(12) United States Patent
Yu et al.

(10) Patent No.: US 9,915,659 B2
(45) Date of Patent: Mar. 13, 2018

(54) SYSTEMS AND METHODS FOR PROGNOSTICATING BRAIN TUMORS

(71) Applicant: Cedars-Sinai Medical Center, Los Angeles, CA (US)

(72) Inventors: John S. Yu, Los Angeles, CA (US); Lincoln A. Edwards, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/186,188

(22) Filed: Jun. 17, 2016

(65) Prior Publication Data

US 2016/0363594 A1 Dec. 15, 2016

Related U.S. Application Data

(63) Continuation-in-part of application No. PCT/US2014/071282, filed on Dec. 18, 2014.

(60) Provisional application No. 61/917,878, filed on Dec. 18, 2013, provisional application No. 61/923,516, filed on Jan. 3, 2014.

(51) Int. Cl.
| | |
|---|---|
| G01N 33/574 | (2006.01) |
| C12Q 1/68 | (2006.01) |
| A61K 45/06 | (2006.01) |
| A61K 31/436 | (2006.01) |
| A61K 31/404 | (2006.01) |
| A61K 31/4188 | (2006.01) |

(Continued)

(52) U.S. Cl.
CPC ..... *G01N 33/57407* (2013.01); *A61K 31/404* (2013.01); *A61K 31/4188* (2013.01); *A61K 31/436* (2013.01); *A61K 31/44* (2013.01); *A61K 31/506* (2013.01); *A61K 45/06* (2013.01); *C12Q 1/6886* (2013.01); *C12Q 2600/106* (2013.01); *C12Q 2600/118* (2013.01); *C12Q 2600/158* (2013.01); *G01N 2333/904* (2013.01); *G01N 2800/52* (2013.01)

(58) Field of Classification Search
CPC .............. A61K 2300/00; A61K 31/404; A61K 31/4188; A61K 31/436; A61K 31/44; A61K 31/506; A61K 45/06; C12Q 1/6886; C12Q 2600/106; C12Q 2600/118; C12Q 2600/158; G01N 2333/904; G01N 2800/52; G01N 33/57407
See application file for complete search history.

(56) References Cited

FOREIGN PATENT DOCUMENTS

| WO | 2011106709 A2 | 9/2011 |
| WO | 2013003384 A1 | 1/2013 |
| WO | 2015095598 A1 | 6/2015 |

OTHER PUBLICATIONS

Nagane et al. (Jpn J clin Oncol, 2012, 42(10) pp. 887-895).*

(Continued)

*Primary Examiner* — Savitha M Rao
(74) *Attorney, Agent, or Firm* — Nixon Peabody LLP; Linda B. Huber

(57) ABSTRACT

The present invention describes methods of prognosticating patient survival based on an analysis of the ZEB1 gene or gene product. The present invention also describes methods of selecting and/or selecting various therapies based on the analysis of ZEB1, IDH1, PTEN, MGMT and/or RET. Further describes are systems for analyzing ZEB1, IDH1, PTEN, MGMT and/or RET as well as selecting and/or selecting the therapies.

6 Claims, 58 Drawing Sheets

(51) Int. Cl.
*A61K 31/44* (2006.01)
*A61K 31/506* (2006.01)

(56) References Cited

OTHER PUBLICATIONS

Siebzehnrubl et al. (EMBO mol med (2013), 5, 1196-1212.*
Zhang et al. (Neuro-Oncology 15(9), pp. 1114-1126, 2013).*
International Search Report and Written Opinion for PCT/US2014/071282 dated Apr. 20, 2015, 25 pages.
International Preliminary Report on Patentability for PCT/US2014/071282 dated Jun. 21, 2016, 21 pages.
Arslantas et al., The Importance of Genomic Copy Number Changes in the Prognosis of Glioblastoma Multiforme, Neurosurg Rev., 2003, vol. 27(1), pp. 58-64.
Denardo et al., Quantitative Phosphoproteomic Analysis Identifies Activation of the RET and IGF-1R/IR Signaling Pathways in Neuroblastoma, PLoS One, 2013, vol. 8(12), pp. 1-16.
Edwards et al., Effect of Brain- and Tumor-Derived Connective Tissue Growth Factor on Glioma Invasion, J. Natl. Cancer Inst., 2011, vol. 103(15), pp. 1162-1178.
Iwamoto et al., Phase II Study of Pazopanib (GW786034), An Oral Multi-Targeted Angiogenesis Inhibitor for Adults with Recurrent Glioblastoma, 2010, vol. 12(8), pp. 855-861.
Kahlert et al., Activation of Canonical WNT/β-Catenin Signaling Enhances in Vitro Motility of Glioblastoma Cells by Activation of ZEB1 and other Activators of Epithelial-to-Mesenchymal Transition, Cancer Lett., 2012, vol. 325(1), pp. 42-53.
Nagane et al., Phase II Study of Single-Agent Bevacizumab in Japanese Patients with Recurrent Malignant Glioma, Japan Journal of Clinical Oncology, 2012, vol. 42(10), pp. 887-895.
Ramirez et al., Loss of 1p, 19q, and 10q Heterozygosity Prosecptivity Predicts Prognosis of Oligodendroglial Tumors—Towards Individualized Tumor Treatment, Neuro Oncol, 2010, vol. 12(5), pp. 490-499.
Siebzehnrubl et al., The ZEB1 Pathway Links Glioblastoma Initiation Invasion and Chemoresistance, EMBO Mol. Med., 2013, vol. 5(8), pp. 1196-1212.

* cited by examiner

| Mutation | Exon | MP Score | Species | AA alignment | SEQ ID NO: |
|---|---|---|---|---|---|
| N603S | 7 | 0.99 | Human | DSVNLPLDVVK | 54 |
| | | | Mutated | -SV⑤LPLDVVK | 55 |
| | | | Mmusculus | --VNLPLDVVK | 56 |
| | | | Ptroglodytes | DSVNLPLDVVK | 57 |
| G709D | 7 | 0.99 | Human | NTQGYLYTAE | 58 |
| | | | Mutated | NTQ⑩YLYTAE | 59 |
| | | | Mmusculus | NTQGYLYTAE | 60 |
| | | | Ptroglodytes | NTQGYLYTAE | 61 |

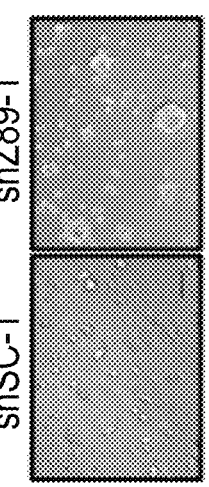
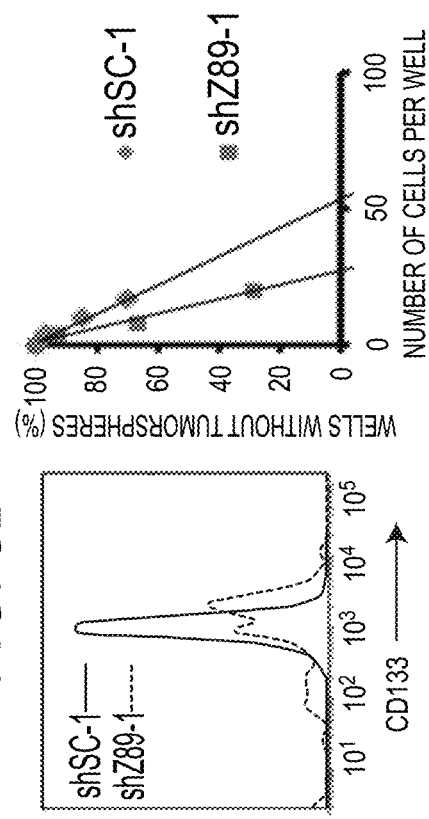
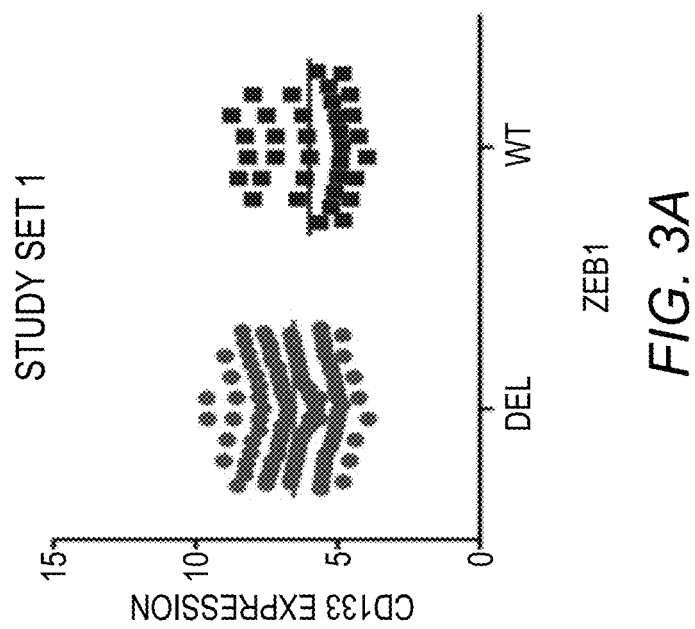
FIG. 3A
FIG. 3B
FIG. 3C

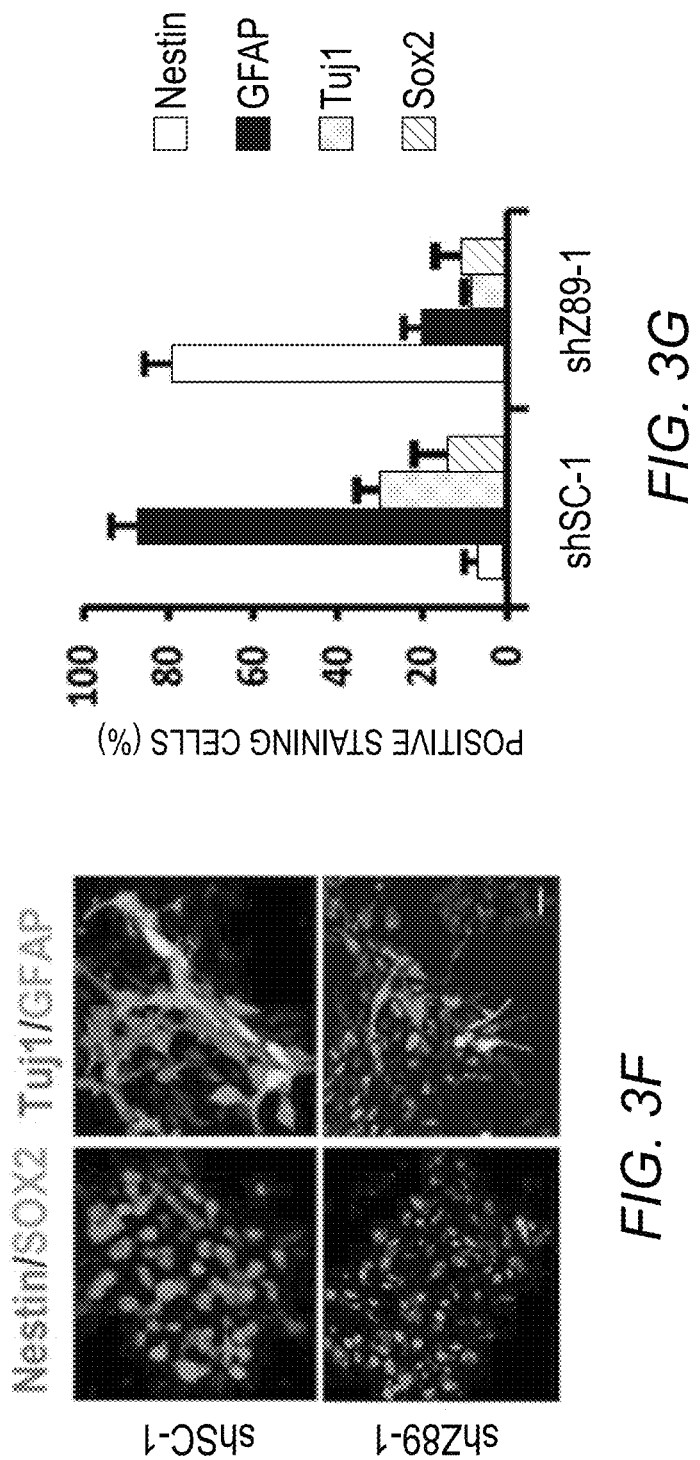

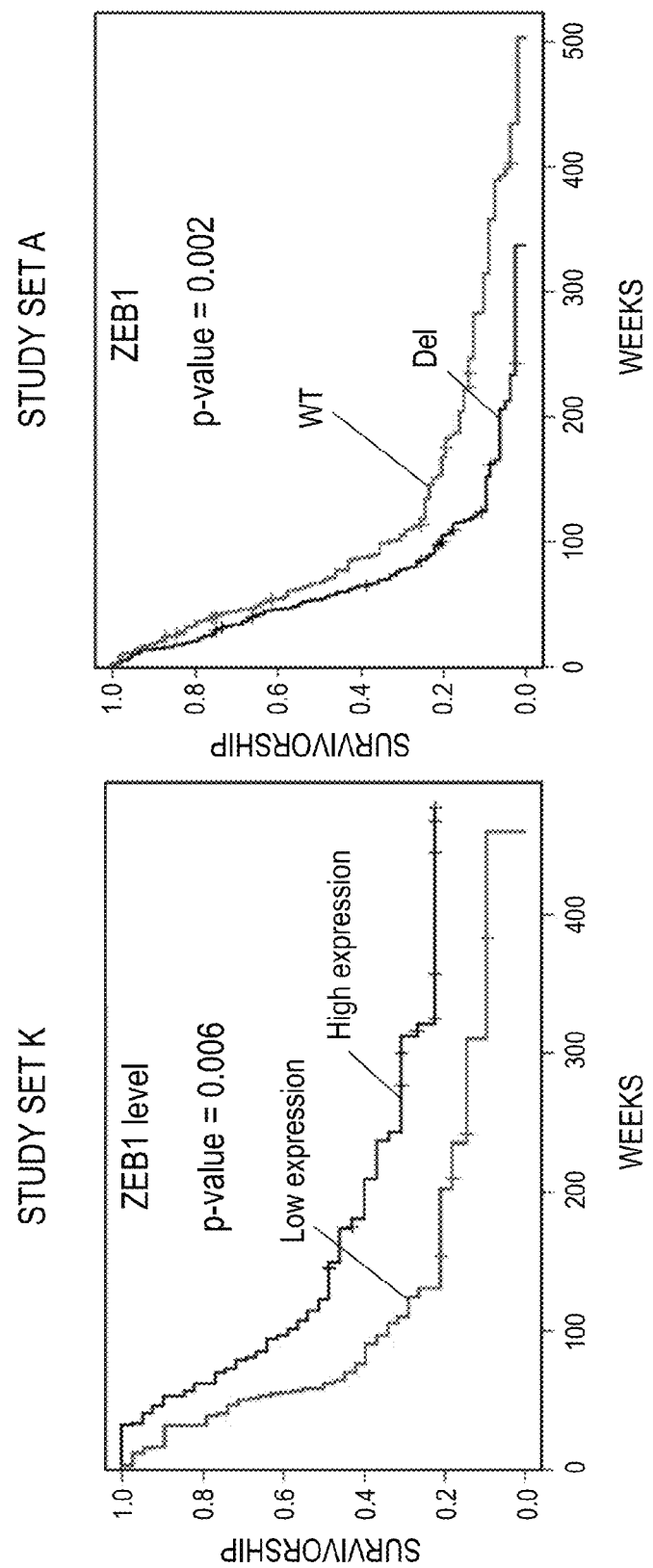

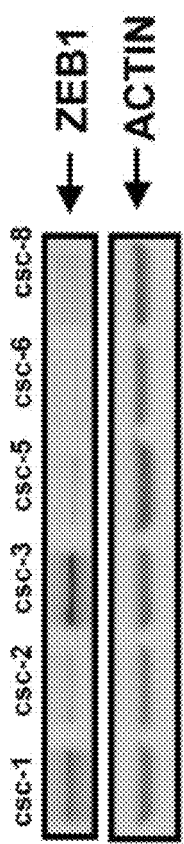
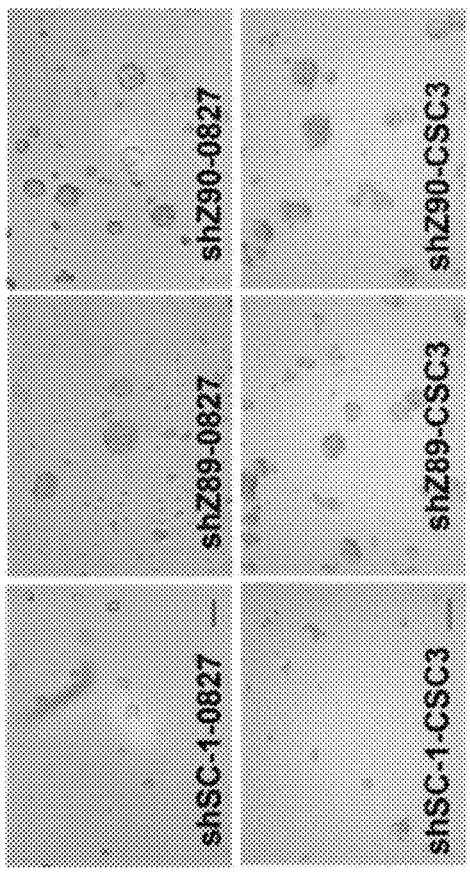
FIG. 14D
FIG. 14E
FIG. 14F

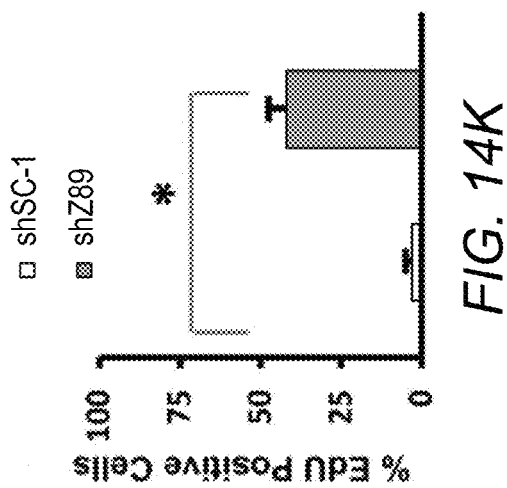
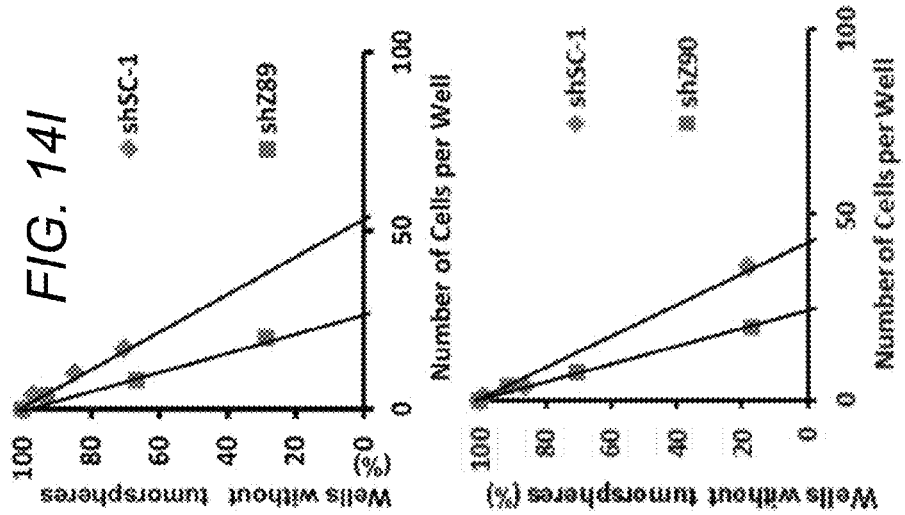
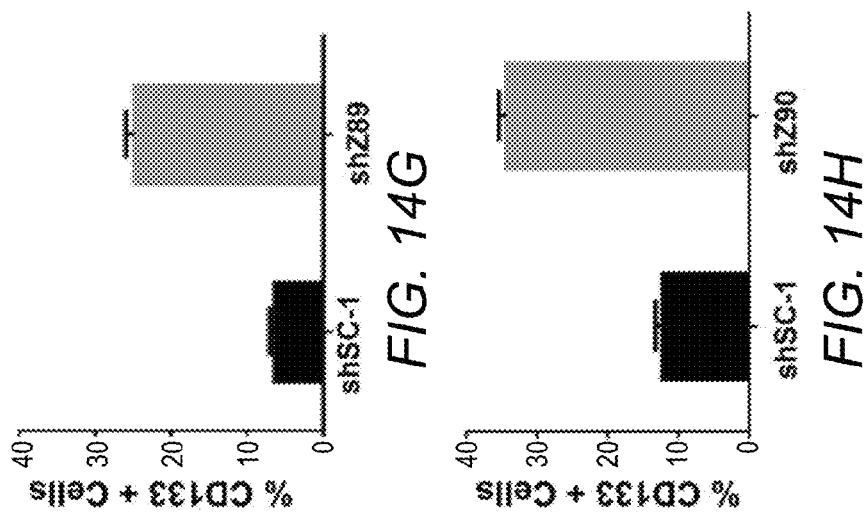

Concordance RET and ZEB1 rev
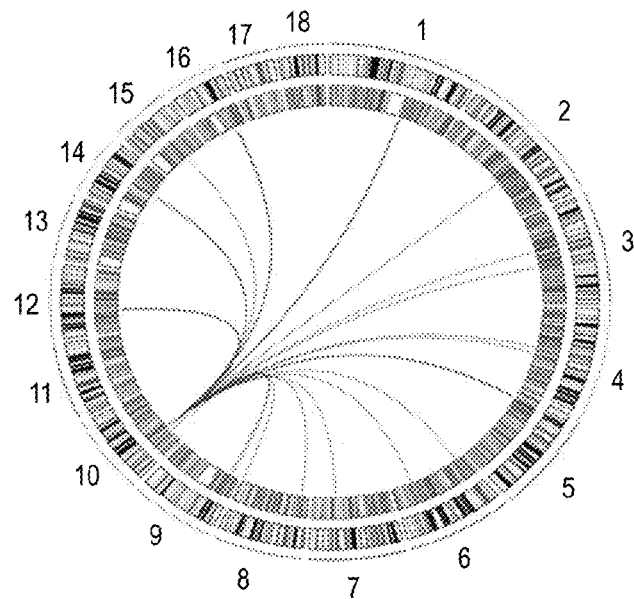
RET and ZEB1 Associations
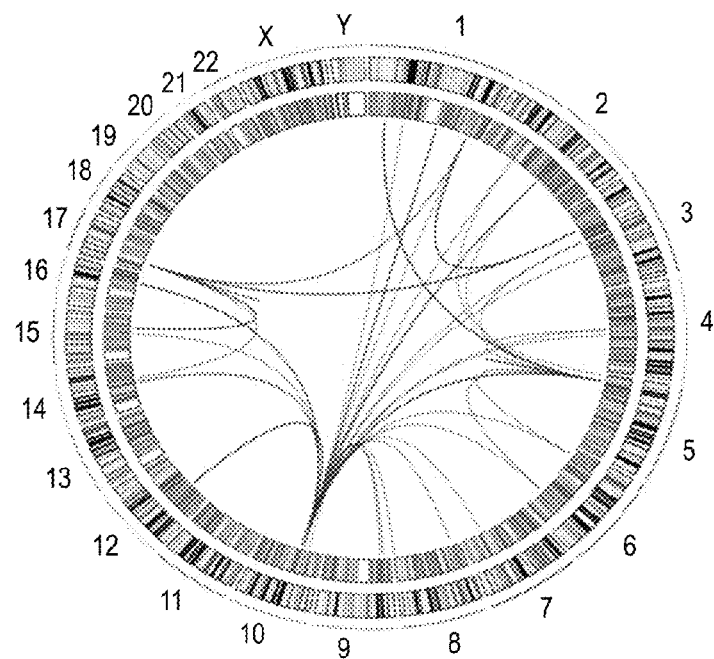
FIG. 20A

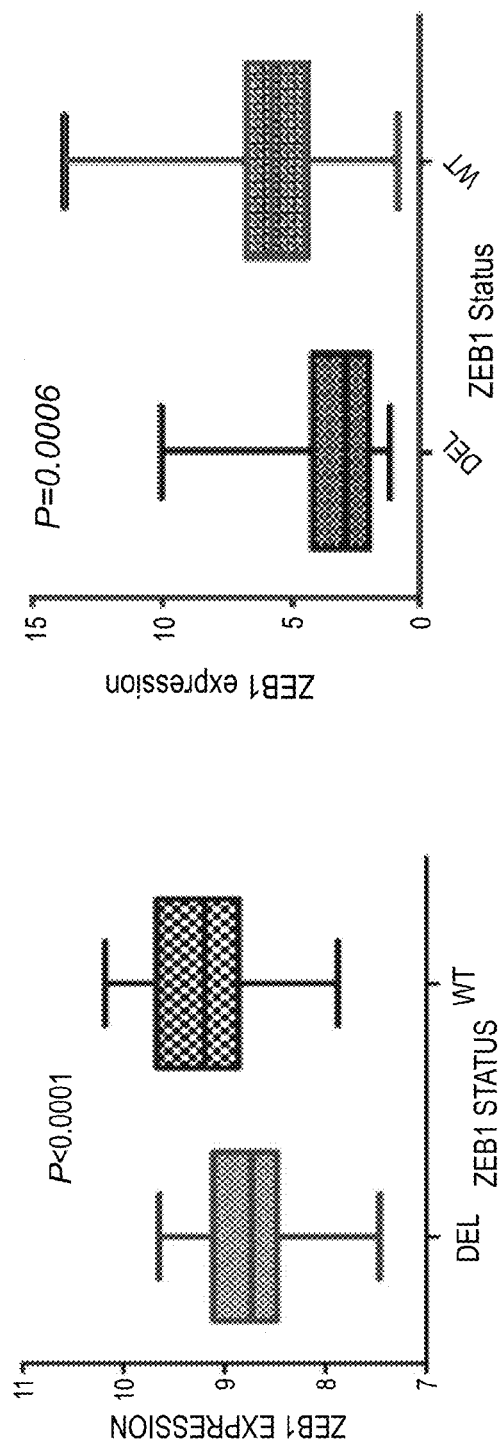
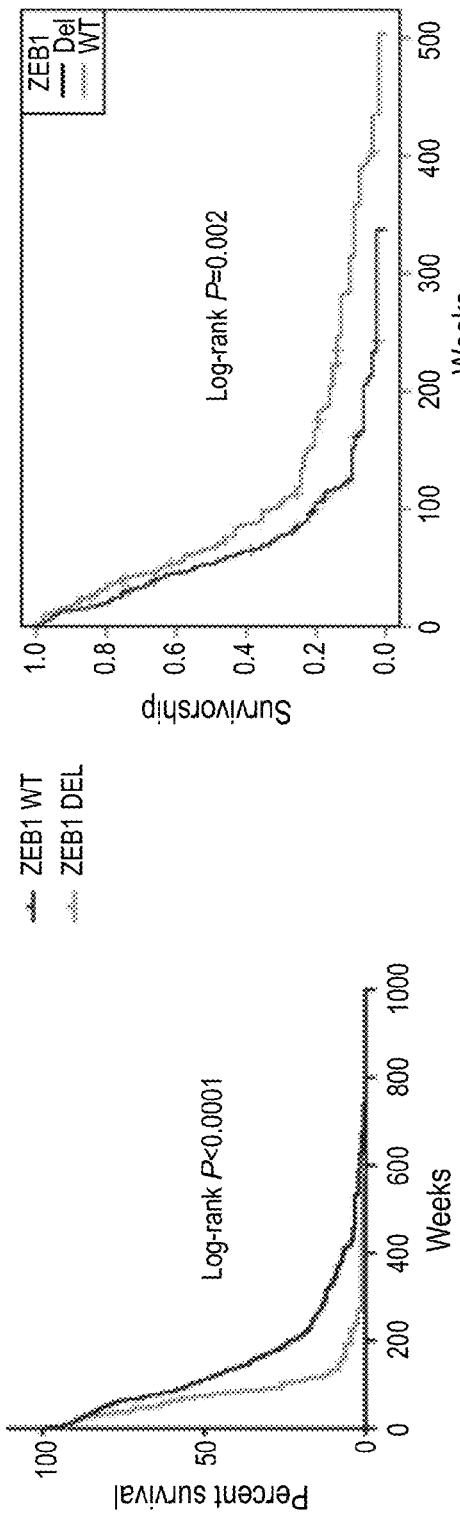
FIG. 28D
FIG. 28E
FIG. 28F
FIG. 28G

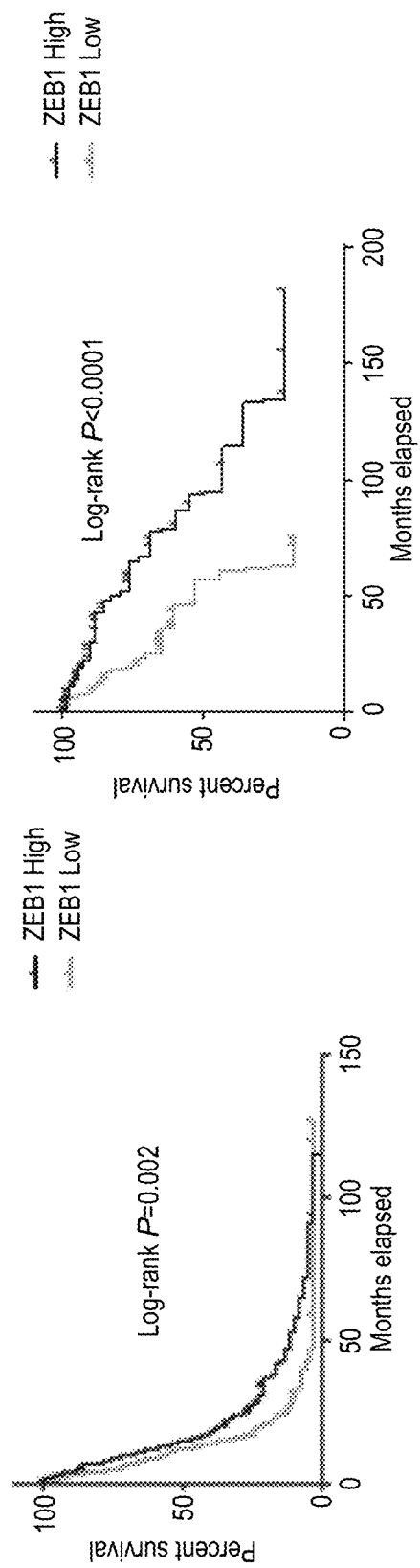

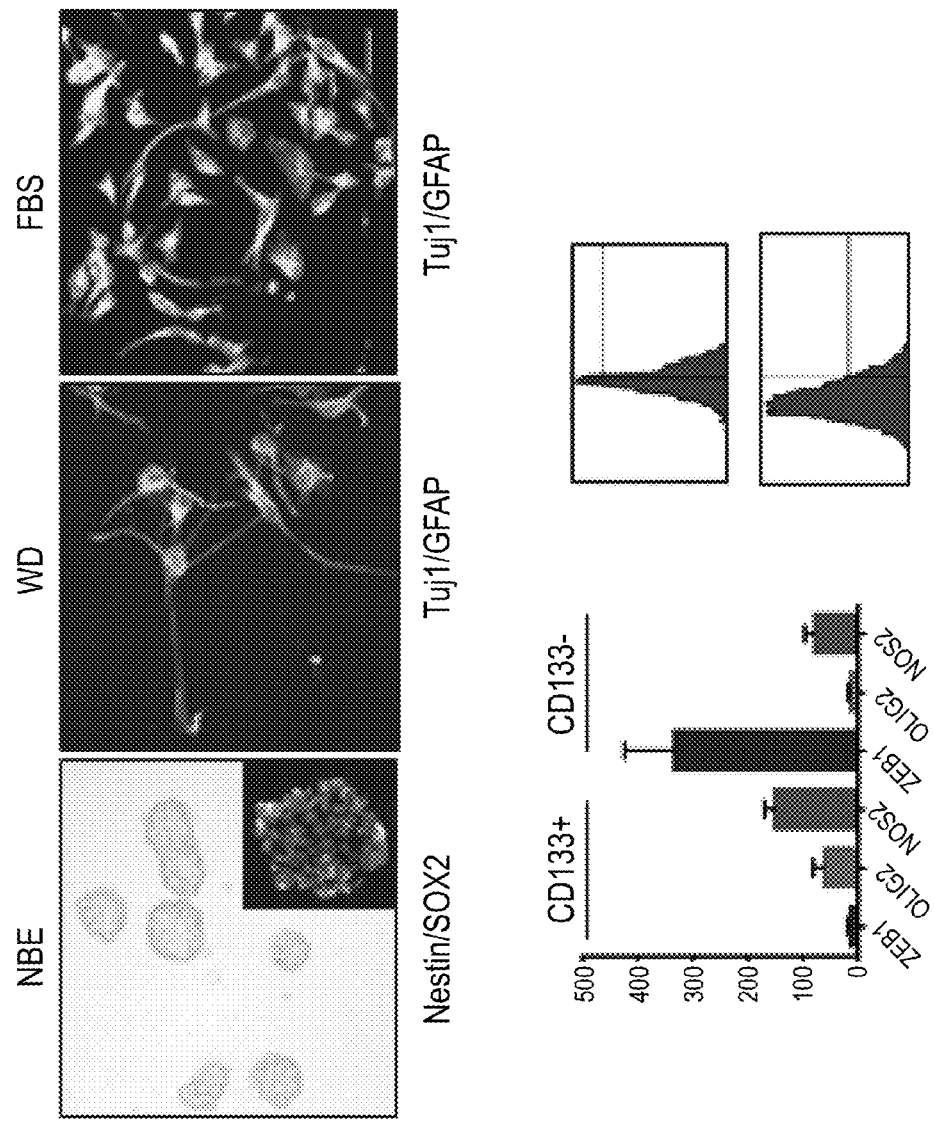

SYSTEMS AND METHODS FOR PROGNOSTICATING BRAIN TUMORS

CROSS-REFERENCE TO RELATED APPLICATIONS

This application is a continuation-in-part of International Application No. PCT/US2014/071282, filed on Dec. 18, 2014, which designated the U.S., was published under PCT Article 21(2) in English, and claims priority under 35 U.S.C. §119(e) to U.S. provisional patent application No. 61/917,878, filed on Dec. 18, 2013, and to U.S. provisional patent application No. 61/923,516, filed on Jan. 3, 2014. The contents of all the related applications cross-referenced herein are herein incorporated by reference in their entirety as though fully set forth.

STATEMENT REGARDING FEDERALLY-SPONSORED RESEARCH

This invention was made with government support under Grant No. NS048959 awarded by the National Institutes of Health. The government has certain rights in the invention.

FIELD OF INVENTION

This invention relates to the fields of oncology and pathology.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Glioblastoma is the most frequent and most lethal form of primary brain cancer. Despite advances in stereotactic surgical resection, radiation therapy and chemotherapeutics, patients diagnosed with a glioblastoma multiforme (GBM) have a median survival of 14.6 months. This disease is complicated by the fact that along with aberrant signal transduction pathways at the protein level, GBMs are marred in chromosomal alterations and instability at the genomic level. For this reason, biologically relevant targets remain elusive. The introduction of subdividing glioblastoma patients based on molecular signatures has increased our knowledge of patient response to therapy, patient outcome and the stem cell component found within GBMs. Among the glioblastoma subtypes, the proneural (PN) subytpe has the most favorable outcome. In contrast, the proliferative (Prolif) and mesenchymal (Mes) subtypes have a poor survival outcome. The stem cell component of GBMs may play an important role in both patient response to therapy and patient survival.

As such, there is a need in art for methods, kits and systems for determining molecular subsets for the prognostication of brain tumors, such as GBMs, and for selecting and administering treatment for these patients.

SUMMARY OF INVENTION

Various embodiments of the present invention provide for a process, comprising: obtaining a sample comprising a tumor cell from a subject desiring a prognosis of a tumor; assaying the sample to determine a presence or absence of a ZEB1 dysregulation in the sample; and determining the subject has a poor prognosis if a ZEB1 dysregulation is present, or determining the subject has a good prognosis if a ZEB1 dysregulation is absent.

In various embodiments, the process further comprises detecting a presence or absence of a PTEN deletion in the sample; and determining the subject has a poor prognosis if a ZEB1 dysregulation and a PTEN deletion are present, or a ZEB1 dysregulation is present and a PTEN deletion is not present, or determining the subject has a good prognosis if a ZEB1 dysregulation and a PTEN deletion are absent.

In various embodiments, the process further comprises detecting a presence or absence of a RET dysregulation in the sample; and determining the subject has a poor prognosis if a ZEB1 dysregulation and a RET dysregulation are present, or ZEB1 dysregulation is present and RET dysregulation is not present or determining the subject has a good prognosis if a ZEB1 dysregulation and a RET dysregulation are absent.

In various embodiments, the process further comprises detecting a presence or absence of an IDH1 dysregulation in the sample; and determining the subject has a poor prognosis if ZEB1 dysregulation is present and IDH1 dysregulation is absent.

In various embodiments, the tumor can be glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, assaying the sample to determine a presence or absence of a ZEB1 dysregulation in the sample can comprise: assaying the sample for a chromosome 10p11.2 copy number; comparing the chromosome 10p11.2 copy number to a reference value; and determining the presence of a ZEB1 dysregulation that is indicative of a poor prognosis if there is a chromosome 10p11.2 copy number loss, and determining the absence of a ZEB1 dysregulation if there is not a 10p11.2 copy number loss.

In various embodiments, assaying the sample to determine a presence or absence of a ZEB1 dysregulation in the sample can comprise: assaying the sample to determine if there is a loss of heterozygosity (LOH) of the ZEB1 gene; and determining the presence of a ZEB1 dysregulation indicative of a poor prognosis if there is a LOH of the ZEB1 gene and determining the absence of a ZEB1 dysregulation if there is not a LOH of the ZEB1 gene.

In various embodiments, assaying the sample to determine a presence or absence of a ZEB1 dysregulation in the sample can comprise: subjecting the sample to an analysis for ZEB1 expression; comparing the ZEB1 expression to a ZEB1 expression reference value; and determining the presence of a ZEB1 dysregulation that is indicative of a poor prognosis if the ZEB1 expression level is lower than the reference value, and determining the absence of a ZEB1 dysregulation if the ZEB1 expression level is not lower than the reference value.

In various embodiments, the ZEB1 expression reference value can be a median or mean ZEB1 expression level from a population of subjects with an intact ZEB1 gene, or a population of subjects without a brain tumor, or a population of subjects with a brain tumor. In various embodiments, the ZEB1 expression reference value can be a ZEB1 expression level from the subject's own blood sample or from a normal blood sample.

In various embodiments, assaying the sample to determine a presence or absence of a ZEB1 dysregulation in the sample can comprise: subjecting the sample to an analysis for ZEB1 mutation or a ZEB1 deletion; and determining the presence of a ZEB1 dysregulation that is indicative of a poor prognosis if there is a ZEB1 mutation or a ZEB1 deletion; and determining the absence of a ZEB1 dysregulation if there is not a ZEB1 mutation or a ZEB1 deletion.

In various embodiments, assaying for a presence or absence of a ZEB1 dysregulation can comprise detecting ZEB1 mRNA with a polynucleotide capable of hybridizing with ZEB1 mRNA under stringent hybridization conditions.

In various embodiments, assaying for a presence or absence of a ZEB1 dysregulation can comprise detecting a ZEB1 protein with an antibody capable of specifically binding to a ZEB1 protein.

In various embodiments, assaying for the presence or absence of a ZEB1 dysregulation can comprise: sequencing the ZEB1 gene from the subject's brain tumor; and comparing the brain tumor ZEB1 sequence to a ZEB1 sequence from the subject's own blood sample, or a normal blood sample, or a reference ZEB1 sequence.

In various embodiments, assaying the ZEB1 dysregulation can comprise using DNA sequencing, comparative genomic hybridization (CGH), array CGH (aCGH), SNP analysis, mRNA expression assay, RT-PCR, real-time PCR, Fluorescence in situ hybridization (FISH), or a combination thereof.

In various embodiments, the poor prognosis can comprise decreased survival likelihood, shortened life expectancy, or enhanced tumor stemness.

In various embodiments, the process can further comprise selecting a first therapy to the subject if the subject has a good prognosis or selecting a second therapy, or both the first therapy and the second therapy, to the subject if the subject has a poor prognosis.

In various embodiments, the first therapy can be a selected from the group consisting of: surgery, radiation, chemotherapy, and combinations thereof. In various embodiments, the first therapy can be temozolomide.

In various embodiments, the second therapy can be selected from the group consisting of: an agent that inhibits the self-renewal pathways of cancer stem cells. In various embodiments, an agent that inhibits the self-renewal pathways of cancer stem cells can be selected from the group consisting of an agent that inhibits the sonic hedgehog pathway, an agent that inhibits the WNT pathway, an inhibitor of BMX, an inhibitor of IDH1, an inhibitor of IDH2 and combinations thereof. In various embodiments, the second therapy can be rapamycin or bevacizumab (AVASTIN).

In various embodiments, the process can further comprise administering the first therapy to the subject if the subject has a good prognosis or administering the second therapy, or both the first therapy and the second therapy, to the subject if the subject has poor prognosis.

Various embodiments provide for a system for determining a prognosis of a subject suspected of having or having a tumor, comprising: a sample analyzer configured to produce a signal for ZEB1 dysregulation from a sample comprising a tumor cell from the subject; and a computer sub-system programmed to calculate whether the signal is greater or not than a reference value.

In various embodiments, said computer sub-system can be programmed to determine that the subject has a poor prognosis if a ZEB1 dysregulation is present, or to determine that the subject has a good prognosis if a ZEB1 dysregulation is absent.

In various embodiments, the sample analyzer can be further configured to produce a signal for a PTEN deletion in the sample; and the computer sub-system can be further programmed to calculate whether the PTEN signal is greater or not than a reference value. In various embodiments, said computer sub-system can be further programmed to determine that the subject has a poor prognosis if a ZEB1 dysregulation and a PTEN deletion are present, or a ZEB1 dysregulation is present and a PTEN deletion is not present, or to determine that the subject has a good prognosis if a ZEB1 dysregulation and a PTEN deletion are absent.

In various embodiments, the sample analyzer can be further configured to produce a signal for a RET dysregulation in the sample; and the computer sub-system can be further programmed to calculate whether the RET signal is greater or not than a reference value. In various embodiments, said computer sub-system can be further programmed to determine that the subject has a poor prognosis if a ZEB1 dysregulation and a RET dysregulation are present, or to determine the subject has a good prognosis if a ZEB1 dysregulation and a RET dysregulation are absent.

In various embodiments, the sample analyzer can be further configured to produce a signal for a MGMT expression level in the sample; and the computer sub-system is further programmed to calculate whether the MGMT signal is greater or not than a reference value. In various embodiments, said computer sub-system can be further programmed to determine that the subject has a poor prognosis if a ZEB1 dysregulation is present and a MGMT expression level is lower than the reference value, or if a ZEB1 dysregulation is present and MGMT expression level is equal or higher than the reference value, or to determine the subject has a good prognosis if a ZEB1 dysregulation is absent and a MGMT expression level is lower than the reference value.

In various embodiments, the sub-system can be programmed to determine the presence of ZEB1 dysregulation if there is a chromosome 10p11.2 copy number loss and the absence of ZEB1 dysregulation if there is not a chromosome 10p11.2 copy number loss.

In various embodiments, the reference value can be chromosome 10 centromere copy number in the sample.

In various embodiments, the sub-system can be programmed to determine the presence of ZEB1 dysregulation if there is a loss of heterozygosity (LOH) of the ZEB1 gene and the absence of ZEB1 dysregulation if there is not LOH of the ZEB1 gene. In various embodiments, the sub-system can be programmed to determine the presence of ZEB1 dysregulation if a ZEB1 expression level is lower than a reference value, and the absence of ZEB1 dysregulation if a ZEB1 expression level is not lower than the reference value. In various embodiments, the sub-system can be programmed to determine the presence of ZEB1 dysregulation if there is a ZEB1 mutation or a ZEB1 deletion, and the absence of ZEB1 dysregulation if there is not a ZEB1 mutation or a ZEB1 deletion.

Various embodiments of the present invention provide for a computer program product embodied in a computer readable medium that, when executing on a computer, performs steps comprising: detecting the presence or absence of a ZEB1 dysregulation in sample comprising a tumor cell from a subject.

In various embodiments, the steps can further comprise: detecting the presence or absence of a PTEN deletion in the sample. In various embodiments, the steps can further comprise: detecting the present or absence of a RET dysregulation in the sample. In various embodiments, the steps can further comprise: detecting MGMT expression levels.

In various embodiments, detecting the presence or absence of the ZEB1 dysregulation can comprise detecting the presence or absence of a chromosome 10p11.2 copy number loss. In various embodiments, detecting the presence or absence of the ZEB1 dysregulation can comprise detection the presence or absence of a loss of heterogeneity of the ZEB1 gene. In various embodiments, detecting the presence or absence of the ZEB1 dysregulation can comprise detection expression level of ZEB1 and comparing the expression level to a reference level. In various embodiments, detecting the presence or absence of the ZEB1 dysregulation can comprise detecting the presence or absence of a ZEB1 mutation or a ZEB1 deletion.

Various embodiments provide for a process for determining a subject's susceptibility to treatment with an angiogenesis inhibitor, comprising: obtaining a sample comprising a tumor cell from a subject desiring a determination regarding the susceptibility to treatment with an angiogenesis inhibitor; assaying the sample to determine a presence or absence of a ZEB1 dysregulation in the sample; and determining the subject is susceptible to treatment with the angiogenesis inhibitor if a ZEB1 dysregulation is present.

In various embodiments, the process can further comprise: assaying the sample to determine a presence or absence of a PTEN deletion in the sample; and determining the subject is susceptible to treatment with the angiogenesis inhibitor if a ZEB1 dysregulation and a PTEN deletion are present, or a ZEB1 dysregulation is present and a PTEN deletion is not present. In various embodiments, the process can further comprise: assaying the sample to determine a presence or absence of a RET dysregulation in the sample; and determining the subject is susceptible to treatment with the angiogenesis inhibitor if a ZEB1 dysregulation and a RET dysregulation is present. In various embodiments, the process can further comprise: assaying the sample to determine MGMT expression levels in the sample; and determining the subject is susceptible to treatment with the angiogenesis inhibitor if a ZEB1 dysregulation is present and MGMT expression levels are low, or if a ZEB1 dysregulation is present and MGMT expression levels are high.

In various embodiments, the angiogenesis inhibitor can be bevacizumab. In various embodiments, the angiogenesis inhibitor can be selected from the group consisting of sorafenib (Nexavar®), sunitinib (Sutent®), pazopanib (Votrient®), and everolimus (Afinitor®).

In various embodiments, the tumor can be glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, assaying the sample to determine a presence or absence of a ZEB1 dysregulation in the sample can comprise: assaying the sample for a chromosome 10p11.2 copy number; comparing the chromosome 10p11.2 copy number to a reference value; and determining the presence of a ZEB1 dysregulation that is indicative susceptibility to the angiogenesis inhibitor if there is a chromosome 10p11.2 copy number loss.

In various embodiments, assaying the sample to determine a presence or absence of a ZEB1 dysregulation in the sample can comprise: assaying the sample to determine if there is a loss of heterozygosity (LOH) of the ZEB1 gene; and determining the presence of a ZEB1 dysregulation indicative of susceptibility to the angiogenesis inhibitor if there is a LOH of the ZEB1 gene.

In various embodiments, assaying the sample to determine a presence or absence of a ZEB1 dysregulation in the sample can comprise: subjecting the sample to an analysis for ZEB1 expression; comparing the ZEB1 expression to a ZEB1 expression reference value; and determining the presence of a ZEB1 dysregulation that is indicative of susceptibility to the angiogenesis inhibitor if the ZEB1 expression level is lower than the reference value.

In various embodiments, the ZEB1 expression reference value can be a median or mean ZEB1 expression level from a population of subjects with an intact ZEB1 gene, or a population of subjects without a brain tumor, or a population of subjects with a brain tumor. In various embodiments, the ZEB1 expression reference value can be a ZEB1 expression level from the subject's own blood sample or from a normal blood sample.

In various embodiments, assaying the sample to determine a presence or absence of a ZEB1 dysregulation in the sample comprises: subjecting the sample to an analysis for ZEB1 mutation or a ZEB1 deletion; and determining the presence of a ZEB1 dysregulation that is indicative of a susceptibility to the angiogenesis inhibitor if there is a ZEB1 mutation or a ZEB1 deletion.

In various embodiments, assaying for a presence or absence of a ZEB1 dysregulation can comprise detecting ZEB1 mRNA with a polynucleotide capable of hybridizing with ZEB1 mRNA under stringent hybridization conditions.

In various embodiments, assaying for a presence or absence of a ZEB1 dysregulation can comprise detecting a ZEB1 protein with an antibody capable of specifically binding to a ZEB1 protein.

In various embodiments, assaying for the presence or absence of a ZEB1 dysregulation can comprise: sequencing the ZEB1 gene from the subject's brain tumor; and comparing the brain tumor ZEB1 sequence to a ZEB1 sequence from the subject's own blood sample, or a normal blood sample, or a reference ZEB1 sequence.

In various embodiments, assaying the ZEB1 dysregulation can comprise using DNA sequencing, comparative genomic hybridization (CGH), array CGH (aCGH), SNP analysis, mRNA expression assay, RT-PCR, real-time PCR, Fluorescence in situ hybridization (FISH), or a combination thereof.

In various embodiments, assaying the ZEB1 dysregulation comprises using ELISA, immunohistochemistry, flow cytometry, fluorescence in situ hybridization (FISH), radioimmuno assays, affinity purification or combinations thereof.

In various embodiments, the process can further comprise selecting a therapy comprising the angiogenesis inhibitor to the subject if the subject is determined to be susceptible to the angiogenesis inhibitor. In various embodiments, the process can further comprise administering the therapy comprising the angiogenesis inhibitor to the subject if the subject is determined to be susceptible to the angiogenesis inhibitor.

Various embodiments provide for a process, comprising: obtaining a sample comprising a tumor cell from a subject desiring a prognosis of a tumor; detecting a presence or absence of a ZEB1 dysregulation in the sample; detecting a MGMT expression level in the sample; and determining the subject has a poor prognosis if a ZEB1 dysregulation is present and the subject has a low MGMT expression level, determining the subject has a poor prognosis if a ZEB1 dysregulation is present and the subject has a high MGMT expression level, or determining the subject has a good prognosis if a ZEB1 dysregulation is absent and the subject has a low MGMT expression level.

In various embodiments, the process can further comprise selecting a first therapy if a good prognosis is determined, or selecting a second therapy or a both the first therapy and the second therapy, if a poor prognosis is determined.

In various embodiments, the process can further comprise administering a first therapy if a good prognosis is determined, or administering a second therapy or a both the first therapy and the second therapy, if a poor prognosis is determined. In various embodiments, temozolomide is not selected as a therapy if ZEB1 dysregulation is present and the subject has a high MGMT expression level. In various embodiments, bevacizumab is selected if ZEB1 dysregulation is present and the subject has a high MGMT expression level.

Various embodiments provide for a process, comprising: obtaining a sample comprising a tumor cell from a subject desiring a prognosis of a tumor; assaying the sample to determine a presence or absence of a RET dysregulation in the sample; and determining the subject has a poor prognosis if a RET dysregulation is present, or determining the subject has a good prognosis if a RET dysregulation is absent.

In various embodiments, the tumor can be glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, assaying the sample to determine a presence or absence of a RET dysregulation in the sample can comprise: assaying the sample for a chromosome 10q11.2 copy number; comparing the chromosome 10q11.2 copy number to a reference value; and determining the presence of a RET dysregulation that is indicative of a poor prognosis if there is a chromosome 10q11.2 copy number loss, and determining the absence of a RET dysregulation if there is not a 10q11.2 copy number loss.

In various embodiments, assaying the sample to determine a presence or absence of a RET dysregulation in the sample can comprise: assaying the sample to determine if there is a loss of heterozygosity (LOH) of the RET gene; and determining the presence of a RET dysregulation indicative of a poor prognosis if there is a LOH of the RET gene and determining the absence of a RET dysregulation if there is not a LOH of the RET gene.

In various embodiments, assaying the sample to determine a presence or absence of a RET dysregulation in the sample can comprise: subjecting the sample to an analysis for RET expression; comparing the RET expression to a RET expression reference value; and determining the presence of a RET dysregulation that is indicative of a poor prognosis if the RET expression level is lower than the reference value, and determining the absence of a RET dysregulation if the RET expression level is not lower than the reference value.

In various embodiments, the RET expression reference value can be a median or mean RET expression level from a population of subjects with an intact RET gene, or a population of subjects without a brain tumor, or a population of subjects with a brain tumor.

In various embodiments, the RET expression reference value can be a RET expression level from the subject's own blood sample or from a normal blood sample.

In various embodiments, assaying the sample to determine a presence or absence of a RET dysregulation in the sample can comprise: subjecting the sample to an analysis for RET mutation or a RET deletion; and determining the presence of a RET dysregulation that is indicative of a poor prognosis if there is a RET mutation or a RET deletion; and determining the absence of a RET dysregulation if there is not a RET mutation or a RET deletion.

In various embodiments, assaying for a presence or absence of a RET dysregulation can comprise detecting RET mRNA with a polynucleotide capable of hybridizing with RET mRNA under stringent hybridization conditions.

In various embodiments, assaying for a presence or absence of a RET dysregulation can comprise detecting a RET protein with an antibody capable of specifically binding to a RET protein.

In various embodiments, assaying for the presence or absence of a RET dysregulation can comprise: sequencing the RET gene from the subject's brain tumor; and comparing the brain tumor RET sequence to a RET sequence from the subject's own blood sample, or a normal blood sample, or a reference RET sequence.

In various embodiments, assaying the RET dysregulation can comprise using DNA sequencing, comparative genomic hybridization (CGH), array CGH (aCGH), SNP analysis, mRNA expression assay, RT-PCR, real-time PCR, Fluorescence in situ hybridization (FISH), or a combination thereof.

In various embodiments, assaying the RET dysregulation comprises using ELISA, immunohistochemistry, flow cytometry, fluorescence in situ hybridization (FISH), radioimmuno assays, affinity purification or combinations thereof.

In various embodiments, the poor prognosis can comprise decreased survival likelihood, shortened life expectancy, or enhanced tumor stemness.

In various embodiments, the process can further comprise selecting a first therapy to the subject if the subject has a good prognosis or selecting a second therapy, or both the first therapy and the second therapy, to the subject if the subject has a poor prognosis.

In various embodiments, the first therapy can be a selected from the group consisting of: surgery, radiation, chemotherapy, and combinations thereof. In various embodiments, the first therapy can be temozolomide.

In various embodiments, the second therapy can be selected from the group consisting of: an agent that inhibits the self-renewal pathways of cancer stem cells. In various embodiments, an agent that inhibits the self-renewal pathways of cancer stem cells can be selected from the group consisting of an agent that inhibits the sonic hedgehog pathway, an agent that inhibits the WNT pathway, an inhibitor of BMX, an inhibitor of IDH1, an inhibitor of IDH2 and combinations thereof. In various embodiments, the second therapy can be rapamycin or bevacizumab (AVASTIN).

In various embodiments, the process can further comprise administering the first therapy to the subject if the subject has a good prognosis or administering the second therapy, or both the first therapy and the second therapy, to the subject if the subject has poor prognosis.

Various embodiments provide for a method of treating a brain tumor in a subject, comprising: analyzing a biological sample from the subject to determine the presence or absence of ZEB1 dysregulation; and administering a first therapy to the subject when ZEB1 dysregulation is not present which is indicative of a good prognosis, or administering a second therapy or the first and second therapies when ZEB1 dysregulation is present which is indicative of a poor prognosis.

In various embodiments, the method can further comprise analyzing the biological sample to determine the presence or absence of a PTEN deletion; and administering a first therapy to the subject when ZEB1 dysregulation is not present and PTEN deletion is not present which is indicative of a good prognosis, or administering a second therapy or the first and second therapies when ZEB1 dysregulation is present and PTEN deletion is present or when ZEB1 dysregulation is present and PTEN deletion is not present which are indicative of a poor prognosis.

In various embodiments, the method can further comprise analyzing the biological sample to determine the presence or absence of a RET dysregulation; and administering a first therapy to the subject when ZEB1 dysregulation and RET dysregulation are not present which is indicative of a good prognosis, or administering a second therapy or the first and second therapies when ZEB1 dysregulation and RET dysregulation are present or when ZEB1 dysregulation is present and RET dysregulation is not present which are indicative of a poor prognosis.

In various embodiments, the method can further comprise analyzing the biological sample to determine MGMT expression levels; and administering a first therapy to the subject when ZEB1 dysregulation is not present and MGMT expression levels are low is indicative of a good prognosis, or administering a second therapy or the first and second therapies when ZEB1 dysregulation is present and MGMT expression levels are low, or when ZEB1 dysregulation is present and MGMT expression levels are high which are indicative of a poor prognosis.

Various embodiments provide for a method of treating a brain tumor in a subject, comprising: obtaining the results of an analysis of ZEB1 dysregulation in a biological sample comprising a tumor cell from a subject; and administering a first therapy to the subject when ZEB1 dysregulation is not present which is indicative of a good prognosis, or administering a second therapy or the first and second therapies when ZEB1 dysregulation is present which is indicative of a poor prognosis.

In various embodiments, the method can further comprise obtaining the results of an analysis of PTEN deletion in the biological sample; and administering a first therapy to the subject when ZEB1 dysregulation is not present and PTEN deletion is not present which is indicative of a good prognosis, or administering a second therapy or the first and second therapies when ZEB1 dysregulation is present and PTEN deletion is present or when ZEB1 dysregulation is present and PTEN deletion is not present which are indicative of a poor prognosis.

In various embodiments, the method can further comprise obtaining the results of an analysis of RET dysregulation in the biological sample; and administering a first therapy to the subject when ZEB1 dysregulation and RET dysregulation are not present which is indicative of a good prognosis, or administering a second therapy or the first and second therapies when ZEB1 dysregulation and RET dysregulation are present or when ZEB1 dysregulation is present and RET dysregulation is not present which are indicative of a poor prognosis.

In various embodiments, the method can further comprise obtaining the results of an analysis of MGMT expression levels in the biological sample; and administering a first therapy to the subject when ZEB1 dysregulation is not present and MGMT expression levels are low is indicative of a good prognosis, or administering a second therapy or the first and second therapies when ZEB1 dysregulation is present and MGMT expression levels are low, or when ZEB1 dysregulation is present and MGMT expression levels are high which are indicative of a poor prognosis.

In various embodiments, the method can further comprise obtaining the results of an analysis of the presence or absence of an IDH1 dysregulation; and administering a first therapy to the subject when ZEB1 dysregulation is not present which is indicative of a good prognosis, or administering a second therapy or the first and second therapies when ZEB1 dysregulation is present and IDH1 dysregulation is not present (e.g., IDH1 wildype is present) which are indicative of a poor prognosis. In various embodiments, the first therapy and second therapy do not comprise procarbazine, lomustine, and vincristine (PCV).

Various embodiments provide for a method of treating a brain tumor in a subject who has been determined to have ZEB1 dysregulation in a brain tumor cell, comprising: administering a second therapy or a first therapy and a second therapy when ZEB1 dysregulation is present which is indicative of a poor prognosis.

In various embodiments, the subject has also been determined to have a PTEN deletion in the brain tumor cell, and the method comprises: administering a second therapy or a first therapy and a second therapy when ZEB1 dysregulation is present and PTEN deletion is present which are indicative of a poor prognosis.

In various embodiments, the subject has also been determined to have a RET dysregulation in a brain tumor cell, and the method comprises: administering a second therapy or a first therapy and a second therapy when ZEB1 dysregulation and RET dysregulation are present which are indicative of a poor prognosis.

In various embodiments, the subject has also been determined to have low MGMT expression levels in a brain tumor cell, or determined to have high MGMT expression levels in the brain tumor cell, and the method further comprises: administering a second therapy or a first therapy and a second therapy when ZEB1 dysregulation is present and MGMT expression levels are low, or when ZEB1 dysregulation is present and MGMT expression levels are high which are indicative of a poor prognosis.

In various embodiments, the subject has also been determined to not have an IDH1 dysregulation in a brain tumor cell, and the method comprises: administering a second therapy or a first therapy and a second therapy when ZEB1 dysregulation is present and and IDH1 dysregulation is not present which are indicative of a poor prognosis. In various embodiments, the first therapy and the second therapy do not comprise procarbazine, lomustine, and vincristine (PCV).

Various embodiments of the present invention provide for a method, comprising: obtaining a sample comprising a tumor cell from a subject; assaying the sample to determine a presence or absence of a ZEB1 dysregulation; and determining that the subject is responsive to an angiogenesis inhibitor and resistant to a chemotherapeutic agent, upon determining the presence of the ZEB1 dysregulation in the sample. In various embodiments, the method further comprises: assaying the sample to determine a presence or absence of an IDH1 dysregulation; and determining that the subject is responsive to an angiogenesis inhibitor and resistant to a chemotherapeutic agent, upon determining the presence of the ZEB1 dysregulation and the absence of the IDH1 dysregulation in the sample. In various embodiments, the method further comprises selecting the angiogenesis inhibitor but not the chemotherapeutic agent for the subject as a tumor treatment. In various embodiments, the method further comprises instructing the subject to receive the angiogenesis inhibitor but not the chemotherapeutic agent as a tumor treatment. In various embodiments, the method further comprises administering the angiogenesis inhibitor but not the chemotherapeutic agent to the subject as a tumor treatment. In some embodiments, wherein the chemotherapeutic agent is already being administered to the subject, the method further comprises stop administering the chemotherapeutic agent to the subject. In some embodiments, the chemotherapeutic agent is temozolomide. In some embodiments, the chemotherapeutic agent is procarbazine, lomustine, and vincristine (PCV).

Various embodiments of the present invention provide for a method of treating a tumor in a subject, wherein a ZEB1 dysregulation has been determined to be present in a tumor cell of the tumor, comprising: providing an angiogenesis inhibitor; and administering a therapeutically effective amount of the angiogenesis inhibitor to the subject, thereby treating the tumor in the subject. In various embodiments, an absence of an IDH1 dysregulation has also been determined to be in the tumor cell. In various embodiments, the method further comprises not administering a chemotherapeutic agent to the subject, or stop administering the chemotherapeutic agent to the subject. In some embodiments, wherein the chemotherapeutic agent is already being administered to the subject, the method further comprises stop administering the chemotherapeutic agent to the subject. In some embodiments, the chemotherapeutic agent is temozolomide. In some embodiments, the chemotherapeutic agent is procarbazine, lomustine, and vincristine (PCV).

BRIEF DESCRIPTION OF THE DRAWINGS

Exemplary embodiments are illustrated in referenced figures. It is intended that the embodiments and figures disclosed herein are to be considered illustrative rather than restrictive.

(FIG. 1A): ZEB1 deletion (DEL), defined as copy number less than or equal to −0.5 (n=188); wildtype (WT) defined as copy number greater than or equal to zero (n=62). Two-tailed student t-test identified a significant difference between these two groups with a p<0.001. (FIG. 1B): Identification of LOH (n=14) with glioblastoma and matched controls indicated that within the ZEB1 locus (10p.11.2) LOH could be inferred in a retrospective SNP analysis of GBM patients indicated by colors yellow-no LOH, blue-LOH in 29% of patients.

FIGS. 3A-3G show decrease or loss of ZEB1 expression results in poor survival, enhances stemness and resistance to differentiation. FIG. 3A: ZEB1 deletion (DEL), defined as copy number less than or equal to −0.5 (n=117); wildtype (WT) defined as copy number greater than or equal to zero (n=152) analyzed against CD133 expression. FIG. 3B: representative neurospheres from 0827 GSCs transduced with either non-targeting shRNA (shSC-1) or ZEB1 targeting shRNA (shZ89-1) utilized in (FIG. 3C) and (FIG. 3F). FIG. 3C: Left, FACs analysis of CD133 staining 0827 GSCs transduced with shSC-1 (shown in solid line) compared to shZ89-1 transduced into 0827 GSCs (shown in dotted line). Right, limiting dilution assay of 0827 infected shSC-1 and 0827 infected shZ89-1. FIG. 3D: Estimated Kaplan-Meier survival curves for 507 glioblastoma patients from study set J (left) for high and low ZEB1 expression. FIG. 3E: The same cohort was used (right) stratified with CD133 high and low expression. ZEB1 median expression was used to stratify patients in both curves. Patients with GBMs having high vs low ZEB1 expression had estimated median survival times of 580 vs 310 weeks in study set J (left) and 540 vs 220 weeks in study set J (right). FIG. 3F: Representative immunofluorescent micrographs of 0827 GSCs transduced with either shSC-1 (top) or shZ89-1 (bottom) under differentiation conditions. Differentiation was inhibited in ZEB1 targeted (shZ89-1) 0827 GSCs. 3G: Histograms indicating the percentage of Nestin,Tuj1,GFAP and Sox2 positive 0827 GSCs transduced with either shSC-1 or shZ89-1.

FIG. 4A: Kaplan-Meier estimates of ZEB1 copy number analysis in association with low MGMT expression in GBM patients treated with temozolomide. ZEB1 deletion, defined as copy number less than or equal to −0.5 (n=70); ZEB1 wildtype (WT) defined as copy number greater than or equal to zero (n=45). FIG. 4B: ZEB1 copy number analysis in association with high MGMT expression in GBM patients treated with Temozolomide. ZEB1 (DEL), defined as copy number less than or equal to −0.5 (n=57); ZEB1 (WT) defined as copy number greater than or equal to zero (n=64). FIG. 4C: Kaplan-Meier estimates of overall survival of GBM patients either treated with bevacizumab (n=83) or without (n=282). FIG. 4D: Kaplan-Meier estimates of overall survival of ZEB1 wildtype (WT) GBM patients either treated with bevacizumab (n=67) or without (n=10). P-value was determined by log rank test p=0.839. FIG. 4E: Kaplan-Meier estimates of overall survival of ZEB1 deleted GBM patients either treated with bevacizumab (n=12) or without (n=67). P-value was determined by log rank test p=0.045. FIG. 4F: Relative Zeb1 expression and relative LIF expression.

(FIG. 7A) A panel of primary patient derived glioma stem cells (GSCs) from 5 patients were analyzed for ZEB1 expression, actin served as a loading control. (FIG. 7B) RT-PCR and Western blot confirmation of ZEB1 knockdown in 0827 GSCs with shRNA targeting ZEB1 (shZ89-1) a non-targeting shRNA (shSC-1) was included as a control. (FIG. 7C) Representative bright-field images of neurospheres in CSC3 GSCs infected with either non-targeting shRNA (shSC-1) or a shRNA targeting ZEB1 (shZ90-1). (FIG. 7D) FACs analysis of CSC3 GSCs infected with shSC-1 or shZ90-1 indicate an increase in CD133 expression with ZEB1 knockdown in CSC3 infected with shZ90-1. (FIG. 7E) RT-PCR of a GSCs from Cedars-Sinai designated as cancer stem cells (CSCs)

for ZEB1 expression and CD133 expression where there appears to be an inverse correlation in trend.

FIGS. 8A-8B show ZEB1 expression and its effect on patient survival and cell proliferation. (FIG. 8A) Estimated Kaplan-Meier survival curve for 77 glioblastoma patients from study set K for high and low ZEB1 expression, p-value was determined by log rank test p=0.006. (FIG. 8B) Kaplan-Meier estimates of overall survival of ZEB1 wildtype (WT) GBM patients compared to ZEB1 deleted patients from study set A. P-value was determined by log rank test p=0.002.

Figure 9:
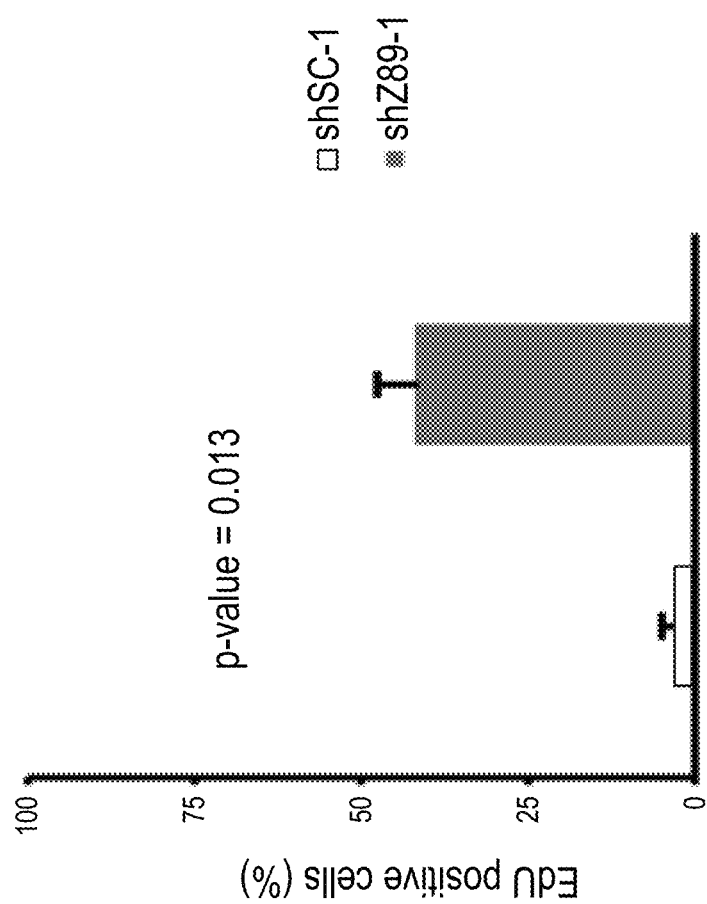

FIG. 9 shows Quantitation of 0827 GSCs transduced with either shSC-1 or shZ89-1 and cell proliferation of each was determined as measured by 5-ethynyl-2'-deoxyuridine (EdU) incorporation.

Figure 10B:
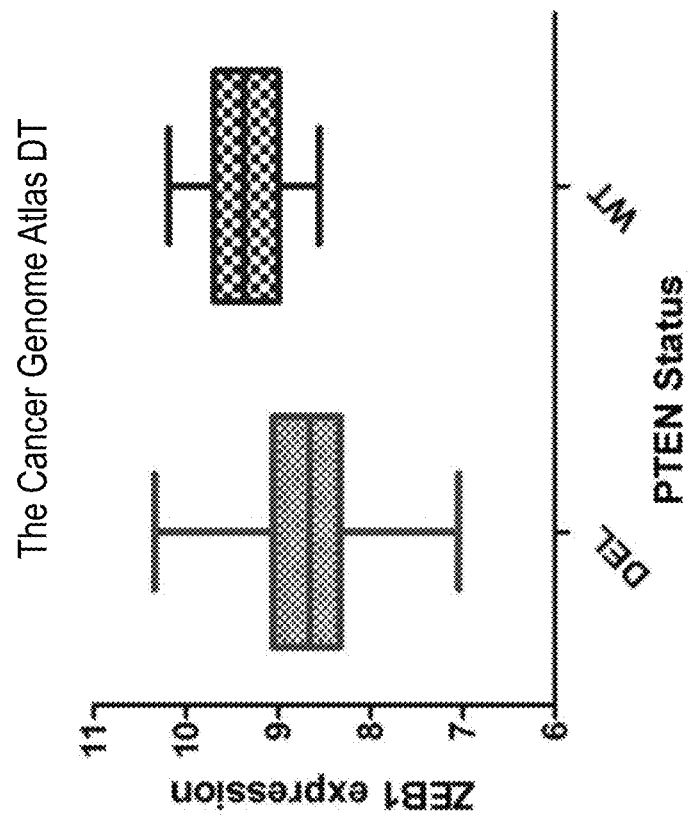
Figure 10A:
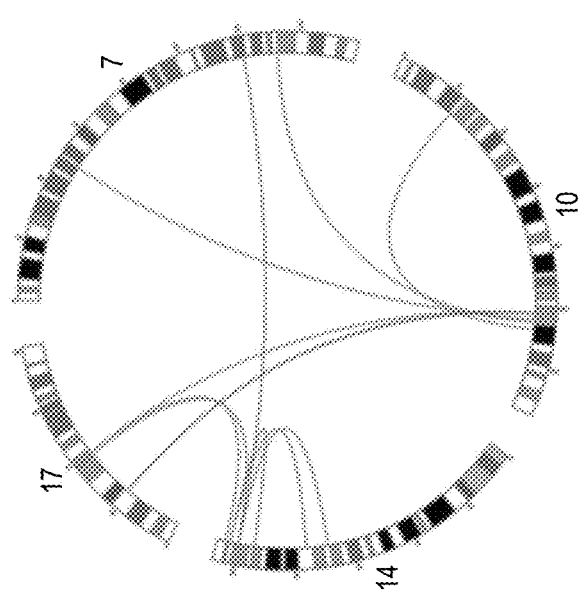
Figure 10C:
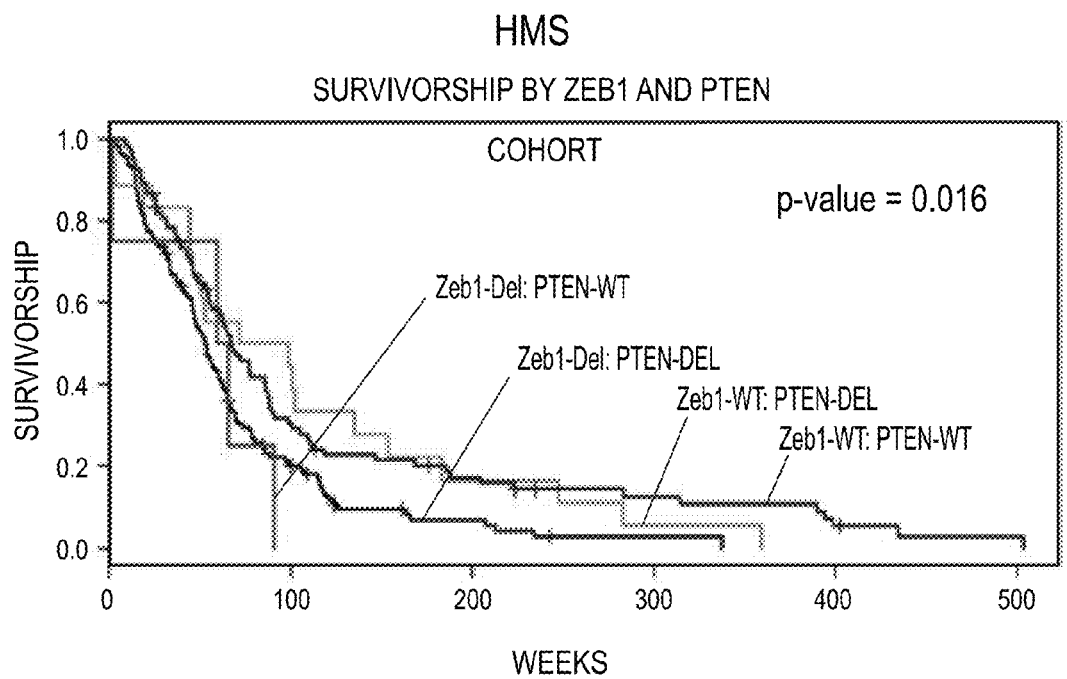
Figure 10D:
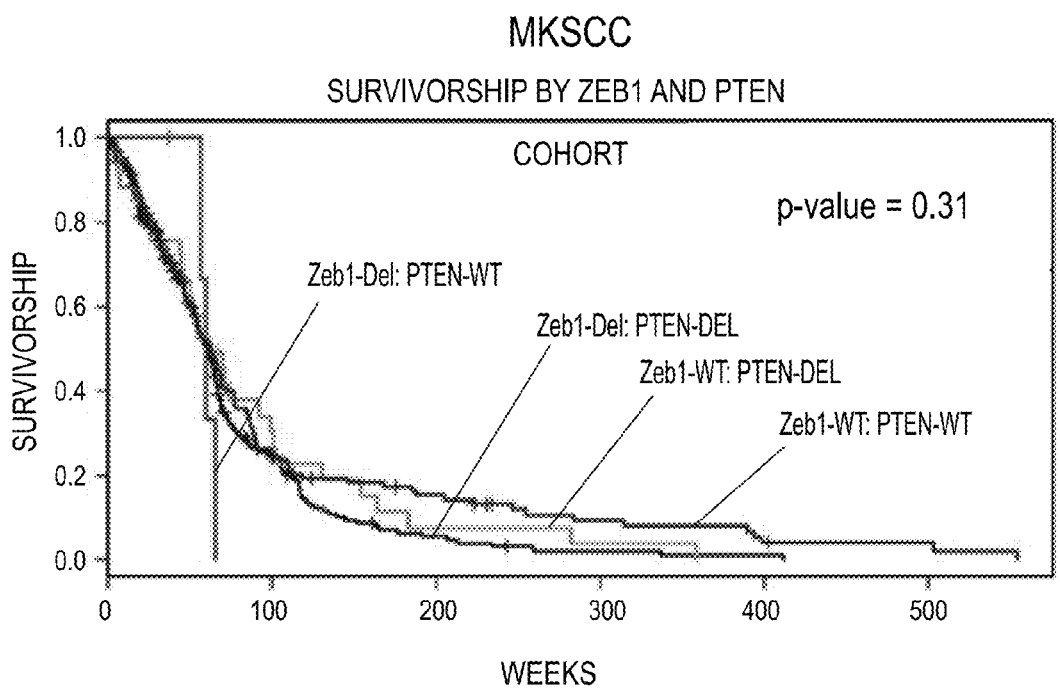

FIGS. 10A-10D depict ZEB1 and its association with PTEN in accordance with various embodiments of the present invention. FIG. 10A: Representation of ZEB1 and its associations with genes known to be implicated in GBM development. FIG. 10B: ZEB1 expression in association with PTEN expression in GBM patients. ZEB1 and PTEN deletion (DEL), defined as copy number less than or equal to −0.5 (n=179); ZEB1 and PTEN wildtype (WT) defined as copy number greater than or equal to zero (n=58). Two-tailed student t-test identified a significant difference between these two groups with a p<0.001. FIG. 10C: Estimated Kaplan-Meier survival curves for 238 glioblastoma patients from cohort A (left) and FIG. 10D: 406 glioblastoma patients cohort B (right). ZEB1 and PTEN copy number expression which defined deletion (del) or wildtype (wt) was used to stratify patients in both cohort A and B.

Figure 11A:
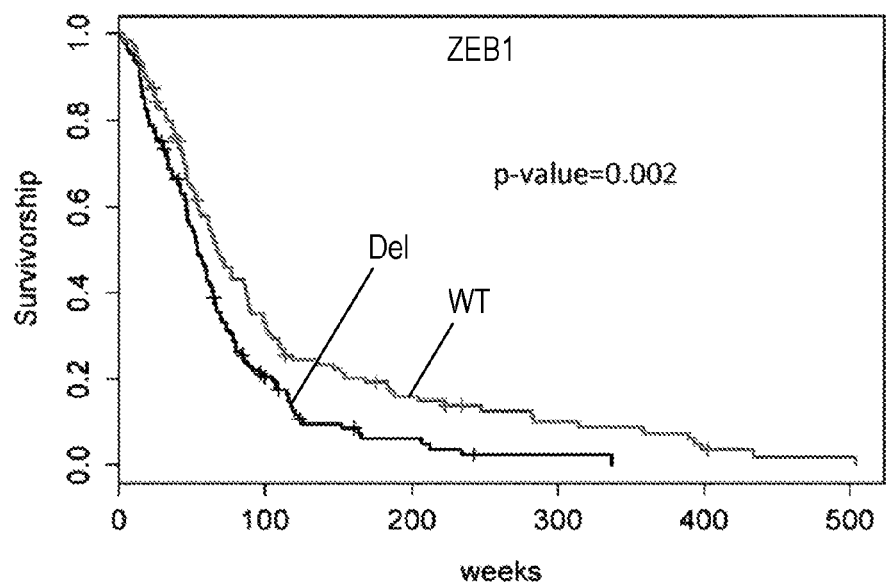
Figure 11B:
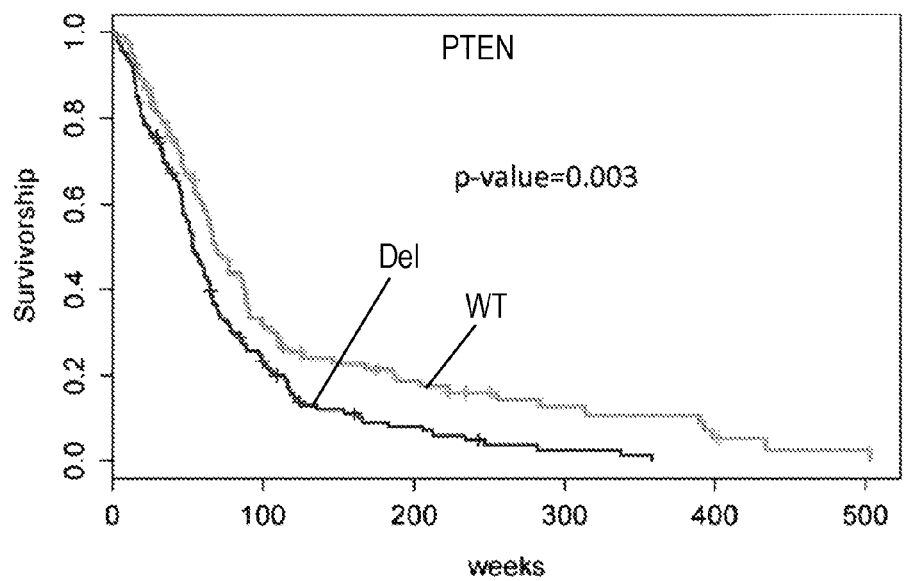

FIGS. 11A-11B depicts survival analysis of GBM patients in accordance with various embodiments of the present invention. Correlation between ZEB1 expression and patient survival. (FIG. 11A) GBMs were categorized into those containing ZEB1 expression (ZEB1 wildtype-WT, (top line on graph)) and those containing no ZEB1 expression (ZEB1 deleted-DEL, (bottom line on graph)). P-value was determined by log-rank test p=0.002. (FIG. 11B) GBMs were categorized into those containing PTEN expression (PTEN wildtype-WT, (top line on graph)) and those containing no PTEN expression (PTEN deleted-DEL, (bottom line on graph)). P-value was determined by log-rank test p=0.003.

Figure 12:
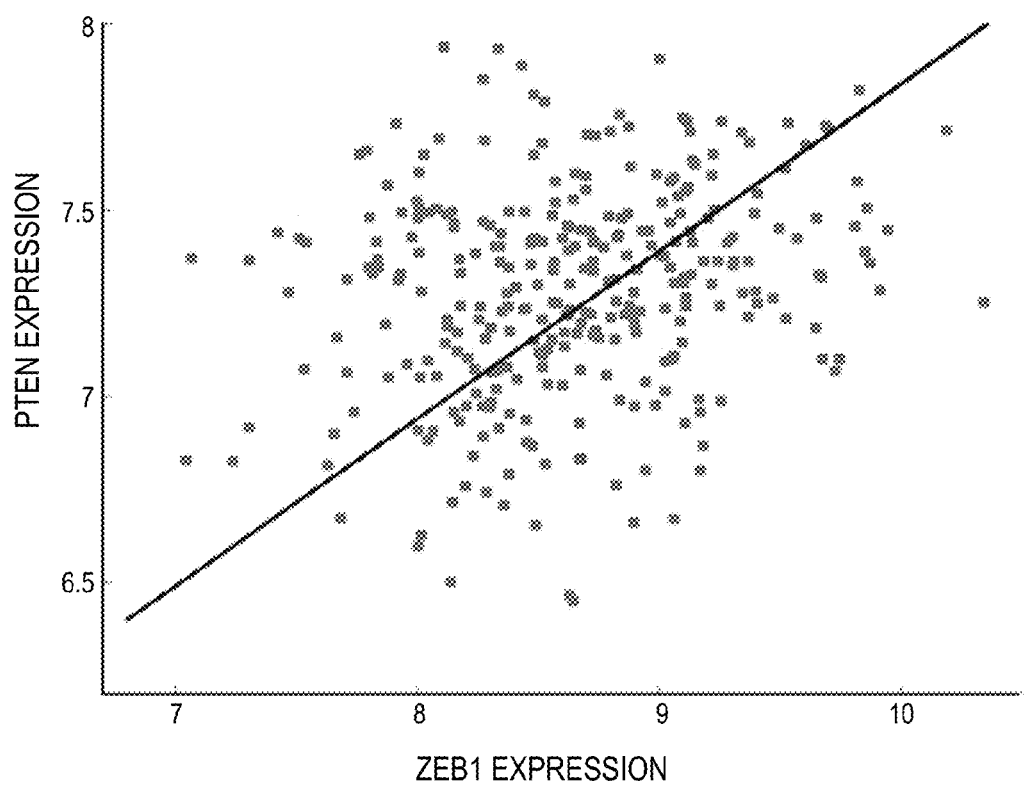

FIG. 12 depicts relationship between PTEN and ZEB1 in accordance with various embodiments of the present invention. Correlation analysis between the levels of PTEN and ZEB1 (N=313; p<0.002).

FIGS. 13A-13G depict, in accordance with various embodiments of the present invention, ZEB1 copy number variation. (FIG. 13A) From a collection of 238 glioblastomas, copy number variation was visualized across chromosome 10 and specifically ZEB1 was identified to have significant copy number loss (over 50% of cases-shown by orange line) indicative of ZEB1 deletion. Gene dosage profiles are indicated below copy number visualization. Aggregate copy number loss from the most significant copy number loss genes from genome-wide analysis in (FIG. 13B) Primary and (FIG. 13C) Recurrent glioblastomas. (FIG. 13D) aCGH ratio plots showing chromosome 10 from GBM tumor tissue compared to (FIG. 13E) specific ZEB1 region. (FIG. 13F) normal patient blood highlights loss of ZEB1. (FIG. 13G) ZEB1 expression measured by qPCR in Anaplastic Astrocytoma=AA n=8, Anaplastic Oligoastrocytoma=AOA n=7, Anaplastic Oligodendroglioma=AOD n=11 and Glioblastoma=GBM n=59.

FIGS. 14A-14K depict, in accordance with various embodiments of the present invention, suppression of ZEB1 expression and its effect on CD133 and stemness. (FIG. 14A) ZEB1 deletions (DEL), defined as copy number less than or equal to −0.5 (n=117); wildtype (WT) defined as copy number greater than or equal to zero (n=152) analyzed against CD133 expression (p=0.023). (FIG. 14B) Paenel of primary GBMs from 8 patients were analyzed for ZEB1 expression where the reference was normal brain. (FIG. 14C) RT-PCR of GSCs from Cedars-Sinai designated as cancer stem cells (CSCs) were quantified for ZEB1 expression and CD133 expression with an apparent inverse correction in trend. (FIG. 14D) Protein determination by Western blot of ZEB1 loss in GSCs. (E) RT-PCR and Western blot confirmation of ZEB1 knockdown in 0827 GSCs with shRNA targeting ZEB1 (shZ89) a non-targeting shRNA (shSC-1) was included as a control. Panel of primary GBMs from 8 patients were analysed for ZEB1 expression. (FIG. 14F) Representative images of GSC neurosphere formation after transduction with shRNAs targeting ZEB1 (shZ89 or shZ90) or non-targeting shRNAs (shSC-1). Scale bar=200 μM. (14G) The percentage of CD133$^+$ 0827 GSCs targeted with either ZEB1 targeted shRNAs (shZ89 or SHZ90) or non-targeting shRNAs (shSC-1) were determined by flow cytometry. (FIG. 14H) Limiting dilution sphere-forming assay indicated that cells transduced with shRNAs targeting ZEB1 (shZ89 or shZ90) increased self-renewal in vitro. (FIG. 14I, FIG. 14J) Same as (G,H) only 0323 GSCs were used. (FIG. 14K) Quantitation of 0827 GSCs transduced with either shSC-1 or shZ89 and cell proliferation of each was determined as measured by 5-ethynyl-2'-deoxyuridine (EdU) incorporation. *p<0.05. Error bars represent the mean±SEM of at least 3 measurements.

FIGS. 15A-15J depict, in accordance with various embodiments of the present invention, effect of IFN-γ on LIF and ZEB1 activation in patient derived glioma cancer stem cells (GCSCs). (FIG. 15A) GCSCs were treated with IFN-γ for 3-days and ZEB1 expression levels were determined by qRT-PCR. (FIG. 15B) The percentage of CD133$^+$ GCSCs in the presence and absence of IFN-γ were determined by flow cytometry. GCSCs were incubated with IFN-γ for 7-days. (FIG. 15C) The effects of IFN-γ on secondary neurosphere formation. (FIG. 15D) Limiting dilution sphere-forming assay indicated that cells not exposed to IFN-γ had increased self-renewal in vitro. (FIG. 15E) Spearman correlation between LIF and ZEB1 GBM patients (n=28), rank correlation (R) and two-tailed significance is shown. (FIG. 15F) ZEB1 binding motifs within the LIF promoter (CAGGTG, *P<0.0001 and CAGGTA, *P<0.0001). (FIG. 15G) Schematic of LIF deletion constructs. (FIG. 15H) GCSCs transfected with LIF luciferase deletion constructs −773/+10, −592/+10, −272/+10, or −109/+10 or with ZEB1 binding sites deleted/mutated (DEL). The GCSCs were then incubated with IFN-γ to cause ZEB1 induction. (FIG. 15I) Oligonucleotide precipitation assay. Nuclear extracts from untreated GCSCs or GCSCs treated with IFN-γ were incubated with biotinylated double-stranded oliognucleotides corresponding to the putative ZEB1 binding motifs in the LIF promoter or a mutant version of that site (bottom western). Similarly, GFP-tagged ZEB1 was transiently transfected into GCSCs and the oligonucleotide precipitation assay was done (top western). (FIG. 15J) Western blot indicating GCSCs ZEB1 knockdown with shRNA targeting ZEB1 (shZ89,shZ90) or a non-targeting scrambled control (shSC-1, top western right). Determination of secreted LIF protein levels by ELISA after 72 hr treatment with IFN-γ of GCSCs 0323 (left) and 0827 (right). Error bars represent the mean of ±SEM of at least 3 experiments.

Figure 16A:
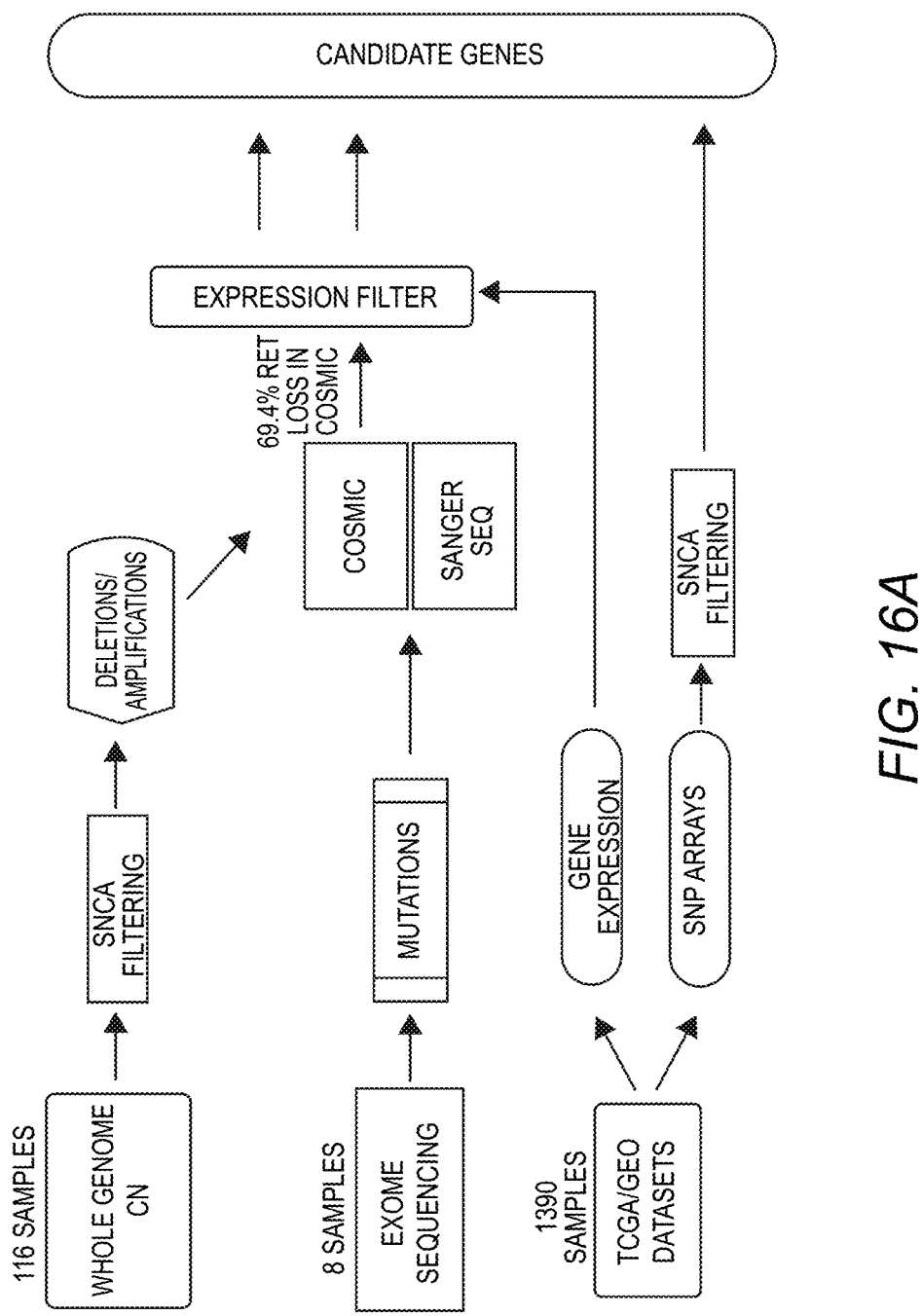
Figure 16B:
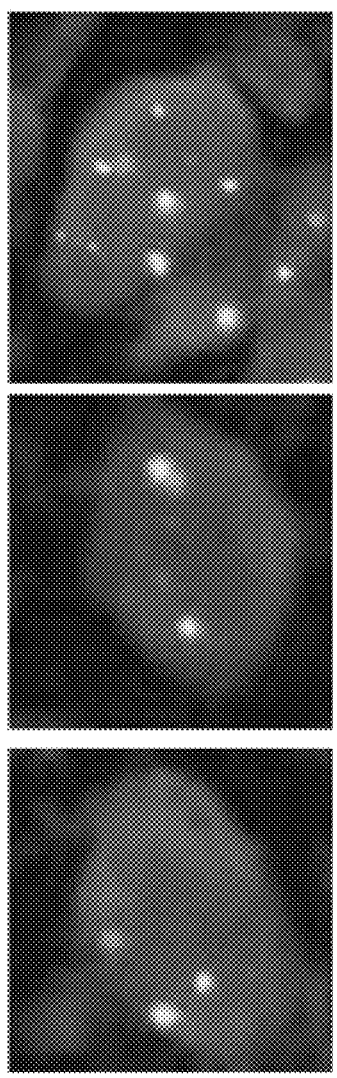
Figure 16C:
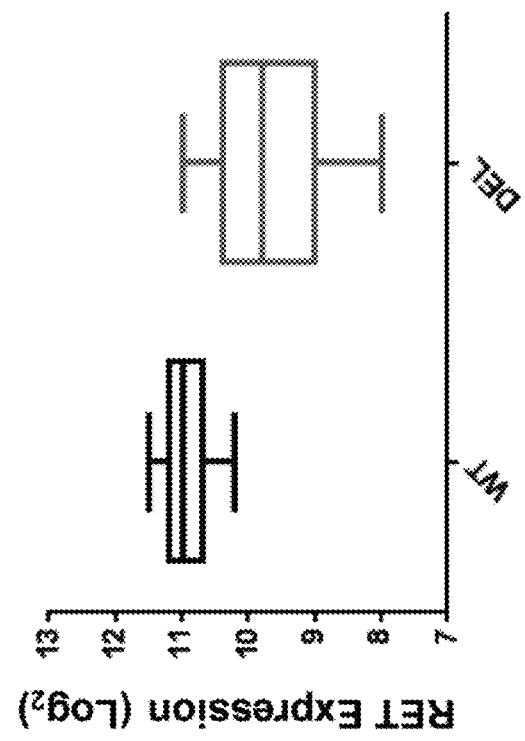

FIGS. 16A-16C depicts RET loss in glioblastoma patients. (FIG. 16A) A general overview of the analysis steps in the retrospective and prospective studies in glioblastomas. (FIG. 16B) Representative FISH performed on GBM patients using a probe covering the entire RET gene region labeled with Rhodamine (red) and a centromere reference probe labeled with FITC (green). (FIG. 16C) RET deletion (DEL), defined as copy number less than or equal to −0.5 (n=41); wildtype (WT) defined as copy number greater than or equal to zero (n=43). Two-tailed student t-test identified a significant difference between these two groups **P<0.0080.

Figure 17A:
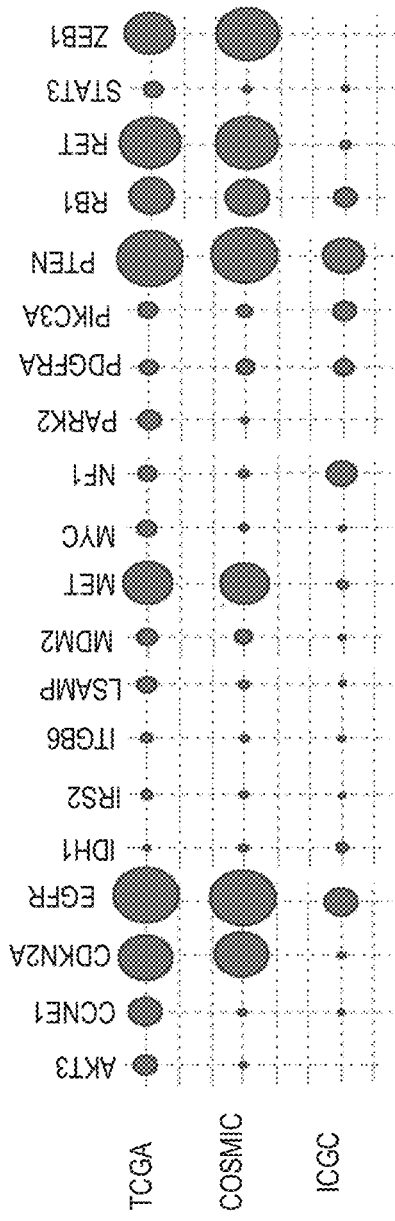
Figure 17B:
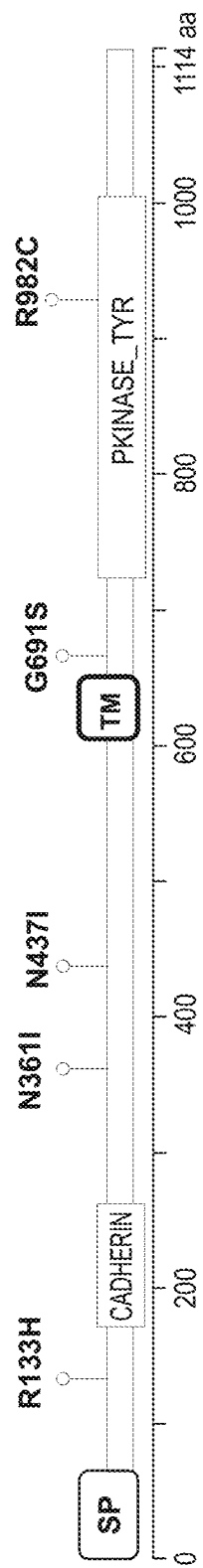

FIG. 17A-17B depicts in (FIG. 17A) Significant genomic alterations are given per database where colored gene names indicate amplification (red), deletion (blue). The size of the circle represents the frequency of alteration. (FIG. 17B) RET protein domain structure with somatic mutations are summarized from GBM patient samples.

Figures 18A, 18B:
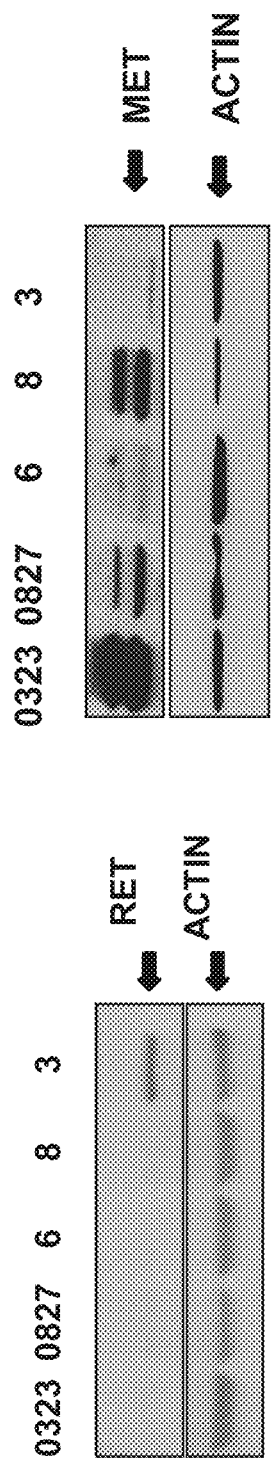

FIGS. 18A-18B depicts Western blot analysis of RET and MET expression from patient derived glioma stem cells.

Figure 19A:
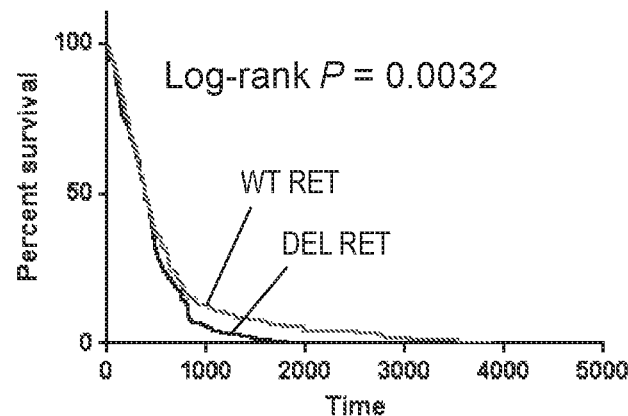
Figure 19B:
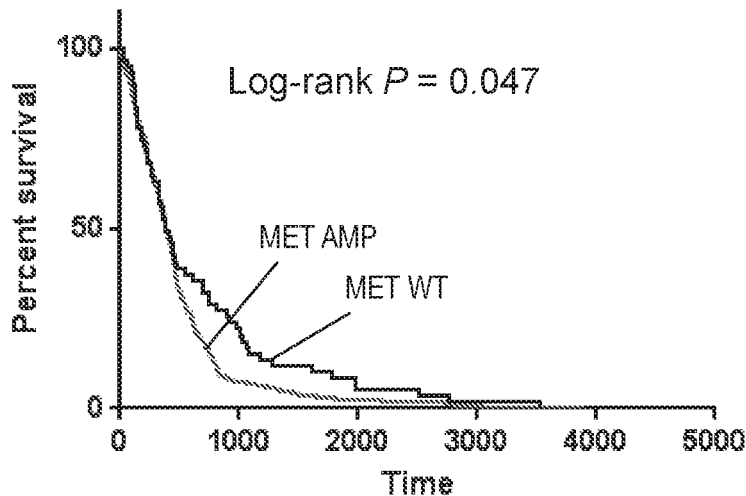

FIG. 19A depicts Kaplan-Meier survival curves for 963 glioblastoma patients samples (left) for high and low RET expression. P-value was determined by log rank test **P=0.032, hazard ratio 1.24. FIG. 19B depicts Kaplan-Meier survival curves for 428 glioblastoma patient samples (right) for high and low MET expression. P-value was determined by log rank test *P=0.047, hazard ratio 1.32.

Figure 20B:
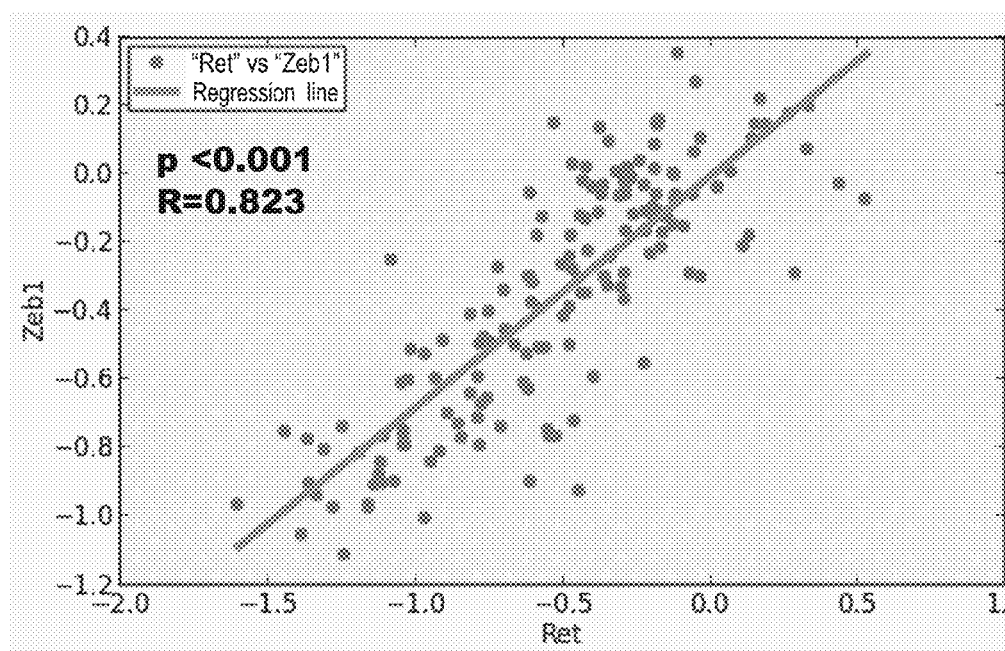
Figure 21A:
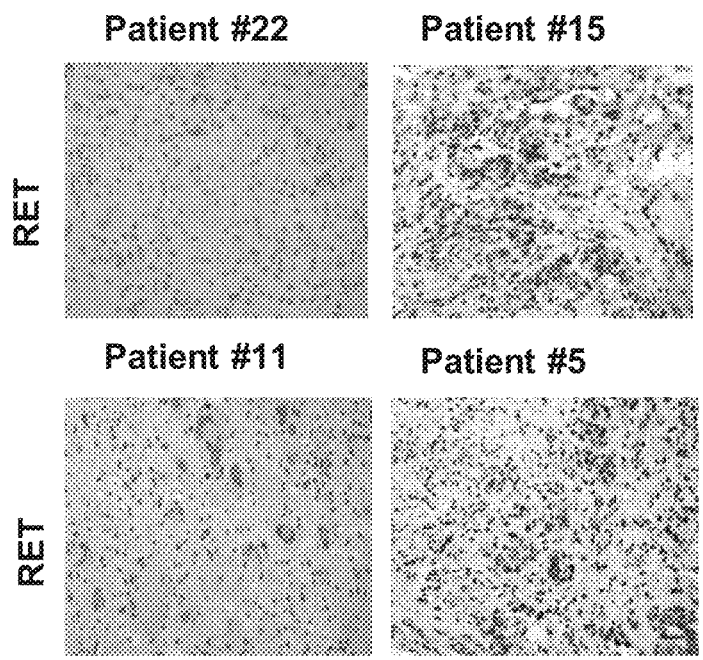
Figure 21B:
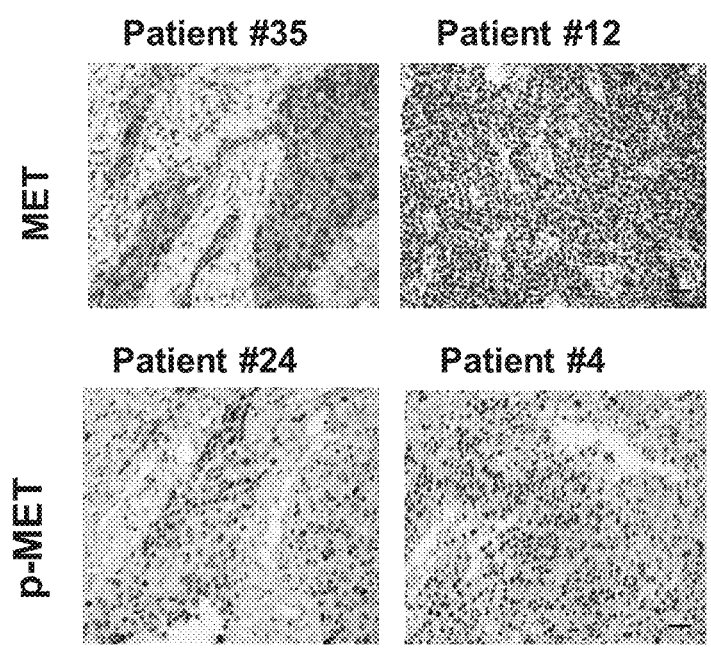
Figure 21C:
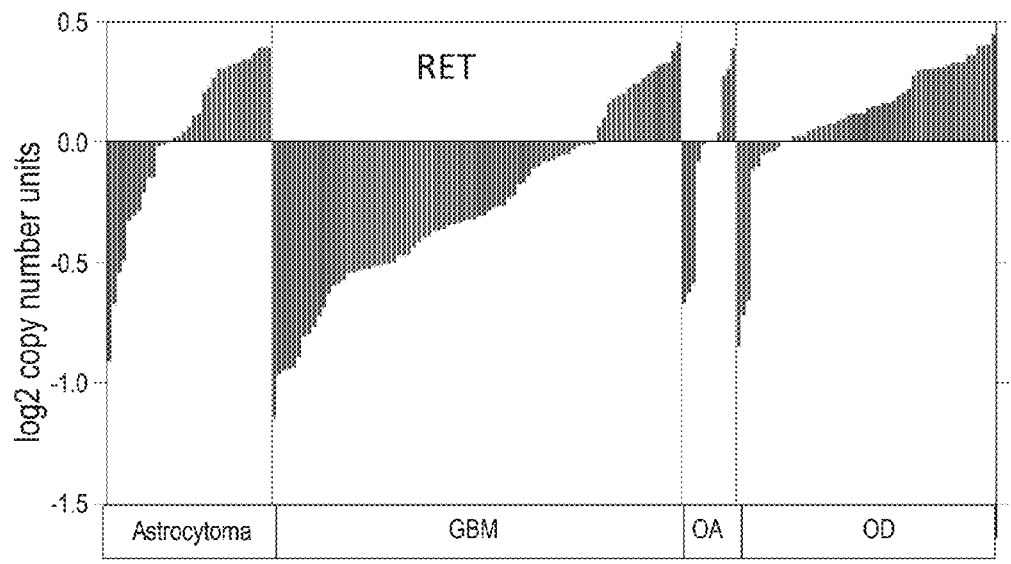
Figure 21D:
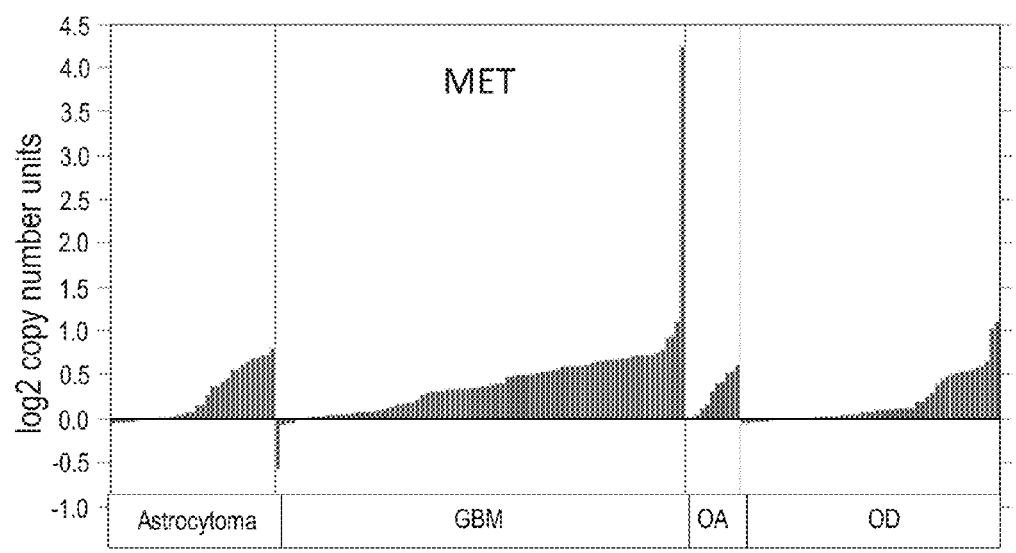

FIG. 20A depicts concordant analysis of ZEB1 and RET genes and implicates likely gene changes (amplifications or deletions) associated with ZEB1 and RET genes. FIG. 20B depicts Strong Pearson's correlation between ZEB1 and RET in glioblastoma multiforme patient samples FIGS. 21A-21D depict IHC staining of glioblastoma multiforme patient tissue samples for (FIG. 21A) RET and ZEB1 (FIG. 21B) protein expression. mRNA expression of RET (FIG. 21C) and MET (FIG. 21D) across different types of brain tumors (i.e. Astrocytoma, GBM=glioblastoma multiforme, OA=Oligoastrocytoma, OD=Oligodendroglioma)

Figure 22:
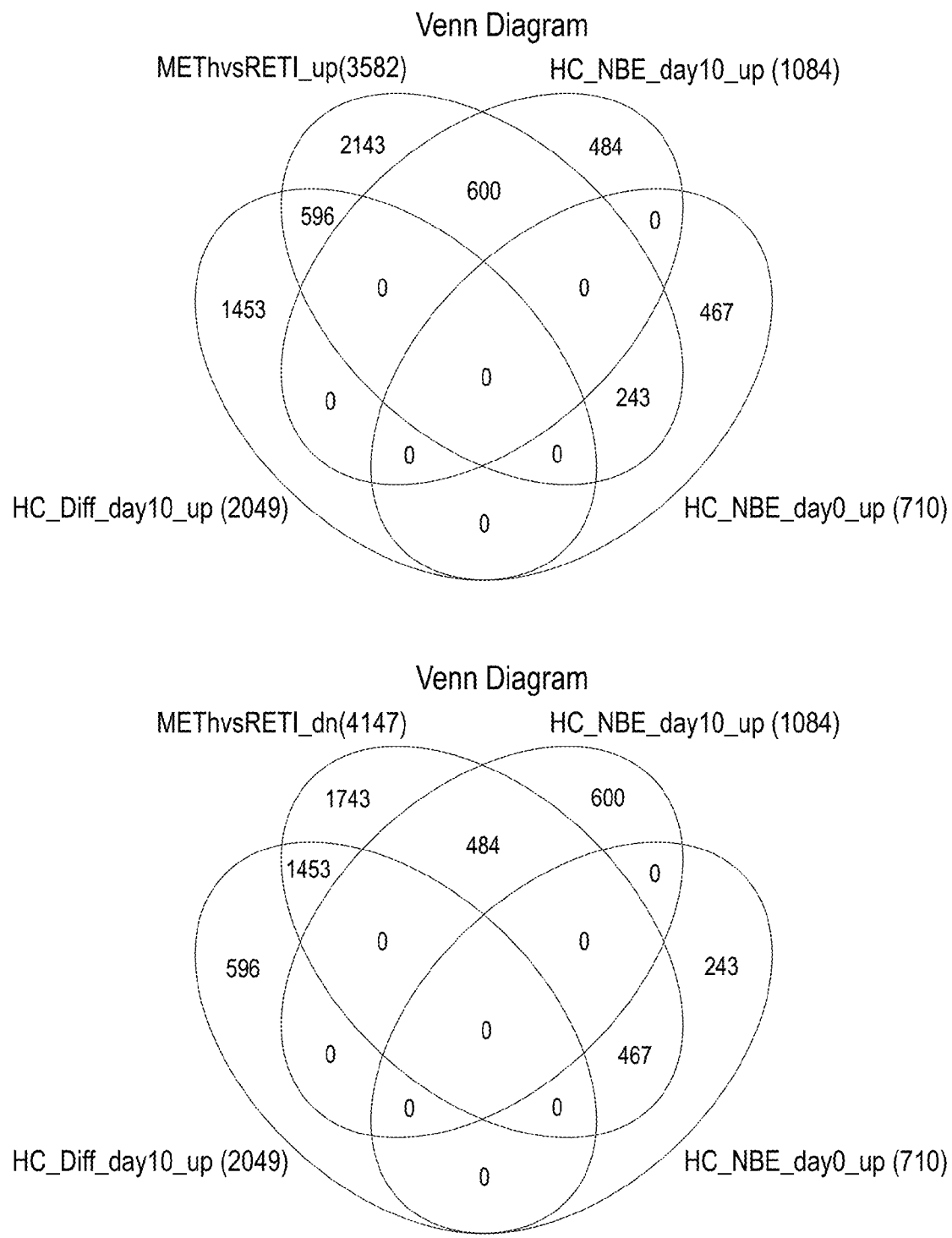

FIG. 22 depicts Venn diagrams showing RET and ZEB1 high and low expression under conditions of differentiation or normal stem cell conditions with intersecting associated genes that are also expressed highly or have low expression under conditions differentiation or normal stem cell conditions.

Figure 23A:
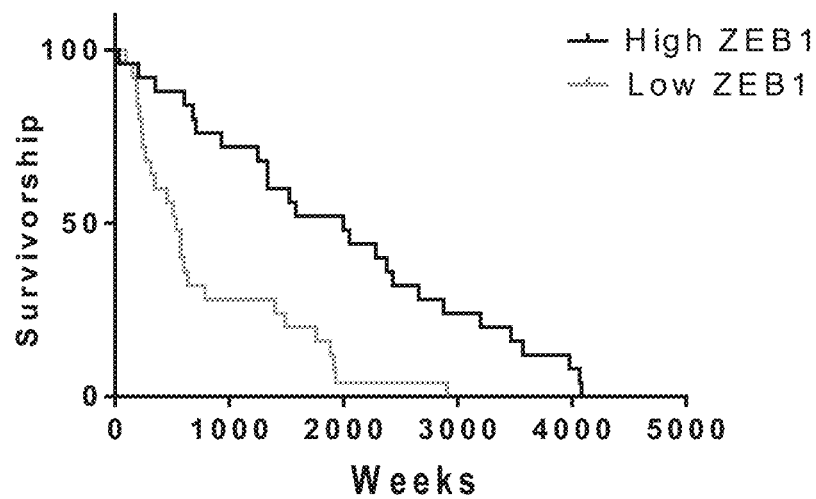
Figure 23B:
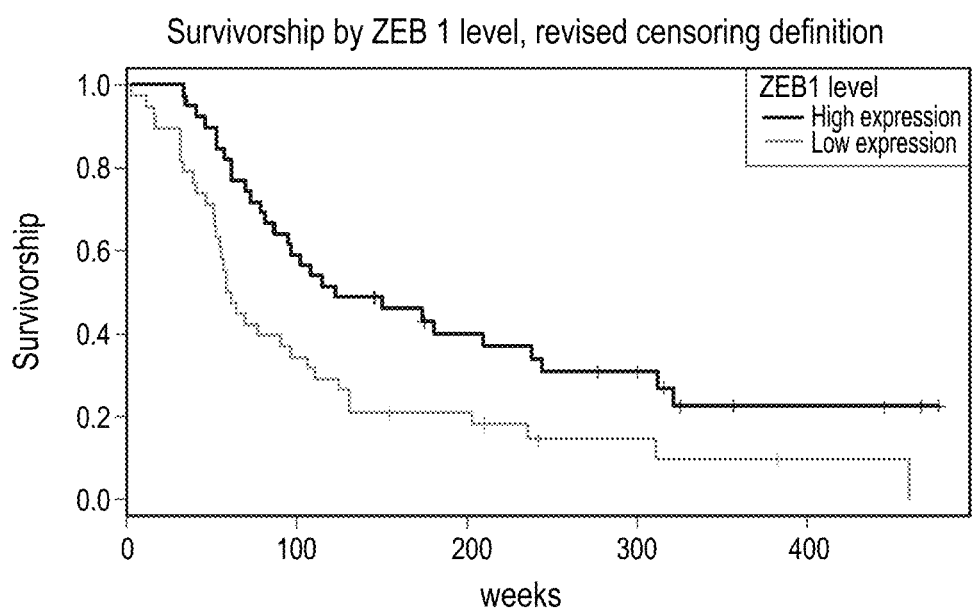

FIGS. 23A-23B depict, in accordance with various embodiments of the present invention, survivorship by ZEB1 levels.

Figure 24A:
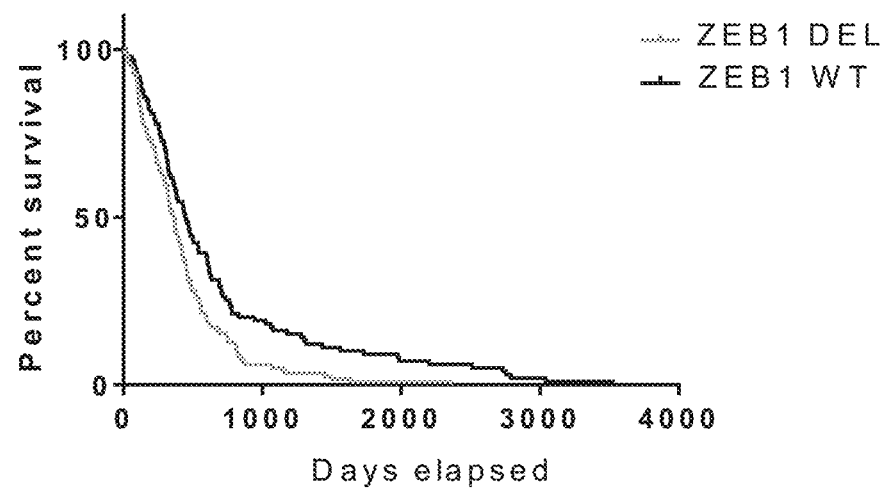
Figure 24B:
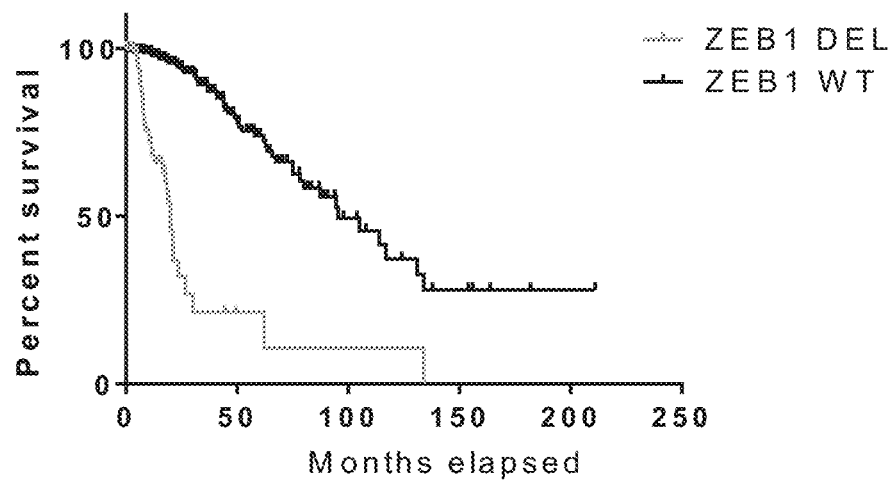

FIGS. 24A-24B depict, in accordance with various embodiments of the present invention, survivorship by ZEB1 proportions.

Figure 25A:
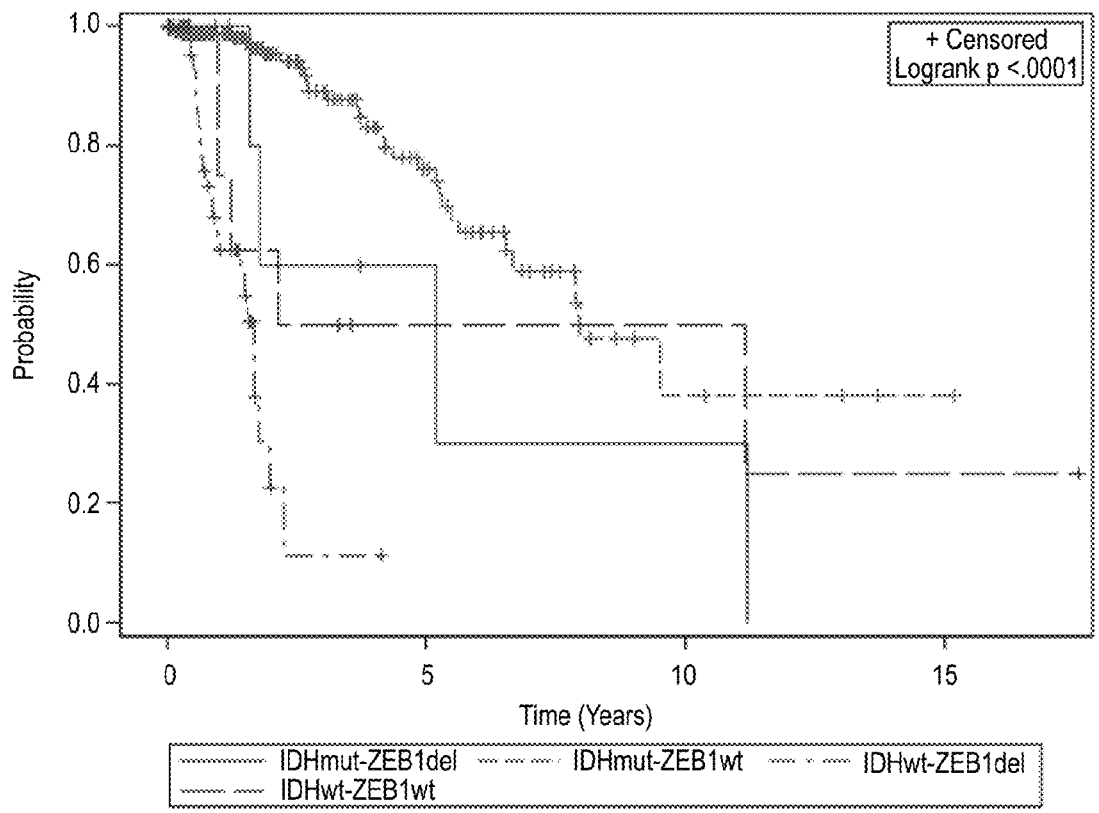

FIG. 25A depicts, in accordance with various embodiments of the present invention, KM Curve for IDH/ZEB1 group in LGG patients.

Figure 25B:
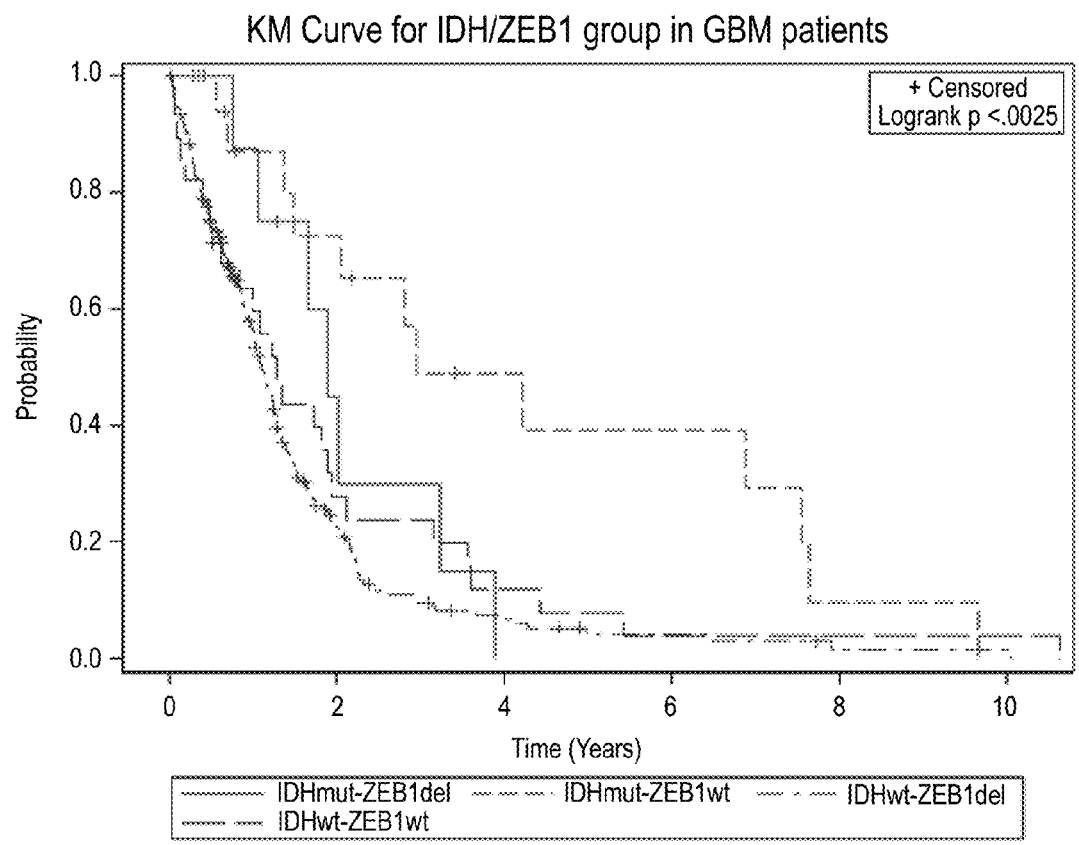

FIG. 25B depicts, in accordance with various embodiments of the present invention, KM Curve for IDH/ZEB1 group in GBM patients.

Figure 26A:
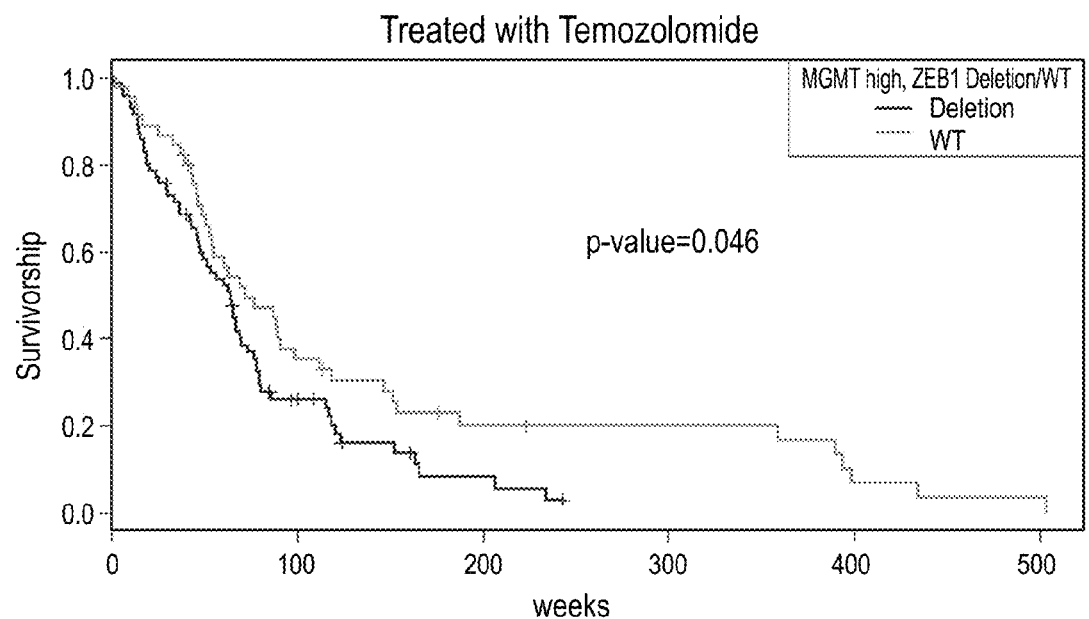
Figure 26B:
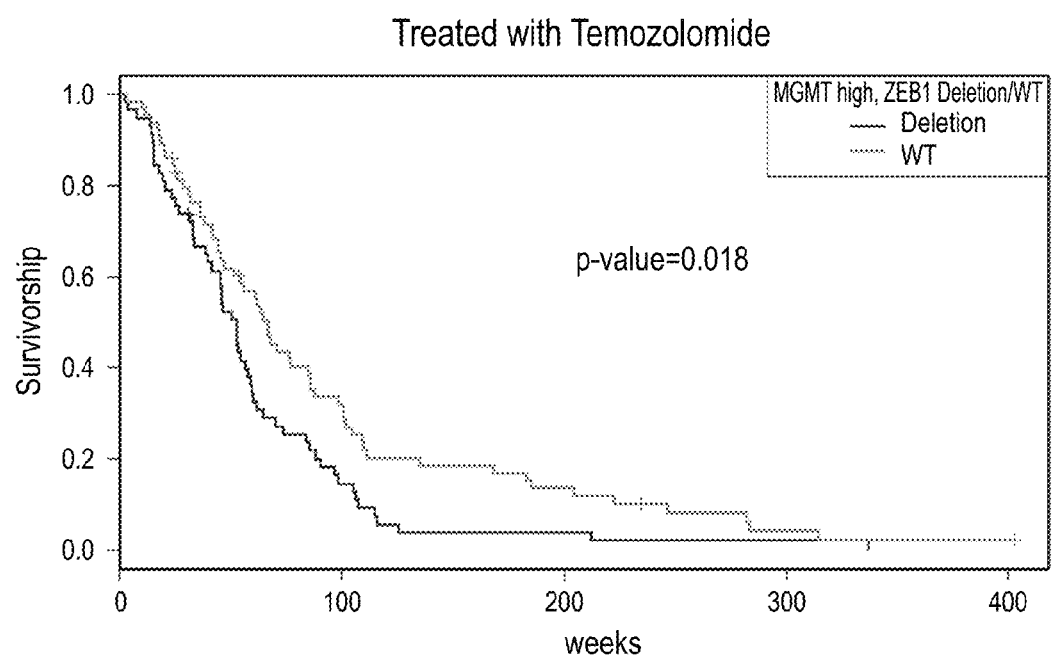

FIGS. 26A-26B depict, in accordance with various embodiments of the present invention, survivorship in patients treated with Temozolomide.

Figure 26C:
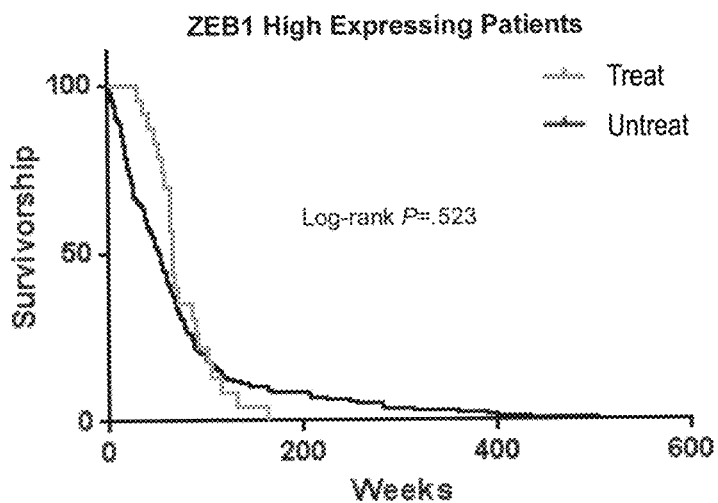
Figure 26D:
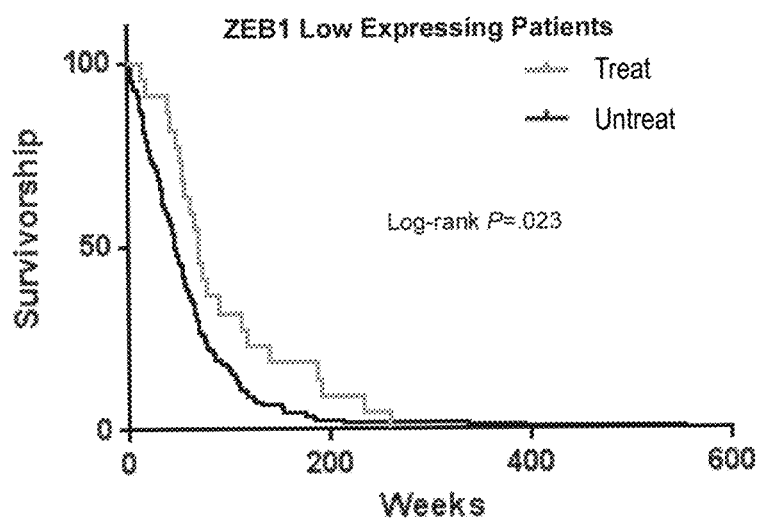

FIGS. 26C-26D depict, in accordance with various embodiments of the present invention, survivorship by ZEB1 levels with or without bevacizumab treatment.

Figure 27A:
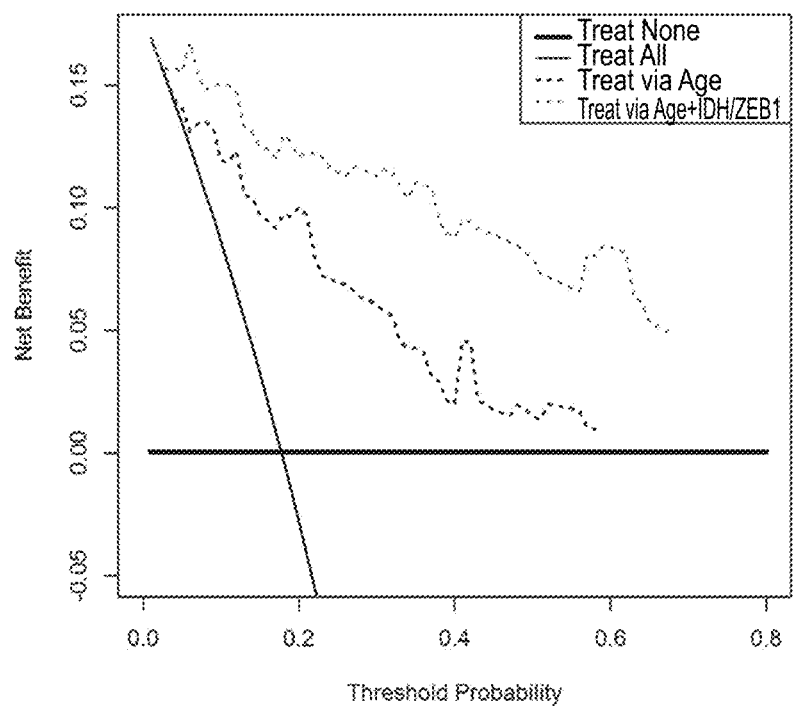
Figure 27B:
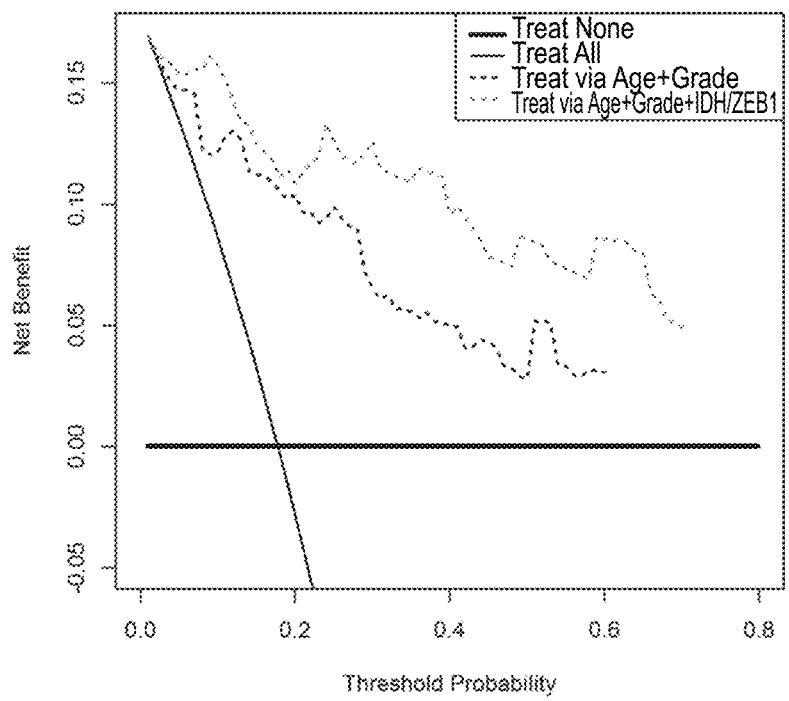
Figure 27C:
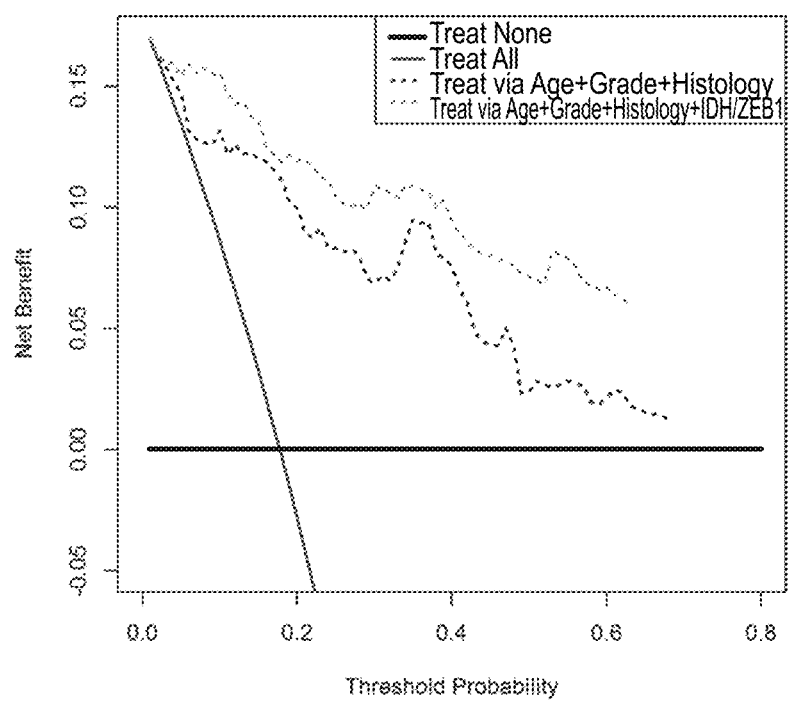

FIGS. 27A-27C depict, in accordance with various embodiments of the present invention, risk to harm predictions.

FIGS. 28A-28G depict, in accordance with various embodiments of the present invention, somatic copy number alterations. (FIG. 28A) Copy number alterations determined for 70 low grade gliomas (grade II and III) by single nucleotide polymorphism (SNP) arrays. Significant amplifications (red) and deletions (blue) were determined for the chromosomal regions and are plotted as q-values (significance<0.05). (FIG. 28B-FIG. 28C) Copy number alterations for ZEB1 in low grade gliomas (n=527) and GBM (n=595) patients identified through cBioportal. Deep deletions indicate homozygous deletions. Shallow deletions indicate heterozygous deletions. Diploid represents wildtype. (FIG. 28D) ZEB1 deletion (DEL) for glioblastomas, defined as copy number less than or equal to −0.5 (n=188); wildtype (WT) defined as copy number greater than or equal to zero (n=62). Two-tailed student t-test identified a significant difference between these two groups *P<0.0001. (FIG. 28E) ZEB1 deletion (DEL) for low grade gliomas (n=79); wildtype (WT) (n=372), copy number was previous called for DEL or WT in cBioportal. Two-tailed student t-test identified a significant difference between these two groups P=0.0006. (FIG. 28F) Estimated Kaplan-Meier survival curves for 451 low grade gliomas patients (left) for deleted (DEL) and wildtype (WT) copy number. Patients with low grade gliomas having DEL vs. WT ZEB1 had estimated median survival times of 16.82 vs. 25.46 months. P-value was determined by log rank test *P<0.0001, hazard ratio 1.96. (FIG. 28G) Kaplan-Meier estimates of overall survival of ZEB1 WT GBM patients compared to ZEB1 DEL patients (n=238). P-value was determined by log rank test P=0.002, hazard ratio 1.54.

Figure 29A:
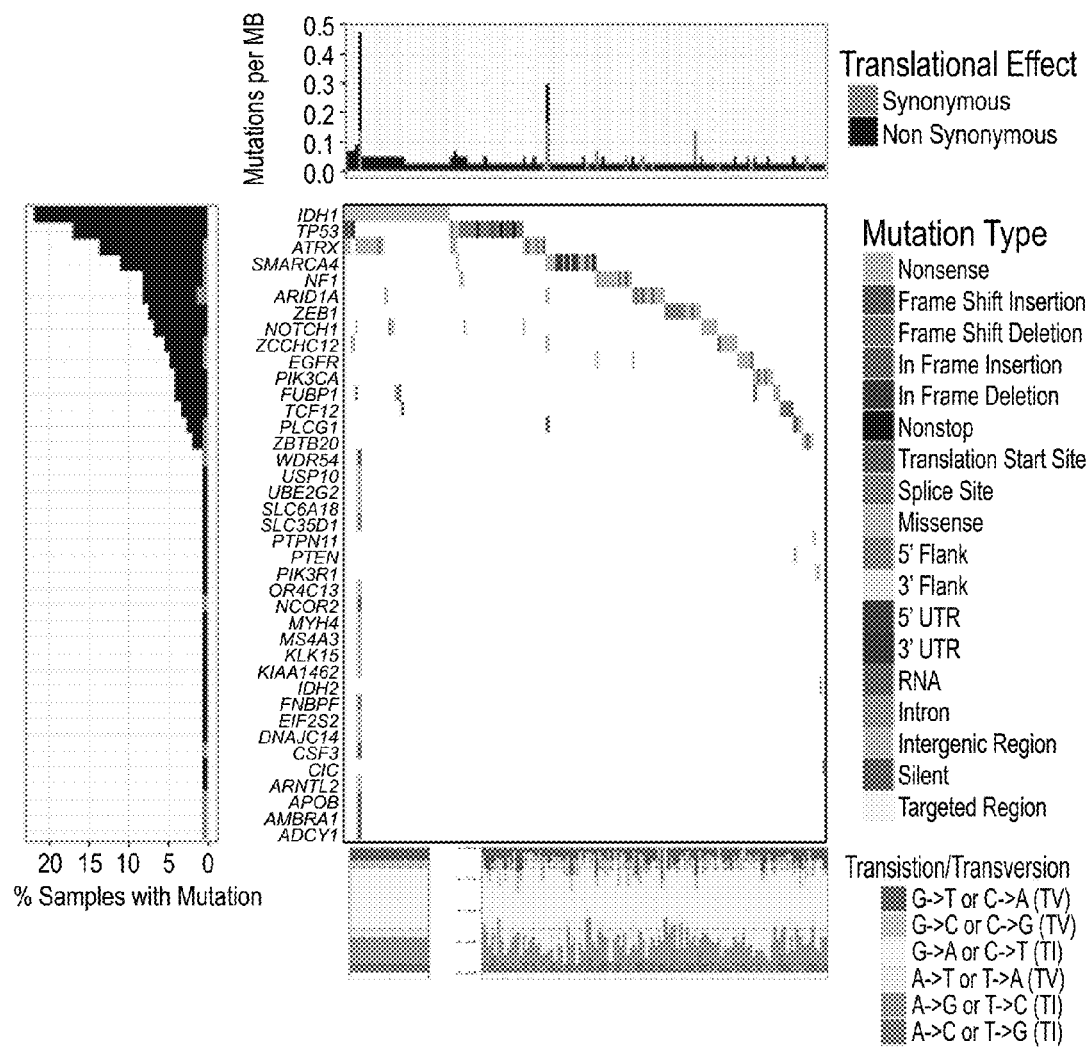

FIGS. 29A-29C depict, in accordance with various embodiments of the present invention, genomic alterations in gliomas. (FIG. 29A) Glioma samples are arranged from left to right. Alterations of low grade gliomas and GBM candidate genes are annotated for each sample according to the colour panel (right). The somatic mutation frequencies for each candidate gene are plotted on the left panel. Mutation rates and type of base-pair substitution are displayed in the top and bottom panel, respectively. (FIG. 29B) Estimated Kaplan-Meier survival curves for 507 glioblastomas patients (left) for high and low ZEB1 expression. Patients with GBMs having high vs. low ZEB1 expression had estimated median survival times of 580 vs. 310 weeks. p-value was determined by log rank test *P=0.02, hazard ratio 1.25. (FIG. 29C) Estimated Kaplan-Meier survival curves for 249 low grade gliomas patients (right) for high and low ZEB1 expression. P-value was determined by log rank test ***P<0.0001, hazard ratio 3.341.

FIGS. 30A-30F depict, in accordance with various embodiments of the present invention, ZEB1 loss enhances stemness and resistance to differentiation. (FIG. 30A) Left, GCSCs forming neurospheres and expressing Nestin and Sox2. Middle, Right, GCSCs induced to differentiate expressing TUJ1 and GFAP. NBE=Neural Basal A media, WD=growth factor withdrawal, FBS=fetal bovine serum. Scale bar represents 100 μm (FIG. 30B) real time qRT-PCR expression of ZEB1, OLIG2 and NOS2 in enriched CD133 GCSCs (wildtype ZEB1) and matched CD133 depleted GCSCs. (FIG. 30C) Top panel, Flow cytometry of GCSCs indicates CD133 positivity in contrast to GCSCs that were cultured under differentiation conditions that do not. (FIG. 30D) Validation of GCSC tumorigenicity. Top, schematic of GCSC isolation and subsequent intracranial injection. Bottom, Kaplan-Meier estimate of survival from injected GCSCs 0827 to form intracranial xenograft mouse (n=5) models, representative H&E of brain tumor formation. (FIG. 30E) Determining ZEB1 expression stratified for CD133 expression (n=251). Median survivals were 540 weeks for the high CD133, low ZEB1 group vs. 220 weeks for the low CD133, high ZEB1 group. P-value was determined by log rank test ***P=0.0003 hazard, ratio 1.73. (FIG. 30F) Immunofluorescent micrographs of 0827 GCSCs transduced with either shSC-1 (top) or shZ89 (bottom) under differentiation conditions. Differentiation was inhibited in ZEB1 targeted shZ89 0827 GCSCs. Scale bars represent 60 µm. Bottom, histograms indicating the percentage of Nestin,Tuj1,GFAP and Sox2 positive 0827 GCSCs transduced with either shSC-1 or shZ89. Error bars represent the mean of ±SEM of at least 3 experiments.

Figure 31A:
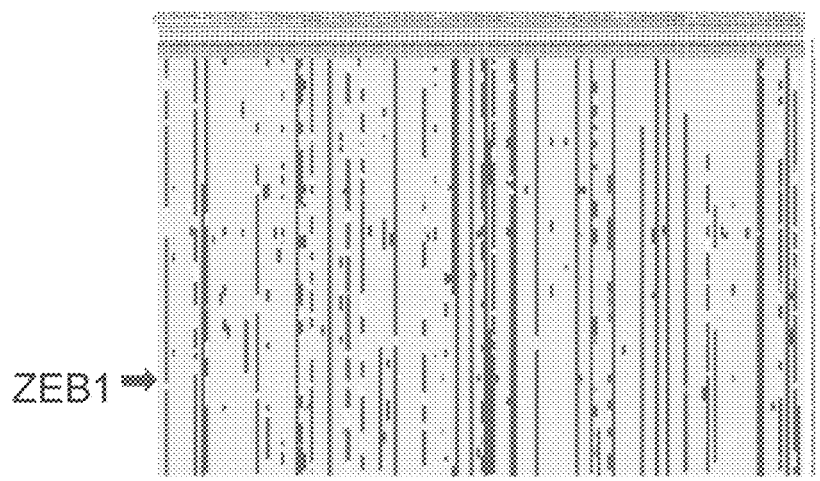
Figure 31B:
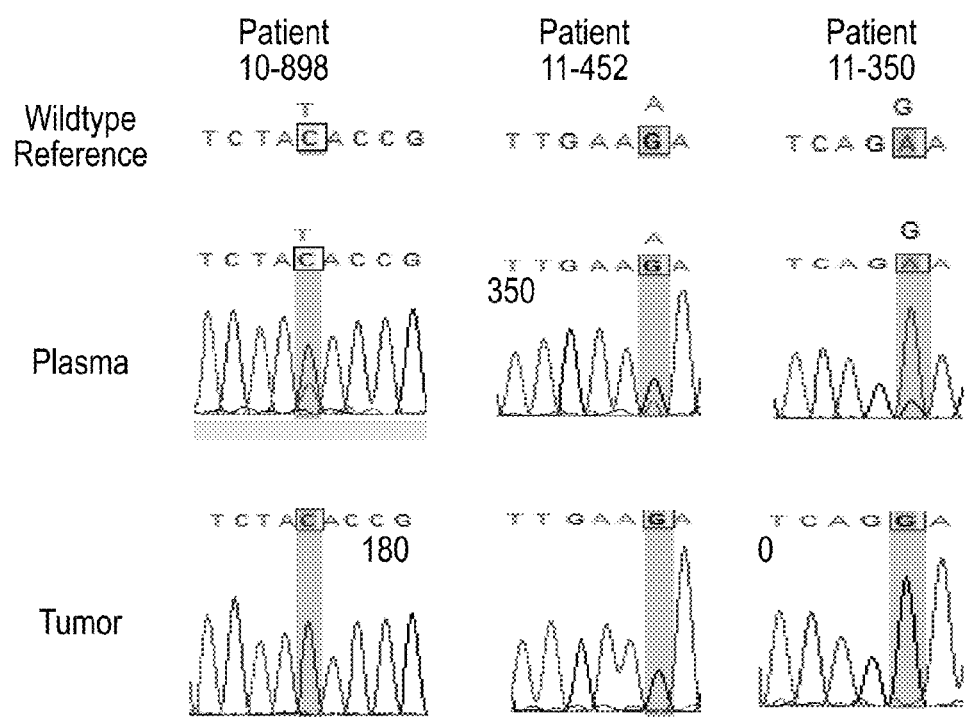
Figure 31C:
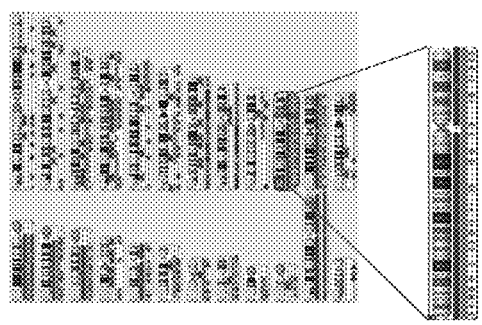

FIGS. 31A-31C depict, in accordance with various embodiments of the present invention, representative mutations and loss of heterozygosity in ZEB1. (FIG. 31A) HuSNP analysis to determine genome-wide LOH on 178 patient GBM samples. Approximate location of ZEB1 gene across GBM patient samples from left to right is given by the arrow. Blue=LOH; yellow=retention. Threshold=0.46. (FIG. 31B) Sanger sequencing of GBM patients and matching blood plasma. (FIG. 31C) Karyotype analysis of patient derived GBM GSC 0827 indicating copy number changes loss=orange, copy number changes gain=light blue, LOH=purple, deletions=red arrows, amplifications=blue arrows. Chromosome 10 where ZEB1 resides is blown up.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); March, *Advanced Organic Chemistry Reactions, Mechanisms and Structure* 7$^{th}$ ed., J. Wiley & Sons (New York, N.Y. 2013); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9): 1126-36).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is cancer.

"Patient outcome" refers to whether a patient survives or dies as a result of treatment. A more accurate prognosis for patients as provided in this invention increases the chances of patient survival as a more appropriate treatment can be selected and administered to the patient.

"Poor Prognosis" means that the prospect of survival and recovery of disease is unlikely despite the standard of care for the treatment of brain tumors (i.e., conventional therapy; e.g., surgery, radiation, chemotherapy). Poor prognosis is the category of patients whose survival is less than that of the median survival.

"Good Prognosis" means that the prospect of survival and recovery of disease is likely with the standard of care for the treatment of the disease (i.e., convention therapy; e.g., surgery, radiation, chemotherapy). Good prognosis is the category of patients whose survival is not less than that of the median survival.

"ZEB1 dysregulation" as used herein refers to a chromosome 10p11.2 copy number loss, a loss of heterozygosity of the ZEB1 gene, a decrease in ZEB1 expression (gene or protein), ZEB1 mutation resulting in a decrease in ZEB1 function, or ZEB1 deletion (e.g., one or more nucleic acid deleted from the ZEB1 gene) resulting in a decrease in ZEB1 function. In some embodiments, a ZEB1 deletion refers to a ZEB1 gene that has lost a significant portion of its sequence or the entire sequence such that it is no longer transcribing the appropriate RNA transcript and subsequent protein that allows for normal function of the gene.

"RET dysregulation" as used herein refers to a chromosome 10q11.2 copy number loss, a loss of heterozygosity of the RET gene, a decrease in RET expression (gene or protein), RET mutation resulting in a decrease in RET function, or RET deletion (e.g., one or more nucleic acid deleted from the RET gene) resulting in a decrease in RET function. In some embodiments, a RET deletion refers to a RET gene that has lost a significant portion of its sequence or the entire sequence such that it is no longer transcribing the appropriate RNA transcript and subsequent protein that allows for normal function of the gene.

"IDH1 dysregulation" as used herein refers to an IDH1 mutation (e.g., one or more nucleic acid mutated in the IDH1 gene), an IDH1 deletion (e.g., one or more nucleic acid deleted from the IDH1 gene), a change (e.g., decreases or increases) in IDH1 expression (mRNA and/or protein), an IDH1 gene copy number loss, a chromosome 2q33.3 (or 2q34) copy number loss, or a loss of heterozygosity of the IDH1 gene. In some embodiments, an IDH1 mutation or deletion alters the normal enzymatic function of IDH1. In certain embodiments, an IDH1 mutation or deletion causes IDH1 to produce 2-hydroxyglutarate and to not produce NADPH. In some embodiments, an IDH1 mutation or deletion changes (decreases or increases) the enzymatic activity level of IDH1. In some embodiments, an IDH1 mutation or deletion changes (decreases or increases) the expression level of IDH1 (mRNA and/or protein). In some embodiments, an IDH1 mutation results in that the IDH1 gene is no longer transcribing the appropriate RNA transcript and subsequent protein that allows for normal function of the IDH1 gene. In some embodiments, an IDH1 deletion involves a loss of a significant portion of the IDH1 gene sequence or the entire IDH1 gene sequence such that the IDH1 gene is no longer transcribing the appropriate RNA transcript and subsequent protein that allows for normal function of the IDH1 gene. IDH1 gene copy number loss at Cytogenetic band is defined by Entrez Gene as 2q33.3 or by Ensembl or HGNC as 2q34.

Select or selecting a therapy as used herein, includes but is not limited to selecting, choosing, prescribing, advising, recommending, instructing, or counseling the subject with respect to the treatment.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Examples of cancer treatment include, but are not limited to, active surveillance, observation, surgical intervention (such as craniotomy, computer-assisted brain surgery, awake brain surgery, and intraoperative MRI), chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof.

"Tumor," as used herein refers to all neoplastic cell growth and proliferation, whether malignant or benign, and all pre-cancerous and cancerous cells and tissues.

"Cancer" and "cancerous" refer to or describe the physiological condition in mammals that is typically characterized by unregulated cell growth. Examples of cancer include, but are not limited to brain tumor and brain cancer.

"Brain cancer" and "brain tumor" can be benign (in the case of brain tumor, not brain cancer) or malignant, can occur in different parts of the brain, and may or may not be primary tumors. A primary tumor is one that has started in the brain, as opposed to a secondary tumor, which is a metastatic tumor that has invaded the intracranial sphere from cancers originating in other organs. The most common primary brain tumors are gliomas, meningiomas, pituitary adenomas, and nerve sheath tumors. Examples of brain tumor include, but are not limited to, glioblastoma multiforme, gliomas, mixed gliomas (such as oligoastrocytomas that contain cells from different types of glia), astrocytomas, anaplastic astrocytomas, medulloblastomas, ependymomas, meningiomas, oligodendrogliomas, gangliocytomas, neuroblastomas, pituitary adenomas, retinoblastomas, and choroid plexus tumors.

"Glioma Stem Cells (GSCs)" as used herein is an operational term and refers to a glioma tumor cell that has the ability to self-renew giving rise to another malignant stem cell and/or give rise to another malignant cell with the potential to differentiate into another malignant cell type where stem cell potential is limited.

"Loss of Heterozygosity (LOH)" refers to the situation where a population of brain tumor patients is heterozygous for the gene (e.g., ZEB1) and there is loss of one of two alleles at one or more loci in brain cell or brain tumor cell population due to chromosome loss, deletion, or mitotic crossing-over.

"Chemotherapy resistance" as used herein refers to partial or complete resistance to chemotherapeutic drugs. For example, a subject does not respond or only partially responds to a chemotherapeutic drug. A person of skill in the art can determine whether a subject is exhibiting resistance to chemotherapy.

A "recurrence" means that the cancer has returned after initial treatment.

Being "non-recurrent" or "recurrence-free" means that the cancer is in remission; being recurrent means that the cancer is growing and/or has metastasized, and some surgery, therapeutic intervention, and/or cancer treatment is required to lower the chance of lethality. The "non-recurrent subjects" are subjects who have non-recurrent or recurrence-free disease, and they can be used as the control for recurrent subjects who have recurrent disease or recurrence.

The transcriptional repressor zinc-finger E-box binding homeobox1 (ZEB1) is an inducer of the epithelial-mesenchymal transition (EMT) in cancers and has been shown to promote cancer infiltration including in glioblastomas. The sequence of chromosome:GRCh37:10:31606824:31819342:1 (SEQ ID NO:63) contains the ZEB1 wild-type exons. Given the pleiotropic actions of ZEB1 and its implication in stem cell processes we hypothesized that ZEB1 expression would be associated with a negative outcome in GBM patients. In contrast, our findings demonstrate that the loss of ZEB1 and LOH of this gene are common in glioblastomas.

The comprehensive nature of our analysis allowed us to investigate the significance of ZEB1 copy number, LOH and the effect of these on response to therapy and survival in patients with GBM. Our data indicates that ZEB1 expression is lost in a significant number of GBM patients, and that ZEB1 is a tumor suppressor. Congruent with this idea, is the LOH in a subset of GBM patients identified by SNP analysis, as well as in primary patient derived GSCs. Our data also indicates that ZEB1 loss results in resistance to differentiation of GSCs shown by increased cell proliferation under differentiation conditions and decreased expression of markers associated with differentiation. A further increase in the enrichment of the stem cell marker CD133 after knockdown of ZEB1 in patient derived GSCs all indicate gain of function attributes associated with the loss of a tumor suppressor. The impact of ZEB1 loss can also be seen at the clinical level as patients who are burdened with the loss of ZEB1 have a shortened survival and patients who have both loss of ZEB1 with high CD133 expression have a shorter survival still, consistent with our analysis of ZEB1 loss classifying into the Mes subtype of GBM tumors.

We and others have reported ZEB1's role in the activation of GSC invasion. Given the dual nature of ZEB1 to be both activator and repressor the presence and absence of ZEB1 affects divergent GSC function. Others have reported that ZEB1 expression increases GSC stemness as evidenced by CD133 expression and chemoresistance. These divergent data would suggest that sample size and genetic evaluation drastically affects the analysis of the role of ZEB1 in patient outcome and stemness. We have addressed this with analyzing several data sets of significant patient numbers. The fact that when ZEB1 expression is decreased, ZEB1 falls into the Mes subtype, is consistent with ZEB1 loss contributing to a decrease in patient survival.

Although from a small data set, recurrent tumors tend to be more frequently ZEB1 deleted and classify into the mesenchymal subtype. Furthermore, loss of ZEB1 leads to therapy resistance and increased self-renewal, further indications that the loss of ZEB1 promotes cancer stem cell propagation and retention of "stemness."

Loss of ZEB1 in GBM patients impacts both a favorable patient response to temozolomide chemotherapy due to MGMT hypermethylation as well as an unfavorable response due to a lack of methylation of this gene. ZEB1 loss significantly decreases the survival of patients in both groups. This finding may improve our ability to stratify outcomes more precisely in glioblastoma patients. In addition, although bevacizumab has been shown to provide no survival advantage in GBM patients in two recent phase III trials, patients with ZEB1 deletion treated with bevacizumab have a significant survival benefit when receiving this anti-angiogenic agent. It has been demonstrated that glioma stem cells secrete VEGF to support the vascular microenvironmen which in turn supports glioma stem cell self-renewal. These are preliminary data fraught with the caveats of post-hoc analysis, bevacizumab initiation at different times during the therapeutic regimen, and heterogeneity of concurrent therapies.

Here, for the first time, we have demonstrated that the loss of a gene with pleiotrophic effects on glioma stem cells consistently enhances GSC stemness while preventing differentiation both at a cellular and clinical level. The role of ZEB1 loss on chemoresistance has a significant effect on survival.

The comprehensive nature of our analysis allowed us to investigate the significance of ZEB1 mutation, deletion, copy number loss, and LOH in GBMs. Our data clearly demonstrate that ZEB1 is consistent with the features of a tumor suppressor, congruent with this idea, is the LOH in a subset of GBM patients identified by aCGH, SNP and retrospective analysis, not only in primary derived patient GSCs, but also in newly diagnosed primary GBM patient samples. An intriguing question within our analysis is how important is ZEB1 mutation/deletion with respect to PTEN. We find that statistically, ZEB1 has a smaller p value than PTEN when comparing survival outcome of wildtype versus gene deleted patients. This raises the question: is ZEB1 more important and perhaps a greater indicator of patient prognosis than PTEN. Our further analysis indicated this is believed to be the case as ZEB1 deletion with wildtype PTEN appears to have a worse patient survival outcome than does the reverse group of PTEN deletion with ZEB1 wildtype, and interestingly, worse than the double deletion of PTEN and ZEB1. Further, a positive correlation could be seen between PTEN expression and ZEB1 expression, and the second worse patient survival group (ZEB1 deletion with PTEN deletion) was also statistically significant with respect to the PTEN deletion with ZEB1 wildtype GBM patients and the ZEB1 wildtype with PTEN deleted GBM patients, suggesting that co-deletion may be a mechanism utilized by GBMs to rid itself of two important tumor suppressor genes that are involved in stem cell control. The fact that PTEN and ZEB1 are located on two separate arms of the same chromosome, the q arm where PTEN is located and the p arm where ZEB1 is located on chromosome 10, suggests that this is not a random stochastic event or due to gene proximity with deletion of the entire chromosomal arm. We have observed in previous studies that GBM subtype classification into Mes, Prolif and PN has revealed that Mes and Prolif represent stages of neural stem cell like and transit amplifying stages within GBM development. Further the Mes and Prolif GBM subtype classification results in the poorest survival outcome for GBM patients. Comparatively, the PN GBM subtype represents a significantly improved patient survival outcome. Our analysis indicates that ZEB1 deletion classifies into primarily the Mes GBM subtype which, consistent with our data has the worst patient survival outcome. This not only indicates that ZEB1 is a predictor of GBM patient survival outcome, but suggests that ZEB1 negatively regulates glioma stemness and upon its deletion or decreased expression results in an enhancement and increase in GSC proliferation resulting in a poorer prognosis for GBM patients.

Despite advances in stereotactic surgical resection, radiation therapy and chemotherapeutics, patients diagnosed with a glioblastoma multiforme (GBM) have a median survival of 14.6 months. Along with aberrant signal transduction pathways at the protein level, GBMs are marred by chromosomal alterations and instability at the genomic level. For this reason, biologically relevant targets remain elusive. The stem cell component of GBMs impacts both patient response to therapy and patient survival. Identifying genes that control stem cell regulation, especially when mutations or a loss in copy number of these stem cell regulatory genes can support the propagation of the cancer, is fundamental to the basic understanding of GBM lethality and its implications for clinical practice.

The leukemia inhibitory factor (LIF) is a cytokine that is widely known to induce stem cell self-renewal in mice and humans in such cell types as embryonic stem cells and neuroprogenitor cells. Furthermore, LIF induction has been shown to activate glioblastoma stem cell self-renewal, inhibit differentiation, promote neurosphere formation and enrich for GSCs including CD133+ GSCs.

In contrast, the proinflammatory cytokine interferon gamma (IFN-γ), has been shown to negatively regulate neuroprogenitor cells, to decrease neurosphere formation and decrease stem cell self-renewal and has re-emerged as a possible treatment for glioblastomas.

ZEB1 is an inducer of the epithelial-mesenchymal transition (EMT) in cancers and has been shown to promote cancer invasion including in glioblastomas. ZEB1 has also been implicated in stem cell processes.

Retrospective clinical analysis, whole genome copy number analysis and DNA sequencing resulted in the identification of significant loss of the ZEB1 gene in glioblastoma multiforme (GBM). Current literature would suggest that ZEB1 expression would be associated with a negative outcome in cancer patients based on increased tumorigenicity and stemness (self-renewal and inhibition of differentiation). To our knowledge there is only one report in opposition to ZEB1 overexpression being associated with tumorigenicity. Our findings illustrate that the loss of the ZEB1 gene is common in glioblastomas and is associated with decreased survival. Moreover, we see a distinct association of ZEB1 loss with propagation of the glioma stem cell population. This implies a biologically selective role for ZEB1 that when mutated or deleted favors glioblastoma tumorigenicity and propagation, particularly of the glioma stem cell component. We investigated the mechanistic role of ZEB1 in cancer stem cell regulation in GBM.

The cancer stem cell component of glioblastoma multiforme (GBM) is thought to be responsible for conferring chemotherapeutic resistance, self-renewal and likely cancer recurrence resulting in shortened patient survival. To overcome these challenges in treating GBM requires identification of glioma stem cell (GSC) regulatory genes and there mechanisms that directly result in GBM patient mortality. The deletion and loss of heterozygosity (LOH) of ZEB1 in GBM patients resulting in poor patient outcome, in part, as a result of inhibition of differentiation and chemotherapeutic resistance. Genomic and concordant analysis of ZEB1 comprising of over 400 GBMs identifying the RET receptor similarly having deletion and LOH. We demonstrate through FISH, copy number, whole-exome and Sanger sequencing that RET is deleted in over 40% of gliomas. RET is involved in the regulation of glioma stem cell differentiation, and results in shortened patient survival upon its deletion (P=0.0032). Expression of RET in GSCs leads to the attenuation of MET signaling in GBMs. While not wishing to be bound by any particular theory, we believe that RET negatively regulates the MET receptor a known contributor to GBM malignancy and when RET is deleted results in the dis-inhibition of MET and the enhancement of tumorigenicity.

The present invention is based, at least in part, on these findings. The present invention addresses the need in the art for methods of determining molecular subsets for the prognostication of brain tumors, such as GBMs, and for guiding treatment options for these patients, and further provides a method for determining which treatments would provide a more favorable patient outcome. The present invention also acts as a biological indicator of patient prognosis in the midst of acquiring a GBM or the likelihood of acquiring a GBM. This invention provides a prognostic indicator for patients with GBMs.

In this invention, we provide systems, kits and methods for predicting treatment outcomes for brain tumor, particularly GBM, by detecting ZEB1, IDH1, MGMT, PTEN, and/or RET gene mutation, deletion, loss of heterozygosity (LOH), loss of copy number, or by detecting decreased or lost ZEB1, IDH1, MGMT, PTEN, and/or RET gene expression. We also provide systems, kits and methods for prognosticating brain tumor, for monitoring brain tumor progression, and for selecting patient-specific treatment plans for brain tumor.

Prognosis

Various embodiments of the present invention provide for a process for prognosticating a tumor, comprising: obtaining a sample comprising a tumor cell from a subject desiring a prognosis of a tumor; assaying the sample to determine a presence or absence of a ZEB1 dysregulation in the sample; and determining the subject has a poor prognosis if a ZEB1 dysregulation is present, or determining the subject has a good prognosis if a ZEB1 dysregulation is absent.

Various embodiments of the present invention provides for a process for prognosticating a tumor, comprising: obtaining a sample comprising a tumor cell from a subject desiring a prognosis of a tumor; detecting a presence or absence of a ZEB1 dysregulation in the sample; detecting a presence or absence of a PTEN deletion in the sample; and determining the subject has a poor prognosis if a ZEB1 dysregulation and a PTEN deletion is present, or if a ZEB1 dysregulation is present and a PTEN deletion is not present, or determining the subject has a good prognosis if a ZEB1 dysregulation and a PTEN deletion are absent. In some embodiments, PTEN deletion not being present indicates that the subject has a wild-type PTEN gene.

Various embodiments of the present invention provides for a process for prognosticating a tumor, comprising: obtaining a sample comprising a tumor cell from a subject desiring a prognosis of a tumor; detecting a presence or absence of a ZEB1 dysregulation in the sample; detecting a MGMT expression level in the sample; and determining the subject has a poor prognosis if a ZEB1 dysregulation is present and the subject has a low MGMT expression level, determining the subject has a poor prognosis if a ZEB1 dysregulation is present and the subject has a high MGMT expression level, or determining the subject has a good prognosis if a ZEB1 dysregulation is absent and the subject has a low MGMT expression level.

Various embodiments of the present invention provides for a process for prognosticating a tumor, comprising obtaining a sample comprising a tumor cell from a subject desiring a prognosis of a tumor; assaying the sample to determine a presence or absence of a ZEB1 dysregulation and RET dysregulation in the sample; and determining the subject has a poor prognosis if ZEB1 dysregulation and a RET dysregulation is present, or ZEB1 dysregulation is present and RET dysregulation is not present, or determining the subject has a good prognosis if a ZEB1 dysregulation and a RET dysregulation are absent.

Various embodiments of the present invention provides for a process for prognosticating a tumor, comprising obtaining a sample comprising a tumor cell from a subject desiring a prognosis of a tumor; assaying the sample to determine a presence or absence of a ZEB1 dysregulation and an IDH1 dysregulation in the sample; and determining the subject has a poor prognosis if ZEB1 dysregulation is present and IDH1 dysregulation is absent. When a subject does not have an IDH1 dysregulation, the subject has IDH1 wild type.

In various embodiments, the subject is human. In various embodiments, the subject is suspected to have a brain tumor. In various embodiments, the subject is diagnosed to have a brain tumor. In various embodiments, the subject is treated for a brain tumor.

In various embodiments, the tumor is glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, the sample is obtained before, during, or after tumor treatment.

In various embodiments, assaying the sample to determine a presence or absence of a ZEB1 dysregulation in the sample comprises: assaying the sample for a chromosome 10p11.2 copy number; comparing the chromosome 10p11.2 copy number to a reference value; and determining the presence of a ZEB1 dysregulation that is indicative of a poor prognosis if there is a chromosome 10p11.2 copy number loss, and determining the absence of a ZEB1 dysregulation if there is not a 10p11.2 copy number loss.

In various embodiments, assaying the sample to determine a presence or absence of a ZEB1 dysregulation in the sample comprises: assaying the sample to determine if there is a loss of heterozygosity (LOH) of the ZEB1 gene; and determining the presence of a ZEB1 dysregulation indicative of a poor prognosis if there is a LOH of the ZEB1 gene and determining the absence of a ZEB1 dysregulation if there is not a LOH of the ZEB1 gene. In various embodiments, the absence of a ZEB1 dysregulation if there is not a LOH of the ZEB1 gene is indicative of a good prognosis.

In various embodiments, assaying the sample to determine a presence or absence of a ZEB1 dysregulation in the sample comprises: subjecting the sample to an analysis for ZEB1 expression; comparing the ZEB1 expression to a ZEB1 expression reference value; and determining the presence of a ZEB1 dysregulation that is indicative of a poor prognosis if the ZEB1 expression level is lower than the reference value, and determining the absence of a ZEB1 dysregulation if the ZEB1 expression level is not lower than the reference value. In various embodiments, the absence of a ZEB1 dysregulation if the ZEB1 expression level is not lower than the reference value is indicative of a good prognosis.

In various embodiments, the ZEB1 expression reference value is a median or mean ZEB1 expression level from a population of subjects with an intact ZEB1 gene, a population of subjects without a brain tumor, a population of subjects with a brain tumor, or a population of subjects with a nonrecurrent disease state (e.g., for 1, 2, 3, 4, 5, 6, 7, 8, 9, 10, 11, 12 or more months, or for 1, 1.5, 2, 2.5, 3, 3.5, 4, 4.5, 5, 6, 7, 8, 9, 10, 15, 20, 25, 30, 35, 40, 45, 50, 60, 70, 80, 90 or more years.)

In various embodiments, the ZEB1 expression reference value is a ZEB1 expression level from the subject's own blood sample or from a normal blood sample.

In various embodiments, assaying the sample to determine a presence or absence of a ZEB1 dysregulation in the sample comprises: subjecting the sample to an analysis for ZEB1 mutation or a ZEB1 deletion; and determining the presence of a ZEB1 dysregulation that is indicative of a poor prognosis if there is a ZEB1 mutation or a ZEB1 deletion; and determining the absence of a ZEB1 dysregulation if there is not a ZEB1 mutation or a ZEB1 deletion. In various embodiments, the absence of a ZEB1 dysregulation if there is not a ZEB1 mutation or a ZEB1 deletion is indicative of a good prognosis.

In various embodiments, assaying for a presence or absence of a ZEB1 dysregulation comprises detecting ZEB1 mRNA with a polynucleotide capable of hybridizing with ZEB1 mRNA under stringent hybridization conditions. In various embodiments, assaying for a presence or absence of a ZEB1 dysregulation comprises detecting a ZEB1 protein with an antibody capable of specifically binding to a ZEB1 protein. In various embodiments, assaying for the presence or absence of a ZEB1 dysregulation comprises: sequencing the ZEB1 gene from the subject's brain tumor; and comparing the brain tumor ZEB1 sequence to a ZEB1 sequence from the subject's own blood sample, or a normal blood sample, or a reference ZEB1 sequence.

In various embodiments, assaying the ZEB1 dysregulation, PTEN deletion, MGMT expression, RET dysregulation comprises using DNA sequencing, comparative genomic hybridization (CGH), array CGH (aCGH), SNP analysis, mRNA expression assay, RT-PCR, real-time PCR, Fluorescence in situ hybridization (FISH), or a combination thereof.

In various embodiments, assaying the ZEB1 dysregulation, PTEN deletion, MGMT expression, RET dysregulation can be done by assaying for the ZEB1, PTEN, MGMT and RET protein expression. Methods and systems to detect ZEB1 protein expression (including for example, ZEB1 deletion, ZEB1 copy number loss which can result in an absence or near absence of ZEB1 protein expression) include but are not limited to ELISA, immunohistochemistry, flow cytometry, fluorescence in situ hybridization (FISH), radioimmuno assays, and affinity purification.

In various embodiments, the poor prognosis includes decreased survival likelihood, shortened life expectancy, or enhanced tumor stemness.

Selecting Therapy

Various embodiments of the present invention provide for a process for selecting a therapy for a subject in need thereof, comprising: obtaining a sample comprising a tumor cell from a subject desiring a prognosis of a tumor; assaying the sample to determine a presence or absence of a ZEB1 dysregulation in the sample; determining the subject has a poor prognosis if a ZEB1 dysregulation is present, or determining the subject has a good prognosis if a ZEB1 dysregulation is absent; and selecting a first therapy for the subject if the subject has a good prognosis or selecting a second therapy, or both the first therapy and the second therapy, for the subject if the subject has a poor prognosis.

Various embodiments of the present invention provides for a process for selecting a therapy for a subject in need thereof, comprising: obtaining a sample comprising a tumor cell from a subject desiring a prognosis of a tumor; detecting a presence or absence of a ZEB1 dysregulation in the sample; detecting a presence or absence of a PTEN deletion in the sample; and determining the subject has a poor prognosis if a ZEB1 dysregulation and a PTEN deletion is present, or if a ZEB1 dysregulation is present and a PTEN deletion is not present, or determining the subject has a good prognosis if a ZEB1 dysregulation and a PTEN deletion are absent; and selecting a first therapy if a good prognosis is determined, or selecting a second therapy or a both the first therapy and the second therapy, if a poor prognosis is determined.

Various embodiments of the present invention provide for a process for selecting a therapy for a subject in need thereof, comprising: obtaining a sample comprising a tumor cell from a subject desiring a prognosis of a tumor; detecting a presence or absence of a ZEB1 dysregulation in the sample; detecting a MGMT expression level in the sample; determining the subject has a poor prognosis if a ZEB1 dysregulation is present and the subject has a low MGMT expression level, determining the subject has a poor prognosis if a ZEB1 dysregulation is present and the subject has a high MGMT expression level, or determining the subject has a good prognosis if a ZEB1 dysregulation is absent and the subject has a low MGMT expression level; and selecting a first therapy if a good prognosis is determined, or selecting a second therapy or a both the first therapy and the second therapy, if a poor prognosis is determined.

Various embodiments of the present invention provides for a process for selecting a therapy for a subject in need thereof, comprising obtaining a sample comprising a tumor cell from a subject desiring a prognosis of a tumor; assaying the sample to determine a presence or absence of a ZEB1 dysregulation and RET dysregulation in the sample; determining the subject has a poor prognosis if ZEB1 dysregulation and a RET dysregulation are present, or if ZEB1 dysregulation is present and RET dysregulation is not present, or determining the subject has a good prognosis if a ZEB1 dysregulation and a RET dysregulation are absent; and selecting a first therapy if a good prognosis is determined, or selecting a second therapy or a both the first therapy and the second therapy, if a poor prognosis is determined.

Various embodiments of the present invention provides for a process for selecting a therapy for a subject in need thereof, comprising obtaining a sample comprising a tumor cell from a subject desiring a prognosis of a tumor; assaying the sample to determine a presence or absence of a ZEB1 dysregulation and an IDH1 dysregulation in the sample; determining the subject has a poor prognosis if ZEB1 dysregulation is present and IDH1 dysregulation is absent; and selecting a second therapy or both a first therapy and the second therapy, if a poor prognosis is determined.

In various embodiments, the process further comprises administering a first therapy if a good prognosis is determined, or administering a second therapy or a both the first therapy and the second therapy, if a poor prognosis is determined.

In various embodiments, the subject is human. In various embodiments, the subject is suspected to have a brain tumor.

In various embodiments, the subject is diagnosed to have a brain tumor. In various embodiments, the subject is treated for a brain tumor.

In various embodiments, the tumor is glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, the sample is obtained before, during, or after tumor treatment.

In various embodiments, assaying the sample to determine a presence or absence of a ZEB1 dysregulation in the sample comprises: assaying the sample for a chromosome 10p11.2 copy number; comparing the chromosome 10p11.2 copy number to a reference value; and determining the presence of a ZEB1 dysregulation that is indicative of a poor prognosis if there is a chromosome 10p11.2 copy number loss, and determining the absence of a ZEB1 dysregulation if there is not a 10p11.2 copy number loss.

In various embodiments, assaying the sample to determine a presence or absence of a ZEB1 dysregulation in the sample comprises: assaying the sample to determine if there is a loss of heterozygosity (LOH) of the ZEB1 gene; and determining the presence of a ZEB1 dysregulation indicative of a poor prognosis if there is a LOH of the ZEB1 gene and determining the absence of a ZEB1 dysregulation if there is not a LOH of the ZEB1 gene. In various embodiments, the absence of a ZEB1 dysregulation if there is not a LOH of the ZEB1 gene is indicative of a good prognosis.

In various embodiments, assaying the sample to determine a presence or absence of a ZEB1 dysregulation in the sample comprises: subjecting the sample to an analysis for ZEB1 expression; comparing the ZEB1 expression to a ZEB1 expression reference value; and determining the presence of a ZEB1 dysregulation that is indicative of a poor prognosis if the ZEB1 expression level is lower than the reference value, and determining the absence of a ZEB1 dysregulation if the ZEB1 expression level is not lower than the reference value. In various embodiments, the absence of a ZEB1 dysregulation if the ZEB1 expression level is not lower than the reference value is indicative of a good prognosis.

In various embodiments, the ZEB1 expression reference value is a median or mean ZEB1 expression level from a population of subjects with an intact ZEB1 gene, a population of subjects without a brain tumor, a population of subjects with a brain tumor, or a population of subjects with a nonrecurrent disease state (e.g., for 1, 2, 3, 4, 5, 6, 7, 8, 9, 10, 11, 12 or more months, or for 1, 1.5, 2, 2.5, 3, 3.5, 4, 4.5, 5, 6, 7, 8, 9, 10, 15, 20, 25, 30, 35, 40, 45, 50, 60, 70, 80, 90 or more years.)

In various embodiments, the ZEB1 expression reference value is a ZEB1 expression level from the subject's own blood sample or from a normal blood sample.

In various embodiments, assaying the sample to determine a presence or absence of a ZEB1 dysregulation in the sample comprises: subjecting the sample to an analysis for ZEB1 mutation or a ZEB1 deletion; and determining the presence of a ZEB1 dysregulation that is indicative of a poor prognosis if there is a ZEB1 mutation or a ZEB1 deletion; and determining the absence of a ZEB1 dysregulation if there is not a ZEB1 mutation or a ZEB1 deletion. In various embodiments, the absence of a ZEB1 dysregulation if there is not a ZEB1 mutation or a ZEB1 deletion is indicative of a good prognosis.

In various embodiments, assaying for a presence or absence of a ZEB1 dysregulation comprises detecting ZEB1 mRNA with a polynucleotide capable of hybridizing with ZEB1 mRNA under stringent hybridization conditions. In various embodiments, assaying for a presence or absence of a ZEB1 dysregulation comprises detecting a ZEB1 protein with an antibody capable of specifically binding to a ZEB1 protein. In various embodiments, assaying for the presence or absence of a ZEB1 dysregulation comprises: sequencing the ZEB1 gene from the subject's brain tumor; and comparing the brain tumor ZEB1 sequence to a ZEB1 sequence from the subject's own blood sample, or a normal blood sample, or a reference ZEB1 sequence.

In various embodiments, assaying the ZEB1 dysregulation, PTEN deletion, MGMT expression, RET dysregulation comprises using DNA sequencing, comparative genomic hybridization (CGH), array CGH (aCGH), SNP analysis, mRNA expression assay, RT-PCR, real-time PCR, Fluorescence in situ hybridization (FISH), or a combination thereof.

In various embodiments, assaying the ZEB1 dysregulation, PTEN deletion, MGMT expression, RET dysregulation can be done by assaying for the ZEB1, PTEN, MGMT and RET protein expression. Methods and systems to detect ZEB1 protein expression (including for example, ZEB1 deletion, ZEB1 copy number loss which can result in an absence or near absence of ZEB1 protein expression) include but are not limited to ELISA, immunohistochemistry, flow cytometry, fluorescence in situ hybridization (FISH), radioimmuno assays, and affinity purification.

In various embodiments, the poor prognosis includes decreased survival likelihood, shortened life expectancy, or enhanced tumor stemness.

In various embodiments, the first therapy is a selected from the group consisting of: surgery, radiation, chemotherapy, and combinations thereof. In various embodiments, the first therapy is temozolomide.

In various embodiments, the second therapy is selected from the group consisting of: an agent that inhibits the self-renewal pathways of cancer stem cells. In various embodiments, an agent that inhibits the self-renewal pathways of cancer stem cells is selected from the group consisting of an agent that inhibits the sonic hedgehog pathway, an agent that inhibits the WNT pathway, an inhibitor of BMX, an inhibitor of IDH1, an inhibitor of IDH2 and combinations thereof. In various embodiments, the second therapy is rapamycin or bevacizumab (AVASTIN).

In various embodiments, the process further comprises administering the first therapy to the subject if the subject has a good prognosis or administering the second therapy, or both the first therapy and the second therapy, to the subject if the subject has poor prognosis.

Determining Susceptibility to Treatment, Selecting Treatment, and/or Administering Treatment Various embodiments of the present invention provide for a method, comprising: obtaining a sample comprising a tumor cell from a subject; assaying the sample to determine a presence or absence of a ZEB1 dysregulation; and determining that the subject is susceptible, sensitive and/or responsive to an angiogenesis inhibitor upon determining the presence of the ZEB1 dysregulation in the sample. In various embodiments, the method further comprises selecting the angiogenesis inhibitor for the subject as a tumor treatment. In various embodiments, the method further comprises instructing the subject to receive the angiogenesis inhibitor as a tumor treatment. In various embodiments, the method further comprises administering the angiogenesis inhibitor to the subject as a tumor treatment.

Various embodiments of the present invention provide for a method, comprising: obtaining a sample comprising a tumor cell from a subject; assaying the sample to determine a presence or absence of a ZEB1 dysregulation; and determining that the subject is resistant to (or not susceptible, sensitive or responsive to) a chemotherapeutic agent upon determining the presence of the ZEB1 dysregulation in the sample. In various embodiments, the method further comprises: assaying the sample to determine a presence or absence of an IDH1 dysregulation; and determining that the subject is resistant to (or not susceptible, sensitive or responsive to) the chemotherapeutic agent upon determining the presence of the ZEB1 dysregulation and the absence of the IDH1 dysregulation in the sample. In various embodiments, the method further comprises not selecting the chemotherapeutic agent for the subject. In various embodiments, the method further comprises instructing the subject not to receive the chemotherapeutic agent. In various embodiments, the method further comprises not administering administering the chemotherapeutic agent to the subject, or stop administering the chemotherapeutic agent to the subject. In some embodiments, wherein the chemotherapeutic agent is already being administered to the subject, the method further comprises stop administering the chemotherapeutic agent to the subject.

Various embodiments of the present invention provide for a method, comprising: obtaining a sample comprising a tumor cell from a subject; assaying the sample to determine a presence or absence of a ZEB1 dysregulation; and determining that the subject is responsive to an angiogenesis inhibitor and resistant to a chemotherapeutic agent, upon determining the presence of the ZEB1 dysregulation in the sample. In various embodiments, the method further comprises: assaying the sample to determine a presence or absence of an IDH1 dysregulation; and determining that the subject is responsive to an angiogenesis inhibitor and resistant to a chemotherapeutic agent, upon determining the presence of the ZEB1 dysregulation and the absence of the IDH1 dysregulation in the sample. In various embodiments, the method further comprises selecting the angiogenesis inhibitor but not the chemotherapeutic agent for the subject as a tumor treatment. In various embodiments, the method further comprises instructing the subject to receive the angiogenesis inhibitor but not the chemotherapeutic agent as a tumor treatment. In various embodiments, the method further comprises administering the angiogenesis inhibitor but not the chemotherapeutic agent to the subject as a tumor treatment. In some embodiments, wherein the chemotherapeutic agent is already being administered to the subject, the method further comprises stopping the administration of the chemotherapeutic agent to the subject.

Various embodiments of the present invention provide for a method, comprising: obtaining a sample comprising a tumor cell from a subject; assaying the sample to determine a presence or absence of a ZEB1 dysregulation; and selecting an angiogenesis inhibitor but not a chemotherapeutic agent as a tumor treatment for the subject, upon determining the presence of the ZEB1 dysregulation in the sample. In various embodiments, the method further comprises: assaying the sample to determine a presence or absence of an IDH1 dysregulation; and selecting an angiogenesis inhibitor but not a chemotherapeutic agent as a tumor treatment for the subject, upon determining the presence of the ZEB1 dysregulation and the absence of the IDH1 dysregulation in the sample. In various embodiments, the method further comprises instructing the subject to receive the angiogenesis inhibitor but not the chemotherapeutic agent as a tumor treatment. In various embodiments, the method further comprises administering the angiogenesis inhibitor but not the chemotherapeutic agent to the subject as a tumor treatment. In some embodiments, wherein the chemotherapeutic agent is already being administered to the subject, the method further comprises stopping the administration of the chemotherapeutic agent to the subject.

Various embodiments of the present invention provide for a method, comprising: obtaining a sample comprising a tumor cell from a subject; assaying the sample to determine a presence or absence of a ZEB1 dysregulation; and instructing the subject to receive an angiogenesis inhibitor but not a chemotherapeutic agent as a tumor treatment, upon determining the presence of the ZEB1 dysregulation in the sample. In various embodiments, the method further comprises: assaying the sample to determine a presence or absence of an IDH1 dysregulation; and instructing the subject to receive an angiogenesis inhibitor but not a chemotherapeutic agent as a tumor treatment, upon determining the presence of the ZEB1 dysregulation and the absence of the IDH1 dysregulation in the sample. In various embodiments, the method further comprises administering the angiogenesis inhibitor but not the chemotherapeutic agent to the subject as a tumor treatment. In some embodiments, wherein the chemotherapeutic agent is already being administered to the subject, the method further comprises stopping the administration of the chemotherapeutic agent to the subject.

Various embodiments of the present invention provide for a method, comprising: obtaining a sample comprising a tumor cell from a subject; assaying the sample to determine a presence or absence of a ZEB1 dysregulation; and administering an angiogenesis inhibitor but not a chemotherapeutic agent to the subject, upon determining the presence of the ZEB1 dysregulation in the sample, thereby treating the tumor in the subject. In various embodiments, the method further comprises: assaying the sample to determine a presence or absence of an IDH1 dysregulation; and administering an angiogenesis inhibitor but not a chemotherapeutic agent to the subject, upon determining the presence of the ZEB1 dysregulation and the absence of the IDH1 dysregulation in the sample, thereby treating the tumor in the subject. In some embodiments, wherein the chemotherapeutic agent is already being administered to the subject, the method further comprises stopping the administration of the chemotherapeutic agent to the subject.

Various embodiments of the present invention provide for a method of treating a tumor in a subject, wherein a ZEB1 dysregulation has been determined to be present in a tumor cell of the tumor, comprising: providing an angiogenesis inhibitor; and administering a therapeutically effective amount of the angiogenesis inhibitor to the subject, thereby treating the tumor in the subject. In various embodiments, an absence of an IDH1 dysregulation has also been determined to be in the tumor cell. In various embodiments, the method further comprises not administering a chemotherapeutic agent to the subject, or stop administering the chemotherapeutic agent to the subject. In some embodiments, wherein the chemotherapeutic agent is already being administered to the subject, the method further comprises stopping the administration of the chemotherapeutic agent to the subject.

Various embodiments of the present invention provides for a process for determining a subject's susceptibility to treatment with an angiogenesis inhibitor, comprising: obtaining a sample comprising a tumor cell from a subject desiring a determination regarding the susceptibility to treatment with an angiogenesis inhibitor; assaying the sample to determine a presence or absence of a ZEB1 dysregulation in the sample; and determining the subject is susceptible to treatment with the angiogenesis inhibitor if a ZEB1 dysregulation is present.

Various embodiments of the present invention provides for a process for determining a subject's susceptibility to treatment with an angiogenesis inhibitor, comprising: obtaining a sample comprising a tumor cell from a subject desiring a determination regarding the susceptibility to treatment with an angiogenesis inhibitor; assaying the sample to determine a presence or absence of a ZEB1 dysregulation and a presence or absence of a PTEN deletion in the sample; and determining the subject is susceptible to treatment with the angiogenesis inhibitor if a ZEB1 dysregulation and PTEN deletion are present, or a ZEB1 dysregulation is present and a PTEN deletion is not present.

Various embodiments of the present invention provides for a process for determining a subject's susceptibility to treatment with an angiogenesis inhibitor, comprising: obtaining a sample comprising a tumor cell from a subject desiring a determination regarding the susceptibility to treatment with an angiogenesis inhibitor; assaying the sample to determine a presence or absence of a ZEB1 dysregulation and an MGMT expression level in the sample; and determining the subject is susceptible to treatment with the angiogenesis inhibitor if a ZEB1 dysregulation is present and the subject as a low MGMT expression level, or subject is susceptible to treatment with the angiogenesis inhibitor if a ZEB1 dysregulation is present and the subject as a high MGMT expression level. In various embodiments, subjects with ZEB1 dysregulation present and high MGMT expression level are to be treated with an angiogenesis inhibitor as they have an even poorer survival as compared to those who have a ZEB1 dysregulation and a low MGMT expression level.

Various embodiments of the present invention provides for a process for determining a subject's susceptibility to treatment with an angiogenesis inhibitor, comprising: obtaining a sample comprising a tumor cell from a subject desiring a determination regarding the susceptibility to treatment with an angiogenesis inhibitor; assaying the sample to determine a presence or absence of a ZEB1 dysregulation and a presence or absence of a RET dysregulation in the sample; and determining the subject is susceptible to treatment with the angiogenesis inhibitor if a ZEB1 dysregulation and RET dysregulation are present.

In various embodiments, the angiogenesis inhibitor is bevacizumab.

In various embodiments, the angiogenesis inhibitor is selected from the group consisting of sorafenib (Nexavar®), sunitinib (Sutent®), pazopanib (Votrient®), and everolimus (Afinitor®).

In various embodiments, the chemotherapeutic agent is an alkylating agent. In various embodiments, the chemotherapeutic agent is temozolomide. In various embodiments, the chemotherapeutic agent is procarbazine, lomustine, or vincristine, or a combination thereof. In various embodiments, the chemotherapeutic agent is a combination of procarbazine, lomustine, or vincristine. In some embodiments, the chemotherapeutic agent is procarbazine, lomustine, and vincristine (PCV).

In various embodiments, the chemotherapeutic agent being not selected, not administered, or stopped is an alkylating agent. In various embodiments, the chemotherapeutic agent being not selected, not administered, or stopped is temozolomide. In various embodiments, the chemotherapeutic agent being not selected, not administered, or stopped is procarbazine, lomustine, or vincristine, or a combination thereof. In various embodiments, the chemotherapeutic agent being not selected, not administered, or stopped is a combination of procarbazine, lomustine, or vincristine. In some embodiments, the chemotherapeutic agent being not selected, not administered, or stopped is procarbazine, lomustine, and vincristine (PCV).

In various embodiments, the method further comprises selecting a therapy comprising the angiogenesis inhibitor for the subject if the subject is determined to be susceptible to the angiogenesis inhibitor.

In various embodiments, the method further comprises administering the therapy comprising the angiogenesis inhibitor to the subject if the subject is determined to be susceptible to the angiogenesis inhibitor.

In various embodiments, the subject is human. In various embodiments, the subject is suspected to have a brain tumor. In other embodiments, the subject is diagnosed to have a brain tumor. In other embodiments, the subject is treated for a brain tumor.

In various embodiments, the tumor is glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, the sample is obtained before, during, or after tumor treatment.

In various embodiments, assaying the sample to determine a presence or absence of a ZEB1 dysregulation in the sample comprises: assaying the sample for a chromosome 10p11.2 copy number; comparing the chromosome 10p11.2 copy number to a reference value; and determining the presence of a ZEB1 dysregulation that is indicative susceptibility to the angiogenesis inhibitor if there is a chromosome 10p11.2 copy number loss.

In various embodiments, assaying the sample to determine a presence or absence of a ZEB1 dysregulation in the sample comprises: assaying the sample to determine if there is a loss of heterozygosity (LOH) of the ZEB1 gene; and determining the presence of a ZEB1 dysregulation indicative of susceptibility to the angiogenesis inhibitor if there is a LOH of the ZEB1 gene.

In various embodiments, assaying the sample to determine a presence or absence of a ZEB1 dysregulation in the sample comprises: subjecting the sample to an analysis for ZEB1 expression; comparing the ZEB1 expression to a ZEB1 expression reference value; and determining the presence of a ZEB1 dysregulation that is indicative of susceptibility to the angiogenesis inhibitor if the ZEB1 expression level is lower than the reference value.

In various embodiments, the ZEB1 expression reference value is a median or mean ZEB1 expression level from a population of subjects with an intact ZEB1 gene, or a population of subjects without a brain tumor, or a population of subjects with a brain tumor.

In various embodiments, the ZEB1 expression reference value is a ZEB1 expression level from the subject's own blood sample or from a normal blood sample.

In various embodiments, assaying the sample to determine a presence or absence of a ZEB1 dysregulation in the sample comprises: subjecting the sample to an analysis for ZEB1 mutation or a ZEB1 deletion; and determining the presence of a ZEB1 dysregulation that is indicative of a susceptibility to the angiogenesis inhibitor if there is a ZEB1 mutation or a ZEB1 deletion.

In various embodiments, assaying for a presence or absence of a ZEB1 dysregulation comprises detecting ZEB1 mRNA with a polynucleotide capable of hybridizing with ZEB1 mRNA under stringent hybridization conditions.

In various embodiments, assaying for a presence or absence of a ZEB1 dysregulation comprises detecting a ZEB1 protein with an antibody capable of specifically binding to a ZEB1 protein.

In various embodiments, assaying for the presence or absence of a ZEB1 dysregulation comprises: sequencing the ZEB1 gene from the subject's brain tumor; and comparing the brain tumor ZEB1 sequence to a ZEB1 sequence from the subject's own blood sample, or a normal blood sample, or a reference ZEB1 sequence.

In various embodiments, assaying the sample to determine a presence or absence of an IDH1 dysregulation in the sample comprises: assaying the sample for a chromosome 2q33.3 (or 2q34) copy number; comparing the chromosome 2q33.3 (or 2q34) copy number to a reference value; and determining the presence of an IDH1 dysregulation if there is a chromosome 2q33.3 (or 2q34) copy number loss.

In various embodiments, assaying the sample to determine a presence or absence of an IDH1 dysregulation in the sample comprises: assaying the sample to determine if there is a loss of heterozygosity (LOH) of the IDH1 gene; and determining the presence of an IDH1 dysregulation if there is a LOH of the IDH1 gene.

In various embodiments, assaying the sample to determine a presence or absence of an IDH1 dysregulation in the sample comprises: subjecting the sample to an analysis for IDH1 expression; comparing the IDH1 expression to an IDH1 expression reference value; and determining the presence of an IDH1 dysregulation if the IDH1 expression level is lower than the reference value.

In various embodiments, the IDH1 expression reference value is a median or mean IDH1 expression level from a population of subjects with an intact IDH1 gene, or a population of subjects without a brain tumor, or a population of subjects with a brain tumor.

In various embodiments, the IDH1 expression reference value is an IDH1 expression level from the subject's own blood sample or from a normal blood sample.

In various embodiments, assaying the sample to determine a presence or absence of an IDH1 dysregulation in the sample comprises: subjecting the sample to an analysis for IDH1 mutation or an IDH1 deletion; and determining the presence of an IDH1 dysregulation if there is an IDH1 mutation or an IDH1 deletion.

In various embodiments, assaying for a presence or absence of an IDH1 dysregulation comprises detecting IDH1 mRNA with a polynucleotide capable of hybridizing with IDH1 mRNA under stringent hybridization conditions.

In various embodiments, assaying for a presence or absence of an IDH1 dysregulation comprises detecting an IDH1 protein with an antibody capable of specifically binding to an IDH1 protein. In some embodiments, the IDH1 protein is a mutant IDH1 protein (i.e., an IDH1 protein with one or more IDH1 mutations).

In various embodiments, assaying for the presence or absence of an IDH1 dysregulation comprises: sequencing the IDH1 gene from the subject's brain tumor; and comparing the brain tumor IDH1 sequence to an IDH1 sequence from the subject's own blood sample, or a normal blood sample, or a reference IDH1 sequence.

In various embodiments, assaying the ZEB1 dysregulation, PTEN deletion, MGMT expression, RET dysregulation, and/or IDH1 dysregulation comprises using DNA sequencing, comparative genomic hybridization (CGH), array CGH (aCGH), SNP analysis, mRNA expression assay, RT-PCR, real-time PCR, Fluorescence in situ hybridization (FISH), or a combination thereof In various embodiments, assaying the ZEB1 dysregulation, IDH1 dysregulation, PTEN deletion, MGMT expression, and/or RET, dysregulation can be done by assaying for the ZEB1, IDH1, PTEN, MGMT, and/or RET protein expression. Methods and systems to detect ZEB1, IDH1, PTEN, MGMT, and RET, protein expression (including for example, ZEB1 mutation, ZEB1 deletion, ZEB1 copy number loss which can result in an absence or near absence of ZEB1 protein expression) include but are not limited to ELISA, immunohistochemistry, flow cytometry, fluorescence in situ hybridization (FISH), radioimmuno assays, and affinity purification.

Treatments

Various embodiments provide for methods of treating a subject based on the analysis of ZEB1, IDH1, MGMT, PTEN, and/or RET.

Various embodiments provide for a method for treating a brain tumor in a subject, comprising: analyzing a biological sample from the subject to determine the presence or absence of ZEB1 dysregulation; and administering a first therapy to the subject when ZEB1 dysregulation is not present which is indicative of a good prognosis, or administering a second therapy or the first and second therapies when ZEB1 dysregulation is present which is indicative of a poor prognosis.

Various embodiments provide for a method for treating a brain tumor in a subject, comprising: analyzing a biological sample comprising a tumor cell from the subject to determine the presence or absence of ZEB1 dysregulation and IDH1 dysregulation; and administering a first therapy to the subject when ZEB1 dysregulation is not present which is indicative of a good prognosis, or administering a second therapy or the first and second therapies when ZEB1 dysregulation is present and IDH1 dysregulation is not present which are indicative of a poor prognosis. In various embodiments, the first therapy and second therapy do not comprise procarbazine, lomustine, and vincristine (PCV).

Various embodiments provide for a method for treating a brain tumor in a subject, comprising: analyzing a biological sample comprising a tumor cell from the subject to determine the presence or absence of ZEB1 dysregulation and a PTEN deletion; and administering a first therapy to the subject when ZEB1 dysregulation is not present and PTEN deletion is not present which is indicative of a good prognosis, or administering a second therapy or the first and second therapies when ZEB1 dysregulation is present and PTEN deletion is present or when ZEB1 dysregulation is present and PTEN deletion is not present which are indicative of a poor prognosis.

Various embodiments provide for a method for treating a brain tumor in a subject, comprising: analyzing a biological sample comprising a tumor cell from the subject to determine the presence or absence of ZEB1 dysregulation and a RET dysregulation; and administering a first therapy to the subject when ZEB1 dysregulation and RET dysregulation are not present which is indicative of a good prognosis, or administering a second therapy or the first and second therapies when ZEB1 dysregulation and RET dysregulation are present or when ZEB1 dysregulation is present and RET dysregulation is not present which are indicative of a poor prognosis.

Various embodiments provide for a method for treating a brain tumor in a subject, comprising: analyzing a biological sample comprising a tumor cell from the subject to determine the presence or absence of ZEB1 dysregulation and to determine MGMT expression levels; and administering a first therapy to the subject when ZEB1 dysregulation is not present and MGMT expression levels are low is indicative of a good prognosis, or administering a second therapy or the first and second therapies when ZEB1 dysregulation is present and MGMT expression levels are low, or when ZEB1 dysregulation is present and MGMT expression levels are high which are indicative of a poor prognosis. In various embodiments, the second therapy comprises an angiogenesis inhibitor. In various embodiments, the angiogenesis inhibitor is bevacizumab. In various embodiments, the second therapy does not comprise temozolomide if MGMT expression levels are high.

Various embodiments provide for a method for treating a brain tumor in a subject, comprising: obtaining the results of an analysis of ZEB1 dysregulation in a biological sample comprising a tumor cell from a subject; and administering a first therapy to the subject when ZEB1 dysregulation is not present which is indicative of a good prognosis, or administering a second therapy or the first and second therapies when ZEB1 dysregulation is present which is indicative of a poor prognosis.

Various embodiments provide for a method for treating a brain tumor in a subject, comprising: obtaining the results of an analysis of ZEB1 dysregulation and IDH1 dysregulation in a biological sample comprising a tumor cell from a subject; and administering a first therapy to the subject when ZEB1 dysregulation is not present which is indicative of a good prognosis, or administering a second therapy or the first and second therapies when ZEB1 dysregulation is present and IDH1 dysregulation is not present which are indicative of a poor prognosis. In various embodiments, the first therapy and second therapy do not comprise procarbazine, lomustine, and vincristine (PCV).

Various embodiments provide for a method for treating a brain tumor in a subject, comprising: obtaining the results of an analysis of ZEB1 dysregulation and PTEN deletion in a biological sample comprising a tumor cell from a subject; and administering a first therapy to the subject when ZEB1 dysregulation is not present and PTEN deletion is not present which is indicative of a good prognosis, or administering a second therapy or the first and second therapies when ZEB1 dysregulation is present and PTEN deletion is present or when ZEB1 dysregulation is present and PTEN deletion is not present which are indicative of a poor prognosis.

Various embodiments provide for a method for treating a brain tumor in a subject, comprising: obtaining the results of an analysis of ZEB1 dysregulation and RET dysregulation in a biological sample comprising a tumor cell from a subject; and administering a first therapy to the subject when ZEB1 dysregulation and RET dysregulation are not present which is indicative of a good prognosis, or administering a second therapy or the first and second therapies when ZEB1 dysregulation and RET dysregulation are present or when ZEB1 dysregulation is present and RET dysregulation is not present which are indicative of a poor prognosis.

Various embodiments provide for a method for treating a brain tumor in a subject, comprising: obtaining the results of an analysis of ZEB1 dysregulation and MGMT expression levels in a biological sample comprising a tumor cell from a subject; and administering a first therapy to the subject when ZEB1 dysregulation is not present and MGMT expression levels are low is indicative of a good prognosis, or administering a second therapy or the first and second therapies when ZEB1 dysregulation is present and MGMT expression levels are low, or when ZEB1 dysregulation is present and MGMT expression levels are high which are indicative of a poor prognosis. In various embodiments, the second therapy comprises an angiogenesis inhibitor. In various embodiments, the angiogenesis inhibitor is bevacizumab. In various embodiments, the second therapy does not comprise temozolomide if MGMT expression levels are high.

In various embodiments, the analysis of ZEB1 dysregulation, IDH1 dysregulation, PTEN deletion, RET dysregulation, and/or MGMT expression levels are performed via the methods described herein.

Various embodiments provide for a method for treating a brain tumor in a subject who has been determined to have ZEB1 dysregulation in a brain tumor cell, comprising: administering a second therapy or a first therapy and a second therapy when ZEB1 dysregulation is present which is indicative of a poor prognosis.

Various embodiments provide for a method for treating a brain tumor in a subject who has been determined to have ZEB1 dysregulation and IDH1 wildtype (i.e., no IDH1 dysregulation) in a brain tumor cell, comprising: administering a second therapy or a first therapy and a second therapy when ZEB1 dysregulation is present and IDH1 wildtype (i.e., no IDH1 dysregulation) is present which are indicative of a poor prognosis. In various embodiments, the first therapy and second therapy do not comprise procarbazine, lomustine, and vincristine (PCV).

Various embodiments provide for a method for treating a brain tumor in a subject who has been determined to have ZEB1 dysregulation and PTEN deletion in a brain tumor cell, comprising: administering a second therapy or a first therapy and a second therapy when ZEB1 dysregulation is present and PTEN deletion is present which are indicative of a poor prognosis.

Various embodiments provide for a method for treating a brain tumor in a subject who has been determined to have ZEB1 dysregulation and RET dysregulation in a brain tumor cell, comprising: administering a second therapy or a first therapy and a second therapy when ZEB1 dysregulation and RET dysregulation are present which are indicative of a poor prognosis.

Various embodiments provide for a method for treating a brain tumor in a subject who has been determined to have ZEB1 dysregulation and low MGMT expression levels in a brain tumor cell, or determined to have ZEB1 dysregulation and high MGMT expression levels in a brain tumor cell comprising: administering a second therapy or a first therapy and a second therapy when ZEB1 dysregulation is present and MGMT expression levels are low, or when ZEB1 dysregulation is present and MGMT expression levels are high which are indicative of a poor prognosis. In various embodiments, the second therapy comprises an angiogenesis inhibitor. In various embodiments, the angiogenesis inhibitor is bevacizumab. In various embodiments, the second therapy does not comprise temozolomide if MGMT expression levels are high.

In various embodiments, the determination of ZEB1 dysregulation, IDH1 dysregulation, PTEN deletion, RET dysregulation and/or MGMT expression levels are performed via the methods described herein.

Various embodiments provide for a system for prognosticating a brain tumor in a subject, comprising: a biological sample comprising a tumor cell from the subject; and an assay to detect ZEB1 dysregulation. In various embodiments, the system further comprises a machine to run the assay to detect ZEB1 dysregulation.

Various embodiments provide for a system for prognosticating a brain tumor in a subject, comprising: a biological sample comprising a tumor cell from the subject; and an assay to detect ZEB1 dysregulation and IDH1 dysregulation. In various embodiments, the system further comprises a machine to run the assay to detect ZEB1 dysregulation and IDH1 dysregulation.

Various embodiments provide for a system for prognosticating a brain tumor in a subject, comprising: a biological sample comprising a tumor cell from the subject; and an assay to detect ZEB1 dysregulation and PTEN deletion. In various embodiments, the system further comprises a machine to run the assay to detect ZEB1 dysregulation and PTEN deletion.

Various embodiments provide for a system for prognosticating a brain tumor in a subject, comprising: a biological sample comprising a tumor cell from the subject; and an assay to detect ZEB1 dysregulation and RET dysregulation. In various embodiments, the system further comprises a machine to run the assay to detect ZEB1 dysregulation and RET dysregulation.

Various embodiments provide for a system for prognosticating a brain tumor in a subject, comprising: a biological sample comprising a tumor cell from the subject; and an assay to detect ZEB1 dysregulation and MGMT expression. In various embodiments, the system further comprises a machine to run the assay to detect ZEB1 dysregulation and MGMT expression.

Various embodiments provide for a composition for prognosticating a brain tumor in a subject, comprising: a biological sample comprising a tumor cell from the subject; and an assay to detect ZEB1 dysregulation.

Various embodiments provide for a composition for prognosticating a brain tumor in a subject, comprising: a biological sample comprising a tumor cell from the subject; and an assay to detect ZEB1 dysregulation and IDH1 dysregulation.

Various embodiments provide for a composition for prognosticating a brain tumor in a subject, comprising: a biological sample comprising a tumor cell from the subject; and an assay to detect ZEB1 dysregulation and PTEN deletion.

Various embodiments provide for a composition for prognosticating a brain tumor in a subject, comprising: a biological sample comprising a tumor cell from the subject; and an assay to detect ZEB1 dysregulation and RET dysregulation.

Various embodiments provide for a composition for prognosticating a brain tumor in a subject, comprising: a biological sample comprising a tumor cell from the subject; and an assay to detect ZEB1 dysregulation and MGMT expression.

Samples

Samples, such as tumor cells, tumor tissue and blood, could be collected at the time of biopsy for diagnosis of the tumor. This would allow the design a course of treatment that would serve the patient from the time of the diagnosis. For example, if ZEB1 has undergone deletion, loss of heterozygosity, or mutation in a patient's tumor, the patient may require a more aggressive treatment course compared to another patient with a tumor that does not have a ZEB1 deletion, loss of heterozygosity or mutation. It is also possible to obtain tumor tissue and blood after cancer treatment (e.g., surgery) or during cancer treatment (e.g., radiation). This would allow for a change in treatment course or decision on the course of treatment with the prospect of recurrence. In various embodiments, the tumor is a brain tumor. Examples of brain tumors include but are not limited to glioblastoma multiforme (GBM), glioma, mixed glioma, astrocytoma, anaplastic astrocytoma, medulloblastoma, ependymoma, meningioma, oligodendroglioma, gangliocytoma, neuroblastoma, pituitary adenoma, retinoblastoma, or choroid plexus tumor.

In various embodiments, the steps involved in the current invention comprise obtaining either through surgical biopsy or surgical resection, a sample of the patient's brain tumor and matching blood sample from the patient. Alternatively, a sample can be obtained through primary patient harvested brain cancer stem cells, primary patient brain tumor derived cell lines, or archived patient samples in the form of FFPE (Formalin fixed, paraffin embedded) samples, or fresh frozen brain tumor samples. This invention also allows for the possibility of retrospectively evaluating the above mentioned parts of this invention (e.g., likelihood of survival, estimated life expectancy and the potential of acquiring this mutation in the future).

Patient brain tumor sample is then used to extract Deoxyribonucleic acid (DNA) using the standard protocol designated "QIAamp DNA Mini and Blood Mini kit" or for FFPE samples "QIAamp DNA FFPE Tissue kit" commercially available from Qiagen®. Informed consent is obtained from patients.

ZEB1, PTEN, MGMT, and RET Expression Analysis

Analysis of ZEB1 expression to determine the complete loss of ZEB1 expression can be determined by sequence analysis which can provide a yes or no answer to ZEB1 expression. Alternatively, ZEB1 copy number in a patient's brain tumor can be compared to that of a control sample, such as the patient's own blood sample as a matched control or a normal blood sample. Also, ZEB1 copy number in a patient's brain tumor can be compared to a reference value that is generated by using a computer algorithm to pool many control samples. For example, a ZEB1 dysregulation resulting in low ZEB1 expression (such as ZEB1 deletion, mutation or loss of heterozygosity) can be defined as a brain tumor ZEB1 with a copy number less than or equal to $-0.5$ as compared to a normal blood sample or the patient's own blood sample, which has a copy number greater than or equal zero. A two-tailed student t-test with unequal variation can be used to measure the differences between patient's brain tumor and a normal blood sample, or the patient's own blood (matched control), or a reference generate by computer algorithm pooling many control samples. A significant difference can be achieved where the p value is equal to or less than 0.05. ZEB1 mRNA expression will also be used to determine patient's prognosis, where ZEB1 mRNA expression will be separated into two groups: those with high ZEB1 expression and those with low ZEB1 expression. The groups will be separated by the median ZEB1 expression and plotted over time with a Kaplan-Meier curve.

A patient with a brain tumor can have their ZEB1 gene in the brain tumor sequenced and compared to ZEB1 sequence from the patient's own blood or a normal blood sample, or a reference generated by using an algorithm that pools many control samples and accounts for population variation. In various embodiments, this is used to determine ZEB1 mutation, deletion or loss of heterozygosity.

The analysis for PTEN, MGMT, and RET expression can be similarly performed.

Therapies

After a ZEB1, PTEN, MGMT, and/or RET mutation, deletion, loss of heterozygosity, copy number loss, or expression level is examined, one can design appropriate treatment plans according to tumor patients' individual situations; in particular, brain tumor patients' individual needs.

In some embodiments, ZEB1, PTEN, MGMT and/or RET deletants may warrant more cancer stem cell growth inhibiting therapies such as vaccine therapies targeting cancer stem cells or inhibitors of the canonical Wnt or Sonic hedgehog pathways.

If a patient falls into the "good prognosis" category, one can select a "first therapy" to the patient. "First therapy" as used herein refers to standard or convention therapy for the tumor type. In some embodiments, it is the standard or conventional therapy at the time if the present application's filing date. Examples of standard and conventional therapy for newly diagnosed glioblastomas include surgery, radiation and temozolomide chemotherapy.

If a patient falls into the "poor prognosis" category, one can select a "second therapy" or a combination of both the first therapy and the second therapy to the patient. Examples of "second therapy" include therapies to selectively target brain cancer stem cells, therapies with drugs that affect the self-renewal pathways of cancer stem cells, AVASTIN, agents that inhibit the sonic hedgehog pathway, the WNT pathway, vaccine therapy, viral therapy, molecular targeted therapy, angiogenesis inhibitors; inhibitors of BMX including BMX-IN-1 (Liu et al., 2013 ACS Chemical Biology), as BMX are involved in brain cancer stem cells (Guryanova et al., 2011 Can Cell); and inhibitors of IDH1 and IDH2 including AGI-5198 (Pamela Feliciano, *Inhibitors of mutant IDH1 and IDH2* (2013) Nature Genetics 45:477), as IDH1 and IDH2 are involved in brain cancer stem cells (Yan et al., 2009 NEJM). Other therapies to selectively target brain cancer stem cells involve targeting CD133, a stem cell marker that identifies brain cancer stem cells. Studies have indicated that selective targeting of CD133 on brain cancer stem cells can be achieved through carbon nanotubes conjugated to a CD133 monoclonal antibody allowing for more specific targeting of CD133 brain cancer stem cells with near infrared laser light (Wang et al., *Photothermolysis of glioblastoma stem-like cells targeted by carbon nanotubes conjugated with CD133 monoclonal antibody*. Nanomedicine 2011; 7: 69-79). Several lines of research have led to the elucidation of a number of cell signaling pathways utilized by cancer stem cells which hold the potential to be targeted: the PTEN pathway, the Wnt/β-catenin pathway, the PI3K/Akt pathway, the NF-κB pathway, the Notch pathway, the ABC superfamily pathway, the JAK/STAT pathway, and the Hedgehog pathway (Ke Chen et al. *Acta Pharmacol Sin* 2013; 34: 732-740). Furthermore, specific cancer stem cell targets have been identified and drugs have been developed. Surface markers, such as CD44, CD90, CD133 and CD33, can be targeted; the ABC cassette can be targeted by agents such as Verapamil, MS-209, VX-710, and Tariquidar; tumor microenvironment, such as CXCL12/CXCR4; VEGF/VEGFR, weakly acidic pH, can be targeted; and some signal cascades, such as Notch, Hedgehog, Wnt, and NF-κB pathways, can be targeted. "First therapy" and "second therapy" do not mean that the therapies will be tried first or second, it is just a convenient way to differentiate the two classes of therapies.

Nucleic Acid Sample Preparation
Nucleic Acid Isolation

Nucleic acid samples derived from cancerous and non-cancerous cells of a subject that can be used in the methods of the invention to determine the genetic signature of a cancer can be prepared by means well known in the art. For example, surgical procedures or needle biopsy aspiration can be used to collect cancerous samples from a subject. In some embodiments, it is important to enrich and/or purify the cancerous tissue and/or cell samples from the non-cancerous tissue and/or cell samples. In other embodiments, the cancerous tissue and/or cell samples can then be microdissected to reduce the amount of normal tissue contamination prior to extraction of genomic nucleic acid or pre-RNA for use in the methods of the invention. In still another embodiment, the cancerous tissue and/or cell samples are enriched for cancer cells by at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range in between, in cancer cell content. Such enrichment can be accomplished according to methods well-known in the art, such as needle microdissection, laser microdissection, fluorescence activated cell sorting, and immunological cell sorting. In one embodiment, an automated machine performs the hyperproliferative cell enrichment to thereby transform the biological sample into a purified form enriched for the presence of hyperproliferative cells.

Collecting nucleic acid samples from non-cancerous cells of a subject can also be accomplished with surgery or aspiration. In surgical procedures where cancerous tissue is removed, surgeons often remove non-cancerous tissue and/or cell samples of the same tissue type of the cancer patient for comparison. Nucleic acid samples can be isolated from such non-cancerous tissue of the subject for use in the methods of the invention. In certain embodiments of the methods of the invention, nucleic acid samples from non-cancerous tissues are not derived from the same tissue type as the cancerous tissue and/or cells sampled, and/or are not derived from the cancer patient. The nucleic acid samples from non-cancerous tissues may be derived from any non-cancerous and/or disease-free tissue and/or cells. Such non-cancerous samples can be collected by surgical or non-surgical procedures. In certain embodiments, non-cancerous nucleic acid samples are derived from tumor-free tissues. For example, non-cancerous samples may be collected from lymph nodes, peripheral blood lymphocytes, and/or mononuclear blood cells, or any subpopulation thereof. In a preferred embodiment, the non-cancerous tissue is not pre-cancerous tissue, e.g., it does not exhibit any indicia of a pre-neoplastic condition such as hyperplasia, metaplasia, or dysplasia.

In one embodiment, the nucleic acid samples used to compute a reference value are taken from at least 1, 2, 5, 10, 20, 30, 40, 50, 100, or 200 different organisms of that species. According to certain aspects of the invention, nucleic acid "derived from" genomic DNA, as used in various methods of the invention, e.g., in hybridization experiments to determine ZEB1 expression, 10p11.2 copy number, RET expression, 10q11.2 copy number, PTEN, or MGMT expression or copy number can be fragments of genomic nucleic acid generated by restriction enzyme digestion and/or ligation to other nucleic acid, and/or amplification products of genomic nucleic acids, or pre-messenger RNA (pre-mRNA), amplification products of pre-mRNA, or genomic DNA fragments grown up in cloning vectors generated, e.g., by "shotgun" cloning methods. In certain embodiments, genomic nucleic acid samples are digested with restriction enzymes.

Amplification of Nucleic Acids

Though the nucleic acid sample need not comprise amplified nucleic acid, in some embodiments, the isolated nucleic acids can be processed in manners requiring and/or taking advantage of amplification. The genomic DNA samples of a subject optionally can be fragmented using restriction endonucleases and/or amplified prior to determining analysis. In one embodiment, the DNA fragments are amplified using polymerase chain reaction (PCR). Methods for practicing PCR are well known to those of skill in the art. One advantage of PCR is that small quantities of DNA can be used. For example, genomic DNA from a subject may be about 150 ng, 175, ng, 200 ng, 225 ng, 250 ng, 275 ng, or 300 ng of DNA.

In certain embodiments of the methods of the invention, the nucleic acid from a subject is amplified using a single primer pair. For example, genomic DNA samples can be digested with restriction endonucleases to generate fragments of genomic DNA that are then ligated to an adaptor DNA sequence which the primer pair recognizes. In other embodiments of the methods of the invention, the nucleic acid of a subject is amplified using sets of primer pairs specific to ZEB1 or chromosome 10p11.2, RET or chromosome 10q11.2, or PTEN or MGMT and in instances wherein a housekeeping gene is also to be assessed, sets of primer pairs specific to the housekeeping gene. Such sets of primer pairs each recognize genomic DNA sequences flanking ZEB1, chromosome 10p11.2, RET, chromosome 10q11.2, PTEN, MGMT or the housekeeping gene wherein the expression is also to be assessed. A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

In other embodiments, where genomic DNA of a subject is fragmented using restriction endonucleases and amplified prior to analysis, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook and Russel, *Molecular Cloning: A Laboratory Manual* 4$^{th}$ ed., Cold Spring Harbor Laboratory Press (Cold Spring Harbor, N.Y. 2012)).

In yet other embodiments, where the DNA of a subject is fragmented using restriction endonucleases and amplified prior to analysis, the amplification comprises expressing a nucleic acid encoding a gene, or a gene and flanking genomic regions of nucleic acids, from the subject. RNA (pre-messenger RNA) that comprises the entire transcript including introns is then isolated and used in the methods of the invention to analyze and provide a genetic signature of a cancer. In certain embodiments, no amplification is required. In such embodiments, the genomic DNA, or pre-RNA, of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

Hybridization

The nucleic acid samples derived from a subject used in the methods of the invention can be hybridized to arrays comprising probes (e.g., oligonucleotide probes) in order to identify ZEB1, chromosome 10p11.2, PTEN, chromosome 10q11.2 or MGMT and in instances wherein a housekeeping gene expression is also to be assessed, comprising probes in order to identify the housekeeping gene. Hybridization can also be used to determine whether the ZEB1, chromosome 10p11.2, RET, chromosome 10q11.2, PTEN, or MGMT identified exhibit total copy number change, copy number gain, and copy number loss in nucleic acid samples from cancerous tissues and/or cells of the subject. In particular embodiments, the probes used in the methods of the invention comprise an array of probes that can be tiled on a DNA chip (e.g., SNP oligonucleotide probes). In some embodiments, ZEB1, chromosome 10p11.2 copy number, RET, chromosome 10q11.2 copy number, PTEN, or MGMT is determined by a method that does not comprise detecting a change in size of restriction enzyme-digested nucleic acid fragments. In other embodiments, SNPs are analyzed to identify ZEB1, chromosome 10p11.2 copy number, RET, chromosome 10q11.2 copy number, PTEN, or MGMT. Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays such as those used to analyze SNPs in MIP assays. The single-stranded synthetic oligodeoxyribonucleic acid DNA probes of an array may need to be denatured prior to contact with the nucleic acid samples from a subject, e.g., to remove hairpins or dimers which form due to self-complementary sequences.

Optimal hybridization conditions will depend on the length of the probes and type of nucleic acid samples from a subject. General parameters for specific (i.e., stringent) hybridization conditions for nucleic acids are described in Sambrook and Russel, *Molecular Cloning: A Laboratory Manual* 4$^{th}$ ed., Cold Spring Harbor Laboratory Press (Cold Spring Harbor, N.Y. 2012); Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization with Nucleic Acid Probes, Elsevier Science Publishers B. V. and Kricka, 1992, Nonisotopic DNA Probe Techniques, Academic Press, San Diego, Calif.

Oligonucleotide Nucleic Acid Arrays

In some embodiments of the methods of the present invention, DNA arrays can be used to determine total copy number change, copy number gain, and copy number loss by measuring the level of hybridization of the nucleic acid sequence to oligonucleotide probes that comprise complementary sequences. Hybridization can be used to determine the presence or absence of heterozygosity. Various formats of DNA arrays that employ oligonucleotide "probes," (i.e., nucleic acid molecules having defined sequences) are well known to those of skill in the art. Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

In some embodiments, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes. Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. Using DNA array assays, complex mixtures of labeled nucleic acids, e.g., nucleic acid fragments derived a restriction digestion of genomic DNA from non-cancerous tissue, can be analyzed. DNA array technologies have made it possible to determine the expression level of ZEB1, copy number of chromosome 10p11.2, expression level of RET, copy number of chromosome 10q11.2, expression level of PTEN, expression level of or MGMT, or copies of PTEN and a housekeeping gene in instances where housekeeping gene expression is also assessed.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors And Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules corresponding to each informative locus of interest (e.g., SNPs, RFLPs, STRs, etc.).

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof. The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

In various embodiments, the high-density oligonucleotide arrays used in the methods of the invention comprise oligonucleotides corresponding to ZEB1, chromosome 10p11.2, RET, chromosome 10q11.2, PTEN, or MGMT or in instances wherein a housekeeping gene expression is also assessed, the arrays also comprise oligonucleotides corresponding to the housekeeping gene. The oligonucleotide probes may comprise DNA or DNA "mimics" (e.g., derivatives and analogues) corresponding to a portion of each informative locus of interest (e.g., SNPs, RFLPs, STRs, etc.) in a subject's genome. The oligonucleotide probes can be modified at the base moiety, at the sugar moiety, or at the phosphate backbone. Exemplary DNA mimics include, e.g., phosphorothioates. For each SNP locus, a plurality of different oligonucleotides may be used that are complementary to the sequences of sample nucleic acids. For example, for a single informative locus of interest (e.g., SNPs, RFLPs, STRs, etc.) about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more different oligonucleotides can be used. Each of the oligonucleotides for a particular informative locus of interest may have a slight variation in perfect matches, mismatches, and flanking sequence around the SNP. In certain embodiments, the probes are generated such that the probes for a particular informative locus of interest comprise overlapping and/or successive overlapping sequences which span or are tiled across a genomic region containing the target site, where all the probes contain the target site. By way of example, overlapping probe sequences can be tiled at steps of a predetermined base interval, e. g. at steps of 1, 2, 3, 4, 5, 6, 7, 8, 9, or 10 bases intervals. In certain embodiments, the assays can be performed using arrays suitable for use with molecular inversion probe protocols such as described by Wang et al. (2007) *Genome Biol.* 8, R246. For oligonucleotide probes targeted at nucleic acid species of closely resembled (i.e., homologous) sequences, "cross-hybridization" among similar probes can significantly contaminate and confuse the results of hybridization measurements. Cross-hybridization is a particularly significant concern in the detection of SNPs since the sequence to be detected (i.e., the particular SNP) must be distinguished from other sequences that differ by only a single nucleotide. Cross-hybridization can be minimized by regulating either the hybridization stringency condition and/ or during post-hybridization washings. Highly stringent conditions allow detection of allelic variants of a nucleotide sequence, e.g., about 1 mismatch per 10-30 nucleotides. There is no single hybridization or washing condition which is optimal for all different nucleic acid sequences. For particular arrays of ZEB1, chromosome 10p11.2, RET, chromosome 10q11.2, PTEN, MGMT or the housekeeping genes these conditions can be identical to those suggested by the manufacturer or can be adjusted by one of skill in the art. In some embodiments, the probes used in the methods of the invention are immobilized (i.e., tiled) on a glass slide called a chip. For example, a DNA microarray can comprises a chip on which oligonucleotides (purified single-stranded DNA sequences in solution) have been robotically printed in an (approximately) rectangular array with each spot on the array corresponds to a single DNA sample which encodes an oligonucleotide. In summary the process comprises, flooding the DNA microarray chip with a labeled sample under conditions suitable for hybridization to occur between the slide sequences and the labeled sample, then the array is washed and dried, and the array is scanned with a laser microscope to detect hybridization. In certain embodiments there are at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 50,000, 60,000, 70,000, 80,000, 90,000, 100,000 or more or any range in between, of ZEB1, chromosome 10p11.2, RET, chromosome 10q11.2, PTEN, MGMT or the housekeeping gene for which probes appear on the array (with match/mismatch probes for a single locus of interest or probes tiled across a single locus of interest counting as one locus of interest). The maximum number of ZEB1, chromosome 10p11.2, RET, chromosome 10q11.2, PTEN, MGMT or the housekeeping gene being probed per array is determined by the size of the genome and genetic diversity of the subjects species. DNA chips are well known in the art and can be purchased in pre-5 fabricated form with sequences specific to particular species. In some embodiments, the Genome-Wide Human SNP Array 6.0™ and/or the 50K XbaI arrays (Affymetrix, Santa Clara, Calif.) are used in the methods of the invention. In other embodiments, SNPs and/or DNA copy number can be detected and quantitated using sequencing methods, such as "next-generation sequencing methods" as described further above.

Signal Detection

In some embodiments, nucleic acid samples derived from a subject are hybridized to the binding sites of an array described herein. In certain embodiments, nucleic acid samples derived from each of the two sample types of a subject (i.e., cancerous and non-cancerous) are hybridized to separate, though identical, arrays. In certain embodiments, nucleic acid samples derived from one of the two sample types of a subject (i.e., cancerous and non-cancerous) is hybridized to such an array, then following signal detection the chip is washed to remove the first labeled sample and reused to hybridize the remaining sample. In other embodiments, the array is not reused more than once. In certain embodiments, the nucleic acid samples derived from each of the two sample types of a subject (i.e., cancerous and non-cancerous) are differently labeled so that they can be distinguished. When the two samples are mixed and hybridized to the same array, the relative intensity of signal from each sample is determined for each site on the array, and any relative difference in abundance of an allele of ZEB1, chromosome 10p11.2, RET, chromosome 10q11.2, PTEN, or MGMT. Signals can be recorded and, in some embodiments, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the array, a ratio of the emission of the two fluorophores can be calculated, which may help in eliminating cross hybridization signals to more accurately determining whether a particular SNP locus is heterozygous or homozygous.

Labeling

In some embodiments, the nucleic acids samples, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, 32P and 14C. Fluorescent molecules suitable for the present invention include, but are not limited to, fluorescein and its derivatives, rhodamine and its derivatives, texas red, 5'carboxy-fluorescein ("FAM"), 2',7'-dimethoxy-4',5'-dichloro-6-carboxy-fluorescein ("JOE"), N,N,N',N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art.

Electron rich indicator molecules suitable for the present invention include, but are not limited to, ferritin, hemocyanin, and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto. Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) *Genome Res.* 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) *Genome Res.* 6, 639-645. Alternatively, a fiber-optic bundle can be used such as that described by Ferguson et al. (1996) *Nat. Biotech.* 14, 1681-1684. The resulting signals can then be analyzed to determine the expression of ZEB1, copy number of 10p11.2, PTEN or PTEN copy number, or MGMT using computer software.

Algorithms for Analyzing ZEB1, Chromosome 10p11.2, RET, Chromosome 10q11.2, PTEN, or MGMT Once the hybridization signal has been detected the resulting data can be analyzed using algorithms. In certain embodiments, the algorithm for determining the expression of ZEB1, copy number of 10p11.2, PTEN or PTEN copy number, or MGMT is based on well-known methods.

Systems, Computers, Kits and Uses
Computer Implementation Systems and Methods

In certain embodiments, the methods of the invention implement a computer program to calculate a copy number, copy number loss, copy number gain, LOH, mutation, deletion and expression levels. For example, a computer program can be used to perform the algorithms described herein. A computer system can also store and manipulate data generated by the methods of the present invention which comprises a plurality of hybridization signal changes/profiles during approach to equilibrium in different hybridization measurements and which can be used by a computer system in implementing the methods of this invention. In certain embodiments, a computer system receives probe hybridization data; (ii) stores probe hybridization data; and (iii) compares probe hybridization data to determine the state of ZEB1, chromosome 10p11.2, RET, chromosome 10q11.2, PTEN, or MGMT or housekeeping gene in said nucleic acid sample from cancerous or pre-cancerous tissue. The copy number, copy number loss, copy number gain, LOH, mutation, deletion and expression levels is then calculated. In some embodiments, a computer system (i) compares the determined copy number, copy number loss, copy number gain, LOH, mutation, deletion and expression levels to a threshold value or reference value; and (ii) outputs an indication of whether said copy number, copy number loss, copy number gain, LOH, mutation, deletion and expression levels is above or below a threshold value, or a genetic signature based on said indication. In certain embodiments, such computer systems are also considered part of the present invention.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; CRLMM software described in Silver et al. (2007) *Cell* 128, 991-1002; Aroma Affymetrix software described in Richardson et al. (2006) *Cancer Cell* 9, 121-132. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.). In certain embodiments, the computer comprises a database for storage of hybridization signal profiles. Such stored profiles can be accessed and used to calculate a copy number, copy number loss, copy number gain, LOH, mutation, deletion and expression level. For example, of the hybridization signal profile of a sample derived from the non-cancerous tissue of a subject and/or profiles generated from population-based distributions of ZEB1, chromosome 10p11.2, RET, chromosome 10q11.2, PTEN, or MGMT in relevant populations of the same species were stored, it could then be compared to the hybridization signal profile of a sample derived from the cancerous tissue of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Once a laboratory technician or laboratory professional or group of laboratory technicians or laboratory professionals determines whether a sample has a copy number, copy number gain, copy number loss, or expression level as described above (e.g., step (1) in many of the methods above), the same or a different laboratory technician or laboratory professional (or group) can analyze a plurality of test ZEB1, chromosome 10p11.2, RET, chromosome 10q11.2, PTEN, or MGMT to determine whether there is a copy number, copy number loss, copy number gain, LOH, mutation, or deletion to determine the expression levels (e.g., step (2) in many of the methods above). Next, the same or a different laboratory technician or laboratory professional (or group) can combine copy number, copy number loss, copy number gain, LOH, mutation, or deletion, or expression level data from the test to ZEB1, chromosome 10p11.2, RET, chromosome 10q11.2, PTEN, or MGMT to derive a copy number, copy number loss, copy number gain, LOH, mutation, or deletion, or expression level (e.g., step (3) in many of the methods above). Optionally, the same or a different laboratory technician or laboratory professional (or group) can correlate the copy number, copy number loss, LOH, mutation, or deletion, or expression level to an increased or decreased likelihood of response to a particular therapy (e.g., those mentioned above).

In various embodiments, provided herein is a computer readable storage medium comprising: a storing data module containing data from a sample comprising a cancer cell obtained from a subject that represents an expression level from an assay for ZEB1, copy number of chromosome 10p11.2, RET, copy number of chromosome 10q11.2, PTEN, or MGMT; a comparison module that compares the data stored on the storing data module with a reference data and/or control data, and to provide a comparison content, and an output module displaying the comparison content for the user, wherein the decrease expression of ZEB1, copy number loss of 10p11.2, decreased expression of RET, copy number loss of chromosome 10q11.2, decreased PTEN expression, copy number loss of PTEN, and/or high MGMT expression level indicates that the subject is has poor prognosis and a "second therapy" should be selected and administered to the subject as the subject may not adequately respond to standard or conventional therapy alone.

In various embodiments, the control data comprises data from a population of non-cancerous healthy individuals. In various embodiments, the control data comprises data from a housekeeping gene expression.

Embodiments of the invention can be described through functional modules, which are defined by computer executable instructions recorded on computer readable media and which cause a computer to perform method steps when executed. The modules are segregated by function, for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks), BLU-RAY disc or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include for example, at a measuring module, a storage module, a comparison module, and an output module. The functional modules can be executed on one, or multiple, computers, or by using one, or multiple, computer networks. The measuring module has computer executable instructions to provide e.g., expression information in non-transitory computer readable form.

The measuring module can comprise any system for detecting the expression of ZEB1, chromosome 10p11.2 copy number, expression of RET, chromosome 10q11.2, expression of PTEN or PTEN copy number, or expression of MGMT. Such systems can include DNA microarrays, RNA expression arrays, any ELISA detection system and/or any Western blotting detection system.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon expression level or protein level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment the reference data stored in the storage module to be read by the comparison module is, for example, expression data obtained from a population of non-cancer subjects, a population of cancer subjects or expression data obtained from the same subject at a prior time point using the measuring module.

The "comparison module" can use a variety of available software programs and formats for the comparison operative to compare expression data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to expression of ZEB1, the 10p11.2 copy number, expression of RET, chromosome 10q11.2 copy number, PTEN expression or PTEN copy number, or MGMT expression in an individual, efficacy of treatment in an individual, and/or method for treating an individual.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets. An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content-based in part on the comparison result that may be stored and output as requested by a user using an output module.

The content based on the comparison result, may be an expression value compared to a reference showing the susceptibility/adequate response or nonsusceptibility/non-adequate response from standard or conventional therapy.

In various embodiments of the invention, the content based on the comparison result is displayed on a computer monitor. In various embodiments of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The present invention therefore provides for systems (and computer readable media for causing computer systems) to perform methods for selecting treatment of cancer in an individual.

Systems and computer readable media described herein are merely illustrative embodiments of the invention for detecting ZEB1 expression, 10p11.2 copy number, RET expression, 10q11.2 copy number, PTEN expression, or PTEN copy number, or MGMT expression in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

In some cases, a computing system provided herein can include computer-executable instructions or a computer program (e.g., software) containing computer-executable instructions for formatting an output providing an indication of ZEB1 expression, 10p11.2 copy number, RET expression, 10q11.2 copy number, PTEN expression or PTEN copy number, or MGMT expression or a likelihood that a cancer patient will respond to a particular cancer treatment regimen (e.g., a regimen as described above), or a combination of these items. In some cases, a computing system provided herein can include computer-executable instructions or a computer program (e.g., software) containing computer-executable instructions for determining a desired cancer treatment regimen for a particular patient based at least in part on decreased expression of ZEB1, 10p11.2 copy number loss, decreased expression of RET, 10q11.2 copy number loss, decreased expression of PTEN, PTEN copy number loss, or high MGMT expression level.

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

Reference Values

ZEB1 Expression Reference Value

In various embodiments, the reference value can be the median or mean ZEB1 expression level from a population of subjects with an intact ZEB1 gene, or a population of subjects without a brain tumor, or a population of subjects with a brain tumor. In various embodiments, the reference value can be from the subject's own blood, serum, or plasma sample.

The nucleic acid samples used to compute a reference value when taken from a population of subjects are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine ZEB1 expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

In various embodiments, the reference value for ZEB1 expression is the expression level of one or more of the genes listed in Table 3, and the ZEB1 expression is decreased by at least or about 10, 20, 30, 40, 50, 60, 70, 80, or 90% compared to the reference value.

In various embodiments, the reference value for ZEB1 expression is the expression level of one or more of the genes listed in Table 3, and the ZEB1 expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold, 2.8-fold, 2.9-fold, or 3-fold, 4-fold, 5-fold, 6-fold, 7-fold, 8-fold, 9-fold or 10-fold compared to the reference value.

PTEN Expression Reference Value

In various embodiments, the reference value can be the median or mean PTEN expression level from a population of subjects with an intact PTEN gene, or a population of subjects without a brain tumor, or a population of subjects with a brain tumor. In various embodiments, the reference value can be from the subject's own blood, serum, or plasma sample.

The nucleic acid samples used to compute a reference value when from a population of subjects are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine PTEN expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

In various embodiments, the reference value for PTEN expression is the expression level of one or more of the genes listed in Table 3, and the PTEN expression is decreased by at least or about 10, 20, 30, 40, 50, 60, 70, 80, or 90% compared to the reference value.

In various embodiments, the reference value for PTEN expression is the expression level of one or more of the genes listed in Table 3, and the PTEN expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold, 2.8-fold, 2.9-fold, or 3-fold, 4-fold, 5-fold, 6-fold, 7-fold, 8-fold, 9-fold or 10-fold compared to the reference value.

MGMT Expression and Reference Value

MGMT positivity is determined usually by lack of methylation of the MGMT gene. If it is methylated the MGMT gene is turned off and hence there is no chemoresistance. Immunohistochemistry assay can be used to determine whether the MGMT gene is expressed in the nucleus. The means by which this expression is considered positive is listed below.

A high percentage of tumor cells (e.g., greater than 20%) immunostaining for MGMT has been reported to be diminished response to temozolomide (TEMODAR) (*J Clin Onc* 16: 3851-3857; 1998). Hence, the 40% result in this case can suggest the possibility of a relatively diminished response to TEMODAR. In various embodiments, high MGMT expression can be 40, 45, 50, 55, 60, 65, 70, 75, 80, 85, 90, or 95% or more tumor cells immunostaining for MGMT. In various embodiments, high MGMT expression can be 20, 25, 30, 35, 36, 37, 38, 39% or more tumor cells immunostaining for MGMT. In other embodiments, high MGMT expression can be 20, 25, 30, 35, 40, 45, 50, 55, 60, 65, 70, 75, 80, 85, 90, or 95% or more tumor cells found to be expressing MGMT A low percentage of tumor cells (e.g., 20% and less) immunostaining for MGMT has been reported to be associated with a relative response to temozolomide (TEMODAR) (J Clin Onc 16: 3851-3857; 1998). Hence, the 10% result in this case can suggest a likelihood of being responsive to temozolomide (TEMODAR). In various embodiments, low MGMT expression can be 10, 9, 8, 7, 6, 5, 4, 3, 2, 1% or less tumor cells immunostaining for MGMT. In other embodiments, low MGMT expression can be 20, 15, 14, 13, 12, or 11% or less tumor cells immunostaining for MGMT. In other embodiments, low MGMT expression can be 20, 15, 14, 13, 12, 11, 10, 9, 8, 7, 6, 5, 4, 3, 2, 1% or less tumor cells found to be expressing MGMT.

In various embodiments, the reference value can be the median or mean MGMT expression level from a population of subjects with an intact MGMT gene, or a population of subjects without a brain tumor, or a population of subjects with a brain tumor. In various embodiments, the reference value can be from the subject's own blood, serum, or plasma sample.

The nucleic acid samples used to compute a reference value when taken from a population of subjects are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine MGMT expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

RET Expression Reference Value

In various embodiments, the reference value can be the median or mean RET expression level from a population of subjects with an intact RET gene, or a population of subjects without a brain tumor, or a population of subjects with a brain tumor. In various embodiments, the reference value can be from the subject's own blood, serum, or plasma sample.

The nucleic acid samples used to compute a reference value when from a population of subjects are taken from at least 1, 2, 5, 10, 20, 30, 40, 50, 100, or 200 different organisms of that species. According to certain aspects of the invention, nucleic acid "derived from" genomic DNA, as used in the methods of the invention, e.g., in hybridization experiments to determine RET expression can be fragments of genomic nucleic acid generated by restriction enzyme digestion and/or ligation to other nucleic acid, and/or amplification products of genomic nucleic acids, pre-messenger RNA (pre-mRNA), or post-messenger RNA (the mature form of mRNA), amplification products of pre- or post-mRNA, or genomic DNA fragments grown up in cloning vectors generated, e.g., by "shotgun" cloning methods. In certain embodiments, genomic nucleic acid samples are digested with restriction enzymes.

In various embodiments, the reference value for RET expression is the expression level of one or more of the genes listed in Table 3, and the RET expression is decreased by at least or about 10, 20, 30, 40, 50, 60, 70, 80, or 90% compared to the reference value.

In various embodiments, the reference value for RET expression is the expression level of one or more of the genes listed in Table 3, and the RET expression is increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold, 2.8-fold, 2.9-fold, or 3-fold, 4-fold, 5-fold, 6-fold, 7-fold, 8-fold, 9-fold or 10-fold compared to the reference value.

Housekeeping Genes

In various embodiments, the house keeping gene can be selected from the genes listed in Table 3. Accordingly, in some embodiments, the housekeeping gene is one of the genes from Table 3, and in other embodiments, the housekeeping gene is a combination of any number or all of the genes from Table 3. (See e.g., Eisenberg and Levanon, Human housekeeping genes are compact. Trends in Genetics, Volume 19, Issue 7, 362-365, 1 Jul. 2003; Valeria Valente et al., Selection of suitable housekeeping genes for expression analysis in glioblastoma using quantitative RT-PCR (2009), BMC Molecular Biology; Thomas Hrus et al., RefGenes: identification of reliable and condition specific reference genes for RT-qPCR data normalization (2011), BMC Genomics). Some of the genes in table 3 name/description are followed by their geometric average expression levels according to the data published by Su et al. One of ordinary skill in the art can easily determine what the cut-off points for increased expression for any one of these genes are. For example, genes designated by asterisk are in popular use as reference in real-time PCR or quantitative PCR (qPCR), which is most often used in gene expression analysis.

In some aspects of all the embodiments on the invention, the assays, methods, kits, and systems incorporate qPCR as the gene expression analysis method to determine the amount compared to a reference value.

TABLE 3

Housekeeping Genes

| Accession No. | Description |
|---|---|
| *NM_001002.3/ NM_053275.3 | *Homo sapiens* 60S Acidic Ribosomal Protein (RPLPO), mRNA |
| *NM_021130.3 | *Homo sapiens* Cyclophilin (PPIA), mRNA |
| *NM_005255.2 | *Homo sapiens* cyclin G-Associated Kinase (GAK), mRNA |
| *NM_017840.3 | *Homo sapiens* 39S Ribosomal protein L16 (mRpL16), mRNA |
| *NM_006947.3/ NM_001267722.1 | *Homo sapiens* Signal Recognition Particle 72 kDa (Srp72), mRNA |
| *NM_013245.2 | *Homo sapiens* vacuolar protein sorting 4 homolog A (VpS4A), mRNA |
| *NM_003194.4/ NM_001172085.1 | *Homo sapiens* TATA-Box Binding Protein (TBP), mRNA |
| *NM_001402.5 | *Homo sapiens* eukaryotic translation elongation factor 1 alpha 1 (EF1A), mRNA |
| *NM_001030018.1/ NM_000485.2 | *Homo sapiens* Adenine phosphoribosyltransferase (APRT) mRNA |
| *NM_000194.2 | *Homo sapiens* Hypoxanthine Phosphoriboxyltransferase (HPRT), mRNA |
| *NM_022551 | *Homo sapiens* ribosomal protein S18 (RPS18), mRNA |
| NM_000977 | *Homo sapiens* ribosomal protein L13 (RPL13), transcript variant 1, mRNA 6407 |
| NM_033547.3 | *Homo sapiens* integrator complex subunit (INTS4), mRNA |
| NM_001159736.1/ NM_032725.3 | *Homo sapiens* Functional Spliceosome-Associated Protein 71 (BUD13), mRNA |
| NM_001242924.1 | *Homo sapiens* Zinc Finger Protein APA-1 (ZNF410), mRNA |
| NM_004096.4 | *Homo sapiens* Eukaryotic Translation Initiation Factor 4E-Binding Protein 2 (EIF4EBP2), mRNA |
| NM_001015 | *Homo sapiens* ribosomal protein S11 (RPS11), mRNA 7614 |
| NM_003973 | *Homo sapiens* ribosomal protein L14 (RPL14), mRNA 3135 |
| NM_000973 | *Homo sapiens* ribosomal protein L8 (RPL8), transcript variant 1, mRNA 8138 |
| NM_001028 | *Homo sapiens* ribosomal protein S25 (RPS25), mRNA 4683 |
| NM_001022 | *Homo sapiens* ribosomal protein S19 (RPS19), mRNA 6683 |
| NM_001013 | *Homo sapiens* ribosomal protein S9 (RPS9), mRNA 6868 |
| NM_001009 | *Homo sapiens* ribosomal protein S5 (RPS5), mRNA 6739 |
| NM_000995 | *Homo sapiens* ribosomal protein L34 (RPL34), transcript variant 1, mRNA 5424 |
| NM_002948 | *Homo sapiens* ribosomal protein L15 (RPL15), mRNA 5450 |
| NM_002952 | *Homo sapiens* ribosomal protein S2 (RPS2), mRNA 8825 |
| NM_001026 | *Homo sapiens* ribosomal protein S24 (RPS24), transcript variant 2, mRNA 5701 |
| NM_001020 | *Homo sapiens* ribosomal protein S16 (RPS16), mRNA 7477 |
| NM_001018 | *Homo sapiens* ribosomal protein S15 (RPS15), mRNA 6261 |
| NM_001017 | *Homo sapiens* ribosomal protein S13 (RPS13), mRNA 5430 |
| NM_000969 | *Homo sapiens* ribosomal protein L5 (RPL5), mRNA 4653 |
| NM_000985 | *Homo sapiens* ribosomal protein L17 (RPL17), mRNA 4369 |
| NM_000937 | *Homo sapiens* polymerase (RNA) II (DNA directed) polypeptide A, 220 kDa (POLR2A), mRNA 753 |

TABLE 3-continued

Housekeeping Genes

| Accession No. | Description |
|---|---|
| NM_001016 | *Homo sapiens* ribosomal protein S12 (RPS12), mRNA 8265 |
| NM_001014 | *Homo sapiens* ribosomal protein S10 (RPS10), mRNA 8074 |
| NM_004587 | *Homo sapiens* ribosome binding protein 1 homolog 180 kDa (dog) (RRBP1), mRNA 658 |
| *NM_004048 | *Homo sapiens* beta-2-microglobulin (B2M), mRNA 4992 |
| NM_002950 | *Homo sapiens* ribophorin I (RPN1), mRNA 495 |
| NM_005418 | *Homo sapiens* suppression of tumorigenicity 5 (ST5), transcript variant 1, mRNA 2305 |
| NM_006510 | *Homo sapiens* ret finger protein (RFP), transcript variant alpha, mRNA 420 |
| NM_006711 | *Homo sapiens* RNA binding protein S1, serine-rich domain (RNPS1), transcript variant 1, mRNA 1376 |
| NM_006145 | *Homo sapiens* DnaJ (Hsp40) homolog, subfamily B, member 1 (DNAJB1), mRNA 667 |
| NM_006362 | *Homo sapiens* nuclear RNA export factor 1 (NXF1), mRNA 729 |
| NM_021134 | *Homo sapiens* mitochondrial ribosomal protein L23 (MRPL23), mRNA 771 |
| NM_021974 | *Homo sapiens* polymerase (RNA) II (DNA directed) polypeptide F (POLR2F), mRNA 1169 |
| NM_006808 | *Homo sapiens* protein translocation complex beta (SEC61B), mRNA 679 |
| NM_005617 | *Homo sapiens* ribosomal protein S14 (RPS14), mRNA 7764 |
| NM_006867 | *Homo sapiens* RNA-binding protein gene with multiple splicing (RBPMS), mRNA 1255 |
| NM_006743 | *Homo sapiens* RNA binding motif protein 3 (RBM3), mRNA 2949 |
| NM_005381 | *Homo sapiens* nucleolin (NCL), mRNA 2043 |
| NM_018955 | *Homo sapiens* ubiquitin B (UBB), mRNA 6074 |
| NM_006442 | *Homo sapiens* DR1-associated protein 1 (negative cofactor 2 alpha) (DRAP1), mRNA 561 |
| NM_024011 | *Homo sapiens* cell division cycle 2-like 2 (CDC2L2), transcript variant 1, mRNA 430 |
| NM_005105 | *Homo sapiens* RNA binding motif protein 8A (RBM8A), mRNA 785 |
| NM_006013 | *Homo sapiens* ribosomal protein L10 (RPL10), mRNA 10721 |
| NM_007104 | *Homo sapiens* ribosomal protein L10a (RPL10A), mRNA 3006 |
| NM_012423 | *Homo sapiens* ribosomal protein L13a (RPL13A), mRNA 9545 |
| NM_021128 | *Homo sapiens* polymerase (RNA) II (DNA directed) polypeptide L, 7.6 kDa (POLR2L), mRNA 1524 |

Copy Number Reference Value

In various embodiments of the present invention, the reference value is chromosome 10 centromere copy number. In various embodiments, the reference value for chromosome 10p11.2 copy number is chromosome 10 centromere copy number. In various embodiments, the reference value for chromosome 10q11.2 copy number is chromosome 10 centromere copy number.

The chromosome 10p11.2 copy number, chromosome 10q11.2 copy number, and chromosome 10 centromere copy number can be ascertained by various methods. For example, they can be ascertained by using centromeric FISH probes, which is an assay for testing for copy number changes using microscopy.

In various embodiments, the number of chromosome 10 centromere probes is compared to the number of 10p11.2 probes, in each cell using a microscope. If the numbers match, there is no relative gain or loss of 10p11.2. Decrease in this context can be a numerical increase, e.g., 2 copies→1 copy. In various embodiments, copy loss can be defined by the absolute copy number determined in an interphase FISH assay averaged by counting a minimum of 20 tumor cells. In various embodiments, copy loss can be defined as the ratio of 10p11.2/centromere 10 determined in an interphase FISH assay counting both spots (10p11.2 and cent10) in the same cells and averaging over a minimum of 20 cells. In various embodiments, copy loss can be determined using a normalized genome wide assay such as SNP array, genome sequencing and the like, wherein the normalization is done using the allele-specific copy number analysis of tumors (ASCAT) algorithm or other appropriate algorithms. In various embodiments, the cutpoints can be anything below normal, which is 2 absolute copies of 10p11.2, or ratio<1 for 10p11.2/cent10. Due to the typical noise in these assays, in certain embodiments, the cutoff is defined by adding a standard error. Accordingly, copy<2 or ratio<1 signify copy number loss. Thus, in various embodiments, a copy number of less than 2 or a ratio of less than 1 indicates a copy number loss in the sample.

In various embodiments, the number of chromosome 10 centromere probes is compared to the number of 10q11.2 probes, in each cell using a microscope. If the numbers match, there is no relative gain or loss of 10q11.2. Decrease in this context can be a numerical increase, e.g., 2 copies→1 copy. In various embodiments, copy loss can be defined by the absolute copy number determined in an interphase FISH assay averaged by counting a minimum of 20 tumor cells. In various embodiments, copy loss can be defined as the ratio of 10q11.2/centromere 10 determined in an interphase FISH assay counting both spots (10q11.2 and cent10) in the same cells and averaging over a minimum of 20 cells. In various embodiments, copy loss can be determined using a normalized genome wide assay such as SNP array, genome sequencing and the like, wherein the normalization is done using the allele-specific copy number analysis of tumors (ASCAT) algorithm or other appropriate algorithms. In various embodiments, the cutpoints can be anything below normal, which is 2 absolute copies of 10q11.2, or ratio<1 for 10q11.2/cent10. Due to the typical noise in these assays, in certain embodiments, the cutoff is defined by adding a standard error. Accordingly, copy<2 or ratio<1 signify copy number loss. Thus, in various embodiments, a copy number of less than 2 or a ratio of less than 1 indicates a copy number loss in the sample.

In other embodiments, the reference value for chromosome 10p11.2 is determined from a non-cancer cell sample from the subject or a member of the same species to which the subject belongs. In certain embodiments, the reference value is determined from a non-cancerous cell or tissue sample that is the same type of cell or tissue as the cancer cell from the subject. In certain embodiments, the reference value is determined from a non-cancerous cell or tissue sample that is not the same type of cell or tissue as the cancer cell from the subject. In various embodiments, array-based or sequencing-based technologies can be used wherein the reference can be from patients' normal cells (e.g., blood), or it can be a collection of blood samples.

In other embodiments, the reference value for chromosome 10q11.2 is determined from a non-cancer cell sample from the subject or a member of the same species to which the subject belongs. In certain embodiments, the reference value is determined from a non-cancerous cell or tissue sample that is the same type of cell or tissue as the cancer cell from the subject. In certain embodiments, the reference value is determined from a non-cancerous cell or tissue sample that is not the same type of cell or tissue as the cancer cell from the subject. In various embodiments, array-based or sequencing-based technologies can be used wherein the reference can be from patients' normal cells (e.g., blood), or it can be a collection of blood samples.

Copy number abnormalities can be detected using methods, such as, for example, array aCGH using BAC, cDNA and/or oligonucleotide arrays; microsatellite markers; STRs, RFLPS; etc.

Among these techniques, array comparative genomic hybridization (aCGH) is preferable. In order to indicate cut-off points and values that define copy number loss. Differentially fluorescently labeled brain tumor DNA and normal DNA (e.g. patient blood DNA) are co-hybridized to normal DNA chromosomes. The ratios of normal DNA and brain tumor DNA that hybridize are determined by the signal intensity of the fluorescent labeled normal DNA and brain tumor DNA, and then the ratios determine the copy number value. This is done after the signal intensities of the normal and brain tumor DNA are normalized, which would ideally be normalized so that the log ratio of 1.0 is the baseline for the analysis, and corresponds to two DNA copies in diploid (2n) tumors. The copy number changes are identified from the ratios deviating from the baseline, using statistical methods. A possible problem with this approach however, is that in the use of aCGH the total DNA in tumors and particularly in brain tumors is in many cases is not diploid (ploidy) and the analysis can further be confounded by the proportion of normal cells within the tumor sample, therefore biasing the results. Furthermore, in aneuploid tumors with gross alterations in the DNA content, the baseline represents a copy number other than 2, like 3 or 4 in tri- or tetraploid tumors, or a non-integer value when the DNA content differs from n, 2n, 3n, etc. In order to alleviate the above difficulties to determine copy number values the following methods have been implemented: (1) exclusion of samples with low purity—that is the removal of brain cancer samples that are "contaminated" with normal DNA; and (2) An algorithm is used that sets the log ratio (the signal intensity of the fluorescent label) to 0 given the fact that the normalized aCGH ratio, which is supposed to increase with increasing DNA copy number is not truly reflected in the signal intensity and therefore must be compensated by setting the log ratio to 0 (Bilke et al, Bioinformatics, 2005). Therefore, the log ratio 0 represents the normal diploid condition and the values<0 indicate copy number loss and values>0 represent copy number gain.

Additional methods for evaluating copy number of nucleic acid in a sample include, but are not limited to, hybridization-based assays. One method for evaluating the copy number of encoding nucleic acid in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal mRNA (e.g., a non-amplified portion of the same or related cell, tissue, organ, etc.) provides an estimate of the relative copy number of the target nucleic acid. Similar methods for determining copy number can be performed using transcriptional arrays, which are well-known in the art.

An alternative means for determining the copy number is in situ hybridization (e.g., Angerer (1987) Meth. Enzymol 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases.

In some applications it is necessary to block the hybridization capacity of repetitive sequences. Thus, in some embodiments, tRNA, human genomic DNA, or Cot-I DNA is used to block non-specific hybridization.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

The methods of the invention are particularly well suited to array-based hybridization formats. Array-based CGH is described in U.S. Pat. No. 6,455,258, the contents of which are incorporated herein by reference. In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) *PCR Protocols, A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) Genomics 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In still other embodiments of the methods provided herein, sequencing of individual nucleic acid molecules (or their amplification products) is performed, as an alternative to hybridization-based assays, using nucleic acid sequencing techniques. In one embodiment, a high throughput parallel sequencing technique that isolates single nucleic acid molecules of a population of nucleic acid molecules prior to sequencing may be used. Such strategies may use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380; U.S. Pat. Nos. 6,274,320; 6,258,568; 6,210,891), by Heliscope™ system from Helicos Biosciences (see, e.g., U.S. Patent App. Pub. No. 2007/0070349), and by others. Other sequencing strategies such as stochastic sequencing (e.g., as developed by Oxford Nanopore) may also be used, e.g., as described in International Application No. PCT/GB2009/001690 (pub. no. WO/2010/004273). All of the copy number determining strategies described herein can similarly be applied to any of other nucleic acid-based analysis described herein, such as for ZEB1, or 10p11.2 the like described further below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1A

Tumor Samples and Patients

Over 2000 samples mainly consisting of primary glioblastoma multiformes (GBMs) were compiled and investigated. The original institution and the subsequent reference data obtained are indicated in Table 1.

TABLE 1

Summary of Patient Cohorts

| Cohort | Source Institution | Tumor Type | No. of Patients | FIG.(s) | Reference |
|---|---|---|---|---|---|
| A | HMS | Primary GBM | 238[Π] | 1, 10 | TCGA |
| B | MSKCC | Primary GBM | 406[Π] | 5 | TCGA |
| C | NCI | Primary/Recur | 428 | 5 | TCGA |
| D | TCGA | Primary/GBM | 250 | 1 | TCGA |
| E | Kyushu | Primary GBM | 14 | 1 | GEO |
| F | NCI | Primary GBM | 178[Π] | 6 | GEO |
| G | Genentech | Primary/Recur | 140*[Π] | 2 | Phillips et al. |
| H | TCGA | Primary/Recur | 313 | 8 | TCGA |
| I | TCGA | Primary/Recur | 152 | 3 | TCGA |
| J | UNC | Primary GBM | 507 | 3, 4 | TCGA |
| K | Genentech | Primary/Recur | 77 | 10 | GEO |

*Samples were obtained before treatment,
[Π]Samples were from newly diagnosed patients
TCGA = the cancer genome atlas Glioma Stem Cells (GSCs)

Patient brain tumor samples classified as GBM based on the World Health Organization (WHO) criteria were obtained in accordance with the appropriate Institutional review Boards (Kleihues et al., 2004) and isolated as previously described (Yuan et al., 2004). Glioma stem cells (GSCs) were cultured in NBE media as previously described (Lee et al., 2006)

Immunohistochemistry

Tissue microarrays (TMAs) were obtained from US BioMax, Inc (Rockville, Md.). Immunohistochemistry was performed on paraffin TMAs as previously described (Spoelstra et al., 2006)

Antibodies for Immunohistochemistry and Immunoblotting

The following antibodies were used: GFAP (Dako, Carpinteria, Calif.), TUJ1 (Covance, Dallas, Tex.), Nestin (Covance, Dallas), Sox2 (Millipore, Billerica, Mass.), ZEB1 (Cell Signaling Technologies, Danvers, Mass.), ZEB1 (Santa Cruz Biotechnology, Dallas, Tex.), Actin (Sigma-Aldrich, St. Louis, Mo.), CD133 (Miltenyi Biotech, Auborn, Calif.), Alexa-Fluor conjugated antibodies (Life Technologies), FITC (Sigma-Aldrich), HRP-secondaries IgG (Promega, Madison, Wis.).

Immunostaining

0827 GSCs were plated onto chambered slides (Labtek) coated with polyornithine (Sigma-Aldrich) and Fibronectin (Sigma-Aldrich) with the appropriate media. Cells were fixed with 4% Formalin and permeabilized with 0.1% Triton-X-100 in PBS and blocked with 5% goat serum. GSCs were incubated with primary antibodies overnight at 4° C. and then washed in PBS before addition of the corresponding Alexa Fluor-conjugated secondary antibody (Life Technologies) for 1 hr at room temperature and mounted with mounting medium containing DAPI (Life Technologies) and analyzed by confocal microscopy.

Western Blotting

Protein content was extracted from 0827 GSCs in lysate form and protein concentration was determined using a Bradford protein assay (Bio-Rad Laboratories, Hercules, Calif.). Equivalent amounts of protein were resolved by electrophoresis on premade 4%-15% gradient SDS-polyarcylamide gels (Bio-Rad Laboratories) and transferred to nitrocellulose membranes (Invitrogen). The membranes were incubated with either a ZEB1 antibody (Santa Cruz Biotechnology), or an Actin antibody (Sigma-Aldrich) was used to control for equal protein loading. The secondary antibodies were horseradish peroxidase-conjugated anti-mouse IgG and anti-rabbit IgG (Promega). Proteins were detected with the use of SuperSignal West Pico Chemiluminescent substrate (Pierce) and visualized after exposure to Kodak BioMax MS autoradiography films (Sigma).

GSCs and Stable Infections

To generate GSCs that stably express short hairpin RNAs (shRNAs) that target ZEB1, we co-transfected shRNA (Origene, Rockville Md.),—that target ZEB1 into our 0827 or 0323 GSCs, with a VSV-G expression plasmid (Clontech, Mountain View, Calif.) into the GP2-293 packaging cell line (Clontech) according to the manufacturer's instructions. The resulting retroviral super-natants containing shRNA were used to infect 0827 and 0323. We used two shRNAs for targeting ZEB1, shRNA was not used together but were separately infected into either GSCs. The shRNAs were designated as shZ89-1 or shZ90-1 for infection into GSCs. Similarly, a non-targeting shRNAs shSC-1 was infected into either the 0827 or infected into 0323 GSCs. Forty-eight hours after infection, the medium was replaced with complete medium containing 0.1 µg/mL puromycin (Gibco) to select for shRNA-expressing GSCs. Cells that were resistant to puromycin were characterized for ZEB1 expression by immunoblotting and subsequent cell proliferation immunofluorescence and fluorescence activated cell sorting (FACs) analysis.

FACs

GSCs were washed with 1× PBS buffer 3 times and resuspended in 1× PBS. GSCs were fixed in 4% formaldehyde for 15 min at room temperature. Cells were washed with 1× PBS buffer and were incubated in 0.1% Triton X-100 for 5 min, washed and then incubated with FcR Blocker (Mitenyi Biotech) followed by incubation with CD133 antibody conjugated to Phycoerythrin (PE) or although not shown an isotype control was also performed (Mitenyi Biotech), protected from light for 1 hr at room temperature. Cells were washed and analyzed on a FACscan flow cytometer (BD Biosciences, San Jose, Calif.).

Data Sources

Level 3 exon expression data generated from glioblastoma patients using Affymetrix Human Exon ST Arrays platform, level 3 copy number data generated from glioblastoma patients using Agilent Human Genome CGH microarray 244A platform, as well as the patient clinical data were downloaded from the cancer genome atlas (TCGA) data portal (https://tcga-data.nci.nih.gov/tcga/). The data processing details could be found in the following URL: https://gforge.nci.nih.gov/docman/view.php/265/5004/Data_Preparation_and_Transfer_SOP.zip Data was also obtained from Gene Expression Omnibus (GEO) from the following data sets represented in Table 1. GSE4271, GSE6109, GSE10922.

Mutational Analysis

Data inferred mutations were analyzed from study sets and from tissue microarray sections for the presence or absence of the ZEB1 protein. Analysis was performed at the Advanced Health Sciences Pavilion at Cedars-Sinai Neurosurgery department or the National Cancer Institute, Neuro-Oncology Branch. Loss of Heterozygosity (LOH) was inferred using dChip software from cohorts (E and F) followed by a clustering analysis based on a chosen threshold LOH score previously described (Lin et al., 2004). GSCs were prepped using QiaAmp DNA kit (Qiagen) for genomic DNA extraction. DNA from GSCs and newly diagnosed GBM patients were analyzed for LOH using Cytoscan HD (Affymetrix, Cleveland, Ohio) at the UCLA Clinical Microarray Core. All arrays were performed using the Cytoscan HD arrays and Cytoscan reagent kits in accordance with the manufacturer's instructions. Analysis was performed with Chromosome Analysis Suite software for ZEB1 loss and determination of LOH.

Clinical data for 238, 406, 250, 313, 152 and 507 glioblastomas (study sets A,B,D,H,I and J) were obtained from Open and controlled access data Tiers Portal (https://tcga-data.nci.nih.gov/tcga/). Normal brain samples data was obtained from The Repository of Molecular Brain Neoplasia Data (REMBRANDT; http://caintegrator-info.nci.nih.gov/rembrandt) of the National Cancer Institute and the National Institute of Neurological Disorders and Stroke.

LOH Analysis

The resulting loss of heterozygosity (LOH) data were analyzed with DNA-Chip Analyzer 2010.01 (www.dchip.org; Li & Wong 2001a).

The dChip program allows for copy number as well as LOH analysis against a user defined reference or matched-pair samples. The data used for analysis were taken from gene expression omnibus (GEO) and the cancer genome atlas (TCGA), cohorts E and F. We normalized arrays using invariant set normalization. Signal intensities were used to infer copy number and LOH by the hidden Markov model (HMM). HMM inferred probablity of LOH based on LOH calls (from the paired tumor/normal samples) and this is displayed from blue (1) to white (0.5) to yellow (0). The dChipSNP was then used to visualize the LOH model for each sample and mapped to chromosome regions. No further analysis was done on regions where LOH was more than 10% of the reference data.

Copy Number Analysis

The ZEB1 gene was extracted for glioblastoma aCGH datasets in retrospective analysis. The deletion is defined as copy number less than −0.5 and wild type is defined as copy number greater than zero. The genomic alteration heatmap of individual genes were generated using Partek Genomic Suite v. 6.5.

The whisker boxplots of ZEB1 expression analysis associated with ZEB1 genomic status was created using Prism v. 6.0. A two-tailed student t-test with unequal variation was used to measure the differences between groups. For study set A and B the analysis was performed as previously described (Bredel et al., 2011). Briefly, copy number was analyzed using snapCGH package for Rstudio or Gitools v. 2.00. Chromosomal gains and losses using snapCGH were defined by predicted values more than 0.75 times the interquartile range of the difference between observed and predicted for each region.

Stratifying TCGA Glioblastoma Patients into Phillip's Molecular Subtypes

Figures 4A, 4B:
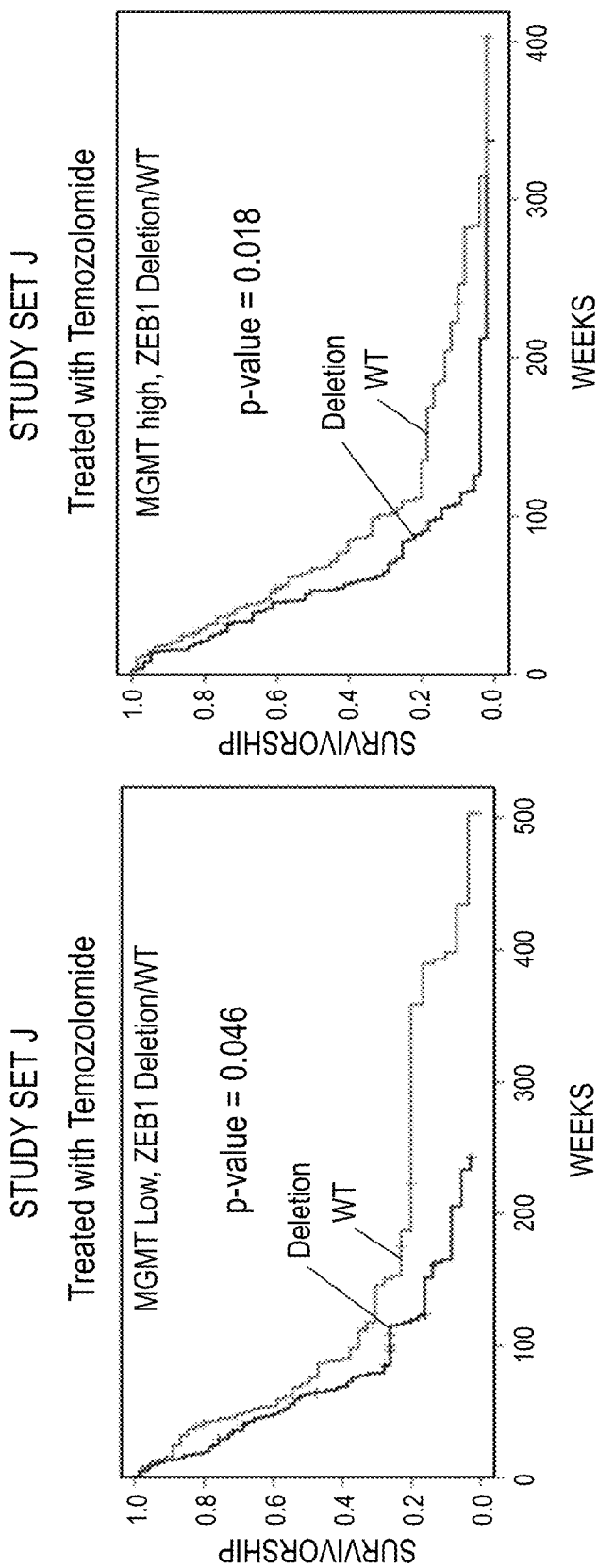
FIGS. 4A-4F depict ZEB1 loss impact on treatment.

Using the level 3 exon expression dataset, glioblastoma patients were stratified into mesenchymal, proliferative and proneural subtypes with supervised hierarchical clustering method using the classifiers derived by original authors (Phillips et al., 2006). To stratify TCGA glioblastoma patients into Phillip's molecular subtypes, the expression values of thirty-three classifiers (two genes were not available in the exon platform) and eight marker genes derived from original paper (Phillips et al., 2006) were extracted from 313 glioblastoma (study set H) patients expression data set. Similarly, glioblastoma patients were stratified into Phillip's molecular subtypes, the expression values of 35 classifiers were extracted from 140 glioblastoma patients (study set G) expression data set. A two-way supervised hierarchical clustering was then applied to these data sets using Pearson correlation as distant measure and complete linkage method. The classifier genes charactering original subtypes form three distinct clusters with one exception of SRRM2 gene, in the case of study set H which as a proneural classifier falls into mesenchymal group. Each group of classifier genes with a unique up-regulated expression pattern corresponds to a group of samples representing one of the Phillip's subtype (sup. FIG. 4A). Partek Genomic Suite v 6.5 was used for the classification analysis. Data was also obtained from supplemental data and manuscript with respect to classification of primary and recurrence and GBM subtypes.

Results

ZEB1 Deletions are Common in Glioblastoma, with a Significant LOH Component

Figures 1A, 1B:
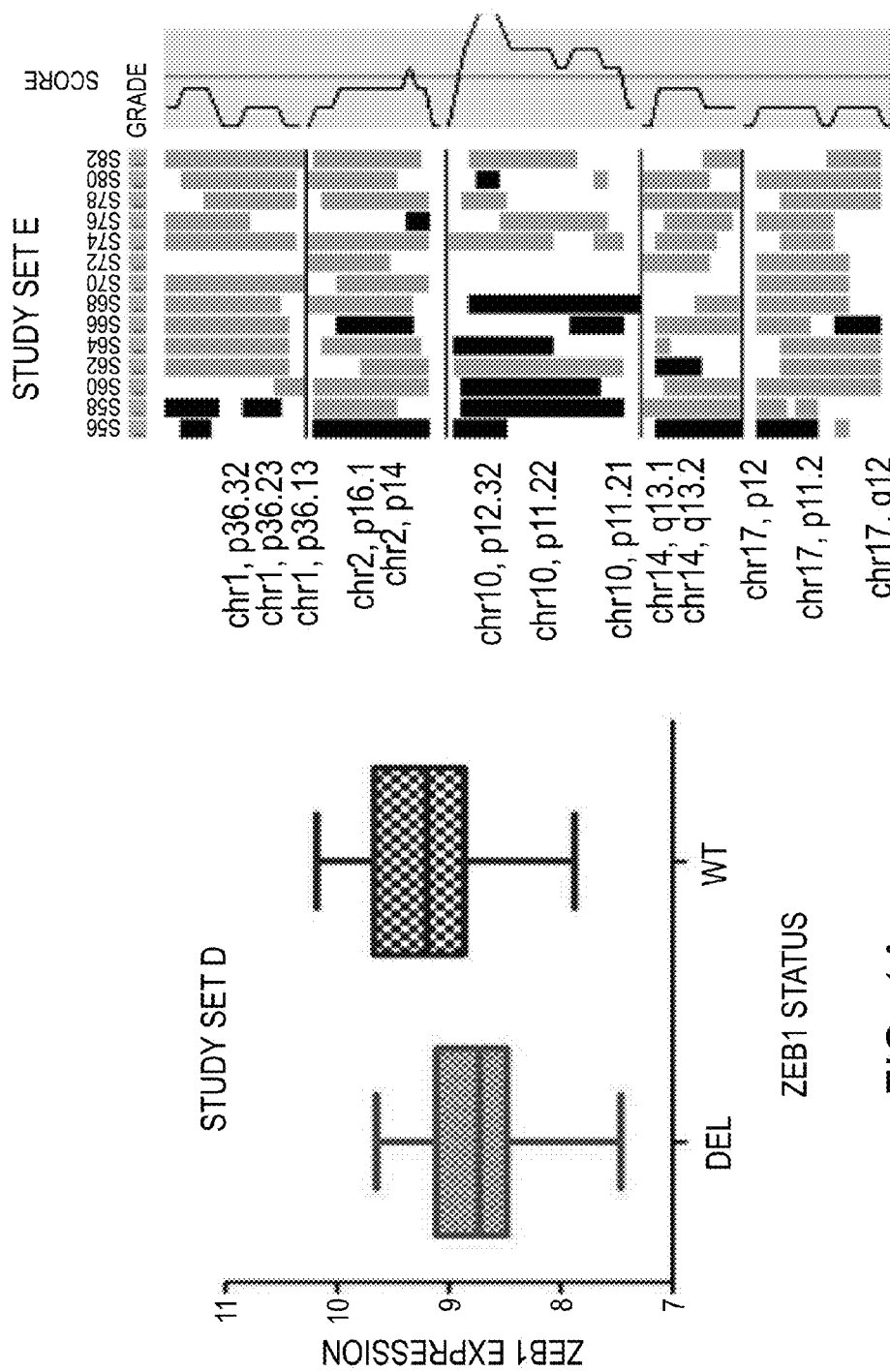
FIGS. 1A-1B depict ZEB1 deletion and loss of heterozygosity in glioblastomas.
Figure 5A:
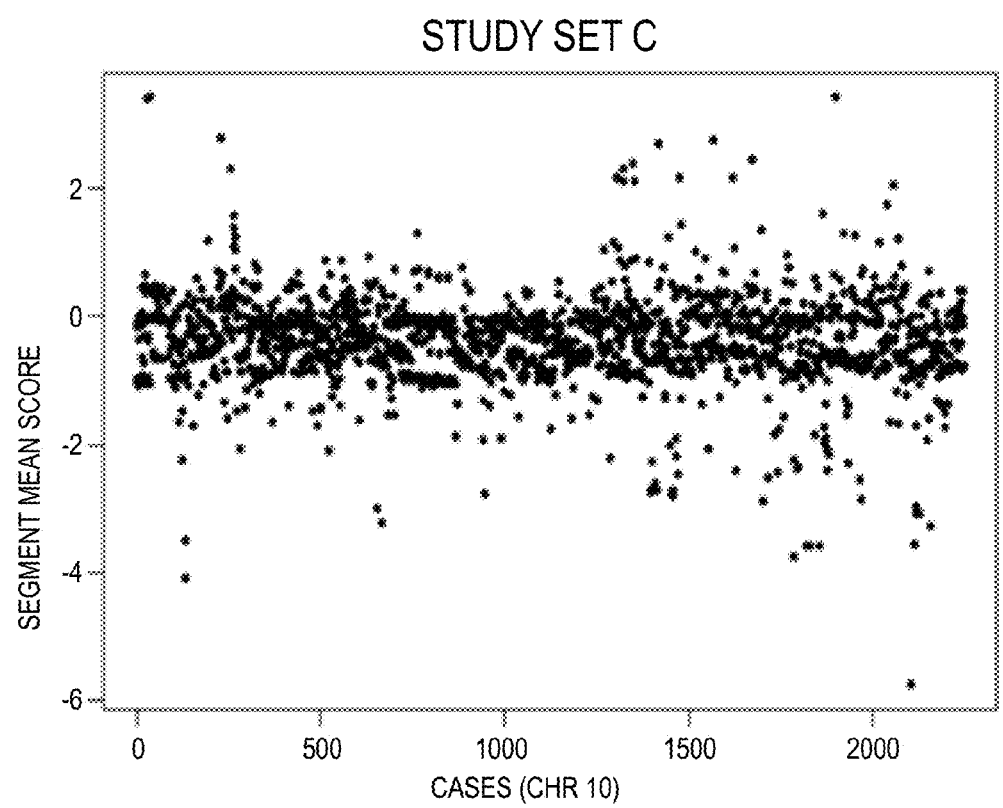
FIG. 5A-5C depicts aCGH ratio plots showing chromosome 10 from GBM tumor tissue (FIG. 5A), compared to normal patient blood (FIG. 5B), and compared to the specific ZEB1 region (FIG. 5C). Significant loss of ZEB1 can be seen compared to normal patient blood.
Figure 5B:
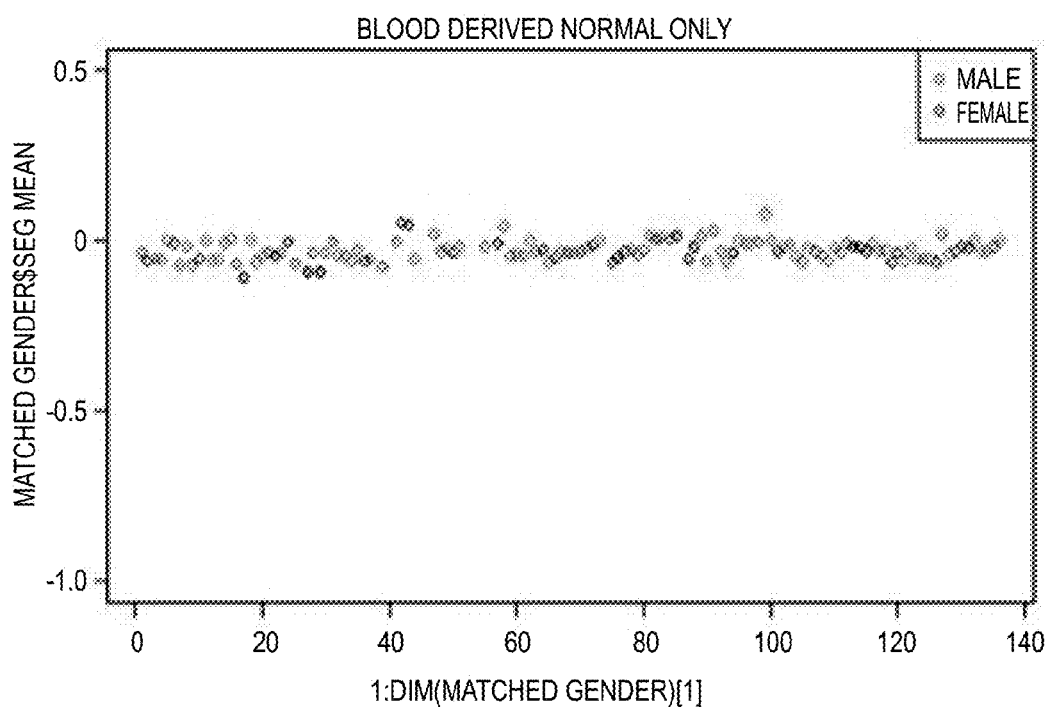
Figure 5C:
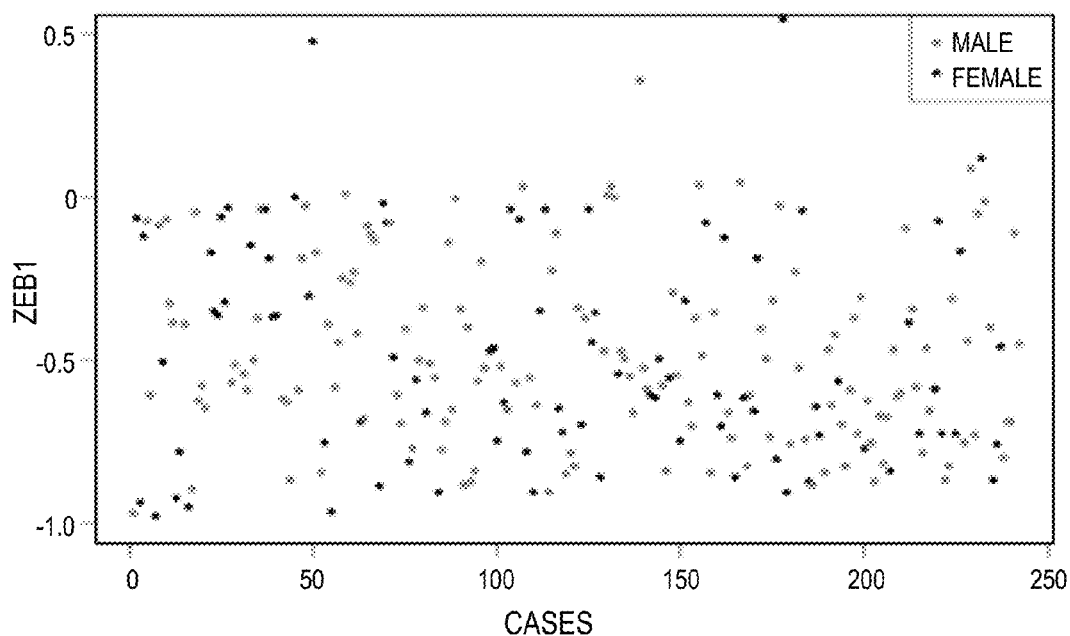

In over 51% of cases from study set A we observed a deletion that included ZEB1 on chromosome 10 (FIG. 1A), similar results were seen in study set B, which was from a collection of 406 glioblastomas, copy number variation was visualized across chromosome 10 and specifically ZEB1 was identified to have significant copy number loss (over 50% of cases) indicative of ZEB1 deletion. Retrospective copy number analysis (aCGH) of primary GBMs on chromosome 10 (FIG. 5A) compared to normal blood samples of men and women (FIG. 5B) indicated significant copy number loss in the 10p11.2 chromosomal region where ZEB1 is located, regardless of gender (FIG. 5C). We observed a dramatic decrease in ZEB1 expression in patient tumors where ZEB1 was deleted compared to patient tumors where the ZEB1 gene was intact (p<0.0001, 95% CI, −0.63 to −0.32), i.e. wildtype (FIG. 1B). We sequenced a number of exons for ZEB1 and found no mutations, suggesting the result of ZEB1 loss was due to a reduction in gene dosage (i.e. loss of copy number).

Figures 1C, 1D:
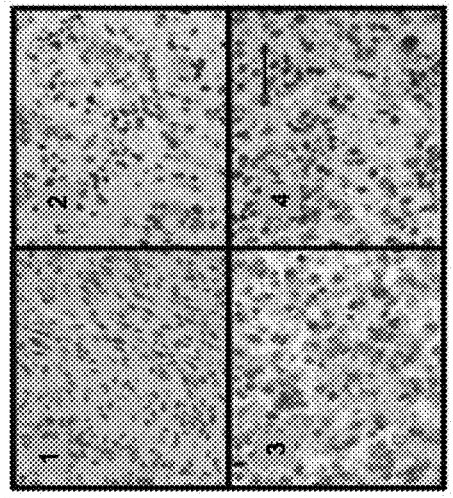
(FIG. 1C): panels 1-4, representative immunohistochemistry of tissue microarrays indicated the presence of ZEB1 protein expression (EB and ED) in some GBM patients and the absence (EA and EC) of ZEB1 protein expression in others.
(FIG. 1D) Sanger sequencing (primers) from primary GBM patients from Cedars-Sinai Medical center (n=7) indicated mutations in exon 7. Mutation algorithms revealed driver gene capability 80% (0.8) and 99% (0.99) in a highly conserved area.
Figure 6:
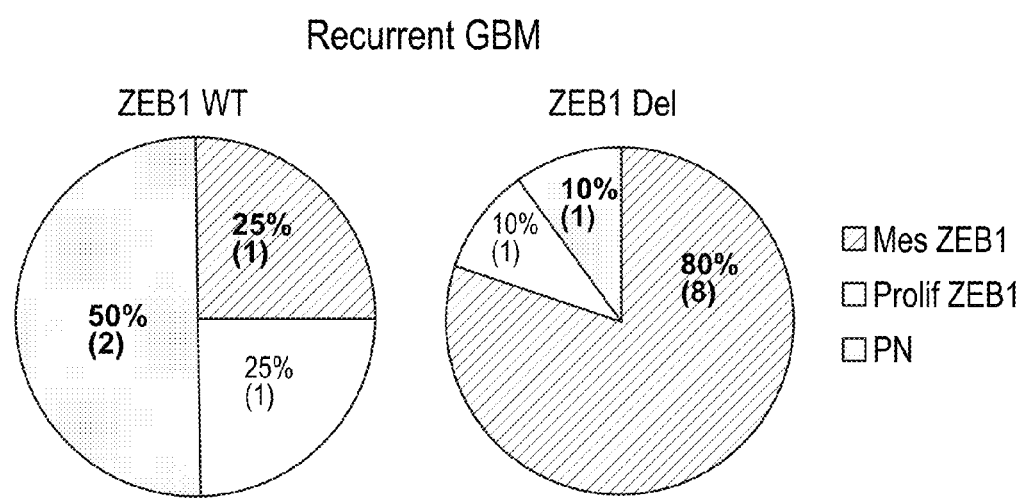
FIG. 6 shows ZEB1 classification into Mes subtype and disproportionally found in Recurrent GBMs. Classification of ZEB1 wildtype (left) and ZEB1 deletion (right) GBM patients. ZEB1 deleted patients reside primarily in the Mes GBM subtype in recurrent GBM tumors.

A defining feature of a tumor suppressor gene is the identification of loss of heterozygosity (LOH) at a tumor suppressor locus.[18] We set out to determine if LOH was present at the ZEB1 locus. Analysis of an initial 14 glioblastoma patients with matched normal controls (study set E) identified LOH in approximately 29% of patients (FIG. 1C). We further expanded this analysis to 178 glioblastoma patients and found LOH in 22% of patients (FIG. 6 study set F).

Copy number and SNP analysis of primary GBM patient derived glioma stem cells (GSCs) revealed regions of chro- Sequences of ZEB1 Wild Type and Mutations

| Patient | Gene Name | Exon | Flanking Sequence | SEQ ID NO: | Mutation Type | Peptide Flanking Sequence | SEQ ID NO: |
|---|---|---|---|---|---|---|---|
| 11-054 | ZEB1 | 2 | CAACAGACCAG | 1 | C I T | QRDTQQRD | 2 |
| 10-898 | ZEB1 | 7 | TACACAGGGTTA | 3 | G I A | SRNTQGYLYTA | 4 |
| 10-999 | ZEB1 | 7 | CTTTCAGCAT | 5 | G I T | LFFSQSAHIS | 6 |
| 11-452 | ZEB1 | 7 | CAGTAAACCT | 7 | A I G | DSVNLPLDV | 8 |
| 10-898 | ZEB1 | 8 | TGATTCTACACC | 9 | C I T | SDSTPPKKK | 10 |
| 11-177 | ZEB1 | 8 | AAATGTAGAG | 11 | A I G | NMCVRERGD | 12 |
| 11-177 | ZEB1 | 8 | AAAAAGAAAAT | 13 | A/G | KKREKKNMC | 14 |
| 11-350 | ZEB1 | 8 | TAGCTCAGAAG | 15 | A/G | DTSSEGVSN | 16 |
| 11-452 | ZEB1 | 8 | CAAATGTAGAG | 17 | A/G | KNMCVRERG | 18 |
| 11-036 | ZEB1 | 9 | GAGGAAGGAAG | 19 | Ins A | ERGERRGEKRE | 20 |
| 11-555 | ZEB1 | 9 | GACAAGGGAA | 21 | G I A | DTQKRGGEKRE | 22 |
| 11-555 | ZEB1 | 9 | CAAGGGAAGAG | 23 | Silent | ESLTREEDED | 24 |

| Patient | Mutation Nomenclature | Germline or Somatic | Matching Blood | Mutations Confirmed |
|---|---|---|---|---|
| 11-054 | c141t = Q475 | Somatic | NO | Confirmed |
| 10-898 | g2105a = G702D | Germline | YES | Confirmed |
| 10-999 | g904t = A301T | Somatic | NO | Confirmed |
| 11-452 | a1808g = N6035 | Germline | YES | Confirmed* |
| 10-898 | c2621t = T874I | Germline | YES | Confirmed |
| 11-177 | a2595g = R865G | Somatic | YES | Confirmed |
| 11-177 | a1438g = N479D | Somatic | YES | Confirmed |
| 11-350 | a2579g = E860G | Germline | YES | Confirmed |
| 11-452 | a2591g = R863E | Somatic | YES | Confirmed |
| 11-036 | A3156 = R1052 | Somatic | NO | Confirmed |
| 11-555 | g3042a = G1014R | Somatic | YES | Confirmed |
| 11-555 | g3042a = R1014R | Germline | YES | Confirmed | mosomal deletions and amplifications such as CDKN2A and EGFR respectively, consistent with GBM pathology[19] (FIG. 7).

We identified LOH at the ZEB1 locus in our GSCs 0827 (FIG. 1D) as well as from newly diagnosed GBM patient samples (data not shown). Immunohistochemistry of GBM tissue microarrays (FIG. 1E) revealed the presence (FIGS. 1Eb and 1Ed) and absence (FIGS. 1Ea and 1Ec) of ZEB1 in grade IV GBMs consistent with the loss of ZEB1 in certain patients and the preservation of ZEB1[20] in other GBM patients. Out of 88 GBMs 58% had weak to no indication of ZEB1 staining with respect to nuclear staining and only 11% of GBMs analyzed had strong nuclear staining consistent with the majority of GBMs having a reduction in gene dosage.

Loss of ZEB1 Promotes a Stem-Cell Like Signature

Figure 2:
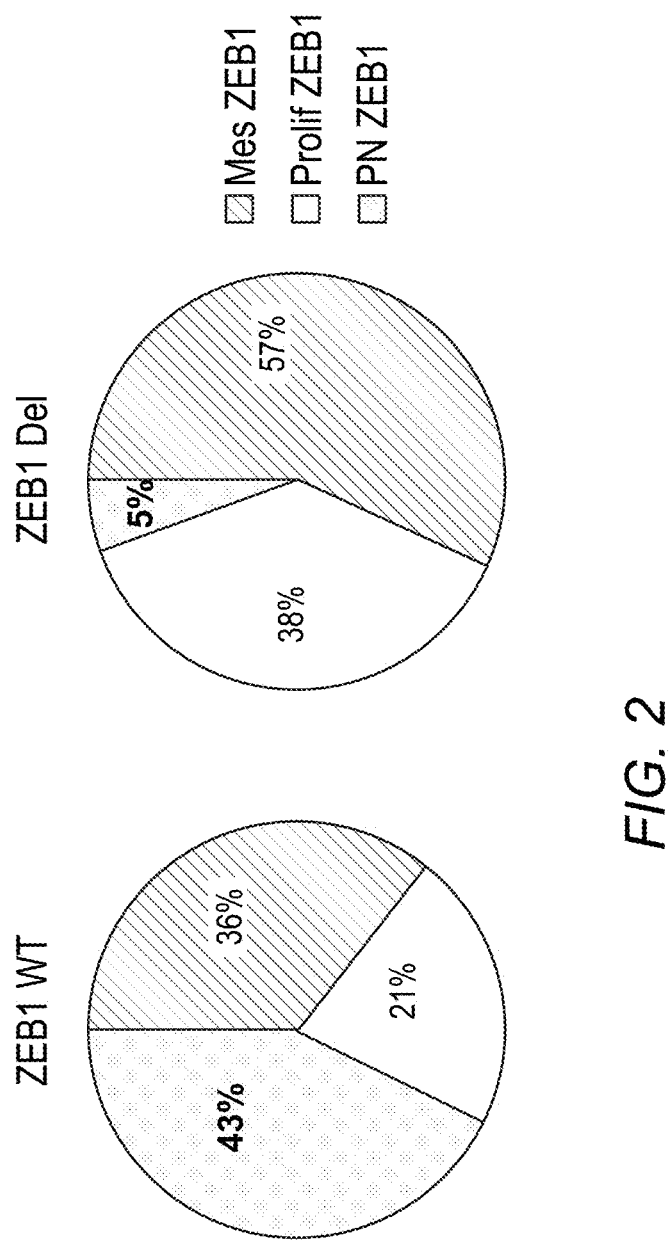
FIG. 2 shows that ZEB1 deletion classifies in the neural stem cell/transit amplifying class. Classification of ZEB1 wildtype (left) and ZEB1 deletion (right) GBM patients. ZEB1 deleted patients reside primarily in the Mes GBM subtype.

Analysis of study set G where ZEB1 wildtype and ZEB1 deleted tumors were stratified by their transcriptional signatures into the GBM subtypes mesenchymal, proliferative or proneural[2] revealed that ZEB1 deleted tumors were mostly of the mesenchymal subtype (FIGS. 2A and 2B); known for having a shortened patient survival and having arisen from a neural stem cell-like stage.[2,21] This was in contrast to the wildtype ZEB1 tumors that were mostly of the proneural subtype (FIG. 2B, left), known for having a more favorable prognosis of the three subtypes[2].

A similar analysis of study set H resulted in the same classification (FIG. 8A). Interestingly, we found in a small patient pool that almost all recurrent GBM patients contained ZEB1 deletion and were of the Mes subtype (FIG. 8B).

ZEB1 Loss Enhances GSC Stemness and Results in Shortened Patient Survival

Figure 3E:
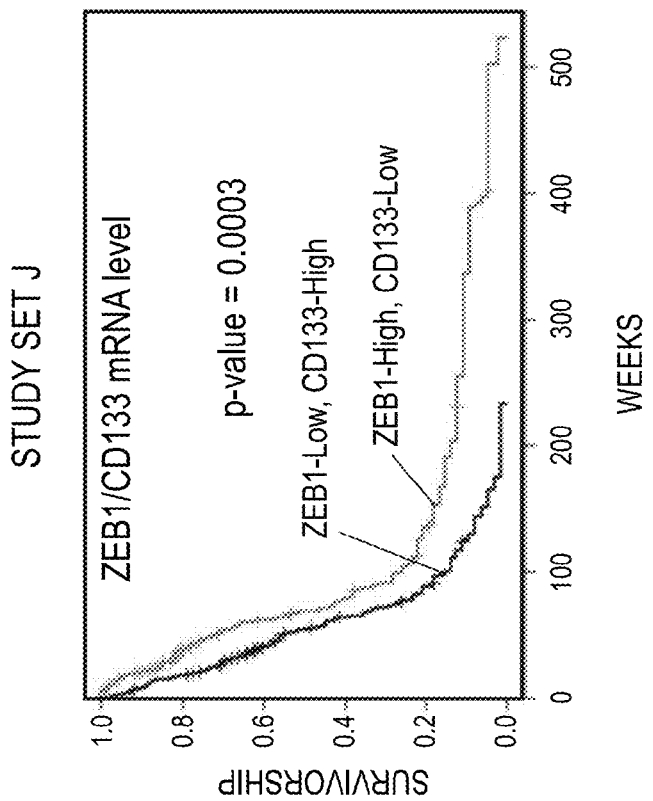
Figure 3D:
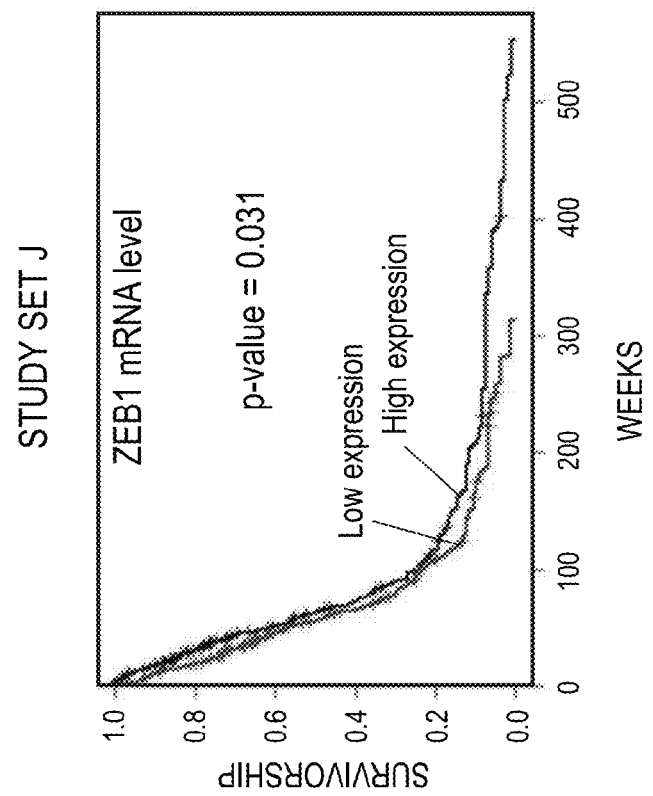
Figures 7A, 7B, 7C:
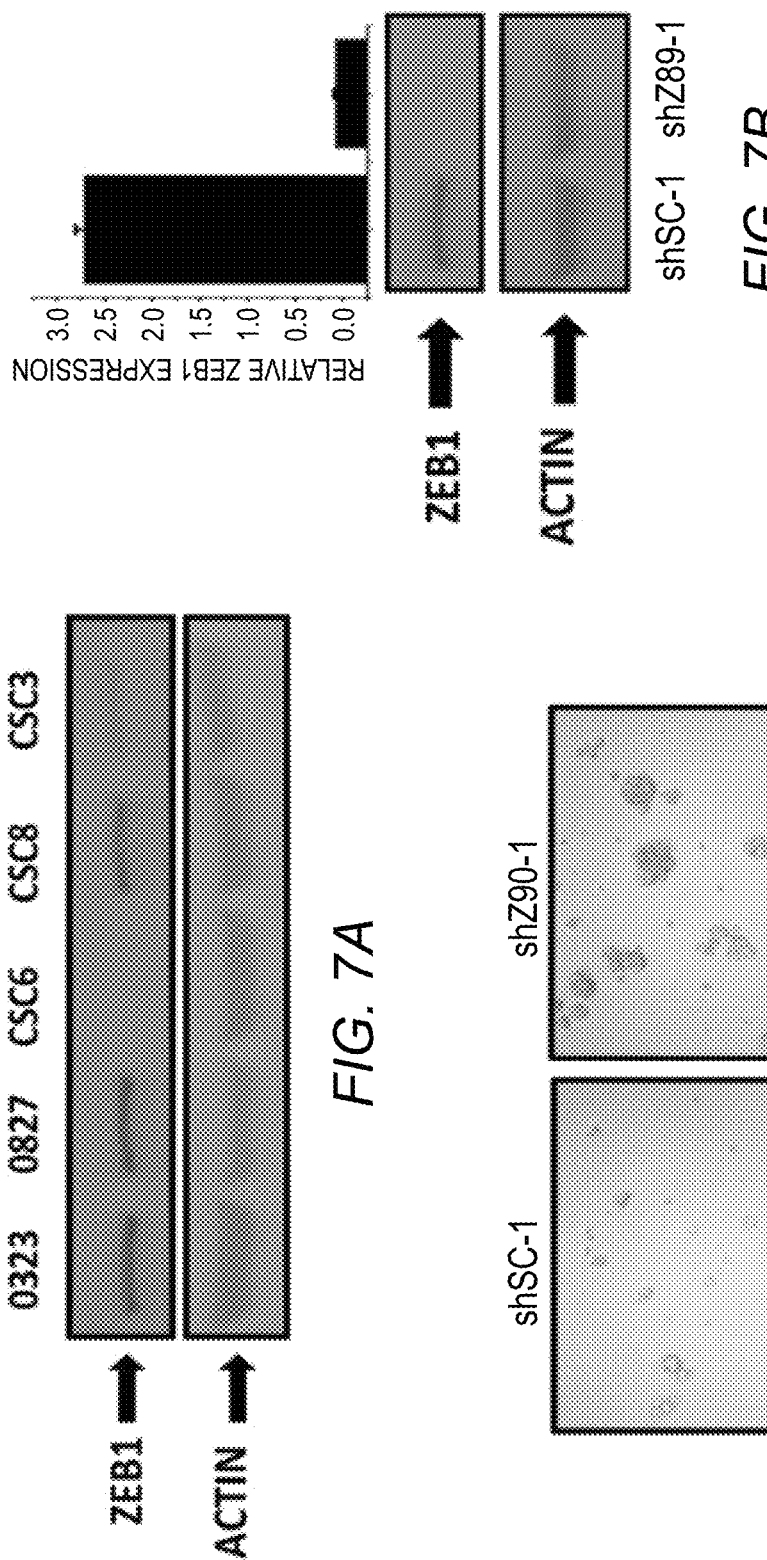
FIGS. 7A-7E show ZEB1 expression and its effect on patient survival and cell proliferation.
Figures 7D, 7E:
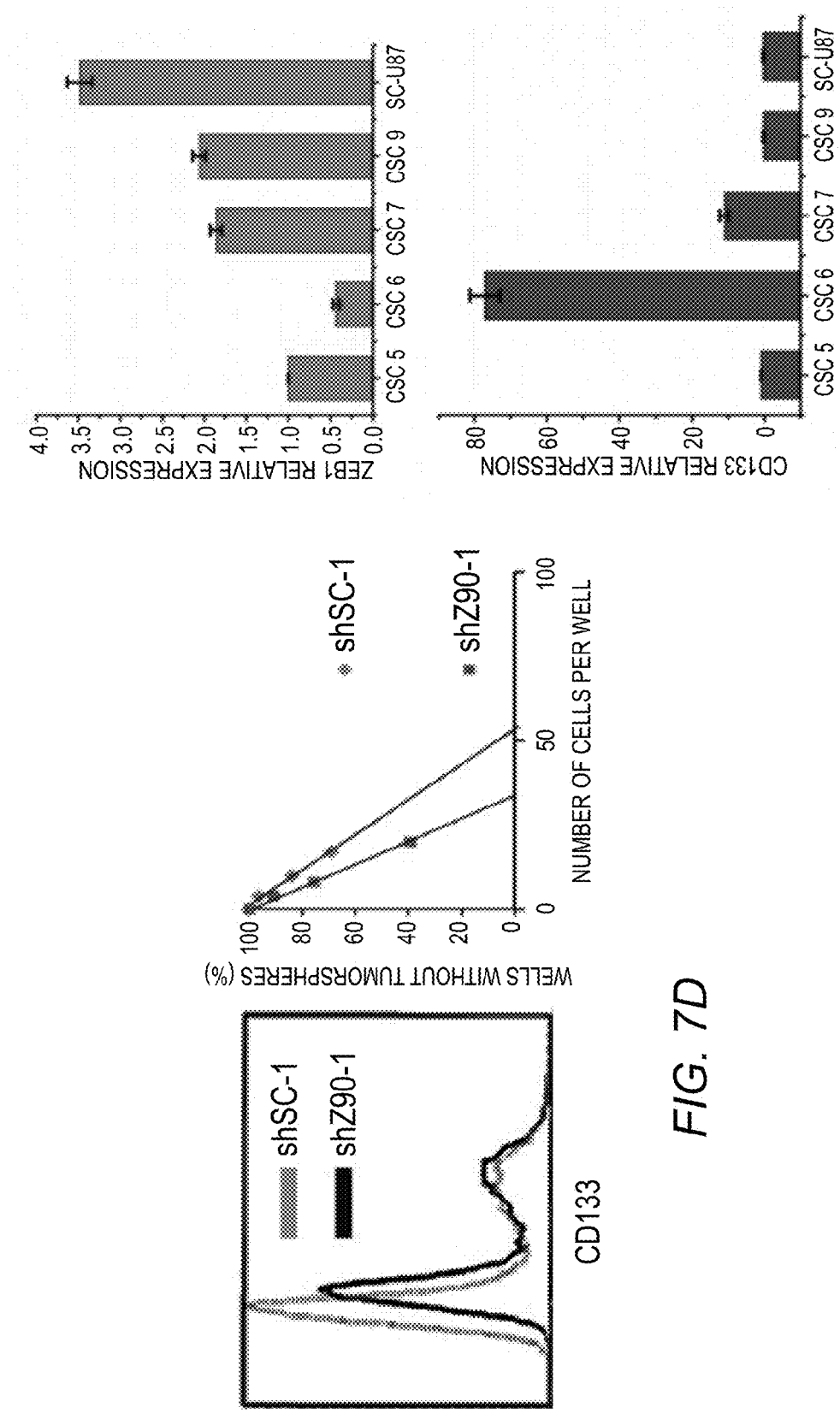

Based on the loss of ZEB1 and the classification of deleted ZEB1 tumors into a more stem cell-like subtype (i.e. mesenchymal), we wanted to determine if loss of ZEB1 enriched for stemness. We examined over a 150 GBM patient tumors with copy number and gene expression data (study set I) and found that ZEB1 deletions were consistent with increased CD133 expression compared to ZEB1 wildtype patients (FIG. 3A) who had lower CD133 expression (p=0.023). CD133 is a cell surface marker used to prospectively identify and isolate GSCs. 15,22,4,16,23 From a panel of 5 primary patient derived GSCs, three expressed ZEB1 (FIG. 7A). This led us to investigate if knockdown of ZEB1 (FIG. 7B) would maintain or enhance stem cell like properties and reinforce the notion of ZEB1 as a tumor suppressor. Suppression of ZEB1 expression by targeting shRNA (shZ89-1) led to an increase in neurosphere size (FIG. 3B) and revealed a 3.9-fold increase in the CD133 subpopulation (6.4% vs 25%±1.8%) compared to a non targeting shRNA (shSC-1) transduced into 0827 GSCs (FIG. 3C, left) and an increase GSC self-renewal (FIG. 3C, right); similar results were seen in another GSC, CSC3, using another shRNA targeting ZEB1 (FIGS. 7C and D). A panel of patient derived GSCs further indicated that with ZEB1 loss CD133 expression was higher on average as determined by RT-PCR (FIG. 7E). The loss of ZEB1 expression and yet high CD133 expression in GBM patients (FIG. 3A), and the loss of ZEB1 leading to increased CD133 expression in our GSCs (FIG. 3C) prompted us to determine if ZEB1 expression was critical to GBM patient survival (FIG. 3D and FIG. 8A).

Study set J indicated that low expression of ZEB1 in GBM patients resulted in a worse patient outcome (FIG. 3D, hazard ratio 1.25, 0.95% CI=1.02 to 1.54, p=0.031) Likewise, GBM patients with ZEB1 deletion compared to wildtype ZEB1 expressing patients had an unfavorable survival outcome (FIG. 10B, hazard ratio 1.54, 0.95% CI=1.16 to 2.04, p=0.002) and when ZEB1 loss of expression was stratified with CD133 expression (FIG. 3E, hazard ratio 1.73, 0.95% CI=1.28 to 2.34, p=0.0003) the survival difference increased suggesting that the effect of ZEB1 loss on survival was consistent with an increase in the proportion of the glioma stem cell population in the tumor.

Under certain conditions GSCs, similar to other stem cells can undergo differentiation[24]. We observed a difference in the expression of the stem cell marker CD133 in the ZEB1 deletion population as well as in ZEB1 deleted GSC lines (FIGS. 3C, 3E and FIGS. 7D and E). Our interest was in determining if ZEB1 loss would lead to resistance toward differentiation. 0827 GSCs transduced with a nontargeting shRNA (shSC-1) placed in culture conditions conducive to differentiation resulted in a precipitous change in cell morphology starting with decreased expression in Nestin, a marker attributable to a stem cell like state.

Reciprocally, there was a significant increase in GFAP, an astrocytic marker and Tuj1 a neuronal differentiation marker (FIG. 3F, top panels). 0827 GSCs transduced with ZEB1 targeted shRNA (shZ89-1) exposed to the same differentiation conditions showed little change in morphology with over 78% of infected GSCs maintaining their Nestin expression while there was little increase in GFAP or Tuj1 (FIG. 3F, bottom and FIG. 3G). These findings indicate that loss of ZEB1 expression retained the GSC-like state and resisted differentiation.

It is has been reported that cellular proliferation of GSCs are inhibited under differentiation conditions[25] which led to investigations into GSC differentiation as a means of glioma therapy.[26,27] Consistent with this notion, we saw a significant slow-down in cell proliferation of our GSC 0827 infected with a non-targeting shRNA-shSC-1 under differentiation conditions compared to NBE conditions (data not shown), however 0827 GSCs infected with ZEB1 targeted shRNA-shZ89-1 maintained a similarly high proliferative rate regardless of NBE or differentiation conditions (FIG. 9). These data support our conclusion that decreased expression of ZEB1 enhances or at least maintains the cancer stem cell-like state even under differentiation conditions.

ZEB1 Deletion Confers a Resistance and Sensitivity to Therapeutics Used in GBM

Given our observations that ZEB1 and CD133 expression imparts GSC resistance to differentiation and impacts patient survival, we considered if ZEB1 loss would impact response to therapy. To do this, we explored the role of 06-methylguanine-DNA methyltransferase (MGMT) which removes DNA alkylating agents and therefore hinders the effectiveness of chemotherapeutic alkylating agents including temozolomide.[28] The MGMT promoter region has been shown when hypermethylated to suppress MGMT activity conferring chemosensitivity resulting in favorable prognosis compared to the hypomethylated state of MGMT which results in poor patient outcomes. MGMT expression is inversely correlated to its methylated state. We sought to determine the effect of ZEB1 loss on the clinical impact of hypermethylation of MGMT in the presence of temozolomide.

We stratified patients with these characteristics and found that low ZEB1 loss expression even in the presence of low MGMT expression, and therefore favorable chemosensitivity, in the presence temozolomide treatment had a shorter patient survival (hazard ratio 1.56, 0.95% CI=1.01 to 2.38, p=0.046) than patients with low MGMT and wildtype ZEB1 (FIG. 4A). Worse yet, patients who had high MGMT expression consistent with previous reports did poorly, but patients with ZEB1 deletions in addition to high MGMT (FIG. 4B) also had a shorter survival (hazard ratio 1.59, 0.95% CI=1.08 to 2.27, p=0.018).

To further explore the role of ZEB1 loss and therapy response, we compared in study set J, patients treated with bevacizumab versus patients not treated with bevacizumab. We found that bevacizumab therapy did little to alter patient survival in the general patient population (FIG. 4C, hazard ratio 0.77, 0.95% CI=0.56 to 0.1.06, p=0.11) consistent with what has been shown in two randomized phase III trials.[31,32] The ZEB1 intact patients showed no effect from bevacizumab on survival (FIG. 4D, hazard ratio 0.91, 0.95% CI=0.21 to 0.39, p=0.837). However, ZEB1 deleted patients demonstrated a statistically significant improvement in survival when treated with bevacizumab as compared to those patients in the study set who did not receive bevacizumab (FIG. 4E, hazard ratio 0.4, 0.95% CI=0.22 to 0.98, p=0.045).

Inactivating Mutations in IDH I and II

Inactivating mutations in isocitrate dehydrogenase (IDH) I and II (R132 and R172 respectively) have been found to be an independent favorable prognostic marker in infiltrating gliomas (Yan et al. IDH1 and IDH2 Mutations in Gliomas. N Engl J Med 2009; 360:765-773). There were no inactivating mutations identified immunohistochemically in one patient. In another patient, there were inactivating mutations identified immunohistochemically.

Example 1B

Archival Sources of Specimens

Tissue from GBM cancer patients was provided by multiple institutions (listed below) by way of The Cancer Genome Atlas which was downloaded from the TCGA data portal (https://tcga-data.nci.nih.gov/tcga/) and the Gene Expression Omnibus (GEO)-Accession Numbers GSE6109, GSE10922, GSE13041, GSE4412. Note we obtained our initial 87 GBMs (FIG. 1a) from TCGA using the Nexus biodiscovery application which contained curated copy number information for both primary and recurrent GBMs Patient tumors material derived from:

Harvard Medical School; Broad Institute; Memorial Sloan Kettering Cancer Center; National Cancer Institute; University of North Carolina, Chapel Hill; Kyushu University, Japan; Genentech; University of California at Los Angeles; Clinical Data Selection Fifteen patient brain tumor samples classified as GBM based on the World Health Organization (WHO) criteria and seven samples with matching patient blood were obtained in accordance with the appropriate institutional review boards32 as were primary patient glioma stem cells (GSCs) designated 0827 and 0323.33,34 All tumors were obtained following surgical resection at Cedars-Sinai Medical Center as part of clinical care and snap frozen. Examination of the tumors was done by a neuropathologist to confirm histologically the GBM diagnosis at Cedars-Sinai Medical Center. DNA and RNA was extracted using QiaAmp DNA kit (Qiagen) for genomic DNA extraction and RNeasy RNA kit (Qiagen) for RNA extraction in accordance with the manufacturer's instructions.

Genomic Analysis

Level 3 exon expression data generated from glioblastoma patients using Affymetrix Human Exon ST Arrays platform and Affymetrix SNP6, level 3 copy number data generated from glioblastoma patients using Agilent Human Genome CGH microarray 244A platform, as well as the patient clinical data were downloaded from TCGA data portal (https://tcga-data.nci.nih.gov/tcga/) or from GEO. The data processing details could be found in the following URL: (https://gforge.nci.nih.gov/docman/view.php/265/5004/Data_Preparation_and_Transfer_SOP.zip). Note all data collection was in the last 6 years with the exception of the initial LOH dataset, but was later validated with a dataset from 2009 (FIG. 14).

Loss of Heterozygosity

Loss of Heterozygosity was performed in three different ways and analyzed by three different methods 1) Loss of Heterozygosity (LOH) found through clinical datasets in GEO. The resulting LOH data were analyzed with DNA-Chip Analyzer 2010.01 (www.dchip.org). The dChip program35 allows for copy number as well as LOH analysis against a user defined reference or matched-pair samples. We normalized arrays using invariant set normalization. Signal intensities were used to infer copy number and LOH by the hidden Markov model (HMM). HMM inferred the probability of LOH based on LOH calls (from the paired tumor/normal samples) and this is displayed from blue (1) to white (0.5) to yellow (0). The dChipSNP was then used to visualize the LOH model for each sample and mapped to chromosome regions. 2) GSCs from the National Cancer Institute and GBM patient tumors from Cedars-Sinai Medical Center were analyzed for LOH using Affymetrix Chromosome Analysis Suite (ChAS) and/or Nexus Copy Number software for ZEB1 loss and determination of LOH after samples were run on Cytoscan HD (Affymetrix, Cleveland, Ohio) at the UCLA Clinical Microarray Core. All arrays were performed using the Cytoscan HD arrays and Cytoscan reagent kits in accordance with the manufacturer's instructions. 3) LOH was also determined through matching patient blood plasma and patient GBM tumor obtained from Cedars-Sinai Medical Center (n=7) using DNAbaser for sequencing alignment after Sanger sequencing of exons in both patient blood plasma and GBM tumor.

Methodology of Copy Number Loss of ZEB1

Our approach to the role of ZEB1 copy number loss utilized the following methods assembling a variety of resources. We obtained an initial 87 TCGA (The Cancer Genome Atlas) GBM patients using the Nexus biodiscovery application which contained curated copy number information for both primary and recurrent GBMs. We compared well characterized genes in GBM pathology for copy number alterations (e.g. PTEN, EGFR, NF1) as determined by the TCGA GBM Analysis Working Group, to the ZEB1 gene in primary and recurrent cohorts. Our findings were supported by analyzing 238 glioblastoma patient samples for ZEB1 deletion downloaded from the the cancer genome atlas (TCGA) data portal (https://tcga-data.nci.nih.gov/tcga/).

Copy Number Analysis

The ZEB1 gene was extracted for glioblastoma aCGH datasets in retrospective analysis. A deletion is defined as copy number less than −0.5 and wild type is defined as copy number greater than zero. The genomic alteration heatmap of individual genes were generated using Partek Genomic Suite v. 6.5. The whisker boxplots of ZEB1 expression analysis associated with ZEB1 genomic status were created using Prism v. 6.0. A two-tailed student t-test with unequal variation was used to measure the differences between groups. Analysis was performed as previously described.36 Briefly, copy number was analyzed using snapCGH package for Rstudio or using ChAS or Nexus copy number software. Chromosomal gains and losses using snapCGH were defined by predicted values more than 0.75 times the interquartile range of the difference between observed and predicted for each region. The percent aggregation and survival curves of copy number were determined using Nexus copy number software 7.2v.

Sanger Sequencing

Coding sequences of ZEB1 from GBM patient samples and patient blood were obtained using PCR and Sanger sequencing on genomic DNA. Primers (Table 2) were designed to cover the coding sequences plus at least 10 nucleotides in the intron region on both ends. Primer extension sequencing was performed by GENEWIZ, Inc. (South Plainfield, N.J.) using Applied Biosystems BigDye version 3.1. Both forward and reverse strands were sequenced. The reactions were then run on Applied Biosystem's 3730xl DNA Analyzer.

The sequencing data were analyzed with Lasergene SeqMan software and DNAbaser (DNASTAR, Madison, Wis.) to detect any mutations compared to the genomic DNA reference sequence.

IFN-γ (eBioscience) temozolomide was obtained through Cedars-Sinai Medical Center. ZEB1 constructs: GFP tagged (Origene), shRNA-ZEB1 (Origene), shRNA-nontargeting control (Origene).

Immunohistochemistry

Immunohistochemistry was performed on paraffin TMAs as previously described. (Spoelstra, N. S. et al. The Transcription Factor ZEB1 is Aberrantly Expressed in Aggressive Uterine Cancers. Can. Res. 66, 3893-3902 (2006)).

Immunostaining

GSCs were plated onto chambered slides (Labtek) coated with poly-ornithine (Sigma-Aldrich) and Fibronectin (Sigma-Aldrich) with the appropriate media. Cells were fixed with 4% Formalin and permeabilized with 0.1% Triton-X-100 in PBS and blocked with 5% goat serum. GSCs were incubated with primary antibodies overnight at 4° C. and then washed in PBS before addition of the corresponding Alexa Fluor-conjugated secondary antibody (Life Tech-

TABLE 2

ZEB1 Exon Sequencing Primers

| Exon | Forward Primer | SEQ ID NO: | Reverse Primer | SEQ ID NO: |
|---|---|---|---|---|
| 1 | TTCGAGCCATCATTAAAATCAC | 25 | CTGGGTGGTTCAGACTCACA | 26 |
| 2 | GGGTAGCTACTATTTGTCATTTTGG | 27 | TTGATTTCAAACTTTTCATCCAAT | 28 |
| 3 | TCGGGAAGTTAAAATGTTTGTG | 29 | GGAAACGGACTAAATTCAGGA | 30 |
| 4 | TTCTGCAGATTCAAGAACAATCA | 31 | TGCATGGTCATCATAGTGTTCC | 32 |
| 5 | TGGAACATAGCATAGGGACTCA | 33 | TCAGGAATGACCAGATAACTCAAA | 34 |
| 6 | TTCTGTCCCCACTATCACTATCC | 35 | GCCAAAAGAAATGCAAGGAG | 36 |
| 7-1 | CCGCTTGTTTTAGGGAAATG | 37 | ATGGCCACCTTGTTGTATGG | 38 |
| 7-2 | CGTCTCTTTCAGCATCACCA | 39 | CTCCTGGACAATCATCACACA | 40 |
| 7-3 | AGCCATCAGTCTTCCTTTGG | 41 | ACTTTGCCTGGTTCAGGAGA | 42 |
| 7-4 | TACTCAGCCTCCTCCACTCC | 43 | TGTCCTTTTGTGGCTCCTTT | 44 |
| 7-5 | CCACCAATGGTTCCAGAAGT | 45 | AGTTGGCTCTACGGGACTGA | 46 |
| 8 | GATCAGTGTGCTTGCTTTGG | 47 | AAAGAAAGAAAATTCTAAAAC | 48 |
| 9-1 | TTGGGACCTGGAAATGTTTT | 49 | TCATCAGACCTTCAGTTTTTGC | 50 |
| 9-2 | GAGAAGCGGAAGAACGTGAC | 51 | GCACACCCGGATTTATTTTG | 52 |
| 9* |  |  | TGAACAGGAATCACAGCATACA* | 53 |

*The ZEB1-Ex9-2SeqR primer was used

Genomic and Mutational Analysis Methodology

We then assessed the relevance of observed mutations using the algorithm MutationTaster (http://www.mutationtaster.org/) Current build: NCBI 37/Ensembl 69 (ref 37) to determine their disease-causing potential and DriverDB (http://driverdb.ym.edu.tw/DriverDB/intranet/init.do) to determine the mutational hotspots in the exons of ZEB1 and the driver gene capability.

Reagents

The following antibodies were used: GFAP (Dako), TUJ1 (Covance), Nestin (Covance), Sox2 (Millipore), ZEB1 (Cell Signaling Technologies), ZEB1 (Santa Cruz Biotechnology), Actin (Sigma-Aldrich), CD133 (Miltenyi Biotech), Alexa-Fluor conjugated antibodies (Life Technologies), FITC (Sigma-Aldrich), HRP-secondaries IgG (Promega).

nologies) for 1 hr at room temperature and mounted with mounting medium containing DAPI (Life Technologies) and analyzed by confocal microscopy.

Western Blotting

Protein content was extracted from GSCs in lysate form and protein concentration was determined using a Bradford protein assay (Bio-Rad Laboratories). Equivalent amounts of protein were resolved by electrophoresis on premade 4%-15% gradient SDS-polyacrylamide gels (Bio-Rad Laboratories) and transferred to nitrocellulose membranes (Invitrogen). The membranes were incubated with either a ZEB1 antibody (Santa Cruz Biotechnology), or an Actin antibody (Sigma-Aldrich) was used to control for equal protein loading. The secondary antibodies were horseradish peroxidase-conjugated anti-mouse IgG and anti-rabbit IgG (Promega).

Proteins were detected with the use of SuperSignal West Pico Chemiluminescent substrate (Pierce) and visualized after exposure to Kodak BioMax MS autoradiography films (Sigma).

GSCs, Transient and Stable Infections

To generate GSCs that stably express short hairpin RNAs (shRNAs) that target ZEB1, we co-transfected shRNA (Origene, Rockville Md.),—that target ZEB1 into our 0827 or 0323 GSCs, with a VSV-G expression plasmid (Clontech) into the GP2-293 packaging cell line (Clontech) according to the manufacturer's instructions. The resulting retroviral supernatants containing shRNA were used to infect 0827 and 0323. We used two shRNAs for targeting ZEB1, shRNA was not used together but were separately infected into either GSCs. The shRNAs were designated as shZ89 or shZ90 for infection into GSCs. Similarly, a non-targeting shRNAs shSC-1 was infected into either the 0827 or infected into 0323 GSCs or CSC3. Forty-eight hours after infection, the medium was replaced with complete medium containing 0.1 µg/mL puromycin (Gibco) to select for shRNA-expressing GSCs. Cells that were resistant to puromycin were characterized for ZEB1 expression by immunoblotting and subsequent cell proliferation using 5-ethynyl-2'-deoxyuridine (EdU) Click-IT assay (Life Technologies) using fluorescence activated cell sorting (FACs) analysis according to the manufacturer's instructions. GSCs were incubated with IFN-γ for either 3 days (200 ng/ml) or 7 days (100 ng/ml). GSCs were incubated with temozolomide for 48 hr (25 µM). Transient transfection of ZEB1-GFP was done using X-treme gene HP DNA (Roche) according to the manufacturer's instructions.

Limiting Dilution Assay

Neural Basal A media (Invitrogen) supplemented with EGF and bFGF (R&D Systems) were used to culture primary patient derived glioma stem cells (GSCs) which were dissociated into single cells sorted for CD133 expression and plated onto 24 well plates with various seeding densities (4-100 cells/well). GSCs were incubated at 37° C. at 5% CO2 for 2 to 3 weeks. GSCs were then quantified for neurosphere formation.

Fluorescence Activated Cell Sorting

GSCs were washed with 1× PBS buffer 3 times and resuspended in 1× PBS. GSCs were fixed in 4% formaldehyde for 15 min at room temperature. Cells were washed with 1× PBS buffer and were incubated in 0.1% Triton X-100 for 5 min, washed and then incubated with FcR Blocker (Mitenyi Biotech) followed by incubation with CD133 antibody conjugated to Phycoerythrin (PE) or although not shown an isotype control was also performed (Miltenyi Biotech), protected from light for 1 hazard ratio at room temperature. Cells were washed and analyzed on a FACscan flow cytometer (BD Biosciences).

Oligonucleotide Precipitation Assays

Were performed as previously described17 with the exception of the identification of the ZEB1 binding sites within the LIF promoter which were identified by Pscan (http://www.beaconlab.it/pscan, and by comparing known E-box binding sites for ZEB1 and using the TOMTOM alogorithm.

Luciferase Reporter Assays

To measure transcriptional activity of LIF, 0827 GSCs ($1 \times 10^4$ cells per transfection, three replicates per condition) were transiently transfected with one of several deletion LIF luciferase reporter plasmids (1 ug; Switchgear) with the use of X-treme gene HP DNA (Roche), seeded in six-well plates ($1 \times 10^4$ cell per well), and incubated for 48 hrs. IFN-γ cytokine (200 ng/mL) was added to the cultures and the cells were incubated for 72 hrs. The cells were harvested and the luciferase activity was measured with the use of a GloMax 20/20 Luminometer (Promega, Madison, Wis.). These experiments were carried out in triplicate on three different occasions.

Note the original LIF luciferase reporter plasmid obtained from Switchgear was then subjected to site directed mutagenesis to obtain the appropriate deletion constructs.

Quantitative Real Time RT-PCR

Total RNAs from either GSCs or GBM patient samples were isolated using RNeasy mini kit (Qiagen). Real-time PCR was performed using the IQ5 (Bio-rad) system according to the manufacturer's instructions. Template controls and samples were assayed in triplicate. The relative number of target transcripts was normalized to the number of human GAPDH transcripts found in the same sample. The relative quantitation of target gene expression was performed using the comparative cycle threshold ($C_T$) method. Human primers (Qiagen) used in the real time PCR were the following ZEB1, LIF, GAPDH and CD133.

ELISA

To determine quantitatively the total LIF secreted protein amount we used a LIF Human Quantikine ELISA kit (R&D systems) according to the manufacturer's specifications. The kit presents >95% cross-reactivity with human LIF relative to related molecules. 72 hrs after treatment with IFN-γ GSC culture supernatants stably infected with either shRNAs targeting ZEB1 or non-targeting control were centrifuged to remove particles and concentrated with Amicon Ultra-4 Centrifugal Filters-10K (Millipore) to a final volume of 200 µl.

Differentiation of GSCs

Was performed as previously described. (Spoelstra, N. S. et al. The Transcription Factor ZEB1 is Aberrantly Expressed in Aggressive Uterine Cancers. Can. Res. 66, 3893-3902 (2006)).

Statistical Analysis

Data are expressed as mean±s.e.m. Kaplan-Meier curves and p values were generated using Prism 6.0v. Two-tailed student's t-test, were used. A P value of *<0.05 was considered significant.

Accession Numbers

Data obtained from Gene Expression Omnibus (GEO) were from the following data sets. GSE6109, GSE10922, GSE13041, GSE4412.

Results

In over 51% of cases of GBM, we observed a deletion that included ZEB1 on chromosome 10. Similarly, we observed significant copy number alterations of ZEB1 in both primary and recurrent (n=87) GBM patients in relation to well characterized genes determined by the TCGA GBM Analysis working group (P=0.033, Chi-Square Pearson, FIG. 13). Copy number loss and expression at the ZEB1 locus of GBM patients on chromosome 10 (FIG. 13, P<0.0001, 95% CI, −0.63 to −0.32) could be seen relative to patient blood with normal copy number and expression across other brain cancer types (FIG. 13).

Sanger sequencing (Table 2 (primers)) from primary GBM patients from Cedars-Sinai Medical center (n=7) indicated mutations in exon 7. Mutation algorithms revealed driver gene capability 80% (0.8) and 99% (0.99) in a highly conserved area (FIG. 1D). ZEB1 mutations and copy number loss prompted us to determine if ZEB1 expression was critical to GBM patient survival. In either case GBM patients with low ZEB1 expression or ZEB1 deletion resulted in shorter patient survival. ZEB1 deletion was found to be secondary to loss of heterozygosity at the ZEB1 locus. Taken together these data suggest that ZEB1 loss is an important prognostic indicator and determinant of unfavorable outcome for GBM patients.

To confirm ZEB1 loss at the protein level, we performed immunohistochemistry using tissue microarrays, which revealed the presence and absence of ZEB1 in grade IV GBMs consistent with the loss of ZEB1 in certain patients and the preservation of ZEB1 in other GBM patients. Only 11% of GBMs analyzed had strong nuclear staining.

Given the deleterious effects of ZEB1 loss on patient survival, we wanted to determine if loss of ZEB1 enriched for stemness. We utilized CD133, a cell surface marker used to prospectively identify and isolate glioma stem cells. Examining GBM patient tumors (n=269) for copy number and gene expression data revealed that ZEB1 deleted tumors demonstrated increased CD133 expression compared to ZEB1 wildtype tumors (FIG. 14, P=0.023). Primary GBMs and patient derived GSCs revealed, that the majority expressed low levels of ZEB1 with GSCs inversely correlating with CD133 expression as determined by RT-PCR (FIG. 14). GSCs were also confirmed at the protein level to have low expression of ZEB1 protein (FIG. 14). This led us to investigate if knockdown of ZEB1 (FIG. 14) would maintain or enhance stem cell properties. Suppression of ZEB1 expression using shRNAs revealed a significant increase in neurosphere size, the CD133 subpopulation (6.4% vs 25%±1.8%) and self-renewal compared to non-targeting shRNAs in GSCs (FIG. 14).

The loss of ZEB1 expression was associated with an increase in CD133 expression in GBM patient tumors. In addition, the loss of ZEB1 led to an increase in CD133 expression in our GSCs. This encouraged us to determine whether ZEB1 loss in association with high CD133 expression would result in a worsened patient outcome. Indeed, when ZEB1 loss of expression was stratified with CD133 expression (hazard ratio 1.73, 0.95% CI, 1.28-2.34; P=0.0003) the result was shortened patient survival, suggesting that the effect of ZEB1 loss on survival was consistent with an increase in the proportion of the glioma stem cell population in the tumor.

To examine ZEB1 loss and resistance to differentiation, we compared targeting ZEB1 using shRNAs in GSCs to non-targeting shRNAs in GSCs for neurosphere size under normal GSC media conditions. There was a substantial difference in neurosphere size between targeted ZEB1 in GSCs which were larger compared to non-targeted GSCs. Non-targeting shRNAs in GSCs placed in culture conditions conducive to differentiation resulted in cell morphology changes starting with decreased expression in Nestin. Reciprocally, there was a significant increase in end terminal differentiation markers for astrocytes (GFAP), and neurons (Tuj1). Knockdown of ZEB1 in GSCs exposed to the same differentiation conditions showed little change in morphology with over 78% of infected GSCs maintaining their Nestin expression while there was little increase in GFAP or Tuj1. These findings indicate that loss of ZEB1 expression led to the maintenance of the GSC-like state and resistance to differentiation.

It is has been reported that certain stem cell factors can block differentiation, essentially conferring some resistance to differentiation. Allowing cancer stem cells to proliferate and continue tumor propagation even under differentiation conditions. To investigate if loss of ZEB1 would confer GSC resistance to differentiation, we cultured GSCs under conditions of maintaining the stem cell-like state and under differentiation conditions. Consistent with this notion, we saw a significant decrease in cell proliferation of our GSC targeted with non-targeting shRNAs under differentiation conditions however GSCs infected with ZEB1 targeted shRNAs maintained a similarly high proliferative rate in differentiation conditions (FIG. 14). Under normal stem cell media conditions both our GSCs targeted with either non-targeting or ZEB1 targeting shRNAs were similar. These data support our conclusion that decreased expression of ZEB1 enhances or at least maintains the cancer stem cell-like state even under differentiation conditions.

IFN-γ has been shown to have opposing effects to maintaining stemness including decreased neurosphere formation, decreased self-renewal and the promotion of differentiation. We wanted to determine if IFN-γ would cause induction of ZEB1, reinforcing the notion that ZEB1 activation leads to decreased stem cell activation. Exposure of GSCs to IFN-γ resulted in a significant increase in ZEB1 induction compared to untreated GSCs (FIG. 15). Strikingly, in contrast to ZEB1 knockdown of expression by targeted shRNA which resulted in increased CD133 expression, induction of ZEB1 by IFN-γ resulted in decreased CD133 expression (FIG. 15). IFN-γ also resulted in decreased secondary neurosphere formation (FIG. 15). Similarly, IFN-γ treated GSCs had decreased self-renewal capabilities compared to untreated GSCs (FIG. 15).

Through our analysis of GBMs for copy number we also looked at gene expression and found that a strong negative correlation was apparent between ZEB1 and LIF (FIG. 15), a known regulator of stem cell self-renewal in gliomas. Given that ZEB1 is also known to have repressive functions we explored a ZEB1 mediated suppression of LIF. Our attention was focused on a 2 kb region prior to the transcriptional start site of the LIF promoter. Analysis of the LIF promoter identified known ZEB1 E-box binding motifs (CAGGTG, P<0.0001 and CAGGTA, P<0.0001) within the LIF promoter region (FIG. 15). We cloned the human LIF promoter into a luciferase reporter construct and made subsequent deletion constructs, which systematically eliminated the E-box binding sites to which ZEB1 could bind (FIG. 15). We transfected our GSCs with these constructs and treated our GSCs with IFN-γ for ZEB1 induction. A suppressive effect was observed in all constructs with the exception of −109/+10 region where ZEB1 binding sites were eliminated (FIG. 15). Similarly, the deletion of the ZEB1 binding sites via the introduction of mutations in those sites also resulted in the rescue of LIF transcriptional activation (FIG. 15). A DNA pull-down of a biotinylated oligonucleotide of the ZEB1 binding site within the LIF promoter in GSCs resulted in ZEB1 binding of exogenously expressed GFP tagged ZEB1 or to endogenously expressed ZEB1 through IFN-γ treatment (FIG. 15). GSCs targeted with shRNAs against ZEB1 (shZ89 or shZ90) confirmed by immunoblot analysis (FIG. 15) resulted in increased LIF protein secretion compared to GSCs targeted with non-targeting shRNA (shSC-1) as measured by ELISA (FIG. 15, bottom) in normal stem cell media.

We previously demonstrated that CD133 expressing GSCs exhibit chemoresistance compared to their differentiated daughter cells. We sought to determine if ZEB1 loss affected chemoresistance given that ZEB1 loss increased CD133. We stratified patients with ZEB1 loss to either high or low expression of MGMT (a DNA repair enzyme that can reverse the effects of a DNA alkylating agent) and found that ZEB1 deletion even in the presence of low MGMT expression, and therefore chemosensitive, in the presence of temozolomide treatment had a shorter patient survival (hazard ratio 1.56, 0.95% CI, 1.01-2.38; P=0.046) than patients with low MGMT and wildtype ZEB1. Patients with ZEB1 deletions in addition to high MGMT also had a shorter survival than those patients with wildtype ZEB1 and high MGMT (hazard ratio 1.59, 0.95% CI, 1.08-2.27; P=0.018). Consistent with our findings among GBM patients, temozolomide exposure to GSCs resulted in increased LIF expression coincident with decreased ZEB1 expression. This raises the provocative and worrisome possibility that temozolomide treatment may lead to the enrichment of GSCs while killing a portion of tumor cells.

Our analyses investigated the significance of ZEB1 copy number, loss of heterozygosity (LOH) and the association of these with response to therapy and survival in patients with GBM. These findings have the potential of impacting medical practice by demonstrating a novel gene deletion and loss of heterozygosity that impacts chemoresistance to temozolomide, the only approved systemic chemotherapy for newly diagnosed glioblastoma. ZEB1 deletion and expression can be used to prognosticate glioblastoma patients with greater accuracy. These findings enable the actionable testing of therapies that increase intratumoral IFN-γ release, not only for immunologic ends but also to increase tumor differentiation and inhibit self-renewal. The likely decision to tend toward a more cancer stem cell-like phenotype rests on ZEB1 not binding the LIF promoter As IFN-γ activates ZEB1, which in turn suppresses LIF expression, ZEB1 expression can be queried as a surrogate for therapies that invoke tumor differentiation. We and others have reported ZEB1's role in the activation of GSC invasion. It is not surprising given the dual nature of ZEB1 to be both activator and repressor that the presence and absence of ZEB1 affects divergent GSC functions. Others have reported that ZEB1 expression increases GSC stemness as evidenced by CD133 expression and chemoresistance. These divergent data would suggest that sample size and genetic evaluation dramatically affects the analysis of the role of ZEB1 in patient outcome and stemness. We have addressed this by analyzing several datasets of significant patient numbers. Finally, the downregulation of ZEB1 by temozolomide raises the disconcerting potential of chemotherapeutics, which when not killing cancer cells, may engender greater tumor virulence and chemoresistance, not only by proportionally reducing the daughter cell population but by expanding the cancer stem cell compartment.

Example 2

ZEB1 and PTEN Deletion in Glioblastomas

There have been several genes linked to the development and/or progression of glioblastomas, notably, NFKB1A (Bredel et al., 2011), NF1 (Reilly et al., 2000), EGFR (Mellinghoff et al., 2005) and PTEN (Unnisa et al., 1999). We attempted to determine if there were any associations between ZEB1 and any of these important genes in glioblastoma development (FIG. 10A). We focused our attention on PTEN. Consistent with published data (Smith et al., 2001) our analysis showed PTEN deletion was associated with poor patient outcome (FIG. 11C). In the context of PTEN deletion and wildtype, we identified a positive correlation between ZEB1 deletion and PTEN deletion (FIG. 10B, 95% CI=−0.587 to −0.270). Stratifying patients in cohort A indicated that ZEB1 deletion in the context of PTEN wildtype (FIG. 10C) gave a statistically significant worse patient outcome (hazard ratio 0.631, 0.95% CI=0.39 to 1.00, p=0.0016). Interestingly, cohort B (hazard ratio 0.853, 0.95% CI=0.58 to 1.25, p=0.31) was not statistically significant (FIG. 10D) and in both cases there were very few ZEB1 deleted and PTEN wildtype patients, and in at least one other dataset analyzed no ZEB1 deleted with PTEN wildtype patients could be found.

In accordance with the invention, the use of ZEB1 deletion and PTEN deletion increases the accuracy in terms of the subgroups of good prognosis patients and poor prognosis patients. The use of the two markers together increases the degree of accuracy in defining the prognosis group for a brain tumor patient. Also, this has a bearing on combination therapies. For instance, for a brain tumor patient with both ZEB1 and PTEN deletions or mutants, one may select a combination of drugs that affect PI3 kinase pathway such as rapamycin and drugs that affect cancer stem cell self-renewal pathways including but not limited to AVASTIN, agents that inhibit the sonic hedgehog pathway, the WNT pathway, etc.; inhibitors of BMX including BMX-IN-1 (Liu et al., 2013 ACS Chemical Biology); and inhibitors of IDH1 and IDH2 including AGI-5198.

Example 3

Glioblastoma multiforme (GBM) originates from within the central nervous system and is characterized by chemotherapeutic resistance (1-Bao) and recurrence with poor patient prognosis and survival. Glioma stem cells (GSCs), a subset of cells within GBM appear to be responsible for the propagation of the tumor and conferring characteristics that ultimately result in patient mortality. However, the specific mechanisms by which GSCs confer these characteristics are not well understood. The major impediment to elucidating the genes responsible for GBM pathology is identifying the genes that are associated with the cancer stem cell component of the cancer. The protracted maintenance of GSCs due to self-renewal within GBMs even though a small population, allows for the isolation and whole genomic analysis of GSCs as a means of identifying candidate genes involved in not only the cancer stem cell process, but importantly, in conferring the characteristics that make GBMs difficult to treat. Utilizing retrospective datasets comprising of microarray and comparative genomic hybridization (aCGH) arrays, and our own, Sanger sequencing and whole genome copy number analysis, we have described a link between a specific glioma stem cell regulatory gene, ZEB1, and its effects on differentiation, patient prognosis and survival. We have adopted this approach here to test our belief that GSC genes could be identified by way of concordant (FIG. 20A) and comprehensive genomic analysis that impacts GBM patient survival (FIG. 16A). We identified the RET gene being consistently deleted in GBM patients. RET is a tyrosine kinase receptor that is part of the glial cell-derived neurotrophic factor (GDNF) receptor family complex that binds the ligands GDNF, artemin (ARTN), neurturin (NRTN) and persephin.

RET binds these ligands along with GDNF receptor alpha proteins that lead to RET receptor activation and the initiation of cell signaling pathways including mitogen-activated protein kinase (MAPK), c-Jun N-terminal kinase, p38MAPK and phospholipase-C-gamma pathways. To validate gene deletion of the RET receptor we used fluorescence in situ hybridization (FISH) to analyze tissue microarrays (TMA) containing more than 75 GBMs. Using a human RET-specific probe prepared from a BAC clone with BAC end sequencing and the RET gene itself, we scored FISH results manually, this method has been shown to be clinically robust. Focal deletions affected the chromosomal region 10q11.2 containing the RET gene. FISH analysis of 40 independent specimens validated the deletion of RET in GBMs (n=X, X %, FIG. 16B). An analysis of RET gene dosage and expression (n=86), indicated significantly lower RET mRNA expression (p<0.0080**) in tumors in which RET was deleted compared to those with intact copies of RET (FIG. 16C). Analysis using aCGH profiles showing representative 10 primary GBM specimens further identified the chromosomal region containing the RET gene as a region of deletion or loss (FIG. 16D). RET deletion was further identified through GISTIC-(Genomic Identification of Significant Targets in Cancer) analysis as a driver gene (FIG. 16E), and its significance was analyzed and confirmed by well characterized proto-oncogenes and tumor suppressor genes. Significantly amplified chromosomal regions were 7p(EGFR), 8q(MYC) whereas significantly deleted chromosomal regions were 10p(PTEN), 10p(ZEB1), 10q (RET) (FIG. 16E). The Catalogue of Somatic Mutations (COSMIC), obtained in March 2014, further validated RET deletion (441/636, 69.4%) in GBM patient samples. These results are similar to our findings regarding the ZEB1 gene in glioblastoma and there was a strong positive correlation between ZEB1 and RET (FIG. 20B)

An analysis of copy number from TCGA revealed previously reported genes with significant copy number changes in GBM, such as EGFR, CCNE1, MET, CDKN2A and PTEN. In addition, novel copy number aberrations were detected in the RET gene, which was significantly mutated in over 75% (421/561) of GBM patients. Analysis of GBM patients from Cedars-Sinai Medical Center for copy number also revealed decreased copy number at the RET locus. The gene for MET receptor also appeared prominently in our analysis and had some mutually exclusivity to RET. We classified GBM patients as having ≤−0.3 copy number ratio as a requirement of gene deletion. All other tissues or genomic regions under this value were considered normal.

Due to the frequency of the RET mutation and others we believed that looking globally at several datasets (i.e., TCGA, COSMIC and ICGC) may highlight the frequency of alterations of specific genes (FIG. 17B). Several of the mutations including hallmark genes of GBM such as EGFR, PTEN and MYC occurred in at least two of the three datasets. This was also the case for RET and ZEB1 (FIG. 17B). To delve deeper into genomic alterations in GBM cancer, we examined GBM patient DNA using whole-exome sequencing and Sanger sequencing. The RET gene harbored several silent mutations and one notable non-synonymous mutation determined by whole exome sequencing that occurred in the kinase domain of the RET receptor (R982C, FIG. 17C). We also discovered mutations in ligands of the RET receptor (2 mutations out of 4), notably in the regulatory region of the PSPN ligand (A133T).

The finding that the RET receptor was in part mutually exclusive to the MET receptor suggested to us that there may be an interaction and a regulatory mechanism in GBM between the RET and MET receptor.

The RET receptor has been associated with differentiation and the MET receptor has been associated with cancer stem cell tumorigenicity in glioblastomas, thus, we considered the possibility that glioblastoma stem cells within GBMs would require a low or deleted RET receptor and a highly expressed or amplified MET receptor. Gene expression profiles of GBM patients were analyzed using principal component analysis and indicated a separation between high MET expression and low RET expression in GBM patient samples. Unsupervised microarray analysis for RET and MET expression revealed two distinct clusters of high and low MET and RET expression respectively. We further performed non-negative matrix factorization, and hierarchical clustering and again determined both subgroups. Tissue microarrays and whole genome copy number analysis confirmed RET loss in GBM patients and MET overexpression and activation. Further, we could not detect the RET receptor in the majority of our patient derived glioblastoma stem cells (FIG. 18A). However, we did see MET expression in the majority of our GSCs (FIG. 18B). We decided to test the notion that the RET receptor if present may negatively regulate the MET receptor via protein-protein interaction. The MET receptor interacted with the RET receptor in an in vitro HIS pull-down experiment, HIS-RET but not HIS alone resulted in pull-down in purified MET. Surface Plasmon Resonance (SPR) analysis confirmed a RET and MET receptor interaction. Differentiation markers were induced with introduction of a wildtype RET construct into GBM patient derived MET receptor containing GSCs that are RET deficient. In contrast, we made a mutant RET construct that mimicked the RET kinase inactivating mutation we detected by exome sequencing (mutant RET R982C) and transfected this into RET deficient GSCs and found that RET (R982C) along with RET deficient GSCs were resistant to differentiation compared to RET wildtype GSCs containing the MET receptor. Gene expression sets of stratified GBM patients with high MET expression with low RET expression compared to GBM patients with low MET expression and high RET expression revealed that differentiation genes were found to be in GBM patients with low MET and high RET expression. We evaluated patient survival with respect to RET copy number loss and MET copy number amplification from GBM patient samples and found that patients with RET deletion had shorter survival compared to RET wildtype GBM patients (FIG. 19 P=0.0032). GBM patients with MET amplification similarly had shorter survival compared to MET wildtype GBM patients (FIG. 19 P=0.0470).

These findings demonstrate a novel receptor-receptor interaction impacts cancer stem cell regulation. Similar to our previous work with ZEB1 whole genome copy number analysis along with focused gene mutational analysis and gene expression analysis clearly identify further targets of cancer stem cell regulation that have a significant effect on patient survival. Copy number loss of the RET receptor particularly in the context of MET receptor amplification can be used to prognosticate glioblastoma patients with greater accuracy. These findings indicate that RET regulation of MET can have a positive effect on driving cancer stem cell containing glioblastomas to a more favorable prognosis with the activation of differentiation pathways. The potential for actionable therapies that not only target MET but also activate the RET receptor differentiation pathways may indicate positive patient outcome.

Example 4

Effectiveness of ZEB1 as a Prognostic Indicator Alone, with IDH1, and with Respect to Adjuvant Chemotherapy (A Meta-Analysis)

To uncover brain cancer stem cell regulatory genes that affect glioma patient outcome and response to therapeutic agents, we identified ZEB1 as a brain cancer stem cell regulatory gene and investigated its effects and its impact as compared to other known genes that impact patient outcome. We determined the utility of ZEB1 as a prognostic indicator of patient survival in glioblastomas and low grade gliomas. We retrospectively identified patients with ZEB1 deletions or decreased ZEB1 expression in both low grade gliomas and glioblastomas from TCGA, cBioportal, COS- MIC, and GEO databases for studies published or deposited between 2006 and 2016. Additionally, we confirmed by whole genome sequencing, exome sequencing and expression analysis using glioblastoma samples ZEB1 loss of expression or deletion. We showed feasibility of using ZEB1 status in prognostication and treatment decision making. Deletion of ZEB1 was associated with decreased patient survival in both low grade gliomas (log rank P<0.0001 and glioblastomas (P=0.0009). For patients with glioblastoma, ZEB1 deleted patients demonstrated resistance to temozolomide chemotherapy and decreased patient survival regardless of their MGMT status: low MGMT in 115 glioblastoma patients (log rank P=0.046) and high MGMT in 121 glioblastoma patients (log rank P=0.018). When ZEB1 deleted patients were treated with bevacizumab, there was an increase in survival as compared to ZEB1 wt patients in which no change in survival was note. (log rank P=0.023 vs. log rank p=0.0523). Decision curve analysis confirmed ZEB1 status with IDH1 was more beneficial to clinical decision making than conventional information such as age, tumor grade and histology. Taken together, we demonstrated that ZEB1 deletion is associated with chemotherapy resistance and decreased survival in glioblastoma and low grade gliomas.

Glioblastoma is the most common and most aggressive form of primary brain cancer. However even with advances in stereotactic surgical resection, radiation therapy and chemotherapeutics, patients diagnosed with a glioblastoma have a median survival of 14.6. In contrast lower grade gliomas (WHO classified as grade II and grade III) have a longer patient survival but ultimately progress to secondary high grade gliomas. Treatment efforts has been confounded due to the variation in the complex nature of obtaining actionable information. Although histologic classification has been part and parcel to the classification of gliomas and the subsequent treatment, the variation that accompanies histologic classification (due to intraobserver and interobserver variability) does not satisfactorily predict clinical outcomes. Next generation sequencing has led to the identification of genes that acquire somatic mutations such as IDH1, TERT and TP53 which contribute to low grade gliomas and gene mutations have been previously identified for glioblastomas such as PTEN and NF1. Already genetic classification is more readily being incorporated into clinical decision making. To gain a more comprehensive understanding of how molecular markers can capture a more accurate picture in the assessment of patient prognosis, glioma classification and subsequent clinical decision making for therapy we performed multi-dimensional analysis from over 2900 brain cancer genomes consisting of both glioblastomas and low grade gliomas for copy number analysis, and over 1,000 gliomas for mRNA expression analysis. We further analyzed genomic alterations and performed our own whole copy number genome and exome sequencing analysis of glioblastoma patients for alterations and applied these data to the clinical data to arrive at survival outcomes. Here we demonstrated that ZEB1 can be used to prognosticate glioblastoma and low grade glioma patients with greater accuracy. In addition, ZEB1 Deletion may be evaluated with other gene mutations of gliomas to further aid prognostication and treatment decision making.

Search and Selection Criteria

Over 2500 samples consisting of primary glioblastomas and low grade gliomas were compiled and investigated. The original institution and the subsequent reference data obtained are indicated in Table 1.

With the exception of one of The Cancer Genome Atlas (TCGA) data sets containing 87 patients (this information can be found at the Cancer Genome Atlas (TCGA) Data Portal by National Cancer Institute and National Human Genome Research Institute (https://tcga-data.nci.nih.gov/tcga/)). Copy number, mutation, loss of heterozygosity and gene expression analysis and all clinical data were collected from datasets, TCGA, cBioportal, Gene Expression Omnibus (GEO), Nexus Biodiscovery and Cedars-Sinai Medical Center.

Three reviewers accessed databases and datasets and all data was screened independently by each reviewer. Specifically, one reviewer screened cBioportal, GEO and Nexus Biodiscovery; another reviewer screened TCGA and GEO; and the third reviewer screened TCGA and Nexus Biodiscovery. To be eligible, datasets had to meet the following criteria: grades II,III and IV gliomas, with either ZEB1 expression or ZEB1 copy number data and/or IDH1, TERT, CD133 and MGMT copy number or expression or mutation data, neoadjuvant therapy using either Temozolomide or bevacizumab, MGMT expression status, IDH1 status and/or TERT status, Patient Age and histology. Due to the narrow focus of the patient population we were able to find and we incorporated a few manuscripts that also provided data in the supplemental sections. We included cohorts whether prospectively or retrospectively defined and studies that pooled datasets, manuscripts and patient data from Cedars-Sinai Medical Center. All data was consolidated by two reviewers. Discrepancies in cohorts, datasets or selection criteria were resolved by discussion between the two reviewers until an agreement was reached.

Data Extraction

Data extraction consisted of collecting information regarding the (1) tumor grade, (2) histology, (3) genes and/or expression or copy number or mutation information, (4) treatment, and (5) outcomes such as survival. Survival included survival rates ranging from 1 year to beyond 8 year survivals, which were reported in the datasets or derived from the survival curves. Gene expression was dichotomized at the median to determine high and low expression of mRNA. Copy number was determined either by previous analysis that was deposited in TCGA or Nexus biodiscovery, or by looking at the raw copy number data and using the algorithm CGARS.

Hazard Rates for OS

Studies reported OS results by ZEB1 status and permutations of ZEB1/IDH1 status via (1) Kaplan-Meier curves, (2) hazard ratios (HRs) and corresponding 95% confidence intervals, (3) c-statistic. We translated all reports of survival outcomes to the number of events and the survival time. Patients not experiencing event were censored at the last follow-up date.

Statistical Methods

Data are presented as frequency (percentage, %) for categorical variables and median (IQR, interquartile range) for continuous variables. ZEB1 and IDH1 mRNA values were log base 2 transformed. Univariate associations between variables were examined with Wilcoxon rank-sum test, chi-square test, or Spearman rank correlation, where appropriate. A Cox proportional hazards regression model was employed in univariate and multivariable analyses to identify variables that predict OS. The proportional hazards assumption was evaluated with Schoenfeld residuals and a Kolmogorov-type supremum test. Hazard ratios (HRs) were expressed as an increase from the 25th to 75th percentile in continuous variables. Multivariable analysis was further carried out with the Cox proportional hazards model to examine whether an improvement in predictive discriminatory power was obtained when ZEB1 was added to the model containing the known marker, IDH1 and age. The models with and without ZEB1 were compared in terms of the bias-corrected c-statistic, corrected for possible overfitting using the bootstrap method with 1000 replicates. All analyses were done using SAS 9.3 (SAS Institute, Inc., Cary, N.C.) and R package version 3.2.2 (The R Foundation for Statistical Computing) with a significant level of 0.05.

Study Selection

In total 13 study sets containing over 4500 patients of both glioblastomas and low grade gliomas were accessed. An initial set of 240 patients with differing histological type and grade where copy number status of ZEB1 was identified in our initial search (Table 4). Studies that were excluded were mainly due to lack of copy number information for ZEB1, lack of grade, age or histological tumor type, chemotherapeutic agent or MGMT, IDH1 or TERT data. Two study sets were taken from supplemental data from published manuscripts. Following examination of the study sets and given the nature of the portals and databases, specifically using TCGA data, duplicates TCGA samples were removed from analysis.

TABLE 4

Descriptive statistics

| Variable | N = 240 |
|---|---|
| ZEB1 | |
| CN Deletion | 42 (17.5) |
| Wildtype | 198 (82.5) |
| Histologic type | |
| Astrocytoma | 77 (32.08) |
| Oligoastrocytoma | 59 (24.58) |
| Oligodendrogliomas | 104 (43.33) |
| Grade | |
| II | 120 (50) |
| III | 120 (50) |
| Histological type and grade | |
| Astrocytoma Grade II | 24 (10) |
| Astrocytoma Grade III | 53 (22.08) |
| Oligoastrocytoma Grade II | 34 (14.17) |
| Oligoastrocytoma Grade III | 25 (10.42) |
| Oligodendrogliomas Grade II | 62 (25.83) |
| Oligodendrogliomas Grade III | 42 (17.5) |

TABLE 4-continued

Descriptive statistics

| Variable | N = 240 |
|---|---|
| Median (IQR) | 12.29 (11.8-12.71) |
| Missing | 0 |
| Age at diagnosis | |
| Median (IQR) | 41 (33-54.5) |
| Missing | 0 |
| Data are presented as number of patients (%) or median (IQR, interquartile range). | |
| ZEB1 | |
| CN Deletion | 15 (4.36) |
| Wildtype | 327 (95.06) |
| Missing | 77 |
| Age at diagnosis | |
| Median (IQR) | 56.96 (14.66) |
| Median | 58 (10-89) |
| High Copy Gain | 2 (0.58) |

Study Characteristics

The study percentages that indicated the mean age of the patients was 61.5% ($8/13$); grade 4 glioblastoma made up the bulk of the study sets 85% ($11/13$). In addition, there were several datasets that had both primary and recurrent glioblastomas 38.4% ($5/13$). Not all glioblastoma patients were treated with the same treatment regimens, some were on radiation only or radiation and temozolomide or further adjuvant treatment with bevacizumab. Only 1 study focused on bevacizumab treatment as the main treatment option. 15.3% of the studies ($2/13$) had MGMT data. 2 studies were used in the stratification of CD133 and ZEB1 expression (15.3%).

ZEB1 and Patient Survival

To evaluate the significance of ZEB1 decreased expression we compared the overall survival of low grade glioma patients with ZEB1 low expression to ZEB1 high expression patients. This resulted in significantly poor patient outcome (***$P<0.0001$). This study consisted of 249 low grade glioma patients with ZEB1 expression data dichotomized at the median (FIG. 23A). Similarly, glioblastoma patients with ZEB1 low expression had a worse outcome (*$P=0.005$) than ZEB1 high expressing glioblastoma patients (FIG. 23B). Consistent with this data, we observed that ZEB1 copy number loss in both low grade gliomas (*$P<0.0001$) and glioblastomas (*$P=0.0009$, FIGS. 24A-24B) resulted in shorter patient survival. To further validate our survival plots univariate and multivariate analysis was used this time accounting for covariates (age, grade and histology) and indicated an improvement in the predictive accuracy of patient outcome with an improvement in the concordance index (c-index) of 0.028 demonstrating that ZEB1 copy number was still a significant predictor of overall survival (Table 5).

TABLE 5

Univariate and multivariable OS analyses with ZEB1 CN

| | | | | Multivariable | | | |
|---|---|---|---|---|---|---|---|
| | | Univariate | | Model 1 | | Model 2 | |
| Variable | N | Hazard Radio (95% CI) | HR P-value | Hazard Ratio (95% CI) | HR P-value | Hazard Ratio (95% CI) | HR P-value |
| Age at diagnosis | 240 | 1.08 (1.05-1.10) | <.001 | 1.08 (1.05-1.10) | <.001 | 1.07 (1.04-110) | <.001 |
| Histologic type | | | 0.008* | | 0.065* | | 0.153* |

TABLE 5-continued

Univariate and multivariable OS analyses with ZEB1 CN

| | | | | | | | |
|---|---|---|---|---|---|---|---|
| Astrocytoma | 77 | 2.63 (1.37-5.02) | 0.003 | 1.87 (0.97-3.61) | 0.062 | 1.75 (0.88-3.47) | 0.110 |
| Oligoastrocytoma | 59 | 1.17 (0.49-2.75) | 0.725 | 0.82 (0.34-1.96) | 0.648 | 0.89 (0.37-2.14) | 0.791 |
| Oligodendrogliomas | 104 | 1 | | 1 | | 1 | |
| Grade | | | | | | | |
| II | 120 | 0.29 (0.16-0.56) | <.001 | 0.33 (0.16-0.66) | 0.022 | 0.44 (0.22-0.90) | 0.024 |
| III | 120 | 1 | | 1 | | 1 | |
| ZEB1 | | | | | | | |
| CN Deletion | 42 | 6.05 (3.33-11.00) | <.001 | | | 3.37 (1.69-6.71) | <.001 |
| Wildtype | 198 | 1 | | | | 1 | |
| Optimism-corrected c-statistic | | | | 0.825 (0.725, 0.926) | | 0.843 (0.743, 0.944) | |
| Change in optimism-corrected c-statistic (95% Ci); p-value | | | | | | 0.017 (−0.006, 0.041); 0.150 | |

| | Multivariable | | | | Multivariable | | | |
|---|---|---|---|---|---|---|---|---|
| | Model 3 | | Model 4 | | Model 5 | | Model 6 | |
| Variable | Hazard Ratio (95% CI) | HR P-value | Hazard Ratio (95% CI) | HR P-Value | Hazard Ratio (95% CI) | HR P-value | Hazard Ratio (95% CI) | HR P-value |
| Age at diagnosis | 1.08 (1.05-1.10) | <.001 | 1.07 (1.04-1.10) | <.001 | 1.07 (1.05-1.10) | <.001 | 1.07 (1.04-1.10) | <.001 |
| Histologic type | | | | | | | | |
| Astrocytoma | | | | | | | | |
| Oligoastrocytoma | | | | | | | | |
| Oligodendrogliomas | | | | | | | | |
| Grade | | | | | | | | |
| II | | | | | 0.30 (0.16-0.59) | <.001 | 0.41 (0.21-0.80) | 0.009 |
| III | | | | | 1 | | 1 | |
| ZEB1 | | | | | | | | |
| CN Deletion | | | 4.55 (2.40-8.63) | <.001 | | | 3.52 (1.81-6.82) | <.001 |
| Wildtype | | | 1 | | | | 1 | |
| Optimism-corrected c-statistic | 0.813 (0.713, 0914) | | 0.841 (0.741, 0.941) | | 0827 (0.727, 0.928) | | 0.844 (0.744, 0.945) | |
| Change in optimism-corrected c-statistic (95% Ci); p-value | | | 0.028 (−0.006, 0.062); 0.102 | | | | 0.017 (−0.008, 0.042); 0.178 | |

*Overall p-value
240 observations were used in multivariable models.
Models 1 and 2 include all variables of interest; Model 3 includes age only; Model 4 includes age only; Model 4 includes age and ZEB1; Model 5 includes all variables but ZEB1 significant in the model 6; Model 6 includes variables significant in the final multivariable model.

ZEB1 Versus IDH1

In order to determine the true consequence of ZEB1 deletion on patients in low grade gliomas and glioblastomas we analyzed ZEB1 deletion alone and in conjunction with the status of IDH1, the standard molecular marker in defining patient low grade glioma prognosis. Univariate analysis indicated that ZEB1 indicated a hazard ratio exceeding that of IDH1 in both low grade gliomas and glioblastomas (Table 6). To further compare IDH1 and ZEB1 accounting for histologic classification, age and tumor grade, we classified lower-grade gliomas and glioblastomas into four categories: low grade gliomas with IDH1 mutation and ZEB1 wildtype, IDH1 wildtype and ZEB1 wildtype, IDH1 mutation and ZEB1 deletion and IDH1 wildtype and ZEB1 deletion. We found a strong association between IDH1 and ZEB1 (Table 6).

TABLE 6

Univariate OS analysis

| Variable | N | Hazard Ratio (95% CI) | HR P-value | Type3 P-value |
|---|---|---|---|---|
| Grade II or III | | | | |
| ZEB1 | | | | |
| CN Deletion | 63 | 7.20 (4.24-12.24) | <.001 | <.001 |
| Wildtype | 271 | 1 | | |

TABLE 6-continued

Univariate OS analysis

| Variable | N | Hazard Ratio (95% CI) | HR P-value | Type3 P-value |
|---|---|---|---|---|
| IDH | | | | |
| Wildtype | 69 | 6.54 (3.87-11.05) | <.001 | <.001 |
| Mutation | 265 | 1 | | |
| IDH/ZEB1 | | | | |
| IDHmut-ZEB1wt | 257 | 0.07 (0.04-0.13) | <.001 | <.001 |
| IDHwt-ZEB1wt | 14 | 0.16 (0.05-0.48) | 0.001 | |
| IDHmut-ZEB1del | 8 | 0.18 (0.06-0.57) | 0.004 | |
| IDHwt-ZEB1del | 55 | 1 | | |
| Histologic type | | | | |
| Astrocytoma | 112 | 1.62 (0.82-3.22) | 0.166 | 0.073 |
| Oligodendrogliomas | 135 | 0.86 (0.43-1.74) | 0.677 | |
| Oligoastrocytomoas | 87 | 1 | | |
| Grade | | | | |
| II | 153 | 0.32 (0.18-0.56) | <.001 | <.001 |
| III | 181 | 1 | | |

TABLE 6-continued

| | | | HR | Type3 |
|---|---|---|---|---|
| Variable | N | Hazard Ratio (95% CI) | P-value | P-value |
| Histological type and grade | | | | |
| Astrocytoma Grade II | 32 | 0.40 (0.11-1.39) | 0.150 | 0.001 |
| Astrocytoma Grade III | 80 | 1.88 (0.96-3.67) | 0.066 | |
| Oligoastrocytoma, Grade II | 46 | 0.37 (0.11-1.29) | 0.117 | |
| Oligoastrocytoma, Grade III | 41 | 1.36 (0.59-3.16) | 0.475 | |
| Oligodendrogliomas, Grade II | 75 | 0.49 (0.22-1.10) | 0.085 | |
| Oligodendrogliomas, Grade III | 60 | 1 | | |
| Age at diagnosis | 334 | 1.07 (1.05-1.10) | <.001 | <.001 |
| Grade IV | | | | |
| ZEB1 | | | | |
| CN Deletion | 249 | 1.74 (1.22-2.50) | 0.003 | 0.003 |
| Wildtype | 48 | 1 | | |
| IDH | | | | |
| Wildtype | 270 | 2.25 (1.40-3.62) | <.001 | <.001 |
| Mutation | 27 | 1 | | |
| IDH/ZEB1 | | | | |
| IDHmut-ZEB1wt | 19 | 0.36 (0.20-0.65) | <.001 | 0.004 |
| IDHwt-ZEB1wt | 29 | 0.77 (0.50-1.17) | 0.218 | |
| IDHmut-ZEB1del | 8 | 0.63 (0.30-1.34) | 0.233 | |
| IDHwt-ZEB1del | 241 | 1 | | |
| Age at diagnosis | 297 | 1.03 (1.02-1.04) | <.001 | <.001 |

The IDH1/ZEB1 group had strong associations with histologic type, grade and age. With histologic type, patients with IDH1 mutation and that are ZEB1wildtype were more likely to have oligodendrogliomas than those patients with IDH1wildtype with ZEB1 deletions (p<0.001). Patients with IDH1wildtype and ZEB1wildtype were less likely to have oligodendrogliomas than those with IDH1 mutation and ZEB1 deletion (p<0.001) but more likely to have oligodendrogliomas than those with IDH1 wildtype and ZEB1 deletion (p=0.013). With tumor grade, patients with IDH1wildtype with ZEB1 deletions were more likely to have grade III tumors than patients with IDH1 mutation with ZEB1 wildtype (P<0.001 With age, patients with IDH1wildtype with ZEB1 deletions were more likely older than patients who had IDH1 mutation with ZEB1 wildtype (P<0.001, Table 7).

TABLE 7

Univariate association of IDH/ZEB1 group with covariates

| | IDH/ZEB1 | | | | |
|---|---|---|---|---|---|
| Variable | IDH1mut-ZEB1wt (N = 174) | IDH1wt-ZEBwt (N = 24) | IDH1mut-ZEB1del (N = 5) | IDH1wt-ZEB1del (N = 37) | P-value* |
| Histologic type | | | | | |
| Astrocytoma | 46 (26.44) | 6 (25) | 1 (20) | 24 (64.86) | <.001 |
| Oligoastrocytoma | 48 (27.59) | 3 (12.5) | 0 (0) | 8 (21.62) | |
| Oligodendrogilomas | 80 (45.98) | 15 (62.5) | 4 (80) | 5 (13.51) | |
| Grade | | | | | |
| II | 102 (58.62) | 12 (50) | 2 (40) | 4 (10.81) | <.001 |
| III | 72 (41.38) | 12 (50) | 3 (60) | 33 (89.19) | |
| Histological type and grade | | | | | |
| Astrocytoma Grade II | 19 (10.92) | 5 (20.83) | 0 (0) | 0 (0) | <.001 |
| Astrocytoma Grade III | 27 (15.52) | 1 (4.17) | 1 (20) | 24 (64.86) | |
| Oligoastrocytoma Grade II | 31 (17.82) | 1 (4.17) | 0 (0) | 2 (5.41) | |
| Oligoastrocytoma Grade III | 17 (9.77) | 2 (8.33) | 0 (0) | 6 (16.22) | |
| Oligodendrogliomas Grade II | 52 (29.89) | 6 (25) | 2 (40) | 2 (5.41) | |
| Oligodendrogilomas Grade III | 28 (16.09) | 9 (37.5) | 2 (40) | 3 (8.11) | |
| Age at diagnosis | 39 (33-54.5) | 34 (33-54.5) | 38 (33-54.5) | 58 (33-54.5) | <.001 |

Data are presented as number of patients (%) or median (IQR, interquartile range).

*P-value is calculated by Kruskal-Wallis test for age; and chi-square test or Fisher's exact test for categorical covariates, where appropriate.

IDH1/ZEB1 group remained a significant predictor of OS after adjusting for age, histologic type, and grade and after adjusting for age only. By adding IDH/ZEB1 group I to the model with age, histologic type, and grade or model with age only, and this was true for both lower grade gliomas and glioblastomas (Table 8A and Table 8B).

chemosensitivity resulting in favorable prognosis compared to the hypomethylated state of MGMT which results in poor patient outcomes.

MGMT expression is inversely correlated to its methylated state. We sought to determine the effect of ZEB1 deletion on the clinical impact of hypermethylation of

TABLE 8A

Pairwise comparisons between IDH/ZEB1 group on univariate and multivariable OS analyses in LGG patients

| | | Univariate | | Multivariable | | | | | |
|---|---|---|---|---|---|---|---|---|---|
| | | | | Adjusted for age | | Adjusted for age and grade | | Adjusted for age, grade, and histologic type | |
| Variable 1 | Variable 2 | Hazard Ratio (95% CI) | HR P-value | Hazard Ratio (95% CI) | HR P-value | Hazard Ratio (95% CI) | HR P-value | Hazard Ratio (95% CI) | HR P-value |
| IDH1mut-ZEB1wt | IDH1wt-ZEB1wt | 0.43 (0.16-1.16) | 0.094 | 0.38 (0.14-1.01) | 0.052 | 0.42 (0.15-1.16) | 0.096 | 0.48 (0.17-1.38) | 0.174 |
| | IDH1mut-ZEB1del | 0.39 (0.13-1.12) | 0.08 | 0.39 (0.13-1.11) | 0.078 | 0.50 (0.17-1.49) | 0.216 | 0.49 (0.16-1.48) | 0.208 |
| | IDH1wt-ZEB1del | 0.07 (0.04-0.13) | <.001 | 0.11 (0.05-0.21) | <.001 | 0.13 (0.06-0.27) | <.001 | 0.15 (0.07-0.31) | <.001 |
| IDH1wt-ZEB1wt | IDH1mut-ZEB1del | 0.89 (0.24-3.35) | 0.868 | 1.02 (0.27-3.84) | 0.974 | 1.19 (0.31-4.51) | 0.801 | 1.02 (0.26-4.01) | 0.979 |
| | IDH1wt-ZEB1del | 0.16 (0.05-0.48) | 0.001 | 0.28 (0.09-0.85) | 0.024 | 0.31 (0.10-0.97) | 0.044 | 0.31 (0.10-0.96) | 0.042 |
| IDH1mut-Zeb1del | IDH1wt-ZEB1del | 0.18 (0.06-0.57) | 0.004 | 0.28 (0.09-0.88) | 0.03 | 0.26 (0.08-0.85) | 0.026 | 0.30 (0.09-0.99) | 0.049 |

TABLE 8B

Pairwise comparisons between IDH/ZEB1 group on univariate and multivariable OS analyses in GBM patients

| | | Univariate | | Multivariable Adjusted for age | |
|---|---|---|---|---|---|
| Variable 1 | Variable 2 | Hazard Ratio (95% CI) | HR P-value | Hazard Ratio (95% CI) | HR P-value |
| IDH1mut-ZEB1wt | IDH1wt-ZEB1wt | 0.47 (0.23-0.93) | 0.03 | 0.55 (0.27-1.10) | 0.091 |
| | IDH1mut-ZEB1del | 0.57 (0.22-1.45) | 0.234 | 0.62 (0.24-1.59) | 0.321 |
| | IDH1wt-ZEB1del | 0.36 (0.20-0.65) | <.001 | 0.52 (0.28-0.97) | 0.039 |
| IDH1wt-ZEB1wt | IDH1mut-ZEB1del | 1.21 (0.52-2.82) | 0.65 | 1.13 (0.49-2.63) | 0.772 |
| | IDH1wt-ZEB1del | 0.77 (0.50-1.17) | 0.218 | 0.95 (0.62-1.46) | 0.813 |
| IDH1mut-Zeb1del | IDH1wt-ZEB1del | 0.63 (0.30-1.34) | 0.233 | 0.84 (0.39-1.80) | 0.652 |

Although patients with IDH1 wildtype and ZEB1 deletion was associated with shortened patient survival and appears to be a robust prognostic indicator, conversely, we find that patients with IDH1 mutations with ZEB1 wildtype predicts longer patient survival. This observation was true for both low grade gliomas (FIG. 25A) and glioblastomas (FIG. 25B).

We have been able to show the prognostic benefits of ZEB1 alone and in conjunction with IDH1 for predicting patient outcome. However, although this data is useful we wanted to determine if there were further benefits that could gleaned from ZEB1 dysfunction with respect to chemotherapy and chemotherapeutic resistance. We previously demonstrated that CD133 expressing GSCs exhibit chemoresistance to therapeutics used in GBM as compared to their differentiated daughter cells.

Given our observations that ZEB1 attenuation and CD133 expression imparts GSC resistance to differentiation and impacts patient survival, we asked whether ZEB1 loss would impact response to therapy. To do this, we explored the role of O6-methylguanine-DNA methyltransferase (MGMT) which repairs mutagenic lesions caused by DNA alkylating agents and therefore hinders the effectiveness of chemotherapeutic alkylating agents including temozolomide.

The MGMT promoter region has been shown when hypermethylated to suppress MGMT activity conferring MGMT in the presence of temozolomide. We stratified patients with these characteristics and found that ZEB1 deletion even in the presence of low MGMT expression, and therefore favorable chemosensitivity, in the presence of temozolomide treatment (n=115) had a shorter patient survival (HR, 1.56; 0.95% CI, 1.01-2.38; P=0.046) than patients with low MGMT and wildtype ZEB1 (FIG. 26A). Furthermore, patients with ZEB1 deletions in addition to high MGMT (n=121) (FIG. 26B) also had a shorter survival than those patients with wildtype ZEB1 and high MGMT (HR, 1.59; 0.95% CI, 1.08-2.27; P=0.018).

To further explore the role of ZEB1 loss and therapy response, we compared 403 glioblastoma, patients treated with bevacizumab versus patients not treated with bevacizumab. We found that bevacizumab therapy did little to alter patient survival in the general patient population (P=0.06) consistent with what has been shown in two randomized phase III trials.

Figures 4C, 4D:
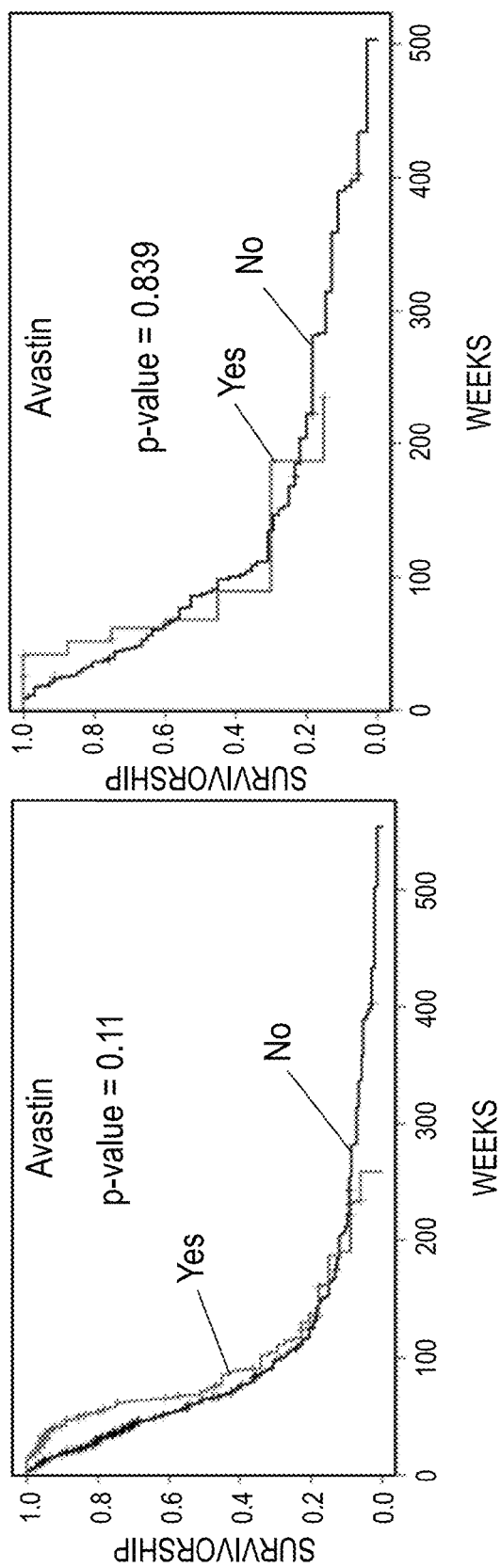
Figure 4F:
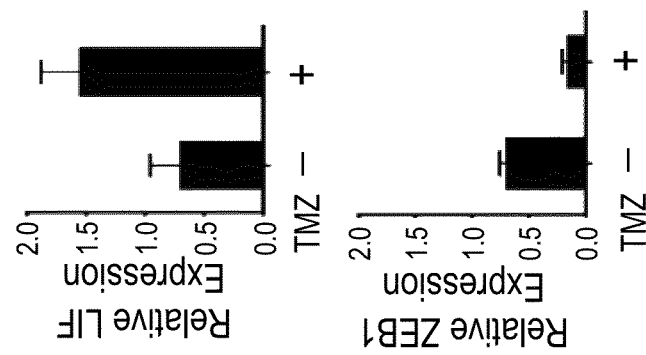
Figure 4E:
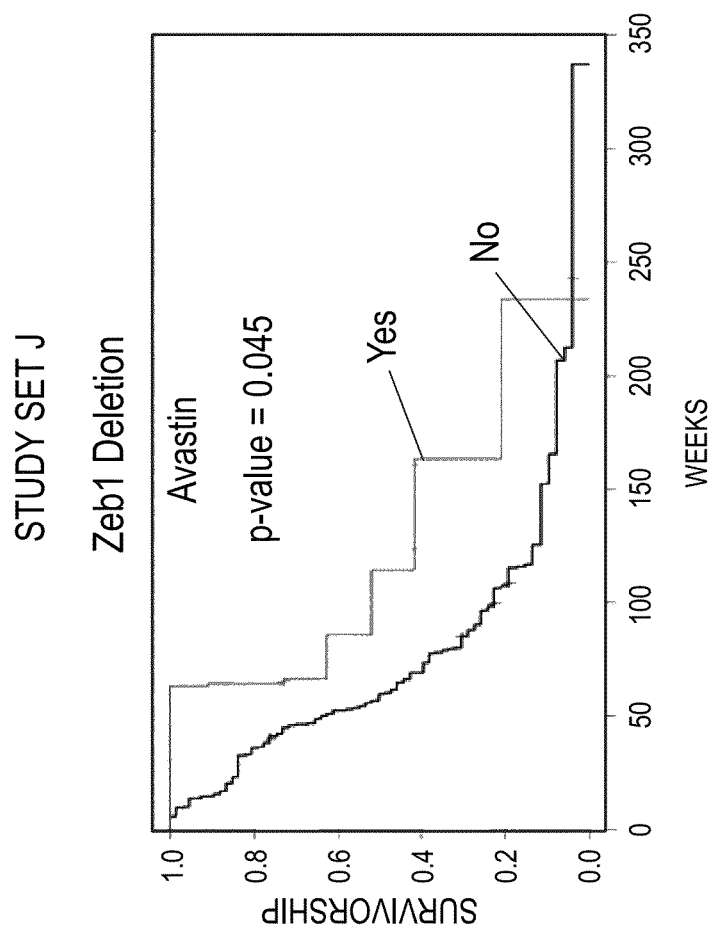

The ZEB1 high expressing patients showed no effect from bevacizumab on survival (FIG. 26C, HR 1.14, 0.95% CI, 0.76-1.74; P=0.523). However, ZEB1 low expressing patients demonstrated a statistically significant improvement with a greater survival benefit when treated with bevacizumab as compared to those patients in the study set who did not receive bevacizumab (FIG. 26D, HR 1.65, 0.95% CI, 1.07-2.27; P=0.023). Similarly, looking at ZEB1 wildtype and ZEB1 deleted GBM patients in an independent data set of 78 GBM patients we found that bevacizumab therapy did little to alter patient survival in the general patient population (P=0.11). ZEB1 intact patients showed no effect from bevacizumab on survival (FIG. 4D, P=0.839). However, ZEB1 deleted patients demonstrated a statistically significant improvement in survival when treated with bevacizumab as compared to those patients in the study set who did not receive bevacizumab (FIG. 4E, HR, 0.4 0.95% CI, 0.22-0.98; P=0.045). ZEB1 deleted patients treated with bevacizumab did not have a significant difference in survival as compared to ZEB1 wildtype patients treated with bevacizumab in this small group of patients (P=0.74).

The risk to harm ratio is an important concept when deciding whether to give treatment or not. The accuracy of such risk to harm predictions can be achieved using decision curve analysis (DCA). In low grade gliomas (grade II and III) we wanted to determine if the molecular markers IDH1 in conjunction with ZEB1 would be beneficial in determining the risk/harm ratio to these patients. Unlike other types of risk prediction attempts, DCA takes into account the clinical implications associated with the prediction. The goal here is to identify high risk low grade glioma patients by efficiently maximizing the benefit and decreasing the potential harm, where harm is defined as the percentage of false positives relative to the benefit defined as true positives which in DCA produces a value measure that can aid the clinician in determining over a threshold to either treat a patient or not treat a patient. The conventional methods of assessing a patient such as age, histology and tumor grade are compared to combining these factors with IDH1 and ZEB1 molecular markers to determine if greater predictive accuracy can be achieved FIGS. 27A-27C).

When we analyzed the DCA for how this predictive risk/harm may affect the decision to treat low grade glioma patients. We looked at DCA in the context of using Procarbazine, CCNU and Vincristine (PCV) treatment. The DCA revealed to us that at a mortality rate of 50%, 8.542 fewer false-positive results per 100 low grade glioma patients occurred when including the molecular markers ZEB1 and IDH1 as compared to the null model (assuming every patient will get PCV treatment). In other words, including our proposed molecular markers will give the equivalent of 8.54% fewer cases of unnecessary PCV treatment to low grade glioma patients who would not benefit from PCV compared the null model (Table 9).

TABLE 9

Net benefit according to prediction models across a threshold of probability of death at 2-year, 50% <= Pt <= 71% in LGG patients with grade II/III

| Pt (%) | Net Benefit over Null model Assuming no one will die and so everyone will get RT + PCV | | Net Benefit for model with IDH/ZEB1 + | Advantage of model: Reduction in the number of avoiding PCV when it would be of benefit per 100 patients | | Advantage of model with IDH/ZEB1 + |
|---|---|---|---|---|---|---|
| | Prediction model with age + grade | Prediction model with IDH/ZEB1 + age + grade | age + grade over model with age + grade | Prediction model with age + grade | Prediction model with IDH/ZEB1 + age + grade | age + grade over model with age + grade |
| 50 | 0.0280 | 0.0854 | 0.057 | 2.803 | 8.542 | 5.740 |
| 51 | 0.0518 | 0.0842 | 0.032 | 4.980 | 8.093 | 3.113 |
| 52 | 0.0515 | 0.0830 | 0.032 | 4.752 | 7.661 | 2.908 |
| 53 | 0.0511 | 0.0763 | 0.025 | 4.532 | 6.767 | 2.235 |
| 54 | 0.0338 | 0.0750 | 0.041 | 2.879 | 6.387 | 3.510 |
| 55 | 0.0332 | 0.0734 | 0.040 | 2.717 | 6.002 | 3.289 |
| 56 | 0.0295 | 0.0720 | 0.043 | 2.318 | 5.659 | 3.339 |
| 57 | 0.0289 | 0.0707 | 0.042 | 2.183 | 5.335 | 3.153 |
| 58 | 0.0316 | 0.0693 | 0.038 | 2.286 | 5.021 | 2.730 |
| 59 | 0.0312 | 0.0867 | 0.056 | 2.166 | 6.024 | 3.857 |
| 60 | 0.0308 | 0.0858 | 0.055 | 2.050 | 5.719 | 3.667 |
| 61 | NA | 0.0848 | NA | NA | 5.424 | NA |
| 62 | NA | 0.0849 | NA | NA | 5.201 | NA |
| 63 | NA | 0.0839 | NA | NA | 4.928 | NA |
| 64 | NA | 0.0808 | NA | NA | 4.547 | NA |
| 65 | NA | 0.0798 | NA | NA | 4.298 | NA |
| 66 | NA | 0.0624 | NA | NA | 3.215 | NA |
| 67 | NA | 0.0610 | NA | NA | 3.006 | NA |
| 68 | NA | 0.0526 | NA | NA | 2.475 | NA |
| 69 | NA | 0.0510 | NA | NA | 2.292 | NA |
| 70 | NA | 0.0494 | NA | NA | 2.116 | NA |
| 71 | NA | 0.0477 | NA | NA | 1.947 | NA |

We have shown the utility in including the molecular marker ZEB1 in determining the prognostic value to both glioblastoma and low grade glioma patients. We have shown the benefit of ZEB1 in conjunction with IDH1 at improving the risk to harm predictions in decision curve analysis compared to the conventional models of just age, tumor and histology in low grade gliomas and how this impacts the clinical decision to treat patients with PCV. Here we have extended the use of DCA to help enhance the clinician's decision to treat a low grade glioma patient armed with the knowledge that at a 50% mortality rate in low grade gliomas there is an 8.54% false positive rate without the introduction of the molecular markers ZEB1 and IDH1. This indicates that a DCA model that includes ZEB1 and IDH1 would lower the false positive rate leading to more applicable treatment. In addition, low grade glioma patients with a mortality rate of 70% have a significantly reduced false positive rate of 1.9% when using a model incorporating ZEB1 and IDH1. Our conclusions are based molecular platforms involving microarrays and copy number analysis for both glioblastomas and low grade gliomas. Previous work has indicated that the majority of ZEB1 alterations is due to heterozygous ZEB1 deletions. Loss of ZEB1 in GBM patients impacts both a favorable patient response to temozolomide chemotherapy due to MGMT hypermethylation as well as an unfavorable response due to a lack of methylation of this gene. ZEB1 loss significantly decreases the survival of patients in both groups. This finding can improve our ability to stratify outcomes more precisely for patients. In addition, although bevacizumab has been shown to provide no survival advantage in GBM patients in two recent phase III trials, patients with ZEB1 deletion treated with bevacizumab appear to have a significant survival benefit when receiving this anti-angiogenic agent. It has been demonstrated that glioma stem cells secrete VEGF to support the vascular microenvironment which in turn supports glioma stem cell self-renewal. The role of ZEB1 loss on chemoresistance has a significant effect on survival and should be determined on patient prognostication and therapeutic development.

Example 5

ZEB1 Regulates Glioma Stemness Through LIF Repression

The identification of a stem cell regulatory gene which is aberrantly expressed in glioma and associated with patient survival would increase the understanding of the role of glioma cancer stem cells (GCSCs) in the virulence of gliomas. Interrogating the genomes of over 4000 brain cancers we identified ZEB1 deletion in ~15% (grade II and III) and 50% of glioblastomas. Meta-analysis of ZEB1 copy number status in 2,988 cases of glioma revealed disruptive ZEB1 deletions associated with decreased survival. We identified ZEB1 binding sites within the LIF (stemness factor) promoter region, and demonstrate LIF repression by ZEB1. ZEB1 knockdown in GCSCs caused LIF induction commensurate with GCSC self-renewal and inhibition of differentiation. IFN-γ treatment to GCSCs induced ZEB1 expression, attenuating LIF activities. These findings implicate ZEB1 as a stem cell regulator in glioma which when deleted leads to increased stemness, tumorigenicity and shortened patient survival.

The genetic underpinnings of how glioma cancer stem cells (GCSCs) propagate tumors and how this affects patient survival is not well understood. Identifying genes that control stem cell regulation, especially those in which mutations or a loss in copy number of these stem cell regulatory genes can support the propagation of the cancer, is fundamental to the basic understanding of brain cancer lethality. To address this question, we utilized 2,988 brain cancer genomes for copy number analysis, 339 glioma genomes for mutations indicative of loss of function and 1,007 gliomas for mRNA expression analysis. Our primary focus involved searching for genes showing enrichment for copy number loss, loss of heterozygosity (LOH) and mutations. We identified several genes which have previously been described in glioblastoma (GBM) and lower grade (WHO grade II and grade III) gliomas such as PTEN, NF1 and IDH1 and concentrated our efforts on a gene not previously implicated to have copy number loss, LOH or mutations in GBMs or low grade gliomas namely, Zinc Finger E-Box Binding Homeobox 1 gene (ZEB1). ZEB1 is an inducer of the epithelial-mesenchymal transition (EMT) in cancers and has been shown to promote cancer invasion in glioblastomas among other cancers. Most insights into its action would suggest that ZEB1 expression would be associated with a negative outcome in cancer patients based on increased tumorigenicity and stemness. We have identified ZEB1 as a stem cell regulator in brain cancer which when deleted leads to increased stemness, tumorigenicity and shortened patient survival. Although evidence of decreased ZEB1 expression and deletion does exist, studies using The Cancer Genome Atlas (TCGA) datasets have not revealed decreased expression or loss of the ZEB1 gene either by copy number or mutation, particularly not in brain cancer. In contrast, we have observed ZEB1 deletions in more than 50% of GBMs and 15% in low grade gliomas (grade II and grade III) with frequent LOH. The explanation for this discordance is that both GBMs and low grade gliomas do not demonstrate the more frequently observed and investigated homozygous or deep deletions, rather GBM patients and low grade glioma patients have heterozygous or shallow deletions of ZEB1. In addition, our analysis of glioma patients from our institution through exome sequencing revealed previously unidentified mutations. These mutations along with other recently observed mutations of ZEB1 in gliomas could account for the decreased ZEB1 expression. These findings uncover important information about stem cell regulation by ZEB1 expression, copy number level in both GBMs and low grade gliomas with implications for prognostication and treatment of gliomas.

ZEB1 Copy Number Loss and Loss of Heterozygosity

Figure 13A:
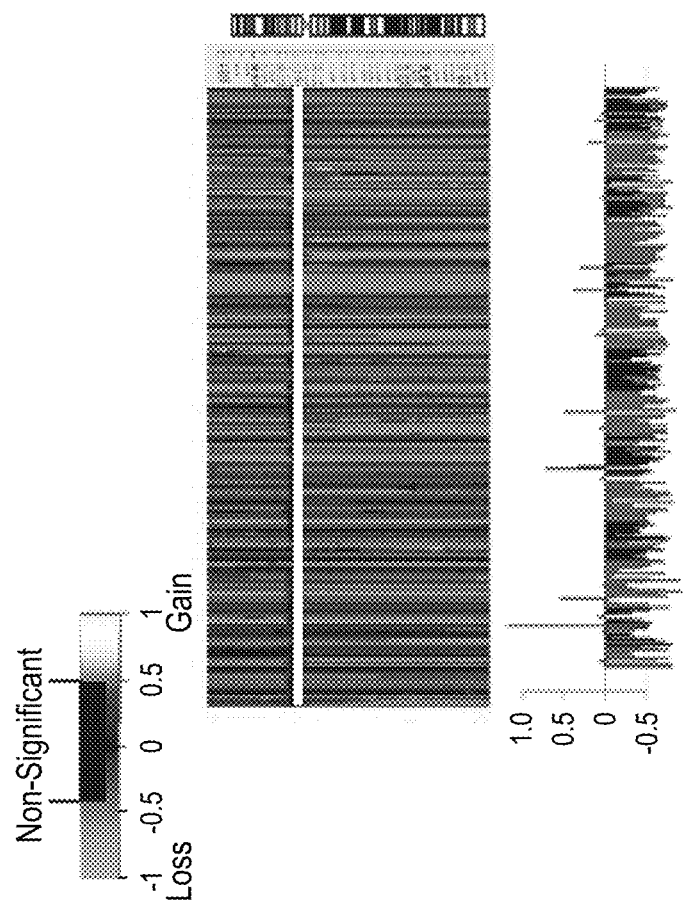
Figures 28A, 28B, 28C:
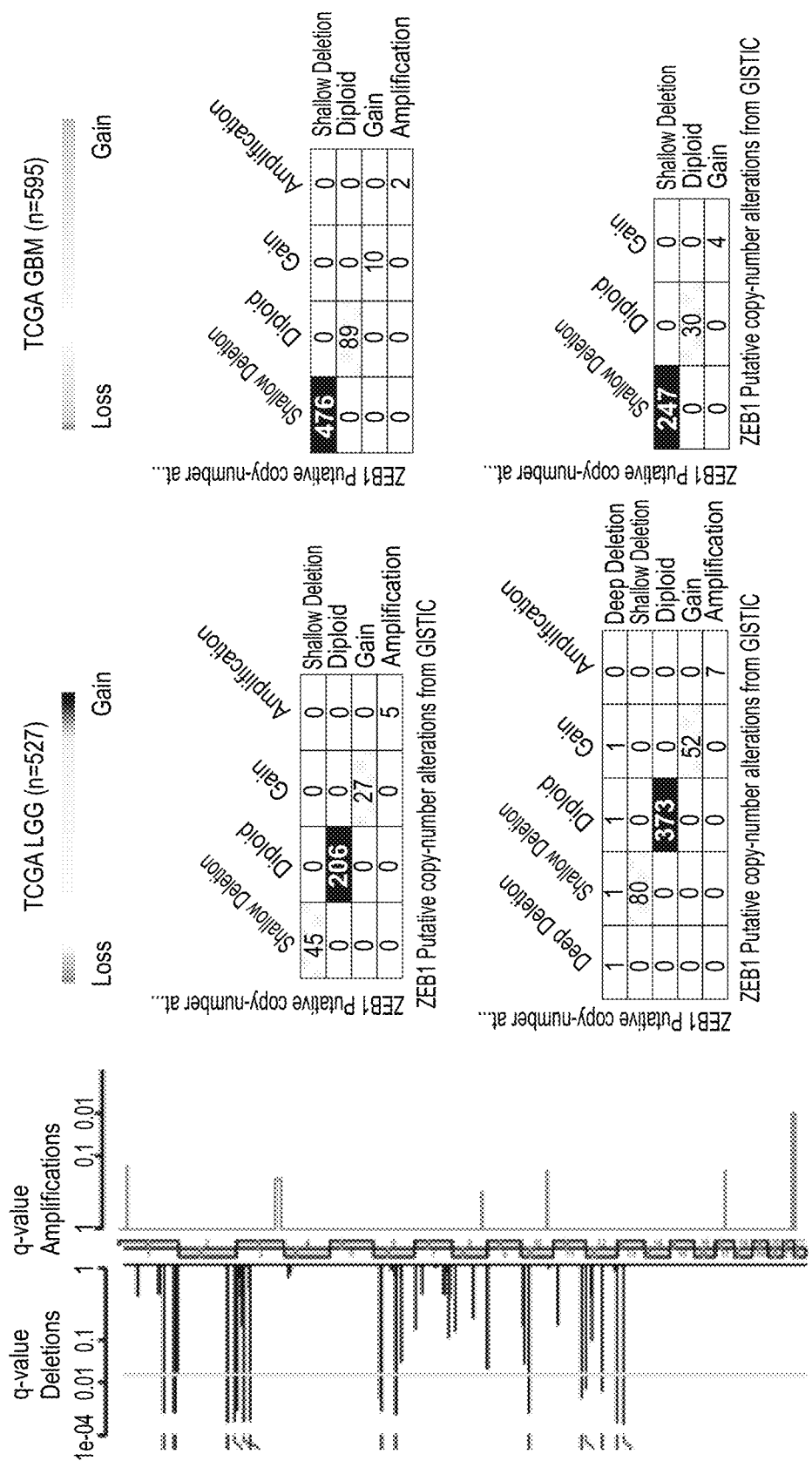

In order to investigate possible heterozygous deletions, we used the CGARS algorithm (see e.g., Lu, X., Thomas, R. K., Peifer, M. CGARS: cancer genome analysis by rank sums. Bioinformatics 30(9), 1295-1296 (2014)) which transforms raw copy number into ranks avoiding copy number base line levels. Using the CGARS algorithm, we identified significant focal copy number alterations and observed deletions affecting 10p11.22, the ZEB1 locus in lower grade gliomas (grade II and III, q-values [False discovery rate] <0.001, FIG. 28A). Similarly, cBioportal revealed in both lower grade gliomas consisting of WHO grade II and grade III gliomas (n=527) and GBMs (n=595) significant heterozygous deletions indicated as shallow deletions (FIGS. 28B-28C). In over 50% of glioma cases, we observed a deletion that included ZEB1 on chromosome 10 (FIG. 13A and Table 10).

TABLE 10

Primary and Recurrent Aggregate Copy Number gain and loss

| Gene | CN Loss % | Homozygous Copy Loss % | CN Gain % | High Copy Gain % |
|---|---|---|---|---|
| Primary | | | | |
| PTEN | 67.21 | | 1.64 | |
| NF1 | 8.2 | | 21.31 | |
| CCNE1 | 3.28 | | 49.18 | |
| CDK4 | 9.84 | | 24.59 | |
| EGFR | | | 50.82 | 1.64 |
| HYDIN | 6.56 | | 21.31 | |
| LSAMP | 8.2 | | 21.31 | |
| MDM4 | | | 31.15 | 1.64 |
| MYC | 3.28 | | 22.95 | 1.64 |

TABLE 10-continued

Primary and Recurrent Aggregate Copy Number gain and loss

| Gene | CN Loss % | Homozygous Copy Loss % | CN Gain % | High Copy Gain % |
|---|---|---|---|---|
| PDGFRA | | | 13.11 | 4.92 |
| CDKN2A | 18.03 | 40.98 | 13.11 | |
| ZEB1 | 52.46 | 8.2 | 3.28 | |
| Recurrent | | | | |
| PTEN | 61.54 | | | |
| NF1 | 3.85 | | 23.08 | |
| CCNE1 | 3.85 | | 53.85 | 3.85 |
| CDK4 | 19.23 | | 15.38 | |
| EGFR | | | 26.92 | 23.08 |
| HYDIN | 19.23 | | 11.54 | |
| LSAMP | 7.69 | | 19.23 | |
| MDM4 | | | 38.46 | |
| MYC | 7.69 | | 19.23 | 3.85 |
| PDGFRA | 7.69 | | 19.23 | |
| CDKN2A | 30.77 | 53.85 | 3.85 | |
| ZEB1 | 76.92 | | 3.85 | |

Figures 13B, 13C:
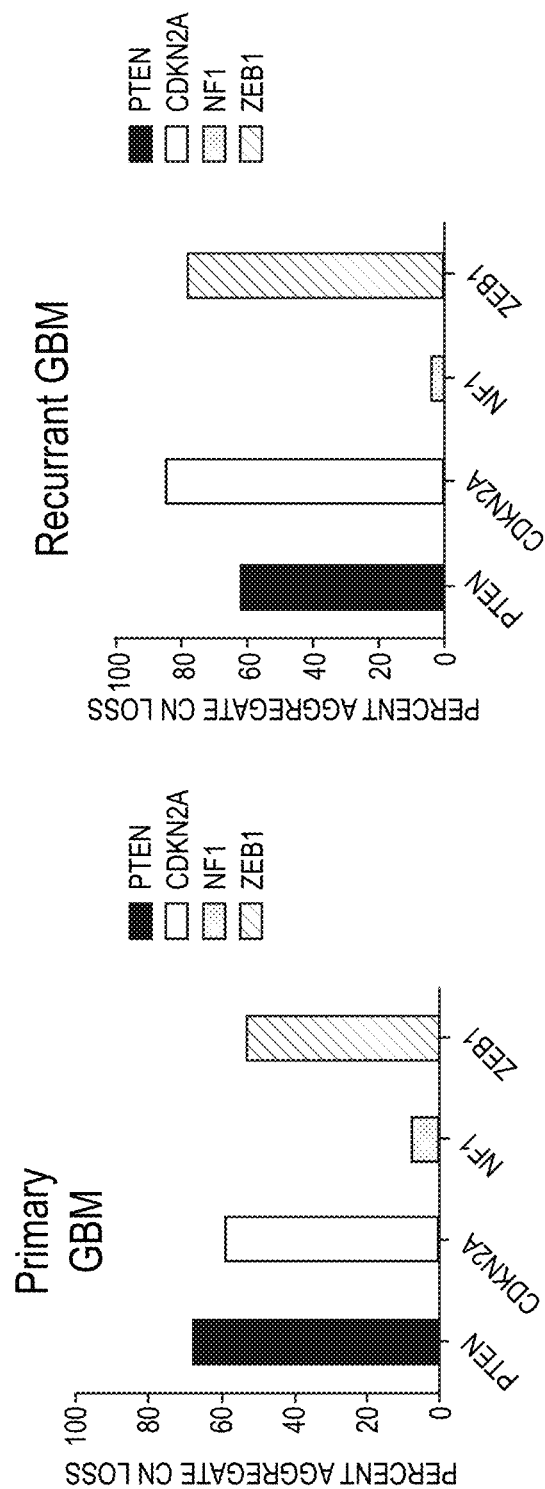
Figure 13D:
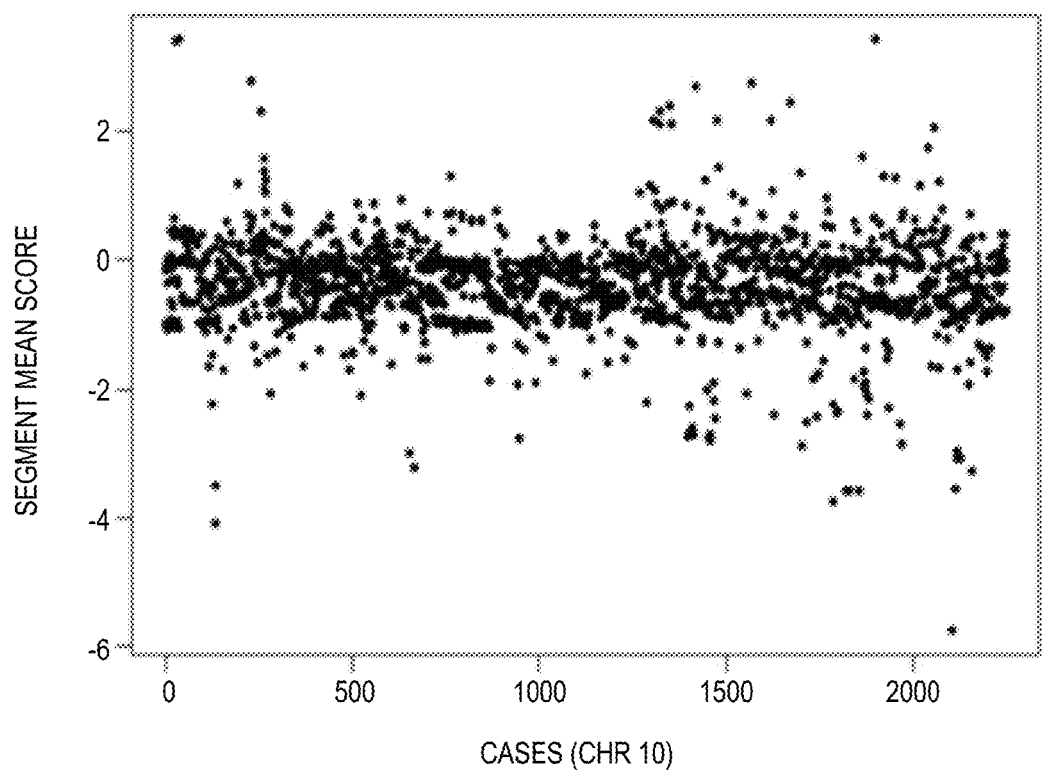
Figure 13E:
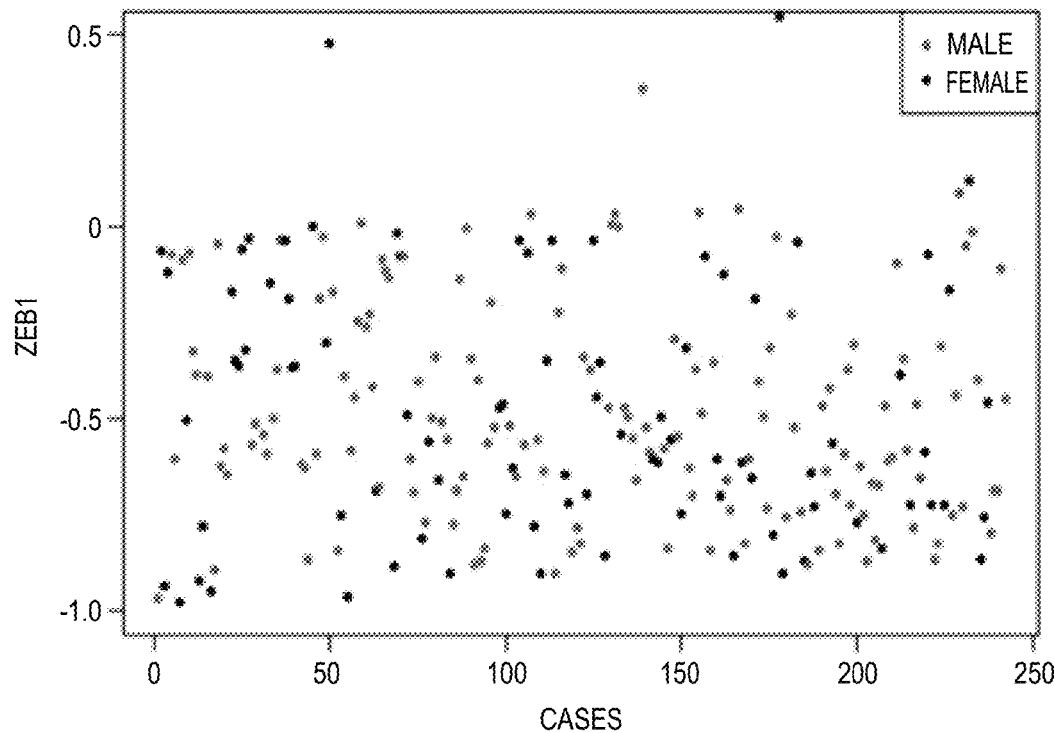
Figure 13F:
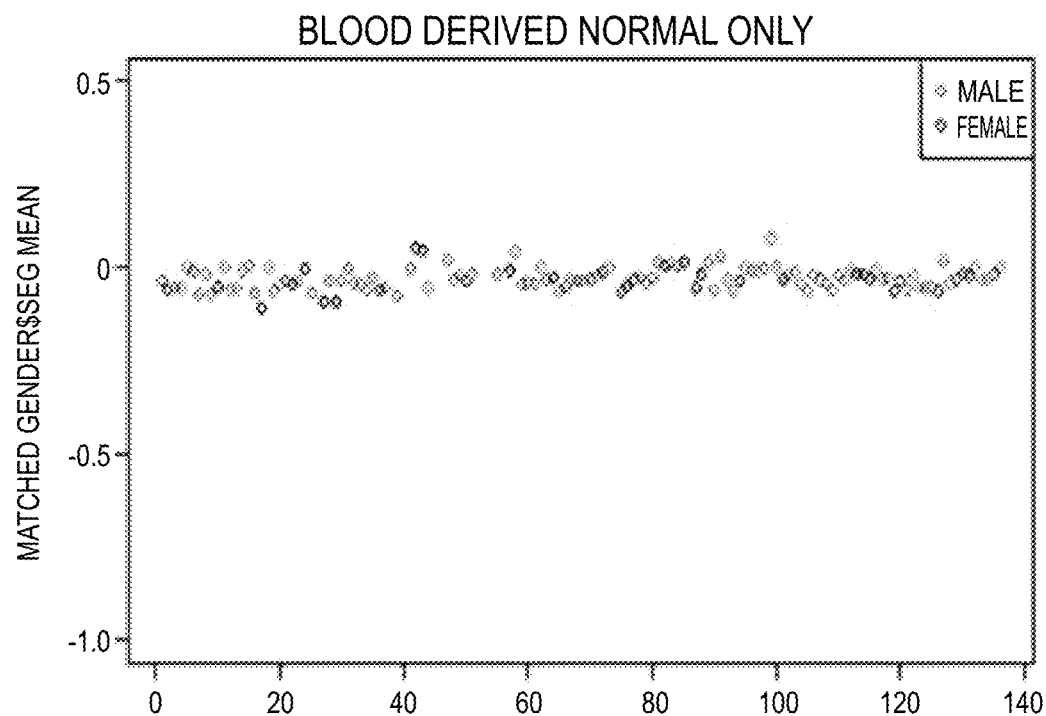
Figure 13G:
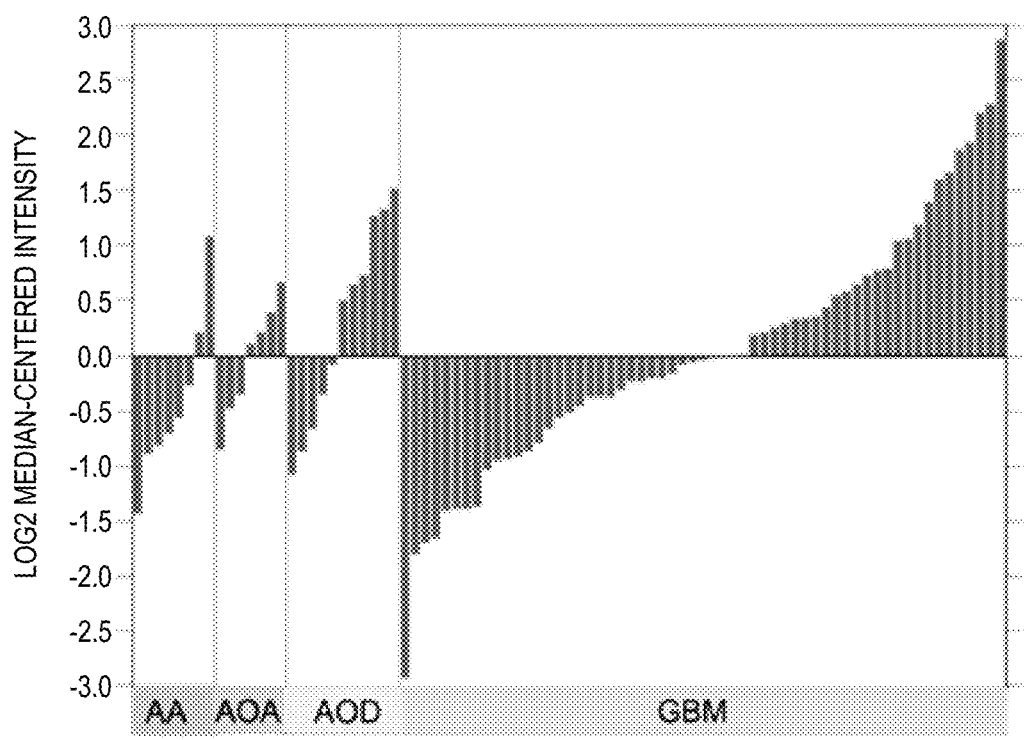

Copy number alterations in ZEB1 could be identified in both primary and recurrent (n=87) GBM patients in relation to well characterized genes determined by the TCGA GBM Analysis working group (FIGS. 13B-13C). Analysis of TCGA data for copy number along with expression data where we correlated expression and copy number data, revealed a dramatic decrease in ZEB1 expression in both GBM and low grade glioma patients (FIGS. 28D-28E, P<0.0001 and P=0.0006 respectively) or comparing the whole of chromosome 10 and the specific ZEB1 locus in glioblastoma patients (FIGS. 13D-13E, respectively) indicated significant copy number loss relative to patient blood with normal copy number (FIG. 13F) and expression across other brain cancer subtypes (FIG. 13G). Importantly, copy number loss of ZEB1 correlated with shortened patient survival in both lower grade gliomas (*P<0.0001) and GBMs (P=0.002, FIGS. 28F-28G). In addition, data from the COSMIC database (data freeze January 2014) also revealed significant copy number loss where 110 of 138 GBMs (79.7%) had copy number loss at the ZEB1 locus (Table 11).

TABLE 11

COSMIC copy number loss of ZEB1 in GBM patient tumors

| CNV_id | Gene | Study | Sample | Copy Number | Type |
|---|---|---|---|---|---|
| 322742 | ZEB1 | 329 | TCGA-06-0133-01 | 1 | loss |
| 323243 | ZEB1 | 329 | TCGA-06-0138-01 | 1 | loss |
| 323402 | ZEB1 | 329 | TCGA-06-0166-01 | 1 | loss |
| 323641 | ZEB1 | 329 | TCGA-06-0138-01 | 1 | loss |
| 323766 | ZEB1 | 329 | TCGA-06-0152-01 | 2 | loss |
| 324154 | ZEB1 | 329 | TCGA-06-0158-01 | 1 | loss |
| 324489 | ZEB1 | 329 | TCGA-06-0154-01 | 1 | loss |
| 324777 | ZEB1 | 329 | TCGA-06-0174-01 | 1 | loss |
| 325045 | ZEB1 | 329 | TCGA-06-0195-01 | 2 | loss |
| 325209 | ZEB1 | 329 | TCGA-06-0197-01 | 1 | loss |
| 325266 | ZEB1 | 329 | TCGA-06-0201-01 | 2 | loss |
| 325569 | ZEB1 | 329 | TCGA-06-0211-01 | 1 | loss |
| 325596 | ZEB1 | 329 | TCGA-06-0206-01 | 2 | loss |
| 325682 | ZEB1 | 329 | TCGA-06-0166-01 | 1 | loss |
| 325848 | ZEB1 | 329 | TCGA-06-0208-01 | 1 | loss |
| 325920 | ZEB1 | 329 | TCGA-06-0184-01 | 1 | loss |
| 326127 | ZEB1 | 329 | TCGA-06-0185-01 | 1 | loss |
| 326236 | ZEB1 | 329 | TCGA-06-0209-01 | 1 | loss |
| 326262 | ZEB1 | 329 | TCGA-06-0168-01 | 1 | loss |
| 326446 | ZEB1 | 329 | TCGA-06-0168-01 | 1 | loss |
| 326493 | ZEB1 | 329 | TCGA-06-0187-01 | 1 | loss |
| 326551 | ZEB1 | 329 | TCGA-06-0214-01 | 1 | loss |
| 326631 | ZEB1 | 329 | TCGA-06-0210-01 | 1 | loss |
| 326825 | ZEB1 | 329 | TCGA-06-0169-01 | 1 | loss |
| 326884 | ZEB1 | 329 | TCGA-06-0188-01 | 1 | loss |
| 327011 | ZEB1 | 329 | TCGA-06-0210-01 | 2 | loss |
| 327319 | ZEB1 | 329 | TCGA-06-0219-01 | 1 | loss |
| 327468 | ZEB1 | 329 | TCGA-06-0190-01 | 2 | loss |
| 327627 | ZEB1 | 329 | TCGA-06-0211-01 | 1 | loss |
| 327844 | ZEB1 | 329 | TCGA-06-0173-01 | 1 | loss |
| 328113 | ZEB1 | 329 | TCGA-06-0237-01 | 1 | loss |
| 328183 | ZEB1 | 329 | TCGA-06-0238-01 | 2 | loss |
| 328765 | ZEB1 | 329 | TCGA-06-0241-01 | 1 | loss |
| 328966 | ZEB1 | 329 | TCGA-06-0644-01 | 2 | loss |
| 329182 | ZEB1 | 329 | TCGA-06-0645-01 | 1 | loss |
| 329528 | ZEB1 | 329 | TCGA-06-0646-01 | 1 | loss |
| 329738 | ZEB1 | 329 | TCGA-06-0648-01 | 2 | loss |
| 333837 | ZEB1 | 329 | TCGA-08-0244-01 | 1 | loss |
| 334402 | ZEB1 | 329 | TCGA-08-0347-01 | 2 | loss |
| 334518 | ZEB1 | 329 | TCGA-08-0357-01 | 2 | loss |
| 334859 | ZEB1 | 329 | TCGA-08-0353-01 | 1 | loss |
| 334920 | ZEB1 | 329 | TCGA-08-0246-01 | 1 | loss |
| 335005 | ZEB1 | 329 | TCGA-08-0348-01 | 2 | loss |
| 335317 | ZEB1 | 329 | TCGA-08-0349-01 | 1 | loss |
| 335577 | ZEB1 | 329 | TCGA-08-0354-01 | 1 | loss |
| 312509 | ZEB1 | 329 | TCGA-02-0009-01 | 1 | loss |
| 312588 | ZEB1 | 329 | TCGA-02-0016-01 | 2 | loss |
| 313479 | ZEB1 | 329 | TCGA-02-0021-01 | 1 | loss |
| 314046 | ZEB1 | 329 | TCGA-02-0023-01 | 1 | loss |
| 314178 | ZEB1 | 329 | TCGA-02-0027-01 | 1 | loss |
| 314418 | ZEB1 | 329 | TCGA-02-0003-01 | 1 | loss |
| 314534 | ZEB1 | 329 | TCGA-02-0033-01 | 1 | loss |
| 314891 | ZEB1 | 329 | TCGA-02-0034-01 | 1 | loss |
| 315001 | ZEB1 | 329 | TCGA-02-0006-01 | 2 | loss |
| 315139 | ZEB1 | 329 | TCGA-02-0037-01 | 1 | loss |
| 315432 | ZEB1 | 329 | TCGA-02-0052-01 | 1 | loss |
| 315848 | ZEB1 | 329 | TCGA-02-0055-01 | 2 | loss |
| 315882 | ZEB1 | 329 | TCGA-02-0068-01 | 2 | loss |
| 315982 | ZEB1 | 329 | TCGA-02-0043-01 | 2 | loss |
| 316065 | ZEB1 | 329 | TCGA-02-0057-01 | 2 | loss |
| 316212 | ZEB1 | 329 | TCGA-02-0046-01 | 1 | loss |
| 316391 | ZEB1 | 329 | TCGA-02-0102-01 | 1 | loss |
| 316569 | ZEB1 | 329 | TCGA-02-0089-01 | 1 | loss |
| 317014 | ZEB1 | 329 | TCGA-02-0048-01 | 1 | loss |
| 317138 | ZEB1 | 329 | TCGA-02-0070-01 | 1 | loss |
| 317555 | ZEB1 | 329 | TCGA-02-0071-01 | 2 | loss |
| 317586 | ZEB1 | 329 | TCGA-02-0086-01 | 2 | loss |
| 317820 | ZEB1 | 329 | TCGA-02-0084-01 | 3 | loss |
| 317974 | ZEB1 | 329 | TCGA-02-0064-01 | 1 | loss |
| 318035 | ZEB1 | 329 | TCGA-02-0099-01 | 1 | loss |
| 318248 | ZEB1 | 329 | TCGA-02-0075-01 | 2 | loss |
| 318507 | ZEB1 | 329 | TCGA-02-0085-01 | 2 | loss |
| 318630 | ZEB1 | 329 | TCGA-06-0124-01 | 2 | loss |
| 318884 | ZEB1 | 329 | TCGA-06-0125-01 | 1 | loss |
| 319304 | ZEB1 | 329 | TCGA-06-0125-01 | 1 | loss |
| 319539 | ZEB1 | 329 | TCGA-02-0107-01 | 1 | loss |
| 319934 | ZEB1 | 329 | TCGA-02-0113-01 | 3 | loss |
| 320128 | ZEB1 | 329 | TCGA-06-0126-01 | 1 | loss |
| 320204 | ZEB1 | 329 | TCGA-06-0122-01 | 1 | loss |
| 320727 | ZEB1 | 329 | TCGA-06-0126-01 | 1 | loss |
| 320826 | ZEB1 | 329 | TCGA-06-0122-01 | 1 | loss |
| 320961 | ZEB1 | 329 | TCGA-02-0116-01 | 1 | loss |
| 321267 | ZEB1 | 329 | TCGA-06-0124-01 | 1 | loss |
| 321363 | ZEB1 | 329 | TCGA-06-0127-01 | 1 | loss |
| 321750 | ZEB1 | 329 | TCGA-02-0038-01 | 1 | loss |
| 321814 | ZEB1 | 329 | TCGA-06-0130-01 | 1 | loss |
| 321912 | ZEB1 | 329 | TCGA-06-0154-01 | 1 | loss |
| 321946 | ZEB1 | 329 | TCGA-06-0130-01 | 1 | loss |
| 322276 | ZEB1 | 329 | TCGA-06-0147-01 | 1 | loss |
| 322374 | ZEB1 | 329 | TCGA-06-0132-01 | 1 | loss |
| 322700 | ZEB1 | 329 | TCGA-06-0157-01 | 1 | loss |
| 335961 | ZEB1 | 329 | TCGA-08-0358-01 | 1 | loss |
| 336163 | ZEB1 | 329 | TCGA-08-0345-01 | 1 | loss |
| 336277 | ZEB1 | 329 | TCGA-08-0355-01 | 2 | loss |
| 336312 | ZEB1 | 329 | TCGA-08-0359-01 | 2 | loss |
| 336567 | ZEB1 | 329 | TCGA-08-0346-01 | 2 | loss |
| 336722 | ZEB1 | 329 | TCGA-08-0373-01 | 1 | loss |
| 336823 | ZEB1 | 329 | TCGA-08-0352-01 | 1 | loss |

TABLE 11-continued

COSMIC copy number loss of ZEB1 in GBM patient tumors

| CNV_id | Gene | Study | Sample | Copy Number | Type |
|---|---|---|---|---|---|
| 336857 | ZEB1 | 329 | TCGA-08-0356-01 | 1 | loss |
| 337930 | ZEB1 | 329 | TCGA-12-0615-01 | 1 | loss |
| 338322 | ZEB1 | 329 | TCGA-12-0616-01 | 1 | loss |
| 338900 | ZEB1 | 329 | TCGA-08-0386-01 | 1 | loss |
| 338949 | ZEB1 | 329 | TCGA-12-0618-01 | 2 | loss |
| 339525 | ZEB1 | 329 | TCGA-08-0389-01 | 1 | loss |
| 339587 | ZEB1 | 329 | TCGA-12-0619-01 | 2 | loss |
| 340005 | ZEB1 | 329 | TCGA-12-0620-01 | 1 | loss |
| 340342 | ZEB1 | 329 | TCGA-08-0390-01 | 1 | loss |

Taken together these data suggest that ZEB1 loss is an important prognostic indicator and is associated with unfavorable outcome for both lower grade gliomas and GBM patients.

Given the heterozygous nature of the observed copy number loss in both lower grade and GBM patients for ZEB1, we set out to determine if loss of heterozygosity (LOH) was present at the ZEB1 locus, we found that ZEB1 deletion was secondary to LOH at the ZEB1 locus. Analysis of an initial 14 GBM patients with matched normal controls at our institution identified LOH in approximately 29% of patients (FIG. 1B). We further expanded this analysis to 178 glioblastoma patients (both datasets taken from the Gene Omnibus Expression database) and found LOH in 22% of patients (FIG. 31A). We sequenced all exons of ~14 GBM patients matched for tumor and blood plasma from samples at Cedars-Sinai Medical Center. Sanger sequencing also revealed LOH at the ZEB1 locus in 21% (3/14) of samples (Table 2 and FIG. 31B). Lastly, GBM patient samples from Cedars-Sinai Medical Center were analyzed for whole genome copy number where we validated LOH at the ZEB1 locus. In addition, glioma patient derived GCSCs (0827) also revealed LOH (FIG. 31C). Collectively, we examined two independent datasets, as well as in house GBM patient samples with matching blood plasma from Cedars-Sinai Medical Center and patient derived GCSCs to validate LOH by Sanger sequencing.

Having examined four independent datasets for genome wide copy number and two datasets for LOH, and confirmed LOH in our own Cedars-Sinai Medical Center patients validated through Sanger sequencing, we wanted to determine if ZEB1 gene loss would extend to ZEB1 protein loss. To confirm ZEB1 loss at the protein level, we performed immunohistochemistry using tissue microarrays (FIG. 1C), which revealed the presence (FIG. 1C, panels 2 and 4) and absence (FIG. 1C, panels 1 and 3) of ZEB1 in grade 4 GBMs consistent with the loss of ZEB1 in certain patients and the preservation of ZEB1 in other GBM patients. Only 11% of GBMs analyzed had strong nuclear staining, with 58% of GBM patients having weak to no staining, 28% having moderate staining and 3% of GBM patients unscored due to poor quality tissue.

ZEB1 Mutations

Having identified copy number loss as a means of ZEB1 loss we turned our attention to mutations that may be affecting ZEB1 expression. To comprehensively characterize mutations that affect gliomas we enriched for ZEB1 by combining low grade glioma data, GBM patient data including previously reported ZEB1 mutations, and exome sequencing data from Cedars-Sinai Medical Center. The data analyzed consisted of an initial 203 samples representing already reported mutations in gliomas (n=7), GBMs (n=108) and low grade gliomas (n=88). Of the initial 203 samples 41 were excluded from the analysis because of insufficient quality or amount of DNA or insufficient information for analysis, these were all GBMs. Somatic single-nucleotide variants (SSNVs) were called by comparison to the NCI build 37, with a median of 19 SSNVs identified per sample (range of 3 to 877). G>A and C>T transitions made up the bulk of the mutations accounting for 61% collectively with 3% or more mutations occurring in 38% of the genes listed. The bulk of the genes were characterized by missense mutations (FIG. 29A). Although it is unclear the impact of the identified ZEB1 mutations, the degree to which ZEB1 mutations occur suggests that these mutations contribute to ZEB1 loss in both low grade gliomas and GBMs. In support of ZEB1 mutations carrying out a pro-tumorigenic function, the top 10 genes which included well known contributors to both GBMs and low grade gliomas such as IDH1, TP53, NF1 and ZEB1 were for the most part mutually exclusive and strongly associated with missense or splice site mutations (FIG. 29A).

Given the copy number loss and increased number of mutations now identified for ZEB1, this prompted us to determine if there was a relationship between ZEB1 expression that was critical to both low grade gliomas and GBM patient survival. Consistent with our observation of poor patient survival due to ZEB1 deletion (FIGS. 28D-28E); patients with low ZEB1 expression resulted in shorter patient survival in both GBMs (*P=0.002) and lower grade gliomas (***P<0.0001, FIGS. 29B-29C).

ZEB1 Loss Increases GSC Stemness

Figures 14A, 14B, 14C:
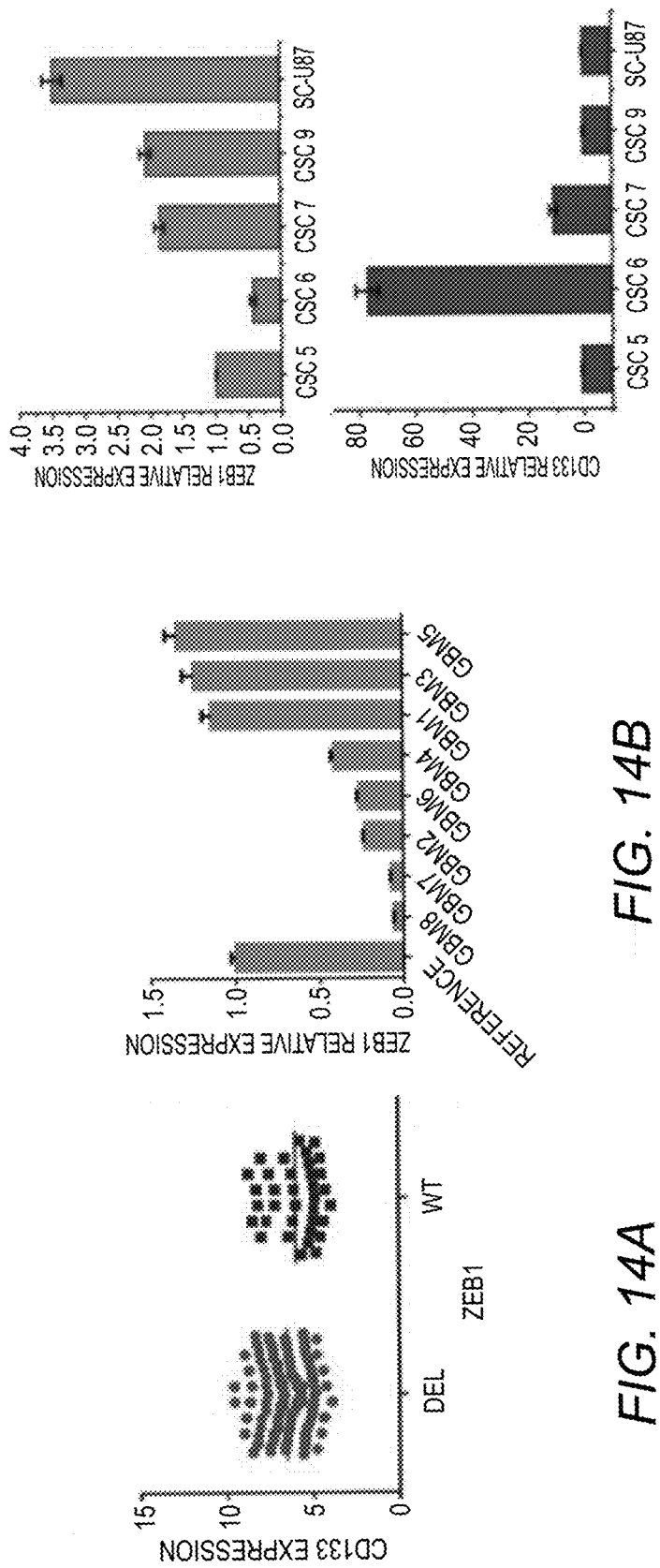
Figure 30D:
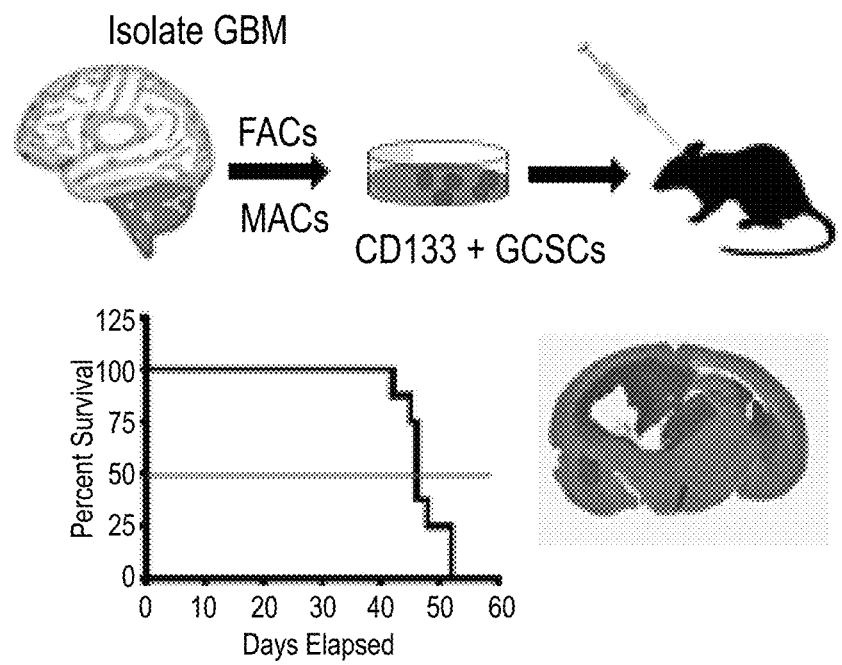
Figure 30E:
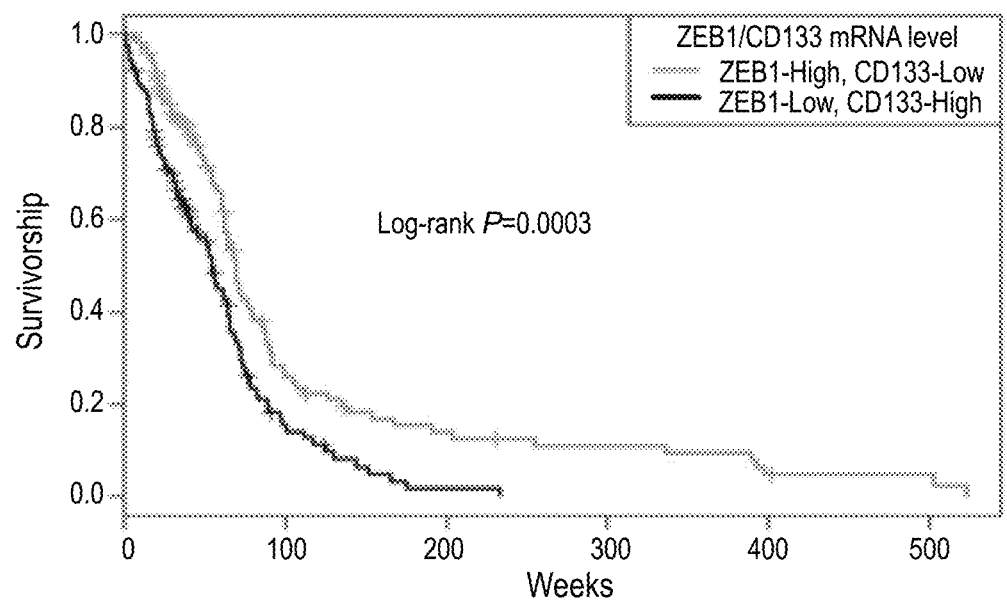
Figure 30F:
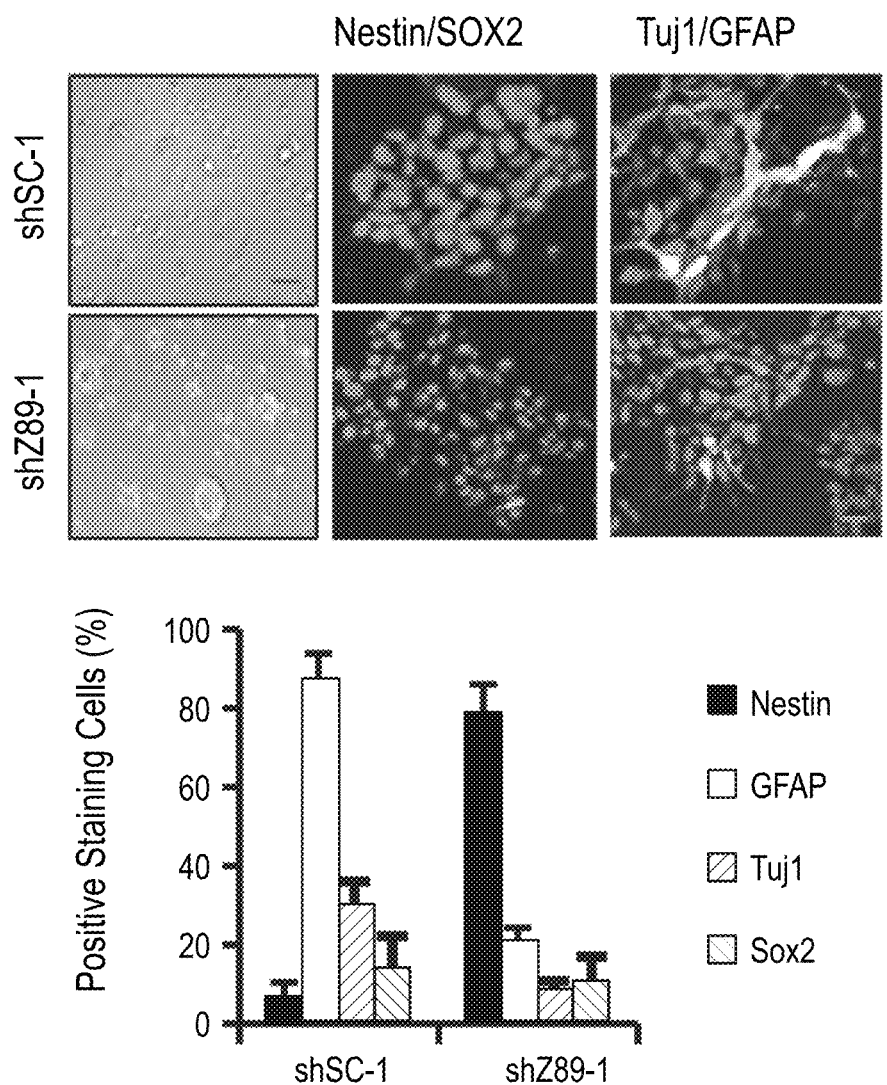

Given the deleterious effects of ZEB1 loss on patient survival, we wanted to determine if loss of ZEB1 was associated with increased stemness as the basis and link to both tumor virulence and poor patient survival. We utilized CD133, a cell surface marker used to prospectively identify and isolate glioma cancer stem cells. Examining GBM patient tumors (n=269) for copy number and gene expression data revealed that ZEB1 deleted tumors demonstrated increased CD133 expression compared to ZEB1 wildtype tumors (FIG. 14A, P=0.023). We next turned to glioma patient derived cancer stem cells (GCSCs), and undertook a series of studies to characterize their stem cell properties. GCSCs grown under stem cell conditions, select against survival of terminally differentiated cells, maintaining neurosphere fidelity (FIG. 30A, left) and GCSC marker expression (inset). Consistent with previous studies we further demonstrated that GCSCs have the potential to differentiate along neuronal and/or glial lineages (FIG. 30A, middle and right respectively). To validate our GCSCs we used magnetically activated cell sorting (MACs) to acutely isolate GCSCs into $CD133^+$ and $CD133^-$ populations and observed high expression of the reported stem cell markers OLIG2 and NOS2 in $CD133^+$ GCSC populations along with low ZEB1 expression. In contrast, $CD133^-$ GCSC populations had low levels of NOS2 and OLIG2 with high levels of ZEB1 expression (FIG. 30B). GCSC expression of CD133 (FIG. 30C, top) was eliminated when GCSCs were cultured under differentiation conditions (FIG. 30C, bottom) consistent with what has been reported. A hallmark feature of GCSCs is their tumorigenic potential. Implantation of our GCSCs in an orthotopic xenograft mouse model resulted in brain tumor formation (FIG. 30D). Primary GBMs and patient derived GCSCs revealed, that the majority expressed low levels of ZEB1 with GCSCs inversely correlating with CD133 expression as determined by RT-PCR (FIGS. 14B-14C). GCSCs were also confirmed at the protein level to have low expression of ZEB1 protein (FIG. 14D). This led us to investigate whether knockdown of ZEB1 (FIG. 14E)

would maintain or enhance stem cell properties. Suppression of ZEB1 expression using shRNAs revealed a significant increase in neurosphere size, the CD133$^+$ subpopulation (6.4% vs 25%±1.8%), and self-renewal compared to non-targeting shRNAs in GCSCs (FIGS. 14F-J).

The loss of ZEB1 expression was associated with an increase in CD133 expression in GBM patient tumors. In addition, the loss of ZEB1 led to an increase in CD133 expression in our GCSCs. This encouraged us to determine whether ZEB1 loss was associated with high CD133 expression and would result in a worsened patient outcome. Indeed, when loss of ZEB1 expression was stratified with CD133 expression (FIG. 30E, hazard ratio 1.73, 0.95% CI, 1.28-2.34; **P=0.0003) the result was shortened patient survival, suggesting that the effect of ZEB1 loss on survival was consistent with an increase in the proportion of the glioma stem cell population in the tumor.

To examine ZEB1 loss and resistance to differentiation, we compared targeting ZEB1 using shRNAs in GCSCs to non-targeting shRNAs in GCSCs. Non-targeting shRNAs in GCSCs placed in culture conditions conducive to differentiation resulted in cell morphology changes (FIG. 30F, top left) starting with decreased expression in Nestin, (FIG. 30F, top-middle and lower panel quantification). Reciprocally, there was a significant increase in end terminal differentiation markers for astrocytes (GFAP) and neurons (Tuj1) (FIG. 30F, top-right and lower panel quantification). Knockdown of ZEB1 in GCSCs exposed to the same differentiation conditions led to little change in morphology (FIG. 30F, bottom-left) with over 78% of infected GCSCs maintaining their Nestin expression (FIG. 30F, bottom-middle and lower panel quantification) while there was little increase in GFAP or Tuj1 (FIG. 30F, bottom-right and lower panel quantification). These findings indicate that loss of ZEB1 expression led to the maintenance of the GCSC-like state and resistance to differentiation.

It has been reported that certain stem cell factors can block differentiation, essentially conferring resistance to differentiation, allowing cancer stem cells to proliferate and continue tumor propagation even under differentiation conditions. To investigate if loss of ZEB1 would confer GCSC resistance to differentiation, we cultured GCSCs under conditions of maintaining the stem cell-like state and under differentiation conditions. We saw a significant decrease in cell proliferation of our GCSC targeted with non-targeting shRNAs under differentiation conditions, however, GCSCs infected with ZEB1 targeting shRNAs maintained a similarly high proliferative rate in differentiation conditions (FIG. 14K). Under normal stem cell media conditions both our GCSCs targeted with either non-targeting or ZEB1 targeting shRNAs were similar. These data support our conclusion that decreased expression of ZEB1 enhances or at least maintains the cancer stem cell-like state even under differentiation conditions.

IFN-γ Induces ZEB1 Activation

Figure 15A:
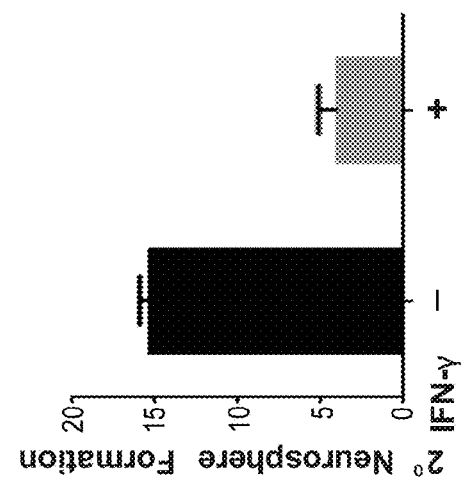
Figure 15B:
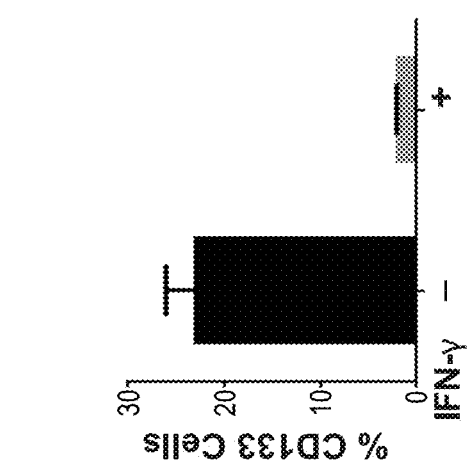
Figure 15C:
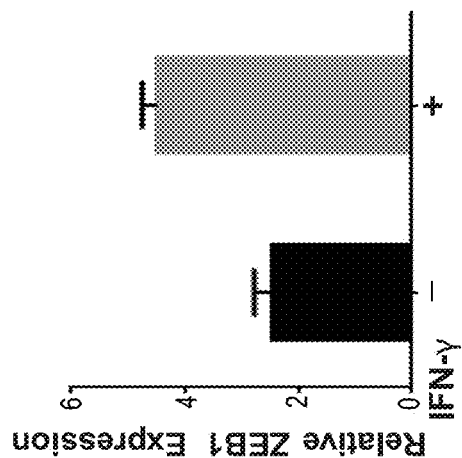
Figures 15D, 15E:
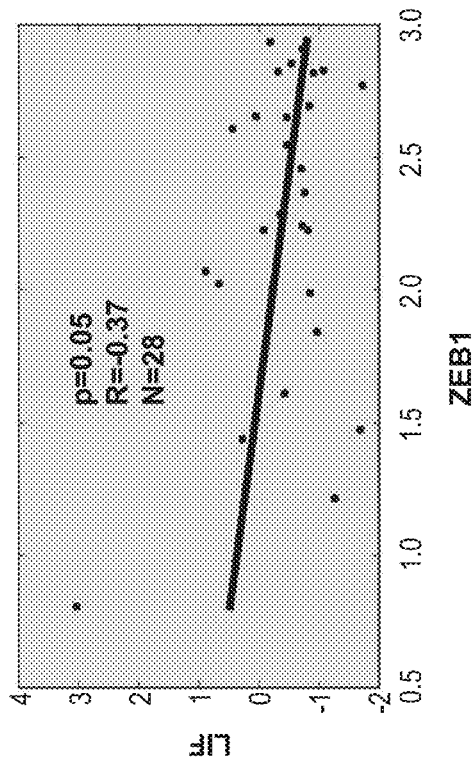

IFN-γ has been shown to have antagonistic effects on stem cell maintenance including decreased neurosphere formation, decreased self-renewal, and the promotion of differentiation. We sought to determine whether IFN-γ would cause induction of ZEB1, reinforcing the notion that ZEB1 activation leads to decreased stem cell activation. Exposure of GCSCs to IFN-γ resulted in a significant increase in ZEB1 induction compared to untreated GCSCs (FIG. 15A). Strikingly, in contrast to ZEB1 knockdown of expression by targeted shRNA which resulted in increased CD133 expression, induction of ZEB1 by IFN-γ resulted in decreased CD133 expression (FIG. 15B). IFN-γ also resulted in decreased secondary neurosphere formation (FIG. 15C). Similarly, IFN-γ treated GCSCs had decreased self-renewal capabilities compared to untreated GCSCs (FIG. 15D).

ZEB1 Represses LIF Expression in GCSCs

Figure 15G:
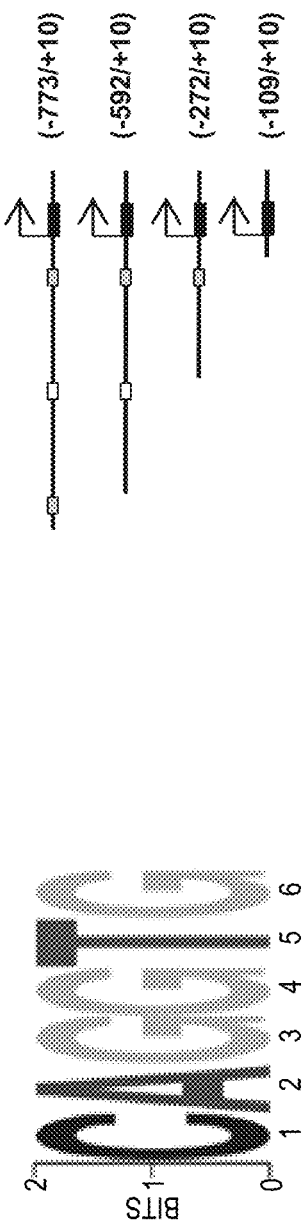
Figure 15H:
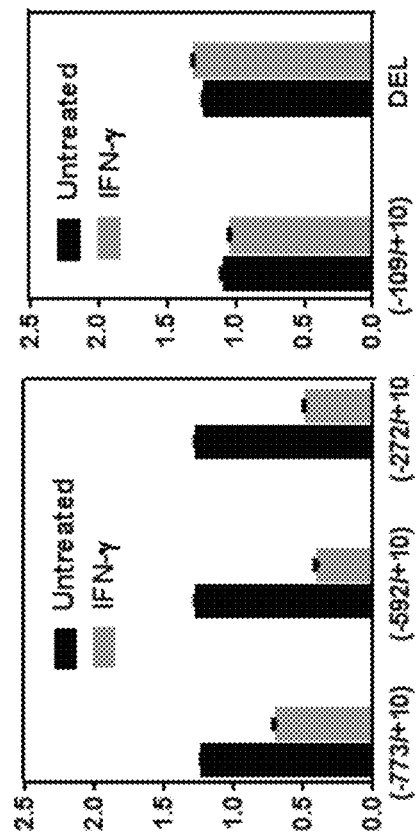
Figure 15F:
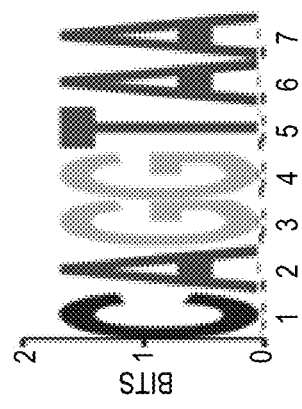
Figure 15I:
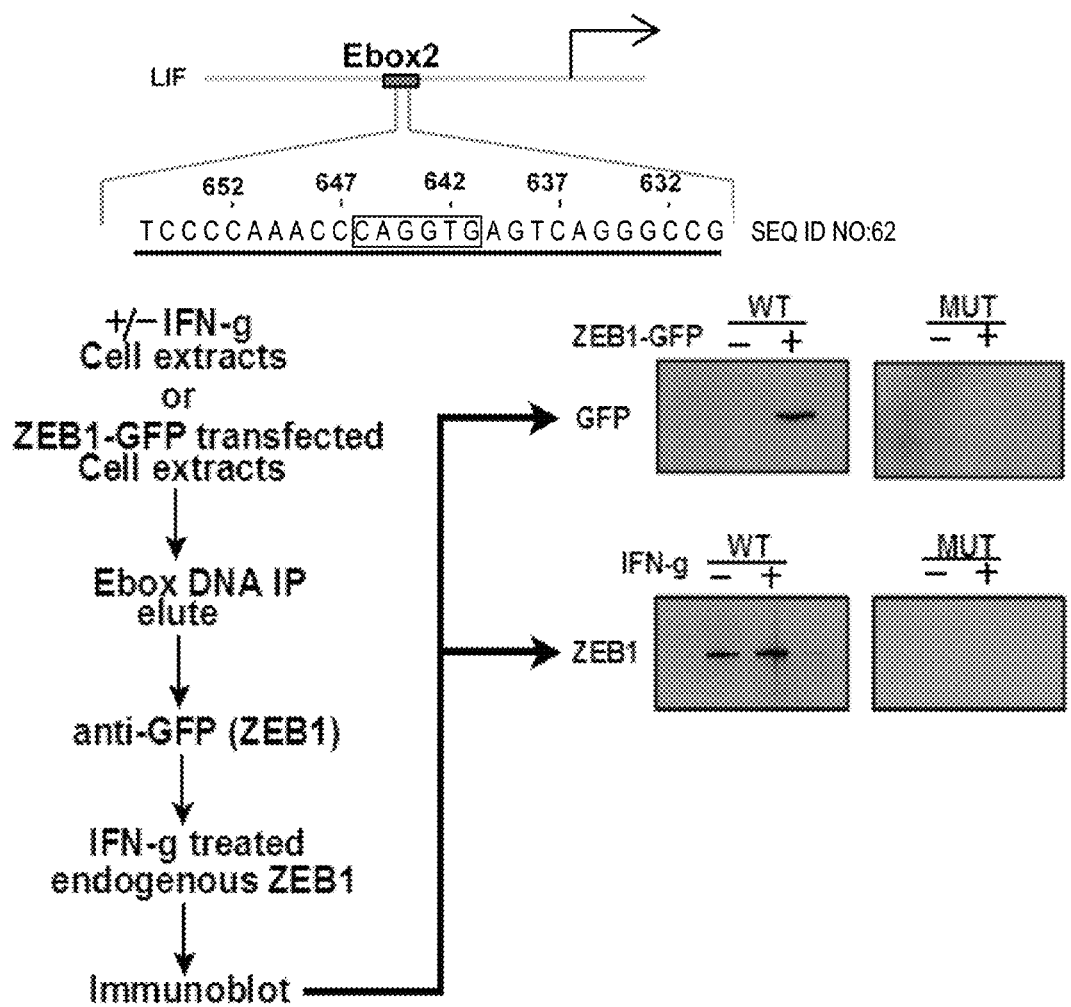
Figure 15J:
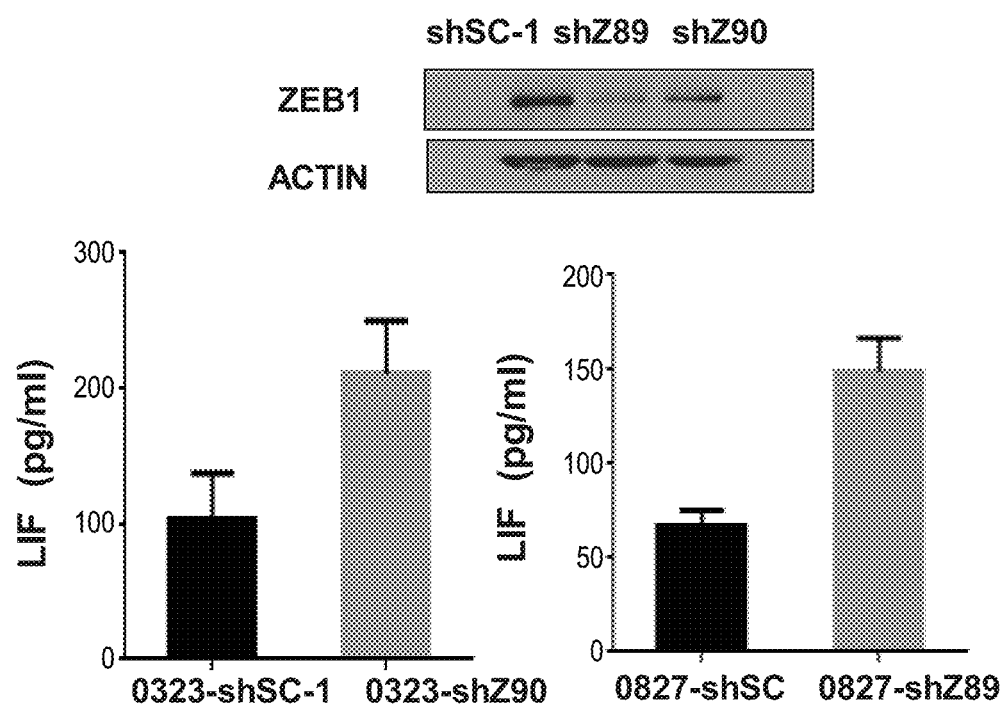

Through our analysis of GBMs for copy number we also looked at gene expression and found that a strong negative correlation was apparent between ZEB1 and LIF (FIG. 15E), a known regulator of stem cell self-renewal in gliomas. Given that ZEB1 is also known to have repressive functions we explored a ZEB1 mediated suppression of LIF. Our attention was focused on a 2 kb region prior to the transcriptional start site of the LIF promoter. Analysis of the LIF promoter identified known ZEB1 E-box binding motifs (CAGGTG, P<0.0001 and CAGGTA, P<0.0001) within the LIF promoter region (FIG. 15F). We cloned the human LIF promoter into a luciferase reporter construct and made subsequent deletion constructs, which systematically eliminated the E-box binding sites to which ZEB1 could bind (FIGS. 15G-15H). We transfected our GCSCs with these constructs and treated our GCSCs with IFN-γ for ZEB1 induction. A suppressive effect was observed in all constructs with the exception of −109/+10 region where ZEB1 binding sites were eliminated (FIG. 15H, left). Similarly, the deletion of the ZEB1 binding sites via the introduction of mutations in those sites also resulted in the rescue of LIF transcriptional activation (FIG. 15H, right). A DNA pull-down of a biotinylated oligonucleotide of the ZEB1 binding site within the LIF promoter in GCSCs resulted in ZEB1 binding of exogenously expressed GFP tagged ZEB1 or to endogenously expressed ZEB1 through IFN-γ treatment (FIG. 15I). GCSCs targeted with shRNAs against ZEB1 (shZ89 or shZ90) confirmed by immunoblot analysis (FIG. 15J, top) resulted in increased LIF protein secretion compared to GCSCs targeted with non-targeting shRNA (shSC-1) as measured by ELISA (FIG. 15J, bottom) in normal stem cell media.

We studied the role of ZEB1 loss in maintaining glioma cancer stem cell properties and its impact on patient survival in gliomas. Our data indicated that ZEB1 expression is lost in a significant number of glioma patients, and that the cause of ZEB1 loss is due in large part to heterozygous deletions in both GBMs and low grade gliomas with frequent LOH in at least 20% of glioma patients. Despite ZEB1 not being identified for copy number loss or mutations in TCGA analysis before, other cancers have shown the propensity for ZEB1 to be deleted recent evidence and a re-examination of the data indicates that ZEB1 does not carry deep or homozygous deletions which are consistently identified through various types of analysis using TCGA data and databases when looking at copy number, but is rather identified through looking at raw copy number where heterozygous deletions can be more readily detected. The impact of ZEB1 copy number loss or decreased expression appears to be in the dysregulation of stemness-as the stem cell promoting factor LIF becomes unregulated and increases, there is a resistance to differentiation, an increase in the stem cell marker CD133, and a significant association with shorter patient survival, which is further exacerbated when we stratify patients who have ZEB1 loss and increased CD133. Furthermore, recent papers now reveal mutations in ZEB1 as did our own sequencing. Data portal sites that utilize TCGA data also identify the heterozygous deletions consistent with our findings, however, the implications of ZEB1 heterozygous deletions have never been explored. Given the observed shortened patient survival in both low ZEB1 expressing patients and patients with ZEB1 deletion that in the absence of mutations or LOH that would affect ZEB1, there is a haploinsufficiency that results in a shortened survival for patients who have low expression of ZEB1 or a deletion of ZEB1. Methylation is also another possibility although this has not been seen on large datasets with respect to gliomas. Furthermore, if we incorporate the mutations observed in ZEB1 with LOH, ZEB1 inactivation may be observed, which is suggestive of ZEB1 being a tumor suppressor. Congruent with this idea is the frozen data from COSMIC, cBioportal and our own copy number analysis of glioma patient samples at Cedars-Sinai Medical Center, GEO dataset analysis, and our own LOH analysis and the recently discovered ZEB1 mutations and our primary tumor and patient derived glioma stem cell functional analysis. Our data also indicated that ZEB1 loss results in resistance to differentiation of GCSCs shown by increased cell proliferation under differentiation conditions and decreased expression of markers associated with differentiation. A further increase in the enrichment of the stem cell marker CD133 after knockdown of ZEB1 in patient derived GCSCs all indicate gain of function attributes associated with the loss of a tumor suppressor.

ZEB1's role in the activation of GCSC invasion is reported. It is not surprising given the dual nature of ZEB1 to be both activator and repressor that the presence and absence of ZEB1 affects divergent GCSC functions. It is also reported that ZEB1 expression increases GCSC stemness as evidenced by CD133 expression.

These divergent data would suggest that sample size and genetic evaluation dramatically affects the analysis of the role of ZEB1 in patient outcome and stemness. We have addressed this by analyzing several datasets of significant patient numbers.

IFN-γ treatment of GCSCs like that of subventricular zone neural stem cells and neural progenitor cells, results in decreased self-renewal and neurosphere formation due to LIF suppression. ZEB1 has been shown to carry out both repressive and active functions in cancer. The likely decision to tend toward a more cancer stem cell-like phenotype rests on ZEB1 not binding the LIF promoter. Although IFN-γ has been suggested by some as a treatment for glioblastomas, our data suggest a more focused treatment strategy of IFN-γ targeting GCSCs may inhibit the propagation of this virulent subset of cells. These findings enable the actionable testing of therapies that increase intratumoral IFN-γ release, not only for immunologic ends but also to increase tumor differentiation and inhibit self-renewal. As IFN-γ activates ZEB1, which in turn suppresses LIF expression, ZEB1 expression can be queried as a surrogate for therapies that invoke tumor differentiation. These findings can impact medical practice by demonstrating that ZEB1 mutation, gene deletion and LOH impacts patient survival. ZEB1 deletion and expression can be used to prognosticate glioblastoma patients with greater accuracy. Deletion may be evaluated with other gene mutations of gliomas to further aid prognostication. In particular, given the role of ZEB1 in stem cell maintenance, its expression can be used to query the stem cell properties of the tumor and assess the effect of differentiation therapies.

Tumor Samples

Patient brain tumor samples were classified as GBM based on the World Health Organization (WHO) criteria (see e.g., Kleihues, P. et al. The who classification of tumors of the nervous system. J Neuropathol. Exp. Neurol. 61, 215-225 (2002)). All blood, brain tumors and patient derived GCSCs were approved by the Cedars-Sinai Medical Center institutional review board (IRB). Informed patient consent was obtained from all patients. All methods were carried out in accordance with the relevant guidelines of the IRB at Cedars-Sinai Medical Center.

Archival Sources of Specimens

DNA or RNA from GBM samples, GCSCs and patient blood were analyzed from TCGA and GEO datasets or samples were obtained from Cedars-Sinai Medical Center and extracted for whole genome copy number analysis, Sanger sequencing, real-time PCR and Exome sequencing. base calling, mutations and LOH identification were called using various software (dChip, MutsigCV, Phred, Chromosome Analysis Suite).

Glioma Cancer Stem Cells (GCSCs)

GCSCs were isolated as previously described (see e.g., Yuan, X. et al. Isolation of cancer stem cells from adult glioblastoma multiforme. Oncogene 23, 9392-9400 (2004) and Lee, J. W. et al. Tumor stem cells derived from glioblastomas cultured in bfgf and egf more closely mirror the phenotype and genotype of primary tumors than do serum-cultured cell lines. Can. Cell 9, 391-403 (2006)) and cultured in NBE media or differentiation media and infected with shRNAs as previously described (see e.g., Edwards, L. A. et al. Effect of brain- and tumor derived connective tissue growth factor on glioma invasion. JNCI. 103, 1162-1178 (2011)) and used in limiting dilution assays, neurosphere formation assays, ELISA, FACs or orthotopic xenograft mouse models. Some of these assays were also done with GCSCs exposed to IFN-γ for 3 or 7 days.

Animals

Tumorigenicity was determined using GCSCs cultured in NBE media that were resuspended in HBSS and injected stereotactically into SCID mice. SCID mice were housed in a specific pathogen-free environment. Mice were sacrificed in accordance to NIH guidelines for the Care and Use of Laboratory Animals. All animal experiments were reviewed and approved by the Institutional Animal Care and Use Committee at Cedars-Sinai Medical Center.

Methodology of Copy Number Loss of ZEB1

Our approach to the role of ZEB1 copy number loss utilized the following methods assembling a variety of resources. For example, we obtained an initial 87 TCGA (The Cancer Genome Atlas) GBM patients using the Nexus biodiscovery application which contained curated copy number information for both primary and recurrent GBMs. We compared well characterized genes in GBM pathology for copy number alterations (e.g. PTEN, EGFR, NF1) as determined by the TCGA GBM Analysis Working Group, to the ZEB1 gene in primary and recurrent cohorts. Our findings were supported by analyzing GBM patient samples from Cedars-Sinai Medical Center and 238 glioblastoma patient samples for ZEB1 deletion downloaded from the TCGA data portal (https://tcga-data.nci.nih.gov/tcga/). We further confirmed ZEB1 deletion through cBioportal and the COSMIC database (frozen January 2014). LOH and decreased ZEB1 expression was confirmed through GEO datasets and GBM patient samples (Cedars-Sinai Medical Center).

Statistical Analysis

Data are expressed as mean±s.e.m. Kaplan-Meier curves and p values were generated using Prism 6.0v. Two-tailed student's t-test, were used. A P value of *<0.05 was considered significant.

Accession Numbers

Data obtained from Gene Expression Omnibus (GEO) were from the following data sets. GSE6109, GSE10922, GSE13041, GSE4412.

Clinical Samples and Cell Lines

We analyzed a total of 4,589 tumor genomes from which 22 were acquired from Cedars-Sinai Medical Center. Whole genome copy number was run by the UCLA Clinical Microarray Core for 6 GBMs and copy number was determined by Cytoscan® HD arrays. Due to the availability of the matched-normal blood plasma, tumor content, and amount of DNA we Sanger sequenced 7 tumor/normal pairs (FIG. 31B). Exome sequencing was performed on 16 samples (FIG. 29A). 3 patient derived glioma cancer stem cell lines (GCSCs) were analyzed using Cytoscan® HD (FIG. 31C). The fresh-frozen GBM samples were from primary tumors diagnosed as grade IV GBM tumors, and snap-frozen. All GBMs were assessed by a pathologist to confirm the diagnosis by H&E with no extensive signs of necrosis. Matching normal material was provided in the form of blood plasma. In addition, matching normal material was confirmed to be acquired from the same patient (n=7). Patient material was stored at −80° C. GBM samples were obtained from patients under IRB-approved protocols following written informed consent as were primary patient GCSCs designated 0827 and 0323, CSC-1-3,5,6,8. All other tumor genomes analyzed from low grade gliomas and GBM cancer patients were provided by multiple institutions (listed below) by way of The Cancer Genome Atlas which was downloaded from the TCGA data portal (https://tcga-data.nci.nih.gov/tcga/) and the Gene Expression Omnibus (GEO) or Nexus Biodiscovery which was TCGA data.

Patient tumor material derived from: Harvard Medical School; Broad Institute; Memorial Sloan Kettering Cancer Center;—National Cancer Institute; University of North Carolina, Chapel Hill; Kyushu University, Japan; Genentech; University of California at Los Angeles; and Cedars-Sinai Medical Center DNA and RNA Extraction DNA and RNA was extracted using QiaAmp DNA kit (Qiagen) for genomic DNA extraction and RNeasy RNA kit (Qiagen) for RNA extraction in accordance with the manufacturer's instructions.

Loss of Heterozygosity

Loss of Heterozygosity was performed in three different ways and analyzed by three different methods 1) Loss of Heterozygosity (LOH) found through clinical datasets in GEO. The resulting LOH data were analyzed with DNA-Chip Analyzer 2010.01 (www.dchip.org). The dChip program (see e.g., Lin, M., Wei, L. J., Sellers, W. R., Lieberfarb, M., Wong, W. H., Li, C. dChipSNP: Significance Curve and Clustering of SNP-Array-Based Loss-of-Heterozygosity Data. Bioinformatics 20, 1233-1240 (2004)) allows for copy number as well as LOH analysis against a user defined reference or matched-pair samples. We normalized arrays using invariant set normalization. Signal intensities were used to infer copy number and LOH by the hidden Markov model (HMM). HMM inferred the probability of LOH based on LOH calls (from the paired tumor/normal samples) and this is displayed from blue (1) to white (0.5) to yellow (0). The dChipSNP was then used to visualize the LOH model for each sample and mapped to chromosome regions (FIG. 1B and FIG. 31A). 2) GCSCs from the National Cancer Institute and GBM patient tumors from Cedars-Sinai Medical Center were analyzed for LOH using Affymetrix Chromosome Analysis Suite (ChAS) (FIG. 31C) and/or Nexus Copy Number software for ZEB1 loss and determination of LOH after samples were run on Cytoscan® HD (Affymetrix, Cleveland, Ohio) at the UCLA Clinical Microarray Core. All arrays were performed using the Cytoscan® HD arrays and Cytoscan reagent kits in accordance with the manufacturer's instructions. 3) LOH was also determined through matching patient blood plasma and patient GBM tumor obtained from Cedars-Sinai Medical Center (n=7) using FinchTV (FIG. 31B) for sequencing alignment after Sanger sequencing of exons in both patient blood plasma and GBM tumor.

Copy Number Analysis

Human DNA extracted from fresh-frozen GBM samples were hybridized to Cytoscan® HD arrays following the manufacturer's instructions. Signal intensities were processed to analyze for chromosomal gene copy number data. The raw, unsegmented copy number signals were used to analyze for significant copy number alterations applying the CGARS method. Significant amplifications were determined with the upper quantiles 0.25, 0.15, 0.1, and 0.05; deletions were computed in reference to the 0.25 lower quantile. The significance threshold was set at a q-value of 0.02 (FIG. 28A). Additionally, copy number was analyzed using snapCGH package for Rstudio (FIGS. 13D-13F). Chromosomal gains and losses using snapCGH were defined by predicted values more than 0.75 times the interquartile range of the difference between observed and predicted for each region. The whisker boxplots of ZEB1 expression analysis associated with ZEB1 genomic status were created using Prism v. 6.0. A two-tailed student t-test with unequal variation was used to measure the differences between groups (FIG. 28D-28E and FIG. 14A).

Dideoxy Sequencing for Validation of LOH

Initially exome sequencing was used to look for somatic mutations. Alternatively, dideoxynucleotide chain termination sequencing (Sanger sequencing) was performed to validate mutations and LOH. Coding sequences of ZEB1 from GBM patient samples and patient blood were obtained using PCR and Sanger sequencing on genomic DNA. Primers (FIG. 31B and Table 11) were designed to cover the coding sequences plus at least 10 nucleotides in the intron region on both ends. Primer extension sequencing were performed by GENEWIZ, Inc. (South Plainfield, N.J.) using Applied Biosystems BigDye version 3.1. Both forward and reverse strands were sequenced. The reactions were then run on Applied Biosystem's 3730xl DNA Analyzer. The sequencing data were analyzed with Lasergene SeqMan software and Finch TV (Geospiza, Inc) to detect any mutations compared to the genomic DNA reference sequence.

Data Processing

The raw sequencing reads of human samples acquired from whole-genome, whole-exome were aligned to the respective human (NCBI37/hg19) reference genome. The data processing details could be found in the following URL: (https://gforge.nci.nih.gov/docman/view.php/265/5004/Data_Preparation_and_Transfer_SOP.zip). Briefly, alignment was performed with the BWA aligner (version0.6.1-r104). The quality of the sequencing data was determined and genome sequencing data of human samples was analyzed for purity and ploidy. Somatic mutations were either already determined in retrospective analysis with additional enrichment to customize the maf files or called at the UCLA CMC Mircoarray Core or called using MutSigCV and copy number alterations were determined as described above.

Reagents

The following antibodies were used: GFAP (Dako), TUJ1 (Covance), Nestin (Covance), Sox2 (Millipore), ZEB1 (Cell Signaling Technologies), ZEB1 (Santa Cruz Biotechnology), Actin (Sigma-Aldrich), CD133 (Miltenyi Biotech), Alexa-Fluor conjugated antibodies (Life Technologies), FITC (Sigma-Aldrich), HRP-secondaries IgG (Promega). IFN-γ (eBioscience) temozolomide was obtained through Cedars-Sinai Medical Center. ZEB1 constructs: GFP tagged (Origene), shRNA-ZEB1 (Origene), shRNA-nontargeting control (Origene). Temozolomide was obtained from either Cedars-Sinai Medical Center or the National Cancer Institute.

Immunohistochemistry

Immunohistochemistry was performed on paraffin TMAs as previously described (see e.g., Spoelstra, N. S. et al. The Transcription Factor ZEB1 is Aberrantly Expressed in Aggressive Uterine Cancers. Cancer Res. 66, 3893-3902 (2006)).

Immunostaining

GCSCs were plated onto chambered slides (Labtek) coated with poly-ornithine (Sigma-Aldrich) and Fibronectin (Sigma-Aldrich) with the appropriate media. Cells were fixed with 4% Formalin and permeabilized with 0.1% Triton-X-100 in PBS and blocked with 5% goat serum. GCSCs were incubated with primary antibodies overnight at 4° C. and then washed in PBS before addition of the corresponding Alexa Fluor-conjugated secondary antibody (Life Technologies) for 1 hr at room temperature and mounted with mounting medium containing DAPI (Life Technologies) and analyzed by confocal microscopy.

Intracranial Glioma Cancer Stem Cell Injection into SCID Mice

The procedure is performed as previously described (see e.g., Son, M. J., Woolard, K., Nam, D-H., Lee, J., Fine, H. A. SSEA-1 Is an Enrichment Marker for Tumor-Initiating Cells in Human Glioblastoma. Cell Stem Cell 4, 440-452 (2009)). Briefly, To evaluate the tumorigenicity of GCSCs, stem cell media cultured GCSCs were resuspended in 2 µl of HBSS and injected stereotactically into adult SCID mice ~6-8 weeks of age. Tumor histology was evaluated by Hematoxylin and Eosin staining after removal of the mouse brain. Coordinates for stereotactical injections into SCID mice were 3 mm distal to the midline, 2 mm anterior to the coronal suture, and 2.5 mm deep from the dura.

Western Blotting

Protein content was extracted from GCSCs in lysate form and protein concentration was determined using a Bradford protein assay (Bio-Rad Laboratories). Equivalent amounts of protein were resolved by electrophoresis on premade 4%-15% gradient SDS-polyacrylamide gels (Bio-Rad Laboratories) and transferred to nitrocellulose membranes (Invitrogen). The membranes were incubated with either a ZEB1 antibody (Santa Cruz Biotechnology), or an Actin antibody (Sigma-Aldrich) was used to control for equal protein loading. The secondary antibodies were horseradish peroxidase-conjugated anti-mouse IgG and anti-rabbit IgG (Promega). Proteins were detected with the use of SuperSignal West Pico Chemiluminescent substrate (Pierce) and visualized after exposure to Kodak BioMax MS autoradiography films (Sigma).

GCSCs, Transient and Stable Infections

To generate GCSCs that stably express short hairpin RNAs (shRNAs) that target ZEB1, we co-transfected shRNA (Origene, Rockville Md.) that target ZEB1 into our 0827 or 0323 GCSCs, with a VSV-G expression plasmid (Clontech) into the GP2-293 packaging cell line (Clontech) according to the manufacturer's instructions. The resulting retroviral supernatants containing shRNA were used to infect 0827 and 0323. We used two shRNAs for targeting ZEB1, shRNA was not used together but were separately infected into either GCSCs. The shRNAs were designated as shZ89 or shZ90 for infection into GCSCs. Similarly, a non-targeting shRNAs shSC-1 was infected into either the 0827 or infected into 0323 GCSCs or GCSC-3. Forty-eight hours after infection, the medium was replaced with complete medium containing 0.1 µg/mL puromycin (Gibco) to select for shRNA-expressing GCSCs. Cells that were resistant to puromycin were characterized for ZEB1 expression by immunoblotting and subsequent cell proliferation using 5-ethynyl-2'-deoxyuridine (EdU) Click-IT assay (Life Technologies) using fluorescence activated cell sorting (FACs) analysis according to the manufacturer's instructions. GCSCs were incubated with IFN-γ for either 3 days (200 ng/ml) or 7 days (100 ng/ml). GCSCs were incubated with temozolomide for 48 hr (25 µM). Transient transfection of ZEB1-GFP was done using X-treme gene HP DNA (Roche) according to the manufacturer's instructions.

Limiting Dilution Assay

Neural Basal A media (Invitrogen) supplemented with EGF and bFGF (R&D Systems) were used to culture primary patient derived GCSCs which were dissociated into single cells sorted for CD133 expression and plated onto 24 well plates with various seeding densities (4-100 cells/well). GCSCs were incubated at 37° C. at 5% $CO_2$ for 2 to 3 weeks. GCSCs were then quantified for neurosphere formation.

Fluorescence Activated Cell Sorting/Magnetic Activated Cell Sorting

GCSCs were washed with 1× PBS buffer 3 times and resuspended in 1× PBS. GCSCs were fixed in 4% formaldehyde for 15 min at room temperature. Cells were washed with 1× PBS buffer and were incubated in 0.1% Triton X-100 for 5 min, washed and then incubated with FcR Blocker (Mitenyi Biotech) followed by incubation with CD133 antibody conjugated to Phycoerythrin (PE) or although not shown an isotype control was also performed (Miltenyi Biotech), protected from light for 1 hazard ratio at room temperature. Cells were washed and analyzed on a FACscan flow cytometer (BD Biosciences). MACs sorting was performed as previously described (see e.g., Son, M. J., Woolard, K., Nam, D-H., Lee, J., Fine, H. A. SSEA-1 Is an Enrichment Marker for Tumor-Initiating Cells in Human Glioblastoma. Cell Stem Cell 4, 440-452 (2009)).

Oligonucleotide Precipitation Assays

Were performed as previously described (see e.g., Son, M. J., Woolard, K., Nam, D-H., Lee, J., Fine, H. A. SSEA-1 Is an Enrichment Marker for Tumor-Initiating Cells in Human Glioblastoma. Cell Stem Cell 4, 440-452 (2009)) with the exception of the identification of the ZEB1 binding sites within the LIF promoter which were identified by Pscan (http://www.beaconlab.it/pscan, and by comparing known E-box binding sites for ZEB1 and using the TOMTOM alogorithm (see e.g., Zambelli, F., Pesole, G., Pavesi, G. Pscan: finding over-represented transcription factor binding site motifs in sequences from co-regulated or co-expressed genes. Nucleic Acids Research 37, W247-W252 (2009); and Gupta, S., Stamatoyannopolous, J. A., Bailey, T., Noble, W. S. Quantifying similarity between motifs. Genome Biology 8, R24-R32 (2007)).

Luciferase Reporter Assays

To measure transcriptional activity of LIF, 0827 GCSCs ($1 \times 10^4$ cells per transfection, three replicates per condition) were transiently transfected with one of several deletion LIF luciferase reporter plasmids (1 ug; Switchgear) with the use of X-treme gene HP DNA (Roche), seeded in six-well plates ($1 \times 10^4$ cell per well), and incubated for 48 hrs. IFN-6 cytokine (200 ng/mL) was added to the cultures and the cells were incubated for 72 hrs. The cells were harvested and the luciferase activity was measured with the use of a GloMax 20/20 Luminometer (Promega, Madison, Wis.). These experiments were carried out in triplicate on three different occasions. Note the original LIF luciferase reporter plasmid obtained from Switchgear was then subjected to site directed mutagenesis to obtain the appropriate deletion constructs.

Quantitative Real Time RT-PCR

Total RNAs from either GCSCs or GBM patient samples were isolated using RNeasy mini kit (Qiagen). Real-time PCR was performed using the IQ5 (Bio-rad) system according to the manufacturer's instructions. Template controls and samples were assayed in triplicate. The relative number of target transcripts was normalized to the number of human GAPDH transcripts found in the same sample. The relative quantitation of target gene expression was performed using the comparative cycle threshold ($C_T$) method. Human primers (Qiagen) used in the real time PCR were the following ZEB1, LIF, GAPDH, OLIG2, NOS2 and CD133.

ELISA

To determine quantitatively the total LIF secreted protein amount we used a LIF Human Quantikine ELISA kit (R&D systems) according to the manufacturer's specifications. The kit presents >95% cross-reactivity with human LIF relative to related molecules. 72 hrs after treatment with IFN-γ GCSC culture supernatants stably infected with either shRNAs targeting ZEB1 or non-targeting control were centrifuged to remove particles and concentrated with Amicon Ultra-4 Centrifugal Filters-10K (Millipore) to a final volume of 200 µl.

Differentiation of GCSCs

Was performed as previously described (see .e.g., Son, M. J., Woolard, K., Nam, D-H., Lee, J., Fine, H. A. SSEA-1 Is an Enrichment Marker for Tumor-Initiating Cells in Human Glioblastoma. Cell Stem Cell 4, 440-452 (2009))

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.)

What is claimed is:

1. A method of treating a brain tumor in a subject, wherein a zinc-finger E-box binding homeobox 1 (ZEB1) dysregulation has been determined to be present in a tumor cell of the brain tumor, comprising:
   providing an angiogenesis inhibitor; and
   administering a therapeutically effective amount of the angiogenesis inhibitor to the subject, thereby treating the brain tumor in the subject, wherein said brain tumor is selected from glioblastoma or glioma, and wherein said angiogenesis inhibitor is bevacizumab.

2. The method of claim 1, wherein an absence of an isocitrate dehydrogenase I (IDH1) dysregulation has also been determined in the brain tumor cell.

3. The method of claim 1, further comprising not administering a chemotherapeutic agent to the subject, or stop administering the chemotherapeutic agent to the subject.

4. The method of claim 3, wherein the chemotherapeutic agent is procarbazine, lomustine, and vincristine (PCV).

5. The method of claim 1, wherein the brain tumor is a glioblastoma.

6. The method of claim 1, wherein the brain tumor is a glioma.

* * * * *

SEQUENCE LISTING

```
<160> NUMBER OF SEQ ID NOS: 63

<210> SEQ ID NO 1
<211> LENGTH: 11
<212> TYPE: DNA
<213> ORGANISM: Homo sapiens

<400> SEQUENCE: 1
caacagacca g                                                          11

<210> SEQ ID NO 2
<211> LENGTH: 8
<212> TYPE: PRT
<213> ORGANISM: Homo sapiens

<400> SEQUENCE: 2

Gln Arg Asp Thr Gln Gln Arg Asp
1               5

<210> SEQ ID NO 3
<211> LENGTH: 12
<212> TYPE: DNA
<213> ORGANISM: Homo sapiens

<400> SEQUENCE: 3
tacacagggt ta                                                         12

<210> SEQ ID NO 4
<211> LENGTH: 11
<212> TYPE: PRT
<213> ORGANISM: Homo sapiens

<400> SEQUENCE: 4

Ser Arg Asn Thr Gln Gly Tyr Leu Tyr Thr Ala
1               5                   10

<210> SEQ ID NO 5
<211> LENGTH: 10
<212> TYPE: DNA
<213> ORGANISM: Homo sapiens

<400> SEQUENCE: 5
ctttcagcat                                                            10

<210> SEQ ID NO 6
<211> LENGTH: 10
<212> TYPE: PRT
<213> ORGANISM: Homo sapiens

<400> SEQUENCE: 6
```

Leu Phe Phe Ser Gln Ser Ala His Ile Ser
1               5                   10

<210> SEQ ID NO 7
<211> LENGTH: 10
<212> TYPE: DNA
<213> ORGANISM: Homo sapiens

<400> SEQUENCE: 7
cagtaaacct                                                          10

<210> SEQ ID NO 8
<211> LENGTH: 9
<212> TYPE: PRT
<213> ORGANISM: Homo sapiens

<400> SEQUENCE: 8

Asp Ser Val Asn Leu Pro Leu Asp Val
1               5

<210> SEQ ID NO 9
<211> LENGTH: 12
<212> TYPE: DNA
<213> ORGANISM: Homo sapiens

<400> SEQUENCE: 9
tgattctaca cc                                                       12

<210> SEQ ID NO 10
<211> LENGTH: 9
<212> TYPE: PRT
<213> ORGANISM: Homo sapiens

<400> SEQUENCE: 10

Ser Asp Ser Thr Pro Pro Lys Lys Lys
1               5

<210> SEQ ID NO 11
<211> LENGTH: 10
<212> TYPE: DNA
<213> ORGANISM: Homo sapiens

<400> SEQUENCE: 11
aaatgtagag                                                          10

<210> SEQ ID NO 12
<211> LENGTH: 9
<212> TYPE: PRT
<213> ORGANISM: Homo sapiens

<400> SEQUENCE: 12

Asn Met Cys Val Arg Glu Arg Gly Asp
1               5

<210> SEQ ID NO 13
<211> LENGTH: 11
<212> TYPE: DNA
<213> ORGANISM: Homo sapiens

<400> SEQUENCE: 13
aaaaagaaaa t                                                        11

<210> SEQ ID NO 14

```
<211> LENGTH: 9
<212> TYPE: PRT
<213> ORGANISM: Homo sapiens

<400> SEQUENCE: 14

Lys Lys Arg Glu Lys Lys Asn Met Cys
1               5

<210> SEQ ID NO 15
<211> LENGTH: 11
<212> TYPE: DNA
<213> ORGANISM: Homo sapiens

<400> SEQUENCE: 15
tagctcagaa g                                                          11

<210> SEQ ID NO 16
<211> LENGTH: 9
<212> TYPE: PRT
<213> ORGANISM: Homo sapiens

<400> SEQUENCE: 16

Asp Thr Ser Ser Glu Gly Val Ser Asn
1               5

<210> SEQ ID NO 17
<211> LENGTH: 11
<212> TYPE: DNA
<213> ORGANISM: Homo sapiens

<400> SEQUENCE: 17
caaatgtaga g                                                          11

<210> SEQ ID NO 18
<211> LENGTH: 9
<212> TYPE: PRT
<213> ORGANISM: Homo sapiens

<400> SEQUENCE: 18

Lys Asn Met Cys Val Arg Glu Arg Gly
1               5

<210> SEQ ID NO 19
<211> LENGTH: 11
<212> TYPE: DNA
<213> ORGANISM: Homo sapiens

<400> SEQUENCE: 19
gaggaaggaa g                                                          11

<210> SEQ ID NO 20
<211> LENGTH: 11
<212> TYPE: PRT
<213> ORGANISM: Homo sapiens

<400> SEQUENCE: 20

Glu Arg Gly Glu Arg Arg Gly Glu Lys Arg Glu
1               5                   10

<210> SEQ ID NO 21
<211> LENGTH: 10
<212> TYPE: DNA
<213> ORGANISM: Homo sapiens

<400> SEQUENCE: 21
```
gacaagggaa 10

<210> SEQ ID NO 22
<211> LENGTH: 11
<212> TYPE: PRT
<213> ORGANISM: Homo sapiens

<400> SEQUENCE: 22

Asp Thr Gln Lys Arg Gly Gly Glu Lys Arg Glu
1               5                   10

<210> SEQ ID NO 23
<211> LENGTH: 11
<212> TYPE: DNA
<213> ORGANISM: Homo sapiens

<400> SEQUENCE: 23
caagggaaga g 11

<210> SEQ ID NO 24
<211> LENGTH: 10
<212> TYPE: PRT
<213> ORGANISM: Homo sapiens

<400> SEQUENCE: 24

Glu Ser Leu Thr Arg Glu Glu Asp Glu Asp
1               5                   10

<210> SEQ ID NO 25
<211> LENGTH: 22
<212> TYPE: DNA
<213> ORGANISM: Homo sapiens

<400> SEQUENCE: 25
ttcgagccat cattaaaatc ac 22

<210> SEQ ID NO 26
<211> LENGTH: 20
<212> TYPE: DNA
<213> ORGANISM: Homo sapiens

<400> SEQUENCE: 26
ctgggtggtt cagactcaca 20

<210> SEQ ID NO 27
<211> LENGTH: 25
<212> TYPE: DNA
<213> ORGANISM: Homo sapiens

<400> SEQUENCE: 27
gggtagctac tatttgtcat tttgg 25

<210> SEQ ID NO 28
<211> LENGTH: 24
<212> TYPE: DNA
<213> ORGANISM: Homo sapiens

<400> SEQUENCE: 28
ttgatttcaa acttttcatc caat 24

<210> SEQ ID NO 29
<211> LENGTH: 22
<212> TYPE: DNA

```
<213> ORGANISM: Homo sapiens

<400> SEQUENCE: 29
tcgggaagtt aaaatgtttg tg                                    22

<210> SEQ ID NO 30
<211> LENGTH: 21
<212> TYPE: DNA
<213> ORGANISM: Homo sapiens

<400> SEQUENCE: 30
ggaaacggac taaattcagg a                                     21

<210> SEQ ID NO 31
<211> LENGTH: 23
<212> TYPE: DNA
<213> ORGANISM: Homo sapiens

<400> SEQUENCE: 31
ttctgcagat tcaagaacaa tca                                   23

<210> SEQ ID NO 32
<211> LENGTH: 22
<212> TYPE: DNA
<213> ORGANISM: Homo sapiens

<400> SEQUENCE: 32
tgcatggtca tcatagtgtt cc                                    22

<210> SEQ ID NO 33
<211> LENGTH: 22
<212> TYPE: DNA
<213> ORGANISM: Homo sapiens

<400> SEQUENCE: 33
tggaacatag catagggact ca                                    22

<210> SEQ ID NO 34
<211> LENGTH: 24
<212> TYPE: DNA
<213> ORGANISM: Homo sapiens

<400> SEQUENCE: 34
tcaggaatga ccagataact caaa                                  24

<210> SEQ ID NO 35
<211> LENGTH: 23
<212> TYPE: DNA
<213> ORGANISM: Homo sapiens

<400> SEQUENCE: 35
ttctgtcccc actatcacta tcc                                   23

<210> SEQ ID NO 36
<211> LENGTH: 20
<212> TYPE: DNA
<213> ORGANISM: Homo sapiens

<400> SEQUENCE: 36
gccaaaagaa atgcaaggag                                       20

<210> SEQ ID NO 37
<211> LENGTH: 20
```

```
<212> TYPE: DNA
<213> ORGANISM: Homo sapiens

<400> SEQUENCE: 37
ccgcttgttt tagggaaatg                                              20

<210> SEQ ID NO 38
<211> LENGTH: 20
<212> TYPE: DNA
<213> ORGANISM: Homo sapiens

<400> SEQUENCE: 38
atggccacct tgttgtatgg                                              20

<210> SEQ ID NO 39
<211> LENGTH: 20
<212> TYPE: DNA
<213> ORGANISM: Homo sapiens

<400> SEQUENCE: 39
cgtctctttc agcatcacca                                              20

<210> SEQ ID NO 40
<211> LENGTH: 21
<212> TYPE: DNA
<213> ORGANISM: Homo sapiens

<400> SEQUENCE: 40
ctcctggaca atcatcacac a                                            21

<210> SEQ ID NO 41
<211> LENGTH: 20
<212> TYPE: DNA
<213> ORGANISM: Homo sapiens

<400> SEQUENCE: 41
agccatcagt cttcctttgg                                              20

<210> SEQ ID NO 42
<211> LENGTH: 20
<212> TYPE: DNA
<213> ORGANISM: Homo sapiens

<400> SEQUENCE: 42
actttgcctg gttcaggaga                                              20

<210> SEQ ID NO 43
<211> LENGTH: 20
<212> TYPE: DNA
<213> ORGANISM: Homo sapiens

<400> SEQUENCE: 43
tactcagcct cctccactcc                                              20

<210> SEQ ID NO 44
<211> LENGTH: 20
<212> TYPE: DNA
<213> ORGANISM: Homo sapiens

<400> SEQUENCE: 44
tgtccttttg tggctccttt                                              20

<210> SEQ ID NO 45
```

```
<211> LENGTH: 20
<212> TYPE: DNA
<213> ORGANISM: Homo sapiens

<400> SEQUENCE: 45
ccaccaatgg ttccagaagt                                              20

<210> SEQ ID NO 46
<211> LENGTH: 20
<212> TYPE: DNA
<213> ORGANISM: Homo sapiens

<400> SEQUENCE: 46
agttggctct acgggactga                                              20

<210> SEQ ID NO 47
<211> LENGTH: 20
<212> TYPE: DNA
<213> ORGANISM: Homo sapiens

<400> SEQUENCE: 47
gatcagtgtg cttgctttgg                                              20

<210> SEQ ID NO 48
<211> LENGTH: 21
<212> TYPE: DNA
<213> ORGANISM: Homo sapiens

<400> SEQUENCE: 48
aaagaaagaa aattctaaaa c                                            21

<210> SEQ ID NO 49
<211> LENGTH: 20
<212> TYPE: DNA
<213> ORGANISM: Homo sapiens

<400> SEQUENCE: 49
ttgggacctg gaaatgtttt                                              20

<210> SEQ ID NO 50
<211> LENGTH: 22
<212> TYPE: DNA
<213> ORGANISM: Homo sapiens

<400> SEQUENCE: 50
tcatcagacc ttcagttttt gc                                           22

<210> SEQ ID NO 51
<211> LENGTH: 20
<212> TYPE: DNA
<213> ORGANISM: Homo sapiens

<400> SEQUENCE: 51
gagaagcgga agaacgtgac                                              20

<210> SEQ ID NO 52
<211> LENGTH: 20
<212> TYPE: DNA
<213> ORGANISM: Homo sapiens

<400> SEQUENCE: 52
gcacacccgg atttattttg                                              20
```

```
<210> SEQ ID NO 53
<211> LENGTH: 22
<212> TYPE: DNA
<213> ORGANISM: Homo sapiens

<400> SEQUENCE: 53
tgaacaggaa tcacagcata ca                                              22

<210> SEQ ID NO 54
<211> LENGTH: 11
<212> TYPE: PRT
<213> ORGANISM: Homo sapiens

<400> SEQUENCE: 54

Asp Ser Val Asn Leu Pro Leu Asp Val Val Lys
1               5                   10

<210> SEQ ID NO 55
<211> LENGTH: 10
<212> TYPE: PRT
<213> ORGANISM: Homo sapiens

<400> SEQUENCE: 55

Ser Val Ser Leu Pro Leu Asp Val Val Lys
1               5                   10

<210> SEQ ID NO 56
<211> LENGTH: 9
<212> TYPE: PRT
<213> ORGANISM: Mus musculus

<400> SEQUENCE: 56

Val Asn Leu Pro Leu Asp Val Val Lys
1               5

<210> SEQ ID NO 57
<211> LENGTH: 11
<212> TYPE: PRT
<213> ORGANISM: Pan troglodytes

<400> SEQUENCE: 57

Asp Ser Val Asn Leu Pro Leu Asp Val Val Lys
1               5                   10

<210> SEQ ID NO 58
<211> LENGTH: 10
<212> TYPE: PRT
<213> ORGANISM: Homo sapiens

<400> SEQUENCE: 58

Asn Thr Gln Gly Tyr Leu Tyr Thr Ala Glu
1               5                   10

<210> SEQ ID NO 59
<211> LENGTH: 10
<212> TYPE: PRT
<213> ORGANISM: Homo sapiens

<400> SEQUENCE: 59

Asn Thr Gln Asp Tyr Leu Tyr Thr Ala Glu
1               5                   10

<210> SEQ ID NO 60
<211> LENGTH: 10
<212> TYPE: PRT
```

```
<213> ORGANISM: Mus musculus

<400> SEQUENCE: 60

Asn Thr Gln Gly Tyr Leu Tyr Thr Ala Glu
1               5                   10

<210> SEQ ID NO 61
<211> LENGTH: 10
<212> TYPE: PRT
<213> ORGANISM: Pan troglodytes

<400> SEQUENCE: 61

Asn Thr Gln Gly Tyr Leu Tyr Thr Ala Glu
1               5                   10

<210> SEQ ID NO 62
<211> LENGTH: 27
<212> TYPE: DNA
<213> ORGANISM: Homo sapiens

<400> SEQUENCE: 62
tccccaaacc caggtgagtc agggccg                                         27

<210> SEQ ID NO 63
<211> LENGTH: 212519
<212> TYPE: DNA
<213> ORGANISM: Homo sapiens

<400> SEQUENCE: 63
cagttttctc aatttctcta tcaataactg ctacattgtt aatttataac tatattactt      60
gaaatacagc tcagcttatt tattccataa agttggtccc aaagacgttt ccttattcga     120
aggaggtggg aagcaggaag gaaacctaaa tctaaattct acttaatact gaagacgact     180
ttcttgatat ttgtggttat ctgtatggtc ttttcagaaa tcccaaaact tgtaccaagt     240
caaggataaa ataagataaa atcagcaatc tatcaggttc agagatcaca tctgtcagcc     300
gatgcttctt gccttaaggt cctgcacggc gatgaccgct catttaggaa ggaattcatg     360
gcctgtggat accttagctc tgagtcctgc cacctaggat cccacggttc tacgcgagga     420
agagggcggg gagcgcggac cgggtgtggg aggccgaggt gacagcaggt gagggccggg     480
tgcggatggg gaagtgagac aagcaccgtg tgggtattac tcattccgct ctactaagga     540
ggctgctggc aagcggaact tctagcctct cttcaatcc agctgaagtt caatctcatt      600
gaagtcactt cccatcccgg ttcgcttggg gggaaaccag cgtccctgg aagggaaggg      660 aagggagtcc gggctgcgcg ggtcaggtag cctctctccg gtcgccgcgt gtcctcgccg     720
tccccaaacc tgcccttccc ctcatcaagg gaactcccg gggagtccag accgcgatcc      780
ctttccttgg ccccggggtg cggggggcgg acacgcgagg cgtgggactg atggtagccc     840
tgcctccagg aagcaggcag gcggggacct ctgggcgctc ggaggggcag ctccgagggc     900
acagggtaca gggagaatca gccagatccc tccctgcccc gggcagccgc ggcgggtgtg     960
gccagcgcgg aggcaggacg ccgccgagcc tccaacttta cctttccaac tccgacagcc    1020
cgtcgccttt ctgaccgcgt ccctacggtt tccggcatc cgcctccctc tccccaccac     1080
acctgaggaa aacttttccc tcgcccctca attcaaattc agcagtgccc acggttgccg    1140
caaaccgccc ggtccctagc aacaaggttc cggccgtaga gcgagagcct ctaggtgtaa    1200
ggaaggtgat gtcgtaaagc cgggagtgtc gtaaaccagg tgcggtgggg aggggggagg    1260
ggtggaggcg gaggggtggg ggggaagggg gagggagggg gaggaggtga ctcgagcatt    1320
```

```
tagacacaag cgagaggatc atggcggatg gccccaggtg taagcgcaga aagcaggcga    1380
acccgcggcg caataacggt gagtggcgga ggggaccggg gagcggcgga gtcaggggga    1440
gctgggcagc cggggcgccc ccggggtga gggggcgag ccgggctggg ggcagccggg      1500
gcagggacgg caaagtggag tgggaaagta gaaagtagtg ctctctgccc ccctccgctg    1560
ccgccgctgc cggagccgcg ccgcggccgc tcgctctccc tgaaccgtta tgtctcttac    1620
ctggtctctc tccgcctagc ggctcccgcc gcccctgccg cctccctgga ccgttagccg    1680
gcgccgacgc cgccgcatcc ccggcgcagg gcgggcggcc gggacgcact ggccactttt    1740
ctggtcccgg gtggagcggc tgttgcttct ttccgcactt ttccccactc ttgtgccctt    1800
cggcgcctcc ctctccccct cctcctggcc ccctcagcgc gattctccct cagcgcccag    1860
gcccccggga gccgcggaac aaacttgtgc ccggcgctga ccgtgcaaag tggcttccgc    1920
gcgccgcggc cccggccggc gccgtcgctg tcgctcgggc cccgcgactc gggccgggct    1980
gtgggcgcgc ggcaggcggg ctgcggcggc ggcgggacgg ggcggccgcg ggttgcgtgg    2040
ggtttgtgcg cgcgtgtgcg cgggcgccgg ctgtgcgcgc cgcgggcgga cagggttcgg    2100
ccggcggcgg taaagttggg acccgcgggc cgggcgcgct cgcgtaacgg ggattagagg    2160
cgcggggcg cgggtcccta agcgcccctc ctccctggcg cctcccgctg cccggcccag     2220
agccccggcc tggggactcc gcggcgagcc ccgcgagtgg ggtccacgtt tggcggggcg    2280
cggcggggcg gcgcggggaa caaggcagga aaggtaccca cttaacgccg ccgggagccg    2340
cgccgatggg ggcgagctgg gcggcgggtg tgtttgcgga gttgttacct gggcttagag    2400
accgggaagc accacagaca gatcccccct ccggggcaga cgaggtctct gcgccgggat    2460
gggccggtgt gcgtgcgcct cgcgcttttc tctttcggtt tttggggaag ttgttacctg    2520
ggccggacgc acggagcgct gaagccggat aatgggctt ggatggcgct ctgggtctcg     2580
ggtggaagga gggtggggga ggggcggac ggaccgacgg acgcgcgggg ctgctacttg     2640
caccgcagct gcagtgttta ttgatttgtg ctgctgtgcc aagggaaaca cacacccctc    2700
tgcctggcgt gagagttaaa aaaaaagaga gacagcccga gggatcgaga cctgaacatg    2760
tggtggtggt tgcacagtcg ccttttccag tttggagaga cgttgtaagt tgattgtatt    2820
tctggttatc tcggggcgat gctatgcttt ctctccctct cgtgcagcag cgaaatgtct    2880
gctgattgtt attgtctgga cagttcctgt ggcgagaggg gcgagacttg tccgcccggg    2940
ggcggcggga gcgcagggag agcagccccc gcctgcgccg ccccggtacc tgtttgtata    3000
ataatgggcg gcaacggccc tgccgccggc cgcagcccag gctatataag gaattacacg    3060
tacatttcgg accgaggggc tcgctttggt tcctgcgtta ttttaaaac gacttttaag      3120
agaggggcaa taaatgcgtc tataatggga ccgctgcagc gtcgagaaaa cgaggaaata    3180
cgtgtttagg agaaaactct ctcgtgctcc cccagcccca cccccgcgc ctgggctccc     3240
tttctccctc ccctctggga tgcgaaacgc gaggttttgt aacctttcct ggcaatttta    3300
gattttgtgt gggatttcct gtctagaagc agatacgaag attttttaagc tgtttcaaga   3360
tgtttccttc caatccataa ttatatttt aatatattcg agccatcatt aaaatcactg     3420
ctttcgtgat tttaattatt caaataaaca cttgcatttt aaagacgtct gttgattata    3480
aacgaaaggt attttggtat tctcattgtg gagagatgac ttgttatagc aaggagtgga   3540
gcataggcta ttgcaatttt aatttcctgt tttagcgtca aatagtgtgt gttccatatt    3600
gagctgttgc cgctgttgct gatgtggctt tatgaaaggt aagttggttc ggaaagagct    3660
```

```
gttcgctttt taccttattt aaaatgttga tcgccagaga aaggggcttt tcttgttgct    3720
gacgacatgt gtgtgacatg tgagtctgaa ccacccagcg tctgtgcagc tgctgtaaac    3780
atgtttacct gaacaggaaa gaatggattt ttctccttga gatcctgtga tatgaatatt    3840
acactcgtaa ggcatatcaa cagatgactt aaggggggaa aagcgatcct gaaagatact    3900
tgaaatcaac aggaaagaga ggttcttgat cgctgcagca aatggcaact tgtgcaggta    3960
gaaaaaaaga tggtgtttag ttttctcctg catgtatgtc agccccctcc tgtctgctgc    4020
tttcattctc aagggaggga tttatttacc acgcttgctg tcagtgtttt tcctttgtgt    4080
ttaatattag aaaaacagat ttgcgtctgt ttagcacaaa acgtcttgtc tgcagtatgc    4140
attactctca gaaaacaaaa ggtgtttaag atagcactgt actactacag gtatcttcca    4200
ttttcatcac ttttggctct gtccttgtat ttcttttttgt tctcaaatgc atttcatcca    4260
ttgctggtga ttatagccat gctatttgat ttagccttat attttgcaaa ttaaaaatga    4320
agttatattc cattgtgttg tgaaacctca gtatatgtgc tggttaatat ttcttagcag    4380
tgcagtcata tttaagttgc agatgtttat tggagaaaat tgcctggcaa aacgttaact    4440
ctcaaatctt tttaatgaag aaatatgtga tatatacagt ggaagattgt cgtagagata    4500
gtttatgttg ttatatatgt aaataatgtt ttattcattt tgaaataaga tacgtggatt    4560
ttgctgctaa gccttctgta aaatatttta atttcctttc tggaatatgt ctgaaggtag    4620
gatattaaaa ggagtatcag gtaatgtaac tgacaggggt aaaccaattg agtaaggttt    4680
ggccaaagca tcaaaccttg tgtggtaact taatgatgtt agtcatccgt aaaggagtga    4740
cattagaatt gcttgaatta gttttttacca tttataattt catgctttgt tgcattttaa    4800
aaaatctgtc tttttctttt tctgctttct tctatgtggt tttcttcttg ttctaccttt    4860
tttttttttg agagagagat gtactctact aatgaccaca tgctgattaa ttctctttag    4920
atggaataga aggtacatat ccttctgtca tcagcaccat ttccccttgc tgtcattgga    4980
aaccaccagt agaggatgct aacaaaaatg attattggtg tggtagcatc ataagtctct    5040
ctatcgactg tgctgattgg gaccttcagt ataattctga gtcttattgt tacttaaaac    5100
tagccttggt taaattaggc ataagcattt tctagtttgc cgaaactaga aagaagcagg    5160
actgttttaa cttgaataat tttataaatt tgagttattt aagtctctaa ttgagattgc    5220
tgttaattca ttccttgtttt agagcagttg tattactcct tattttaaaa agattttgtt    5280
ttatgttctt aggtttggag aagaatatgt aataattgac ccatatttat gttgcatatt    5340
tagaatactt tttaatcacc ccttttttaaa attcatagta agatccctta aaatatatat    5400
tttagatgtt aaaatacatc taaaatggtc aaagtttaag agtagcaagg aaaattacaa    5460
ttgattgata atactgtgta attattttta tataacttat gtagacttag actatggatg    5520
ggttggcaga gagctactaa cggaggtggt aactagcagt cacttagatg ttagtgattt    5580
ttagatttta tcttttcctt ccccttcagg tcttttccta ctggtagccc tcccccacct    5640
ttttagttaa gaatcagtga gtgcatacgt tttaaatttg tcagttgtaa ttaaggaata    5700
taagtttgct ttgagatctt atatgcagta aaactctgta gttcgtacgt tgctgtatgc    5760
ttgtatttaa ataattcctt tcaagaaact atataaattg catataaata attgcatgag    5820
actgtattta gttatgtctt ttcattttgt gttcttatag gtatattaat ataactgtaa    5880
attttaagcc tctcattagg tagaacatta gaagtattta tttccttaat tattttttagt    5940 ggtgttttta taaatgcatc aatatcagta ccgtaatgga atagccatac tgtttatctt    6000
gaactaagta ggtattgaat tgccaggtaa gcctgtgtta atttcttatt ttaggatgtc    6060
```

```
atggttcttc gtgtgtgtgt gtgtgtgtgt gtgtgtgtgt gtaaatagtt tttcatttcc    6120
tgacaggtat ttcttgaatt tagtattcta attcctgagg gctcagtagt gaataggtgt    6180
gattcactta aatgtttatg aactcagaaa ctttgccaca aagtcacgag atacattgta    6240
gcatggagca aaacttaaag tatcttataa attgaaaata ttaatcgttt atgaagatga    6300
ccctgatata aaaagcatgt gaaatatttg tttaatactg ttttcttcct ttctctagtc    6360
tctagtatgt ttgaaatggc atacctccta tgtagtagct tttgaagcat gtgctgagaa    6420
acttctgtta aattgagaat gatattttta aaataagagc ataatgattt ctcatagttg    6480 tgttttttctt ttgctttatc ctcttgtgga tttacctgta taaatcactt ttaagcatgt    6540
ggttagagcc agatgtaaac acagatgcag tatcatgtgg aattatattg ttagctactc    6600
ttaactacct gtattgaatt gcagcagagg aggagaaaaa tcatgcagat gttggaagaa    6660
gatatgcatt agtgtgcaag agtacagcga gaggttagaa aacttgaagc tgtagaaata    6720
ggattgaaaa aggtttcttt gcagtacagt cactaattta tgtggaaatg catgctcttt    6780
atttctaatt gagatataag ctaaaataaa agtccattgt tgaaagaaaa ctcaaaaaat    6840
tttaaactag aaaaagtgtc ctgattagga aatatgataa aatgattttt taaactactt    6900 tttaagggt agatgttgta catattactg gctaaataat cattcaacta gatatgaact    6960
aaaagtagta agcaagtaga aatatatgta gtagagaaag ttttgtagca accctagtta    7020
aaattaaatt tgatctatta tgtaggcatt gccatataaa ctaatcattc ttttgcatgg    7080
ggcagtgttt tgagtattat gtcactaaag gaaacatctt taggacatta gttttactaa    7140 ataaaattt caatatgtta tgagcatgtc tggattttag ccttgatgga ggtgggttac    7200
gctgttaact aaaactggg ttgcttaaaa agatggcaat ataatacagt acttaagtag    7260
caaaatgctc tctaataagt aaaatttgct ttatgattgt tttcagagaa aacaacttaa    7320
tttttagaac ttcattaatt ttgttaaagc atattttttgg attatataat atggatgtag    7380
ataaatggaa agattatgaa aggaaaagca aaaaattgaa ttcaagtgtc tatttgtatt    7440
atagctgtga aacttaagc ttttttcatt ctctacaaag ttactttct ctttcttcaa    7500 acagctccct gttgtttaat acacgttccc tctatacata gggattgcat ttatctgtcc    7560
atatgcacat ttctcctcct aatcaacatt atgtatttat tgagacttgg tacatggagg    7620
ttgaggtatg aactatgttt gtagaaaacc ttacagtatg gcaacctggg aaaaccttca    7680
tctcttttgc agtaacaact acatctgtgc tgaaattatt cataacagat gttttgtgat    7740
ctcttaattc cctccctctc ccttcccctc cccattcag atttaaaatt aaatgtgaat    7800
ggaagataaa tttataaatt atgttaattt cttttttattg ttttattcta tattgaaagt    7860
cctctgtttt ctcttttaa aatattctaa ttttaaatgt ttaagatatt ttaagtactc    7920
tgatttcaat tatcttttaa taaaatatga caccattatt tatatatctg ttactattca    7980
tgctcacggc ctaaaatata ttctgatttc ccttactctt aaggtctttg tattcattta    8040
atccacaatt ctagcagagt gtttggtttt gggttttttt ttttttttt aagtagatag    8100 tgctgagtgt aactagtttg ctgatgaaaa aaactcattt tcttggaatc atatattttt    8160
aatatggaag attcatcttt tccaaaataa cttttttatct gaaaactgac acagataagc    8220
tgaaatttag ggtctttaag tagaaactct agaagagact ttaatgtgtg ttttaagaag    8280
gggtaatgcc aggcagatac agtgacatat ggaataacat gtagtgaaat ccttcaagga    8340
gtagattttc tgaacctggg ctcagggtaa ccttgctctg ccttgaatac ttgaaaaggc    8400
```

```
tgtcaaaatc actgtatctc tttaacgttt tctcctttct accctaaagt taagttgcta    8460
tttgctccta ttgctacatc acttttctga atctcttttg atacacttgg cttttgcttt    8520
atttgggagg gagaaagtaa aggaaggagg aattggagta gacaaaaaat aactttatat    8580
gaataaatat tcattaagaa aatgaagtgg aataattttg gactggagag atttgggaga    8640
atcatccaaa gccatttttgc agtaaagcag acagtcaaag agataagatg actttgccaa    8700
gtttatgtta ctagttagct tggactaggt cacagctttt tgggttccta gttcggtatt    8760
cttttcatta ggtcatttga gcatatttat ctaagacggt aacaagcaag aactagatac    8820
catgaatttt caaatttatt atacttaaaa ccaaaatgtg tagaatgctt catcatctca    8880
aaggcaagtt ctaatacata tgcatacatc tgtcaaattt agtagttgat gtagttatat    8940
cacttaaaat atttcagatg cagagcatta gtattattta gaggcatcct ctcatttgga    9000
ttatactttt ggtcactatt cccaatttca gctcccattc actctatcct tcctaccttg    9060
gacccaatct aatatgtttt ttatatgctg ttggttttgt agctagcctt gtaaaatttt    9120
gtacctcttt tgtgtgtttt gtatttacat aagtgctata agtgctactt tgctctatca    9180
tttactttct ttttcttttc tttttctttt tttttttttt ttttttttgag acagtttgac    9240 agtttgactc ttgtcaccca ggctggagtg taaaggcgcg atatcagctc actgcaacct    9300
ctgtctccca ggttcaagtg attctcccgc ttcagcctcc caagtagctg ggattacagg    9360
cacacaccgc catgcctggc tgatttttgt attttagta aagatggggt tttgccatgt    9420
tagccaggct ggtctcaaac tcctgacctc agctgatcca cctgcctcag cctcccaaag    9480
tgctgggatt acaggtgtga gccactgcac ctgacatata atttactttc tttacttagc    9540
attgtttgat agctagatat gttgctatat gtacagctag ttcattgctt ttaaccttgc    9600
agtagttcat ttatgtagta agcacaaatt acctatcaat tccctaatg gcagattccc    9660 agattgactc caattcttag ataccaataa ttctgtaata aacatcctcc tacgtgttgc    9720
taatggctgt ggaagagttt ctcagcacta ccatatctag ggacatggta ttgtccagac    9780
atagtattgc tgagtatagg tcaatcacat atttaataat tactaaattc tgtcagatta    9840
ttttaaaaac agcaacacca ttttttacgc tcaccaacaa tgtaaaagaa ctattttctc    9900 acgttttgc cagccttcgg tattgtacaa cattctacat tttgctaatt tttcagttgc    9960
taaatataat ctgatagttg ctttaatta tgtttctctg tttattaggg aggttgatca    10020
tttcttcata tccttgctag ctgtttgggt ttcccttttcc atatctggcc tattcatacc    10080 ctttaccect cttttttggat agatttccat ttctcttgtg tatttaagat gataatcccc    10140
aacgtttcag tcatttgact ttggtacagg aatccttaat tttaatgtca aaattttgac    10200
tttatgggta gtaagaagtc cttcctaatc tatagattat aaagatattt tcctggattt    10260
tcttctatta gtttcttagt tgtatttttt gtatttatat gtctaatgca tcaggagttc    10320
accttttgaa tacacccttt cttaagagga acaagtatag cagttaagag tttgggttga    10380
tcctgtaact tactacctat caccctggcc gggttactta gtcttttat gcttgagttt    10440 ctctgcatgt aaattggaca tgacagtcta agaattggga aagtttaaat gaagcatatg    10500
acgcattgtg cctaatacat gttttaagtt ttcaacacat gttcatttaa aattttactt    10560
atttatttta aatatatctt ggatcagctg acaattttt atccttttga ccagtattaa    10620
ctccagctaa tgtaactacc atctgaaagg gggttgctgt aaaatttgta cattgtttgt    10680
gtaactttga catttaacat tgcttagttc agaccttgga caaagctgtt aaatgatcaa    10740
tagacactga agcttcatct taatgctact tttggtatgt cttcagctt taggaaggat    10800
```

```
tccttggatc ttttaagggg ccattatatg agagagacct taccatatca cttttatgta   10860
taacattgac atgaacttca aggataatgt cccattgtta ttctgttaca taaatcaaag   10920
aactcaagtc caaggaataa aagctgtgca ttctatattt gaatagtcta agcaacatgg   10980
agtctgcacc ttctcatata tccatttggc tgggaatgta tttaagaaga tggctgtctt   11040
actgtgttcc tatggtatag atcaggacta ttctaagcca aaagttaaaa ccatacccctg  11100 gtgtgtgtgt gtgtgtgtgc gtgtgaactt aattgaggta taatttatat acaataagat   11160
ataccactat gcatgtacat tttgatagag ttttgacata cttgcataca tgtgtaactg   11220
ctaccacagt caagatgtaa tagaacatta tttccatcat cctaaagagt tcttgtgtac   11280
ttaatctcag ccaatcttcc ccacctattg cccctagca atgatctgct tttggtcact    11340
agaggttaga tttaatgttt ctagagtttc atataaaccg aatcatgcag tatgtccttt   11400
ctgtgcacct tcttttgcac aggatattat caaaattaat aagtatcagt agctcattcc   11460
ttttgtattg ctgagtagta ttccattgta tgaatgttat atcaccaaat acacaatttg   11520
tgtcgccatt cacctgcagt ggaactatta acttgggttg tttctggttc tttgctctaa   11580
tgaataaagc tactgtgaac atttacataa aatttatatg catatatatc ttacattttt   11640
cttgagtcaa tacttaagag tacagttata gtacaggtaa ctgtacttct aagtacatat   11700
agtaagtata tgtttaactt ggtaagaagc tgcaaaattg caactgctt gtaacaaaca    11760 tttttacatt tccaccagcc atgtatgaga gttctggttg ttccacatcc ttgcaaacaa   11820
ttgtccatgt ttttaatttt aaccattcta gtagatgagt ggtagtatca ttttggtttt   11880
gattggattt caccggtgac taatgatgtt tgaagatctt ttggtgtatg tattggccac   11940
ttgtatattt tcctttgtga actgtctgtt caaataattt gtccatttt aattggattg    12000 tttgtctttt tattattcag ttgtaagagt tcttgtata ttctggacca aaattttttg    12060
ttggatacaa gtattaaaga tatttctctc tttctgttgg cttatcagtt ttcttaatgg   12120
taccattgaa gtgccaaagc tttaaatttt gatggagttt aattcataat tttattcatt   12180
taagctttgt gtcctttctg agaaatcttt gcctattcca gatcttcagg atttctccca   12240
tgtattttta gaagcttata gctttaccat ttaggtctgt aatccatttc aggttaatgt   12300
ttggtcttaa ctcaccagaa tttggcataa gaattttttat ttgaaatttt taaaaatgtt  12360
tctcagggcc caactaatac ccaaagctca ggattataga ggaacacaag tcctacttcc   12420
ctggttttga acatttttaa ctgagagtga gtacattgtg cctagttggg gttttcaagg   12480
ttcttcatgt ccttgacaca ttttaattca ctgaaatata cttattgag gatacagtttc    12540 cagagaaaga tgcctaagga gagtggccct agttagggga atgcgagtgt tgtcttcaag   12600
gtttcttatt tcctacaagg ttttaaggaa tttagcacta taccaattca ttttcatgtt   12660
ccgtagcttt tatctttaga tggggagttt gtttaaacct aacatttatc ttgagttttt   12720
aagggatgta gttttctcct tgagataaat gcttgatctt actgattttt ggctacatat   12780
tttacctcct cactttgtta tagctaaaga aaaagttttt agttactttt aactttgata   12840
agttgattac agatgggttt attatattta tttctttcat ttcttagaaa atatagatgt   12900
tacttattcc tatgtaattc ttattttaag atagtttttt aacttttctg ttttatttta   12960
tcacctattc ctattccttg aaaattcgtt ataagtaacc tgtgccttat ttttgttttt   13020
acagatctcg ctttttaata ctccttttag ctctgtgtct gtcttgaacg ttctgtatat   13080
taatgcataa ttccttctga gctggtatcc ttaggtgcat ttatagaaaa agcattgaac   13140
```

```
tgggaaggag tcttaaattt cattttcttt tctttttcct ttctttcttt tttttttttt    13200
tttttttttt tttgagacgg agtcttgctg tgttgcccag gctggaatgc agtggcatct    13260
cggttcactg caacctccgc ctcctgggtt caagtgattc tcctgcctca acctcctgag    13320
tagctgggat tacaggcgcg tgccaccatg cccgactaat ttttttgtatt tttagtagag    13380 atggggtttc accgtgttag ccaggatggt ctccatctcc tgacatcgtg atctgcctgc    13440
ctcagcctcc caaagtgctg ggattacagg cgtgagccac cacgcctggc cgaagtgtt    13500 aaattctaat attgaatctg ccattatttg gcctctgaaa ttgagaaaat aattccattt    13560
atctgggcct atgtttgttc atctgtggga tgaatatgat ggattattgt atgcaaggta    13620
atgagaccct gaagatgaga gatgtagtac cttgccctaa ggagattata gtgtggtagg    13680
gaagaaaaat gaggaaagaa acctttagaa tacagtttgg taactgatgt gatattctgt    13740
cttatatgca tagaggggat ggtgcttaaa ccaagtctta aagtatgtgt gtgggttatc    13800
ctagtaaaat atcctagtgg aaaataatat tccatacagg gggaatatta tgtgcaaagg    13860
cataacacac atgcacacac atattgtggg actcaagtca cgtttggtaa aactgtaggg    13920
tgagcggaag aatggctaga gatgaggctg gagaattgga tagtaagcaa atgaagaaaa    13980
aatgctttat attgctttcc tgaatttaga ttttatcttg acatgatgg gaaattacca    14040 caggtcttga agcaaagagt gacatgatta catttatata cagtaattta taatattatg    14100
tttctttata tactcagtgt taatatgatt aaaaatttaa gaatatatat gcttgcttta    14160
ctaaaagtga aaaagttgt aaaacctgat gtatcctgct ttcctgagtt tttgcttatc    14220
tattctgata atactaatag atttgcatag taattgcttc gaaatggtgc tgccactacc    14280
acttctacca ccaccataaa ttagtagaag acttacgcta ctagaagcat aagcagcctt    14340
acgttatagt ggctggtatc tgtgcaccaa gtttggctgt gcatttctag tccctgcact    14400
gttaggggga attgtatatt ttttttttcct tttctcaaat cagtaaatca gtgcaaacaa    14460
atgtgttgtg gatttacaaa cctatggaat aaaatgtttt tacttctatc aattatggct    14520
ctccaaagac ataaaatact cttcattcac tattactagt taattttcta gattatttct    14580
ggcatttatt aatggttctg catagagctc caccttgtga acatgttatt gtactttgat    14640
atcagttctg tgtcatagat atttaataaa taaaataaaa ctttatttac ctgaatgttt    14700
ctcattcaga atagctgtaa ttcaggcctg tatatgttt ttatttgaat agaaacagtt    14760
cactgttttt ttggaggtta tgctgtatac tacaagatag attaaaacca gtgcctttt    14820 ttagaccagc tgctgaggaa ataccttat catgtttcaa cctcttaagt ttaataattc    14880
tcatgtaaaa attagtgctt gatttatgca tcaatttct aaacatttca catgtgatct    14940
actttgtata ttcagggact tttgtgttct atgttattat atagcgtatt ttttaaccaa    15000
aactttaaaa attaacctca tttcattagt atttgtttat actttactat accttgttta    15060
catgcttaac ctgcctatgt attatctgtg acagtaatga aactgaatgg ttataaaatg    15120
ctatataatt ttatcaagtt aagctgactt ttttggtggg gaacatcatc ttcctcttgc    15180
taatagataa aggagttta ctgtactaat ttcaaaaatg gtataaagca gtaaggcaga    15240
tcttcacagc ctattctttg acagtatatt aagcatgtgg agaggaaagc aaggtgttag    15300
ctattttaag gtttcacagc aacactccca tcttgttcat tttcacctga gttgtataga    15360
gcctgggaat tgctatatat ctttaatgta aagtcagcag tgcaagtaac agtattggat    15420
catacttcca ccattacatt ctctgagttt ctgatcacca cattctcaca gataaggaaa    15480
atagttgtag atggatggtc tgaaatgtaa aaaggataaa gaacacaaga agtggtaaat    15540
```

```
atgtttagtt tcagacagac attatataaa acttgggagg agggtaaaat tattgattag    15600
ctacgggtag gcttggtaag ttttaacgca tgttaaaatt tctaagataa ggaataaaaa    15660
tctagaaggt atgtgtacct tacaaactag tagagaaggg aagtagaaca agaaacaata    15720
ttcaatctga aaaaaggta aagaagctga agaaagaaaa catggaaaag agaagacaag     15780
tagcacaaaa gtacatagca gcaataagtg caaatatatt agtaattaca gtgcatatga    15840
gttgaaaaaa tcctccactt aacagaaact ggttattaga tgggataaaa taacaaaata    15900
tatttatatg ctgtttacaa gcaatacctt aaaaagcata ttctcgcttg aaagtaaaaa    15960
ggatttaaaa agatattcct gacactacta accaatagaa atgttgtatg gctatatata    16020
tcatgtaaag ttgactttga ggcagaaaac ctgtccgaga gagtgagggt cactcaatag    16080
ttataaaagg aaggtataat tttaaataag tgactacctg ataatacact ttcaaaatac    16140
attaagcaga aactaggact gcagaagaaa taggtaaatt tatcattatt atagcttatt    16200
taaaataatc tctgttaatg tgagaacaag cagaaaaaaa ttaagaaaaa tatagatgat    16260
tttaataaca ggacttacaa gcctgctgta atggacacgt atggaacatt gtattccaca    16320
actaaagtag aggaggaaca cttagaaaaa ctgatcacat tctggtcaaa tacagccagc    16380
tttaacaaat ttcagtggat tggcatcaca ttacactttc tgtttacaat tccattaact    16440
taaatagaaa ttttgtgtgt gtgtgttttg gaaattaaca tgtttatttc aaaataactt    16500
gtggatcaaa gaaaaacttg taatgatagc agtaaattat tgtacacgac aacttatgta    16560
tagctaaaat gggaatttat agattttaat gcttatatta tgggactaaa ggttgaggaa    16620
taataaacat gcaattttaa gaattagaaa aaaagcatac tccccgattg aaataacagg    16680
ggaataatta tgaactaga gaaagtaaaa gtaattcaaa aaggaaacaa tgcaactaaa    16740
aatagattat ttgagaagag taacaaaatt agcaaaccac tggcaagatt aataggtggg    16800
gaaagaagtc ataaagcagt atctggaatg aaaatgggaa tgttactaca ggtgtttcat    16860
gaatgatcaa ctttatttta atgcagttga aagattaagt ggaccaattc ctaaaaaaaa    16920
atgtagctca tgctggccca agaagtaata gaaaatggaa taccctaaa acaaaaagga    16980 aaaatattct tacaaagaaa aaaataccaa ttctagacag gtttactggc aaattctaca    17040
aaacattcaa ggaacaataa ttccagttgt acagagagta tttcatggtt tggaaaaga    17100 aatgactgtc cccaactttt ttttacgaag ctctaagtat aaaaaatgat gattgtctt    17160 aactcagacc tatgtacaaa aattcataga ttagatatca tcacatggta gtaccccctt    17220
atccatctgt aggtggttac ctatgctcaa tcacagtccg aaaatattaa atggaaaatt    17280
caagaaataa aaattcatat gttttaaatt gtacgcccag gatgtggatc ctcccttgt    17340 ccagcatatc cacactgtat atgctacctg cccattagtt accattggta gccgtcttgg    17400
tcatcagata ataaaaaaaa acatagtatt tatagggctt ccatgctatc catggtttca    17460
ggcatcctca gggggtcttg aaacgtatgc cctgttgata aagggaatt actgtacttg    17520 accaataatg tgtaagaaag taacccatca taaccaagtt gggtttactc tagaatttca    17580
aagttggttt tatattagaa agtcacttaa tagaatttac cacatcatct gtttaaagga    17640
aaagaatcat gtgagcatct caatagatcc atctgtgata aaactcttag caagtcgta    17700 aatgagaagg cccctttctt aacctgataa aggcattttt ttccaaagaa aatttccagc    17760
cctaccttct ttccacttca tggtaaagta ttgaaggcat tggttcccct tgatatcaaa    17820
ggacaagtgt gcctgctaat gccactttta gtcaacattg tactagaagt atagctagta    17880
```

```
cagtaaacaa acaaagatac aatgattaga aagaaaaagc tattattatt tgcagattat    17940
atgattatct gtgtaaccca gaaaaattca cagatgaatt actcaaagtt taaatttgga    18000
tgcagaatta ttatacaaat tcaattattt ttcagacttt ttgctggcat agaaatgcaa    18060
ttaagaggta gcattatatc atcataaaag tataaaacac tgtgagtaaa tctaacaacg    18120
tgctcaatat ctttatggag aaattatgaa acattggcag acataaagat ctaattaaat    18180
agcataatgt accatgttta taaaggaga cttgaacatt gtaatggtgc catttctccc     18240
caattttatc tgtaagttct gtgccatctg atcaaatat tgacaggttt ttgttgaatt     18300
tgacacgcta atccaaaaac ttacatggaa gaactaagag ataatagcaa gatactcatt    18360
catgaaatgg atctgtgatg gcactgggat tgccaatgag tgaaatagga tgacccttc     18420 aataattggg gttgttggtt aattaaatgg aaaaaattgg ggttggactg ctgcctcaca    18480
ctatttagag aaaccagtgg aaggattata gatctaaatc tgtaggtaag gtaaaggtat    18540
aggtaaagta aaatggtaac actttataaa gatgataggc tagaatatct ctatgacttt    18600
gagtaaagat aaaaaggcat aaaacacaga gcaaagatt ggcaaatatg actacatcaa     18660
aattaagaat tttgtttcac taatagatac tgtagagtgc ctaatcccgt atttagcaca    18720
tatcaaaatc taccacccag ggaaataaag atgaacaatc tgatagaaaa ctgggcttga    18780
ataggcactt cacaaaagaa taaactcgtt tggccaagga gtgtattata agatattcaa    18840
cctcattagg aatcagggaa atgcaaatta aaaccacgtt aagaaggcat ttcatgtctc    18900
ctagattctc aaaacttaga agccagctaa tactgctgtt ggtatagaca tggaacaact    18960
gaacacttag gcgttgcaga tgctaatgta agtaggtaca ttcactttgg gaaataattt    19020
cacattatta aagttgaaga tacacataac actatgaccc agtattccta tgtcttagag    19080
aaatctctat acagacatac caggtaatgt atgtagttgt ttatacagta ctgatcacaa    19140
taacaaaaca aaaaaataaa taataggata agtaaattgt agtatattta tacaatggaa    19200
tgcaacacaa tactgaaaaa tgaatgaatt acacctgtgc ttaacaactt ggatcatcct    19260
aggaaaataa tgttcgaaca aaacaaatca ctgaagaata tagtgtgatt ccatttatat    19320
agaatcaaag aacacgcaaa attaagtaat atattgttta aggataccaa tacacataat    19380
acaagtctat gataaacata aaatttagga atgagtgaat ttggacacag agtagatatc    19440
acaggtcagg ataatgtgtg tttaaaaaaa aacgatggtg gaactcagat atttattgta    19500
ttacttatta taccttaaat ttattttata gaattcttta atgtttgata ttaataatta    19560
ctgatagtaa tttatggcta ctgataatca acatttaatc taaaatagta actgaaaaaa    19620
taaaagtgaa tgattttgg gggaactcag tatttgccat gtatttccta tgtacgtatg     19680
tttaattttt gtgagttctc aaatgtaatc aatttctttt gagtatcttt agtattttat    19740
actatctttg tatttaatat agcagataaa gcttaataat ttctttctgt ttttttttt     19800 tttttttt tgatggagtc ttgctgtgtc tcccaggctg gagtgcaatg gcgcaatctc       19860
ggctcactgc tgcctccgtc tccccggtca gcgattctc ctgcctcagc ctccccagta     19920
gctgggatta caggcaccca ccaccacgct ggctaatttg tgtatttta gtagagacag     19980 ggtttcacca tcttggccag gcaggtcttg aactcctgac cctcatgatc cacctgcctt    20040
ggcctcccat agtgttggga ttacaggcat gagacaccgc gcccggccta agcataataa    20100
tttctaaccc tggttgtgtg atactccaaa atgtattcat ttattttag gggtataggc     20160 atttttaatt cttttatatt tttgtagtca ctaaatttac ttggcttcta cctttacata    20220
ttttctgttt attgaccacc ttttaggaag tttgagaaag gtattacctt attatatttt    20280
```

```
tttctaactt aaaatatgtg tgttactatt gcacttgtgg atataacatt tcattttaga   20340
atatttacat tttattttgt ttatcaaaca atagcatttt tgtatcaggc actattctca   20400
atatcgttaa aatattaatt tatttagtat tcattgcaac cctatgagaa agatcctgct   20460
atctttgata ggtaaaggga aactgaggca cggaaagtgt tgggtaaggt cacttagcta   20520
gtaagtggag cctgtgttca aacctaggca gtctggttcc acagtctgtg cacttaacca   20580
ctaagctgta agagaccata tgaagtagat ctctaagagg agtatgtcat ctatttcaat   20640
gttctttaat aaacagggta ctattttga gcggtgccag catattgtca gattatgatg   20700
aaataattat attattccct ttgtttgatc tgagaatgta aaaagcaata ctggtaaatt   20760
acacactgct ggacattgct tagatttact cttcaatgaa ttttgtgtcc gtacgttcat   20820
gagatgagaa aaatagatag gcaaaagtac ctgttagtct gattgcagat ctacccgtaa   20880
tgcacaaatg gtgatagtgt actttcttct tccaaaggtg ggttaatgga gtcatgattt   20940
aaaataagag tttaacagta gcgtgtataa atttgatatt tatacatcat aaatgatgta   21000
taaatcattt atgggagagt gatatttgat tcagggatgt tgacatgata cctttgggaa   21060
attctcatag taaaatagag ttagactgtc aacagggaaa attctaagta atttgtgaag   21120
aaactagtag tagtagtcta aagtgaggca ccaggcaaag agagaagaat cagacaaatc   21180
ctttagagta atagttcttt acccattcag acccacactc catttagagc atttactgta   21240
gaagttcttg agagaagatc tcatcctgta gccatatatg ctcactatat atatagatat   21300
aaaacatctc taagaatttc agcttctctt tgtgcttttt gttagctact ttaaatagct   21360
taactttcag tgacacatgg ttttaacagg caaaacacat gactgttaat gatttttctt   21420
tagagcagaa atggtttata tggcctaaat tcacttttag agaatcttct gagagagagt   21480
atttcctgtc tctttgcaca tgtgtggcat attgtaagga cttatttact tttaaataaa   21540
aaggaaagct cttgcagtga agtagacatt tattttgtta agaacctata taaggccagg   21600
cgccgtggct cacatctgta gtcccagcac tttgggaggc tgaggtgggt ggatcacaag   21660
gtcaggagtt cgagaccagc ctgaccaatg tggtgaaacc ccttctctac taaaaataca   21720
aaaaacttag ccaggtgtgg tggtgcacac ctgtaatctc agctactcag gaggctgaga   21780
caggagaatc gcttgaaccg gggaggcaga ggttgcagtg aactgagatt gcaccactca   21840
ctccagcgac agagagagac tctgtctcaa attaaaaaaa aaaaaaaacc tatataaaat   21900
agtttatagc agtttatagc tgtgaccatc aagtcagata atttgggatg ttcacagaga   21960
gctctgggtg attatgacag tgtaccaccc acatctctta tttgttttgc ttcatttctc   22020
tactagggag aggaggtcat ataatatatg gtatttttat gttatttag ataaatccat   22080 atcaacacag cacaggagaa caaattatac ccctggtaga ttttggggta taaacgtcat   22140
gaaatgtttc tcagaaagtg agaaatattt cttgattgta tctttaaaat taatgcaaaa   22200
ttgttatgtt actccataat ttatttgtgt gcattactgt aaggttcatg tgtattcata   22260
ttaaattttt tcttttaaaa attgggttca atgaattatc taggatgatt gcattgtttg   22320
tggcatcaag tgttgtttct cccttttccat accaagcata tcctgctttt ggtacaggat   22380
atattttttt cagatgtcaa aacacctagg gatacatttt tgaattact aacttacttt   22440 tttaggacag acttgaaatc atttagaggg taaactctag caatatagaa atctgttttt   22500
tgttgaatgg agtagcagct aatctttaag acccattgat agcatttag tagtagcact   22560 taacattcag aaaagaaaaa caaatcatcc agcttctgat cttcagtttt atgtaacttt   22620
```

```
acaatttggt acttgatgac ttggtattgg tatgagactg aatagtgtga tgttacaaac    22680
atgtgatgtt tgcctaccat gttctaggca ctgtgccaag tgctagagat ggaatggtag    22740
gtaaagctgt ggtctatact tagggagttc acagtcaaat gaaggataca gtcacaaaac    22800
agacacttgt ataaagcatg gtcactataa tacagagaaa tggaaagaat ggccagagaa    22860
agcttacttg aaaagataat gcctgaactg aatactaaag ggaggtcagt gggagagaca    22920
aggaagggta gatattgatt gtgagtgcat gagcattgaa atgagagggc caggggaat     22980 aggaagagag gaatagccta aaggagaaca ggagcaaagg cacatgggtg agaaacaaca    23040
tggaatgttc tggacataca agcagatctc tgttggaagg agtatgagat aagggtaaga    23100
gagtgattgg agttgagtct ggagagatac gaaaccaaat catggaagct ttttaaatgc    23160
catgtttagg agcttgaact tcatcttttt gtgagttgga cagtcattga agggttttaa    23220 gtagggccc aatttgattg tattcaggtt gagtagagta ctctgatagc tgatgtgaag     23280
gataaatttg aagggaaaaa gattggaggc agagaggcca tttgggaagt agttagcttg    23340
ataagaggtg acgagggctt aaactgacac ttaatagaaa tggagaagag ggagtagatt    23400
tcagagtctg tactttttt gttgttgata aatagtaaat ttagtaggac tcgatgcttg      23460
gaaatgacca gtgggagaga aaaaatggac gagattaact ccaaagtttc tagctgaggt    23520
gattccaggg atagcgatga caccaaacag agtgaatata tgaataatca gttgaggaga    23580 caaacgaag tcagttttgg atattttgag tttaagatgg ttgtgacatc actaatggag     23640
gaaggctaac aaggcagtta acctttgaac ttgatgctgt gggatataga tgggggtcct    23700
gggctggaaa tacagcttga agagttcatc agtttgcagg agtgattga aagcataaga     23760 ccatcaaggg aaggtgtgtg ggctgaagag aaaaaaaggt cagaagacag gagcttggag    23820
aacagaagtg tttcagagtc aagtagagaa aaagaagccc cacaaagata agaaaaggaa    23880
ctgaaaaaaa tgaaataatc agtgggccaa cctgaagatc caagcaagac tagaaaccac    23940
acatttttaa tggaacaaat ctatatcgtt gtgatttcct tagaagcctt aaattggtgg    24000
gggagatcag aatgtaacat tagtctagga ttgaggtttt accagatggt acagtaaaag    24060
ttgtgagttt agggaaacca agttgtttga agttagagca gtttagatga tcagctgtgc    24120
caaatattgc aaattatgtg ctgtacatta ttctttacgt atattaactc ttaaccctca    24180
ccacaaccat agttgttaca gaagattcta gaatgtaagt tccataagag caaggtgggt    24240
atgctttgtt gtctgtgcta ttctcagtgc ctgacataca gaataggctc aaatacttgt    24300
tgaataaatg agagaatatg agatacatac tattattccc attttacaga tatggaaacc    24360
gggtaagaag agattaagta acttacattc acaattttta gtggtagagc cagtaggaaa    24420
ggaattgagc ccaggattag ggagctgatg gaaaatagag aaattttagg tctgagatc     24480 tctctgagga tagtggaaat aaaggcatga gagatgtaga aggggagaaa gttatcatca    24540
gagagtaaaa tggtggaggt tatgattttt tgagataggg ttgttcagtg ttatgacaaa    24600
gggtcaagtc ttagcagtgg agtaaaggat gtttattatt gaatctctgt aggcgtcgat    24660
gtagatgttg aaggctccta aggttatact agaagtttga atagagagga acattatgat    24720
accatcctca taaatgaagt ggtataattg gagatctata gataagaagc agcagagagt    24780
ggaatagata agcttcttta tttcaattct agcttttaa acgtagattg aggttagatc     24840
tggtttgctg aaaagacagg aataaattgg gcttgctgca tataatttat ttcccccata    24900
tggataagct cgttggaaag ctccagaaat attcagaata taaatacaaa agtttcaaat    24960
tttacctgac atgccagctc tacttaaggt atgaattcta aatcttgtat ctctcccctg    25020
```

```
caagaaaagc tacctcctcc tttttatata gtagtagaac aaaatttttg tttgtgtttg    25080
tggcagcaca tctcacctct ttgtttcata gctgttgggt acacattcca aggacggtaa    25140
aaacaaaatg cacttgctct tctaaatctt tagccactgg ctagtggatt gcatttattc    25200
tcagtttcct tgccgatcct tttacccttc ccctccccca ttttctttt tgaatggttt    25260 tgtttcatga agctcttgag agctttctat gttatattgt ggcacaggaa aaagtttatt    25320
cattttagca ctaaactgta gttaacattt taagttaatc attttagaa tgttttgatg    25380 agcaatcctg tttcattttt agagatgatt caatctgata tttcatttgc ttttaaagtc    25440
tctaatttct tttcatctat ttccatagca ttgtaattg tatcctgaac gtttctcttc    25500
agagaaatat aaaaatccag caatccatta tagtattgta ttaagcctaa gatttcatta    25560
tttatcatac acatttattt atttatttt attttttatc atacacattt aaagtacggc    25620
ctttgattta tagaattttt cattttgtgg ttgtgcctgc ttatctttgt ttttgtgtgt    25680
gtatgtcttt cacagaaatt agtatcattc tgtcatagct cttaggaaat tcagagttaa    25740
tcaaatatgt tataaaatgt gtttgtataa tgaaaaggtt ggaggagatg attctgaagg    25800
tgccatttag agcaggtgtg ctatggtttg gtggctctct attctctgcc cgctttaaat    25860
cttagtaggc agcagatgaa atactactaa gtgaccttg acacagaacc catgaatgct    25920
ccaagtatga tttcatttta ccgtgttctt tgtaaactca aatgcctgtc aaatcagatg    25980
tgtgtttcga tgttttttact gaatgcgcct tgaggaggag actaaagctt ggggtcaatt    26040
tggcataatc cccacgtttt tcttttctta ttatagaggt ttcttgggga agggtgaca    26100 tttctttctg aggaaaaggt gcaggctaag tgtaggtgga ctttctgtct tctccatact    26160
ttttctgaca gcctcactgg atcctggtga tatcatacat aaatgcagag cagactagat    26220
gggttgctgg ttggtatttt tggttaccat ttgatctggt gtctttggtt atgtaatagg    26280
cacattaact gacaaattat attaagtaaa tatatagcca tgggctttt aaaatctcac    26340 ttttaaagt caataattag attagattgt ctcccagtaa ttaagtttt catatgttca    26400 tggatatatg tagtatatat aaaagatta tttgtgtatt ttttacatta atttggtaat    26460
tttgacaatt tgtcaactca agtataaaat acttacatat aaatatactt aaataagtat    26520
ttaagattta atgtcaactt tacagtaatg aaatagaaaa ttcttgaatg ttactcattt    26580
aaattttctg atttgagttc tgataatctg ttagaaaatt agtaatatgc ttaggctcac    26640
ttcaatttcc ccagcagaaa ctattgtatc cttactggtt agaagctgcc aatagtcatt    26700
aattgttaaa atataagaag gttgtagggg accatatgac aaaagaacta gttacctta    26760 cagtttgttc gctgtacctc atacactttg tgttagaaga aagctctat tcagtgcctt    26820 gagtgaaaag atccttacct cctttagac tccgattgtg ggaattttct tgctatcctg    26880
gacattttaa cttgttctgg gttatttga acatattaag gtggactcct ggaatagttg    26940
agaactaatt catgttgtt tgtttttctg aatcagcagt ttagtgatta agcttaaga    27000 ttctttaat agatttaatg aaaagaaat cttaacttga aatttaaatt aatgaaaaat    27060
attaccagag gagatgtctg atattttgat acgggaaaat acagaaaata aaacatttta    27120
aaaatttatc cagatgttaa tgtttgactg gaagttttct actggaagaa ttagtttgga    27180
ttttacaatt tgggagaggc agaagggagt tggggaggtg gtcaagccca aattagcatg    27240
ttgaatatcc agattcacag acatttcact aaaccattta tgtacttagc atttttgttg    27300
actagtcttt tcatttatag tgctcttaaa tcactccatt tgtcagttac tccatttacc    27360
```

```
tgaagattaa agtatacact gtgatagaaa aaaatagatt ggcaggggcg ggggttgtat    27420
tatataatgt aataaatcct attaaacctg ttaaagtaga aacattaatt ttacgtttta    27480
gaattttctt aatgacagga aagtaaactg gtaactaaaa ttcattttgt tctgtaggtt    27540
tgtggcattt tatgtgggga atgtagatgc taagtgttat gagttgtcca cctgtataaa    27600
actacttccc agaagccttg atgttcccat aaagagctaa agacaaaacc aaatcaactg    27660
ctaacacctt ttatgggaga tcaacttgtg tgggttatga ggcccacctt gactaagcag    27720
gatatgtagg taaacctgcc cagttggaat tagtagctga tactctaaaa ggagaatggt    27780
gaacaggagg ccattagcag aaacagcctc attcatttat agagatcatc ttgttaaaag    27840
ggaaatcagc ttccctagat cccaagggg tattgaaaat gctaggagag agcctagaaa    27900
acttttctgt gcagattgtc agaaaaaggt gaaaatattt tcttttactg taaaaagaaa    27960
gaaattcttt tccttcttcc aaagatgcct taccacctt gaaaaagatt tttaaaagtc    28020
tcagagaaaa tgaaatatag attcttaaag tggaaaggga ccttaaaaat ccatctggtc    28080
tggttcattt tatagataga actgagaacc tcaaaaagtt atgtaatttg gcttacatca    28140
caagagctag tttgaagcag aagctacgat tttcttactg tgtccagttg tttggaagta    28200
tgaatagtca tcattaaaat gtagggagtt tataggggaag cttatgacaa ctattagtta    28260
atttacaatt tgttcactgt agctcatctg ctttgtttca gaagaaaaat tctatgtctt    28320
gtgtggaaaa actcttacct ccctatgaac agaactatag gaaatttctt gctaacttgg    28380
atgtttcagc tacttcaggg ttattttaag taactggata gttggttttc agaattctag    28440
ttacagaaac tagtaaaaga atatgagttg ttgatacgtg gaaactttag acccaaaata    28500
aaggtaggat gatgtgagtt tagtgcttac aaatttgaat gaaatagtac cttttttgagg    28560 tgttttagta gttgcccta atgatttatt ttaaattaga tggctttggg agtaaaaata    28620
ctgcttttag caaaaaataa atataaaatt gaaacttttg cacgtagagt ttttttttc    28680 tttttgagat agataaagcc atctaatgtc cttttctatc atgtcttgat aagtcaagag    28740
cagaccactt gatgaagaaa atgaaatat catctaaaat agaaaaatat cctgttagga    28800
aaaataccac cgttttttcg ctgcctttag tctggttgtt cttattgtgt gaagggaact    28860
taaatcttgt caaattacat acattgtaag tcccattct gtcttaaaag tataaccatg    28920
catgctcaat taagtcagtt atcgtcttca gactgtactt ttgctaatta agtcttttcc    28980 ttgggggttaa gataagacaa gatttacaga tttttaagtt taaggcctgt aactactgag    29040
gatggtttaa agctttgata agtgagatgt ggtgctttaa aggaggactt tcctttagtc    29100
tcttaaaaac acttggaaga tatttattac agttttccaa agtaagataa agctcagctt    29160
taataatgag gaccttgaag ttttttttatg tggtggggag gtgttaggaa actcattttt    29220
taactacctt caagtgatta tcgaggcagg ttttttcttcc ctatgaggaa gaaaatgaat    29280
tgtgcaatgc cagtttaaag aaactaaagc aatgtatttc ttacataaag tagatcattc    29340
tctctccctg tgtaactgcc acctgtttaa aataagattc cagtcttgcc tctgtcagtc    29400
ttaatgtgat agactctcac tcagtgaaga tctatggatt tatttttattg aaaacatttg    29460 tttagcatat atctgtgtta tttttaatttt aatgttttta gagatgaggt ctagctattt    29520
tgcccaggct ggccttgaac tcctgggttc aagtgatcct cctgtttggc ctcctaggta    29580
gctgggacta caggcatgag ccaccatgcc tgggtaagat ctaatgatt atttgattga    29640 aaacacttat ttagcataca ttcatgtatt tttgtaactt gttgcctcct gacaggtcac    29700
tagacatagg aaagtgcctc ttttaacact ttcataaacc tttaacataa acattttaaa    29760
```

```
tttcttcatt atagtggaaa tagcgtctcc ccttattatt ggacattttg aaaaattaaa   29820
aaaattttaa aacaattttt atcataaata ctagatggga ataattatat atgaagcttg   29880
tctgacaagt tggatttta tgataggata gaatcccagg agtagaatta ttgggcatac    29940
ccttttaagc ctcacagtaa attattacta agtgtgttg caaagatttt atcagttgta    30000
tagactccca gatatgaatt ccagggccct tcagggaat tagtggggac attttgcaaa    30060
gagcaacaga tggtgtctgg aaacatgttc tttaatcttt gctgtgccac atactagtta   30120
tagatatctg ggttagtaac ataggttgtg tgggccttac tttcctcacc ataactcagg   30180
tgaattttaa ctattctact ggccttaatt ctcattctgt aaaatatgag tataatcaag   30240
gagaatcagt gcctatatat taccaagtga tttgtctggg aaaaagcag aagcagggaa    30300 tgtcagatgt acctagaaaa aggagcaagt taggggaaat gcacaaaaca tgatttgctc   30360
ttctggtttt tttaagaata gagtctaggc tgggtgcagt ggctcacacc tgtaatccca   30420
gcactttggg aggctgaggt gggtggatca cttgaggtca ggagtctgag accagccttg   30480
ccaacatagc gaaaccccat ctctactaaa aatacaaaaa ttagccgggt gtggtggcgg   30540
gctcctgtaa tcccagctac tcaggaggct gagacaggag aatcacttgc acctgggtgg   30600
tggaggttgc agtgagctga gattgcacca ttgcattcca gcctgggtga cagagtgaga   30660
ctcggtctca aaaataaaa agaaaaaaga aaaatagag tcccataaaa ttatgtcaga     30720
tagacactcc tcctgagact tagggatttt caaaccattt caaatagaaa atgaaagtgt   30780
aaggagacaa gtgtgtaact ttccaaaaga agttgtgttc tgtgtccgtt ttaggttaca   30840
gaatgactca agccaaaaaa aaagtatgtt attcattcat ttacacaaaa tacaaaatat   30900
tttcattatc ttctgttatt tgtttaaatt gataaaatta tatttatggt gtacaacttt   30960 atttttgat atatgtacac attgtggaat ggctaaatca agctaattaa catatgcatt    31020
acctcacata cttttttgttg tgagaacacc taaaatctac tcttcacaat tttcaggtgt  31080
acagtatatt aactgtaggc ctatgattta ccatggatct cttgaattta ttcctcctgt   31140
ttagatgaaa ttttgtatcc tttgaccaac atttccccac cccttctaca ccccagcctc   31200
tggttaccac cattctactc tctgcttcca tgatttagac tgttttagat tccacgtata   31260
agtgagatca ttggcatttc tctttctgtg ccttagctta tttcacttat tataatgtcc   31320
tccaggttca tccgtgtcgt tgcaactgac aggattttct tctctttgaa ggaagaatag   31380
tattctgttg tgtgcgtata ctacattctc tctatcagtt catctgttga tggatactta   31440
ggttgattcc atatcctggc tcttacgaat aatgctgaaa tgaacagggg agtacagata   31500
cctcatcaac acactgattt catttctttt gtatttataa ctattggtga gactggtgga   31560
tcatatgata gctccaatgt tagttttga ggaccctcca tactgttttc catagtggct    31620
gtaccaattt acattcccag caacagcgta caggggtttc cttctctctg catcctcatc   31680
agcacttgtt ctgtttcatc ttttttgataa tcaccattct aacaggtgtg aggtagtctc   31740
tcattgggtt ttaatttgca tttccctgat gattagtcat gctgagcact atttcatata   31800
cctgttggca atttgtatgt catcccttat gaaatgtctg cacccttgtc tgtttttta   31860 ttaggtttat ttattttctt gctatttagt tgctttagct ttttacatgt tttggatact   31920
aatgtcttat cagttgtatg gtgtgttttc aaatatttc tcccattctg caggttgtct   31980
cttcactctt gattgtttta tttgctgagc agaaattttt agtttgatgt aatcctattt   32040
gtctattttt gttttttgttg cctatacttt tagggtcata tttagaaagt cattgcccat   32100
```

```
accagtgtca gagagctttt tccctatgtt ttcttgtagg agttttatag tgtcgggttt    32160
catgtttaag tatttaatca attttgagtt gattttcgta aatgatgtga gatgagggtc    32220
taatttcatt cttctgcatg gggacattca gttttcccaa caccatttat tgaggagact    32280
gttttttccc cattgtgtgt tcttggcatc tttattgaaa atcaattgac cataaatgtg    32340
tggtctctct attatattca tatttttaa gtaaattatt ttatgatgag aaaggtggca     32400
aaaattctgc attatctttg atatgtaaga aaaggccatt tgggcacaga ttggacctga    32460
ttatttctct tttcaagaag caagtacctt atctctattc ttattccaaa gtgatttaat    32520
ctctattaat aatttaggca actaaacatc attactgatt gtaggagaaa tctgagtcta    32580
gtctgtctat actgatcaag aaccaggact acctcatgga gactttggta aaataaatct    32640
caacagcact caccagatga ataaaggttt tcttgaacta gtttaagata cttggttatc    32700
agttgaacac aaatagtaat aatttaaggt ttcatgaatt gacatgtcta taattagctt    32760
cctaaactaa gaataacaaa aaatgagtag tttgttaatt cctaatagcc tgtgatgaaa    32820
gttattatct ggggtttttt ttgggtctgt tttaaaaatt aacactttgg ctctgattat    32880
aaaatttata aattggaaat tgaaattact ggataaaata caatttatgt tttaaaaaca    32940
ttttcaagtg gaaaaaatta cagcttggct gaatagtgat aattttcaaa ctaagccttt    33000
gagttcacta tttagagttc tctgataaat tgttagagtt agaagtagtg agttcattgc    33060
ttgactgaat aaataattca tatggcacaa aagcagcttt ttctttctct tcagttccct    33120
tctcccccat tatgttcact ttctctcttg taaaaggctc ctttgcagcc aaatagcaac    33180
cttgtgtgaa tatgcaggga cttgggcata gtttcaacct cagtgttagc tgagtatctg    33240
gagtcatgga agagaattaa gaatctgtct tgaatgtata ttttctagta gcaactgaaa    33300
agaaatatag tagttgtaaa ttgctagacc ttactcttac ggtacagttg ctctggaaat    33360 ctcttttag caaaatagga ttttatttct ggatatagaa tctttcgtag tgtctgcgtc      33420
aaaacaaaat taagttttaa aattgagtaa atcatttatt ttttctagtt ttttcagaaa    33480 tgcttttta ctagactaaa taacttttca gcatcagtct gataagcata gaattttcaa      33540
aattctttac ttgctatttt agaattcttt attttctaag aattatgaag actgtattag    33600
gtatttatgt ggacttcctt ttttttcctac cttttattat agcaccaaaa ttggaattac    33660
gctagattat tttctctctg ctgttaaat cataagagac tcttttattg ggtcagggca     33720
attgtctttc tagcacaata atcttctttg ataatgtcac tactggaaat tatgtttatc    33780
cttcataaat taactaatcc ttatttttgt aataaattat ctgatatcct tcagaggtta    33840
tctaaaaata ttcctttaag tctgcatgta ttcagcatat ttcatggtat aacaagactt    33900
ttacagttgt ataacagaaa tttaaaataa ggcaacggac tgtaatccag acttctgtca    33960
actggaaatt tttatgaagt agtattttgc tggtatactg atacttcacc aaatacaatg    34020
tttatcttta aagaagtttc taaataagac aaaacattat gtttagtaaa attcaatgta    34080
gtatgtttta ctgtatacta attctttata tagcccataa tcataataca taggctatat    34140
aatacatgta aagcatataa ttcataatac ataggataca aatcaaatat atgagctta     34200 ttttgatata atcagacttt attctgttac ctatttgcct ttctttttca aactttaag     34260 cgttgccctt attttcataa gacttagtgt ttcactcagt attaaattta tccaaagtca    34320
tgtgattttt atgaaacatt gtgatttaa gtgctgaacc atgttgtttt tcaatgtaaa     34380
atgagtgtaa cttttagtaa ttattgaaat ttaagcgtta ctgtgatttt ccataattct    34440
atttcggtag tcacaaaaaa acaaaaattt ggcttcttat tggcccttct agtgccaaca    34500
```

```
ctggcattgt tgaaatacat ttctaaggaa gatggtgagt gtttcacttc attagtagct    34560
gcatgacaag ccaccccaaa gtttaatggc ttaaaacaac agtaattcat tatttctcat    34620
aattttgaga gttgactgag tgagtcttct gctttgtgtg gtcttggctg gggtgctagg    34680
aaagagggca gtccacagtg gcctcactta catagctggc agtggatgca ggctgctggc    34740
gtggagcaca gttggggggtg gcctgggtgc ctcagctctc cttaagtgtg cctctctgtg    34800
aagttagttg ggcttgctta caacatggta gctggattcc aaaaagaaat gttccaaggg    34860
caaagaagct gcagccttttt aaagggccat atttagaagt tacttagcat tacttctgcc    34920
cattctgttg atcaaaacaa gtcacaaggc cagcccagat caacaggaag agaaataggc    34980
ttcatttgtt aaagatggag tagcaagatt acactgtaga agagcaaatg gtttgggatg    35040
tattgttgca gccatctatg gaaatgcaaa ctaccacaag gaagtgcagt ttttgctgag    35100
catgggtatt tgccattacc acatttcaga aactggtata gtcaagcaca catggatttg    35160
accactggat ttacactagg gtcacttaag agctatcagc cactgtcttc tcatctgtat    35220
gacagtagta gtatcaacct cacaggattg acagttaagt gagataattt ggaagtacac    35280
agcgtagtgc tggaaattcc attactccca tcctgtttct tttcccatgt ccctcatgtt    35340 taattttttat atttgtgatt ataatactta aaggtatgtt ttaaagataa atcataattc    35400
atctaaagtc tttgtcttac caagatagtt caatagttcc aatctgaata agtttataa    35460 cattaacata atttatagat cttctaatac aagcatctgt ctaatgctag aattctttat    35520
aaaccactgt atataggcta ctcacaatgt aatgagctac taattggtag aaacaagtgg    35580
ctatttgcca tagttctaca ttctgttcta ccttctattt tgcagaaaaa tcttacagct    35640
ttcctaagcc atcttttttag gtcaattcca gaatttgttt atgatcaaat tgacaagtac    35700
ctagccaaag agattaagat actgaatcag agaaagaagt ctaaagagat aattttccaa    35760
tgatcatttc taaagaagga atagagataa aatattttaa aacaggtact gaatagtcac    35820
agtcaaaggt ttgattatga gtcagctttg ttggttttag tctcattagt caccagcacc    35880
accaacctgt catattggca atacatagtt ttggtcacca ggagaaggag tcacagaaaa    35940
ccagtactac tacttacaga agattaactg aaagcacatg tcctgatttg ttcttgaaga    36000
taagactgag gtgaatattg cttaaaacag tatcagcaaa atacaaaatc aagtgaaata    36060
ttacattgaa tataataatt gaaagaatga ggatagacac aaagaacttt tggatgctag    36120
tgattagata ttagaattag ttttctcagaa tattttaaag aatttaacaa atgacagtgt    36180
tatgaattat gtgggcagtg cttaaagtgg gaacagagca aaagaagtgg atttagtttt    36240
gtcaagtctg tctgttcagc gttaggggga acattttatt tcttctgaaa caatgatatt    36300
ggaatcccat ttcatctttt cattttcaaa cactgacttt ataagtgact ttgggagaag    36360
cttttaagtt ttatataaag cactttttttt gtacttagca caaagtgggc accttttaaaa    36420 ttacctgttt gtatagcagt taatttaaag aatatgttca tgcatattac tatattttct    36480
cgattctaaa agctcatcaa ttgtaaggca cattctttga tttcataaca actttttaat    36540 gtctctttttt ggaaaaataa aacacttttc ttggggggagg aggagaattt ttctaaggat    36600
tattctgaat tcctttgggc cataggcact gtagcaaatg ctgctcttcc tgatctttaa    36660
cacttttagg attgatagtg tcgttctgag ccatgtccag gaattacttt ggcgaggttt    36720
ccatttccta tttaattaaa attttttttac taattatatt acatttcact agaagttaaa    36780
taacttctct tgaaagtcat ccagaagact ttaacagcca gatatttggt atctgctcag    36840
```

```
aattatcact tgtgaaacct tcattaaaca taattcagcc acatgtcaca gaaagttctg    36900
catgtataat aacttttgt ttcaatgctg cattatagtg atctttaaaa gacattttaa    36960
gaggtaattt agggatttca aattaagtta aaatttagct gtgcatagtt ctgttgatgc    37020
tgataagtga acagaaggta aattcttagt catgtctaag ttcacacaga gatacaataa    37080
tacacgtggg tgtaatacaa agcattatag tattttgtat agtatctcct ttgttattaa    37140
aagttctttt gatatctttg gtaagactcc tattgatttg aaaaatgtta ctgtgaaaaa    37200
aatgtgcttt aagagttgag aaagtaaatt attcctttt ttctctcagc agctgtttaa     37260
ggaagacaga gcaggcattg gataatattc ttattaaggt aaagaatctg ggtgtttgag    37320
ccctaaagtc atacagcaag tagtccacct ggaatcatga accaggtctt caggacttcc    37380
agatatttgt gctgtatact atgctgcatt ttcaacaata attcatttat ctgtgggttt    37440
gatttaatga gactcattta ttcaacaaat atttattaaa tgctattctt gccagtcatt    37500
gtgttaaatg atagtgtaac acagtaaaca agacagatat cttttccatgt cctcacgaaa   37560 ccagcagctt tggaactaaa caataatta taactaagat gagcattaag ggagaaattg     37620
taagatgata ggaaagaata taacaggcgg acttaacctg ctctgggatg gtgggggagt    37680
gttgaatgtg aactgagggt aggacatgag aaataacttt tgggctgaga ttggaagaat    37740
cagcatgagt tagcttaagc ctaggaatta ggagaagggt taggatggaa cattgcaggc    37800
aacagaaata gcatctacaa aagtaaaagg aagaactgaa aagattccag tgtgagcgtt    37860
gaaaagaagg ataagtaaat gtagagaaga atgtaggaaa gagattatgc attcttcagg    37920 atttttttgac ctatatccta agggatattg ggaaaccatg gaaaggtttt aagcatcggg   37980
gtatgccatg attaaatttt tcatttgaaa atcatgagtc tgactatagt atatatagaa    38040
gcattgttgt tagatgctat ttcggtaggc caggttggag atgatggtta cagcagtgga    38100
gctggagaga agggaataga tttgaaattt gggatgtgaa caaagccttg tatttgacag    38160
aaatgtaaaa ctattaatag tattgttatt gttccaccta tagaatctga ttataagatt    38220
atctctaaaa tactttcagg taacttgtac ttaatgttag gaggaagtga ctatattata    38280
aatataattt agaaaacatc gttccttaaa aaataatttt tgaattgtgc taattcttgt    38340
tattgtttga cttcattaac taatatatggg agtataggga gaacttagtt ttaaaagata   38400
atttgacttc ctgatttata cataaaaacac ataagtaatt ttggacatat atgatgtgta   38460
tatatatata tatatagtgc aggtcatctt gtttacacca cttattaatg aatatcagat    38520
ttggaaggtg actctttagg attttcctat tggttgattg attgaaactt acatgaagaa    38580
tttaaccctt ttgtttcaaa tagctttcta ttaagaaaca cttttttcat gattattcag    38640
agaatttatt gctggatcat tggctctaga gatagactgc tggttaaatt aaaagatgcc    38700
ggaggaaaca ttttggaaac agacttcaca gaattcctta tgaacttctg tactttctta    38760
accaatctta tttctttcat gtacctatgg ctgttactag cctgttgtat cagggatacc    38820
atagtcaact acctatacgg gccttaacta taaagaatta ggccatttag ggaaataata    38880
atgagactgg ggctttagag aatttgtgct catctaactg agtagaggga cagctaatat    38940
tctgctccat ctgatggtga tcatgggagt attcaggctg attgttaccc aatatttcag    39000
tttttccaaa ggatcctaaa atacagattt ttatgtaaat tagttggtaa ttaatttagg    39060
tgtttttaag atactctgtg acaataactc tacagggcaa aatcgacctg ttaaatatat    39120
ttggcccata ggctgttgtt ttatagcctt gaccatatag aaatcttcaa tatctattta    39180
aaagtaagag gtcaaaagta tttctaggaa aagtgaatgc caaaagaagg gaggaaggga    39240
```

```
aggcataaat gagatacttt ttaaaagaag tacaaaacta gttatctagg ttatatttt   39300 aaactaagtt caaaagaaa ttcactgtcc tgagaataat tttcatatgc ttcagaacat   39360
acttctagca acttcagcca tctgcgtgtg tataactggg aactcagagt aggatgagaa   39420
tgcacagggc gtagagaacc aatgaactgt agatgagagt gtagtggttc tctgaaactg   39480
ttgtgagcag agtacagcag gaacaagaga cagttgatat tggagcaaaa tcaggctata   39540
agaacatagc gatctgagta catcatgggc ccctgaaagc attactagac taaaagcata   39600
attttttata ctgatgatca agaagaggtc atattggtac actaagattg aataactctg   39660
ctcccaatag cacatgtaat acacaatcac tgtaggaaat caggaaaata tacaaaaagt   39720
agcatatggt ttttttttaa agctaggaat gggtaaaatt ctaaagttt ctaaagtaa   39780 tgaaaataga acttggcaat tgttagtttc ctaatagcta attagtttcc aaattagtct   39840
aatttggctt aaataaaaag aatattggtt agctcacata agaaaataca tatattagga   39900
ttagttacgc cagtggctca gtgattttt tcaaggactc agtttgtcgt ctactctact   39960
ctttatccat aatatttcct ttatcccaac actgtagttg ccaaatggct gctggctgca   40020
atcaggatty tgtgtttcct ccttcagatc caaagagaga aataaacttc tcttggcgtt   40080
ctcatgggca atataggttc ttttctctga gaagtcctta tgcactcctg cccccaactt   40140
gctccttatt gtcctaaatt agcttaattc taaatatgcc ttaactaatc gttggcaaaa   40200
gggatgagct taccataatg gattagatta attgtggtct acccttgcag ctcaggacag   40260
tcagcttacc ctgaggcgca ttgaccactg ggagagatgt ggatatagaa atccaatcat   40320
ggatcattag gaagaaggaa gcgttggata ggctctcagc atggtccacc acagttgcat   40380
taaggattgt gtattacgtt ttttacttat gtgaaacacc accttccccc atcaagcctg   40440
taagtatgaa gtcgagtccc tagtgaatct actctctgac tcctgtgttt caagcaccct   40500
cattagcaga gcttatatag ttcggagttg aagaattttt ttttcccaaa aattctcttc   40560
tcatttaata gacacctgtc tgtagagtaa actatgcagg ccataaatgg aacaaagata   40620
gtttaggaaa atacagtttc ttaaataaat tactttaaa aagtatattt tctctcagct   40680
cttctctcca aaggagtttt gtatcataac ctctgtagta aatagtgtca tctttattgt   40740
ctgattataa aggtgaagta taattatgg gataatttac aaagcaaaaa agaaatactt   40800
atttttaaag tttaaaaatt ttctgtgtag aaaatactat aataatgcat gattttaaga   40860
atctgttatt ttggctaaaa tatttaacca gccaaccata tatcttattt ctttcagttg   40920
ctagatttct gaatgttagc caaatatttt agtatctggg tcacatagtc attacaaaca   40980
aatgtaggcc aaaatggttt atgcttctca gttgccagct cagttctctc tttgactttt   41040
tattatttgt ttctctttga actaaacttt atttacttat attagcacag tactgtgtta   41100
attcttgtgt tagaactggt cttcttgtgt cgttttgccc caaatcaagg taacaaacaa   41160
ataaatgact gtgctcttgg ctgttatta gaattgttac tatacaaaag gtcacacatg   41220
ttaaattacc tactgcagtg ctaattattg tgaaaccttg ttcaaaatgc tagagagact   41280
gtgttttggc acttctgctg taacagtttt taaagatcca acctgtatgc attttggtat   41340
tgaaatcctc aaaactccta aagaccctat gttaatttaa aatgcaaagt tgtctcacct   41400
ttttatacta gatgagatag cattttttctt aaagtaaaat gagaactctt atgtgttatg   41460
atatagaggt aagggcaggg aaagagaggg aagaagaaa ggagtacatt ggagtaacaa   41520
aaattccacc ttcatttata aagtgctata ggctctaaaa ctccattctg aaatactctt   41580
```

```
ttaactttga aagggghtatg tttactgcca gcttctgtta acacaggaac catggttttt    41640
ctgttcttaa aattaagaac cttatacctt ttggaatttt taatattttt ctctatgttt    41700
gtaatgcttt taattatgtt tattactaac tgatgttatt aactatattt ataatttgta    41760
cactctattc tgtttggaaa gtacaaaatg ataccataga tacttcctga attttttag     41820 aaaaatcaaa attttattca tctttattca tagcatcatt ggacattcag ttagtaaatt    41880
ttccagataa caaacaccta tcttctttga ttgctagaat agttaatctc aaccctctt     41940 gttataaaat atagtgactg tggattgttg atgaaaattt cttaagacag tgtattcagg    42000
aagacactgc ctcagggcta ctgaggtatg tcatagggcc atttgtcctt tcaaaaataa    42060
ttctcagtag ctattgttgc tttgcatttg tataaagtgt ctgttttttc aaagcttgat    42120
attaattctg atagctacta gtgtacagag aagggtgtct gtgaataaag taagagaaag    42180
aatgttcata atagatttga agagcacttc aatgagtaaa gtacttggac tttacaatgt    42240
ttgcttttac ttcactaagt cctgccctgt gccctgctc ctgcccttt atgccatagt      42300 ctcttttta acatggtact tggcagtgtt ccaggtagtt attgtaagaa ggatgagctt      42360
agacttggag ctagacaaac atgatgggaa ttaaaacagg ataatttaat agctgtgaga    42420
ccttaagcaa gttcacaact gcaaatggg tttgtatata ctatctctca cggttgtaag    42480
gattaaatat aatggatata gtttaggagg tattttaaca aatgctagtt cctttcctta    42540
tactttaaga taaatgaccc acttactttg gaaatggtat ttgcctattt tagtatgatg    42600
ctataaggtt taaagggtca gtatccctaa aatatgacag ctgttaagat ctctttaatt    42660
attcagaaat gaatggtatg tgacaagata ttattggtta attcagtgga tcagatgaat    42720
aaaatgtgct gaaatatttt ggagactgaa aatataaatt tagatgcaag aaatatattt    42780
taaataaaca tggaaaacag ttttttatc cgagtctaat cacgttgaaa tattttatga     42840
atatccccag agagttcgta aattagtgag tgatttttt aaatgcaaag gtaaatacct     42900
agaaatcata tatacactta aagtaaaatc tcacagagtt ctcaaggcca ttttgcattt    42960
actagtgcca cagtagtggc gttacagtga gctgcagtaa cctgaaacag tactgcatgg    43020
atgctctaat aaaattgcatg tctggaggaa gcagctaact atggcgaccg ccacggagca   43080
gtgggttctg gtggagatgg tacaggcgct ttacaaggct cctgcttacc atcttatttt    43140
ggaagggatt ctgatactct ggataatcag acttcttttc tctaagactt acaaattaca    43200
agaacgatct gatcttacag tcaaggaaaa agaagaactg attgaagagt ggcaaccaga    43260
acctcttgtt cctcctgtcc caaaagacca tcctgctctc aactacaaca tcgtttcagg    43320
acgcagtctt gctctgtcac caggctggag tgcagtggtg cgatctcggc tcactgcaac    43380
ctccacttcc cgggttcaag ccattctcct gcctcagcct cctgagtagc tgggactaca    43440
ggcacaagcc accatgcccg cctaattttt gtattttcag tagagacgga gtttcaccat    43500
gttggccaga atgatcttga tctcctttt ttaaattaaa aagtaaactt taatgtcgaa      43560
aatgcaaacc tggggagggc agaaagatca cacacaaggc tgtcacttca cacttggaag    43620
gttgcacagc agccaggcag agaccctcct cacttcccag atggtgaggg gccgggtgg     43680 gggcactcct cacttcccag acggtgcagg ggctgggcag aggcactcct cccttacaaa    43740
tggtgagggg gctgggcaga ggtgctcctc actttccaga cagggcggcg gctgggcagg    43800
ggcgctcctc acttcccaga tgggacggtg gccgggcaga ggcgctcctc atttcccaga    43860
cggtgaggag gccaggcaga ggcactcctc acttcacaga caggacggca gcgggcaga    43920 ggcgctcctc atttcccaga cggtgaggag gccgggcaga ggcactcctc gcttcgcaga    43980
```

```
cgggacggcg gcaaggcagg ggcactcctc atttcccaga cggtgaggag gccgggcaga    44040
ggcactcctc gcttcgcaga cgggacggcg gcagggcaga ggcgctcctc atttcccaga    44100
cggtgaggag gctgggcaga ggcactcctc gcttcgcaga cggggcggcg gcggggcaga    44160
ggcgctcctc atttcccaca cggtgaggag gccgggcagg ggcactcctt acttcgcaga    44220
caggacggcg gcggggcaga ggcgctcctt gtttcccaga tggggcggcg gctgggcaga    44280
ggcgcttctc acttcccata ctgtgaggca gctgggcaga ggtgctcctc acttcccaga    44340
tggggtggag gccaggcaga ggcggcgctc ctcctcaatt cccagatagt gggcggctgg    44400
gcagaggcgc gcctcacttc ccggacgggg cggtggccga gcagaggcgc tcctcacttc    44460
ccagagtgta gggggccgg gcagaggcac tcctcgcttc ccagagtgta ggggggccgg    44520
gcagaggcac tcctcgcttc gcagacggga cggtggctgg gcagaggcgc tcctcacttc    44580
ccagacaggg cggcggcctg gcggaggcac tcctcactgc ccagacgggg cagggcctgg    44640
gcagaggcgc tcctcacttc ccagactgtg aggctgctgg gcagaggctc ttgtcgcttc    44700
ccagacaggg cgggggccgg gcagaggcgc tcctcactgc ccagatggtg cggtggccgg    44760
gcacaggcgc tcctcacttc ccagatggtg gagcagcagg gcagaggcgc tcctcacttc    44820
ccagatggtg caggcagaga tgctcctcag gtctcaatct cttgatctcc tgatccgccc    44880
gcctgggcct cccaaagtgc tggattacag gcatgagcca ccacgcctgc cctgccgtgt    44940
cttctttctc ctcctaagca actgtcttag tctcctgaat tttgatattc tacttaacac    45000
tctcatgttc ttacgcatgt tgccatgctg gaggcgtcct tctctttggg aagcctgacc    45060
caccaacagt gcctcaggag atagacatgg aagctttgcc ggtgggggcc gctcgtctct    45120
atcacacctc agttgcaggg gagggtcgg ttgcagctgc agcggtggcc ccgacagttt    45180
tcttttgtgg gacctgtggc cggcagctct gggtggagaa gacctacttg atccaagagc    45240
tgcaggatcc ttgggctgca tgtcctcccc caccatcagc aagcctggag agctgggcag    45300
gtggtcttca cccagcacct tcaaggccgc cttctctggc cacagggagc agcccggaac    45360
tggggcaggg agcactgttg gaagtgggtc aggcttccca aagggaagga tgcctccagc    45420
agggctgtgt gaactggcga ctccatggcc cttggagtag aaactcactg catgcacctg    45480
ggccttgtca gtctgattct tttctgtcaa gctcttgagg tggacatttc cctccaaggg    45540
cctgggattg taccaggaag aagtgaggtt tccctgagtc tccaggggcc tagaggtgga    45600
ggctgcttcc ccattgctac aggggcccct tttattgtcc tcctgcccct gggtctctac    45660
ctggtctttc acctctgttg cttctttggg ctcttctgcg ctcacctccg tcttcggag    45720
cctggctggg atcacctgat catctaatga aggaagttga aggttaaact tgcctctgag    45780
acaagggatc cttacgggc tgaggtgtcc aaacattatg gagttgtgag gagacagcac    45840
gggtttcttc cttgagggg ggctccagac cacaggacgc aggaccctct gtggggtgcc    45900
cgtgttccga gggataagac acagcctcat aggggcgccg tcccacctga ctggaaaaga    45960
aggcccaaga tgtcgctgac ggttgaagag gagtgggaaa cggcccacaa ttccccgggc    46020
aggcacaggt gcaggagctg cagggtgagc ccggccagct gggaaggcct cacgacaag    46080
acgagcaggt tgccgatggc atggccagga cctgcggcag aaccaggaac aaaatacgct    46140
tagcgagttg cccatttga gtgagttgtg cacagacgaa actaagggtc agaagcggag    46200
aggatactcc taagtcaccc acttctctgt ggctgggtgc acactgggca tctgggagtt    46260
tatgacatca ctatggggct ggtgacagag ccagtgtgtg gaggagtgct taggagccca    46320
```

```
gcgagggtgc ctacaagagg agtcaaaggg caaagggtga gacccttcca ccggtccagc    46380
tggactctag cctcagggat atcctgctcc tgggggcaag tgtgtggccc tggatgggcc    46440
cccctgtggg gctgttgggg gtgcgaggct gatccgccag agcccttcca cctggcgcct    46500
ggcccaggtg ctggctagca cccagtggcc ctgttttggc cggccctgtc ccccaggtta    46560
cagggccaga acctggaagc agagcgcagg accagccaga tcgcgccagg cttccccggg    46620
gcctctccag tgcctctgtg ccacctggag ccaggcccgc cttctccatg gctgccgtgg    46680
cctcaagggc caccagcctt gctccgcagg tttccaaaga gaggacgcag tgccctgacc    46740
tgactggatg cacctcttac cacatgcctc cctggcaggc agggtctcca cttttttacaa   46800 atttgcctga gaccattcct caggtcattc aggtggtcat ggcccagcca ggctttgaac    46860
ccaggctgtg cgattccaca gctggcgctc tggcctgtgt gcctcatgat catggataca    46920
gcatctattc ttattttttc atgtagtcct ggggtactta gcaccgtggc atatctgtaa    46980
taagcacatg cacacctcga aggaggtctt cacttcaaca tacgagttga ccatggcatg    47040
ctctgggctc cagtcctcta caaagacgta gggcaggaac taccagttgt cagcacagca    47100
ccatcccaca ttgctcttct aatggagcct ttcaccccag atgttctttc tcgtctgatg    47160
ggaaggatcc aagtatgtaa agattatgtt atagatcagc tttggtctgt cctaaaagaa    47220
atttgccagt ggattattcc atatggataa aagtcagttt ctctggtctt cctggaatgt    47280
gtctagaaag caaatagatt atttacaagt tcatagtaga tcaatgtatt ggattaaaat    47340
atgacaaaca taatttggtc attgtgagca tgccagcttg gtcaactatt caccacacat    47400
gatgccctaa atataactct aggttttctt atgcccaaga gagggacata ctcttgggtg    47460
tctggactag ggaaacatgt atgaaaaacc atttggccac tctacatctt gttattggag    47520
aattgaaacc atctatattc aaagatatta ttaaaaggca agaagttaaa aaataaaaaa    47580
ataaattgca tgtctgttgt tatggaattt tataactgta catacctttt atttaatcca    47640
ttcacaggtc atattatagg atatctttca tttaataagt atactaaatc cataccttat    47700
actgttgagt tttgatagta ccagagggaa aaaagaagaa aagcatggcc tctatcttta    47760
aggagctatt taacagtcat atgaatcact cgattgagaa gatccatatg tgtaatataa    47820
tgaattccac aaaaattgct tattaaaatt ttttgaaaaa gtaggggtga gattgaatat    47880
agcaaagctt tattgttgat ttttgttgtt ggccaggcca aatttgtgaa catttttacat   47940 gatcagctat atcgaaatac atttgtatgc tctactgaat atagggaaca taatttaata    48000
tttaatttaa actccaggtt accatcattt acaggcattc tgtgcattaa accgttttgc    48060
ctcttctttc ttcctcagta acacgtttag ggccttttga tgcattggaa agaaaaggca    48120
gttgcgagct gctggctcta gcaaatcaga gctaatcaac ctgagaataa tgtttgcact    48180
ttcccgcttt caagtctttg ctcaaactgc tctctaccct tgctcccaca ggttagtcct    48240
ttcccccaat ctaaaatctc tctgactagc cctgaactta ctttttatag ctctcactgt    48300
ctaccatctc cttcatcttg aatataccag gacagactgg gaagttccag aaaaaaacag    48360
acataatact taaatcatct ttgatacctta atttgtcctc actgccaatt aattaatttt    48420
gttttgtttt atttaatttt gtaaagacag ggtcttgctg tgtcacgcag gctcctctca    48480
aactcctgga ctcaagtgat cctcccacct cagcctctca aagtgctagg attagaagcc    48540
gtgagccact cgcgcctggcc ataatttaaa taatccttta gattcctgtc tctgtccatt    48600
ttcaaagcca gggttacact atcataacat accccatgat gtacaccatt gctaaaacaa    48660
tcttcctgaa gtactaatta gattttgag cagagaataa aaccatcctt tccagtgttg      48720
```

```
gcaaatattc aacgtactgt cctgaaatac ctgtagtact tccaagtttc tgctttgtgc    48780
tcacactgtt ttctttgacc tgaaatgcaa tttctatcta taaaaatctt agtcattatg    48840
aggtctagca aagatctttt tcttctatga agccttccta tcgaccctaa ctaaaatctc    48900
ttctctgagt tcccagcgta tactgcttga gctggagcaa gactccagtg atccttggaa    48960
gaaagtggga ggttatttc ccagtgcgat tccaggaaag tttaatgtct tatagttcag     49020
tcccctttag cattccacat acagttagtg ctcaaatatt tgataattgc tctactcaca    49080 aatattttg tgtgaaattg ctagctattc tctatccaag aagtaatgaa gtatataagc     49140
ttcttcaact ctttgttgag cccgggacct cttacttatt tctgtatcct atctactctt    49200
gagtagtagg gtcattggaa agcaaccact gggtttgggg ataagttgtg tgtattttag    49260
aggaggaagt aaaggtgtta ctggactttt aaaactgaag cttttctgt tttaaagtat     49320 tttgcttccc gttactgtat ttataagatg atactggtat acgtagtgtc ttggctatt     49380 atctattccc ctttctcttt aacacaatat tccccaactt tggtgtgata ctgaattgaa    49440
atctctggga gtgtggccta ggactctaca cttttactaa caatcagttg agatgcttat    49500
gaaggtggtg gtagtagtga taatggtagt gatgatgatg atgattgtat tagctctgct    49560
ttcgaaggct tatgatgtac ttactgcact tttctaggca gtttgcaact attaacctaa    49620
tgttcacagc aagcctatgt ggtaatacgc tattatcttc attatacaaa tggagaaact    49680
gtggcagata taaattaagt aacttgtcgc caaaatgact ttcttataaa taggtcaaga    49740
atccatgaaa aggatgaggc atatttttt ggttgatagt ttttaaactc actttctaaa     49800
ggattgcttt aagtgatgtg aatgatatga atgtaaactg gttcttatat aaattgaagt    49860
atcaatatgc tgactctata taggaatact tcaacaacta gacctaaata tagatacttg    49920
ctcttgcttt taggaagcct gtcacaattc ttggtgaaaa agtaagcatg cacccaaaaa    49980
cgtagaacat tgaggaaaat ttttaaataa ttacactttc taaaatacat gattttagga    50040
agagtgcttt attatatact atatatatat atatacacac acacatagac atacacacgt    50100
agatgcatat atatttactc tatatggatg tgtgtctata tgtatagtca ttcttcagta    50160
tcctcaggtg gttggtgcca ggacaccctc agataccaaa atccaaatac tgtcccacag    50220
tatttgcatg taagctatgc atatcctctc atgtacttta tttatttatt tatttattga    50280
gacatggtct tgctctgtcg cgcaggcttg agtgcgctgg tacaatcatg gcttactgca    50340
gcctcgacct cctgggctca atcgatcccc ccacttcagc ctcccaagtt agctgggacc    50400
acaggcacgc accaccatgc ccagctaact tttgaacttt tttgtagaga tagagtttca    50460
ttgtgtcgcc caggctggtc ttaaactcct gggtcaagc gatcctccca ccttgacctc     50520
tcaaagtgtt gggattacag gcataagcca ctgcacccac ccatcctctt gtatacgtta    50580
aatcatctct agcttactta taatacctaa tacaatacaa atgctgtgta aatagctatt    50640
atattgattt ttatttgtat tatttttat tgttttgttg tttttaaat ttttttcctg      50700 aatattatgt gtgtgtgtat tgagatgtta ctttgtgatt taatgtaatt caagtaaaac    50760
tcgttaagca tttattttct gttttagtag cataagataa atttggtttt atatgctaaa    50820
atattttatc tttttaataa taaatgataa gaatattttg ttcccttta gttcatagac     50880 tatgggaagt ggagtaggga gtgaaagtgg tggctgtggt ggtggtatgg tggaagtaat    50940
ttgtttacca tcactgcctg tccaaaataa ttttgatgaa tgattttagg tgttgcctaa    51000
taagtgctct gacttttgaa accagttgaa ctaacaagca tgttgtgctt tgctagaaac    51060
```

```
atcttgtaag ttctgacttt gaacagacag tggaatctaa attgagttag tggaggacat    51120
atctttacaa ctaaatctaa agtgtttcaa ctatttcttt ttttaatctc ctgtttattt    51180
ttcttgtaga attaatattt tgattgacc aatcataatt gcatacattt atggggtaca     51240
atgtgatgtt ttgatatatg tatacagtgt gatgtgctta tgctaattaa catatctgtc    51300
acctcaccta taatatttca tattgagaca tttgaaattt gcttttatta ttttgaaata    51360
cttaaaacgt tattattgac tctcgtcaac ttgctacgga atagatctca aacttattct    51420
tcctctctac ctgaaacttc ataccccttg atcaactccc cccaccaccc tcctaccta     51480 gcctctggta accattgttc tattctctac ttctatgaat ttaatcttat tagattccac    51540
atgcaagtga gatcatatgg tatttgtttt tctctgcctg acttatttca cttagcataa    51600
tatcctccag attcatccat gttgttgcaa atgacagaat tttcccctt ttaaatgctg     51660 aatagtattc cattgtctgt ataccaca tttccttgat tcatccattg atagacactt      51720
aggtgtttcc gtatcctggc tattgtaaat aatgcaacaa tgaacatagg agtgcagata    51780 tcccttgac atactgactc cagttccttt ggctatataa ccagaagtgg gatcactaga     51840
tcatacagta gttctatttt tagtttttt gggggaaact tccatactat ttaccataat     51900
ggctgaacta atttgcattc ccaccaacaa tgtactgtat aagagttatc atttctccac    51960
acactgtcca acatttacct ttcatctttt tgataaaagc tactctaaca ggtgtaaagt    52020
aataatgcat tgtggtttta atttgtaatt ctctagtaat tagtgatgcc gagcattttt    52080
tcttgtacta gttggccatt tgtgtgtctt ctgagaaatg cctgtttagg ttctttgccc    52140 attttaaaa attgggttat ttgttgtttt gttattgaga tgttggagtt acttaaatat    52200
tttagatatt aacccttat taaatgtatg atttgcagat atttctttt atatttcctg     52260 tttacaaatt tcctgaactt ctctggctgc tcatttatat agaattggga tgagttatgt    52320
cacctgaagc agtcaagata agactgtttc tactgatatc catatggcag gcttactttg    52380
ttacccaatc caatgaaaaa gggtgccagg atgtgaaaga aaaatagatg tgatggccgg    52440
gcgcagtggt tcacgcctgt aatcccagca ctttgggagg ccaagtcagg tggatcacga    52500
ggtcaggaga tcgaaaaata gatgtgatgc catggaacat tctagggaat taccatttt    52560 agagagagtt ttgataaaaa ttttacgtat ttttaaaact catattctta gtctgaagag    52620
ttggaaataa ggttgaatgt atgtcttaaa gctaatagta taaaagaga agtgtaaaat    52680 ttaagttaat catacaactt tctttcccta actttatgaa ttgacttttt gcaatttccg    52740
gagctaatga ggtgaatgtc tgaaattgag tatgtaggtt aaaaagttga aattttccta    52800
ataaaattgt atctctttct aaggtgtaac tctttctttc tttgattata gtaaaaggag    52860
catctgtggt tcttaagagg tcttgatttt tctgccagct agttgtgtga ctttgggtaa    52920
ataatgtcat atgactggac ctgtttcttt atttgtaaaa ttgtgtgtgg tgttaaattc    52980
taagactgtt tttaaaaaaa ttttgcgga gactgggtgt tgctttgttg ccaaggctgg    53040
tctgaactcc tggtttcaag cagtcttccc caccttgacc tcacaaactg ctgggattac    53100
aggcgtgagc ctccatgcct ggccaaattg taagactctt ataatggatg agtagaatat    53160
atttaagatt atataaaaac acaagtcact tcatgatcat cgtctgctgg aacatgaaac    53220
cagctttctt gtgtagatgt gttatcagta atgttattca caccgagagg atcattctgt    53280
ggtttttaat tcatgatttt gtaatctgat agtgactttt cattatgtct cctgattat    53340 aattacatca cagccattat gattggaatc attgggaaga gttgaaatga gcaatttaga    53400
attgtttctg aaatacagaa agccttattt tttggtgggg gttgttggag gagatatctc    53460
```

```
tgtgttctgt aatttcattt gactaaggaa tttatctttg gtcttctccc agagtgagga    53520
catgaatact tccatagcta tattccgtat taatcacagt ttgctttgtg ggtttcatta    53580
ggctaaataa gaaaaacgtc gttatgtatt ttctgcttta aaaatgctt cttgatataa     53640 agtcttctca gatcagtccc acatgtgata aatctattca aactattaaa ctgcctcaat   53700
gtgcttgttt ctctcttgga aatctatcca tttctgtgtc tttatgtacc actcactctc   53760
ccccatcata ttttaggtta taagctcctt tcctttatat ctcatagcac ccaggaaaga   53820
actttgttag tctctgaata gtttataagt gttattgcta ttgagaattt tggatttaaa   53880
ttattggaat gaatagaata atgctatttc tagtatatct aactgagggt cagtgttatt   53940
aactcaaaga catagcagtt ttattaagct ctaggctttg tttctgaagt cagtttctct   54000
taatcataag tggattattc actttatatt ctcttatata atgccttggt atcaggttat   54060
tgataggtaa acatcagaaa taggctggat agatatgcat gcatgtgtac acatgcacat   54120
gtatgtgaga gagagagaga aggattgcac atagaatata tgagaatttg aggtgtgtgt   54180
aatgtttata actcatctga gtcttacata gctatctagt tatgtacact taattttgca   54240 cctttttatag ttgaaattca gaaacatttt ttaaggaaaa taaggacgtg tttttctttc   54300
cttcatgttt tcagtttagc tttatttgat tgtattttg ctaaagactt aaattgtcaa     54360
taactattga aatgggccaa cttatagctg agcacaaagt atgttaggac actgagatat   54420
atcttaacat ttgggaataa tttaatgtgt ctaatacttg agaaggatca aaacagactg   54480
tacaacccaa taatcataaa gcctatggtc aaaaatcgta tataaatgac aggccctatg   54540
aagagtagcc gtaagaatca agagaaaaag aacctaaatt ggtacagaaa aggagctgag   54600
tcatttttat attataatta gaagttggta acgataaatt ttgtcttccc agtacaaaaa   54660
gtatcatgat caggcaggat tacgctaaag tgtaacctct aacttcttgt ggtatgtact   54720
attacaagta gttgatgatt taataaatat aaatatagat gatactgtca gagtgtttcc   54780
agacattaca gttagctttt aggtgaaggc agtgcttgac agaacctaag tttgtgactc   54840
aataatttat tatataatct aataccattt ttatcttgta ttaatttggg ttataggata   54900
attggggtaa cttttttggtg agggattgaa attttcttaa aagcgttttc agaagatact   54960
agaattttat gggattcttt tattatagca tgtcttctca aatataatat taggactgct   55020
tgaacaggag gcaaatcata ttcacgttat ttttccagttt agagttattg ctcttatcag   55080
ttggtgggtg tgggaacaac ttaataaagt ttgggtaatt tagttttcag tttaaattct   55140
caactggcaa ttggccgaaa actcccatct gaagacatga tcatccaaat gtcatttgt    55200 gatttggcta ctgtctgctt gacataggaa agcactatca agaaagacta atggagtgac   55260
tatcaaaagg aagtcaatgg taagagtttt catttaaatt gtgtgtgtgt gtgtgtgtgt   55320
gtgtaaagcc taccaatgta ttatatttga attaaaattt tagaactttt aaaatctagg   55380
acataatgac aagtgtttga attttatatg tctgtcactt atattttaat aaaatatatg   55440
caaagaatgg ttttatagat aagagatttt acatacttaa tgttgataaa tagtataaaa   55500
gtatggaaaa tcaattatat agttcatgtc tggtttaaaa attcaatttt tgtagttta    55560 ttgtagttat ttaaaatagt atattataaa attgcttgac tgaagtttaa cttctaaaaa   55620
atttgtacta aactgagttt ttctgttcag tttcataagt gcttcttaaa atagacatgc   55680
attttgtggt agtctgttga atgctgtttg gttttttact ttcattataa aataggaaag   55740
aaaaaagtat aatatcatat gacaaaatcc atttagttta acattagttc tttaaaaatg   55800
```

-continued

```
tataattgct actatacttt ggcggaaact attaaatttg taagataaga cgtttatact   55860
ctatacccaa aacaaagtga agtagctgtt cataatatgg cgcagaatca aattttggtg   55920
ataaaatcag acatctctct cctgccttac acatactccc actgagaaaa taatttctaa   55980
atttggttac attttcatat acttcagatg accttaaatt tatattttc tcctgaatat    56040 atttgattcc tgcatatccc tttttttggg catctgtgtc caatcagatc catgattagt   56100
catgttagct ttggacaaga gtggaggtag gatcttagca agtttgaaat ctttaagatt   56160
gatgtttatc tgagattatt ccagcatgtc cacggacata gtagttttgt gataacaagg   56220
taatggctga tgaagattag catattaata atagattata attctgttaa ccattctatt   56280
gtcaaatacg tgattttgc gattcacata gtttaagtaa tttttcatgc ccaattagag    56340
atgtcaaaat tatgttaatt gaatctggcc atgttcttag ctgttttcta gagcttaata   56400
acaaacatat caggaagagc tcttgtgaca agcacccagc acagcatctg tcattatgta   56460
atcattccaa tgtttacagt gaactaagta cttgagatgg caacattcat actttagtcc   56520
ctctgtctag taattcatac ttgtatagtc tgtctactat gtgtcaccca tttaggtagg   56580
tgctgagaat aaaatggtgg ggttaaaaac agatattccc tgttattgaa cttccagtgc   56640
caatggtaat tacagtgtag ataataatta cacactgcaa ctggaaccaa tactataaaa   56700
tggcataagt tcctataagg gtaggaacaa taaagttagt gtataaataa agcacagaac   56760
ctacacattt atttattaga ttgaattgat aacttgcttt tgaacttta aagttaattc     56820 tattaatatc tgctaagcta ggcatcagaa agactaaatt ctaaccatag agaaatacat   56880
tttttatgct gctattctat tttcttagat ttccttaagaa tttacaacaa acccctgtca   56940
aagcagcatt cttacgtgag aatttcactt acgggagagt tcttacagga tttcaagaag   57000
gaaagccctg aagagggaca ctgatttcct caactgaatt taaaattgtt acatgcagac   57060 attttaaag gtagtatgat tttccttaat caagtcaact ttatatcttt ttatcttttt    57120
aaagaaggga atgtgacatt tatgttttc atacacacac acacacacac acacacacac   57180
acacacacac acacacagag aagcatacat gttgattacg ttttggaaaa taaaatccaa   57240
agagcatttg gatgtctgaa tgtttatgct tcatctccgc agtgacttct aaatttagtt   57300
tttttctgga tatactcaaa gtcaccaacc tgagttcaag tattctgatt tgaagatctc   57360
aacttagaga tccaggcagt cccccttgtc agtgctagga gaaagatgtc cttcccatac   57420
cttccagaaa gagtgtcttg aagaaatata ttccttcctg ggtaacgtgc tttggaatgt   57480
acatgatatt catttttctt tgacagctct ttttggttct gtttagttgg ctttgatggg   57540
ttcatgatgc ccagtggaga atttggtatt tagccacaaa aagatattta agacacataa   57600
ttatgtaaat attgcagatg gaggatgata catagcattt cttttatcaa aatgaatttg   57660
aattgacttc tttctaaaac aaaattctac caatagtcat cagttttaa ttatataact    57720 tctcaatata ggaaataatc agtgtctgat tggctgtgta tgttggagtg taatggcttt   57780
tgttttgaat ttggcagttt ctactctcag aagaaatgag ttgcgaatta cagtggtgtt   57840
agaagaaatg aattggaagt tcgaatgaga aaaatttaaa taaaagttat tgtttataga   57900
tatgaaaagg aaaataatgt ttttagttca atatgagaaa gaaccttta aatgtagaaa    57960 taaaatgggg tgcctttcta catccattct taagaatttg gcagaagtta tgaagaagtt   58020
aaaaagaagg agttcctgct gatataagtc acgaggatta tttgaaggaa atttatgtca   58080
catctcgtaa aatcatcata ttgacaatta taaatatgta aaactttatg tgcaatagtt   58140
attactaaaa atactgagct actatttata gtgagatcat tattaaataa atttaacaga   58200
```

```
tagaatagca aatcacattt attcattcag tatattctta ccaacaacct gctgtatgtc   58260
agtcattgca taagactgat gtgatgccat aggtcttgca gggaatgtag acattaagca   58320
agtaattaca ataaagtata gtggcttatg atattataaa aacaaagcag tccttaagta   58380
taccttgcaa ttgatctgta gtatattaat tttaatccgc tcatactcct catgaaatga   58440
ggttgttcat tttgatgtaa aaattagact gacgttcttt gcagttagta gagactgaaa   58500
aagttcttat tatttgtata acttatttaa aatgagaaac tgctgtggaa agatctgcag   58560
gtttctgaga taccaagaaa cgtgaatatg agcagaataa acacatgcat attatataca   58620
ttataaacgt catttaagac aattatatga agcagtttta catttaaaac taccaagttg   58680
taatagttaa gaagttgggc tccagagtca tactggttgg gtgtgagtat taactctgac   58740
acttaccagc tttgcagtct taggaaacct gcataactct actgtgcttc agtttcctta   58800
cctgtaaaat ggggataata agagtatata tcttgtggaa aaatatatta tttgatatat   58860
gaaaatgcta aagagtatc tagcatatgg aaagtgcata gaaagggctc catatgttgt   58920
tttagttaat aattacaata ataatttcct catcttaaaa atatcctgct tcattcataa   58980
agttgtgcca acggaaataa ttgcagatga tgcttaaaat acatacaata tatatttcag   59040
agtggtatgt aaagagcttt tattattact gctaaacaaa aaaaaagtcc gtgaaattct   59100
catctaagct ttggggcctc tttagctgaa tttcagcagt cactcaaagg ctttctagag   59160
atgccatcta gagatacttt ataacctagt gtcttttttt tttttttttt gcaatacaga   59220
attttttttt cattgtaaga tgctgaatga gagaaaatta tttcagtact acaagtatgg   59280
tttcccatga ccacaattag ttctaatgta accagtcaac agttgtctat tgaaaaccac   59340
tagctattaa tatagtatca tggtagccta aaagaattat gctatccttc tacttaggct   59400
ctagggagac aagagccatg taaagaatac ttaaagcaca aaatgtgaga ctgctctgcc   59460
actagttcct gctctgccac taataaacag aggtatctta gatatatgaa cctgttacaa   59520
ttatgaggcc atcttagcat ctcagtaccc ttattatata tatcgtgtgt atacacacat   59580
ggccatccaa tatttctttc ccaaattgaa atgagaggaa ttcattaagg tggttttaat   59640
ttccaaattt actgagtaaa agaattctat tctaaaaatt attttgtata atgcccttca   59700
aattgagttt tacatgtact atttcaaggc ttctcagata ttcccacata aattatctag   59760
tgtttctgca tcactttgcg atcttttcat taatgtcaag tgtaatgttt tttaacttca   59820
caagggaaac atgaaattcc tttagtgtgc ctcattttca gacattttct tgttgattaa   59880
aattcctttt taaataaagt ttcaacatgt actaaataat ttgtttacct ttgaattaac   59940
tttttataaa tgaattttaa ataatgacag cagtcattac aaactctgct gttggcaaca   60000
ctagagggca tttctagttc ttcagacagt gtcatgagtt ctcagaataa tttaccaatt   60060
cattaaacag cagattagca ttttaaggga aaggaactaa aacaagcaca atacatatat   60120
catacatata tatagtatgt atatattatg catagacaga taatataaat atccatatat   60180
aatatataca ttatataata tatggataat acatatatat tggatgtatg tatactcacg   60240
tctgctttac caaatgttct cactgaatca ctactcctaa aaaggcggga gagtatttgt   60300
gatctgctca ctgaagcacc actatattat ccagttgttt attagtgtcg tggaggtcta   60360
tgctctgata ggtttagcat caagtgaaca ttgagtaaaa aagtatatgt atatactcat   60420
acatacatac tcatcagaag ttagttgctg tgcttattga actactagat gctaacatag   60480
tcataattag aataattttt cagataaaaa atgagagtta aaatagatgc cctttatagg   60540
```

```
cttagtagaa gatttaagac tacctatatt ttgaattact gtattttaga tgttaaaata   60600
ttttcaaggg ttttgaatgc aaacatttt agggaaaaga tacaattatg taatattaaa   60660
tatataatat taaatattaa catgcaatga tatgaaagaa gacaagttta taagaaaatt   60720
caattagcgt aaagaaaaac tttttttct tgggaggatt tgcttactgc ggtgtattgg   60780
ggaaaaaatc ttatatatca ttaagtaatc attaacacgg taaaagtaaa gtcaaggacc   60840
agcaaaaaat aacctaattg ttgtgaaaat aaggtgacaa acagacaatc ccatcttaca   60900
ctgtaacata ctttgtataa gagggatac atgataacca ctagaacagt ggtggatgtg    60960
caggtggtag atacacaagg gatataagaa agtctttcta gttcaaatgt atttctgcca   61020
tgtactttac ccagtagaaa tgcatttaca tttttaagag gagcgtataa atctctcaaa   61080
tatttctgtt gatacatata cctatcattc acttaaatac ctgagtacct actaagtata   61140
aaatacccg ttatttatg tttggcacag tgaggctgta acagtttata ctcctattat    61200
gtagctgaga ccagttggtc tcttttagag aggggagtat cagttagtta cagaaggact   61260
catttgaatc atgagataat ttgtgagaat gcagacccaa gtaatatgct ctaataaaat   61320
cagaaggcag catgcttttg ttgagaaatg gaggtaggaa ggtaacaaca taaaataacc   61380
tactttgtac tggttcagta taccccataa actgtcatct cttttgtttg tttgttttga   61440
gggtacaaat tatttcattt tctgatattc tcttccctaa ggtattgttg gactgaaact   61500
taaccaattc tcctcttttt ctgtctctgt ctgtctgtct ctctctctgt gtgtgtatat   61560
atatatacat atatatacac atatattctt tctacacaca cacagtaaca gtatgtgcaa   61620
gtcaaattta attttaaaat aaatctttta aagcgtgggt caatctgtgc cagtcacaca   61680
cagggcagtc tgccgtatct tttgcatcct tgttttgtac tgctcgtgaa tgttcgttat   61740
atagtagagt aggtaattcc atatttactt gtactagaat atatctggct taatagatga   61800
tgttccaaag gcttgaatta aaaaaaaaa accttagtgt aaaaaatttc aggcatacac   61860
ttaagagaga ctagtgtaat aaaccccatg gcctagattt aacaatcagc aaaatttgc    61920
cacatttgct tcatctactc tcttctttt cctcaactat ttttaaagta gatcccagac    61980
ttcaagtctt ttcactcctg cattctttca tatgcatttc tttaaaagaa ggaattttc    62040
ttatataacc acaataccct tattacatcc aacaaaatta acaataacta ctaaccacct   62100
catattctct ctgtattcag tttctctgct tttaactgaa aaatgtcctt tttacgttta   62160
gattgttctt tcagaatcca accaagatct gtatagcatt tggttgtttg gactgctgta   62220
taattaaaag gtctttctt tcccaccact tgtttaccct actcacccc aaacccctt      62280
cttcctcctt ccctcccctt ttccctttaa tgtgttaatg aaaaaactgg gtaaactatc   62340
ctgtagaata tcctccattc tggatttctc tgttgccttc taacttgttc ctgtagcctc   62400
tgaatttcct gcgaactaaa agttggcttg aaagacttaa ttagtttcag gttcagcttt   62460
ggttttggtg ttgaggatgg aaggcatgca ggaatacttt gcacatgaa ctgtttcttc    62520
atactgcatc acatcaagga gcatataatg tctgcttgtc atactcttat caatgctaaa   62580
attgggcagt ggtgccaacc caatctctct attgagagtt ttctaccaat ctttcctccc   62640
gtgggaaaag ttgctgactg ttctccaaat caattctgtc attagggttt gcaagagaat   62700
gaattttaa atctgccacc ccttacacat ttattagtgg aaattcttct gtaagaagaa    62760
gtttccttca taaattacac cttttgatt tatctgaaac aatgtatact ggaaagaagc    62820
ctggtgtctt aaatatcatc tgttaatacc tagtgtaaca ttccaaaggt aacttgagat   62880
actgcaagga ccacatagca ccttgagtac ctattttaca tgtgactctg aggactttca   62940
```

```
cagaataaag atatttctta ttttaatgaa cgttgtcagt atcaggataa ttttatgtag  63000
tcaacatata tacagtgttg gtcctatagg agttggagac cttttgccag ttttatttgg  63060
tcaaatacat tattttgtga tgaaataact gtgagtgatg agttgagcct caaagaacat  63120
gatacttcat taaatcaaca agctgaacag tatcatctaa ccaaagctgt agaataaatg  63180
gtgataaact taaattcagg aatgaaacaa tcaccatttt tgttacaaat ttgtccaccc  63240
gtcatcacta accccatttt tatttaatac tggtaatgaa caaaacctga agaagaaata  63300
aaactaaaat atttcatttg tagatgacat gattaattat ctagaaaaat ctacagcaat  63360
cagctctaaa atgatttatt aaataataaa aatttaataa agtaccagat atactgtatc  63420
tttataccat gtgaaaatca ttctgggaaa atatcccatt cagaattgca acaaacgatg  63480
taatatctag caatacattt gagagagatg ttagatcttt ggaaaataaa ttaacatcca  63540
gtgtatttga aacaatttta agattcaaat aaaagcagag aaactgtttc taaatcaaga  63600
atattggcaa attatttgac taaaagtaag atttttgggt ttaacctcta acttccaaaa  63660
tttctagtga tttattttat agtgattctg taatgagaag tctcgtccta ctaaatatca  63720
aaaggtttta aagcaagaat gtctaaaaca gtgatgatga tgtaagaata ggtgtgttac  63780
ccagatacca gaagagactt ctctgtctgt tggagattta agtatacatt ttctggccag  63840
gcccagtggc tcacgcttgt aatcccagca ctttgggagg ccaaggaggt cagatcactt  63900
gagatcagga gttcaagacc agcctggcca acatggtaaa accccatctc tactaaaaat  63960
agagaaatta gctgggtgtg gtggtgcacg cctgtagtct cagctactcg ggaggctaag  64020
gcagaagagt cacttgaccc caggtggcag gggttgcagt gagatgagat tgtgccactg  64080
cactccagac tgggcgacag tgagactgtc tcaaaaaaaa aaaaaaaaaa aaaaaaaaa  64140
caaagtaaat ttcccttgaa gcccgacttc atggccggtg agagtcaaga gacatggcct  64200
ggatcccgtg acttacacaa atccctgtgg ctgactcaga ccttagtttc tctgcctctg  64260
cttgcatgcc accttggttt ctgccagtgt caatacatat gtgaaaccag cccctttact  64320
agtttcaaac atttaacatt ttgtgagtta agaaatcctg aataggtgat agaccagcaa  64380
atgattttct taattttga gtggaacatg ctatctatgt tcattctttt cttctactca  64440
tactttactg aattaataca gttgttttct taagaggaat actgaacaaa taagcttgtt  64500
ttcattttgt aaaacataga ttactggagc actatgagga atacaaaatt tgtcccatct  64560
gttatcatat acagtaacta aatgtatgac aaaataatct ttcctaagag aggggcactt  64620
aaaggatatt tgttcagtgg tgttggatag tactattcag tgatatgtct taaaactaat  64680
tagacaaaaa tcatccgtat attacacaac cataggaata aaaagaaaa ggtaacagag  64740
agaataccctt tacatctcat atttgaagaa ttagtagaac tcacccagaa gatacttgaa  64800
tattaaaaat ttttgttgga ccaaaatatt atgattaaaa ggataataga aaattgtgga  64860
aactacatta aaaattataa ggaaagtgat aataggtata agttatatat tgttgtaaat  64920
atgcaagttt agatatcaag attataatac ataagtgaga aatgaatatg acagattaag  64980
aatatgaaag taaagacaca tgaataataa agaaatatga ggttttttc attgtattaa  65040
aggacataaa ttttaaaaa gagaaatcta atatttgcaa gtaagcagtg ctaacagacc  65100
cttttgggaa ataatgcagt aatacatgct gagagtcaca ataatgttta gaaatttcat  65160
aataacatat taggaaacac tatgctaatt attttacata tatatatata taaaatgccc  65220
agcttaaaaa ctaattatag aacagcaaca taaaatatta catttaaatg attattttg  65280
```

```
gagactatag aacaacactg ttcaggagag ctttgtggtg atagaaatat tctgtgattg    65340
cactatccaa tatgtagcca tttggcacat gtggctgctg agcccttaaa atgtggctag    65400
ggcaactgag aaactgaatt tttaatttaa tgttaattat ttaaatttaa atagataaat    65460
ggggctagtg gccacaattt tagatagtgt agttccagaa ataaagagaa atgtttggta    65520
taagtgaaaa taaaatagta aatttatatg ccatgattac aagtatgtac ataactaaat    65580
gtacgtatgg aaagtgatag tcataattaa aatatttgtg ttaggattga aggaaatagg    65640 taatttttt aaaatgctaa attttaaaa ggttacatga caataatgta acacttcagc      65700
attgtactgg tactgttcag tatggtagcc accagcctga tgtgcaattt aaacttacat    65760
ctgtttaagt aaaattaaaa attcagtacc ttaatcacac tagccacatt ccaaatgagc    65820
agtagtcata tatggctaat gtttgccttt tcgaacaatg aagctataga acattttgc     65880 cattgccaaa agttctattg tacagtgttg tagaaagaac tggtaaaagg aatatactgg    65940
aatcagtcac tgatagttta tttgtcagta gtttctaagg gcacatgaga attaaaactg    66000
gaaattggat tcagtaaaaa gtaaaagga agagtaacat aagatcctac tcctgtaact    66060
tagattagtg cttttttttt ttttttttt tttttttgag atagagtctc actctgtcgc    66120
ccagactgga gtgcagtagt gtgatttcag ctcactgcag cctcaccacc tcctgtattc    66180
aagtgattgt cctgcctcag ctacccaagt agctggaatt acaggcatgt ccaccactc     66240 ctgactaatt tttgtacttt tagtagagac ggggtttctc catgtttccc aggctggtct    66300
ggagttcctg agctcaaata attcacttgc cttggcctcc cgaagtgcta ggattacagg    66360
cttgagccac tgcgcatgac ctacaccagt gctccttgaa gaatgggcta tgaactggtg    66420
ctggtttgtt aatcaatcca tgactaaatg cttactctca atttctatat tggtttagaa    66480
actcttacag ccatgtgata tttgtgtcat tcaggcacat cacctgtctc cccggttgaa    66540
gttcaggcca gtagttttaa cgcagttgcc tggagagttt tatgcaaagt gagctgagta    66600
tagtcatgac ggtagtccat gaacctgggt ccccaaaagg gagaaaacag tctttcacta    66660
cagattgcgt gagaaacatt ggccagcatt aaagaaggaa agtagattgc tcagggaagt    66720
tttgtaggga acttaaaatg agatgttagt atggcttagt aatctgtatt tgcaggtgaa    66780
atgaaaaatt cagccctaaa tctctgaata tggtaaactt agacttcatc ttctgcaggt    66840
ggaaatgagg caagggatcc attatccaca gcatgagtaa gtttctagtc agttcctctg    66900
tctagggagt ttgttttccc ttttcgccct tgttggcctg ggagactcaa ccagcttagt    66960
agtcttttcc tttcagtaag atttccaact ttgggttggt cttttacccct ttttagctct    67020 ttttgtcgta ttatctgcac ttagtacttt gtaactgttt tcaccccttc cccccaaagt    67080
tagttcaaag gcttacagca tgttgaaaat aggaaaattg ttttttaaatt aagtgagttt    67140 ttgtgtacac ttatttcttt agtctaaagt tttgttttaa atctctttt cacatttaaa     67200 cctgattccc tgagacaaga tataaaattg aattatttgt gaaatgtgga aaggttttta    67260
ttgcctgtaa tcaaagcata atctgtccat taaagcatta ttttagtgat gaagggtgga    67320
catacatccc aagttactta cctgttttct tactgtggtt ttgaccatac agcaaatggt    67380
attttatact ctgaaatgaa atgcaccata cacattgtcc agtatgtttt gagttttaat    67440
tctacatttt cagattttgg ggtcaaatga aatcaagtac tttataaata gttgtttctt    67500
ctgattctac tggccttaca tgttagattt ttttaaagta tacacattca gtcctttatc    67560
agtaccatta atcaaatgtt gatttcagca tttcttcatt ttgttttctt ttttctttc     67620 ttttttttctt tttcttttct ttttttttt gagacggagt ctagctctgt cacccaggct    67680
```

-continued

```
ggagtgcagt ggcacagtct cagctcactg caacctccac ctcccaggtt caagcagttc  67740
tcctgcctta gccccccccaa gtaactggga ttacaggcgc ttgccaccac atccaactaa  67800
tttttgtatt tttagtagag atggggtttc accatgttgg ccaagctggt ctcgaactcc  67860
tgacctcgta atccgccagc ctcagcctct caaagtgctg gaattacagg catgagccac  67920
cacacctggc cagcgtttct tcttttctc tctaatttat caaatttgga aacagttgga  67980
aaacatttaa aggaaataag tctctgtgtt tttaataata gttaaaagt taaggaaaa  68040 caaatgaata atattctgtt tattatagtc agacaaaatg tacatacgaa aatacataag  68100
gaaatataga atggcatctt ctgattttaa tttaatatta tggtaatgat ttacttaggc  68160
agaattatag ctatagacaa ccattttatc actttattta tatcgatcta ctctctatgg  68220
atgaaaacag ttaatactaa agcattaaga aggtatattg cttttcatct gtattaatat  68280
tcttcttctg atatttgata tttaataata tattttaaaa tactctgcat gatttcctga  68340
tcttaaagca ttccattcct ttcaaggaat ttggattata atgatttatt tatagtattt  68400
ttgtcattaa tatttagga tatggcatct taaaatattg tattcctaac agttatttaa  68460
tatataatta aacatctata ttagtattat tttatataac atatttcaa actcctcaga  68520 acatttgtag gttttttgttt aatttatgt aagtttcacc ttaagaatat tgactaatcg  68580
gttaatattc ttcttaatca tcgcaatttt ttaaaatgct ttctatgtac caggacctat  68640
ttaaggtact acagataatc agtgtgtcaa aaaacaaaac caaaattcct ttcctcatgg  68700
agttttacat tctagtagat tgattctact gttgattcat actaaattaa tttattaatt  68760
atagtagatt attctgtggc atttaacaga attcaaaggg ctacttttct gttgttagga  68820
aatagcatat gccattatct tggaaataca aagggaggac agaatttccg ctggctctaa  68880
cccattgctt tttaatgagt ttagctatgt atatatattt taaaatggaa tttataatta  68940
tgatcatttg gcaacctaca gttttctgt atttttttcaa cttctcaact tcccagtgat  69000
gggggtggat gttgaactag tcacttaagg ttttgggtct aaggagtaat atttgaaaca  69060
tgcagtattt agaggagata ttttttgtgaa tgaagagaat gtgatttttaa gaatactcat  69120 gattttatct aatttctgtt ctcaaaactt catttttgtaa tatagaagat aagcttgatc  69180
aaaatagttt gatcccagta taatcttttta ctcttctctc ctcccttagg acaaccttaa  69240
acttccacca caagaggaat ataaagaggt ccctcctgca ccaagaaaga tctgcagatc  69300
tttttcagtg ttcttggagg tgtgggtgt gagaacttga tcagtttgtg tcagccacct  69360
tgttctctaa aggtaagcac tgtgtagtga gtgcacactc gtgggcccag gctcctaacc  69420
taagactggt tttggaatgc tccattgagg gtgtgagacc ttcagacgtt cgcacagaag  69480
ggaggcccta cctgtgggta ggacatcaca cattcatcaa gaggtgcttt tcgttattta  69540
gaagtgaagc atgtcctggg gatgtatgga tatttttgtt ttgttttact ttaaaaaaaa  69600
tcccagtcat agtaaaacct tccagtttag tctgcattta ttcagttaat aactgctgga  69660
gttaatcaaa aatttttctt gtatgtcttg agatatggat taagaattt gaaacaatga  69720 caccatttag gcaatctagt gacataaatag cttcagttga tagagccagc tgtgaagaat  69780 tactttttcat gatctttttg aagctgtatc ttatctttac ttcagggaaa gcccctcaaa  69840 ccatttttgta ttctgtatta cacttcagaa agtgtggaag caaggtcat ctaatcttta  69900 aaaggtatgt aatcataaaa ttttttatgt cagatcttaa ttgaaaaata ttacttaaaa  69960
cttgaaaaaa ttacttaaaa ttggcaattt ctttttcgtc ttacaacttc ttcctgtctt  70020
```

```
caggaaatga agaataaata tgttggttct atcagggaaa ccttatgaag gataagcaaa    70080
ttaatgtctg tgctttactt ccaaattctg acatcagaaa accttattgt taactaatat    70140
aatctataga tgtctctcaa aatgaccagt cttaaattca aatgtcattt ggatatcatt    70200
aattgactat ggagaagagc agaagcatgc tgatttcgaa aatgtcatta atattaggat    70260
taggtcagtc ttaggcaaga atactttgaa taacaagaga ctaaatgtct agtaaaacat    70320
tttagattgt aattcccagt attctgtagt attaacaatg agacttaaag tactggtgaa    70380
gacattaaat ttgtcccttt catttatctt ttcttaaagc tcttaaagtg atcctgaaga    70440
ctttagttct acaaaatgtg aacttcttat ggaccattaa agtggggagt aatctgctga    70500
tttttgtcta gcaaccctac ctctgatgca ggataatttt tcaaaaccgt tgttcttcct    70560
atagctgtat aatagaagat attaaagagg aaaaatactt gtgtgtttgc tgttagaatg    70620
aggaaaaaat acaaattgga ccttttttgaa aaaccttgag aaccaattta ctttttttgt    70680
atgtaaatgg tcgaggagtt agaactagtc ttggttatta taactgcagg taaacttaaa    70740
agatttaaat cttcaaaaca gatatcatgt aggttttatt agaaaagaaa tatagattat    70800
tgggtgtata gagataatct atatatacgt acagtttttt ttaattttta tttgcaagag    70860
catgctaaat atcttagcct ttataatagc atagaataga atggacaaat atgttatccc    70920
tttttgccag ttgagaaaac actttgaatt aaatctccaa cctaatgaaa attataaggt    70980
gggttataga aataactaaa caggttatta tttcttaacc aaactaaagg tttattctaa    71040
ctaaaatact tgtaatctaa gaagtctccc taaacataca ccttttttaa agtgagtttt    71100
gttttatgat agtacatatt ttagcaacat actttagaaa agaaaagttt atttcactat    71160
cctagaactc gtgttctaat ttcagatcag ttttgtagga tgtataaata aaatggggac    71220
ctatgagatc tatgagatct tgccgtctgt atctacagta tcaaaaataa gatcatttcc    71280
ttaacaattc ttattaataa cttatccatc tcaattcata ggaggtgaca aaatcaactg    71340
ttgttctatg attttgatca taggtaggag ggaaaaccca aaataatggt accgagggct    71400
tcttccattg aaactaatat ctgggagaag atttgatttt catgtgtaca tatacacata    71460
cctatattag tgtttatttc ttttttctaa tcatgtaaga atttgtcaaa gatcaggttt    71520
ctgatttgtc tttcatcggt atctgtatgc cacattttgt ttttgttttt gaagtgttcc    71580
tagccagttc atgctagtcc ctactataaa ttttgtttcc ctggcatgat catgctcttt    71640
acctactctg gtagctggag ggaggtgaga gaagcagtct tatgtgttta ccgtactgat    71700 tttttttttag agatgggaca acaaagaaat tctagccttt ggagacatct agaccagcac    71760
tatatggtac aaagataatt cgagccataa atagaagcta cgtatgtaat tttaagttct    71820
taatggccat attaagaaaa taaaagagg caaaattagt tttcattaca ttttatttaa     71880
cccaatatat acaaaaatat tattccaaca tataattaat agaatgtttt atgagatttt    71940
tttcatactc agcattcaaa atctgtgtat tttatactca cagcacatct tatattggac    72000
tagccacagt tcaagtgctc aatagccgca cgtggctagt aggtaccata ttccacagtt    72060
cagatctaga caatgagtgg aattctcatt ttagcctcat acatgccaaa atccactgga    72120
tgaccctgcg aactcccctt gtttagagtt tccaaattta gcagaaggaa aaaacaaaac    72180
aaaacaggat gtccagtgta atttgaattt caagtaaata acaaataatg gtttagtgta    72240
attttgtccc atgctatatt tgaggcaaac ttttaccaaa gaagttactg cttattcgaa    72300
attcaaattt gactgggtgt cctatatttt atctgacaac ccttctctgg tttaacttga    72360
gaagaggaca tcatcaggct gcctggaatc ttggaggact agaaaataga gcatctcttt    72420
```

```
ctctgcgcag gattttaata atcctccaaa aatcagcctg taaactagaa gatatctcta   72480
gcccatttct tcctaatgac ctagtatgtt taagacagaa gaggggctca aatggcaagg   72540
atttagtcca tacatattta aacattttac atctaaatta ttacattaag atataaggtt   72600
tacgaaattt tacaattttt gaatgattac ttgaatttat aaaatgtaga tcatctaaca   72660
gcacaacgct gctatcattt ctcttgaaaa ctaattctcc tttgacagta accacagcag   72720
ttttcagggt cttggccatt tcaaggtatt ttcctaccat tggtttccat tgcatctgtc   72780
acataaacct ctggtagtca agcatgaaca caaaatacaa ggctactgaa tgcagggatt   72840
aggcttactt cgttacaagt atttaagtac ttgtaattct tagctctggt gttgaccatt   72900
ggatcctgac cagttcagca atcagtctcc taagagcttc ttttacagag gaacatcttt   72960
ccgttttcat tctttaacat ttttaatgta ttgattttag tacattttg aagcatacag    73020
tcacctcctt agtagtgtgg atctaccctc aagtgctata gaagagactg tttgtctcga   73080
aagacagtca ttgcaccacc tctctccaga gaatactttt ccttcacaag gtgcatgact   73140
caagatgaca ggcttacatt attatttatg taggcaggtg gatgccaact gccagtgcag   73200
ggtggcataa gttagcgttc caaagttaag ctatggtgca ttccaaatcc attcacactt   73260
aggagaatgt acccaagagt gtggggatgt tttcaattac tgcatttcct tcagagaaca   73320
agaaccacag gtaagtttgt gtgtgtgtgt gtgtgtgtgt gtgtgtgtgt gtgtgtgtgt   73380
gtgagatcca ataattattt ctaaataaga aatttcagaa tttgaaaata ttgcccctcc   73440
cccaaaacag tcacctgaaa ggtctcaaat atagctttcg gtatatattt ttcttcctca   73500
ctctaagaag gaaggtattg gagttggtgg tgatggtgga gttgggatga gggagacaat   73560
ttactgtcat ttgaaagctg tgaatgtcac acattttcat gtctagaaat atcctgggtt   73620
tatgtaagaa tctgattttg cctaacctct aatgtctcag gtatgaatta ttttgtcaga   73680
ttaacacatc tatataagta agatgttcag ccttgcttag ctaatgtctt caacagcaat   73740
gagtaaacta atgagttgtg tctgcatttt tcacttttat tctcaagact gacttccttt   73800
tgtttaaagg cttttgcctt atttctgaaa ccataattta aagctacaaa agacctgaaa   73860
tataatctag tacccttttt acctggggat ccttggatgg atttcagaga ttctgttgaa   73920
tccctaaaa ttacagtcat atttttgtata tatgtgttt tactggggag aatgtccata    73980
ttttcatcat attctcagag gatttcataa caaaaaattt ggtcgacaac cactgtgatc   74040
tagtctaatg tgatcatttt actgataaac tgaagttgaa agaatttaac ttatcttcat   74100
ttgaaattta atacttgtga aaattaaagt ttatttcttt aaaattcata ctgatttta    74160
aaagaaaaat acatttaact tcaactaatt aaacttgaaa ataccagcct aaatgggagc   74220
agttagttg ctaatgcttt cttctgttct gcccttgag tggactctac tagttaacat     74280
taaaatggcc ttccaataaa gtatgaggct atgtgataag ttcttgaaga tagattaaaa   74340
agaaaaggaa ttatccatta taatttaaat ccctttttct ctcttcaaat tctgtctcca   74400
aaactaaaac tcaagaaaat aggtgaataa tgttattttt atatttccag aatattaaaa   74460
aagtaggtaa ttgccttaat aaacattaca ctgggcatta ttgggacagt tttaggttct   74520
gaaccctagt taaagaaatt cttcagtagc ctatatacac ttcctgttgg ttttcagtga   74580
taagggcatt ttaaggtctt tttgatcata agatgctttt aatgttatag taggacttta   74640
gaaatggtaa gtaagcaagt tctgtattaa ttagggaaac taataccttt ttctcaaaat   74700
gaaggaaata ttatttttc ttttttcttgg tactaaccag taaagtctgc ctagtttaag   74760
```

```
atctagtgca tttataccat aaactgaata ttagaataaa aagaaatata gaggatgtta   74820
tataaaagac aattattttc tgaaaggagt agaaaacaag gcaacttgga acactacata   74880
tatataaatg taaaatatat taatatactt ttatatagat gatattatat atccatatat   74940
atattttttt gtttgtttga gacaaggtct cactctgtca cccagcctag agtgcagtgg   75000
cacaaccaca gctcactgga gcctcgacct ctgaggctca agccatcctc ctgtttcagc   75060
ctcctgagta gctggaacca caggtgtgca ccaagatgct gagctaattt ttctgtgttt   75120
tttgttgaga cggggtctc atcatgttgc ccaggctggt ctcaaacccc tgagctcaag   75180
cgatcctccc accttggtct cccaaagagc tgggactatc aggcatgagc caccatgccc   75240
agctgtacta tttatatttt ttatttaaat taaattgtgc ttaaagattc taaaatttat   75300
agtataaagc tcattataga aaatggtatt gacttctgaa acattatagt tttggttttg   75360
tttttattcc ttcggacatt ttcacttaag gtagttatca ctcatgcttt tctgctatta   75420 taaaagtga ccagattttg cttttttatc caggaagaac agtttgtgaa tgccacttga   75480
taggccacct gtgttatttt ccatgggtat ttctaacaaa taaaaagtta tattttact   75540 ttgtattcat caaattattt tatgtttaat ttagaaaagc ttaaattctt cttaggaata   75600
tttgcaaata tttgtaaata gttttttca aaaagttga ggtagataga tattaaatat   75660
ttttgtgact tctcattaaa agaaactgaa gcaattagtt gacctcactc aattcattaa   75720
aacagtgcta ggttcctggt tttcgtgaca ttaaaaacaa ttcaacatct gtgtgtagac   75780
aatgactaaa actttatgat tttgtttcag agttttatta ccatagatat tgtttaaaat   75840
agaactttca aatacattta agaaccatta aaagtgactt ctccctgtgc ctgaaagata   75900
catgcatggc ttatatcttt ttgtgtataa acaatttaat gtttaacttt tatttccttt   75960
aagtttgcat atcaaacact cttagcaatc tcatcattta tactggagta cttagacttt   76020
gaaactttgc cacagctacc tgccacgtcc ttgtatagga tataagtaaa tatattcagt   76080
catcaaatct atagagaact gtgagaatag agtggtaaac aaaacacatt gcctgccctc   76140
acagctaaag aggagtgatg gtgggaaagt ggaagtgatc agaacccaat ctgaggtcag   76200
aaaacaaaac tacaatctat ttcaggttgc acaaatgaaa ttttaactga atctgaggga   76260
cattagattt aatcaaacca aatgagaagg caaggtggtg ttttgagcta agggcacagc   76320
agatgtaaga gtcataaagg aagaagaaca aaacacattc aagataaaag acacggagag   76380
agggaaagat gacactgtac ggtgaaatat cttgcaagtc aatattagat actagccttt   76440
gggctttagc ttgagaacag tgggaagaca ttgacgctca gattttttt tctaaagttt   76500 tttattaatg cctaatacat atagaagcat tagcatactg cttcgtgaat tttcacagac   76560
ttagcacacc tatgtgatga acacctagat gaagaaaaac aacaatatca gcatcctaaa   76620
agttccccct catttccctt ccagtcagtc ctgtctcttg cccaccaagg gagacctctt   76680
gcctgacttc tcactgtata tggaggatat tgcctacatt gtacttaata taaatagggg   76740
catacaatgt gtattcactt gggtgaagca ttacgattat gagatttatc catattgttg   76800
actgtggttg ctaattgttc tcatagctgt ataatgttcc gtcatatgca tgtactacag   76860
atttgcattt ttctgagatt gctgaatctg catcatgaag gatgggaggg tgtgaattta   76920
gtaagcttca cagtaaatct aggaaagaga tactggggct tgagctagtg tggtgacaat   76980
gaggatgaag agaggtgggt atatagagag atatttacaa gttagaactt aattggatga   77040
ggggatgaag aatcatacac cagagataac tcctgggtcc tgacttgggc aggggttaat   77100
ggcagtgccc ttcattaagt ccaaatactg gagaggaagt gggttgttgc ttgtgcttta   77160
```

```
gtgatacagg ggattaacga attcaatttc tgatacagtt aaggcatctg tgaaacattg    77220
catagatctg ctttatacaa ctgttttatt aactgaatta atgaataacc ttaccttcat    77280
taacaacagt gtgctaacaa atagttctac atatggaaaa ctgcaaatct tgtctagtct    77340
cactgttctt cacctctgaa tctcacgaga tactcttttc ctaaatgtgt taggagtggt    77400
tttgttgcat ctcatgcttt tttttctttt tatttataga atatacttca tctaaactag    77460
tgctaacttt atgcaagaag agtagcactt cctaggtata tgatatgaaa ggcattggtg    77520
aaatgccttc atacttaaag gcattgtttt tccaacatta tggtctttcc tttagcacaa    77580
taaagacacc ttaaaatgag tttgtttata ggaaataacc tacttattta gtaagacttt    77640
aatggactga agtaaatatt catgagattt gggcagggga agaaaagaa agatagggat      77700 gaggtctgac ctgagcacaa acctaggcag ggtgccacag ggggaaccct gaacatcaga    77760
gagcaggttg aatgcacctg atttaaagg aagattatgc caaagagtg acgtaggagc      77820 tgtaaaggag ggacttcacc tcttttcgat gctgcctggg actagttata cttgtggaaa    77880
attttatgtg aagataacta ataattctag cactgaatga aacaaatgcc tgagacctac    77940
tggaacatta aatagacttt tatgccagcc agttatgatt cagtgctata tttagaccac    78000
aaaatttgaa ctaaaatcaa ggcagtttat tcttatccca tcatgtccat ggggtggaga    78060
ggaacaacta agtaatcatg atcatgcact tcagtttata gcgttttctc tagctttggg    78120
cattgtcact taacagacaa tacaaatttta aaaattaaat gctcaatttc atttcactga    78180
ggttttttgt tgttgcacaa cattgtaagt atacagtaag ttgttttttc ttttaaattt    78240
ttgcctctaa ttcaggttta cattgagcaa ccaaatcagt attttcagaa accattgaag    78300
ttaattcatt tatttaataa ttacttatga aatatgtcat gtataatagt gctatagcct    78360
aagatgatga tggtgagaag tactcctacc ttttgttact ggcacgatgg tggcgatact    78420
cagaacaaac aaaaacagtg tgataacaca aattattata tgactcgctg ttttaatagt    78480
gtttacaaaa gcagtgaatc ccaggaaaat aaactattgg ctacaatatc aaaaaagaaa    78540
tgatggaagt ggtagaattt aatttgggtc ctgacaaata ggcaggattt gaacatgtat    78600
ggcaagaaca ctgcaggcaa gggtaacatc tcatgagaac tgatgcagaa aaaaatacag    78660
catatattgg cagagtgaga aactggccag actgtagcag aaatcacaag ctggtgtgag    78720
gagagagaga aaagcttcat taaggaagtt ttgaattact gaaaaattca ccagtcataa    78780
ggcatggatt attgtcttgc tgtttagatt acctataaat gtaatttac tttactcacc      78840 accatgtgat aattatgtag ggtttatct ttttagaaac ctgatgtgaa attacctgaa      78900
ggaatgaagt tagtgtgctt ttaagttaag aatatcttca ctcagtatcc atggataggc    78960
ttcagggaat ctggatctct ttgaaattaa agcaaaagtt tggatgtatt tcttttctg      79020 gaggaaggat ccattgcctt tatgagtatg taacagtcca gaagaagtta ataaaatagc    79080
tcgagctctc ctaactaaa actttttat tttttattat tattatttt ttttttgtag       79140 agatggagtc tcgctctgtc acccaggctg gagtgcagtg catgatctc ggctcactgc     79200 aacctccacc tcccgggttc aagcaattct gcctcagcct cccgagaagc ttcatcttgg    79260
gttttttatt attattatta ttattattat tattattat tttaagttct                79320 agggtacatg tgcacaacat cttggggttt tttaatgca gtaaattaaa atggggaaat     79380
taaaacacgt taaatacttt ccctttattt cactatttac tgatacggta tttaagagat    79440
aatcctgaaa agtatatcag ttgggttgat tatataacca gagatagtgg ctattttatc    79500
```

| | |
|---|---|
| aattccgtgg ctttcagtaa aaggacagct caattgcctt tttagataca gaatgtttct | 79560 |
| gaatatgcta tttcaagtag aaattccttc ctatttttgg acaggcatat gtctgctttc | 79620 |
| tgcagaatac aaagaatttt caatgtgtcc agcttcagtc ctgaaatttg acttacctgg | 79680 |
| atcatattta atcttttgca caactgttta aagcaggagt caacaaatta tatatagccc | 79740 |
| atgggccaaa tccagccctc aaacctattt ttgtatggcc tatgacctaa gaattgtttt | 79800 |
| tacattttaa aattgttaaa tttaaaaaag gattgtaagg gattaggatt ttaaaaagga | 79860 |
| gaatatgcaa cagagatttt atgtggccct caaagtctat ggtatttact aactggccct | 79920 |
| ttttttaaat gccaatccgt ggtttaaagt acagttttta agttctccta gatgcatgtg | 79980 |
| ttattctaca agcagataca atgcttgtgg atagatatta ttttgaagt tgggagtata | 80040 |
| tttatataat tttagcaaag ttgactgaat aagataacct gttttctata ctgaatattc | 80100 |
| agctaatagt ttcgctttct aaagtctgga tttgaaagtg tatgaacaaa gtgtggactt | 80160 |
| agtaatctac ttcaaagaac tatgtgaata tgaaagtaga ttttgttttt catggatata | 80220 |
| ttacacagca accacaattc agatcaagaa aaatattaaa atataatctt tgttttagaa | 80280 |
| gacaccactt aaggcaaaga aggcaaaaga aaacatttgt acctgttaat gagttgggaa | 80340 |
| gggcagctct taaaaattat actattcatt ggtttattca acatttatac ttattttag | 80400 |
| aaccattata tatattggct tctttgtatt atattttatt aatattattg tatgagatac | 80460 |
| tatgattcta aattttggat aaatattgaa attattttta atggggata tgtcataatt | 80520 |
| agtgagtctc aaaaaattgg ggcaattctg ccttctctct ctgcatcatt attttttcctt | 80580 |
| cactactgga tcttttccac caacatacaa ataatgttga gttttttccc ccatcttaaa | 80640 |
| aaaaatctta ctcccagttc tcctttagtt actaccccat gtctttcatg taaagcctat | 80700 |
| atctctgaag tatgtagttg cctgtgctgt ctgaattcag ttcctataac ccctgccatt | 80760 |
| tcaccagaat tgtacttctt aatgactgcc atgctgccaa tcagatggtc atctcagtct | 80820 |
| tcctcttatt tgacctggca acggtgttta acactccttg tttggccttt tagatactat | 80880 |
| actacactgt cctgttttt tttctcctac ccctctggct gctgctttt caatctcttg | 80940 |
| ctgatttctt cttgcctccc catctccaaa ttgggaatgc tccaacattt ggaattttga | 81000 |
| ggcctttaaa actgcatgtt cactccctta gtgacttcat atagtaccat ggctttatat | 81060 |
| gatcatccat ttgctaatga tcagaagtcc tttagtcttt ttttttttt tttgatatg | 81120 |
| gagttttgct ctgtctccca agctggagtg agtgcaatgg catgatctca gctcactgtg | 81180 |
| acctcctcct ccggggttca agcgattctc ctgcctcagc ctcccatgta gcggggatta | 81240 |
| caggcgtgtg ccagcacacc tggctaattt ttgtaatttt agtagaaatg gggtttcacc | 81300 |
| atgtcggccc ggctggtttt gaactcctga cctcaggtga tctgcctgcc acggcctccc | 81360 |
| aaagtgctgg gattacagat gtgagcctcc gtgcctggcc cctgtagtct tcttagaatg | 81420 |
| taatatagta aactgaattc ctcatctttc ccccaccaaa acctcctccg gcagttttc | 81480 |
| ccatctgagt aacagcacct gctgtctttt aatcagcctt ggtgtcacca aggatgcctg | 81540 |
| tcctcctttc attccacata tgataattct tcacatttct gttaccaaaa tattatcttg | 81600 |
| cttctgtccc aaaatatttt ctgagattca gttattgctt accatctcta ctcctacaac | 81660 |
| cctgatccaa atcaccttca tctcttacct gtattgatgc aaaaagcctc ctgtaattgg | 81720 |
| tcttcctgtt ttttcctgtt gacttaactt cagtccattc ttaatatagc aggtaaagta | 81780 |
| gttatattta aatataagcc atattatgtc actcttttga tgaaaatcct ccattgactt | 81840 |
| ttcatctcaa ccagaataaa aactaaagtt cttaaaatag cctaccaggc tctgtgctct | 81900 |

```
gggctgtcat tcccagacag ccactgccaa ccactcctgc ctgctcacac ccactttgct    81960
ctagtcatcc acactggctt ctttgctgtt cttagaacat gccaggcaag ttcttgcttt    82020
agagcctttg cactggttgt tctctgtaat actctttccc tgtatatcta cagggatcaa    82080
tctctcatta cttgagattt gtacttaaat gtcaatttaa tgaagctttc tttagccact    82140
tgatctaaaa ttgcagattt cccctacttc accccaattc tccttcctgc tttatgtttc    82200
ttttcttgaa gacctgttac catctaccat cccatatatt ttacctactt ttttcattta    82260 tttttttgcct tcctccacta gaatataaag cttttttgtt tcctttgttc actggtctgt    82320
cctcagcaca tagaaatata gtgtttggcc cacgttatac acttagttaa tattgatgaa    82380
ttaataaata agtggaattt aaaaatagcc aacacaaaat tttaacatag ttcagggatt    82440
tttgagagct cctgggatca ttgaataagc attcaaatat tccagtaaat gacatgcatg    82500
gagctaaagg tattagaaat atgactgtat acattggtat cattatatat gtagaacttt    82560
cttttttgca cagatcctta gctttgacca tttattctat ttttaaagtg tggaatacta    82620
aaaaaaaata ttatttgaac ttaaatatga ttactatttg agtatgctat gatgtgaata    82680 cttttttaaaa gaatctttta tcattaaaag tagtcattta gtacagtagg aattttttta    82740
caaaaaaact tataaaataa tttaaatttc cagaagagtt tcaaaggcag tacagagact    82800
gaacttttca ggatccttgt tctgtgtctt ataagttttc atcttcaaaa agcatggaac    82860
aaatactaat tcagcctacc aacatagctt ttgttaaagt aactgctttt taaaataatt    82920
tttaaataca taaagctacc aaataattag tttcaaattt cataattatt ttttcttgac    82980
tatatgcata actgatttaa atagagtcat aatccaaatt ttctcaatta tgacatacat    83040
ttcttcatgt ttcattatag tctttttaaa tgactaataa tagaccatct tgctgatgta    83100
tcattattaa taaattgttt tcttcctgtt ggacatctta aggctgtttt gttttactgt    83160
tattaataat atggtaggtg atatatttgt gcatataact tcttgcattt gcctaaatta    83220
tttcctttag ctaattaccc agaattagat tgggcaataa aaatcatagg gcttatgagg    83280
aaaatggggt tggagtacag cccacaataa ttttgtcagt gacacatttt taaaaagaca    83340
gaaaactaat aacaagtgca gcacagtttt acatatgtta aatggttaag aaatacataa    83400
ttactattat acaagtgaca cttttttacct tgaacaaacc ctgatgtttg cttgtggaag    83460
taggtatgga attgtgatct ccaagttaat gtgaagtggt agaaggagga ttatctgaaa    83520
tcagaaggaa agttgtaaca ttgcatgtga tgggtgtggc tcgtaacaga agcacggtga    83580
actgaagtgg ctggtaactt gagatgtgtg caggtgtgct ttttgtttat tcttatgtga    83640
cttagttaag ctggcagcaa ttttctgtgt tcacttagtg tttctcgcag ataaaatcat    83700
gcataagcaa aggtgacatt ctctttatgc tcatgtagtt ctctaataaa ccaactgcac    83760
tgaaacaaat ttgcattttc aaaataagtg ttatggcaga agagactcca ctaatttgtt    83820
atcccatcaa ttttactgca attttaacat cgtgctaggt ttttaagctt ttatatggta    83880 attttttctga tatatttta accagatgcc tttagaatac agtttggtgc agtcttacag    83940
atataactcc aaccataata ggcagtggag atgttatttt aaaataataa taaagcttgg    84000
ttaattgcac agagacaaga aaaaatggag gacaggtttc ttccaagaat gactgaagcc    84060
agaatagagg ttagagaaaa cagaagaaga aaaaaaaaac cctaaaacct gcaaagggag    84120
tttgtaccta ggtagagcag taccttgaat accagattaa agtttcaact tccagaaggc    84180
aaccaaaagt cagtattttg ttgttgttgt tgttgctgtt gttgttgttg ttgttgttgt    84240
```

```
tgttaacagg aaagatgaaa gaccagataa ggaagaaagg ccaaggagga ggacatagga    84300
aaagtgtagg ttggagatgg tatggttacc atccaataag aacagaaaag aaagtataaa    84360
tgtaagggtt ttgttagcag tactatttgc cttctgatta aatgataaag aagatgtaaa    84420
ataaatgttt gtctaagatt actccaaagt attatcctga gtggctaaag aatagcgatc    84480
ctagaaaaaa aaaattgatg atcaggaaga agagctgtat gagtgggagg agaaggtatt    84540
cctgaaatga tgagtttagt ttgaaaggaa gcctgactga gtggacacag cccctgattg    84600
agcattaaga aaattttttga ttaattactg gtggggccct ggacaatagt atacttctct   84660
ggctttcagt tttctcacct gtaaaataag tattgaacta ctagtgactg ctgaagtttc    84720
ttccagcttt gaaacaattg ctgtgtgttt tttttttatt tgaactttat tactgtttct    84780
tcatgattgc tgtctagtga cctttttatga agactttggt ttataatgaa acaaggataa   84840
agtgctcagt cttgagtctg ttggagatta aactttcctg actcctgaaa tgcttgactt    84900
gacaccggaa gtgccacaac tgccatctca ctttatcttt tttctgccaa aggaagcttc    84960
ttgcagatca aaatttgggag caaggagaat tggatgtata aagccaaact tggaaaaagc   85020
attctgcaat ttttcttaat acaatctttt ggggctctat ttgttattag ctgttagaaa    85080
tcccaataaa ttatttggaa agaaattcag tacaaatata ataatgttat agaagtatat    85140
gtatatagta aatataatct aggagaggct taccatagaa aaggtgcagg ctttggaatt    85200
agcttgaatt caaatattag ttttattact ctactagctg tgtaacctta ggtaaacaga    85260
aatgaaaagc tttattttgg aggatgattt tatttctttc tgtgtaaaat ggaaatagta    85320
atactaagtt tcagaattgt tgtgaggatt agagacaatg tttgtaaaga actgagtata    85380
caacctgata cttaataaag agtaaccttt atcagttacc aggtaatagt tattgttgca    85440
gtatgaggac ttggttaaaa cttttttcaaa ttcttacctg tattaaacac ttaacctaca   85500
ttctcctctt gtaatcagaa tctcgtgtgc atgtatgtaa tgatgggttc tctaatattc    85560
agttttctgg cagattaaaa catctgacaa aactaaagaa ttattttaaa aatatttaga    85620
gtgtcaacat attcaattct tagatggaat aatgatcttt aaagagatga gactagtatg    85680
taaaaagttc atttttaaaa gtaagaatct tcatcctaat tatctgctag ctaagacaaa    85740
ataatagaat caacattctt acagattttc gtttacactg cctcctttaa aagatgccca    85800
atactgtgga tattaaagag tgattactag tatattatgt atattatata ttcagctttc    85860
cttttgtaaa ttgattttaa acatttccaa gaaatagttt caaactaggt acttcttaac    85920
atctcttata cttttgcctt aaataaaaac acattgataa tgctaattat atggtaaaac    85980
tgttaggtct gcagaagtca tatttattt ctgaaataat aaaaatacat tttaaaacag     86040
atgcagaaaa tgtgaaaggt agattgctgc tggaaattca catagtcttt aaggaataaa    86100
ctatgtacgt gttgactatg aacagactag tctatattta ctatattaaa ttttcaccaa    86160
gttataaaga ttcagtatgt tatccttttg gaaatttaaa aaatagtaaa acacattctt    86220
tttaagagca ggaacaatgt acttgaagca acaaatttat gactgaagat tatatatcag    86280
tataatcctt gcttctctga ttgctgtgta ccctttttctg cagccgtttt tttttttaact  86340 cttaaagtct gtgctctatt acagtgattc ttttttcttgt ttctaaaaga ataaatgaat   86400
agttttttgt taataattaa tgtaggcctc tgcttacctg ctttatacat tctttacctg    86460
cctgtacgta gcacttgcct atgcaagtat tcatttactg aaaaagttac caactttgta    86520
gccttgaaat catttaaaaa atatgttaac tgacttgaat actctggtta gaagcaaaat    86580 gcatacccttc tacttgaagg aatttgtttt cacctttact gaaaaaaata catatttagt   86640
```

```
tgtattttaa acactactta ttttgacata gtaatcactt tatagttttc taggaagttc    86700
atctttgtat gcattttata tctcctattc ttttcttgta aagattaggt tacaattaaa    86760
ataattcaaa gatcattggg aggtactgca ttaaactgtg ggttggatct tgccttttgt    86820
cttgttcaaa ctgcacctct cctttttattt ttttcaatct gaagatagta gcatgcttag   86880
agcatgaatg taagccatgt ggtggctaag atagagaagg cagagatgga tgacttcaga    86940
ggaagtaagt gtttgacagg agactggact gggtgatggt gtgaaccaaa gtcaaggtca    87000
cagggagaaa aagagcaggc tggcttcatg ggtgtgcaac ctgtacagtt acacaaggct    87060
cagctttttt aatgttctgc tactgctatg ttgaaattct taatcaattt cacacaagag    87120
gccctgaatt tttattttgc actgagtctc acaaattatc tagcctgttc tgcagatgag    87180
aaataacagg aagcagaaat ttcttgtctt tttagttatt aattccttttt cccagattag    87240
ccaaaatggg aattattttt taaatgatga cttacggaca tttaaaaaaa tgtggaaaat    87300
taacctaatt tgaaagcagt tgtgtgtgta tgtatgttat ttagtaattt acccaagtat    87360
tggagagggg aaaaaggagc ttgttaaatt ttcttatgga agtgtcaaag gtggtcaaac    87420
ttccaataga ctttaccaag tcagtatgta atatacatag tttgagaagt aaaaacaatt    87480
ggtattacag aattgtatgt ctgaattacc tactacgtgc tgggctttac ccagaaaagt    87540
gtttctttac ccataaagcc tgatgcttta tattcagtac agtactttat tatttagtaa    87600
ttattctttc ctagtattat ttctaaagtg gtaattgttt cttgccttta tagtgcttgt    87660
aaactttatt ttttaaagat tttggaaatt aaaatttaga aatttataag cccattgtgg    87720
tttttacaca gtcctgtcag tttactagtt ttatttgata gctatctaat acgcacctgt    87780
ttaaagtgga acgtgtttct attacaccta ggctcttttt tttttttaaaa tttaagttct    87840
gggatacatc tgcagtttgt tacataggta tacatgtgtc atggtggttt gttgcaccca    87900
tcaacccgtc atctacatta ggtatttctc ctaatgctat ccccaccta gcctcccaca    87960
cctcaacagg ccccagtgtg tgatgttccc tccctgtgtc catgtgttct cattgttcaa    88020
ctcccactta tgagtgagaa catgcggtgt ttggttttct gttcctgcgt tagtttgctg    88080
agaatgatgg tttccaactt catccatgtc cctgcaaagg acatgaactc atcctttta    88140
tggctgcata gtattccatg gtgtatatgt gccacatttt ctttatccag tctatcattg    88200
atggacattt gaattggttc caagtttttg ctattgtgaa cagtgctgca gtaaacatac    88260
atatgcgtgt gtctttataa gtagaatgat ttataatcct ttgggtatat actcaataat    88320
gggattgctg ggtcaaatgg tatttctagt tgtagatcct tgaagaattg ccacactgtc    88380
ttccataatg gttgaactaa tttacactcc caccaacagt gtaaaagcat tcttagttct    88440
gcacatcctc tccagcatct gttgtttcct gactttttaa tgatcgccat tctaactagc    88500
atgatgatat ctcattgtgg ctttgatttg catttctcta atgaccagtg atgatgagtt    88560
ttttttttt catatatttt ttggccgcat aaatgtcttc ttttgagaag tgtctgttaa    88620
tatcctttgc ccactttttg atggagttgt ttttttcttg taaatttgtt taagttcctt    88680
gtagattctg gatattagcc ttctgtcaga tggataggtt gcaaaatct tctcccattc    88740
tctcagttgc ctgttcactc tgatgatagt ttcttttgct gtgcagaagc tctttagttt    88800
aattacattc atttgtcaat tttggctttt gttgccattg cttttggtgt tttgttcatg    88860
aagtgtttgc tcatgtctgt gtcctgaatg gtattgccta gttttctcc tagagttttt    88920
tatggtttta ggtcttatgt ttaagtgttt aatctatctt gagttaattt ttgtatgagg    88980
```

```
tgtaaggaag ggttccagtt tcagttttct gcatatggct agccagtttt cccaacacca    89040
tttattaaat agggaatcct ttccccattg cttgttttt gtcaggtttg tcaaagatca     89100
gatggttgta gatgtgtggt gttatttctg aggcctctgt tctgttccat tagtctatat    89160
gttttgtttt tttgtttatt tttaacttct tatttattta tttatttatt attattatac    89220
cttaagtttt agggtacatg tgcacaatgt gcaggttagt tacatatgta tacatgtgcc    89280
atgctggtgc actgcaccca ctaactcgtc atctagcatt aggtatatct cccaatgcta    89340
tccctccccc ctccccccac cccaccacag tccccagagt gtgatgttcc ccttcctgtg    89400
tccatgtgtt ctcattcttc aattcccacc tatgagtgag aacatgcggt gtttggtttt    89460
ttgttattgc gatagtttac tgagaatgat gatttccaat ttcatccatg tccctacaaa    89520
ggacatgacc tcatcatttt ttatggctgc atagtattcc atggtgtata tgtgccacat    89580
tttcttaatc cagtctatca ttgtaggaca tttgggttgg ttccaagtct ttgctattgt    89640
gaataatgcc gcaataaaca tacgtgtgca tgtgtcttta tagcagcatg atttatagtc    89700
ctttgggtat atacacagta atgggatggc tgggtcaaag acaaaaacca catgattatc    89760
tcaatagatg cagaaaaggc ctttgacaaa attcaacaac acttcatgct aaaaattctc    89820
aataaattag gtattgatgg gacgtatctc aaaataataa gagctatcta tgacaaaccc    89880
acagccaata tcatactgaa tgggcaaaaa ctggaagcat tcccttttgaa aactggcaca    89940 agacaggggat gccctctctc accactccta ttcaacatag tgttggaagt tctggccagg    90000
gcaattaggc aggagaagga aataaagggt attcaattag gaaagagga agtcaaattg     90060 tccctgtttg cagatgacat gattgtatat ctagaaaacc ccattgtctc agcccaaaat    90120
ctccttaagc tgataagcaa cttcagcaaa gtctcaggat acaaaatcaa tgtacaaaaa    90180
tcacaagcat tcttatatgc caacaacaga caaacagaga gccaaatcat gagtgaactc    90240
ccattcacaa ttgcttcaaa gagaataaaa tacctaggaa tccaacttac aagggatgtg    90300
aaggacctct tcaaggagaa ctacaaacca ctggtcaagg aaataaaaga ggatacaaac    90360
aaatggaaga acattccatg ctcatggcta ggaagaatca atatcgtgaa aatggccata    90420
ctgcccaagg taatttacag attcaatgcc atccccatca agctaccaat gactttcttc    90480
acagaattgg aaaaaactac tttaaagttc atatggaacc agaaaagagc ctgcatcgcc    90540
aagtcaatcc tgagccaaaa gaacaaagct ggaggcatca cactacctga cttcaaacta    90600
tactacaagg ctacagtaac caaaacagca tggtactggt accaaaacag agatatagat    90660
caatggaact gaacagagcc ctcagaaata acgccgcata tctacaacta tctgatcttt    90720
gacaaacctg agaaaacaa gcaatgggga aaggattccc tatttaataa atggtgctgg    90780
gaaaactggc tagccatatg tagaaagctg aaactggatc ccttccttac acctatataca    90840 aaaatcaatt caagatggat taaagactta acgttagac ctaaaaccat aaaaaccta      90900 gaagaaaacc tagacattac cattcaagac ataggcatgg gcaaggactt catgtctaaa    90960
acaccaaaag caatggcaac aaaagccaaa attgacaaat gggatctaat taaactaaag    91020
agcttctgca cagcaaaaga aactaccatc agagtgaaca ggcaacctac aaaatgggag    91080 aaaattttg caacctactc atctgacaaa gggctaatat ccagaatcta caatgaactc     91140
aaataaattt acaagaaaaa aacatacaac cccatcaaaa agtgggcaaa ggacatgaac    91200
agacacttct caaaagaaga catttatgca gccaacaaac acatgaaaaa atgctcatga    91260
tcactggcca tcagagaaat gcaaatcaaa accacaatga gataccattt cacaccagtt    91320
agaatggcaa tcattaaaaa gtcaggaaac aacaggtgct ggagaggatg tggagaaata    91380
```

```
ggaacactttt tacactgttg gtgggactgt aaactagttc aaccattgtg gaagtcagtg   91440
tggcgattcc tcagggatct agaactagaa atggtctata tgttttgata ccagtaccat   91500
gctgttttgg ttactgtagc cttgtagtat agtttgaagt caggtagcat gatgccttca   91560
gctttgttct tttggcttag gattgtcttg gctatacggg ctcttttttg gttccgtatg   91620
aagtttaaag tggttttttc taattctgtg aagagagtca atggtagctt gatggggata   91680
acattcaatt tgtaaattac cttgggcagt atggccattt tcacgatact gattcttcct   91740
atccatgagc atggaatgtt tttccatttg tttgtgtcct ctcttatttc cttgaacagt   91800 ggttttagt tctccttgaa gaggtccttc acatcccttg taagttgtat tcctaagtac   91860
tttattctct ttgtagcagt tgtaaatggg agttcactca tgatttggct ctgtttgttt   91920
attattagtg tataggaatg cttgtgattt ttgcacattg attttgtatc ctgagacttt   91980
gctgaagttg cttatcagct taaggagatt tggggctgag acaatgaggt tttctaaata   92040
tgcaatcatg tcatctgcaa acagagacaa tttgacttcc cctcttccta tttgaatacc   92100
ttttatttct ttctcttgcg tgattgccca agccagactt ccaatactat gttgaatagg   92160
agtggtgaga gagggcatcc ttgtcttgtg ccggttttca aagggaatgc ttctagcttt   92220
tgcccattca gcatgatatt ggctgtgggt ttgtcataaa tggctgttac tgttttgagt   92280
tacgttccat caatacctag ttcctggaga gttttttggca tgaacgggtg ttgaatttta   92340
tcaaaagcct tttctgcatc tattgagata attatgtcgt ttttgtcatt ggttctgttt   92400
atgtgatgga ttatgttgat tgatttgcat gtgttcagc ttcatcccag gtatgaagct   92460
gacctaatcg tggtggataa gcttttgat acactgccgg attcagtttg ccaatatttt   92520
attgaggatt tttgccccaa tgttcatcag ggatattggc ctgaaattct ctttttttgt   92580
tgtgtatcta ccaggttttg gtatcaggat gatgctggcc tcataaaatg agttagggag   92640
gagtccctct ttttctgttg ttcgagatag tttcagaagg aatggtagca gctccttttt   92700
gtacctctgg tagaattcag ctgtgaatcc atctggtcct gggctttttt tggttggtag   92760
gctattaatt actgcctcag tttcagaact tgttattggt ctattcaggg atttgacatc   92820
ttcctggttt agtcttggga gggtatatgt gtccaggaat ttattcattt tttcctagat   92880
tttctagttt atttgcatag aggtgtttat agtattctct gatggtagtt tgtatttctg   92940
tgggatcagt ggtgatatcc cctttatcat ttttttattgt gtctgtttga ttcttctcta   93000
ttagtctggc tagcagtcta tctattttgt taatcttttc aaaaaccag cttctggatt   93060 cattgattat tttaaagggt ttttcgtgtc tctatctttt tcagttgtgc tctgatctta   93120
gttatttctt gtcgtctgct agcttttgaa tttgtttgct cttgcttctc tagttctttt   93180
aattgtgatg cacttattct aaaatcaacc acatagttgg aagtaaaaca ctcctcagca   93240
aatgcaaaag aacggaaatc ataacagtat atcagaccac agtgcaatca aattagaact   93300
caggattaag aaactcactc acaacctcac aactgcatgg aaactgaaca acctgctcct   93360
gaatgactac tgggtaaata attaaattaa ggcagaaaaa aataagttct tgataacaa    93420 tgagaacaaa gacacaccat accagaatct ctgggacaca gttaaagcag ctcacgcctg   93480
taatcccagc actttgggag gccgaggcga gtggatcatg aggtcaggag atcgagacca   93540
tcctggctaa caaggtgaaa ccccgtctct actaaaaata caaaaaatt agccgggcgc    93600 ggtggcgggc gcctgtagtc ccagctactc gggaggctga tgcaggagaa tggcgtgaac   93660
ctgggaagcg gagcttgcag tgagccgaga ttgcgccact gcagtccgca gtccggcctg   93720
```

```
ggcgacagag cgagactccg tctcaaaaaa aaaaaaaaaa aagcagcatt aggagagaaa    93780
tttatagcac taaatgctat aaatttctct cccacaagag aaagcaggaa agaactaaaa    93840
tcgacaccct aacctaggct cttttctgg gtctctttct ttctaaagtt ttgcttattt    93900
tgtttactgc acaatccaac taaaaccaaa tttttacat catttcattt gagagttacc    93960
ttttattcta ataaactgtg gaataactgg ggttggggag ggaattgctt aagttcataa    94020
ggattcttgc aaacttgaat gtgtcgatac aagattttt ttgaaaattt gtaattccat    94080
ttcacgatct caaccagaat tcattatgtt taaaccacct gatatagact aaaacatttt    94140
ttcaggagca caattgtaaa aaggatgcag agaaatattt acaacattac ttatttcttt    94200
gcagatttag tgaaagtatg tcctacttt acaaaatatc ttattttcct ctcttttta    94260 cacatataat agagaactaa cttttataaa ctaaatgaga agggaatact aattttaaa    94320 ttatgatgtc acttgtagaa tttgttttaa aattgataaa atacacctct tttttatta    94380 ttatacttta agttctaggc tacgtgtgca caacatgcag gtttgttaca tatgtataaa    94440
tggccatgtt ggtgtgctgc acccattaac tcatcattta cattaggtat atctcctgat    94500
gctatccctc cccactccct ctaccccatg acaggccctg gtgtgtgatg ttccccttcc    94560
tgtgtccaag tgttctcatt gttcaattcc tacctatgag tgagaacatg cggtgtttgg    94620
ttttctgtcc ttgtgatagt ttgctgagaa tgatggtgtc cagcttcatc catgtccta   94680 cagaggacgt caattcatcc ttttttatgg ctgcatagta ttccatggtg tatatgtgcc    94740 acatttctt aatccagcct atcattgatg ggataaagca cacctcttta agactgctta    94800
tagaatgcta tggactcatt ggcttggttt tttattttcct tggttcagt ccaaagtgta    94860 ataagctttt cagaaagttt ctcctggatg tgtaaagaat accaacagat atcagaaagc    94920
atctggctga agtttaagc agggagtatt gttattcatc cagcgaaggt ggtaaaactc    94980
tcctgtatcc tcgaagtata actaactgag agagagaggc cctatataaa gccagctgac    95040
ttaccctgca attgcttgtc tggcaaacag acaattttta aagactcata tatttaggaa    95100
tttttaaatg ccatagaatc gatggacaaa atgattttca tttatcttaa tccaaaatca    95160
caagattgat tatatactta ggttatatgg aaaatcagca ttagaagcat tagttctaca    95220
cctcatttgc atgacattat tacaagatat taactgtaaa aatgaagtaa atataatatc    95280
tgttcaccag atgcctaaaa catacaacat tagtatagac atatagaagg atctgcaagc    95340
aactaaacaa gtagcgtaaa tcaaagaata tactgataaa gtggtaagtg ccttttgggc    95400
ttcttaggta ataagccctt gtatctgcca gaatagtcta gcaaaaaatg cattttttc    95460 tttagcctag ggaaactttt cacaggagat ggagtttag gtattgtgta gatgatggga    95520
gaaattgctt tgataagct tcagtgaaaa aggaagggaa tgtgtcattg cagatagaga    95580
gggagagaaa cactggtagt tggtcgtaga ctggtagtgg tgtagaaata gaaagcaaaa    95640
cctattggac aaaggaactg aacagatttg ttaaaaagga atgagacaaa cagatatgaa    95700
agataaggag taagctgata caggctggtg agctcactga tagcagagtc caccaagagg    95760
catttagtgg ttttccttca gggcaaaaag tttgaaagag aaaaatatga tctctaaata    95820
gggctactca taaaaatat tgactattaa gaatatagat acagtctgta tctttaagac    95880
tgcaatttag tacaatttaa ttttgtttat aggctaaaca ttttataat ttcatagcga    95940 ttaacttgat aaaaaaggga aaatttcttg gtctttctgc caatctgtgt ttctaactga    96000
ccctaaacag ctctgttggt ttcctgctca tgcattagag cttgtccata gccacaagcc    96060
cctcttttcc tgtcagccct gcaaagaccg cccttccaa attgccttct cctcttgatg    96120
```

```
gcacatccaa gcactagcaa attcggaatc attttttgact tatcgtttcc ttttacccctt    96180
tttaatcata ggtacaatct tttgcaagtt gctttatctc tctgacctta gttttttcat    96240
atataacatg gagttaataa aacaatattg ccattttcag aattcaataa gttaatgtgt    96300
aaaagcacac aacatagtgc atggcacata atagttgagc tttaattgta catgttactt    96360
gttttttcta tcttctcaac tggtaataat aactctactg aataggtagt aatttaatga    96420
aaaaaattaa atgcattgtg gtgtttgcca aaattttttgg tttgtatgta tacactggat    96480
tacagtttta taaatttgtc ctcatgaaat tgattgtcag gtgtttctc tttagttgtt    96540
ttgttaaaag gttaattgga gcataacaaa tgcatcacta tcttatgtag ctcctataaa    96600
aacataaata ctttaaaata aatttgaaaa ttagaggggc tactacatgc aactgattat    96660
agttctaatt ttagttatga aatttacttc tcaactaagg cacaatctct aattctgtat    96720
ctgcattgat gactcagtga ttttagaggt tgtgagttga tattttcaca tttctaccta    96780
tggtaactca ttacagaatg tctgatcatg atatcctgtt ctgtagca tcatagtgga    96840
cacttcatga tatttctgct aaacccttta cctgtcataa ctgtctcctt tctgttttgc    96900
aaattccctc agcaaagtca aattcagtcc tcacttggtt ataaatagca ttataaacca    96960
tattttttgat ttaaataaag cacacaaatc tcaaagaatg ataaaagcat tgttcatact    97020
ttgtaaaact taatcattga ttatagatta aaactgaaac aacatgaagg gatcagactc    97080
actcacagaa ggttattgag aaccaggaat catagatttc attcaattca aattatcagt    97140
tgtacattgt tgcttgttca aaatcatttt acaatccact ttgcccaccct ccatcttctt    97200
acgttacaaa gaactttcat ctgctaggca ctgctgatgg tagaatgcca tgcctttaag    97260
gtttccctttt ggaatataaa gtctatgttt tcaatagaat taactgttcg acagagagag    97320
aacaggattt ctgtgcaaag atggtacagt gctagtaaaa tatatagccc ctttactgtc    97380
tacattaagc aaggatgata ccctaagaat tctagctgct gctgttgatg ctgctgcaac    97440
tattactact actacttcta ctaatcacga gtatagaaaa atatctcttt gatcctgtgt    97500
gtgtggtggt aaggttttgg gagaagccat tatctatggg tggtggaatc acatatattt    97560
taaagtcttt tcgaccatgt tcgttttcta attttttctca agtaaaagat tcttctatac    97620
ttttaaaaaa attataattt aaaaaaaaat cttattggac ttgtttaaat tatcagatat    97680
ttttcagtta tgtaattggt ttctggcata catagacttt tatcatttgc tctgctttaa    97740
catacctttca tcagtttttat aaatacagtt cgaaaggatt gttctaaata tatataaagg    97800
gaaaacttca tttgaaagca aaatctgtat ttgggatatt tgttgtctttt tttgccttct    97860
aaagggcaat ctagaaacac taatattgat tggttatttt gtttcataat actttataagc    97920
tgattcttgg caaaaatggt tgatttctct ttcattgtaa tacaataata aaaaagttac    97980
tcagaattttc tccagtgttt taagagctgt ccaggttgac atccaaaaat ttaagagagc    98040
gttagaacat gggatatcta attgttaatt gagactggaa ttatttctaa taatcttagt    98100
tgtaaatact aatatcttat tagtcttctt atctttgctg gtataaaaat ggttgaaaca    98160
tttgaaatta ttttctcagt tacagtttttg ccctgtgtag aagtgtgatt atctaagaag    98220
tgattttttt tcagatttca aatatgaagt gttgtttaat actaacatat agttacaaag    98280
actatcgtga ctatttttgg tgttcttgat tatgatttaa tacttcatac tttaggaaag    98340
acgatttagt tctaaatata tttataagtg agttcctaat ttttttgtgtg ctgtagactt    98400
ctaagctatt gatataattg aatgttaagc attttcattt tttatggctt actactttaa    98460
```

```
tgcaaagcag aataaaatac taatttattt cttaccctca gatgatgttg tgctgatgta   98520
tattttccag tcttgtcata agctcacaat tacctacata atggtcttga accaaacgat   98580
taaatggaag acaacatttc tggtcttcca ttttaattag tgtggtgcaa gactattatg   98640 taggttttg tgtaaaatgt ggaatgtgaa tcctcaactc tttagtcatt cttcctatta   98700
gatattgaag caaaatttaa aatatgccat ttgactaaag atatcaaagt gctttataaa   98760
gatattacaa tgtacctaag tcctgtttta gagcaccaga gagaaaaata gaagcgcata   98820
gaaggaataa attcagttgc acattttgta tttaatccaa tgactcaaaa acatgggcac   98880
atatttacca aattaaacgc tttcatcaaa catcttcttg atcataccat aaaagccccc   98940
aaagttttta ttggtagcat tgctctgatt aatgaaatga gcttcagtgc aaaaacttgg   99000
gctgttagaa tacttacaaa accattattg tccagttcta tagctgctac cctagtccct   99060
ggctctcatc tttttatacc tggtttacca catcagcatc catgctgaga accatgcctc   99120
agtcttgcac tgctcaaata catttagtca tgaacttatt tattcagcag acctttgagg   99180
acctacaatg tgccaacaat ttatttaaac aatatttgta tattttccat ccccaggcta   99240
ggacttatag tccccagttg gttatcaaat ctaaactaaa ctcagcctaa aaatttagag   99300
ttctccaaat ctcacttatt cttgttcttt catgccagtc tccttatggt aacattcatt   99360
cttagcacaa tgtgtgtctg ttcccacttc ttgtcctagt gcatcatctt tcctcttcaa   99420
ggatgtactc cttctcctcc ttaaaatttt aaaaatcata gctaaaacta ccctgtgagg   99480
tgtgaggttt aggttggtgt agtcatctga cttggatcat tcttttttatt ctggatcctg   99540 agagtatcta gaggaaattg cgtattctgg ttaatgagtg gcttatcaca tactgtctta   99600
acaacactaa gcactcttta ttcagtaaaa gttcacacca taagaaaata tattgtaatg   99660
tatttagtgc ttcttcggtg atatataagg tgttctactt agaaatttag atttgtagga   99720
atgctggtta atagaagttt ctaatattta ctgtcttcca tatttcctga tgttttgttt   99780
attttaagct atttaaata ttttgcattt catattttta accaggcagt atctctgttc   99840
ctcattctga acacccaata tggtactttg aacataatag ggtttcataa agtgcttgat   99900
tcagtaaaaa aaaaaattga acatctacta tgttccaggc atttttgctgg attctctgac   99960 tacaatcatg aaaagacagt ctattctctc agcctgctta tagtctagtg ggaaagatag  100020
gttgacagac atccctaata tagtataagt tcttgaatac aggtaaatac aagagtatag  100080
agtacctagt ctcttctagg agtgtcaagc aaactttttt agtagaagca gcctctgcac  100140
caaggaggga attaggaaat tttagtgcct gataatctcc ttcagtctcc taaattatac  100200
caaatgaaac aaagtaacag tgtgtgtttg ctatgggaat acacctggaa gtcaaatatc  100260
cagcatgcac tccctaaaga gtgccaccct aaaccttccc atgtaggaat gccagcgcca  100320
cctctgagag gaagggatgg ctaaacagag gcaagcagca gacaagagca ggaggattcc  100380
tgcaagggga atatgaacaa atacccagtg gcaaaaacaa aacaaaacac caaggggagt  100440
tggaagaagt cattttccaa ggccagaatg tagatttgtt tggacggagt ggatgggggg  100500
atataggcac agtctttgag ctgcagaaga atgccaggag ccaggtctta aaggatttta  100560
aatcagtgat ttttaaaac ctttatttc ttaacagtag aattcttaag aattttaaaa  100620
ttttaacttt agctcaatat ttaaaaaata aaaacagaac tagtttggtt ttgatgttgt  100680
ttaaggttta ttttgctgtg cgttttggtg gggtggtaga agtgttagtt tccttggttg  100740
cttgcttctc tctgtactct actgaggtta ggaattgtgt tctagagtca catcatgtta  100800
ctaactgggg ctttgtgttc tgactggtag tagcaatagg tttcacccctt tgtgattgag  100860
```

```
taggctccta ggaatttact ttcatctatt caacaaaaat gtgtatacag gttgagcgtc 100920
ccaaatctga aatgctccaa aatctgaaac ttgttgagtg ccaatatgat gctcaaagga 100980
aatgctcagt ggaacatttt tagatttcag attttcagac tagggatgct gaaccagtaa 101040
gtataatgta catattcaaa aaaaaatctg atatccaaac acttcttttc tcaaggattt 101100
tggataaggt atgctcatcc tgtattctta gtactagtaa tgtttctctg agcaaaatag 101160
acacaatccc tgacctcatg gagtttccag tataatgcca gagatggata ttagaaagta 101220
atcctgtaac tataagctgt gagataaatg ctgtacagaa gaggtcactt acattgagag 101280
atctgtaaag aaatgacatt tagatagaaa cttaagtgga gatctgaaca atgagctggt 101340
ggtagacagt ggtgtaggca gaggctgtaa catgcatgaa tgccctgggg ggataaggtt 101400
tgtggcagca gtaaagccgg agagggaggt agaacccaga ttatggacag ccaagttagg 101460
gatttcgatt ttatcctcag tgtaatgaaa aaatcatcaa aaggttttga atagtggaat 101520
aatataagat gacttgtttt attaaaatat taattatact atggctaatg tgtggagatt 101580
tgctaagaga acaggtagaa tgagtgagta tggggacatc agttacagga gtcatattct 101640
catatccgcc acatagtggg cactcattca ccattttgtg gttagctgaa tgatgactag 101700
atcactgcct ctgttgtaac atctcaaatt atttgcactt taaccatgag ttaagttgga 101760
tatttttgag gaatcatgaa gtgttgctga tttgtactaa ttttttcctca taaaacttta 101820 gatatttga actgctgctt catcttgcca agggtgaaaa caaagcattt attcattcat 101880
tcgagaagtg cttaagctgt gccaggtact ggctgagagc tgaggataca gactgaatga 101940
ataagttagg catgatatct gccatcaagt ggcttgtagt ctgggtaacc agagctgagt 102000
agagcaggcg gtatgttggc ctcatacctc cgaagtagta tgtctggaat tagcctgtct 102060
gtagtcccag cctcagtatc tggaatatcc taggtgaaga tgagatctct taacaattta 102120
attacatttt ctcctacctc ctctttgttc taatgtatac tactaaattt ctacttcgat 102180 gaccttgct gaaaatacag ccactcttaa gtcctataac acatgtgccc aggaccggac 102240
aacctaaaaa ttaaatcctg attcttcttt actcttagaa aagctgggac cttccttaat 102300
ggattaacct tctattgctg cgtaacaaat gacaagaaat ttagtgattt aaacaacacg 102360
tatttattgt ctcgtgcttc catgggtcag gagtccaggc actgcttagc tggctcctct 102420
gcttaaggca gcaatcaagg taccagccag gctacattct catatctagc tcagggtcct 102480
cttccaagat cattcaggtt cttgacagaa tttgttccct tgtgcttgta ggaaggttgc 102540
ttctctccac aggcagttca caatatggct cttcaccttt tcacaagtgg cagaatagag 102600
agagtttact gctttgcctc tctgaattca gggaaggcct aactcctctt ttaagggttc 102660
acctgattac atcaggctct cccaggataa tctcctttga taaacacaaa tagctgtttg 102720
ggtaccttaa ttacatatgc agaatcactt cacatttgcc agataacata atcacaacag 102780
taatattcca tcatattctc aggtcctact tatactcaag ggaaggggat gatagaagac 102840
catggatcat tggaggtcag tcatcttaga attgtggcca cctcacttgc ttttttagtaa 102900 aaactctcac atctttttagt ttccaacaag tgatgcttgt ctcagtctca ttatatcttt 102960
gatgacttct tcaccattct ttctcttcct tcattccgta gatatcgaga tttctcaaaa 103020
catctcatca acagtccagc ctgtttcttg accctgtacc tcttattttt cattggctga 103080
ggaccaattt tcttgttcta aaaataaagc taagagcagg cactttttc tccagtcatt 103140 tgctgaaaaa cataaactca tcagataata aaacaaatgc tgtttcttgc ctgccttgta 103200
```

```
ccaatttagg gagaagccta ggggagagtg actgatttta gctccagcca ctccaggtag   103260
ggaaaactgt gcatggatga ttgggagaac cttacttaga tggggacag gcagttgtgt    103320 tagtgagttc tagcagatgc accctccatg gcatggagga gtattgtcct tttatgccag   103380
ggtaccttag aagagtatcg gtgtgggttg tgacttatga gaggggctac acatgcatgg   103440
gttgggacaa ccatgtggta ttaatctacc agtggtttca agttatattg ataaaacaaa   103500
tacattctta caatttaagt gtagccttta cacctgaatt caaccatctg ctatctagca   103560
aaattcagta tcttgcaaac ttaaggctgt caggcgtctg ctgctaattt aaggatagct   103620
tggtggaatt tgcatggagg gagcagttct cttttctctt tctgaaatga ccttcatctc   103680 tcttttatc tgattggttt atctgttaaa acccagctta ggaaaaaaa agcttagaca     103740 ttgcctccct gctaaagcct ttccatttct agaaacctat ctccagtgtc atccttgag    103800 aaagtcaatc cttcttttct ctttgttctc tacctggatt gaagttgttt ctgtcaatta   103860
aaactaccat attttattat aatttattta catgcctgtc tcctctacta gtgagatcct   103920
tggggataga aactgattta ttaattttct taactataaa gtgcctgacc tgtgacaaaa   103980
gctcaataca tgttttgagt aaatcaatca ctgcaccaac tcaaatcaca gtattccccc   104040
cctccccgct gatttcaagt gaccacctct gatcccctta gacacaaaca ttgaccctga   104100
ttaaacctgt gtttgctttg atccatagat acacatttga actacaggcc atcctttctg   104160
gacggggttt tgttactctg gcctacagtt ctttattctt tttctcccca ctgaccagca   104220
tgtattaaag tcacaagacc agtctttcaa atagatgttt tgaatggggc aaagcctttt   104280
catcttgaag ccctgtaagt cactccagag agtgtgggaa aagcaaagtg cttggcatag   104340
ggtacggtag tagcagagga tcttaattat agttcttcac atttgagtga agttctgaag   104400
ctatgaagta gaaagtagga attatcatct cagttacctt agttttgatg tgtggaccaa   104460
agaaaatgtt caggaatctt catattgtga aatgtgcagt acatgtttaa ggttgtagaa   104520
tattggctct aaggagaatt ttatattcat tcttaaaaga gaactaagtt agagacagta   104580
tcttcagatt attgtttccc caaagaccct tacctggttt tactgttgaa ttaaacagta   104640
aaattaaact gttgagttaa acagcattaa agatggtgca gtagcatcat tagatgcatg   104700
gccttggaag aacatagctt tcatatcaga aatgtacttt tcaaaaaatc tatatttcct   104760
tttaaataat tttataatct cagctttcat tttagagttg ggggtacatg tgtaggtttg   104820
ctatgtggat atattgtgtg atgctaaggt tttgggtgca aatgatcctg tcactcaaat   104880
actgagcata gtgcccaata ggtaccttc cagcccttac tccttttctt ttgttccccc    104940
ctttggttgt ccccagtgtc tgttccaatc tttatgtcta tgtgtgccca atgcttagct   105000
cccacttaga agtaaaaaca tgtagtattt ggttttctgt gccagtgtta atttgcttag   105060
gatgacagac tccagctgca tccatgctgc cgcaaaggac atgatttcat tcttttaat    105120 ggctgcgtag catttcatgg tgtgtgtgta tatatatata catgtatata tataaatgta   105180
tatataaatg tactttttca tgtgagaatt cttccaataa aatattgatg actgtggcat   105240
aggagtgtaa aattagaagt gcttcatatg gatacaatgc ctacatttca gaaatcttca   105300
tgcagctctt ctggaatgtg ggcaaattag tctcccggtt ttctctatgg tcaaccatt    105360 tctattatac tcaccttgtc agaagatatt taatttacca caattaacta aaagcttttg   105420
tttaaaaagt atgtcttatg gaaaacagaa cagaggtgac taattttttg tgtgcagtaa   105480 atgttttta gtaagcattt ctacaaccag gtgaaggaaa tgattaagta gaaattggga   105540
cttgcatgta atttttaaa agattgtgaa acttgttaat attatgcatg tatccaactt    105600
```

```
cttttctatt ttcaaattat tccagtaaca aaggtttatg caataggtat actcccaaaa 105660
ggttgtgtta ctatataatg caaatgcatg aggatcagtg tttaagcaat tagtcaaaac 105720
ctctaattta cctcttccca aacataatgt attatctctt gagttatcta taagcggcta 105780
gttgtaggaa aaaatgagaa aagctggcta tatagcaagt ttgttcatcc agaaaacttc 105840
agggttttta gtttgaaacc ttcatgagaa attttttaaat agttaaaagc aactgtaatt 105900
gtagctactt gttatcagtt gttcttcagg cctagttctt aaaagagaaa ttttaggagt 105960
atgctactct aatttcagca gataatcatt taagatgctg tcatgataga aaacgactcc 106020
agaataataa ggatagttta tatgtttctt agagattctg taatgatcaa ttttttagaaa 106080 gtatacttca tacaaagcca aatatttgct tttgttttttt tgttgttgtt gttttttcttt 106140 tgtttggttg atttcagcca accccatttta ccccattata ctcaattttta atttaattgt 106200 tttggaaaat gttcttccat ttcattacaa cattttacgt tttctctaat atgtgtttac 106260
gtaaattcac tttgaagaaa tgcatttata ccatcagctt tatggagtta ttgcaaacca 106320
atgccatcat cagtgagact ataaattttt ttttgcagac tagtcttttc atcatgactt 106380
tgcataacat tgttccagct agatcaacaa attgattatt atattttact atatcatgaa 106440
taatgcccag aggcttagta atatgagtga aacttactgg ggatgatatt ttatttaagc 106500
tgctatattt aaatggtgct gcaatttagg tattccattg aatctacata tagtgcatac 106560
ttgacatagt taagaaaagg ttttgttact tttcttatat tgaatatttg agtaatacac 106620
agttctgttg tacgttagga tttgagtccc ttatgtacaa aaatatttac taccttcttt 106680
gtttcatttc agaatgacct tatttaaaag tgtatgaggc tatttataat caactctgtg 106740
gaagtgatta aagaggtgtg aataataggt tattggaact tgacagctca tagttttgcta 106800 aactagtgtt agaacattta tgctgctcag atgtacctta ttttccttaa gtgagaattt 106860
ctgttttgac atgtggtttg ttgatataat atattgcata ggttttttctc ttttaagtgg 106920 tttaccaaat cttgatattt tattgcctta ttttacatttt tcagcttaat caacattttta 106980 tgcttaataa gaataacctt ggtacaggct ataaacaaaa cagtcagtat agacagagta 107040
cggtccttaa gtggagcatc agccttccat ttcaagctat cctataaaat aaatacaatc 107100
aaattttttt taaatgggaa aaaaactctt ttcttacaga aaatttgaaa acatttggta 107160
ggttaacatt cagcagttgt tactctggga ggaatgttag aactcctgaa gaaatttggg 107220
atagccaata tatccataaa aagaagaggt gtgtatttgg tatttcatta aatctttact 107280
aattttaaat acaaagacca gaaaccacg aatttgaatc aattgaattt gagttagaca 107340 gccttttat ttgagaataa aaagaaatct aggaaagcat ttttaaaatt ttgaaaccat 107400
tacttaatga gtttccactg ttctcatgga ttcagagcat tgtcatttgg tagtactctc 107460
aagtattctc aagatttact aaaatgcatt ttaataatcg caattcagtt ttccctaacc 107520
agccaggagg taatgtttct aaaaagaacg tggttgggaa aactgtggca gagaaaatca 107580
ggcctcatag acaacaaagg ttagagaaat aaaagtaaaa attactgtgt atatattcta 107640
caataaacct gagaaattct ttataaaaaa atccaaaatt aaccacattt ctcaacatga 107700
aaaacttcct agactaattc atcactggac ccatttactc agttgtgatt ttagcattag 107760
tcacccacaa atttttgaatt atgtaaatta cacccatttt aaagttttttg aactatctgg 107820 cttgaaacct aatttttctc ttgatttcct cttgtcttat ttttcaagtc tgagaaatta 107880
ttgtgcagca gtctatattt tggtggaact taagggtata ttttttctaga cctgacttca 107940
```

```
tttattaaaa agttggagta caagtgttta tgaaaggatg gtataattgt ttgaaagtat    108000
cagttgtata tgcatacata taaatagccc aaatgtttta taaaaatgaa gtgtgatgat    108060
atattcaaag aacgctgcaa taatttattt ttggagtacc atggtacttt ggagagaact    108120
ctagagacct gtttttaatc cttttcttct aattactctc tgtgtgaatt tgaatagttt    108180
gcttagcttt actaagcttc ctatatcttt tccttaaaaa gtgatgataa taccaactct    108240
accaatgtta cagtatgttg ttctgaggat gttctggtta aagtgctttg taacttgtga    108300
attgcaaggg aattgtaaga tttgccaatg ttgcacttgt tgccaatctg aagattcaag    108360
ctataagttg aatacaaagt atgtgaccta gagaaaacat tactctgccc cctaccctca    108420
tcccaccccc atgactcagg ttgacagcta ttcttagtta agagatactt ggggaaaaga    108480
ggacagttta gagaacttcc tgtaggtatt cattgactcg tagttccttt tggccttctc    108540
agacactttt cttaaaagac agttttatat cggtaacctc actctaaagt ctgtagaata    108600
atagcacatt ctgattatag agtcagtcta actttataac gctagagtag tacagagaac    108660
tctcatgttg tttaggtttt ccaactgggg acatcctgtg atctgactgt tcctagtgca    108720
caagctaatc ccacccatat cctgtttgtg agtaattgga tggatgcctg gaaaatctag    108780
tgccagattg tatagtgcct ttacaacaga atctctagt ttgaattgat ttaccctcta    108840
cctaaacaaa cacctctcat aggtgagcct ctactctaaa aaggcaagat tatataacat    108900
agatccctag ttcttgtttc catagtcatg ctttggatgg tactcccatt gatctggatc    108960
agagacatat gtaaaataca atttcagggt gttgttttc tgtataactg aagcagtaga    109020
ttttgaattg tatacctctt cccatgaata tagaagacag ctttgtagga aaaaatttct    109080
tcttaaatca tcttttttat ctaaattatt aagaatagga aaataccatt tgcatcattg    109140
tagtctctct tacttcttgg gttctcttta caagatatca aaatatgttt aaaaaaaaaa    109200
cccggatgca tataggtgtg tgcaagcttg tcgtaattca aaaaaaaaat ccattgttaa    109260
atttcaaaga cgtgtaatag tgctagcatt tactacagca ttgtgataaa gggcacaagc    109320
tctagagtca gtatcctgga tataaatgct aaatccacca cttactgaag aattctacca    109380
ggcatggcaa aaataaaacc tttcttctaa ttgccatatt cttagccata atttgtgaat    109440
tattcaaaat taataatttg ttttggaacc ccaactcagt aggtataagc cgaaaaaggg    109500
aaggactgaa aagtatgaaa agtgatagct tcagtgagcc ctggttgata ccagggctca    109560
aattatatta tgactcactc tctttctctc cccccacctc ccttgtattt cttcctccct    109620
ttcctctgtc tgagacatag gcttgaact gattgcttta aaaggcaatg aatcttggcc    109680
aggcgcggtg gctcaacgcc tgtaatccca gcactttggg aggccaaggc gggtggatca    109740
cgaggtcagg agatccagac catcctggct aacatggtga acccccatct ctactaaaaa    109800
tacaaacaaa aaaaattagc cgggcgtggt ggcgggcgcc tgtagtccca gctactcgag    109860
aggctgaggc aggagaatgg catgaaccca ggaggtggag cttgcagtga gccgagattg    109920
cgccactgca ctccagcctg gcaactgag caagactcca tctcaaaaaa aaaaaaagg    109980 caatgaatct ctaatggttg attgtatttc tgtggggtca gtggtaatat ccccttgtt    110040 gttgttctg attgtgttta tttgaatttt tggtctttgt ctagctagca gtctgtttca    110100 ttaattttt tcaaaaaaac tagctcctgg attcgttgat cttttgaatg ttttttcttg    110160
tctctgtctc cttcagttca gctctgattt tggttatttc ttgtcttttg ctagctttgg    110220
gatttgtgtg ctcttgatta tctagttatt ttagttgtga tgtcaggttg ttaactcgag    110280
atctatcttt tcgatgtggg catttggtgc tataaatctc cctcttaaca ctgccttagc    110340
```

```
tgtgtcccag agattctggt acattgtctc tttgttccca ttagttttaa agaactttttt  110400 tattatgtcc ttaatttcat tatttaccca aaagtcattc aggagtaggt tattcagttt  110460
ccatgtaatt gtatgagtga gtgaatttct tagtcttgat tttgaatttg attgcactgt  110520
ggtccaagag actgttaaga tttcagttct tttacagttg ctgaggaggg ttttacttcc  110580
aattatgtga gcagttttag agagaaagtg ccatgtggca atgaaaagaa tgtacattct  110640 gttgttttttg ggtggagagt tctgtaaata tctatcaggt ccatttgatc cagtgctgag  110700
ttcaggtcct gaatatcttt gttaattttc tgtctcagtg atctcatatt gtgagtagag  110760
tgttaagttt cccactatta ctgtatgaga gtctcagtct ctttgaaggt ctcttaagaa  110820
gttactttat gaatctgggt gctcctgtgt tgggcacata catatttagg atagtttgat  110880
cttgttgaat gtaaaccttt accattgtat aatgcccttc tttgcctttt ttaaaatctt  110940
tgtttggttt aaagtctgtt ttgtcagaaa ctagaattgc aacccctgct ttttgttttg  111000
ttttgttttc cgttagcttg gtagattttc ctcattccct ttattttgag cctatgtgtg  111060
tcactgcatg tgagatggat ctcttgaata cagcatacca ttggatcttg gttttttatc  111120
cagtttgcca tcctgtgtct tttaattggg gcattgagcc catttacatt taaggttaat  111180
agtgatatgt gtggatttga tgctgtcata atgatgttag ctagttactt tgcagacttg  111240
tttatgtggt tgactttata gtgccactgg tctgtgtact tcagtatggt tttgtaggat  111300
ctggtaacgg tctttccttt ccctatttaa tgtttccttt aggagctctt gtaaggcaga  111360
tgtggtggta acaaattcag catttgcttg tctgaaaagg atcttgtttt tccttcactt  111420
atgaagctta gtttggctaa ctatgaaatt ctgggttaga atttatttaa gaatgttgaa  111480
tattgactcc caatctcttc tggcttgtag ggtttcggag gccattatcc ttagcaaact  111540
aacacaggca tactgcatgt tctcacatgt taagtaggaa ctaaatgatg agaacacatg  111600
ggcacacaga ggggaacaac agacactggg gcttaccagt ggtggagggt ggaaggagag  111660
gatcagaaga aataactaat gggtactggg cctaatacct gtgtgatgaa ataatctgca  111720
caacaaaccc tcatgacaca agtttaacta tgtaacaaac ctgcacttgt accccctgaat  111780 ttaaaagtta aaaaaaaaaa aaagccagtg aatctgttgt gaatacttac aggcagaact  111840
tttttttttt tttttttttt tttttgaga cgaagtctca ctcttgtccc ccaggctgga  111900
gtgcaatggc ataatctcgg ctcactgtaa cctccacctc ctgggttcaa gcgattctcc  111960
tgcctcagcc tcctgagtag ctgggattac agcctgccac catgcctggc taattttttgt  112020 atttctagca gagacagggt ttcaccatgt tggacaggct ggtctcgaac tcctgacgtc  112080
aggtgatcca cccgccttgg cctcccaaag tgctgagatt acaggcgtga gccaccacgc  112140
ccagccatag gcagaacttt tacttgaggg aaggattgat ataagattct gacattctgt  112200
tttttatgtt ctttgtatat aattgcatat gattttgaaa tataaatctt ttgaatttct  112260
tattaaactt gtaaatgatg tttgtaatcg taggcaattt aagatttcgt actagttaag  112320
gtatagactg ttagaatgaa ttcagggtaa actgtgtgtg tttgtgtact ggggaaactg  112380
tgtagtggta gcttataggg tcatctgtta attagttact gagataggca gtttatataa  112440
attgctcatt cagtccttaa aaaatctttat aagtagttat tattctccca ttatatgtga  112500
ggaaaataca agaaactgct tccttttgca aaccaaacac tgcctttaaa cttagcatct  112560
tagactgcca ctacctgcag acatgactag aacttattaa atattgtctt ttttcagttt  112620
aatagttact tagtaatatg gcctttatct aaatttccta atttttgccat gttaaaatgt  112680
```

```
aatcctatttt gaactatgaa ctttgaattt actttaataa aaataatttc taccactgct    112740
aatacaatgt aaaattttta agcttagctt aagattaatg ttactttgga aataaattgc    112800
tacacattta cacacataat ttatatagga aataaatcag tctatggaaa tatatttaga    112860
ttataagcct ttttagctac agaaacaaaa ttgtttagaa tgaacttaca tagcaagaca    112920
aaattgaaaa cagaggcttt agaagctagt gtaatataaa gtttacaatt tacaaaaatt    112980
acttcattta aatagcagtt attttttactt actttcattg aagaaataaa atcctatgat    113040
tcaacttaca gtatacagtc ttttttgcatg gagggatgat tttgtaaggc ccaaatcagt    113100
actgcttaaa tcagtacaaa gagtgtattt gttttatgga tcatgttttct ggttttttca    113160 cccagaataa aactttaaaa ggaaaaattt tcttctgttt ccaaaaggaa ctattggggt    113220
atgtggaggg gttgatccac aaccctaaac tggcagagag cttgggtgta tatataagca    113280
gctaatctct cacctagttc caggtacata tctttgttgt tgaccagaaa agtgcctgac    113340
cagaagtcca catacctctc ctgttatttt ccttcctata aatgtggcct tgcctgccag    113400
ggagcattgc cttaaactaa actggaaata agaagcagca ttcattatac tatacacttg    113460
atcttagcca aaaggccaag aagcaatcat tcattatact ataaatctct attgtatgag    113520
gagtaataga gggcagatat atcactacag gacatgccta gtattttac atcccagagt    113580 atgttgcagg gatcctagta tgtaaaaatc tcagaagcat aaacaaaatt tattttaaat    113640
tttagtttta ataagctttt ttaaactccg catcctactt ttagtgggat ataagggtta    113700
ttaaatcaca cttcaaaaag ttagaaaccc tacaaaggcc atacagaaaa taaaatcctc    113760
tgaacctagg tgctactaat tcactcaaga taaatttaat cattttatta tttatggata    113820
taatctaatg gaataatttt aatactttaa tgaaaacatt actttcaatc agatgtacag    113880
aactcacagg aaaacttgaa aattcttaat tataactgta agacctacgt agtataacta    113940
acagataaaa ggattgtctt taaatcttta tgaaaacgtg aaatgaagca acataaacat    114000
taattcattg acaaaacagt ttattttaaa cacgtaagaa cagaaaaggt ggagacttgg    114060
tggttgtaaa tttggacagg aatatattga aatatcatgt gtatgtggat acagatatca    114120
gtattctggt tactgccctc aaaaagcata tgttctttttt aaggagttaa caaagatatg    114180
ataaaatact gaaagaataa taccagtgat acttagtaag tgctaataac taccttcaga    114240
atatagtata gaccaacact gtccggtaga acttcttgg atgaaagaaa tgttctctat    114300
tttatctaat agccactggc tacctgtggt tatttgagca cttgaaatgt atgctgtatg    114360
aatgaggaat ttaattttat attttattta gaaatttaat taactaattt aaggatagac    114420
atggtggctc acacctgtaa tcctagcagt ttgggaggcc aaggcaggtg gattgcttaa    114480
gcccaggagt ttgagactag ccttggcaat atggcaaaac cctgtctcta cagaaaattt    114540
aaaaattagc caggtgtggt actgtgtgcc tgtggtccca gctactcagg aggctgagga    114600
aggaggatgt cttgagcctg gaaggttgag gctgcaatga gctgtgatca tgccactgca    114660
ctccagcgtg agcaacagag cgcaataccc tgtctcaatt ttttttttaat tcagtgtgaa    114720 tagatacatt tgattagtgg ctaaccttat taaattctac aattctcaaa agatgcttgt    114780
ctcaggaacc cttcatttaa aagtgattta cggccccaga gtgcttttga ctatgtgggt    114840
tatatttact gatatttaca gcattaaaaa tagaaaaatt ttaaatattt attcattctt    114900
aaagttacta catgttaaca taaaaatatc ttgaggaaaa gctatttttta aaaagagtg    114960 gcattgtttt acatgtttac aaatctcttt aatgtgtggg ttaatagaag gcagttgaat    115020
tctcatatct gcttctatat tctagctgtt gcaatgtgtt gaactgtatt aaaacctaac    115080
```

```
ctcacataga tagttagttg gaattagcct ttttagataa ttgtggatat tctttgatta 115140
ccaaaactca ccaagtagca gtttcttaaa gtttagttgt gatgtaaaat ataaaaccat 115200
atcaatgaat tttatagtta cattaaaaaa tcactgctct cttgaacttt gagtgggcct 115260
tttacccact tactaatttg caacatcatg cattagttat ttggaagata ttggttcact 115320
gaattgtcca gatcttccaa atgttgacac attccatttt acccaatcaa aaaatcacta 115380
atagcagcac caatctcttc agaagggtct tcaaaattag gaaattgcaa aattcaactc 115440
agctgcagtt aacatgtttt ccaaaattct catttacatc tgaaagctca aattttattg 115500
gcaacaaatt tggccaatttt gtcttccttt aaatgacagg cttatttggc ttattttttga 115560 gaaaatatct gccaaatact caaacctgaa taaccattgt ttgtcagttg gttattcttt 115620
caagttaaat agatgtacca tgaaaaaagc agctacttcg gtagcaactt aattccagga 115680
gtgattttcc ataagacatc tgttatactt tgatgtccag cagaagtgtt ttgtgtatac 115740
atcccatttt gttgtacaga acactaaaaa gacatacact acagggtcaa aacttattaa 115800
agtaattttt actacttcat caaggatgta cttaagtgaa actggcaaat ttttaactg 115860 gaaatgagtg gcagtgaggg ctacaaggat atagtttgct gctgctgcct tggtaagtgc 115920
taagatgcca acagtttgac ctaccattgt ctttgtatca tcagtgcaaa tgccaaagaa 115980
gtgaaagggg caagtactgc cttagtatta ttataaaaat ggttttgacc ttgctgaaaa 116040
gacaataatg gaggaaagaa attgcttta gttcaaataa gttaaagaag actccatgat 116100
aaagatcaat gtaatatgca tgccctactt tattttttctt tacctgcttt tttctataaa 116160
aataaaagta ggaaagcaat tagcatgtta aaaattattt aaccatgtta cttttaaaat 116220
cattctttga ttcagcaatt atttattaac tattttgcat aagttatttt tgttgttgat 116280
aagtgggcaa tatgtaatgt ttagaataat gatcatgcca ataaagcatc tgtgcccca 116340 ctataaagca ctgctatgtg ctgggcactg tgtttatgtg cttttaaatg cattcacgga 116400
atcttcatgg taaccttagg aggtaggttt tatagaaagt taactggaat tagtgccagc 116460
tcacaatttt tatataacta gataaattac ttaacttatt tggatttcag ttttctcaag 116520
tataaaatac gaagctgaga catatcttca gatgcttaac caggcttaaa attcattaaa 116580
taaacatata tttcacagca ggataaccct ttattgacac attatcagaa tactctgaat 116640
tttattagga agccataaaa acaattacca aatcattaac ataaactttt tgaaactta 116700 tgtcccttc atttaaaat tcgttgagtc aatacatttt tcataacact taatccttta 116760
ctgacacatg atcagaacac tgaacacttg accaaagacc taatgataga tgtgaacata 116820
atgtaaacat gaagggatat agtcactatt gtagcggaat aaaaaataat acaaagcgc 116880 aaagaacaag agtcaggaaa ggtcaagaag agcatcaata aagcagcagt gttttagttt 116940
gttcattagt tcaacagatg tcttatatgc ctttgttatg ccctgtaaag cttggaattt 117000
agactactgg agggaacaaa atgatgtcct tgccctcatg gagcttacat tttagtgggg 117060
gagtgtggta ggtaggatag tggcctccca aatatgtcca tgtcctaatc cctaaaacct 117120
gtgaatatgt tacattactt aaaaaaagat tattaagtag caaaggaata gggagattac 117180
ttcgggttat gtggctaggc aaaatgcaat gttaaaagtg gaagctggag tttgaagaag 117240
ggtcagtggc agaatgatgc gacatgagaa agtttcaact ggccatttct ggctttgaag 117300
atggaagggg ccatgtgcca aggaatgcag cagcctctac aagctggaaa aggcaggaaa 117360
gtggattctc ccctagagtc tccagaaaga acacagttct gccaacatct tgattttagt 117420
```

```
ccagtgagac ccatattggg catctaattg tgaaataata aatgtatgct attttaagcc   117480
tcttagggat atgtcagttt gttacatcaa caatagaaaa ctaatacaga gtaaagaaaa   117540
gtaaacaagt aactaaacaa gataattaca aactacgatg gatgctttga aggaaatagg   117600
atgatgtgaa agagtaaagg ataaagcatg ttggtttagg tgatcatgga agtcttcttt   117660
ggaactatga cactggagtg gaaaagaaag acccagctgt gtggagttgg aaacagaatc   117720
tcaggccaag ggaaaggcaa gtgtaggggc atggagtaga gaaggcttgc catttacaaa   117780
gaacaaaaac aggtcatttta gcgagaatga atagaatagt ggaaaaggtg caggcccaaa   117840
aatgtggagc cttgcaggaa tgatggaaca atggaaagcc attgaaaggt tttaagaagg   117900
agagtgatac attttgcttt acattttttga aagatcaccc cggctgctgt gtggtaaatg   117960
gaaacaaggg accaatgaca tggtattgta gtcctgagga ggaagtttac aggcggaagc   118020
aaactagtgg cattggtgcc tggagaggat tgttgatgat agacgggata tgagttccaa   118080
aagatgagta ggaatttgcc cctagagaag aggaagaata catagcagaa gcatgaaagt   118140
tcaggatgtc tgggaaattg aatatacttt gcagaacagt agcaagtgaa gatgaagaga   118200
ttgtttaagc gataatgtat gcagtcggga gacccttatt cgccatgtat gggagtttgg   118260
aatttatggc atatgcaatg gagagccatc tgaaatttcg aatcaagaga acaaaacaat   118320
ctcttgacct gaagttttgt gattattatg tatgtccttc attttcattc tgaagtaaag   118380
gagaataata agggtgcttt aagttttatc atcttagatt ctgagaagtt cagaaagatt   118440
tgattaagta cttgtcaatg aagtctttaa taattcattg ggaaccacac ttttattctg   118500
ttttgttttt ttgtaaggac ttttttttca tttatgggct ctactcttct gctgtctttg   118560
gagagacagc acagtaacct gttcagagca tgtccggagc cacatggcct agggtacagt   118620
cctggttacc agtactaact ggtcaacctt tggcaagtta tgtaatctaa gtcttagttt   118680
cattgtctat aaaataagga taataaaaat tcttcaagtg gcttctgtaa ggattaatgg   118740
attcagtgca tataaagcac tgaatatgta ataagcactt tgtggatcag ggttgaagca   118800
gggtgcagaa gtatacgagg agcattggtt gtaagctttt ctatatatca gtagtagaaa   118860
tgtgacaggt cataatttct ttaaagtacg tttaaaatac ctatttccca cttcattttt   118920
atatatggta ttaaattttc tatttgtttg tgttttccaa gaatgtccac ttctttcatc   118980
acaaagccca cttattctcc aaaaagttta tataagaaaa tgggtagtta gtttgcatga   119040
tcttctgctt tattggatat tatttatttt ctggaataag ttatgtccac agatgatttt   119100
aattcacact gctactcagg taacttaggt aaaacaaaac atcaggattt tttggtacta   119160
cagttcaaat ttatttaact tcccaacaat atattttaaa taacaagaa acaaaatact   119220 caattttacc tctgttgcac attagcaagg cataaaagag agattaatat aattaggtaa   119280
ggattcttat agtatttatt ttctgcatca ctttttaattt agcatttaat tatgtactat   119340
gacatttctc tatataatac ttcatgtata ttactcatat ttgcaaagat tacgtatatc   119400
tcagaggtgg agactagata ttaaatgtct tcattctcct atcttctgaa gcacttaagt   119460
cagaggaact aaaattattca ttctaatttg acaactcaag cttgtaacat attataatgc   119520
ttagaaaagc tcagtaaaac taaactctag ttacctataa attgtttgtt tttaatactt   119580
catcaggaaa taaattccaa ttaaaatttc attaattatc ccccttgttc tttcatgtct   119640
ttccaatgaa ggagtagaaa gactttcttt acaaaactag gctcagggaa ttagtgtccc   119700
atgttgaaat ttgctctca ggaaagctcc cagaaaggaa gtctcctagt tggcaaccaa   119760
taagccttac ttagattact atatgttgtc attcccatgg aagtaaggga ggatccgtcc   119820
```

```
tcaaactaca tccttggggt tcatgatctt tttcttttca cttttcctat gatttctctt  119880
cccatggtca ggagttttaa attacacata cagcattact agtttgaagg aatcttggag  119940
aaccaaataa aatgaattag aatgtaattc ttgtcctctt ccttcatctt attttcaca   120000
accagttctg ctactaatcg ataagcctca aagccaatca aaggagaatt accttctggg  120060
attagtaaat gtcaaaatat ttcttaaaat ttttttcataa gatgagaaaa gctgaaaatc  120120
atgccaactc ctgtggttga aactatttaa ataattgact gtgtgtttgg gtgtatgtga  120180
gatactataa cctgtacttt ggggatgctc attgcccttg acaagtgaaa gcgtgcgctc  120240
tccacgaggc ctccctcctg gcgtctgtgc agtaagagag cagcttccct cagcactagc  120300
tggaaggaga agtcacttgt gctggtgttc agcaagtatt accttccttt tcattttata  120360
taatgttatg tagccatgaa taggaaaggt aaatgtttt catactttaa atagactact   120420
atctttcaaa aataagaaaa tagatcttat tattgtctca taaaaccata aaataaaaat  120480
tgttttattt caaaatccac agatatttat ttacaacata gtattcatca actaataaat  120540
gtccttttta ccttcatta ttctttagat tttatttcag tatcctgatt agtgttttta   120600
attatacctc ctattcaccg tgataacaaa ttcaaataac ataaaaatgt taaggaagag  120660
agctgggtgc agtggcacat accagtaatc ctaacacttt ggaaggccaa gccggaggat  120720
tgcttgaggc caggggctca agaccaccat aggcaacata gtgagaccct gtctctataa  120780
aaaaaaaatt ttctttaaat tacctgggtg tggtggcaca ggcctttagt cccagctact  120840
tgacagacta aggcacagag gatcgcttga gcctagcagt acacaggtgc agtgagctac  120900
gatcatgcca ctgcgctcca gcctgggtga cagagtgaga cctcgtgtct aaaatataca  120960
tacatctata gaaatataca catatacata cgtacataca tgcatacata gagagccagc  121020
aaatattttg cccaatccca gttcagtttt ctaaagtttg ccactagcaa cattatgctg  121080
aaaattattt ggcttttct ttgcacattt aaaatatatc tttaaaattt tttaaagta   121140
atataaacat taaaataata tcaaaggaat aagccagaaa aacaagtcac tcctttggta  121200
cctgatttcc tcatttgtat gtcctagaca tcatgaattg atgttaaggc acatgtatag  121260
tatggatact atactgcatc tactgtattt tctggaagga tggaatcaaa ctattttgga  121320
agactttcta tatcagtacc aaacaatata tcttagatga ctattaaggt ttttttgtaa  121380
ttaaaaacaa gttttcagat aaacatatgt atgcatattt gcatacatgt gttaatttgc  121440
acggtgccaa gaaattgtta gatcaacagg tcggcatttt aaattttgat aaatattgcc  121500
aaagtaacac agcatataag agtgtactct tttatttaaa ccttgcatat gtcaggcgtt  121560
actgggactt ttttgccgat ttactaaaca tcatttatct agggattagt atctacagcc  121620
agtgttctag atgaggggaa cagtggtgat cgaaacagaa aaaattcctg tctgaatgga  121680
acttgcattg tagtgtagta gataatcaat caataagata ttatagtgac aagtatttt   121740
aaaagaaata aattgaggga gaataggag  tgcaatgggg gtgggggtgg tatttaaata  121800
gagcagtcat aggagacctc cctgaggagg tggaattggg cagttcataa agaatattac  121860
aggtagagtg atatgaagca agaggccagt atacctggaa tgcagtgagc cggggtaaag  121920
tagaagacaa agtctgagag agacaggtga ggagagtcag cccatggagg gccttggatt  121980
acagtgaata ggatgggaag tcattagatg gtttgacaag attccactga tgctttagaa  122040
ggttttgtct gctgtgttga gaactgacta caggaagaca aaggtggcag cacggagacc  122100
agataggaac cagtgacagt actcgaagtg agagatgatg gtaccatcag gtagttagtg  122160
```

```
gcagggaatt ggtagtgggt ggtcagatct tgaatatatt tttataggta tttccttcca 122220
gagtagatgc atgggatatg agagaaaaag aggagtcaaa actatcactg agactttgg  122280 cctgaacaac tggaggaatg gaattgccgt ttactgaaat agagaagact gagagaccag 122340
gaattgtatt tggctatggt aaaaaatttc ccattagaaa tccaagtggt gatatcacca 122400
aagacaaaag ccacatgatt atctcaatag atgcagaaaa ggcctttgac aaaattcaac 122460
agcccttcat gctaaaaact ctcaataaat taggtattga tgggacgtat ctcaaaataa 122520
taagagctat ttatgacaaa tccacaacca atatcatact gaatgggcaa aaattgggag 122580
cattcccttt gaaaactggc gcaagacagg ggtgcccttt ctcaccactc ctattcaaca 122640
tattgttgga aattctggcc aggacaatca ggcaggagaa ggaaataaag tgtattcagt 122700
taggaaaaga gggagtcaaa ttgtccctgt ttgcagatga catgattgta tatttagaaa 122760
accccattgt ctcagcccaa aatctcctta agctgataag caacttcagc aaagtctcag 122820
gatacaaaat ctatgggcaa aatcacaagc attcttatac accaataaca gacaaacaga 122880
aagccaaatc atgagtgaac ccccattcac aattgcttca aagagaataa aatacctaga 122940
aatccaactt acaagggacg tgaaggacct cttcaaggag aactacaaac cactggtcaa 123000
ggaaataaaa gaggatacaa acaaatggaa gaacattcca tgctcatgga taggaagaat 123060
caatatcgtg aaaatggcca tactgcccaa ggtaatttat agattcaatg ccatccccat 123120
caagctacca atgactttct tcacagaatt ggaaaaaact actttaaagt tcatatgaaa 123180
ccaaaaaaga gcccacattg ccaagacaat cctaagccaa agaacaaag ctggaggcat 123240 cacactacct gacttcaaac tatactacaa ggcaacagta accaaaacag catggtactg 123300
gtaccaaaac agagatatag accaatggaa cagaacagag gcctcagaaa taatgccaca 123360
catctacaac catctgatgt ttgacaaacc tgacaaaaag aagaaatggg gaagaatttt 123420
cctgtttaat aaatggtgct gggaaaactg actagccata tgtggaaagc tgaaactgga 123480
tcctttcctt acacctgata caaaaattaa ttcaagatgg attaaagatt gaatgttag  123540 acctgaaacc ataaaaaccc tagaagaaaa cctaggcaat accattcagg ataggcac   123600 gggcaaggac ttcatgtcta aaacagcaaa agcaatggca acaaaagcca aaattgacaa 123660
atgggatcta attaaactaa agagcttctg cacagcaaaa gaaactacca tcagagtgaa 123720
caggcaacct acagaatggg aaaaaatttt tgcaatctac acatttgaca agggctaat  123780 atccagaatc tacaatgaac tcaaacaaat ttacaagaaa aaacaacccc atcaaaaag  123840 taggtgaagg atatgaacag acacttctca aaagaagaca tttatttatg caaccaaaag 123900
acacatgaaa aaatgctcat tatcactggc catcagagaa atgcaaatca aaaccacaat 123960
gagataccat ttcacaccag ttagaatggc aatcattaaa aagtcaggaa acaacaggta 124020
ctggagagga tgtggagaaa taggaacact tttacactgt tggtgggact gtaaactagt 124080
tcaaccattg tggaagacag tgtggcgatt cctcaaggat ctagaactag aaataccatt 124140
tgacccagcc atcccattac tgggtatata cccaaaggat tataaatcat gctgctataa 124200
agacacatgc acatgtatgt tgattgcggc actattcacg atagcaaaga cttggaacca 124260
acccaaatgt ccatcagtga tagactggtt taagaaaagg tggcacatat acaccatgga 124320
atactatgca gccataagaa atgatgagtt catgtccttt gtagggacat ggatgaagct 124380
ggaaaccatc attctcagca aactatcgca aggacaaaaa accaaacact gtacgttctc 124440
actcttaggt gggaattgaa caatgagaac acttggacac agggtgggga acatcacaca 124500
ccggggtctg tcgtggcatg ggggtagggg ggagggatag cgttaggaga tacacctaat 124560
```

```
gtaaatgaca agttaatggg tgcagcatac caacatggca catgtataca tatgtaacaa   124620
agttgcacgt tgtgcacatg taccctagaa cttaaaagta taataataat aataaaaaaa   124680
aaagaaatcc aagtggagct atcaagtaga taatttggga ttcataggag aagtcacctg   124740
ggatataaaa ctgggagtca acaaatggca tttagagcca tgaaacagat tgaggaagtg   124800
gaggaaagaa acgaaaaaga agcagttggt gagttaagag gaaactgata gagtcaagag   124860
aagagattgt tttgaaaagg agagagtaat gaattatgtc aaatgctgct aaaagatcaa   124920
gtcaaatgag gactgataat tgtcattgca tttagcagtg ctcacagtca tgacaagaac   124980
agtgttggtg gagtgttgta attggagtaa tttaagataa aataggaaga aacaaattag   125040
agacacatgt aggcaacttt tccaaaaagc tttgaagtat agagggactg agatatagaa   125100
ttaggagtgc tggagtttaa tcaaggtaag agattagcca gcatagagat tttgaagcca   125160
gagagagcaa gaaagttgag agtgtacgtg agaagtgatt ataaaaatat aagattaaaa   125220
tggatatttc ttctgttact gaggttgagc atcttttttac atgtttattg ggcattcatt   125280
tttgtgtgtg cgaattgctt gtgcatattc ttactgggtg gttcatctta tgagtgttta   125340
agaattctct gtaaaataaa gatgtcagcc tttagtcata tgtgttgcac atattttttca   125400 caatttgtcg tttgtctttt gacttgattt ttttctgtgt atagttatgg gtttcatttc   125460
atgcttataa tggccttctt attccaggtt tgtaaaagga tttgcctata ttttcttctt   125520
tttttttttt attatacttt aagttttagg gtacatgtgc acattgtgca ggttagttac   125580
atacgtatac atgtgccatg ctggtgcgct gcacccacta actcgtcatc tagcattagg   125640
tatatctccc aatgctatcc ctcccccctc ccccaccccc acaacagtcc ccagagtgtg   125700
atattcccct tcctgtgtcc atgtgctctc attgttcaat tcccacctat gagtgagaat   125760
atgcggtgtt tggtttttttg ttcttgcgat agtttactga gaatgatgat ttccaatttc   125820
atccatgtcc ttacaaagga catgaactca tcatttttta tcgctgcata gtattccatg   125880
gtgtatatgt gccacctttt cttaatccag tctatcattg ttggacattt gggttggctc   125940
caagtctttg ctatcgtgaa tagtgccgca ataaacatac gtgtgcatgt gtctttatag   126000
cagcatgatt tatagtcctt tgggtatata cccagtaatg ggatggctgg gtcaaatggt   126060
atttctagtt ctagatccct gaggaatcgc cacactgtct tccacaatgg ttgaactagt   126120
ttacagtccc accaacagtg taaaagtgtt cctatttctc cacatcctct ccagcacctg   126180
ttgtttcctg acttttttaat gactgccatt ctaactggtg tgagatggta tctcatagtg   126240
gttttgattt gcatttctct gatggctagt gatgatgagc attttttcat gtgttttttg   126300
gctgcataaa tgtcttcttt tgagaagtgt ctgttcatgt ccttcaccca cttttgatg   126360 gggttgtttg ttttttcttg taaatttgt ttgagttcat tgtagattct ggatattagc   126420
cctttgtcag atgagtaggt tgcaaaaatt ttctcccatt ttgtaggttg cctgttcact   126480
ctgatggtag tttcttttgc tgtgcagaag ctctttagtt taatgagatc ccatttgtca   126540
attttgtctt ctgttgccat tgcttttggt gttttagaca tgaagtcctt gcccatgcct   126600
atgtcctgaa tggtaatgcc taggttttct tctagggttt ttatggtttt aggtctaaag   126660
tttaaatctt taatccatct tgaattgatt tttgtataag gtgtaaggaa gggatccagt   126720
ttcagctttc tacatatggc tagccagttt tcccagcacc atttgttaaa tagggaatcc   126780
tttccccatt gcttgttttt ctcaggtttg tcaaagatca gatagtcgta ggtatgcggc   126840
gttatttctg agggctctgt tctgttccat tgatctatat ctctgtttg gtaccagtac   126900
```

```
catgctgttt tggttactgt agccttgtag tatagtttga agtcaggtag tgtgatgcct  126960
ccagctttgt tcttttggct taggattgac ttggcgatgc aggttctttt ttggttccat  127020
atgaacttta aagtagtttt tttccaattc tgtgaagaaa gtcattggta gcttgatggg  127080
gatggcattg aatctgtaaa ttaccttggg cagtatggcc attttcgcga tattgattct  127140
tcctatccat gagcatggaa tgttcttcca tttgtttgta tcctctttta tttccttgac  127200
cagtggtttg tagttctcct tgaagaggtc cttcacgtcc cttgtaagtt ggattcctag  127260 gtatttatt ctcttttgaag caattgtgaa tgggagttca ctcatgattt ggctttctgt  127320
ttgtctgttg ttggtgtata agaatgcttg tgattttgt acattgattt tgtatcctga  127380
gactttgctg aagttgctta tcagcttaag gagattttgg gctgagacaa tggggttttc  127440
tagatataca atcatgttgt ctgcaaacag ggacaaatttg acttcctctt ttcctaattg  127500 aataccctt atttccttct cctgcctaat tgccctggcc agaacttcca acactatgtt  127560
gaataggagc ggtgagagag ggcatccctg tcttgtgcca gttttcaaag ggaatgcttc  127620 cagttttgc ccattcagta tgatattggc tgtgggtctg tcatagatag ctcttattat  127680
tttgaagtac gtcccattaa tacctaattt attgagagtt tttagcatga agtgttgttg  127740
aattttgtca aaggcttttt ctgcatctat tgagataatc atgtggtttt tgtctttggc  127800
tctgtttata tgctggatta catttattga tttgcgtata ttgaaccagc cttgcatccc  127860
agggatgaag cccacttgat catggtggat aagcttttttg atgtgctgct ggattcggtt  127920
tgccagtatt ttattgagga tttttgcatc aatgttcatc aaggatattg gtctaaaatt  127980 ctctttttg gttgtgtctc tgccaggctt tggtatcaga atgatgctgg cctcataaaa  128040
tgagttaggg aggattccct cttttttctat tgattggaat agtttcagaa ggaatggtac  128100
cagttcctcc ttgtacctct ggtagaattc ggctgtgaat ccatctggtc ctggactctt  128160
tttggttggt aaactattga ttattgccac aatttcagat cctgttattg gtctattcag  128220
agattcaact tcttcctggt ttagtcttgg gagagtgtat gtgtcgagga atgtatccat  128280
ctctcctaga ttttctagtt tatttgcata gagctgtttg tagtattctc tgatggtagt  128340
ttgtatttct gtgggatcgg tggtgatatc ccctttatca tttttttattg cgtctatttg  128400 attcttctct ctttttttat tagtcttgct agtggtctat caattttgtt gatcctttca  128460
aaaaaccagc tcctggattc attgattttt tgaaggggttt tttgtctctc tatttccttc  128520
agttctgctc tgattttagt tatttcttgc cttctgctag cttttgaatg tgtttgctct  128580
tgcttttcta gttcttttaa ttgtgatgtt agggtgtcaa ttttggatct ttcctgcttt  128640
ctcttgtggg catttagtgc tataaatttc cctctacaca ctgctttgaa tgcgtcccag  128700
agattctggt atgttgtgtc tttgttctcg ttggtttcaa agaatatctt tatttctgcc  128760
ttcatttcgt taggtaccca gtagtcattc aggagcaggt tgttcagttt ccatgtagtt  128820
gagcagcttt gagtgagatt cttaatcctg agttctagtt tgattgcact gtggtctgag  128880
agatagtttg ttacaatttc tgttctttta catttgctga ggagagcttt acttccaagt  128940
atgtggtcaa ttttggaata ggtgtggtgt ggtgctgaaa aaatgtata ttcttttgat  129000 ttggggtgga gagttctgta gatgtctatt aggtctgctt ggttcagagc tgagttcaat  129060
tccctgggta tccttgttga ctttctgtct cgttgatctg tctaatgttg acagtggggt  129120
gttaaagtct cccattatta atgtgtggga gtctaagtct cttttgtaggt cactcaggac  129180 ttgctttatg aatctgggtg ctcctgtatt gggtgcatat atatttagga tagttagctc  129240 ttccttgttga attgatccct ttaccattat gtaatggcct tctttgtctc ttttgatctt  129300
```

```
tattggttta aaggctgttt tatcagagac taggattgca acccctgcct tttttaattt  129360
tccatttgct tggtagatct tcctccatcc ttttattttg agcctatgtg tgtctctgca  129420
cgtgagatgg gtttcctgaa tacagcacac tgatgggtct tgactcttta tccaatttgc  129480
cagtctgtgt cttttaattg gagaatttag tccatttaca tttaaagtta atattgttat  129540
gtgtgaattt gatcctgtca ttatgatgtt agcaggtgat tttgctcgtt agttcatgca  129600
gtttcttcct agtctcgatg gtctttacat tttggcatga ttttgcagcg gctggtaccg  129660
gttgttcctt tccatgttta gtgcttcctt caggagctct tttagggcag gcctgctggt  129720
gacaaaatct ctcagcattt gcttgtgtgt aaaggatttt atttctcctt cacttatgaa  129780
gcttagtttg gctggatatg aaattctggg ttgaaaattc ttttctttaa gaatgttgaa  129840
tattggcccc cactcttctg gcttgtaggg tttctgccga gagatcagct gttagtctga  129900
tgggcttccc tttgagggta acccgacctt tctctctggc tgcccttaac atttcttcct  129960
tcatttcaac tttggtgaat ctgacaatta tgtgtcttgg agttgctctt cttgaggagt  130020 atcttttttgg cgttctctgt atttcctgaa tctgaatgtt ggcctgcctt gctagattgg  130080
ggaagttctc ctggataata tcctgcagag tgttttccaa cttggttcca ttctccccat  130140
cactttcagg tacaccaatc agatgtagat ttggtctttt cacatagtcc catatttctt  130200
ggaggctttg ctcatttctt tttattcttt tttctctaaa cttcccttct cgcttcattt  130260
cattcatttc atcttccatc gctgataccc tttcttccag ttgatcgcat tggctcctga  130320
ggcttctgca ttcttcacgt agttctcgag ccttggtttt cagctccatc agctccttta  130380
agcacttctc tgtattggtt attctagtta tacattcttc taaattttttt tcaaagtttt  130440 caacttcttt gcctttggtt tgaatgtcct cccgtagctc agagtaattt gatcgtctga  130500
agccttcttc tctcagctcg tcaaagtcat tctccatcca gctttgttcc gttgctggtg  130560
aggaactgcg ttccttttgga ggaggagagg cactctgcgt tttagagttt ccacttttttc  130620 tgttctgttt tttcccccatc tttgtggttt tatctacttt tggtctttga tgatggtgat  130680
gtacagatgg gttttcggtg tggatgtcct ttctgtttgt tagttttcct tcttacagac  130740
aggaccctca gctgcaggtc tgttggaata ccctgccgtg tgaggtgtca gtgtgcccct  130800 gctgggggt gcctcccagt taggctgcta aggggtcagg ggtcagggac ccacttgagg  130860
aggcagtctg cccattctca gatctccagc tgcgtactgg gagaaccact gctctcttca  130920
aagctgtcag acagggacat ttaagtctgc agaggttact gctgtctttt tgtttgtctg  130980
tgccctgtcc ccagaggtgg agcctacaga ggcaggcagg cctccttgag ctgtggtggg  131040
ctccacccag ttggagcttc ctggctgctt tgtttaccta atcaagcctg ggcaatggcg  131100
ggcgcccctc ccccagcctc gctgccgcct tgcagtttga tctcagactg ctgtgctagc  131160
aaccagcgag actccgtggg cgtaggaccc tctgagccag gtgtgggata tagtctcatg  131220
gtgcgccatt ttttaagcca gtctgaaaag cgcaatattc gggtgggagt gacccgattt  131280
tccaggtgcg tctgtcaccc ctttctttga ctcggaaagg gaactccctg accccttgcg  131340
cttcccaggt gaggcaatgc ctcgcccctgc ttcggcttgc gcacagtgcg cgcacccact  131400
ggcctgcgcc tactgtctgg cactcccctag tgagatgaac ctggtacctc agatggaaat  131460
gcagaaatca cccgtcttct gcgtcgctca cgctgggagc tgtagactgg agctgttcct  131520
attcggccat cttggctcct ctctgcctat atttttcttct aatacttttta tggtttcagt  131580 ttttttttcta agttaaagtc tttgatttcg tgtgggtttc attttggtga aagtcttggg  131640
```

-continued

```
gtggggatct gatttttttc caaatgattt ttattaaata atgcattttc cccccactaa  131700
tttgcaagac tcctatttgt ttagggtcta ttttgtatta tattcaagtc cattgattgc  131760
ccatccctgt aatagtacaa atctatttcc atttctgtag cttcaagata agtttactc   131820
tctggtatat ctagtttatg ttctcctacc accaccatta ctattatttt tctgaatttt  131880
cctgagtatt ttaatgtgtt tgttttctca gataataata ccaacagtat gtatcaagaa  131940
tatatgtgca gtattaccaa gtgttttgca tatatcccta ttttcatcat tgtgataacc  132000
atgtcagggg tatactatta atatttcaat cttggcaatg aggaaactga gacattagaa  132060
gaatatataa catgctcaag gtgacaaggc tagtaagcag tgaagctgtg atttgagcca  132120
ggcagttagg ttccagagac catgctccta cttctctata taaactgtag acgtgttgat  132180
ctaagtcatt tagatttaga atccaagata ccatgtgtag catttggatc aaaattgcat  132240
tgaatttata gaaaaattta ggtagaattg acatatttat gacacaaaat cattctattc  132300
aaaaccaaga tatagctttt catttattca aatatttgat gacttttaca tagaatgcta  132360
gttttcttca tgtaggtcct ccatgttttta ttttaagctt tttccttcat gtgtttcatt  132420
tgtgttgcta gtaatagaat ttttcctct ttcgtgtttt tagctggtta ttgttgatta  132480
ttggaaagct gttgatttt ttctgttgga aagatattga ttttttttctt ttaaatttgt  132540
aattaaccat ttaccaaatg tccttactgc taatagtttt tttattgatt tttcctgaat  132600
tttctataaa tgttattctg caaataattt tgcttctcct ttctaatatt tatactttct  132660
cttttattct ttttaaaaat tggtttattc ttgtaaatca ttgttaacta atgatgaaac  132720
taagcatctt tatcttacaa atgcctgtca ttcataatca tttattatga tactaacttc  132780
agttttcttt tcatgcaaaa gtatcagcaa gggaatggtg aattttttc aaatgccttt   132840
ctgtatctat agatgtcgtt tgtcctttat gttaatatag taaaagcaca tatattttct  132900
aatattaagt aatgtttgct tcattctttt aatttaatat tttatttagg accattgcat  132960
atttttattta ggactgagcg tgtgtgtgtg tgtgtgcgtg cgtgcgcatg tgtgcctgtg  133020
tgtgtgtgtg tgcacatgca tgtatatcct tcctcagatt ttaattatta tgttgacttc  133080
ctagaattca gacttttcat tttcctctct ctttaaaaag ttacaaaatt atcagtcctt  133140
tacagatctg aagaaattta cctgtgaaaa cacctggcag ttttgggtgg ttaactacta  133200
tcttcctaaa tttattctat gatgtgtctg tctatgtctc ttaaataatt ttccaagttc  133260
tataatacag tgataattat ttacattttc ctagaaaggg ttttcatcta ggttttcaaa  133320
tttatttgct taggtttgga caaaatattt aaaaagtaag tttcctaaat ttctttatag  133380
ttgtagttaa ctccatttgc attttaatat tgaacattcg tgctgcttaa ttttttctc   133440
taggattaag taggctggta atttatcttt tttcttgatt cttttaaagtt tgggcttttg  133500
gactgatata tcaattacat ggcttctcta ttttttgact aagtactttc cgcatttgta  133560
tttttgattt tgtcttcaca cttagatttc gtcatactac ctatcttcca taagtaacag  133620
tttctatgaa ttaaaagca tcctttttata aatgcagact ttacttatga aggaaatatt   133680
agttataggt aatttagtgt gaattatttt actccaaata cttttcctcaa cacaaaaagg  133740
aatcatcttt tttgggactg aatttaattt aatctcttga ggactttgct ttttcactgt  133800
ttcatctatc tgtgagttgt acgaacactg gctgaaatta gctcattgag tggatgggag  133860
tttagataaa agggggaaaag gggaaggtaa tttgggagga tggctcttgt tgggggcaga  133920
tagatacagg atctgtggag gaagagagaa aggccagaac aagaactgag agagtaacaa  133980
agaaatccta cgaatcctta gtaactttca tgtaatgaga gacaggagaa aataagaact  134040
```

```
agcattctgt gagcaatgac aacccttttcc ctgcgtttgc ctatcagtttt tcattctatt   134100
aatagcatgt atctgaagat attaaaaacc accacccctt ttgcagggggt aaaatttaga   134160
atgattgact tttattggag ttatgtttta aaatatattt tgaaaatata aaaagagttt   134220
atgaagattt tacctagaga aggatttaaa aatttcaccc aaaatttact gaatcattag   134280
aattactaaa atctaacatg ttcatggtac ttggggtact ctaaaccat tatgatacct   134340
atttttagat tatttaaatt aaaattagat aatatacaca ttgttcatta ttatataaca   134400
ttacatttgt atattacatt atatccttca ttatacagta aaatatatat agacagtaag   134460
ctaacattat cagttcggtc aaaagtcaga ttaacaaaaa tttacagtaa atgcttagta   134520
tttatagaca agctcctctt tcctggagta atattatatg cagaagtttt ctctgatcct   134580
atgaattacc acatgacctc tccattccat tttgtgtacc tgtttgcctg gtctggttat   134640
gactgcagtt ttgttttcat tttcctgaat tgttgctaac acttaagtat attgacttgt   134700
ttcttcactg agaaaagaaa aaagtgtggt cccatattca gttcagcaaa taattctata   134760
cctactatgt agaaggcagt atgccagtga ctgtatttag gataaaatgt gtgtgtgtgt   134820
gtgtgtgtgt gtgtgtgtgt gtgtgtgtga gagagagaga gagagagaga gagagagaga   134880
gatgttattg tagtcccaat tgatgttaaa gaataatgga tggaaacact tggtcagtgt   134940
ttccaccgat ctttgcatca ctcagcattc atgcctaaat ttgtggtgtt ctcagaattg   135000
tgctaatgtg taaaatattc ttatacttaa tatgagtaca gtctgttggc tctgtagaac   135060
acaactcaaa gtgtatgtat ttttctagtt atttcttaaa ttatgacaat atgcttatct   135120
gatatatgtg gaaccagttt gttaaaagta gtctgttagt ttttaaggat tagtcttcta   135180
agaaagattt tctctttctt ttctaacatg caaatgagtg catgcttagg ggcttgatgg   135240
caatgagtgg gatatagtta agcacatatt aaaggcataa cataataagg gtgtcctctg   135300
gaaagaaaag cctttacaca acccaaaata ggtaaaaatg tggccttcgc ctgtggcttt   135360
aatcaataca tgccacagtt atcgtcggac aagaattgaa gccctcaaag ttaatctttt   135420
ccatctttct tcccccacttc cctaagtttc ttcctctaca tggccctatc ctgctattcc   135480
aagtcacaat aaatgatgat agtgagattc tttatgaagc atttaggtga tcttgctttc   135540
ataccaatga ataaaaaatt gagaatgtat tggttttgga accatactca tataagttat   135600
ctaatgcttt tttatgattg tacattactt aagaaacaga tatttacatg agactttaat   135660
tactatagtt gatacagtgc tgcatgcaat catgtgctaa aaataatatg tgaaagttct   135720
tgtaaagatt tattgacctc gcaaataaac tagaaaatct ggaagaaatg gataaattcc   135780
tggacacata caccctccca agtctaaacc cagaagaagt cgaatccctg aatagaccaa   135840
taacaagttc tgaaattgag gcagtaatta atagcctccc aataaaaaaa aatgtccagg   135900
accagacgga ttcacagccg aattctacca gaggtacaaa gaggagctgg taccattcct   135960
tctgaaacta ttccaaataa tagaaaaaga gggaatcctc ccgaactcat tttatgaggc   136020
cagcatcatc ctgataccaa aacctggcag agacacaaca aaaaaggaaa atttcaggcc   136080
agtatccctg atgaacatcg atgtgaaaat cctcaataaa atactggcaa actaaatcta   136140
gcaggacatc aaaaagctta tccaccacga tcaaatcagc ttcatacctg ggatgcaagg   136200
ctggctgaac atacacaaat caacaaacgt aatccattgt ataaatggaa caaatcacaa   136260
aaaccacatt attatctcaa tagatgcaga aaaagccttt gataaaattc aacacccctt   136320
catgctagaa actctccacg agctctaggt attgatggaa tgtatctcaa aataataaaa   136380
```

```
gctatttatg acaaacccac agccaatatc ttactgaatg ggtgaaaact gcaagcattc  136440
cctttgaaaa ctagcacaag acaaagatgc cctctctcac cactcctatt caacatagtg  136500
ttggaatttc tggccagggc agagacttgg catgcaagag aaagaaataa agggtattca  136560
aataggaaga gaggaagtca gattgtctct gtttgcagat gacatgattg tatatttaga  136620
aaacccctttt gtctcagccc caaatctcct taagctgata aacaacttca gcaaagtctc  136680
aggatacaaa atcaatgtgc aaaaatcaca agcattccta tacaccaata acagagaacc  136740
aaatcatgag tgaactccca ttcacaatta ctattaaaag aataaagtac ctaggaatac  136800
agcttacaag ggatgtgaag gacctcttca aggagaacta caaaccactt ctcaaggaaa  136860
taagagagga cacaacaaat ggaaaaacat tccatgctca tggataagaa gaatcacaat  136920
atagtgaaaa tggccatact gccgaaagta atttatagat tcaatactgt ccccatcaag  136980
ctaccactga ctttcttcac agaattggaa aaatctactt taaacatcat gtggaaccaa  137040
aaaagagccc acatagccaa gacaatcctg ggcaagaaga acaaagctgg aggcatcaca  137100
ctacctgact tcaaactata ctacctggct acagtaacca aaacagcatg gtactggtat  137160
caaaatagat atatagacca atggaacaga acagaggcct cagaaataac accacacatc  137220
tacaaccatc tgatctttga caaacctgac acaaacaaga aatggggaaa agattccctg  137280
tttaataaat ggtgttggga aaactggcta gccatatgca gaaaactgaa actggacccc  137340
ttccttacac tttatacaaa aatcaactca agacggatca aagactgaaa cgtaagacct  137400
aaaaccatga aaaccctaga agaaaacctg agtaatccat tcaggtcata ggcatgggca  137460
aagacttcat atctaaaaca ccaaaagcaa tggcaacaga agccaaaatt gacaaatggg  137520
atctaattaa actaaagagc ttctgcacag caaaagaaac tatcatcaga gtgaataggc  137580
aacctacaga atgggagaaa attttttgcaa tctatccatc tgacaaaggg ctaatatcca  137640
gaatctacaa agaacttcaa caaatttaca gaaaaaaaac aaccccatca aaaagtgggc  137700
aaggatatga acagacactt ctcaaaagaa gacatttatg cagccagcag acatatgaaa  137760
aaatgctcat catcactggt cattagagaa atgcaaatca aaaccacaat gagataccat  137820
ctcacaccag ttagaatggt ggtcattaaa aagtcaggaa acaacaggtg ctggagagga  137880
tgtggagaaa taggaacact tttacactgt tgtgggtgtg taaattagtt caaccattgt  137940
ggaagacaat gtggcgattc ctcaaggatc tagaactaca ataccatttt gacccagcca  138000
tcccattact cggtatatac ccaaaggatt ataaatcatg ctgctataaa gacacatgca  138060
cacgtatgtt tattgcagca ctatttacaa tagcaaagac ttggaaccaa cccaaatgtc  138120
catcaataat agactggata aagaaaatgt ggcacatatg caccatgaaa tactatgcag  138180
ccctaaaaca ggatgagttc ctctcctttg cagggacatg gatgaagcca gaaaccatca  138240
ttctcagcaa actatcacaa gaacagaaaa ccaaacaccg catgttctca ctcatgggtg  138300
ggagttgaac aataagaaca catggacata ggaagggcag catcacacac cagggcctgt  138360
tggcggggtg ggggtctagg ggagaatagc attagaagaa ataccctaatg taggtgatgg  138420
gttgatggag cagcacatca ccaaggcatg tgtatacta tgtaacctgc acgttctgcg  138480
atgtacccca gaacttaaag tataataata aaaagatttg actataagga tgatattatg  138540
ctataataca ctgttcaaat attatgagat tctaatggtt aaaattgttt agtcattaga  138600
aaatatctgc agtggtaaat tgttaagtat ggaattcag taccccaaaa taagtataca  138660
cacaaaagtt taagaatatt tttcatcagt gtaacgattt tcagtcagga gcctttgcac  138720
ataatgaagt atgtaggctg tggaatctag ccaacctggc tttcactctt caacttagta  138780
```

```
gctacataac ctcagacagg ctacttaggt actctgtttt tctttgtctg tcagagggat   138840
atataataat acctacttct taggagctgc tgtaaagatt taccaagcta atagtagtag   138900
cagaaaacac ttctctagtc cttactgtgt accagacact gatctaagca caatacattt   138960
aaaaatcatt atatcttcac aaccactgta tgcagtggtt actgctgtgt ctggcattaa   139020
atattagcaa ataataccaa caactaccac catcaagaag tcaacatgtc tttacattct   139080
gatgacaata agtatgcatt gaaaatgtta ccatcttcta ttgaagttta aattcatatt   139140
atctaaagtc atgtttaaag attttttaaaa ctgtttacca tatttttttac ccttgctttc   139200 ttcatatttt aattaaaatc agaatcaaga tgtgatgatc acctatgatt gttattttca   139260
gataaactat actatatttt cagccacagg ttaaacagtt caggggtata gagatcattg   139320
gacagaacat ttagataact gaagccctca ttggctacta gaatttatca agggcctgca   139380
ttactctgta tgcttttggt ggtgggccat ttttttaaata agctgtgtag atccacaaac   139440
aaaatgatag attcagaaat acaagtaagc ttgactatta atttaagttt cagtcattaa   139500
tatcagcagt tttcactgtt ttttttctct cagctaagtg acagaagcaa aagacagtaa   139560
aaatcttgga aaatagttat cggtctttttt ttccatctca gcagataaaa tacattgatt   139620
ttttggattt ttcccatttt atgacacata tcaaacatgc tctgggaaaa ttcacaagat   139680
agttataaaa tatatacaat ctctgtgttt tggatttatg acataatcta tcttacaatg   139740
gcagcttata caggggacag gaaggagttc tgctagagtc ccagaaagtg ataggcagtc   139800
tttaagagtg cttttgagcta tggttgactt gggcagaata gaacacccag tatctctggt   139860 taaaagaac tcagtaaaaa aatatgaacc atgcaagcaa gcatttgaac cagaatgcat   139920
atatgtctta aagcctaatt tgggggaagt tttcaagccc aaaatactct agatataaat   139980
gtgttaaatg tgcaatccaa ggtcaaccag agaacctaca gctaacaaaa ttgataatat   140040
aatgctaggc tgcaatattg catcattaaa aggtaagaat ggcatcagca taaaaccatg   140100
gccaactcaa gataccaaag atgtccagaa gcctcccttc gcaaacagc aggaatgtca   140160 gctatctagg catgcagttt cactggtcaa gcatatttga gagccttgca gtgagccaga   140220
ccttacatga tagccagatc ttagtggagt atagaattga ttaatcctca gcaaatactt   140280
accatgttct aattttagct tgtcatatat aaatgccaac ttaaaatgac tttatcaagt   140340
aggttgctaa taagtactga aagtaaaaat gaaagttaat agcattgtgc atcatttgcc   140400
agtaagcatc tccattccgt gtgtgtgtgt gtgtgtgtgt gttgtgtgtg tgtgtgtgtg   140460
tgtgtgtgtg tatttgcctc ttactatgag ttaaaggccc atcaggaaac tcttacagtc   140520
aggaaactta agcttatagt cagctgtgaa acagcctttt aaaaatcatt cccccttaccc   140580 acacacggac ttcactctgc ttgtagtgtg gctgctcata gtgtggctgt ttttccatct   140640
tgacacgtat tttctcatta ctatattaaa gtgactttttt tctttattgt attgatatac   140700
tgaatagacc tcctcagata atatttatgg aaacataaaa ccattctgga aggcagttta   140760
acagtatcta cttcataagt cttccctttt actctaaagt ttcaccccta ctaatctgat   140820
aagtatatat aaggaatggc caaaattata catatttaca agaaaaatta tggcattgtt   140880
gctagtgctt aacacaggca aaaaaattat caatagatca taggttgaag tatatctgta   140940
tgatagaatg ctgtgtagct atccagaggg aaataagaaa gctttatgta tatagatgcc   141000
ccttgactta tgaattatga tggtgttatg tcctgataaa ttcatcgtaa gttgaaaata   141060
ctgtgaaatc gaaaatgcat ttaatatact taacctatca aacatcatag ctgagcttag   141120
```

```
cctgccttaa atatgcctgc aacacttata gcttacagtt gggcaaatca taacatgaag 141180
cctatgtttt aatatgatgt tgaatatctc ttgtcattta ttgaatactg taccaagggt 141240
gaaaaacaga atggtgttgc accatcataa agtcaaaaca ttgtaaatca agccataatt 141300
agtcagggac tgtctgtact gacatagaaa ggcttccaag acatgttata aagtggcata 141360
atataagtgg caaagcagta tgatgtgatc atgtgtattt tgaattatat atacacacat 141420
ttgtatatag gtgatgctgg atttatatta aatataagat aaggtgaggt ttgtgttaca 141480
actaagtaag aaaagtatat aaaatgagtt acatcatgcc tacttagtgc attgaaataa 141540
ttaataaaat ttgccattat ttttatcttt atggagtgga ttgaggaagg aaaaataggg 141600
ctgcctttac taactttaca tgttttgcat tgactgattt tacatgcatt acttttataa 141660
taaaataaga gagaaaacca tttactcttg ggaaaagatc tggaaaagca tattcatact 141720
aaaatattaa tggcataaca aaacttgacg tttttcttct gacacaagat attgaagaac 141780
tcctaatatg tgagcacagt ggtgacctct ggtactcttt tggacaagag tcttcctaaa 141840
gtctataaaa gctgttttgg agttttggtt atttgttttc acctttaaat atctacccat 141900
attttcaatt gtatttcttc cttcgtgttc tcaggagtgt gtgtgtgtgt gtgtgtgtgt 141960
gtgtgtgtgt gtgtgtgtgt gtgtgtgtag agggatatgt atacatatta tttaagcatt 142020
taggtgatta tttttcaaga attgttggaa aatttaagga agcagtggaa agaataactg 142080
atagtaatta ctgcctagtt atctaaataa agtgaagctt cttttctcc cttcttccga 142140 atcttttctt agcaaataag aatcaccctg aaagtagttt aaaagagata ttctagtgac 142200 cataccaat gaagtactaa atattcatcc tgttagagtg attattgcaa ggactctaaa 142260
ggaaaacatt gattatacta gattatttat tttatagaat tttattctca gcttatactc 142320
ctggttctat gaactataga aatcactcag aataataaaa tgctgatgtt atattttatt 142380
gaaattcatt aaaaattata gaaaaggtg ctcatttgaa aacttccaaa tgtcagttat 142440
tcagaatgac aaacttaatt atatagaaat tgactaattt ggttgattct ttctaaagtc 142500
agtgttggat taataatgta atgcatggat cattaacagc ttaaaaatac ttgtggtaaa 142560
cttgatgatg taatgctatt tgttaggaa agatggcctc ttttcttaag ttgcaatcct 142620
ttaaggattc aaagccctaa ttgtacataa gcaatatcgt atgctgtagg ctcgttatca 142680
ttggagggga ggtttaatat agagtttaag agcacaaaat atggaatcag actgttgctg 142740
ttaaaatcct ggctctgcca cttcctagct gtgatcttag acaagttact ctctctctgc 142800
cttgattttc ttacatataa aacaaggata taagtagtaa gtggtagaac tcttatttca 142860
taaggctgtt ataagattgt tgtaagaatt taatgggtta gtatttataa agcaggtcta 142920
tatatagtaa gtattcaata agggtagcta ctatttgtca ttttggtcat gtaatatcta 142980
gtgttacata tgtgtgttgt caaataaatt agttgttaac attatttaaa agaaaacatt 143040
gaattacaat ctgtttttaag catctttttt attttctga gatgtaaaaa ctgattgttt 143100
tactagttgg ttttgattat ttgtttcttg tttgtattac agttacaaat tataaactg 143160 tggtagaaac aaattcagat tcagatgatg aagacaaact gcatattgtg gaagaagaaa 143220
gtgttacaga tgcagctgac tgtgaaggt taccagagga tgacctgcca acagaccaga 143280
cagtgttacc agggaggagc agtgaaagag aagggaatgc taagaactgc tgggaggatg 143340
acagtaagtc tgattttttt ttgtaatatt gtattctcat gattcgtttt ttaaaatata 143400
tattaactga aaagataaat tggatgaaaa gtttgaaatc aatagtaaat ttggctatca 143460
ataaatatta ggtgtcctac ttactaaaaa gtggattatg aagcagaata agcaagttat 143520
```

```
tttgaccata tttacaatgc atataatgta ttgaaattta gtagaattta ttaaccagga   143580
tcaagctttc caaatattgt tgatataatt gaacctacct ttaattttt attgtaaccc   143640 cgaatgaata ctctacttag aaaccaataa atatcatata gatatagtga aattataatt   143700
caatatgcaa aaatcccaaa cacatataaa tcatggaggt atttttagtg cttgtaaacc   143760
tctctataca tacatcagaa tcctttaagt aaggtggttt tttcacttta aatttttact   143820
tttactcaaa gtatggctga gtggaaggag cggtgaaagt aaggagaccc tctacttgct   143880
gcactttcag tgagtaaaca ctgaaagttt aatcttcttc ctcatctgtc aaatggagaa   143940
attggaccta gtcttttatt ctagctctaa aatttcttct ttctactttt cctaataaac   144000
taattaaatt atttagcctg tcttgccagg ttaagcacca atgatataaa aatgggatat   144060
ggaagtggca tagtattaat tagagaggtt ggggatcagg aacaagggca tcagaaaagg   144120
taaacaagta cacgcaataa atcgaatcca agaccagtca aaggagaagc ttcccagcaa   144180
gaattcaagt tcaaagaggt cgtctagaca agatatcaaa actaaaatct ggaaaagtgg   144240
gtcaggcatg caggtcagga tattatctgg ataatgaaat atggaagtgt agataaaagc   144300
tcagataata ggcacagatt ggcagaagtt aagatttcta caatatgaca aatctaatgg   144360
ttaacaaggg acttttgaaa taatgtaatc agccctctca ttttatagtg ttgttcattt   144420
gtccattcag caacctctgt agaaattggt tgcaactgtg ataagactc tctgcatgaa   144480 tgatgtttat atggcttaat ggagaagaga gataaataag tcacaaatac attatagttt   144540
tatttaggta tacattatat ggcagcatca aggaggagca tccgaattag agaaggaagg   144600
agaagtcgta gaagagttct gagtgaaaca gagtggtctt tagttcttaa ggaccgatgg   144660
aggttaatta gacaaagtac agtgaatata aggttttcag gcaaaagagg caacatacat   144720
gaagccacag aggcttgagc aaagtgttca cagaaaatga gatcagagaa gtaaacaagg   144780
gaaaaaatat gaagtgattt gtgtactatg tcaaggaatt tgaacctat catggaagct   144840 atgagaagaa catcattaaa ataatttata aataagtctg gtgtaatatg gaaaagaat   144900 tttagaggga gggaggctga ggtagtgtct tcaacgagac ggctgtaata atcaggcagt   144960
gttaagggtt tttgagttaa agtagttgcc catgggatgg gaatagaagg gagataattg   145020
aaagacagaa aggagataga atatataaga attggaaagg gctgttttta gatacagtcc   145080
caggtttcta gaaagtgaga ctcagagaag ttgacttgct cacttatggc agctggttaa   145140
ttgtagagct atgaacctgt taatgttaat actaagctca acatttttg gagcaagggt   145200 ttcttatgta tttcttatct gtggcctgaa ttacgtagtt gatccagagt cttaataggt   145260
aatcaagaag gaaatgatct gtctggggaa aaaggggggc aataagaata aggtagatga   145320
agggagaaag gaaggtgaaa aaatcagtga acaggtctg cttctgagaa tatgttgggt   145380
tcgattattt gaactaaccc ttttactga aaacaactaa tggtgctaga ttaaaaacaa   145440
aaacaaaaaa cttcttagca cttctaaaga gctaagtaag acactacctt gtcaaaatct   145500
aagtgaaaaa aggaacccat agaagtaaac agagcagatc atagaagaca ctttggtcct   145560
gaatacattt gcctagccag tgaaatgtaa ggtgattttc aggcttctga gaggaaacaa   145620
agcccaagac caccaaagat agtttaatag cagtatggat tatgtctcga ctgtgaggat   145680
gaactaaaag caaaccattt tccatctcta ccatccttga gagtgaacaa gcaaagtttc   145740
cctggttagg tattcaggga atggaggatt gtctttgaga agtagtaacc acaagctgtc   145800
tcgcactgat ttgaagtcca agtttacatt gctgtgtagc ctgaaaaatc tcaagccata   145860
```

```
tttgagttta aagtggaact gctacaaata tctattggca ccaggcagaa gtaaacacaa   145920 gtctttttgga gaaatatacc ttcatcctag tactatagaa gtctcccaaa taatttagca   145980
agaaggtaga aacatgagtg agaattacca gaaacaaaag gaagcagaaa ctgacccata   146040
aaggctaatt actagagtta cgtcatacag atttataaaa tgactactgt cttgtttaaa   146100
gaaaaatcag atggttatct gctatgatat gataaaataa aaccagtgtg ttttaagaat   146160
aatctaatag aactaaaaat aaaaaattga atagtaggaa tttgaaattc agaggataca   146220
tttaacaaca aattaaacag ggttaaagaa aaattaataa tttggaagat agagaaaaat   146280
tacactaaat ggaactcaga gagacacata gaaaaaatat gaaaaacagg tgcctgtagt   146340
cccagctact cgggaggctg aggcaggaga atggcgtgaa cccgggaggc agagcttgca   146400
gtgagccgag atgatgccac tgcactccag cctgggcgac agagtaagac tctatctcag   146460 aaaaaaaga aaaagaaaa gatatgaaaa acaggttaag atacatgaag attcaataca   146520
tcttatgcca ggagaaaaga tactagggca gcagccatac ttgaagaaat aatggctgag   146580
gtttttattt ataatcagtg aaaaacacca tactacagat tcaaaagcc caaatggaca   146640 ttcagatctg taaagatcaa agaagtccaa tagattgaac ataaaagat cttcactaag   146700 gcacattaca atcaaattat gaaaagtcaa cgacagtttt gaaagcagca aaagaaagt   146760 tgcagactcc ataagactgt aggcagattt ctgtgcagaa acctgtcaag caaggagaaa   146820
gtgggatgat atattcaaag tgccaaaaga aaaacactgc tgaccaagca tactataccc   146880
agcaaagtta tacttcagaa atgaagaaga aatactttcc caaaacaaa agctgaggga   146940 ttttgtcact gttaaacctg cttcgtaaga aaaactgaag gcagtttttc aagttgaaac   147000 aaagaacac taattagcaa catgaaaaca tgaaagaata aaactcacta gtaaagaagt   147060
tccaaactat aaatactatt ctatatagtg agaagaatg aataagacct actatttgat   147120
agcacaatag ggtgactgca gtcaataata acttaattttt acattttaaa ataaaagagt   147180
ataattggat tgtttgtaac tcaaggata aatacctgag gggacagtta aaaagaaat   147240 aaattcagaa tgctgtgata ctataatgat gttgtgtaaa tgtcttgtaa ctctaatata   147300
aaaataaaaa acaaggtatt aaaatatagc tacaataatt tttaatagat atacaatata   147360
caagtatgta aattgtggta taaattaaca cagaatgtgg gaggggagag gtaaagtgt   147420 agttttata tgtgatggaa attaagttct tatcagttta aaatagattg ttatgactat   147480
aaaatggttt ttgtaagcct tttggataat taaaagaaaa aaactgtgtt agatacacaa   147540
aagataaacc atgcgattgc aaaaaatata tatatatata taaaatatca atggaagcag   147600
caaagaaaca aaggcactta aaacttttca gaaaacaata aaatggcagt agttttact   147660 tatcaataat tactttaaat gcaaatggat taaactcagt aatcaaaata cattgttact   147720
atgcatgttt ttaatacaga gatagggcct tgctgtgtca ccagggtaga gtgcagtgat   147780
gcagtcacag cccactgtaa cttcaacctc ctggactcaa gcagtcttct tgctttagtc   147840
tcctaagtag ctaggactac aggcatatgc caccacatgt ggctaattta aaaaaaaaaa   147900
aaactttcat ggaaagatgg ggtcttgcta tgttgctcag gctttaaatg catttttaa   147960 aactgaccca actacaagct gcctacagga gacttatttt accttaaaag atacagataa   148020
gatgaaagag gaaggttgga aaaatatgtt ccatgtaagt ggaaccaaaa gagagcagtg   148080
gtggccattt ttacaccagg caaaataaat tttaagtaaa aaattgtcac aagaggcaat   148140
gaaggtcatt gtataatgat aaagaggtca atttatcaag atgatacaat tctaaatata   148200
tttgccacca attttggagc acataaatat gtaaagaaaa aatataactg aagggagaaa   148260
```

```
tagatagcag tacagtaatc ataggggtct tcagtgcttt caataatgga gaaatcatct 148320
agacagaaaa tcaataaaga aacagtggat ttgaacaaca ctagacaaaa tggacctgat 148380
atacagaaca ttccattcaa cagtagcaga atatgcacat ttttctcact caaacatgta 148440
acattctcca ggacagatta tttgttaggc cacaagataa gttttaacaa atttaaaatt 148500
aaaattatat caagtatgtt ttctgtcaac agtggcatga aaccataaat ccgtaacagg 148560
aggaaaattg gaaaattcac aaatatgtgg aaattaagca acacactcct gaacaaccaa 148620
aggtcaaaga agaaatgaaa ggggaagtaa aaaatatctt gaaacaaaca aaaatggaaa 148680
cataacatac caaaacatgg aatgcagcaa aagcagttct aaaagagaat tttatagcaa 148740
taaatgccta cattaagaat aaggaatgat cttaaataaa caacttaata ttggacctca 148800
tggaactaga aaaataagaa caaagtaaaa ccaaagttag aagaaggaat gaaataataa 148860
agattagagc acaaataaat gaaataaaga gtagaaaaac aatacaaaag atcaacaaaa 148920
ctgagttagt tttttgagaa gataaaatca acaaacattt agctagaatt taaaaaagga 148980
gggaatatcc aaatagaata ataaatgaaa aatgaggaga gggattaaag atggccaact 149040
agctggatct gggatgcacc tcttctacag agaggaacca aaatattgag taaaccctca 149100
cactttcaac agatcttttg agagaaaaca ctgaaattta atatataggc catgacagac 149160
atgattgaag aagtaggaag caacactgct ggctcagtat tgccagacac cttaggacca 149220
gaatggaccc aaggaaggtg tgagtgaaga aacccgggaa caccactttc ccactgtcaa 149280
cctctgaaat tctagaggag ttcccacaac ccctgaatac gtttggattg gtaggaggag 149340
ctgcctggag accatacaga ggcactactt gaagccacaa ggagcccaaa agccttcagt 149400
gtgctaggca gctgcagcaa aacgtgactc tgggcaccca cccccgagtg ccctgcatcc 149460
gagcggctac atctgctgtc tgccacacca ggatagagtg gggcccatgc atgttcacat 149520
gaccaattca ggatccacca ccattcctgc aggactgagg tgaatctaaa ccacacacga 149580
ccatgcctgc cagtccctcc taagattgcc tgcctggcca ttgctgtgga gtgggaccca 149640
cagcatagcc tccattgccc cacctgagtg gtttattggc tacctgggaa cactttactc 149700
ctcctatcac tgccagtggt tgatcctaag gagccagagg acaaatccac tggcctggtc 149760
tcagtttgcc aggactcaag cataccaccc aggaatatgg ggatgagatc tgtggcctga 149820
tctcaagcag gggaggaacc cccactgtca gaacacaggg aagagtgtgg tgtgggtttt 149880
tcaggtggta cagaagctgg gcacccctcc cttcatgaga atagactagg aagggtatag 149940
cctcatagcc ttgcttcctg ctgcagggag tcttgcattc tggaatgcct gggatggcat 150000
ggcagtctgg gcacaggtgg tttgggattt gcataactaa ttgggccggc tgccagggtg 150060
gacactggag ggagacccac cagtcagggg tgtagaagct gagtgggcct catggccatc 150120
tgctggaatg aaatcccagg gctagccctc ttaccctgaa ccagctcttg tggcacagaa 150180
gaggtgcctg caccccctccc tagagtgttg ttccagctgc ctgagaactg ccctacagc 150240
cctaccaagg tcacgtctgc ctcagagagc ctgatcacgg gctcaccaga cccagtccca 150300
cccagctttg cccctctag ccagccttgg gagcagagca tgggatggga ccactgagag 150360
ctccacaccc cccacccatc accaagaaca ctcttgtatt ccttatcaac aaaggccaag 150420
taaaaatccc actgtcatca ctgcagctgc ctctcacctg ccagcatcac ctactggcca 150480
ggaggtcaaa actgcatgtc ctgtcgcagc aactgttgat atcattgcac agcactcaga 150540
cagctcttac ctgcaggcat cacctgctgg cctgtagggt gaactgcaca acccaatata 150600
```

```
attcctgctg acaagtacac agctctaagg aatgaggtaa gtttccccca aaagacctcc  150660
aactttgcat ctctatagga gacagtgagc cttaccacat atacagcata ccactactac  150720
aaactacaaa caattaacat ttgagaaaac aactacacta aggctatctg taaccaagga  150780
atttatacag agccttggcc ccctaaaagc acgtagaagc aaagccaaag gacacaaccc  150840
aacatatgca agagtcacac cctcaagggg caacgaaaaa taatcccacc caaatgaaga  150900
taaatccaaa aataataagt gccagcttct acacatgaga aggaaccagc acaagagctc  150960
caacaccagg aagaaataga atgttgtgac acccctaaag gaccacatta gctctctagc  151020
aatgaatctt aatgaaaatg aaaactttga aatgacagat aaagaattta agatatggac  151080
tgttaagaag cctagtgaga tacaagagaa agttgaaaac caaagcaact agagaaacaa  151140
tctaagagat gaaagacaac atagatatat tttttaaaaa acaaatggaa tatctgaaaa  151200
tgataaattt gctgaaggaa cttcaaaaca ctgttgaaag ccttaacaat agactagaca  151260
aaccagaaga aagatttcag agcttgacga ctagtctttc aaattaaccc aatcagaaaa  151320
tggccgaata ggaacagctc cggtctacag ctcccagcgt gagcgacgca gaagacgggt  151380
gatttctgca tttccatctg aggtaccggg ttcatctcac tagggagtgc cagacagtgg  151440
gcacaggtca gtgggtgcgc gcaccatgcg tgagccgaag caggggtgagg cattgcctca  151500 ctcgggaagc gcaaggggtc agggagttcc cttcctagt caagaaagg ggtgacagac  151560 ggcacctgga aaatcgggtc actcccaccc gaatattgcg cttttctgac gggcttaaaa  151620
aacggcacac cacgagatta tatcccgcac ctggctcaga gggtcctacg cccacggagt  151680
ctcgctgatt gctagcacag cagtctgaga tcaaactgca aggcagcagc gaggctgggg  151740 gagggcgcc cgccattgcc caggcttcct taggtaaaca aagcagccca gaagctggaa  151800
ctgggtgaag cccaccacag ctcaaggagg cctgcctgcc tctgtaggct ccacctctgg  151860
gggcagggca cagacaaaca aaaagacagc agtaacctct gcagacttaa atgtccctgt  151920
ctgacagctt tgaagagagc agtggttctc ccagtacgca gctggagatc tgagaacggg  151980
tagactgcct cctcaagtgg gtccctgacc cctaaccccc gagcagccta actgggaggc  152040 acccccagc aggggcacac tgacacctca cacggcaggg tactccaaca gacctacagc  152100
tgagggtcct gtctgttaga aggaaaacta acaaacagaa aggacatcca caccaaaaac  152160
ccatctgtac atcaccatca tcaaagacca aagtagata aaaccacaaa gatgggaaa  152220 aaacagaaca gaaaaagtgg aaactctaaa aagcagagcg cctctcctcc tccaaaggaa  152280
cgcaattcct caccagcaat ggaacaaagc tggacggaga acgactttga cgagctgaga  152340
gaagaaggct tcagacgatc aaattactct gagctacggg aggacattca aaccaaaggc  152400
aaagaagttg aaaactttga aaaaatttta gaagaatgta taactagaat aaccaataca  152460
gagaagtgct taaggagct gatggagctg aaaaccaagg ctcgagaact acgtgaagaa  152520
tgcagaagcc tcaggagcca atgcgatcaa ctggaagaaa gggtatcagc gatgaagat  152580 gaaatgaatg aaatgaagcg agaaggaaag tttagagaaa aaagaataaa agaaatgag  152640 caaagcctcc aagaaatatg ggactatgtg aaaagaccaa atctacatct gattggtgta  152700
cctgaaagtg atgggagaa tggaaccaag ttggaaaaca ctctgcagga tattatccag  152760
gagaacttcc ccaatctagc aaggcaggcc aacattcaga ttcaggaaat acagagaatg  152820
ccacaaagat actcctcgag aagagcaact ccaagacaca taattgtcag attcaccaaa  152880
gttgaaatga aggaaaaaat gttaagggca gccagagaga acgtcaggt taccctcaaa  152940 gggaagccca tcagactaac agcggatctc tcggcagaaa ccctacaagc cagaagagag  153000
```

```
tgggggccaa tattcaacat tcttaaagaa aagaattttc aacccagaat ttcatatcca    153060
gccaaactaa gcttcataag tgaaggagaa ataaaatcct ttacacacaa gcaaatgctg    153120
agagattttg tcaccagcag gcctgcccta aaagagctcc tgaaggaagc actaaacatg    153180
gaaaggaaca accggtacca gccgctgcaa aatcatgcca aaatgtaaag accatcgaga    153240
ctaggaagaa actgcatgaa ctaacgagca aaatcacctg ctaacatcat aatgacagga    153300
tcaaattcac acataacaat attaacttta aatgtaaatg gactaaattc tccaattaaa    153360
agacacagac tggcaaattg gataaagagt caagacccat cagtgtgctg tattcaggaa    153420
acccatctca cgtgcagaga cacacatagg ctcaaaataa aaggatggag gaagatctac    153480
caagcaaatg gaaaattaaa aaaggcaggg gttgcaatcc tagtctctga taaaacagac    153540
cttaaaccaa taaagatcaa aagagacgaa ggccattaca taatggtaaa gggatcaatt    153600
caacaagaag agctaactat cctaaatata tatgcaccca atacaggagc acccagattc    153660
ataaagcaag tcctgagtga cctacaaaga gacttagact cccacacatt aataatggga    153720
gactttaaca ccccactgtc aacattagac agatcaacga gacagaaggt caacaaggat    153780
acccaggaat tgaactcagc tctgcaccaa gcagacctaa tagacatcta cagaactctc    153840
caccccaaat caacagaata tacatttttt tcagcaccac accacaccta ttccaaaatt    153900
gaccacatac ttggaagtaa agctctcctc agcaaatgta aaagaacaga aattgtaaca    153960
aactatctct cagaccacag tgcaatcaaa ctagaactca ggattaagaa tctcactcaa    154020
aaccactcaa ctacatggaa actgaacaac ctgctcctga atgactactg ggtacctaac    154080
gaaatgaagg cagaaataaa gatgttcttt gaaaccaacg agaacaaaga cacaacatac    154140
cagaatctct gggacacatt caaagcagtg tgtagaggga aatttatagc actaaatgcc    154200
cacaagagaa agcaggaaag acccaaaatt gacaccctaa catcacaatt aaaagaacta    154260
gaaaagcaag agcaaacaca ttcaaaagct agcagaaggc aagaaataac taaaatcaga    154320
gcagaactga aggaaataga gacacaaaaa acccttcaaa aaattaatta atcccagagc    154380 tggtttttg aaagggtcaa gaaaatagat agaccactag caagactaat aaaaaaagag    154440
agaagaatca aatagatgca ataaaaaatg ataagggga tatcaccacc gatcccacag    154500
aaatacaaac taccatcaga gaatactaca atacctcta tgcaaataaa gtagaaaatc    154560
tagaagaaat ggatacattc ctcgacacat acactctccc aagactaaac caggaagaag    154620
ttgaatctct gaatagacca ataacaggat ctgaaattgt ggcaataatc aatagtttac    154680
caaccaaaaa gagtccagga ccagatggat tcacagccga attctaacag aggtacaagg    154740
aggaactggt accattcctt ctgaaactat tccaatcaat agaaaaagag ggaatcctcc    154800
ctaactcatt ttatgaggcc agcatcattc tgataccaaa gcctggcaga gacacaacca    154860 aaaagagaa ttttagacca atatccttga tgaacattga tgcaaaaatc ctcagtaaaa    154920
tactggcaaa ccgaatccag cagcacatca aaaagcttat ccaccatgat caagtgggct    154980
tcatccctgg gatgcaaggc tggttcaata tacccaaatc aataaatgta atccagcata    155040
taaacagagc caaagacaaa aaccacatga ttatctcaat agatgcagaa aaggcctttg    155100
acaaaattca acaacccttc atgctaaaaa ctctcaataa attaggtatt gatgggacgt    155160
atttcaaaat aataagagct atctatgaca gacccacagc caatatcata ctgaatgggc    155220
aaaaactgga agcattccct ttgaaaactg gcacaagaca gggatgccct ctctcaccac    155280
tcctattcaa catagtgttg gaatttctgg ccagggcaat taggcaggag aaggaaataa    155340
```

```
agggtattca attaggaaaa gaggaagtca aattgtccct gtttgcagac gacatgattg  155400
tatatctaga aaacccatt gtctcagccc aaaatctcct taagctgata agcaacttca    155460
gcaaagtctc aggatacaaa atcaatgtac aaaaatcaca agcattctta tacaccagta   155520
acagacaaac agagagccaa atcatgagtg aactcccatt cacaattgct tcaaacagaa   155580
taaaatacct aggaatccaa cttacaaggg acgtgaagga cctcttcaag gagaactaca   155640
aaccactggt caaggaaata aaagaggata caaacaaatg gaagaacatt ccatgctcat   155700
ggctaggaag aatcaatatc gtgaaaatgg ccatactgcc caaggtaatt tacagattca   155760
atgccatccc catcaagcta ccaatgactt tcttcacaga attggaaaaa actactttaa   155820
agttcatatg gaaccaaaaa agagcctgca tcgccaagtc aatcctaagc caaagaaca    155880 aagctggagg catcacacta cctgacttca aactatacta caaggctaca gtaaccaaaa   155940
cagcatggta ctggtaccaa aacagagata tagatcaatg gaactgaaca gagccctcag   156000
aaataacgcc gcatatctac aactatctga tctttgacaa acctgagaaa acaagcaat    156060 ggggaaagga ttccctattt aataaatggt tctgggaaaa ccggctagcc atatgtacaa   156120
agctgaaact ggatcccttc cttacacctt atacaaaaat caattcaaga tggattaaag   156180
atttaaatgt taaacctaaa accgtaaaaa ccctagaaga aaacctaggc aataacattc   156240
aggacatagg cacgggcaag gacttcatgt ctaaacacc aaaagcaatg gcaacaaaag    156300
ccaaaattga caaatgggat ctaattaaac taaagagctt ctgtacagca aaggaaacta   156360
ccatcagagt gaacaggcaa cctacaaaat gggagaaaat ttttgcaacc tactcatctg   156420
acaaagggct aatatccaga atctacaatg aactccaaca aatttacaag aaaaaaacaa   156480
acagccccat caaaagtgg gcaaaggaca tgaacagaca cttctcgaaa gaagacattt    156540
atgcagccaa aaaacacatg aaaaaatgct catcatcact ggccatcaga gaaaggcaaa   156600 tcaaaccac aatgagatac catctcacac cagttagaat ggcaatcatt aaaaagtcag    156660
gaaacaacag gtactggaga ggatgtggag aaataggaac acttttacac tgttggtggg   156720
actgtaaact agttcaacca ttgtggaagt cagtgcggcg attcctcagg gatctagaac   156780
tagaaatacc atttgaccca gctatcccat tactgggtat atacccaaag gactataaat   156840
catgctgcta taaagacaca tgcacacgta tgtttattga ggcactattc acaatagcaa   156900
agacttggaa ccaacccaaa tgtccaacaa tgatagactg gattaagaaa aggtggcaca   156960
tatacaccat ggaatactat gcagccataa aaaggatga gttcatgtcc tttgtaggga   157020
catggatgaa attggaaatc atcattctca gtaaactatc gcaagaacaa aaaatcaaac   157080
accgcatatt ctcactcata ggtgggaatt gaacaatgag atcacatgga cacaggaagg   157140
ggaacatcac actctgggga ctgttgtggg gtgggcggg gggagggat agcattggga    157200 gatataccta atgctagatg acgagttagt gggtgcagtg caccagcgtg gcacatgtat   157260
acatatgtaa ctaacctgca caatgtgcac atgtacccta aacttaaag tataataata    157320 aaagaaaaaa aaaacaaat taacccaatc agacaaaaaa taagttttgt aaatgaacaa    157380
agtcttcaag aaatacagga ttatgtaaag ctaccaaaac tgtgacttac aggcattctt   157440
gatggagaag aggaaaaagt agaaagcttg gaaaaatatt tgagggata atttaggaaa    157500 atcacccaat cttctagaga tgtagacatc aagatacaag aaattcagag agcacctgaa   157560
aaatactgta caacattaac atgaccaagg catatagtca ttaggctatt caaagtcaat   157620
atgaaagaaa aatcttaaag gcagctagag acaagtgtca aatcacctat gaaggaagct   157680
catcaaccta atggtagaca tctcagcagc aaccttgtaa aacataagag attagaggcc   157740
```

```
tattttttaac caccttgaaa aaatgtcaga catgaatttt atatcctgcc aaactaagct    157800
tcataattga aggagaaata gtctttccca gataagcaca catagagaga attcatcacc    157860
actacaccat cttacaagaa atgctcaaag gagttctgaa catggcaatg aaaggataat    157920
actcaccatc atataaagca caggtaagta gaaacctcaa agatccaata aagcagttac    157980
acaactgaga ctccaaggca cctagctaac aaaactatga tgggaaaaaa acacacatat    158040
taatattaac cttgaacata aaaggcctaa atattccatt taaaaaataa acactagcaa    158100
attggataaa agaagcagga cttaaccatc tgctgcctac cagagaccca cctaatggca    158160
aaagacaact acagactcaa agtaaaggga ctagcagaag aagagaaata acaaagagca    158220
gaaccaaatg agattgagac caaaaaaaaa tgatgaaaag gatcaacata atgaagagtt    158280
tgttctttga atggataaac aaaattggta gaccactaac tagtttaatg aagaaaaaag    158340
agagaaaatt caagtaagca caatcagaaa tgataaaggt gacagtattg ctgatacaac    158400
agaaatacaa aagctcatca gggggttacta tgagcatctc tatgtgcaca aactagataa    158460
cctagaagaa atatgtgaat tcctggaaca cacaacttcc tgagattgaa tcaggaagaa    158520
atagaaatcc tgaacagaca aattatgagt aaggaaattg aatcaatagt aaaaaaaaac    158580
cttccaacaa caaaaaagcc caggaccaga gagatttaca ggacagtttt gccttatcta    158640
caaaggagag caggtaccag tcttacagaa actattccaa ataccaagg caggaaggat    158700 acctccctaa ctctttctgt gatacttgtt atctccctga tgaatataaa tgtaacaatc    158760
ctcaacaaaa ttctagcaaa ccagatttat cgcacatcaa aaacaaaatg tatcacaatc    158820
aagtgtgttt tatttcaggg atgcaaagat ggttcaacat ttgcaagtca gtaaatgtga    158880
ttcaccatat atgcagaatt aaaaagaaaa acgatatgat catgtcaatc aatagatgca    158940
gaagaggctg ttggtaaaat tcaatgtcac ttcatgttaa aaaccctcaa aaactaggca    159000
ttgaaggaac gtacctaaaa atagtaagaa tcatatatga caaagtcaca gccaacatca    159060
tattgaatgg ggaaacgttg aaagcattca ccctaagaac tggaacaaga caaggatgcc    159120
tactcacacc acttctattc aacatagtac tggaagtcct agacagaaca gttgggcaag    159180
agaaagaaac aaaaggcatc cagattggaa aagaggaaat caaattatct ctggtcactg    159240
atgacatgcc cccatacctc gaaaatccta aagactccta gacttgataa acaacttcag    159300 taaagttttta ggatatagaa tgaatgtaca taaaccagta gcatttctgt atactgttac    159360
tgaatctgag aaccaaatca cgaactctat cccatttaca gtagtcacac acaaaaataa    159420
aataactagg aatacattga accaaagagg tgaaagttct ctacaggaag attacacaaa    159480 tggaaaata tctcgtgctc atggattgga agactcaata ttgttaaaaa tgaccacaat    159540
gcccaaagga atctgcagat tcaaagcaat ccctaattac caatgtcatt cttcacgaaa    159600
ttagaaaaaa caatcctgaa gttcatatgg accaaaaaaa gagcctgaat agccaaagca    159660
atcttaagca aaaagaacaa agccagagac atcagattac ctaacttcag attatactac    159720
aaggctgaac agcatgttac tgatatcgtg ataccatgat aaagatggac acatagatca    159780
gaggaataga acaaagaact cataaataaa gtgacatacc tacaaccaac tgactttcag    159840
cagattcaac aaaaataaac aatggggaaa ggacatccta ttcagtaagt ggtgctggga    159900
aattggccaa ccacatgcag aaaaatgaaa ctggacctct gtgtctcatc atattaaaaa    159960
attaactcaa gatggattaa agacccataa atgtaagatg tgaaacttaa aatcctgaaa    160020
gaaaacctag gaaaaactat tctggacatt ggcttaggca aagaatttat gactaagacc    160080
```

```
ccaaaagaaa ataaaacaag aacaaaagta cacaggtggg acttaattaa accaaaaagc   160140
ctgttcacag caaagaaat aacagagtaa gcagacaacc tacagaatga gagaaaacat    160200
ttgcaagtca tacctccgac aaagaactaa tatccagaat ctacaatgaa cccaaataac   160260
tcagcaagag aaaacaacc ccattaaata ttggtcaaag gacatggaca gacatttctt    160320
aaagaagac ataaagttgc caacaaacat tttaaaaatg cttaatatca ctaatcatca    160380
gagaagtgca aattgaagcc acaatgagat attatcttat accagtcaga atggctatga   160440
ttaaaagtca gaaaacaaca gatgttggca tggatgcaga gagaagggta ttcttataca   160500
ctgttggtgg gaatgcaaat tagtacaacc gctatggaaa acagtttgga gattcctgaa   160560
aaaactaaaa atggaattac cattcaattc agcaatgcca ctactgggct tctacccaaa   160620
ggaaaagaaa tcattatata agaaagacac ctttatgtat gtttatcgca gaactactca   160680
caatagcaga gtcatggaat caacctaagt gtatatcagt ggataattgg ataaagaaaa   160740
tgtggtccat ataccatg aaatactatg cagtcataaa aacaaatgaa attatgtcct     160800
ttttagaagt ttctacatgg atggagctgg aggccattat actaagtgaa ataactcagt   160860
aacagaaaag cgaatactgc acattctcac ttgtaagtgg gagctaaaca gtggttacat   160920
atagatgcaa agatgtaaat atcagacgtt ggagactcca aaaaggggga aggtaaaagg   160980
ggaattcgga ttttttataat tcgaatttac aatttttacaa ttgggtacag cttgttcact  161040
gtttggatta tgggtacatt agaagcccaa acctcactat tatgtaatat atctatgtga   161100
taaacctgca catgtgcccc ccaaatctaa atcttaaaa aagaaatttt ataaggaaaa    161160
gggtacacta caactgatac taaacaaaga cagaggatga taggagactg ttatgaacag   161220
ttatacacta acagattgga taatcctgaa gaaatggata aatgaataga aacgtacaac   161280
ctaccaagat ataccatgaa gaaacagaag atataacaga ccaaggaagg agattgaagc   161340
tgtaatcaaa aatctcccaa caaagacaag tcaagatgag atggcttcat tggttaattg   161400
tactaatcat ttaaggaaga attaatgaca agtggtcaac ttgtagaatc agttcttctc   161460
aaattcttct agaaatttga agataaagga atactgccaa agtcattctg taagaccagc   161520
attgttatga tatcaaattc aaataagaac acaagaaaat tataggccag catctctggt   161580
gaaggtaaat gcaaaaatcc tcaacaagat aatagcaaat tgaattcagt aggaaattta   161640
aaatatcata caccatgatc aactgggact tactcctggg atgcaagaat ggtttaacct   161700
atgcagataa aaaatgtgac ataagacatt aatattctga tattcacaga tctgtaacat   161760
aatgtcaaag atctaaatta tattgggaaa tataatatgc tattgaaatt gttaagtatg   161820
tagtaagtac ctttaaaaag ctattatctg tgaatgaaac tccaaattag gattaagttc   161880
ttaaaagaat catatggaaa aaggagtatt ttattgtaaa tattaaacta ggacatgttt   161940
gttattaaaa ataaaattta tacagtaagt gctattgact taaaatacta tcaactttat   162000
tctctgtaga gaagaaagta taagttggca atgttccaac atgtctgtat taatcttaca   162060
agatcttgtg gttcagccaa aaactctcat gcttgtgtca gttaaacttt ttaagtataa   162120
cttttgaaac acctgtctta aaggcatcct tatgctttca gttttttaaaa catatataaa  162180
actgatctga taatgtgaaa tattgttcaa catgttagct atttcttaat gttttgcaat   162240
tggtgagttt taaaactgtc ccaagttaac agcgatttaa aaacattttt ctcacatgta   162300
gttttttaaag ctctctagaa attgacatgt ttaaaaactg ccaagacaat taaacttttt   162360
atgttaaaaa tgtttaaaac tctgatcata tagcacatag taataacgct ttcttgggca   162420
taaattataa taaaatacta taagtaatac atgtaaagaa tgtatcagtc actatctaag   162480
```

```
ccttgaagca aattgtattc atccttcaag attcagttga acctactctt tggaatcatt   162540
ttcaaccaga ggtggtgtat gatttagaaa agattgagca catggcttct agtcttcgct   162600
gtaccatctc ttgagttcca cttgtacata tgtaaaatga aagcaatggg ccagatgacc   162660
cctgagtgtt gttttatttt ttagctctac ttataaggga acacttccat ttgcactaaa   162720
tatactgtat gaatgtttaa gtatttctgg gtatcttgag tattcagagg tggcactaat   162780
gaaggagtgt aggctttccc tgcaatgttg aaccttggtg tacattttgt cctctttaaa   162840
aaaccaatca aacaaatttg ctacctagaa tacagtgtgt ataggtcttt tggtcattag   162900
ccttataata ggtagtcatt taaaatattt tccaaagtta cttaggtaat ttcttgtttt   162960
ccatacctca ttcataatag ttttattact gttggtattg tatttttcat tctccctatc   163020
tgctggatga tttaaattat ttatttttg agggaatagg aaacattgcc atagttatat   163080
aaataagctc tacaaaaggg tgtactcagg gaagtatcaa tcctccccct atgcctacta   163140
ccctgtttcc attctccttc cagttattaa atttgtcata gagatttggg ttgttctgaa   163200
actacttaag tgtatactgg gatataacaa gtaagtaaat atgtttcaga taataagacc   163260
cagatttctc accgtaagat aaaaggctag tgtgttcagg gctatggtgt tcagttggaa   163320
ttggaagtat cagtatgaac ttatggttct gaatatatat aaaaacagat aaatatgaaa   163380
atatagatgg ggtatgttag tgtacataca tatatttcca agccctgcct actaacaaga   163440
catgaaagca gtgacaccca gtagtagtga acatagaata tacccagatc taggatttaa   163500
ataccattct ccagtagaag gtactatgcc gccttggaga aatggctgat tctatatcta   163560
gggcagggaa aatggaagat gagcctagaa tagtaagtac acataaataa gtaaaaataa   163620
atttcaggtg cagcggcatg cacctgcaat ccctgctact caggaggctt tgtaatccca   163680
actactcggg aggctgaggc aggaggatcg cttgagacca agagtttgag accaacctgg   163740
gcaacttagc aagactccat ctcaaaaaat gaatgactaa atgaatgaat gatgagagca   163800
tgtcaaaaaa acacaggagc caacttgaag gagttcccaa tagccaattc tggagcaatt   163860
ttagcagcaa ataaataat gatagcatta ttataatcca gaaaataaaa gaaatatcca   163920
tccatctgta ttgatataaa tacttaaaca cctgggaggg aaaggacagg tcttccttac   163980
agtagaaatc caattataaa ttaataagta aatatggaaa tggagactca ccattaggca   164040
aatatcatgg taataattgt ttaaaagaac tatcaatgga tattaaaata agtgggtgaa   164100
agtgtcatga gaaaaagat ttttgcata attttgaagt attttcccag aagataatta   164160
ataattgcta agagaaacat cacaactggt gtggaaaaat aaacctggca ggcaccacct   164220
taaccagatg atcaattaca gatgataata tcaccagtaa taagacatag tgacatacca   164280
tgtgccacta gtgtggtata ttgacaaggg caccttattgc tttagttctg tttttgctca   164340
aaatacatca cctcaatcta ataattagaa aacatcagag aaatccaagt tgagggcat   164400 atgacaaaat cagtgcccag tacgcttcaa aagtgtcaat gtcaaggtca taaaatacaa   164460
ataaagacag aagcaacttg tcaaagacaa acagattgga ttatcaaatt ttggtagagg   164520
ttacaggagg ttatggacac atgatacagt gtagcatact aaattggctc ctgggccaga   164580
aaaaaaaaaa aaggattatt agtggggaaa ctggaaaagg gcaaataagg tccctagata   164640
agttaatagc attgtataat gttaatttta tatctttcat aacactgctg tgattatgtc   164700
atgttctctt taggggatac tggttaaagg gtatacaaga atgttgattt tttacagctt   164760
ttctgtaagt ctgaaatttt tcaaattgag atactttgaa aatttctgat caaaatgaag   164820
```

```
caaaatcctt tccttgggct tgttagtat gtattacctg aaaaaagttg gaattttcaa    164880
aaatatttta ataagcagta ataaaacaaa aggaaaaata ttggaatata ataataattc   164940
agtttacaaa gtgcatagta ggtcagagga tcattcctag atctctgact cttgtcccat   165000
tctgttagcc taaaagaatg tcagatatct tgccccaaag gaaagttttt tgtacttttc   165060
ctgatctgcc tccatgttgc agagtgccag cttacttccg cacatttcag acctggtcgc   165120
gataccttga acttcagggg caaggataaa tcaggctaat tctgctttca ttaggctttt   165180
ctgttcaggc ctggttgggg tttgagagaa tatgcctctt ctctaaaaca ctggaggact   165240
gggaaggctg gacacaataa attaacaatc agtggcaatc ccacatttca tatattgggt   165300
aagaaaaata atactgagtg tacctgtaca gacctaatgc taattgcttt cccaaatatt   165360
atttattttc atacttagaa tagctctgtg agatagatgt tggctccttt ctaaaaataa   165420
ggaaaatgag gctcagacag gttaaatatc ttgccaagat ggtacattaa gtaatggaaa   165480
gccaagattc aaacccaggt ctatttgatt ccaaagcatg ctattctttt tttcttatag   165540
gtccaacaga aaaatacata tacattaaat atgatatcca tacatataat agagcagtgc   165600
agaggtaatt ctgtcagtat caatgcccat ccatatagaa acatcttaag agaagttacc   165660
atatcatata ttcttttttaa tttcccatgg cctccaataa ggtagaatcc ggtaattact   165720
acattactgg tgattttcag attcatagta tctgatgaaa gtaaaacagc aaaaagaaaa   165780
aaatattgac ctctgcaggg caatcttatc tgtagctagc tggcagattg ctgttatctt   165840
cattcttctc tctgttctat aaatatttaa ccacctgtat tggttttctg ttgctgccat   165900
aacaaatgac aacacactta cgatttaaac aacacaaatt tactttcttt tggctctgtg   165960
ggttgtgagt ccatcccagg tctcactggg ctaaaatcta agtgttgtat tcctttctgt   166020
aagttcatgg ggaagattca tttttcttcct cagatggtgg catagtcaga tcctttttgat  166080
catacaagga ccccatttcc ttgctggctg aaggccattc ccagcttcta gagggtacct   166140
gcattccttg gcttgtgact tcttttctct aaagccagga aaacaggtca agtttgtttc   166200
atatcgtatc tccactcctg cctcactctc tttcactttt aagagctcgt gattaactgg   166260
cccacccaaa taatccagga taatctcccc accttgaggt ccataatttt aatcacatct   166320
gcaaagtcca tttcaccatt taaagtaata tagtcacagg gtcagagtac taggatgtgg   166380
acatcttcat ggatgcctta ttctgcagac cacaatgtaa aaaaaatcac acaagttcat   166440
aaaccactgg ctaatattaa taatcataac tatactgagc agtttgtgtc aagtaatgtt   166500
ctaaattgtg ttttatatat taatctaatc cttgcaatac tgtaatgaag caggttactt   166560
agccctattt tatggatgag aaaaaataag tacaaaagac attaggtaat ttaccagagt   166620
cactgatagt aattattatc tgtaatttca accaggcggt ctgagtctgt aaactatgcc   166680
attaacttcc gtactatcat aagtcactca gatgattcag gacttcggat atttttactta  166740
actgattagg gtcaaaatgt ttagcaagcc tatactgtat gtgggctggt tattcttagt   166800
ttttacggta aatgaatatt ttttcttgc tggctgacag aaaaggaatg ataatgaggg    166860
tacacagatg actgaaattg aatgttattt ccttagatta ttttactcat tatcactatt   166920
gtataagaat atgtcactgt ttgttatata agttccttca gaacaactta gagaaaaaat   166980
atggtaatta ggttatcatg taatccaatg acatacatct ctgttgcagc acttttgcaa   167040
tgatgttgta attctctgtc tctctctccc ccaacctttg ttctttgatg ttagtggtct   167100
ttccaatttt gtatttcaac atctatagag tttctggctg atggatcctc aaatagtgaa   167160
ttggatgaat ggattagtta attaattaaa tcattcctat aattgtcaat ccatttatac   167220
```

```
cctgctctta aaatttaatg aattaatttg aggtgaaaat gtttcagaca agatgatctt 167280
caaattctac atgtaataaa gataatttta agagtctcaa aacaatttgt atatttatag 167340
aatccctaat aatggccatt tgcagtgtgc taagcattgg gctaaacgag agctcagtat 167400
tcacaacaat cctgtgatgt aatgctctag tcgtatacat gtggaaacta aggactaact 167460
gagttgtatc actccccaaa gtctactcac ggacccagta gagccaatgt cttcacctag 167520
gaataattga ctctaaagcg tttgccctta tccactgcct catttctttt tattcctaaa 167580
gtaaaactac tcataagatt tctggatctg atttctgtac tacttgtgga ttgattaaat 167640
acaaaaacat tattgtgtat tattatcagt tggtctttca ataactgag accaaaacat 167700 taaaatagtt ttaaaaatct gtaaacactc ctattcttct ggatttctac ttacagaatt 167760
agcacctaga actagaaaag taagtttctt ttttttttct gagtgttaag acctcaggaa 167820 atatttttt aattaacata ctataaaatt gacttgatat tcatttattt gagctttaat 167880
acacacacac acaaacagac acacacataa gtgtattcat gtagcaacca tgacgatcag 167940
ggcacagaac agttccatca tcagagcact atcgtgctac ccgttttag tcacattttc 168000 attctaccac aaatcctggc aaccgtgatc ttttgctatc attttctctt cttgagaatg 168060
ttataaaaat gaaatcatac aacatgaaac ataatctgtg tcactcagca tacaatatga 168120
aacatttcta tttcactcag atgtattcaa gttgttgcgt gtatcaatag tttgatcctt 168180
tttattaatg agtagtattt cattgtatgg gtgtgccaca gtttatccat tcattagtgg 168240
aaggacattt gggttgtttc caatttacgg agattatgag taaagttgct gtaaacatta 168300
gtatacaggt tttgggggt gaagttaagt tttcatttct ctagggtaaa tatttagaag 168360
tgtgattgct gcataaatatg ttgtatatat ttaatgtttc aagaaactgc caaacttttc 168420
cagagtggtt gtaccatccc accagtaata aataagagat gatccacttt ctctacatgg 168480
ccacaggcat tttgttttat cagatatttt ttactttaac cattctaata ggtgtgtttt 168540
cataacaggt ttggtttttca tttgcattcc cctaatggct aatgaagtta aacatttat 168600 catgtgttta ttatgtcctc ttcagtgaag tgtctgctta acaccttttg tgtattttct 168660 tttcttttt ttctgtagtg tttttttttt cttttttaa ttatacttta agttctaggg 168720
tacatgttca caatgtgcag gttttgttaca tatgtataca tgtattttct agttgagtta 168780
cttattttat taaattttga gagttcttta gagttgtagt aaagactact gtagcttgtc 168840
ttttcattct cttatcctag tcttcacag aacaaaagtt ttaattgaga tttagtttat 168900 cacttttct ttttatggat catgattttc atcatgcttg gtgtcatgtg caggaactct 168960
gcttaactcc agatcatcag gttttctct ttgttttctt cacctttta ttagggcttg 169020 ttgtatttg acctaattt tttataagat gttagattga ggtgaagttt catttcttca 169080
atatggatgt ccaattgtgc caatactgct tgttgaaaag actattcttt tctctattgaa 169140 tatatttgca ttttttgtcag aaattaattg tctatattta tgtgggtcag tttctggact 169200
ttgttccatt ctgttgatct gtacatccat cctttttgcca ataccacgta atcctgatta 169260
ctgtagcttg atagtaagtc ttaaaattgg aggatgttat ttctctaatt ttatttttca 169320
aaatcatttt ggctattata gttccctttgc cttttcatat aaattttaga taatctcttt 169380 atattaaaa taatcatgct gaaatttga tttgatttgt gttaaatatg cagatcaatt 169440
tggagagaac tgacttcttc cttaaagtgt tgaggagtct tccaattaat gaacatggtg 169500
tgtgtttaca tttatttagg ttttcttttt cttacatcag tgtttcataa tttcagaata 169560
```

```
cagatcatgt acatagtttg ttaaatttac acctatatat ttcttctttg gagataagaa   169620
ctgtgaatgg cttgaagttt ttttcttttta atttggtttc cagttcattg cctatgtaga   169680
cagtcttgtt ttctgcaaat agggacattt ttatttcttc ctttctaatg tgtatgcctg   169740
taattctttt attgacttat tgcaagacat caagagaggt gataacggac attcttggct   169800
ttttcttaat cttgagaaga aagcatagtc tttctccttt aagtgtaatg ttaactgtag   169860
gtttcttgta gatacgcttt atcaaattga gtaacttccc ttctattcct ggttcgctgc   169920
aagttttcat catgaataaa tgttgctttt tttcaaatgc ttttttctgca tcaattgaaa   169980 tgatcatatg gttttacttt aatctgtgaa tatggaggaa tgcactaatc aatttcaaat   170040
attgaatcag gctttattct ctgaaaagcc tcactttatc attttctttt tgtatattgc   170100
taatattttg ttgaagattt ttgtgtcgat gttcataagg tatgttagtc tataatttt    170160 tttcttttttc tttttctttt atttcttcg tactattgtc ctatggtttt ggtattagaa   170220
taatcctggc cttaaaaaaa atatttaaat tggtgttatt tcttctttaa atatctgata   170280
aaatttgcaa gtgaaagttg gtcctggagt tttgttttgc ttaggaggaa gattttctaa   170340
ttcaatttaa aaatatttac aggaatattc aggttttgta ttcatcttgg atgtgtttag   170400
tgtctgattt tcaaggaatt tacttatttc acttctttag gttatgtttt acacaattgt   170460
tcagagcatt cctttatatc cttctaatat ctgctggttc tacagtggta ttctctttc    170520 attcctgata gtagcaattt gtggcttctt ttttgctta ccgatcctac tacagttttg    170580
tccattgcat tgatctttac aaagaaccag ctttttgtct cactgttttt ttttttaatt   170640
ttattgcttt ttgattttta ttacttcttt ctgcttgctt tgggtttatt ttgctccttg   170700
tttactgttg ttttaataca caattcagaa ttttgatctg agaccttctt ttctagcaca   170760
agcatttaat gctataaatt ccctctata cagtgtttta gggacactcc acagattttg    170820 atgttttta tttccctttt tgatccatag attctctcta aatcagttta ttaatttcca   170880
gtgttttgga gattttctta tcttttcct attgacatct ggtcattatg atcatagaac    170940
atactttata gaatttaaat cctttaaaat ttgttttgtt ttatgatctt ggaagtggtg   171000
tgtctacatg aatattttgt gtacatttga aaagaatgtg aatttcgtca ttggggtgtg   171060
ttctataaat ctataaatgt tatttggatc tagttgttaa tgttgcctgg ttcttctata   171120
tccttgctaa ttttttgtct acttgttctg tcagttaatg caagaggagt attagaagcc   171180
tgcaagaata ttgtagattt gtctctactt tttgttctgt tcattttgc tttgcttatt    171240 ttaaagctct gttgttaaag gcatacacat ttaagatctc tctgttttct tggcaaattg   171300
accctcttat cattatgcaa tgttttctt gatctctgat aattttctta tcactgaagt    171360
ctactttgtc tgatattact ataatcacgc tagcttctt ctggttaatg atataatttt    171420
tcatgataga attttttatc cttttacttt taaactatgt aattataatt gaagaaattt   171480
ttgtagatag gatattaatg gggattttt ttattatttt tggtctattc tgatcatctc    171540
tgcccttaat tggtttgttt aggccatta tatttcataa aatgttttat gtttggattt    171600
gggtttatca ttttattatt tgttttttgt ttttctctct gtattttcac tcttctggtc   171660
ctctttttct gccttgtttt ggatcatttg aatattttt agtattccat ttaatttag    171720 ttttgactat gtatctttgt atagatttct tttagtggtt gctctatgga ttagaatgta   171780
catcctaact tttcacagtc tatttagaat caatcttta ccctgccaag tggattgtat    171840
aaatctttca tgtaagtctt gttattctcc ctcctttatt ttatagtttt tatatgtact   171900
acatcatttc tcttcttctt ttattcccga cattccaagt gtccctcatt tcaccttctt   171960
```

```
tatgacagtc ttcctttagt aattcttta gaacagatct gccagcaatg aactatactt 172020
tttatctgag aatgtcttta ttttaccttc gttttttaaa ggatattctt attgaattta 172080
gaattttgag ctgacagata ttttttgttt taaacatgtt ccactttctt atggaatcta 172140
tgatttctga ttataactct gtagtccatt gatcccctat aattatatat tatttcctct 172200
ggctcttttt agtattttt taaactagtt tgattgatgg atttgagcct agtgtttgat 172260
tgatgggttc gagcctagat ttgggggtt aggaggttac tatttgaggt tcagttctta 172320
aatctgttgg tttatgtctt tcactaaatt tgggaaattt ttaaacatta ttcagttttt 172380
tttctgcact acagctcttt tccttctggg actccagtga catgaaagtt agatatttta 172440
ttattgtcct gcattatcct gagactcttt attttttaat aaatatttt actctgtctt 172500 attcaaagtg gatagtttcc attgatgtac tgtcaagttc accagtcttt gctctcttat 172560
ctccatttta ctattaagcc catccagtga tttttaaact ttggttactg tatgtttagt 172620
tctaaaattt tcttttagtt tttatttaaa tatcttccat ttgctgagac attctatctt 172680
tccattcttt tcaacagtgt ttacccttac ttcttggagc attttataa tagttgtctt 172740 aatgtcttag tttaataatt ctaacatctt ttttcccaa tgttgccatt ttttgatcat 172800
cttttcctat gtgacttgag acttttctg attcttcaca tgccaagtaa tttgagatta 172860
tattctggat atttcaagta ttatgttgtg agattaataa gttaaataag actaatactt 172920
cgtcttattt aaatcctatc gagaattttg atatttttg cttaacaggc aatttatcca 172980
gttgtattcg ggatgcagtc tccagccagt atataggttt tgattccaca actggttcac 173040
ttttcaaagc ctttgaaatg ctgttcagat ctgtccttca tgtaccaccc agggtccaat 173100
ctagaacatg ggtaattgtc tgtctatact tagtttctca cagtctgtga tcagattcac 173160
acatgagaag tttgagcata aacccaagag ttcataaaca gccttatgag gtcactttcc 173220
tgagcctctc tcttcatga tctcagtact ttgagttcct ggagactctg cttttcagtc 173280
ctctagccaa aactctggga ctttatttac cctactttgc cacatgcttc ctgcatctat 173340
gcctgtagaa gagctgaaag aagacaggga gagaaagagc tcagtggagt ttatattgta 173400
ctcttagggc cacagctcct cctactggag aggaagtttt ccctccctca aagttttaaa 173460
ttcttgcagt tatcattatc tctgctacta ccttgaaggc taggatgcaa gagaatgaag 173520
gagaaaaggg caattttct cttctttgag acttttcctg ctccttgagc ctaaactata 173580
aggattctcc tagagccttc actgccatgc cccagggccc actttcaggt tttaagctcc 173640
cttgaatcca ggccaggggt acctttttaaa aaaagaagaa gaaagaaaaa ggtaagggga 173700
atcaccctgt gctactctga attcttgtca tgtcatcttc tccagtccac ctgctgtgac 173760 ttaccctta gagtctttaa ataaccgttt ccttcattct caagtttat tatctagatt 173820 cagtagcaga cataaacagt ttgtggattc tccatattaa ctggatctga cctcaggtat 173880
atatttttaa tcattatcta agttaatggg tgttcatgga ggttgtgagt tgcatttgtt 173940
ttaactttgc tatacagtta caccccaaat attcacatac atattataaa ttggaagata 174000
caggagcagg aaaatgaaac tatctggaaa agtatacagt gaaacatttc atctctaaag 174060
tttgaacaca ttcaggtctg aatttaggaa tctgttggca ttcgcttttt tgatagtttt 174120
cccttagcag ggaatagggt aggaatagca gaaagctggc tcagcgatga cttacagaat 174180
gagagagatg tgaattggcc ttttaaaaat ctgtggaagt tactcatttg gactgggtaa 174240
cggctttcta ggcagaggga gcaacttcag gaaaggtata gagaaggtcc ccaacttaca 174300
```

-continued

```
acattgactt aagactttc aactttacag tggtgtgaaa gaaatatgta ttcaatagaa    174360
accacactcc aaggacccat gtaatcgttt ctcattttca atatagtgtt caataaatta    174420
tatgagattt taatacttta ttataaaatg ggcttcatgt tagatgattt tgcccaattg    174480
taggatactg taattgtcct gagcattaag gtagactagg ctgaactgtg ttgttcagta    174540
ggaccggcgt attaaatgca ttttgacatg atattttcca tttataacgg ggtttatcaa    174600
tatttaacct catcataagt caaggagtat ctatacaggt ataaatgtgc atggcatgtg    174660
tgaatgtgtg tcaaagagga gtagacaaac caggaaaggg aaatatgatt cagttaggca    174720
tttactgtgc cttcttagag gttgcagtaa gatattccca tgaacatatt tgaaatggtt    174780
agaaacacat gggtgtgaat ttcaaaaaat acaagttttt gaatttaaca catatgctaa    174840
ataatcagtc cttcagctta aactatgtta tcctgcaaat gatagtaagt cttctggatt    174900
tttattagaa tgaatcacat tttccatcct tgtttttatt tactaggaat ttcatcttat    174960
gactaaaaag aacaagccat aagctctttt ggtctaaatt tgagatattt gcctttgact    175020
tattttttaaa ttaaacttttt tattttgaca taataataga ttcacaaata atacagaaa     175080
atcctgtgta ccctttaccc agtttcctcc aatggtaaca taatataatg tcacaacaag    175140
catattgaca ttgatacagt caagatacag agcagttctg tcactaacag gctctcgttt    175200
cccattacat gttcacccct gtccctctac cttgccgcat tccttacccc tggcaaccac    175260
taatctccat ctttacaatt gtgttatttg aagaaagtta cataaatgaa atcatacagt    175320
atgtaacctt ttagactgac ttttttcattc tctataaatt cttggaaatt catctgagct    175380
gttgcttgta tcaatagttt gttctttttt attgctgagt aatatttcat gacttatttt    175440
ttagcccacc tttttccatt atgtttcatt ttgaaaaaac aaagtcttac tactcaggca    175500
tttttctcac ttacatattt gctttagaat ttatactata aacaaaaacc ttaggagcat    175560
tctagtgttc tttttaaaat tgcatttagg ttaaccagtt aatctgttga cattattacg    175620
tcttacagga aaaaaatatg tacaagtaga ttttattact ttactccccct tttaattcct    175680
aaatccagaa gtaagatcag aacacatgag agatactgct gcttgaaaaa tacttagcac    175740
agcctgtttg cagacacact catgctagtc cacggctgat gcagaaagga gcctatccca    175800
aggcagcatt ttttttgcagt gctaaaggcc aacattagga tgttgtctgt tttcattagg    175860
caccatggtc ttagttgctc aaccaaaact ccagcctcaa taatgaggga aaaaatata    175920
cttctagttt ttaaattgtg ggaaataggt ctgggagtag attctgaagt atgttaaata    175980
ctcatctaaa gagcctagaa tttatcccaa ggggggatga agaaatgaag aaacaaataa    176040
attaatcaaa ttgcagttcc taaaatagtt ataagtagaa aaattagcag tgtccaaaaa    176100
tgtcattta cctttaatat caatgtcata ttccatctta cgaggtagta actctggctg    176160
ttttgatttt cattttagaa gaataaggaa cataggttta caataatcag taactatatt    176220
accatcatat aattacccag ttggcatact gtttattatt ttagtttaag gagacacatt    176280
gaagcgagaa aaagggggtg ctagaggttt gcagacactt agcaaacact agtgtttatc    176340
ctacagcttt gtaaacactt taccaagaat ttttaaactg tcattttgct gatggaaagt    176400
gtaaaatgag acttcagcag aagttaatct catcatctac ttaaaacagt gttttttaca    176460
ttgatctaaa gaggtttgtg catatttaa ctgttttttcc tatatgatca tcttcatgta     176520
ctagtatgaa agttaatgag taaagaaaat ctgctgaata aatccacgtg ataatccaag    176580
gcacttaaaa gaaatacatg ctataatggg atgcaaagat tttacttgat tagtgctcta    176640
tttctcaatt taacaatcaa acctaagaga aatctcaatc aagactttg actaacatag     176700
```

```
tgcaatttga ttagggtgca gataagtaca ctatttcggt gtgactgtat aagtattctg    176760
atcataatta tgacatatac tctgctacta gttagaaaaa gaacagtttt taacttcttc    176820
atgcctttca tttatgcaca tgttcttaat acactattat aataaataaa atgtacctga    176880
aaatataaaa catactttt  gcttgtccaa aaagtatgca tttatttata atacaaaata    176940
tttattctga acctatgctg tatgatagcc cactataaat gtagaggtag caagggaaga    177000
tgacagatat ctaaaaatat tgttagtag  cactatattg ttgattacta catatcagta    177060
attagaataa cgaataaagt gaaagaaaaa gcataatgcc ttaggtgttt actttgggca    177120
cagtaacatt tggtccagtc atctttctag ttttctggta cccaagttaa atgagcaaga    177180
gtgtgatgga aagtgggctt tggagccaat cagacctgca tttatatttc atttctacca    177240
cctaataacg gcatgtcttt gggcaagtta tttaacttct ccaagcctca agtttttaa     177300 cttataaaat atgttgttac aaagcttaaa agaagtaagt tactagcaca gtgcctggaa    177360
catagaaatt tgtgctttag agaagaaata aaaatatata attctaccgt ctataggtag    177420
agctcttttc ccaaaatagt actaaaattc cagtttgctt ataatcctaa aatatttata    177480
attccagaat atctaaatct gtactgcttt tacttctcta agatatcttc gtgagtttgg    177540
taagactgtc cacttaattt cttaaacag  ctttacttt  caaggacaca ttaccatatt    177600
cataaaagga aaaaatccaa attaaatata atctgtactg aaagtttcct tttcagattt    177660
cgggaagtta aatgtttgt  gacaactgga tttgttttt  taatcttta  ttgatatata    177720 atagctgtat atatttgggg agtacatgtg atattttgat acatgtatac aatgtgtaat    177780
gatcagatca gagtaattgg gatatccaaa actttaaaca tttgtctttc gtttgtatta    177840
ggaacactat agatctattt taatttcttc tttgatttca gcaggaaagg aagggcaaga    177900
aatcctgggg cctgaagctc aggcagatga agcaggatgt acaggtactc tgctgcgact    177960
ttctttcata ccatagcctt taaaagaagg tctttgtgtc actgatttcg catttgtgag    178020
tcctgaattt agtccgtttc cttctctttt atcttaccttcc ttaaatgt ttaagtactt    178080 aggcatatgg tgcactacat aaaaagaagt aaatattcct taaatacaga gtaacttaca    178140
gattcatatt atgtagcaga tttctccatt ctataagaat gacaagtata acctacagat    178200
aatccaaaaa ataagtgttt gaatgatgat ttgaacttct atcaagtttt tgaccaaagt    178260
tagagaaatg cagatctaac ttttgagttt cgttattagt tacctgggtc tgctttgaat    178320
tgcccacaag acaaaagca  gaagaaaata gaaaaagcat ggatttatct ataaatccga    178380
tgagaatcat gaatattaat gagttgagtg aacatgtcac agcaaacgag aatcaaaaat    178440
ttttcttaaa ttttctgtga ttgaaaaaga gtaaatgaa  gttgaattat aataaacaag    178500
gaaatttgct tttaggtgac taaaaagtac atattccctg aaacttaagg ctattcctct    178560
gtaatggatt cagatcagat ttaagaagca aaagagtagg tggaaaaatt aaatcagatc    178620
ttatgtatag taataccagt cacttttat  tgtgttccct aagagagcca gaactgttag    178680
aatgtaaact tcaaaaatgc attccagatt tttaaaacat ttcctcaaaa tattatactt    178740
aaacgtagtg taattgtact ttgtatattc aaccataaat tagatatttc tgtcatatag    178800
ttttaattac atttttctttt tccttctctt ctatgagtta tcatttatag atttgttttt    178860
ttactttgct gtgcatttta ggaatattcc ataaaggctt acaaattatc tttcattagg    178920
taagatgagg tatggttcat ggctaataag tgtcaagatt agatttttat ctgtaatata    178980
aacaatagca ctcctatact cgtcagtcat ttctgtaaaa cagagtaaat ctttgtgctg    179040
```

```
ttattaaaag tgaattccaa aataattaaa taataatgga gtatgtgata atttgtggtg    179100
cgtatagcct gcgattttat gttttgcccc taacttcgtt ctgtgtaact tgcatgaata    179160
atgtattcag atatgcttgt tatcaaatat ttgccatgct aagctataga atatgtaaaa    179220
tatttaagct ggacatttgt tagtagtaat acagtagtgt taataaacat aagagtacac    179280
tatttacttt tacctagaat cgttaaactt tgatgactta tattaccaga attacagaag    179340
acaacttgcc cttctaggta aaatgctatc caaaaagatg ctcacaggtt tacagtatt    179400
tatctgtcat gctgttcttc actataaaaa taaatgaatt ctttcagttt gaagtactga    179460
atagtatgta aatttcctca aaaagttgc atctggaagg cagggtaacc ttctcaaatt    179520
tgtgtttaac aaaagttgct gctgaaatgt aaaatctccc ccacgtacac aatgatgatc    179580
cctgctgcat tattcgcctg gaacatgggg agttaggagt aagcaaactt ccattaaagc    179640
tccagtgagt gtagctttaa aaggaaattt agcttttgag acttttgagc agttaaactg    179700
taaaatgatg tcctgccttt gcttttgtta cttccttgac ttctagggaa taatatgctg    179760
acaaaatgag caaaagcatt gtacagcagt cgccatcatt agttcagaat gttgtcagat    179820
cttttttata gcagacttcc ttctgcagct cgtgaagtta aggaactata gtctgaactc    179880
agtaatcaga gtaaaaatt cattgaaaac atccttgtt ccttctgagc gtccctttt    179940
ttgtttatat agttgataat tttagaaagt ttcaaacatg gaggataaag ataagaggaa    180000
gcctgaggat actttattca ggatggaaaa atagatagat agatagatag atagatagat    180060
agatagatag atagatagat ttaaaaatat tcagtgttta tattaaatat ttgctctctc    180120
aaatacatgt atatagtcat ttaattctat actttgtcaa ttttgagttt tatcatattt    180180
aaagaaaacc caattacctt ttatgctgtg tatatttgct catctcccta atatttaaat    180240
atataagttt atcatctaaa gaccaggaca tttgctttat aattgacctt ttcaagatgt    180300
gcatttccca acactttaaa ttttaaaaaa ctgcagaaat tctggtctca gtttgaaatt    180360
gggcctggta aatgtgggtt catggatata gagtgtagtt taatgaaaag agctcagatt    180420
ttatacctga cacctaatac caatttgtct gctctaatag taatacattt tctctctgtg    180480
atctcagaag agcttttctg accctaattt ttctattgag gaaaattt aattgtaaaa    180540
ttatgatgtt caccttgcag gacttcttta aggtgtaaat agctaacaat tacatagtac    180600
ttactacata ccaggtaccc tactaataag tacattacta tattaattaa tctaattctt    180660
acaacaaccc taagaggtac tgttatataa attttatagg atgtaaacat tatatactgt    180720
ctcacaaatt tcttaatgga catataaaat ttttcatttt aaatgtcagt agttacaatt    180780
taatttctgg cagagtaaaa cattgacatt ttaacatcac tattacatat gaaatccata    180840
gtatattaat acctattatc ttttttaaaa atatgaaaat gctctttaag aaatgttgtg    180900
tcataatatt tacttttga gctcatattt ccattctata tgcactatag aattttatgc    180960
aaacgtatat taattacttc ataaacagta attaattgta atagcttaat attacttcta    181020
gaaggaaaag tgttcatcat tcagtttctt ttttttagca ttgaggtacc tttattctca    181080
aataaaaaga tgaaataaaa ttttatgtta taactgagtt gctcagtttt tatgcatctt    181140
cagctataat gtcaaaagtt atttgtcaat gaaaatattt taatgtcctg tcagtatttc    181200
ttcaattttg ttgaaaacaa aatttaaagc catctaattt gcaaaagat tgtttccca    181260
gtcattacaa tcatctattc cctcattttc tgggacgtat accagaaaga ctttaccaat    181320
agttatttat caaaggacta atgatacctg ttttgggctt taaaatgttt tttctcacag    181380
tcactttgtt taatgtattc agaaatgatt aaggaaactg aaatatgtta atttcagtat    181440
```

```
cttttatcag tatattttc atgaaaaaca cttttattac atgaactgta ttttgagcaa   181500
taccttattg gttcacccaa tttctggaaa atttccaata acctacccag caaagccagt   181560
tatcaacatc acaccagcca gccaagtcag acttactttc tgtcaggaaa aaaagcattt   181620
tttcgttttt tgaactcagt gtgtcaatac atattttgag gaattctata aaatctcatc   181680
aataaggaag tgtatgaagg atatatttaa aatacaaaag ttaaccaggc atggtgatgc   181740
acgcttgtaa tcccagctac tcgggaggct gaggcgggag aatcgcttgg acccaggagg   181800
tggaggttgc agtgagccaa gatcgcgcca ttgcactcca acctgggcga caagagcgaa   181860
actcattctc aaaaaaaaaa tagaaattat caataatgaa gaaaacataa agtataagta   181920
aatacatctt ataataatac taagtagtaa agtcaagatt aagattatgt agatcgaatc   181980
taatttgtat gttaaaaaaa tctttatctc taaatgtgta tatttagacc taatcaatgt   182040
ataggaaagc tagaatttat tgaagtagca aaattcatat ataaaataca gatcatgcag   182100
ttctgaaaag tgtatactat ttaaaaactc attattccaa cagctagcac acttataatt   182160
tttattagga tgtagaaaat ataagatgga gattgcttaa ttgaaataaa tattttataa   182220
tataatttga taaaaataat tttaactatc ttagcaactc tacatggaat ctgtaagaaa   182280
tcacataaaa tattaatttc atttttttact tttatctagt ttaaattgaa aaattgaagt   182340
tgctttgaaa agaatgccac tgatttgttc tgctttagct cttcagaaat gcttttttgtt   182400
ctacctaatg acaaatccta ggaatgatgt ttgagaatgt tatttgcttt gctcttatca   182460
gtctcctgaa aagcaatgaa ttttaaata taggggaggt cattaaggga aaattaccct   182520
cacttcctct ggccatatta tatagttaat tgcagcttcc caaccaggac cagcataccc   182580
ccatttcagt tgtgctttat gcctaataga aattcatgta aacaggaaag accagaaaac   182640
ctatagtgat tctctgttgc cttgatttgt cagtaaagaa ggctttccct aatcggtatt   182700
ttgaacttta ctccttttggc accctggagg actttacact ccaagcagtg taccataatc   182760
atgtcatgga tggatagagg aatacgcctt ttctctttt ttcttttaag aaagtgagaa   182820
caaggtatac tgtataaagg agagcaggga gaagaattt caaggatgct aggaaagagt   182880
ttacatggaa gctgaggatc cgggagttga ttcctttaaa cccaacagtc cagcttacat   182940
tttaaaagtc ttcgcttacc tctggatcca ataatcccaa tttggtaact actgacatga   183000
actaaataat gcagttcttg gtatatagca aatgctaaat aattgatagc tattgaaaag   183060
tggggaaaaa aattaggatc accatttgtt actgtcattg gttctcaggt tttaaacagc   183120
agtcaccctg atgagtttgg ttaccgctac agtgcaggag atgtagcaag attgttttaa   183180
taaccatcga acaaacagat gcccatacat ccccatttta atttggccaa acttcagcct   183240
gctggggagt gctgttttac aaatttagac ctgacagttc agtcagagtc tataaagaag   183300
tcatccctga ggcatttggg agccatacta aggcattgca gttgccagca tggagtagag   183360
accctcttct ggagccagtg gaggaaatgg aggaaaacca tagtgcagca ataatgcttt   183420
agaaacttgg cagcacgctg ggctaccttc tcaaagcata agcctttcta attcaagaaa   183480
agttgccact gccttaatcc cacagttaaa catttactga ggcagaaata gagaaagaat   183540
aggcttgttt tatatgaata ctagcgtagc taagaaagag ttttcataga tttgatccc    183600
tttgatgctt attagaaatc cttcttacta tagataatta ttaaaaacta ttttctaaga   183660
aatcatataa ctgaactgaa cgtcagagtg gttatatga gaattattca gatttaaagt    183720
agagctcccc cccccattat ctgtgggaga taaattccaa gagtccccca ttgagtgtct   183780
```

```
taaataaata cttatatata ctatactgtt tcctatacat acatacatat gataaagttt 183840
aatttataaa ttttatacag agttgcaaca agaactataa taaaatacgg ttataacaat 183900
atgctttaat aaatttatgt gaatgtggtc tccctcgctc gctctcaaat tattcttctt 183960
gtactgtatt cacctgattt catattgcag ttgaccacag gtaactgaaa ccatggaaaa 184020
tgaagccaca gataaggggc tgtctattgt ccaactttaa ataagtatta tgatatgata 184080
ggttgctaag aaggtgacct ttgagaacta aagttttttt cttgctttat cattaattga 184140
gaaagaattc agtcaactat attgccttct ctgtgtttta ttagtaaaat gcaatagaag 184200
tatgactttta acatttgaaa gggatactgt gagaatttca cacattcata gcattttaaa 184260
cttataaagc aaagatatat cttaatacat tacaacaaaa tgagtggaat tcatttttaa 184320
ttttcaagaa atattttctg cagattcaag aacaatcata tgttctctca agataaaataa 184380
tttcttattt agaaaacctt tgtaataact tagtggtgag attgctgtct taaaagtatg 184440
cattttttt agtaaaagat gatgaatgcg agtcagatgc agaaaatgag caaaaccatg 184500
atcctaatgt tgaagagttt ctacaacaac aagacactgc tgtcattttt cctgaggcac 184560
ctgaagagga ccagaggcag ggcacaccag aagccagtgg tcatgatgaa aatggtaaat 184620
ggatcttaac agttgtgttt cttccctct ttaaaggatt cttgtttcta ccattctact 184680
atgggaacct gctctactat agggaacatt cttgaagacc aaactttatt acaggtgcct 184740
atagagagta atctgtttta ttaatggaac actatgatga ccatgcagta ataaattatt 184800
agctgctcat gtattgtggt agtaatgcca ctgcacgtga aatgcttaga acagtgtctg 184860
gacatcaaat tccatttact tacatggtag caggcagtag aagtgagaac tatacccttta 184920
ctgcccttttg gattctttcc caccattctt ttaacaaata aaaatatggt tgtctgctttt 184980
ataccagaac atactaattt ggaaacagtg gttttcctga atctgcctta gtccactctg 185040
atatgaatag tcagcgtaca gagtgtggaa aatgcaataa aaatgtgttc agactctcct 185100
gagaagaaat aggctgtgat acagtttggg aggaaaagac tatgttattg tttcaccaga 185160
agaaactagg ttatcaaaga aatgaaaggg aaatacaaaa tttaaaaata tatgtatatt 185220
tacgtaaaat ttttatgtga caaaaggctt tcaaaaagcc tcactgaaag gaaacaatga 185280
aacctaaaga aatgatccat tatgtagttc taataaaggt taaaccttttt aaagtttgtc 185340
aggtccatac agtacgatct aaaaattgag gaactaccat tctgaattag tttgaattat 185400
agaataagtt gttgattttg ttattcatta cttttcagata tttaatgtaa tttaattaaa 185460
tgctaataaa gcattttgaa gtattctgtc atatcagcga catttgttta catatttatc 185520
cctttttata accaaatagt attcattcgt gtgtatatgc cacatttgct tcatccattg 185580
atgtacactg aggttgattc catatctttg ctattgtgaa tagtactgta ataagcatga 185640
agatccaggc atctctttga tataccaact tcctttggat aaatacccag tagtggaatt 185700
gctggatcat ataatagttc tatttttagt ttttttttgag aaatctccgt agtattttca 185760
cagtggctgt cctaattttc attcccacca agaatgtatg agagttccct tttctccaca 185820
tcttcaccag cattcattag ttttttgtctt taatagcaat actaactggg atgaaatgat 185880
atattattgt ggttttgatt tgcatttctc taatgattag tgatggtgag cattttttg 185940
tatatctgtg gctatttgta tgtcttcttt taagaaatgt ttattcatat cctttgccca 186000
cttttcaata ggattatttg ggttttttaa atctgttgaa tagttgtgt attcttcata 186060
ttagtcccctt gtcagatgag taatttgcag atattcactc tgttgtttcc tttgctgagt 186120
cttagcaata aagtctttgc ctacccaaat gtcctgagtg ttttctgtat gttttcttct 186180
```

```
agtttatgg tgttgtgtct tatgtttaag tctttcattg atcttgagtt gatttttgta 186240
tgtggtgaga aataggagtc cagtttcatt cttcacatgt taatattcag ttttcccagc 186300
accatttatt ggagagtgtg tccttttcct ggtgtatgtt tttggtgcct tgtcgaaatc 186360
aaatggctgt taataatgtg gatttttattc tgggttctct gttctcttcc actggtctgt 186420
gtgtctgttt tttactaatg ccatgctgtt ttccttactg taccttgtat tatattttga 186480
agtcaggtag tgcgatgtct ccagctttgt tcttttttgct caggattgct ttggctatat 186540
tggtcttttg tggttccgta aaagttttag gattgttttt tctgcttctg tgaaaaatga 186600
catagatatt ttgataggga ttggattgaa tctgtagatc gctctgggca atatgatcat 186660
tttaatgatg ttaattcttc tgatccatga gcatgggatg tctttccatt tacttgtgtc 186720
ttcttcaatt tctttcatca atattttgta gttttccttg gagaggtctt tcaccttctt 186780
gggtaaattt atccctaggt attttacttt tttgtagcta ctataaatga gatggtcttc 186840
ttgatttatt tctcgtctag ttcattattg gtgtacagaa acactgctga tttttatgtt 186900
gagttttgta tcctgcaact ttcagtttat ttagcagatt gcagtttttt ggttgtgtct 186960
ttaggttttt ctagatatta gatcatatag tctgcaaaga gagactattt gacttctttt 187020
ccaaattgga tggcttttat ttctttctct tgcccaattg ctctggctag gactttccaa 187080
tactgtgttg aataggagtg gtgaaggagt ggaaatcctt ttctgattac acttcttaga 187140
gggacgtctg tcagcttgtt ccatgcagta tgctgtggtt ctgtcatata tgtcctttat 187200
tatatggagg tgaaccatct ttgcatccct gggataaatc ccacttgatc atattgcatt 187260 atcttttga cgtgctgtta gatttagttt gtgaatattt ttttgaggat tttgtatctg 187320
ttgtcatcag ggatattgac ctggatagtt ttccttttttt tgtttcatct ttctctggtt 187380
ttggtatcaa gatagtgatg gacttataga atgaagtagg gagaattccc tcctcttcag 187440
ttttttggaa tagtttgagg agaactagtg ttagctcttc tttgacagtt tggtagaatt 187500
cagcagtgaa cccctttcagt cccggacttg aaatattcat tatggattca atctcattac 187560
tcattattgg tctgttcagg ttttctattt cttttctaatt taatcttggt aggctgtgtc 187620
caggaattta tccatatcct ctaggttttt cagttttttc atgtatagtt gttcataatt 187680
gtctcttttg tatttctgtg gtatcatttg ttagtcttct ttttcatttt ttatttgcat 187740
cttctctgtt cttttcttag tctagctagt ggttatcag ttttgttacc ttttcaaaaa 187800
aaccaacttt ttgttttgtt atttgtgttg ttttttagtc ttcatttcat tgattttgtt 187860
ctgattgtta ttatttcttt ccttcttaaa tcctaattta gggtttgctt tgttcttgct 187920
tttctaagtt cttgaggcac attgttagat tatttgaaat gttctattt tttgttttag 187980 gtatttattg ctatatactt cctcttagtg cttttgctat atttcatagg ttttgatatg 188040
ttctgttttg attttcattt aaagaaattt taattttaat ttcatttaaa gaaattttaa 188100
attttcctcc ttatttcttc cttgaccccg tggttattca aaagcatgtt gtttaatttt 188160
catgtgtgtg tagagtttcc aaagttcctc ttattattaa aatctatagt tgtattactt 188220
tgtggtctaa aagctacttg atatgatttt gattttttaaa aatttgtttg agacttgtca 188280
tgggtcccaa catacagtct atcctagagt atgttctgtg tgttgatgac aagaatatgt 188340
atcctttagt agttggttaa aatgttctgt aagtgtctca catccattcg gtataaaatg 188400
cagtttaaat tcagtgtttc tttgttaagt gtctttctac atgatctgtc taatgctgat 188460
aggggtgttg aagtccctaa ctattattgt attagaatct gtctctccct ttagatctaa 188520
```

```
taatatttcc tttatatagc caggtactcc agtcttgggt acatatatgt taagaattgt  188580
tatatcctct tactgaattg attcctttgt cattctttaa tgaccttctt tgtccccttta 188640
tactgttttg tttactggat ttaagagttt atctcattat agctactcct gctcactatg  188700
gtttccattt gcatggacat cttttctgt ccctttactt tcagtctata tggatctttta  188760
caggtgagat gaatttcttc taggcagcac atagctgggt cacagttttt atccattcag  188820
ccaatctgta cctttaagt ggaaagttta atccgtttat gttattatta ttgatatgtt   188880
agagcctatt tctgtcattt tgatttctgg ttgttttgtg tatcatttgt tcctttcttt  188940
cttactgatt attattgtgg tttgatagtt ttctatagtg gtaacatttg agttctttct  189000
cttttcttatt tgtacttgtt ctaccagtgg attttatatt ttcatgtgtt ttcattatgg  189060
tagatatctt cctgtcactt ccatggataa gactcccctta acatttctt gtagggccag   189120
tctagtggtc atgaattctc tcagctttta cttgtttagg aaagactta ttttctcttttc  189180
atttatgaag gataattttg ctgggtatga tattcttggc tggcagggtt ttttctttc   189240
aatactttga ataaatatat catttctttc tctccttgcc tataaagttt ctgctgataa  189300
actgctatta gtcgtatgga ggttccctta caagtgattg gacactttc tcgtgttgtt   189360
tttagaatat ctctttgtct tttacttttg acagtgaata taatgtgcca tggagaagat  189420
cttttttgaat tgtatctatt tgggggtgcg ctgagctttc tgtatctgga tgtctaaatc  189480
ctttgctaga cttgggaaat ttttggatat tatttcatta aataggtttt ctatcccttt  189540
tgtttcctct ttgccttata acacatcaaa aattcgaata tttggttact ttatagtttc   189600
ttatatgtca cacaggctt gttcattgtt cttttattct tttttctctt actaggttat     189660
tttaaaagac ctgtcttcaa gttctaaaat tcttcttctg cttgacctaa tctattgctg  189720
aagctttcag ttgtcttttg tctttcattc ggtgaattct tcaattccag aatttgttta   189780
gttctttttt atgatactta cctctttggt aaatttctca ttcatatcct gatttgtttt   189840
tctggttcct ttgtgttgct tttctgtttt cttctatctc acttagcttt tataagatca  189900
ttatttttaa tcattttcca ggatttcata aatttatttt gattggaatc tgttgctgga  189960
taattattgt atttttttgga ggtgtcatat ttccttcctt tttcatgttt cttgtattct  190020
taccttgata ccacacatct ggtataatag tcaattattc tggttttttg gatttgcttt  190080
cattggttga gtagggcact ttggctttga ttctgggtac atgtggtagt gtaatttctg  190140
tatgatatct ttcgttataa atagtgtgag tagggtccgt gatttcctcg ttggcttagg  190200
tgcaattgtt agtggaggct gaggtgaagt ttggctggga cagggatgcc aggtggacca  190260
ttccttgggc cctagcagtg gtagtaacgg gcttacagta cctgtcctta gaccacaggg  190320
tggcacattg acaccttgtg ttagcaggtc cagttgggct gatccttgga actccaggtg  190380
gcttgcttgg gtgctggtag tggcagtggt aagctgggca ggtgggcagg ttctcaggct  190440
cctgggcagt ggatgtcact tgggcaatgg cagtagcagt ggcaggacac cctctggttc  190500
cctagtgatt cacgctggtg ttggcagtga ctgcaatggg ctgggtgagt cagtccccag  190560
gcctaccggt ggtgcatgca ggagggtgcc agctgtagtg atagtagcag gttgggtgga  190620
cccaacctca ggcctccagg aggagtgttc aggtgacaac agtgttggac tgggctgggt  190680
catccccacg tccctgaata gcatgctcgg aaactgggga ggaggtaagc tgggccagat  190740
ggacctgtcc tcaggcccct tggtggtgtg tgtaggcatt ggctatcatg gcaggggcag  190800
gatgatccca ggccaccagc agagtgctca ggtaaggaca tcagtggttg cactgtggcc  190860
ttcttactgg ggagggcaag gttgctcttg gtggcagcag ccatagggag ggagctggga  190920
```

```
aatgtgcgct ttagccccag acagcggctg tggatggggt agcctgtcct caggtccctt    190980
ataaatgctt agcagctcag ctgctgagga aattagggtc gctgccagtg gctagcactt    191040
tgtccccagc ggtggaagcc cacagtggca gcagtctgtt ggggagtctg tccttggggc    191100
atgtaaaaat gtgtgcagct cctctgctgg gaggaggtat ggtcactgcc aatggcttgc    191160
acttcagcct tagcagccgc aaccagcatt agtgatgact gggaagggag gtatgtcagt    191220
ggggctcaac aggatgtagt ctgttggggg ttgggctctc aaaatagtgc tgtgctgtag    191280
ctacttagaa ctcagggggt gtacagattc agcataagct ccctctccgg agcagcattg    191340
tcatgtggtc tccacatacc tccctgtgtt agtctcagag cccacgatgg tccaggggtt    191400
ctcccatggc taggattgca ggagtccatg gtgggaatgt ggaccctggg ggtctctca    191460 cttactcttt ccctgcattg gagagccttt gcaggttgct ttacttcctt cttccttact    191520
tgaggtgttt cctgtcactt ttctgttgaa ttccagtgtt ctctcttaga tgatctatgt    191580
gaagtgtgat tattacctca ttattttggt ttttccttgt agaggaggtg agtaccagat    191640
gcctctattc agccatcttg aagcccctct ctcaacatat ttgaccaact atttaacatt    191700
caggtgctca gtctattatt tgcagtctgg tccttgagca agacatttga tttatatgga    191760
cttgaataaa ggaatatatg ttcagaaagc acttggagat tttatgaaat tatctgtggt    191820
ggtttgtttt tctatagtga attcaaaatg aaaatagaga tgatgtttac aaaaagatat    191880
cacttaattt atttcattga agaaatgtca aatatggaaa actactctta gttaaataat    191940
attaattggc aaaatattac attttaggat tgtcaggctt agacagctcc aagtgtaaaa    192000
ataaagttca ttcagtaaac taatttattc agaatgcctt tgttttctaa aagctatata    192060
tattcataca tatacagtta tatagcagat ttgccagtgt atttcaatag gggaaattac    192120
aagcagggtc atgcatggga tgtgtttatg tagcaggcct agatctggcc cccatcagtc    192180
tttccttccc caccttacac actatttttt tggtctgaac tcagtcctat ggccacacct    192240
acctgcaagg gactcttgga aacatagtgt gtgtgtactg tttactcttt gatgatgatg    192300
acttggtagt ttcattttca aaatcagagg aataaacatt aaataaataa tgatacatac    192360
cattgttacc aatagactct gttgtagagc acaaaattcc cctttaatct gtatacactt    192420
acaaagacaa cctacattct aattttactt ttgttttctt ttctagctaa tcacatgaca    192480
aaagggaaga attatggttt agggaaaaag aatgggactt gaaggtcaga cagcccgtat    192540
ttgaaccctg acttcatcat tttctggctc tgtgactttt cttttaagtt atttaacctt    192600
cctggaaacc actgttctct ctcttataaa atagagatga gtatcattgc attgttttga    192660
ggatcaaata taaagtgggt agcacaatat ctggaacata gcatagggac tcagtggaaa    192720
ctttggtaat attttctgaa tgttttaaat ttaaaatata tgatctttct tttacaggaa    192780
caccagatgc attttcacaa ttactcacct gtccatattg tgatagaggc tataaacgct    192840
ttacctctct gaaagaacac attaaatatc gtcatgaaaa gaatgaagat aactttagtt    192900
gctccctgtg cagttacacc tttgcataca gaacccaact tgaacgtcac atgacatcac    192960
ataaatcagg aagagatcaa gtaagtgcaa tgactgagag ttcactaact ttccagattt    193020
tgacaactca gccctcaatg gaaggcaagg attttaatat atttgaaagt taaagaatg    193080 tactaaacag tgctatatct gcagccttat aaaagtgaaa atgattattt atttgagtta    193140
tctggtcatt cctgagatta aaaccacat atgaacgtta ctttagaggt aactcagtat    193200
tttgttcagg taagacccctt tccatcttga cttaattatt ttgcttatgc cataacagtt    193260
```

```
aattcttcaa gtttagaaga tgttaaattg cattctatta aaatgttcag tgtaggaaaa    193320
ataagtactg actatataaa ccacattata ctaaccaaat tgacaagaaa gtcaaattaa    193380
aaagtttaag tttctttgaa ccagttacta tttattctca gtataagcta cgtggttttt    193440
ttcccccgta gtaaagggag ttgcctcctc taaaaatcta aagtttagat ttttttattc    193500
tgaagactca atttttatat ggtttattct acttctgtgt cactgtgccc cagttttcag    193560
aagtataaac caagactgtt ttgtaactat aagttacatt taaattgctg gttctatatt    193620
taggattaaa gtcaaaaaag cttttatcag ttgttcctct tttacaaggt cctcatagtt    193680
atcagccatc aacaatgaaa ttaatattgc cttaattcta actttaaaaa ttaaataaat    193740
tttcagccac acagggtttg tgagggtaca tgttggggtt aggccacatt tccagtttct    193800
tacatcaaag aatgatgtat atctacatac ctgaactctg ccctatggat gtacctaata    193860
tgtgtcacat atcccataga gaacaagtta gaccatttgc taaggtgatg gctaggccaa    193920
acaaacaaca aaaagaatt gtaacagaaa aagaatgact gagcagagtc aacctatttc     193980
cttagtactt tggcaacagt actcatgaaa taacaagata ataagaagag ggtggcaatc    194040
agggagaata gaaccaagat tttataggtt tatggtccat aagcccatga aggagcactt    194100
gaaacaggtg agagctccaa gagaaggacg aaattaatac agagaaggga cgactgaagg    194160
caaactccgt ctccttccta gtgccctat taatgagtct tatcagagag accagcagaa     194220
gagtatgttt tataccttag cgctgtgatg tggccacagt gtagacaagg cttgggaaag    194280
agcctactca cgtgacattc aggaagcaga cccatcctgc agctgctgcc accatattcc    194340
ctctactcca agggccatcg tgaaggaga ggacagattg aactggtggc gaaagcagaa     194400
gatgccatta taaaaacaaa ctccaaaatc tttgatgagc atgaaaacca attctatgat    194460
gatttttcca gtgggtgcaa atgtagtagg atttacatat aaaccgtggg tcagactaag    194520
gtcaggaagg agctgtgata aatatgggga ccagtaatgt gaggaaatat aactgggagg    194580
tcttggaaac aatttagttt gcaaggcagc aaactaaaag gtagaatgta tattttgctg    194640
gcccttgaga atcatactgt gactaacaag cattttcaag tcttattaac ttgtttattc    194700
aacaaacatt tgtgtttctt ttatatgtga ggccctcttc tgggtgttaa aggcacagta    194760
gtcaaaaagg aagtccctga tattagggac catacattag tagattatat aaaacagaaa    194820
taaaataata catactgtga agaaaaatac agcaggataa gaggatagaa agtgatgaaa    194880
gctgctaggt ttcacagaga agggagactt ctctgagaat gggatatctg aatacagtga    194940
aggagccagt catggaatat tggagaaggg cattccagtc agaggaaaca gtgaaacata    195000
agaaagcctt gaggccagaa cctgctgggc acacactgag aacagcagag gccagtgtga    195060
aagggagaaa ggtaaggcca gagaggtgtt gggggctaca tattataggc caagataaag    195120
acgttggatt gtattctaaa gtgcagtggg gatgcctgtc aaggatccag gaattttaa     195180 tttttatttt taggggaaca ctgactgttg gatgatagat aagagagaca agaacggaag    195240
cagggagatc atttagaggc ttttgctgta atctaggcca gaggttttgg tggcagacag    195300
ataaataaga ttgttggctt cagaatatgt tcatatgctt gctgatggat tgggtgaggg    195360
tacatgagta agagggtaat caagaataac tccaaagttt aaggcctaag ctataaccaa    195420
ataaatgata gtgctattca cagagatagg aaatactaaa gacggagctg gcttgcagga    195480
gggaaattaa gagtttggtg ttaatcatgt taagtttcag atctctatca ccttccaact    195540
ggcaatatca aataagcagt tggttgtaaa agtctggagt taaggggaga ggtttagaga    195600
tacaaatgtg ggagtcgcca ccatatattt ggtattttaa gtcatggggtt ttagtgaagt   195660
```

```
aggacctgat tcagagtaag tactaattct ctttccttcc tgtataaaag gcaaaggaag   195720
ggagattcca gctggaagag catgaagcag tagttgagtt aagccgttaa aggctgggta   195780
gaatcttagt agtcaaaatt atgggaaaac acagtgaagg agtaagaaat tatgtaaacc   195840
aaagccaaaa gataaagagg agcaatatgt gtgcagaaaa ccatggctcg ctaaatgact   195900
gaggcataga cttgtcataa aaaactggtg aagaatcatc ttggaaactc agggactata   195960
atcttggaat ctgtagactt ggaatcttta ttgaggggtt aatggggatc cttcagaagt   196020
ttatgaggag gagttgatag aatgcaattc aagcagtgct tttgtaagat taatctaagt   196080
atgaagaata catttgaaat atgtgaaaat gggaatttga taaaccagac agaaagctat   196140
tataataatc cacatttggc tgaaaaaact ggaagtattt ttttaatcat cagattaaag   196200
tacattttgg aaatatcaaa tagaagagac aggataaagt acaggaaaaa tcctgtcttc   196260
tattcaggac cttgttctgt tgagtgagct ttagacaggt tattcagtat ttgtggatgc   196320
ggtttctata tctataaatt ggaaagcaaa caagttaacc tctagttcct agcaaagtat   196380
atattacttt attttttacta attttgaata ttgtttaata aaggatgaac tctgatactt   196440
tagaaagttg gtattttttct gtatcaaatt ctgtccccac tatcactatc cttttttggta   196500 ataaatttcag gagttacatt tttgtgactg ctacaactgc taataatttc aagagttaga   196560 ttttttgtgac tgctgcaatt tgaggtcttt aagaaacaaa acaaacaac catcaggctc   196620 acaaaaatgt cactcttagt agattggatg ttctttagtc taaagatctt ttgcttttca   196680 aataaaaatac cagttcttttt cttacagaga catgtgacgc agtctgggtg taatcgtaaa   196740
ttcaaatgca ctgagtgtgg aaaagctttc aaatacaaac atcacctaaa agagcactta   196800
agaattcaca gtggtaaata ttttttttct ttctataccc tgaatatcat agcatatgtg   196860
gtaataaata aatatcataa catgtaatct acgtacatga tcagaaactc cttgcatttc   196920
ttttggcata cactaattgg gagaaatttt atgtttattt tatgtttat tagagtctta   196980 acctttgact aaagtatatc aaattaatat agtatgacat actccagatt tcctaatcag   197040
aagataatat agcatgtttt agtaagtaca acctgaaaac atattagctt tctgatgaat   197100
gtaaatgtca ttgcctcctt tgcacaatta gcaggggaat ggaaagagt atagagatac   197160 gatttgcaca agagaatagg gaagtgaaga catcctttat ttgagaaaag ttgaaatgga   197220
actcaagatt agaaaatatt ggagagctga tatagaggca atgagaggga gtgaaaggat   197280
tacagcatta atgagaatct gaaagaaaaa tgtgctcacc caccatcttc acctgtctat   197340
tccatgtcat tctgtaaatt attacttaca aggttaatac tattatgcga tgaaagtgtt   197400
gtgtctattt taggaactca gagtaaacag agagctatat ttgcatttct ttggagacac   197460
tacttgaaca aaagcgcaaa aggaaaactt gctggtatcc cacaatgccc tatgaaatct   197520
gttcatctcc tgataaattt tgatatgtta tttagattt aaatcatttt aatgaaaaaa   197580
ttattaacca tgaatgggaa attatgggtt ttcacacatt gcttattttg tgaaaattat   197640
gtattgacat ttacatttta caaacatctt cctacaaaaa agtatagtt ggatagcttt   197700 gtgaagcata gttgatgata tttatgtttt attttggaac tgcatttcta aaagttttac   197760
tgtattgctc attaaggcta accctcaatg ttaaacgtgc tgaagttacc acttgaaaat   197820
gctcaaacca agatccttac caaaacattt attttcacac attgattatt gtttctaaaa   197880
agtagaggtt gtcttttgca gcctgccaca atattctgtt tcttagcttc tatgctattg   197940
aacaattttt atcaataata atatatttta acaacctacc ttcttaccag agatgattta   198000
```

```
aagttgttaa taaagatata gctaattcaa gagggatttt taaatgttga aatcagggca 198060
gaggaaggaa aataaagcta acagtaagat tcatgtatat aatgagtcat attcattttg 198120
tcatattgca gtcatggaag atttatcaga tctataaata atacaaagtt ggaaagtata 198180
aatcagaaca aggattgaaa tactggtcta gaaataagaa gttgaaagtt aagcattggt 198240
atttaaaaat cagtctcaat caagtagtaa atttgaatgg cccagagctt aatatgagct 198300
gactgtatgc tgatactgct caaaagctaa tgcaaattta ggccagatca tggaacacaa 198360
agctcccact gtactctgca ctgtccactc attatgtatg tacttatttc tgtcttgttt 198420
ttaaaacatc taatgtgagg cttgtatacc tttaacatag caagtaattt taatttaaaa 198480
atatgtagga aaaattaaga aacactaaca tggagtaaat tgttgggggg acaaaatgaa 198540
tgctgtgaaa tgccatacat atgctggaag tggaccacaa attaagctct aaggtttagg 198600
aagaaaatga caatcagtaa ccaagaccca gggtgtctgt aagtaaaaaa aaaaaaaaaa 198660
aaaaaaaaaa aaaaaaaaaa aaatcagttg ctagaaaaag gactattctt ccttcctgat 198720
accaagtcca tagaaaacgt tattccttgg aacaacataa agagaaaaga acaaacaga 198780 agttatataa tcctcagaaa tatccttaaa ataacacagc agagaatttg atagggtttc 198840 tttttttaaat cagattattc aatagaagcc agtcatagtt caccaaagtg ctatttagga 198900
aaagcattgc tccagggtgg ccacgtagat acagtttaag tacacagctc tctgatggtc 198960
tggttgattc caagagaaga tttttgagca aaggctaccc aaagtgacat ctcaggactg 199020
gtaccagtct gcaaaccctg tgttactcat tcttgagata agtacagaaa ttgagagtaa 199080
gcatttagca tttattatac caagactttg tgacatttta ctatatttta taaaatattg 199140
gtccacagta gattggaaac ttaaaaaaga accaaacaaa gccaactggt cattcaccac 199200
aaatagtttg aaaagctctg cctagggtat ctaataatgg aagagctgaa tatcttttag 199260
gaaacctcca taactttctt ttcacatgac ttttgaaaag atgttgagaa tcaggatcca 199320
aaattatact ctctaaaatt acctatattg ttgctaaata ctggtaccca aaaaattttg 199380
atcatgaccc tatgcagaac cgtgtgtgtt aataattagt tgattctacc tgtaggaatt 199440
gagctatcat gaggaaaagg ctaccagacc tccactcaga ttagagacaa agaacaccct 199500
gcatatggct gtggtccacc cccaaaaata attttccatg gtcttagtaa tttttgcctg 199560 gaaaatttt gtatcagatg cagccaaaca cccaccttag ccattaaaaa aaaaaaaaag 199620
tcagtataca tagtataccg aactttgagt agtgaaactt cctgatgtaa ccttcaggct 199680
aaaatacttg taaccctaa cctccataga taaattagtg atatgcctaa ctaataaact 199740
gtaaagctat gaagctagaa acaaggagtt ttaaattaac aaatatagtg actttggctt 199800
tagaataatt gttgtgtaaa ctttcttttct ggcaatgata aaatatcaag ataatttta 199860 acaataataa tgataactag cacttattgg atccttagct atgtatagcc acatgttagt 199920
tatttgtatg cattaattca tatagtcctc aggataaccc tatggagtag gttttattat 199980
tttctacttt ttactgatga gaaaattgag gctcagaggg cttaattaac ttgtccaagg 200040
tcactcaggt agtacatggc aaagctaggg ctgtgatgta gtcatcctga cccaaagtca 200100
ttcccttacg taccatttct gtcccctgt tttaaaaaat agtctgtatt tatagatgtt 200160
tatctttcta gcgtctctag aaggaaaata agcatgtagt tcatgtaaaa atgttatcaa 200220
gtaattaaaa gtgttaaaat agagatgtac tagagtatat tccttgtttt accccactg 200280 gaaacttttg tctgttgtat tttgagaatt gaatcctatt ccaggcatcg cattggaaaa 200340
atattgataa attggagaat ccccagaggt gggttaacaa gcaggtaagg gttctaaaac 200400
```

```
ccacatcctg tgcagaatgt ttgaaggacc taggtatatt taacctatat aagagaagtt    200460
taagaataca tatagcagct cttgatccat ttgaaggttt gacttgagaa gaaaagttac    200520
acttgttctg tgtggcatca ggacaaacta ggatagggaa ataggcatca tagctatttt    200580
tttggctcaa actcagcctg tctcttagta gaattgcctt tttaaaaagt gactagcatt    200640
tgttgagagc atactaagag ttttgctata taatctcata tgaccccctat aacagtccaa   200700 tgagaatgta tctgcatttg cacattgaaa aactaaggct tggacaggtt aagaaaatac    200760
tatgtgatgg agccaggatt tgaacccaaa tccatggacc tcaacagaac cagacaggac    200820
catcttgtgc agggctgtcc agcaggtcct aactcccctt ttattaaaga agctcaagca    200880
gagattagct ggtgtcaaga atgatatgaa atgaactctt cattgaaaag gaggctgtac    200940
tacaagggct tcttaaatct cttccaattc ttatatatga ttcttcaaat aatcatattt     201000
attagaaaat ataactcaca tgtttaaact atagcattga agttactatt aagcaatttt    201060
tagtagggct taaattgatt cctcactgct ttcattttaa ttcttaaaaa gagcaggaga    201120
tggagagttt tattttgata ctaagtagac aaatcagtgt catcacatct catcattcaa    201180
caattagcca ttcactcatc caaaaaaggt ttaatgagca tctttgcaac ctgtactttg    201240
atgggtgcaa gggataaatg gcaaacaagc ctcagaggct cctgccttac tgaagcttat    201300
agtctgtaac cttttaaatta taaattagtg aactataact taaaactcaa aggaaacatt   201360
aggtttgtag gaaaatattc catttagctc ggtgctttca aaattttcta ccaaagtatc    201420
cctaacagcc aaggagaata aatgcctttt accccacaga gtctagggaa gcagcttgag    201480
ggaagcctct gcaagccaaa ggctactttg acagtgcgtg gcttttccta gcaagtcaca    201540
caaatgtgtt tttctctgtt ttaatataaa aataatgttt tatcatatcc actgtcacta    201600
aaattgaaac tccaaggtgc tttgataccc actacagtgt ttatcctggg agtatataca    201660 tttcagtttta ataagccaat gcttatagaa tatcttatat aagttttcct cccattaggg   201720
aaaaactatt ttcaagaaag ccctatgggt acaggaatta ttattaatca aagatagata    201780
ttcatacttg ttaagtcata tgggacattt tacttatttt tcttttcttt aatatttctc    201840
ctacagatgg ttgagtagag taaaatatag aaaattatat aggtcggtga atgggataa    201900 gaaaaaacat acttgaaaga gtagaatgta attacttttg atacttgaga attatttgaa     201960
gttataaaga ttggtggaaa tattatacac atatgctgag aagattccat gattggttag    202020
cagaacatgt acctcagact tagttactag cgttcatcac atctatgtag gttttgaagc    202080
taaaaagttt attctaaata cagttctgtc acaagcatgc atggcagtct tcttttttaaa  202140 attgataccg cttgttttag ggaaatgagg atacataaaa atttatatgt aataattcag    202200
tgaatataat ttgtttgttt gtttgtttag gagagaagcc atatgaatgc ccaaactgca    202260
agaaacgctt ttcccattct ggctcctata gctcacacat aagcagtaag aaatgtatca    202320
gcttgatacc tgtgaatggg cgaccaagaa caggactcaa gacatctcag tgttcttcac    202380
cgtctctttc agcatcacca ggcagtccca cacgaccaca gatacggcaa aagatagaga    202440
ataaacccct tcaagaacaa ctttctgtta accaaattaa aactgaacct gtggattatg    202500
aattcaaacc catagtggtt gcttcaggaa tcaactgttc aacccctta caaaatgggg     202560 ttttcactgg tggtggccca ttacaggcaa ccagttctcc tcagggcatg gtgcaagctg    202620
ttgttctgcc aacagttggt ttggtgtctc ccataagtat caatttaagt gatattcaga    202680
atgtacttaa agtggcggta gatggtaatg taataaggca agtgttggag aataatcaag    202740
```

```
ccaatcttgc atccaaagaa caagaaacaa tcaatgcttc acccatacaa caaggtggcc 202800
attctgttat ttcagccatc agtcttcctt tggttgatca agatggaaca accaaaatta 202860
tcatcaacta cagtcttgag cagcctagcc aacttcaagt tgttcctcaa aatttaaaaa 202920
aagaaaatcc agtcgctaca aacagttgta aaagtgaaaa gttaccagaa gatcttactg 202980
ttaagtctga gaaggacaaa agctttgaag ggggggtgaa tgatagcact tgtcttctgt 203040
gtgatgattg tccaggagat attaatgcac ttccagaatt aaagcactat gacctaaagc 203100
agcctactca gcctcctcca ctccctgcag cagaagctga gaagcctgag tcctctgttt 203160
catcagctac tggagatggc aatttgtctc ctagtcagcc acctttaaag aacctcttgt 203220
ctctcctaaa agcatattat gctttgaatg cacaaccaag tgcagaagag ctctcaaaaa 203280
ttgctgattc agtaaaccta ccactggatg tagtaaaaaa gtggtttgaa agatgcaag 203340
ctggacagat ttcagtgcag tcttctgaac catcttctcc tgaaccaggc aaagtaaata 203400
tccctgccaa gaacaatgat cagcctcaat ctgcaaatgc aaatgaaccc aggacagca 203460
cagtaaatct acaaagtcct tgaagatga ctaactcccc agttttacca gtgggatcaa 203520
ccaccaatgg ttccagaagt agtacaccat ccccatcacc tctaaacctt tcctcatcca 203580
gaaatacaca gggttacttg tacacagctg agggtgcaca agaagagcca caagtagaac 203640
ctcttgatct ttcactacca aagcaacagg gagaattatt agaaaggtca actatcacta 203700
gtgtttacca gaacagtgtt tattctgtcc aggaagaacc cttgaacttg tcttgcgcaa 203760
aaaaggagcc acaaaaggac agttgtgtta cagactcaga accagttgta aatgtaatcc 203820
caccaagtgc caacccccata aatatcgcta tacctacagt cactgcccag ttacccacaa 203880
tcgtggccat tgctgaccag aacagtgttc catgcttaag agcgctagct gccaataagc 203940
aaacgattct gattcccccag gtggcataca cctactcaac tacggtcagc cctgcagtcc 204000
aagaaccacc cttgaaagtg atccagccaa atggaaatca ggtaaaaaat aacctccatc 204060
ctgaacctgg ctagtaatat gctatttgac taatttcaat taactttgtc taataaatat 204120
cagtcccgta gagccaacta gattattaca aactgtcatt tttaaaagga tcaatgtttg 204180
ctttaactttt tctggcatga tgtcttcagt tggttgtttg ctaatccagg gtattgttac 204240
cagcttaaag tttgaaatgc tattctactg aaagatgatt tttaagtccc agctaaaaac 204300
ctgtttgaag ttagaaatca aaaaacaaaa ttgaaatact cgctaattgg gtttctgttt 204360
ttatagctaa attcctaaaa ttagtaatag tttctgcctt gattatggtc attaattaat 204420
gaaaatatgt tcccattcac aggttcatac caggcaaact tatctatcac ttttatatac 204480
taatacatct gtttataaaa ggttttaatt aaataaacag gaatgaagta tacaaagaac 204540
gcatcttgtg aatttactga tcattttatg aactgtgcat aaacagtgtt cagtcataat 204600
gtatatgagg aagtgtggct gtgaacctaa aaatacatat gcattttcct ccttaactat 204660
cacagtgttt accacaacag tgtttattct gtccaggaag aacccttgaa ctggtcttac 204720
cccaaaatcc acaatagttt tggatagagc tattgtatgc ctcattgtcc agactttttc 204780
catgtcactg atgttgatgt tttcccattt tttccatcaa tttctgatgg aatcaaatga 204840
atactagaga caaatttgat attttatgca aatattttct ataagtataa taatttcaat 204900
atcctgctca aacttgtatt tgctgctttt gttttcccctt aaatattgct attgattggg 204960
tttcctgtaa ttgtgataac tcttgaaaaa aagttcttac gtgatcattg aattcctcta 205020
aatttttagt gtacagaaca ctttgcatgc ctttgaatag aaaaagagcc atccttagca 205080
tttcatagac tcacgtgtca cgtgactaga tcaagtagca gtgaaagtag aatcaagtta 205140
```

```
cttcagcacc agggccactc acaaatgaca gggacaaatg gctgcacctc tcttgcctca 205200
tagagccata agaaatgttg tgaaaaacct tcaactttta gaaaatgtgt gggtttgagg 205260
caatggcgtg gaacactcta gataaggtag gaagatctta ggggacccag ttccacaaca 205320
ggctccctgc agggttattt ggcttacata agaacgtgct gcccaaaatt atctccatga 205380
gactgcctgg agtttctaaa ggttcatttt gattagcaat tatttctgtt aaaagatag 205440 accctcctgc attgtttttc catcttgctc cttagacaag tggtagagca cacctctctc 205500 tttttcaagga gaccgtggag gttaaagaac cctgaagttc tggaggatac aattgaaaga 205560 ccaggttttta aaatagaat gttagctttt gcttagtgaa acccagaatg agaaaaatga 205620
aggcaaaaga tgcagttagt aatgagcgat taattagcaa actaataagt taaaaccttc 205680
tgcaaatttc tcgtaaagta atgattcaca tgaaactagg taaactctgt tactatatat 205740
tttacatgct ttcttttcgg tgtccttgct ttctttccag taccagttga gtatatgtct 205800
ttgctatggt tttgactgtg ttatccccaa cctcactctt gtctttgtca tctccacctg 205860
tgatctggcc ccaccttgg ggcacatgtg cagtgaagat cagtgtgctt gctttggtca 205920
agtccttgaa agtataaaag tataagttaa agtagttctt tatctcatgc ttttatgtat 205980
atctcttgtt tatcttttaa tgttaaatta cattttctca cacctttctc cctctaggat 206040
gaaagacaag atactagctc agaaggagta tcaaatgtag aggatcagaa tgactctgat 206100
tctacaccgc ccaaaaagaa aatgcggaag acagaaaatg gaatgtatgc ttgtgatttg 206160
tgtgacaaga tattccaaaa gagtagttca ttattgagac ataaatatga acacacaggt 206220
atgtcagtga acacaaacat aaagtgtcca tgatatgata tactggaaga tgcaaaatta 206280
aaaactaaag ttttagaatt ttcttctttt tttttttttt ttattttgtt ttgagacaag 206340
gtctggctct agtcacccag gctggagtgc agtggcacgc aatctcaatc tcggctcact 206400
gcaacctccg cctcccgggc tcaagccatc cttttcatctc agcctcctga gtagctggga 206460
ctataggcac ataccaccac acctggccaa ttttgatata gacgggtttt gccatgttgc 206520
ccaggctggt cttgaactaa tgagctcgag ccatctaccc acctcggcct cccaaagtgc 206580
tggtattaca ggcatgagcc accacgcttg acccagaatt aatttctta tttttactt 206640 atctgatctg gccatttca cctgtttgcc cacttctacc tagtacttaa ggtctgtgcc 206700
tttcttttgg tttttgctt catctgtttt tttgttttt tcatgactta tttcctttaa 206760
gctgacacag catttattct gtccgcattc atttaatgca agcttatgct atattaataa 206820
aaacatagta catagtaccc attaataaaa aatatgagac cagtgggcta aagtcatagg 206880
gagacaggat ctggcttcat aaaagaaaaa gctgcttcat aagcatgcgg caagctgtcc 206940
tggcaagtca agatcttttg ttttaagtaa gaagttctgc ctaagaggtt ggactagaag 207000
attctaagat cctgtaattc tgagatcctg taattctgcc acaaaatatg cctccttagg 207060
ttgactcagg gatggcaaac tatagctcac aggccaaatg tgagcatacg catgtttttc 207120
tatgaggtaa gaatggtagt ttttgatttt gttttacat ttttaaatga ttggaaaaga 207180 tgaaagaat atttatgact gatgaaaatt atgtgaaagt caaatatcag catccgtaaa 207240
taaaattagt tggaagacag catcgcctat tcatttacat tttgtctatg tcagctttca 207300
tgctgttcta caatggcagg attgagaagc tactacagag accatttggc ctgcaaagcc 207360
tttaatactc actacccttt acagaaaata gttgccaact cctggcctat ttcattcctt 207420
ccatcagtga agtactgata aattttaaca cctggttctc tgaagggtgg ggaagccctg 207480
```

```
atttgtagtg tttgcagctt tttgtggcat aaatactccc atcatggtgg atttcgagct    207540
tgaatgtgat gtcagcttgc agaattcctg aaaatttagc agtagactct ctccagccag    207600
tacaaactgg ctccagcaca ctcctgtgtc tctctctaac atgggttgct gtagaagggg    207660
ctgggtttat cctgagctct ttaatcccct acctgctctt ccctgcccccc actaccagcc    207720 attatgacta cagtatccat atttatcttt catattctta actgtttcag tgtatttttt    207780
actcttgtga gaaagatag aattgttttt ccttcttcaa tctgtggatt catacagtga     207840
cacttggaag gttcttggag ctaaaaactg gttacataag agaaagtcac acctctcaaa    207900
atcagcccct tgtaactcag tcctctggtt ttcagagatc taagaagagt tagaaaatcc    207960
ccttcctctt caggcaaagt taaatattag caaatatcaa agtgaaaaat atatatgaaa    208020
aactacacta tttctaaaat taaaaatcat ttctgcattt gttagtgtta actgcttgat    208080
agctctgaaa ttggacatta tcgatcctga ctatgatcag ttgttgccag tccttttcat    208140
gtctgggcag caacactcct gtagcccatg cgttctcagg aggggcaata ttgccctcac    208200
gggccaaaac ttgtttctta gggggcaaaa aagtctgaga tactacaatg gctgtggttt    208260
tctaaagaag ctcagtatat atactgtata tttatgagtt ttatcgtata taaaaagtgt    208320
atagtaaaca ttaaaatttc actgggagca gagcttgtga ctaggaaaac aaaatgacta    208380
aaaagggacc ttgtagtgat aatgaacaca aggtgagcag caagtctgtc cctgtctgcc    208440
ctcactgtgc tcgttcacta ccagacatct cctcccagct gcacttggcc catttttccac   208500 ctcgctgtca tgatgcttgt atttttggca tttcaatgtc atgtagctcc cattgaccta    208560
atcatctgca cagcagagtg tagagcacta cgttttttaa tgtaaagaac aaaccaaatt    208620
gcaatattat attacaaaga gtttgggacc tggaaatgtt ttaaaaatga aactaataac    208680 cctcccctttt ctacaacatg aagtacccca aaaaccgtat aaggatttta tttgctgaat   208740
accaccattt tatttaacag aattcttatt ttgcaggtaa aagacctcat gagtgtggaa    208800
tctgtaaaaa ggcatttaaa cacaaacatc atttgattga acacatgcga ttacattctg    208860
gagaaaagcc ctatcaatgt gacaaatgtg gaaagcgctt ctcacactct gggtcttatt    208920
ctcaacacat gaatcatcgc tactcctact gtaagagaga agcggaagaa cgtgacagca    208980
cagagcagga agaggcaggg cctgaaatcc tctcgaatga gcacgtgggt gccagggcgt    209040
ctccctcaca gggcgactcg gacgagagag agagtttgac aagggaagag gatgaagaca    209100
gtgaaaaaga ggaagaggag gaggataaag agatggaaga attgcaggaa gaaaaagaat    209160
gtgaaaaacc acaaggggat gaggaagagg aggaggagga ggaagaagtg gaagaagaag    209220
aggtagaaga ggcagagaat gagggagaag aagcaaaaac tgaaggtctg atgaaggatg    209280
acagggctga aagtcaagca agcagcttag gacaaaaagt aggcgagagt agtgagcaag    209340
tgtctgaaga aaagacaaat gaagcctaat cgttttctctat gaaggaaaat aaattctaat   209400
tgataatgaa tttcgttcaa tattatcctt gcttttcatg gaaacacagt aacctgtatg    209460
ctgtgattcc tgttcactac tgtgtaaagt aaaaactaaa aaatacaaa atacaaaaca     209520 cacacacaca cacacacaca cacacacaca cacacaaaa ataaatccgg gtgtgcctga     209580
acctcagacc tagtaatttt tcatgcagtt ttcaaagtta ggaacaagtt tgtaacatgc    209640
agcagattag aaaaccttaa tgactcagag agcaacaata caagaggtta aaggaagctg    209700
attaattaga tatgcatctg gcattgtttt atcttatcag tattatcact cttatgttgg    209760
tttattctta agctgtacaa ttgggagaaa ttttataatt ttattggt aaacatatgc      209820 taaatccgct tcagtatttt attatgttttt ttaaaatgtg agaacttctg cactacaaaa   209880
```

```
ttcccttcac agagaagtat aatgtagttc caacccgtgc taactacctt ttataaattc   209940
agtctagaag gtagtaattt ctaatattta gatgtcttag tagagcgtat tatcatttaa   210000
agtgtattgt tagccttaag aaagcagctg atagaagaac tgaagtttct tactcacgtg   210060
gtttaaaatg gagttcaaaa gattgccatt gagttctgat tgcagggact aacaatgtta   210120
atctgataag gacagcaaaa tcatcagaat cagtgtttgt gattgtgttt aatatgtgg    210180
taacatatga aggatatgac atgaagcttt gtatctcctt tggccttaag caagacctgt   210240
gtgctgtaag tgccatttct cagtattttc aaggctctaa cccgccttca tccaatgtgt   210300
ggcctacaat aactagcatt tgttgatttg tctcttgtat caaaattccc aaataaaact   210360
taaaaccact gactctgtca gagaaactga acactggga catttcatcc ttcaattcct    210420
cggtattgat tttatgttga ttgattttca gaatttctct acagaaacga aagggaaatt   210480
ttctaatctg ctttatccat gtacttgcat ttcagacatg gacatgctat tgttatttgg   210540
ctcataactg tttccaaatg ttagttatta tggacccaat ttattaacaa cattagctga   210600
tttttaccta tcagtattat tttatttctt ttagtttata gatctgtgca acatttttgt   210660
actgtatgtc ttcaaacctg gcagtattaa tacccttctt actgacatat gtactttag    210720
ttttagaaaa cttttatatt tatgtgtctt atttttatat ttctttatt attacacagt     210780
gtagtgtata atactgtagt ttgtattaat acaataatat attttagtat gaaaatttgg   210840
aaagttgata agatttaaag tagagatgca attggttctc ctgcattgag atttgattta   210900
acagtgttat gttaacattt atacttgcct tggactgtag aacagaactt aaatgggaat   210960
gtattagttt tacaactaca atcaagtcat tttacctta cccagttttt aatataaaac    211020
ttaaattttg aaattcactg tgtgactaat agcatgatgc tctgcagttt tattaagaaa   211080
tcagcctaac catacaactc tcatttcctt agtaagccaa attaggatta acttctataa   211140
acagtgttgg gaacaatgtt taacattttg tgccaatttg ttcctgtatt catgtatgta   211200
agttacagat ctgactcttc attttttaagt tccttgttac atcatggtca ttttctagtt   211260
ttttaccaga ctcccatctc acaataaaat gcatcaacaa gcctgaactg ctgtcattct   211320
tttcatcatt atcagtattt tctttggaaa actgtgaaat ggggtacatt gtcatcctgc   211380
atttgattca tcttgagctg aatttgggta acactaaatg ttttagacat tctccactaa   211440
attatggatt ttcttgtggc taaatgtttc tggagaggtc agagttgaca aaacctcttc   211500
acaggttgct ccttcttcct gaaatcctta atcctccgca tttcatgctt caggtcattt   211560
cagggaagcc tgggtttaga tgcctttctg actctcagct cctgcacttc tgtcatcata   211620
cctctgatac tattatttat attccttccc cactaggaac aggaaccaca tttgtcatag   211680
tcactctcac attcctcact gcctaacagg gtgcctggca taagtggga caacagatat   211740
ttgttgaata aaaatataat ttgcatgttt atggagctca gctatgttct cacttttttt   211800
gcttctaatt ccagaatata tgttaaatga tctaataatt tgattatttt cttataagtc   211860
ttattaaaca ctagtcataa tagacacaat aaattatgcc ttcttttttct attgccttac   211920
tattttgatt ttttgaaagt gtatttctag gtgtcttcct ggtgcttaac ctcatggtat   211980
atggcacagg tattgctggc ttgtggacat gactacctcc aataggagcg ataggactga   212040
tcctagtcag ctctcctttg tagaattcac ttcccttctt aggacccccat attcgtaggt   212100
gctcgttacc atgttgcctg atttcccctg tcactgagag cagctaccaa taaacagact   212160
gactgaaaag gattaggaac taagaataag atactcttct taggaggtat ccacaatgta   212220
```

-continued

```
atataaagtt caatgagggc agtgcttgat atgtatggat aaatgactaa taaaggaatt 212280
taggcattac cagaactttt cagaaagaaa acgtacatgg acctttccca gtattccctc 212340
atatgacata caacaaaaat aatagcaggg ccatatatta tttattcatg ccatgcacag 212400
gtatttcact actatcaaaa tgttcacaaa agcctcataa aaaatacaaa taaagacaat 212460
gtgcccatga acacatacgt cttaagtagc agaatgagga tatgaacata ggcttatct  212519
```